US006818758B2

(12) United States Patent
Kalush et al.

(10) Patent No.: US 6,818,758 B2
(45) Date of Patent: Nov. 16, 2004

(54) ESTROGEN RECEPTOR BETA VARIANTS AND METHODS OF DETECTION THEREOF

(75) Inventors: Francis Kalush, Rockville, MD (US); Michael J Cassel, San Leandro, CA (US); Stuart Soo-In Hwang, San Carlos, CA (US); Emily S Winn-Deen, Potomac, MD (US)

(73) Assignee: Applera Corporation, Norwalk, CT (US)

( * ) Notice: Subject to any disclaimer, the term of this patent is extended or adjusted under 35 U.S.C. 154(b) by 32 days.

(21) Appl. No.: 09/768,185

(22) Filed: Jan. 24, 2001

(65) Prior Publication Data

US 2004/0185439 A1 Sep. 23, 2004

Related U.S. Application Data

(60) Provisional application No. 60/183,755, filed on Feb. 22, 2000.

(51) Int. Cl.[7] ........................... C12Q 1/68; C12P 19/34; C07H 21/04

(52) U.S. Cl. ......................... 536/24.3; 435/91.2; 435/6; 536/23.5; 536/24.31; 536/25.32

(58) Field of Search .................... 435/6, 91.2; 536/23.5

(56) References Cited

PUBLICATIONS

Stratagene Catalog 1991, p. 66.*

Rosenkranz et al; "Systematic Mutation Screening . . . "; Jnl of Clncl Endocrinology and Metabolism; 1998; vol. 88 No. 12; pp. 4524, 4526.

Albagha O et al.; "Estrogen Receptor –alpha and –beta . . . "; Calcified Thissue International; vol. 64 No. Suppl; 1999, p. S86.

Kazuhiro Tsukamoto et al.; "Isolation and radiation hybrid mapping . . ."; J Hum Genet (1998) 43:73–74.

Mosselman et al.; "Erβ: identification and characterization of . . . "; FEBS Letters (1996) 49–53.

* cited by examiner

*Primary Examiner*—Elizabeth Kemmerer
*Assistant Examiner*—Joseph F. Murphy
(74) *Attorney, Agent, or Firm*—Celera Genomics

(57) ABSTRACT

The present invention is based on sequencing genomic DNA from human chromosome 6 and cDNAs to define the genomic structure of estrogen receptor beta genes and novel polymorphism in the estrogen receptor gene/protein. Such polymorphism can lead to a variety of disorders that are mediated/modulated by a variant estrogen receptor, such as a susceptibility to cancer, osteoporosis, cardiovascular disorder, etc. Based on this sequencing approach, the present invention provides genomic nucleotide sequences, cDNA sequences, amino acid sequences and sequence polymorphism in the ESR-beta genes, methods of detecting these sequences/polymorphism in a sample, methods of determining a risk of having or developing a disorder mediated by a variant estrogen receptor and methods of screening for compounds used to treat disorders mediated by a variant estrogen receptor.

4 Claims, 94 Drawing Sheets

Human Genomic DNA for Estrogen receptor Beta (SEQ ID NO:1)

AGCCCGCTGTTTCAGGCCCCGCCGATCTGGAAGGAGTGTCAGAGCTGGAGCGCGCGTGGCCTCATCGGTG
TTGGGGTCACCCCGGGGTTGCCAGGGCTCATGGAGGGTCGTAGTCTGGATTTTGTCACCCCCACGTCCCC
GCCCCGCAGCAAGTCTGGGGTTGGAGAACTCACGCGGTCTTCGTAAGCTACATGCCAGTTGACCCTCGAG
GAGGGATGCTCCCTCCCCTTAAGCGTCCACGCTGGAGAAGGAGTAAGATGGACAATTGCCTGGGGAGCCT
GACAGGGCGGTGGCAGCTGGGATGCTGGAGAGGACTGGCCCCTTGTGTTACTGAGTCCAAGGAATATGCT
TGCTCTGCTCTAGGAACCGCGTTCAGGTTACAGTCATCCCAGTAGAGTCCTGAAGATGCGTGGTTCAGGT
CACTTAGGACTTGACCAGATACCGGGTTTCTTTTACAAGCCGTTTACTACTGGCAGAGCTCATCTAAAAC
TTTTTTTGTTTGTTTGTTTGAGACGGAGTCTCATTCTGTCGCCCAGGCTGGAGTGCAGTGGCACGATTTT
GGCTCACTGCAACCTCCGCTTCCCGGGTTCAAGCAGTTCTCTGCCTCAGCCTCCCGAGTAGCTGGGATTA
CAGGCACCACCTAATTAGCCCGCCACCACGCCCGGCTAATTTTTGTATTTTTAGTAGAGACGGGGTTTCA
CCATCTTGGCCAGGCTGGTCTTGAACTCCTGACCTCGTGATCCACCCGCCTCGGCCTCCCAGAGTGCTGG
GATTACAGGCGTGAGCCACCGCACCTGGCCTAAAACTGATTTTTTATTAATTTTGGGGCTTTTAATATTT
TTTTCTTATTTCTAAATTCTGAGGTTATTTATAGTAGCCCCATATACGGGATTAGATAATCTCTTGTGAT
TTTCTATTTCTGGTAATTATTTCTAATATATGTTTTTTTGTTTTTGAGACGGAGTCTCGCTATGTCGCTC
AGGGTGGAGTGCAGTGGCATGATCTCCGCTCTTTGTAGCCTCTGCCTCCCGGGTTCAAATGATCCTCCCA
CCTCAGCCCCCCGAGTAGCTTGGACCACAGGTGCATGCCACCACGCCGGCTAATTTTTCTATTTTTGGTA
GAGTTGGGGTTTCACTATGTTGACCAGACTGGTCTAGATCTCAAGGGATTAGTCTCCCTTGGCCTCCCAA
AATGCTGGGATAATGGGCATGAGCCACCGTGCGTGGCCTTAAAGTTACTATTCTTAAAGTTTGCACAAGT
GATATGTTAAAGGCACAGACTTAGTAATATAATGTCATTATAATAATAACCCTAAAACACATTGTCTCAT
ATTGTGTTGTACCTAAACAAGTGAAATTAAGAAGAAAATTGAAGGAAATGTTTCTGGTAAATTGCAGATA
GTGAATCTTTTGTCTTATACTATCAAATAGGTATTGACTATTCCAGCTTTCTTATTTGTTGAGGAAGATG
GCAGAAATCCCATTTTACAGAGGGATAGACTTTGAAGGATAATACCCAAAGCTGCATAGCTGTGGCTGGT
ATAGGCCCCAAACCTGATGTTTCTTCTCTAAATCTACTGCCTTTGCCATCTCAACAGCCTGGTTTTTGAC
AGTTATCTATGTATGAGTTGCATAAATCGTTCATTCATGGAGCAAATAATTATTGAGTGGCCACTATGCC
AACAGCACTGCTATAGATGCTAGAGATACCCTAGTGAACCAGCAAAGTTTCTGCTCTCAGCTCATATTCT
GGTGGAGGAGACAACGATCAAGTTAAAGAAATACATAGGCTAATTTTAGAGATTATGACATGCTATATTT
TAAAAATAGGCAAGCTAAGAGGATAGGCAGTGATGCTGGGAGGTGGGAAAGTTTTGTCTCAGAAATGTGG
TAAGAGATTTCTTTGGGCATCTGACTTCAGCAGAAACCTTAATGAAGAGAGGAACTTGGAATGTAAAAGA
AAGAAAGCAGGGATTTGCTCTGAGCAACTGGAAAGATGGAATTGCCATTCGCTGAGTTGAAATAAAGTAA
AATGTAGGACTAGGTTTTGGGGTTAAGATTATGAATTCGGCTTTAGACATTTTTAGATTTCTCTTAGACA
TCCAAATGGAGAGAAGATATTTAAATCCATGGGATTGAATGAGATCCAACCAAGGGTATTGTAGGTAGAG
AGAGGACCAAAGACTGACACCTAGAACCTTTCAGTGTTCAGAATGCAAGGAGACAGGAGGAACCAAGAGG
GAAGATTGAAAAGGAGAGTCCAGCTGGGAGCTGTGGCTACACCTTTACTAATCCCAGCACTTTGGGAGAC
CAAATACAGGAAGATCACTTGAATCCAGGAGTTTGTAGAACAGCCTTAGCAACATAGCAAGACCCTGTCT
CTACAAAAATAAAAATTAAAAAATTTGCCTGTAATCCGAGCATTTTGGAGGCCGAGGTGGGTGGATCAGC
TGAGGTCAGGAGTTTGAGACCAACTTGGCCAACACAGTGAAACCCCGTCTCTACTAAAAATACAAAAATT
AGCTGGGCGTGATGGCTGGTACCTGTAATCCCAGCTACTCGGGAGGCCGAGGCAGGAGAATCCCTTGAAC
CTAGGAGGCAGAGGTTGCAGTGAGCCGAGATCACGCCACTGCACTCCAGCCTGGGAGACAGAGCGAGACT
CCATCTCAAAATAAATAAATAAATAAAAATTTAAAAAGTTAGCTGGGCGTGGTGGCATGTACCTGTAGTC
CCAGTTACTCAGAAGGCTGAGGTGGGAGGATCCTGTGAGCCTAGGAGTTGGAAACTTCAGTAAGCTATAA
TCATCACACTGCACTCCAACCTAGGCAACAGAGCAAGACCCTGTCTCTTAAAAGGAAAGGAGAGTCCAGT
GTGTTCTAAGGAAAACCCCAAGAGCATCCCACCTTAGAAGACAAGTGAGGAGGCCTGGCATGGTGTCTCA
TGCCTGTAATCCCAGCACTTTGGGAGGCCAAGGTGGGTGGATCACTTGAGGTCAGGAGTTCTAGACCAGC
CTGACAAACATGGCGAAACCTCCGTCTCTATAAAAATACAAAAATTAGCCAGGTGTGGTAGCGCGTGCCT
GTAATCCCAGCTACTAGGGAGGCTGAGGCAGGAGAACTGCTTGAACTCAGGGGGCAGAGTTTGCAGTGAG
CCGAGATAGTGCCACTGCACTCCAGCCTGAGCAACAGAGTGAGACTCTGTCTCAAAAACAAACAAGTAAA
CAAACAAACAAAAAAAACAAGACAAGTGAAGAATGTGTTTCATGGAAAAAGAGGTAATTAATTCTGTCAA
GTGTTGCAAATTGGTCAAATAAAGAATGAAAATCAACCTTTCACAGCAAATAGAAGGAAAAAATATTTTT
ATTTAAATGCTTATAAAGGCAGTTGCTAGAAAAAATGTTTACTTTTTGCAGAGGCCCCGTTTTTACAACC
TTTTTCAGGGGTAATTTGATATGATAATATCTACGGGAAAAAAAATGTTTTTTTTTTGAGTCGCTCTGTC
ACCAGGCTGGAGTGCAGTGGCATGATCTCGGCTCACTGAAACCTCCGCCTCCCAGGTTCAAGCAATTCTT
CTGCCTCAGCCTCCCAAGTAGCTGGGACTACAGGTGGGCGCCACCACACCCAGCTAATTTTTGTATTTTT
AGTAGAGACGGGGTTTCACCATGTTGGCCAGGATGGTCTCAATCTTGACCTCGTGATCTGCCTTCCTTGG
CCTCCCAAAGTGCTGGGATTGGTACAGGTGTGAACCACCATACCTGGCCCGAAAATTTTAAATTTGTATT
TTCTTTGACATTGTAATTCCACTTCCAGGATTTTTTTTTTTGGACAGGATTTTACTCTGTCACCCAGGC
TGGAGTGCAGTAACACAATCAGCTCACTGCAACCCTGAACTCCTGGGCTAAAGTGATCCTTCTGAGTAGT
TGGGACTATAGGCACATGCCACCACCCCTGACTAATTAAAAAATTTTCCTGTAGAGATAGTCTTGCTATG
TTGCCCAGACTGGTCTCCAACTCCTGGCCTCAAACCATCCTCCCACCTTGACCTTCCAAAACGTTGGGAT
TACAGGCGTGAGCCACCTCTCCCAGTTTAGGAATTTATCTTAAAGTAATATTTACATATAAAGAAAGATG
TATAGGCTGGGTGCAGTGGTTCACGCCTGTAATCCCAGCACTTTGGAAGGCCGAGGCTGGTGGATCAACT
GAGGTCAGGAGTTCAAGACCAACCTGGCTAACATGGCGAAACCCCATCTCTACTAAAAATACAAAAATTA
GCTGGGCGTGGTGGCCAGCCCCTGTAATCCCAGCTACTCGGGAGGCTGAGGCAGGAGGATAGCTTAAACC
CAGGAGACGAAGGTTGCAGTGAGCCAAGATTACACCATTGCACTCCAGCCTGAGCAACAAAAGCGAAACT
CCATCTCAAAAAAACAAAAACTAAAACTAAACAAAACAAAAAAACCATGTGTAAAACTGTTAATCACAAC
ACTGATTTCAATAGCAAAAAACAAAATTTCTGTCAGGATGGATGCAGTTGTTAAAGGAACAGCAGATACA
TATGTATAGACATGTAAGATAGCTTTCATACTTTTTTTTTTGAGATGGAATTTCGTTCTTGTCACCCAGG
CTGGAATGCAATGGTGAGATCTAGGCTCCGCTTCTCAGGTTCAAGTGATTCTCCTGCCTCAGCCTCCTGA
GTAAGCTGGGAATACAGGCGCCCGCCACCACGCCCAGGTAATTTTTGTATGTTTAGTAGAGACAGGGTTT
CGCCATATTGGCGAGGCTTGTCTCAAACTCCTGACCTCAGGTGATCCACCCACCTCCAAAAGTGTTGGGA
TTACAGGCATCACCCACCACGCGTGACCAGCTTTTATACATTTTTAAATGATAAAGACAGGTTAATAAAA

TGTATAATATTATGTTGCTATATCCAAAAAAAGGCCTTCTTTGATTACACTATCAAAAGTTACCTCTCCA
TTTACATCCCCATTACTATCTCATTAACCTGTTTTATTCATAGCACTTACTACCATCTAAAATGACTTTA
TTTCTTTATATTTTTGTTTGCTACCTGTCTTTTACACCAGAATTTAATTTTTAAGCTTTTTTTGTTTGTT
TGTTTGTTTGTTTTGAGATGGAGTCTTGCTCTGTTGCCCAGACTGGAGTGCAGTGGTGCGATCTCAGCTC
ACTGCAACCTCTGCCTCCTGGGTTCAATCAATCCTCCTGCCTCAGCCTCCCAAGTAGCTGGGATTACAGG
CATGTGCCACCATGCCCAGCTAATTTTTGCATTTTTAGTACAGCAGGGTGTCACCATGTTGGTCAGGCTG
GTCTCAAACTCCTGACCTCAGGAGATCCGTCAGCCTTGGCCTCCCAAAGTGTTGGGATTACAGGCGTGAG
CCACAGCACCCAGCCAGAATTTAAACTTTATAAGAGATTTCCTGTCTTGTTCATACTTATATACCTGCAG
CTTCGAAACATATATATATGTTTAATATATATAATAGATATATTTTAAATTATATATAGAGAGATGGAGT
TTCACTCTTGTTGCCCAGACTGGAGTGCAATGGCGTGATCTCGGCTCACCACAACCTCTGCCCCCCGGGT
TCAAGCAATTCTCCTGCCTCAGCCTCCAGAGTAGTTGGAATTACAGGCACGTGCCACCATGCCTGGCTAA
TTTTGTATTTTTAGTAGAGACAGAGTTTCTCCATGTTGGTCAGGCTGGTCTCGAGCTCTTGACCTCAGGT
AGTCCGCCTGCCTCGGCCTCACAAAGTGCTGGGATTACAAGCATGAGTCACTGTGCCCTGCCAGAATTTA
AGCTTTATAAGAGATTTCCTGTCTGTTTATACTTAAATACCTGCAGCTTGGAAACATATATATGTTTATA
TGTATATATTACATACATTATATATATATTTTTATATATTATAATTATAAACTCCTGACCTCAGGTGATC
CACCTGCCTCAGTCTCTCAAATGCTGGGATTACAGGCGTGAGCCACCACGCCAGGCCAGAAACATATTTT
TAAAAATCTTGTTTTAGAGGAAAAACAGAGTATTTCTTTTTTTTTTTTATTAGATGGATTCTCACTCTAT
TGCCCAGGCTGGAGTACAGTGGCACAATCTTGGCTCACCGCAACCTCAGCCTCCCGGGTTCAAGCAATTC
TCCTGCCTCAGCCTCCCGAGTAGTTGGAACTATAGGCGTGAGCCACCATGCCCTGCTAATTTTTGTATTT
TTAGTACAGATGGGGTTTCACTATGTTGGCCAGGCTGGTCTCGAACTCCTGACCTTGTGATCTGCCCACC
TCGGCCTCCCAAAGTGCTGGGATTACAGGTGTGAGCCACTGCGCCCGGCCTATTTCTTCTTCTCTTTGTT
TAGTTATTATCTATTACTCTCATTCCTATGAACATAACTTGTTTCTCCCCCCTTAATTTTTATCATACAT
GATTGTAGACAGTGGGCACTGTCTTCAATTATAGTGAATTTAGCAGTAAATTCACATTAGACCAACTTGT
ATAGCTTTAAAAAATATATTTATGTCTAGGTTCCACCCTTGACCAACTAAGTCAGAACTTGGGTGGGTTC
AAGGTTCATTATTCTTTGAAGATAAGATGATGTTTGAATAAAATTCCTGGTGATTCTGGTATCAAAAATA
CAAATTTGGGACATACTTTTTCTGCTGTAAAAATATTTTCCTAAGGCCAGGCGCAGTGGCTCACGCCTGT
AATCCTAGCACTTTGGGAGACGGAGGCGGCAGATCACTTGAGGCCAGGAGTTCAAGACCAGTCTGGCCAA
CATGGTGAAACCCAGTCTCTACTAAAAATAGAAAAAATTAGCCAGGCATGGTGGCACGTGCCTGTAGTCC
CAGCTACTCAAGAGGCTGAGGCAGGAGAATCCTTTGAACCCGGGAGGCAGAGGTTGCAGTGAGCTGATAT
TGCAGCACTGCACTCCAGCCTGGGTGACAGATCAAAACTCTGTCTCAGAAAAAAAAAAAAAAAAAAAAGA
ATTTCCTAGAATTAGAATCGCAGGGGTTTTTTTGTTTTGTTTGTTTGTTTGTTTGTTTGTTTTTGAGAC
AGAGTTTCACTCCTGTCGCCCAGGCTGGAGTGCAATGCCATGATCTCGGCTCATTGCAACCTCTGCCTCC
TGAGTTCAAGCAATCCTCCTGCCTCAGCCTCCCGAATAGCTGGGATTACAGGCACCTGCCACCATGCCCA
GCTAATTTTTGTATTTTTAGTAGAGACTGGGTTTTACCATGTTGGCCAAGCTGGTCTCGAACTCCTGACG
TCAGGTGATCCACCCAGCTCATTCTCCCAAAGTGCTGGAATTACAAGCATGAGCCACTGCACTCGGCCTT
TATTTATTTATTTATTTTTGAGATGAAGTCTTGCTCTGTTGCCCAAGCTGGAGTGCAATGGCATGATCTC
GGCTCACTGCAACCTCCACCTCCCAGGTTCAAGCAATTCTCCTGCCTCAGCCCCCTGAGTAGCTGGGATT
ACAGGCGTGCACCACCACGCCTGGCTAATTTTTGTATTTTTAGTAGAGACAGGGTTTCACTATGTTGGTC
AGGTTAGTCTCGAGCTCCTGACTTCGTGATCCGCCCGCCTCAGCCTTCCAAAGTGTTGGGATTACAGGCG
TGAGCCACCGCGCCTGGCCAGAATCCCAGTTTTTTAACACATCTAATGCTTTAGGAATAGTAAATGGAAA
CATCATTTCCCCTTCTTTCGAAGTACTTCTACCTTGATGAGATGTATGTATTGGAGTACAATATTTGACC
TAGCCAAGAATTTCACAAAAGAAGCCCAAAATATGATTTTCACGTTTACTGGACTGTTCACTTTTGGGGG
GATCACTTTCTTAAGATTACTTAAAGTACTAATGCTTGATGAAAATCATTTGTGTTTTCACTTCATTAAT
TGGAGAAAGAGCTACATGTTTTTGTTGTTGTTGTTGTTGTTTTGAGATGGTGTCTTGCTCTGTCTCCCAG
GCTGGAGTGCAATGGCGTGATCTCAGCTCACTGCAACCTCCGCCTCCCGGGTTCAAGCGATTCTCCTGCC
TCAGCCTCCTGAGTAGCTGGGACTACAGGCGCCTGCCACCACGCCCAGCTAATTTTTATACTTTTAATAG
AGACAGGGTTTCACCATATTGGCCAGGATGGTCTCAATCTCTTGACCTTGTGATCCACCCGCCTTGGCCT
CCCAAAGTGCTGGGATTACAGGCGTGAGCCACTGCGCCCAGCCAGAGCTACAGGTTTTACTGTAACACTT
TAGAAGGTCCTTTTTCTTTGTACCTCTGTGATGTGTTCACCTAGCAACAGCTTCTTTGATATGCAAACAT
TCTACAGGCAAATTGCTCAGAGCAGCTACTCATGTTGGACAATTCAGGTCTCTTCTGGAAACTGGCCTTG
TATTTGGAATTTTCTCCAGAGTCTGATGTGGTAAAAATTTATACTTTTCACTTCTTACTAAATGCAGCAT
AGCATACTACATCTTTTGAGTGTGTAAAAAATAAAGTAGTCATGTACAAACCTAAAATCACAGAATAATC
ATGTAATGGTGCTATATTTTATTTTTACTTTAGATTCCTAATACATTTTTATTGTATCTTTATAAGGTTA
GTTTGGGAGAATAGCACTATCATCATCTATATTAGTTAACTTTGCATTAAGGTTTTTCATTAAGGTTTTT
CCCCTGTTTGGTTCTTTCATTTTACGATCCATATTTTTTGTGCCTGGTATGGGATGATAAAGATAACAGA
AATAGCTCCTGTTTTTAGGTACCTTTATTTGTTTGTTTGTTTGGAGACAGGGTCTTACTCTGTCACCCAG
GCTGGTGGCACAATCATAGCTTACTACAGACTAACTCCTGGCTCAAGCCATCCTCCACCTCAGCCTCCCA
AGTAACTGAGATTACAGGTGCACACCACCACCTCTGGCTAATTATTAAAATTTTCATAGAGACAGGATCT
CACTTGGTTGGCCAGACTGATCTCAAACTCCTGGTCTCAAGTGATCCTCCCACCCCAGCCTCCTGAAGTA
CTAGGATTGCAGGCATGAACCACTGCCCTGGCCTAGATACATTTAATGTAGTAGAGGAGATGAGATTTTT
ACATAGTATAATATTGAATGAGACAACAGTCAAAAGAAAATCACATACTATAAGAGAAGAGATTACCCTT
ACCTTTTAGGAATCAAGAAAACTCCCTGGAGGAGATGGTACTTGAACTTATACTGGAGGATTTATATGTT
CATCCTTCTTGGTTTATATTTGTCCCACACGGTAGCTTGTTTCTTTTTTCTTTTTTTTCTTTTTCTTTT
TTTTTTTTTGAGGCAGAGTTTTGCTCTGTTGCCCAGGCTAGAGTGCAGTGGCGCGATCTCGGCTCACTG
CAACCTCCGCCTCCTGGGTTCAAGCGATTCTCCTGCCTCAGCCTCCCTAGTAGCTTGTTTCTTAGAGACA
GTGTGAGTGAAACTCATTAAGTAAAGTCAATACAGCACAAGTTTCATAAAATGGTAAAGAAATAGAAATA
AAAGTAAAGGATGAAATTCTTAAGAACTTTGTCAGGCCGGGCGTGGTGGCTCATGCCTGTAATCCCAGCA
CTTTGGGAGGCCGAGGTGGGTGGATCACCTGAGGTCAGGAGTTTGAGACCAGCCTGGCCAACATGGCAAA
ACCCTGTCTCTCTAAAAATACAAAAATTAGCTGGGCATGCTGGCGGGTGCCTATAATCCCAGCTACTCGG
GAGGCTGAGGCAGGAGAATCGCTTGAACCCAGGAGGCGGAGGTTGCAGTGAGCCGAGATCACATCATTCC
ACTCCAGCCTGGGTGCCAAGAGCAAAAAACTCCATCTTGAAAAATAAAGAATTTTGTCTCCAGTATCATT

CTTGTTCTAGGACTGAGAAACAGTTCATTCTTCATTTTCGTCTACTAAAATTTAAGTTCTTTGATTTTCT
TCTTTAGGTCTTGGAAAAAGAATTAATAGAGTAATTTTCTTAGGTATCAAGTAATGAAAATGAGAAAAGA
GACTAGTCTCATTATAGATTTTTTTTTTTATTCTTATTTATTTTATTTGAGACAAGGTCTCGCTCTGT
CACCCAGGCTGGAGTGTAGTGGCTCCATTATGGTTCCCTGCAGCCTTGAACTCAGGGGCCCAAGCAATCC
TCCCACCTCAGCATCCCGAGCAGCTGGGACTACAGGTGCATGCCACCATGCCTGGCTAATTTTTGTGCTT
TTTCGTGTATAAAGATGAGATTTCGCCATGTTGCCCAGGCTGGTCTCAAACTCCTGGGCTCAAGAGATCT
GTCCACCTCAGCCTCCTAAAGCGCTGAGATTACAGGCATGAGCCACCACGTCCAGCCTAGAGATATTTAT
ACTTTAATAGCTGCCTGCAATACCAATACACCTAGAATGAATTAGAAGAATTTGAAAACAGATTTCAGGA
TTAGTAAAAGAAAGTCAAGCCCCTATGCCTCCTGTTCTACATTCCTCAAATCACATAATCCTGATTTTTTC
CTCTTCGTATGAAAATTCCTCTCATTTTGGGCCTGTTTGATTTTTTGGGAGACACCACCCAGCAGAAACA
CACCGCACTTACATGCAACCCCTCCATTGCACAGTTTCTAAATGCCCCCCCCCTTTTTTTTCCATTCTCT
GATCCTAAAAAAAGAAATCCAGTGGCACAATCACGGATCTCTGCAGCCTTGATCTCTTAGCCTCAAGTGA
TTCTCCTGCCTCAGCTTCCTAAGTAGCTGGGACCACAGGTGCTTGCCACCATGCCCAGCTATTTTTTTT
CTTTGTTTTTTTGTAAAGATGTGTCTCACTATCTTGCCCAGGCTGATATTGAATTCCTGGGCTCAAGTGA
TCCTCCTACCTTGGCCTCCCAAAGTGCTGGGATTTTATATATATATATATTTCCATTTTACTTATGTTAA
TGCTTTCCCTCTTTTGGCATAGAAAAGCTAATAAAGCTTAAACTTAAATGGAACTTGTATAAACACAATA
TATCTGATGATACCTTTGAGAGATGTCTTACATTTGTCTTTTCTTTCAGCAAAATGTGATGCCAGTCCCT
GAAATGTGTAGCAATTTAATTATGGGTAGCATTCTTCTTTCCCTGTACTTACTATAGTATTAACTTACTA
CTAATGCTAAGAAGTTTATAATTTTTGATAATTCAGATTTGGATTAGATTAAGATTTATGTCTATGCATA
ATTCATTAAAAACTTTTTAAACCAAATTGTCAAAAAAGATTGTAGGTACCTTGTTTAAAGAAAATATATA
AGCTAGTTTCAAGAATTCCAAAATATTTTTTAAAAGCAGCTCTGTACATGTCGATAAATTATTTGCTCAT
TGTAATTTTTTGAATCTGTTTGTCAAAGCAAATGTAGACGGGCTCGAACTCCTGACCTCAAATGATCCAC
CCGCCTCAGTCTCCCAAATGCTGGTATTACAGGCATGAGCCACCGCTCATGGCCTGTTATCATTTTTAAT
TGAAAATTTTACTGAGATAATTGTAGATTCACTTGCCATTATAAGAAATAATTCAGAGATATCACTTGTA
TACTTAGCCCAGTGTCCCCCAAAGGTAAAATTTTGCAAAATTATAGTCTAATGTAACAGCGTGAATATTG
ACATTAATACAATCCACTGAGTTTATTCAGATTTCCCCAGTTTTACTTGTATTCAATTGTGTGTTTGTGT
ATTAAGTTCGATATAACTAGTCAATATACTGAACAGTTCTAACATCACAGTATCCTTCAGGTAGCCCTT
TTGTATCCACATCCACTTCCTTCTCATCCCCAGCTATTGACAACCACTAATCCCTTTTCCATTTCTAAAA
TGTGATTTCAAAAATGTTACATACTTGGCTGGGGGCAGTGGCTCATGCCTGTAATCCCAGCACTTTGGAT
ATACTGTCTCTACTAAAAATACAAAAATTAGCTGGGAGTGGTTGTGCACACCTGTAATCCCAGGTGCTTG
GGAAGCTGAGGCAGGAGAATTGCTTGAACCCAGGAGGCAGAGCTTGCAGTGAGCCGAGAGTGTGCCACTT
CACTCCAGCCTGGGCAACAGAGTGAGACTCTGTTTCAAAAATAAATAAATAAATAAATAAAATGGTCTTC
ATACAGCCTTTGCTGCTAGGAAATATAGTTTCTAATTAATGTAATTTTTTGTCAAATACAAAATGCTTCT
GAACGTTTCTGGTTATCAAGCTGGTAATCTTTCACAGTGTCCTCAATTTTTTTTTCTACTCTCTTACTAG
TTCTCCAGATCACATGCAGGCTATTAAGAAATGTGAACTAACAAGTTAAAGTAGCAGGACGGGCGCTGTG
GCTCACACCTATAATCCCAGCACTTTGGGAAGCTGAGGCAGGTGGATCACTTGAGGTCAGGAGTTTGAGA
GCAGCCTGGCCAACAAGGTGAAACCACATCTCTACTAAAAAAAAAAAAAAATTTGCCAGGTGTGGTGGTGC
ATACCTGTAATCCTAGCTATTTGGGAGGCTGAGGCATGAGAATCGCTTGAACCCAGGAGGCAGAGGCTGC
GGGGAGCCAGGATCATAGCACTGCACTCCAGCCTGGGTGACAGAGCTAGACCCTGTCTGAAAAAAAAAAA
AAATGTTAGTAGCAGCAGAGCACAGTGGCTCATGCCTGTAATCCCAACACTATGGGAGTCTGAGGCAGGA
GGATCTCTTGAGCTTAGGAGTTCAAGACCAGCCTGACAACATAGTAAGACTCCATCTCTACAAATAATCA
TTAAAAAAATTAGCCGGGCGTAGTGGCACCTACCTGTAGTCCCAGCTACTGGGGAGGCTGAGATGGGAGG
ATCACCTGAGCCTGGGAGGTCAAGGCTGCAGTGAGCTGTGATCGCCATTGTACTCCAAACTGGGTGACAA
GAGTGAGACCATGCCTCAAAAATAATAATAATAAATGTATAATTTAAATGTGACCTAACATTATGAAGTT
TTTAAAAACAAAATTATAAATGATTTTAACACTTTCTCATTAGCTAAGAAATCTTCAGAACAAACTTTTC
ATAAAAGAAACTTCACTGCAAGAGTTGAAGCCTGAGCTAGAAAGTTACAAAGAAAATAATGTACGACAGT
CGTTCCAGATAATGTCCCTGAAAGATAATATCAAGGACCTACAGAAACTTACTGCTTCTCTAACCAGAAT
TAAATATTTGAGAAACACCAATATTCAGAGGCTTCAAAGAGGCAACTGGAATTTAACTAAATGAATTATT
GAGCTAGAAACTGTCTAAGGTAGGGATTTTTCCAGTTTGTTTTCAAACATGTCTTTTGTTGTAAGCTTGC
AAATAGCATATGAACTCCATACTCCTGATTGATCATAGAATTTAAATCTGCAGAATTTCACTTAATACCT
GACCCAACATTATTATATTTTGTATTGAGATATAACTTAAATACCTCGGGCCAGGTGTGGTGGCTCATGC
CTATAATCCCAGCACTTTGGGAGGCCAGGGCTGGTGAATCACTTGAGGTCAGGAGTTCAAAACCAGCCTG
GCCAACATGACAAAACCCTGTCTCTACTAAAAATACAAAAAATTAGCTGGGCATGGTGGCATGCACCTGT
AATCCCAGCTACTCAGGAGGCTGAGGTAGAAGAATCACTTGAATCCAGGAGGTGCGAGACTCTGTCTAAA
AAAAAAAAATCCAATTTGAGATATAACTTACATACCTCAAGATTCAGTTAAAGTGTACAATTCAATGGTT
GTACAATCATCACCACTATCTAATTTCAGAACAATTTCATCACACCTCCCCACCCCCCACTGCAAAAAAA
AACCCATGCCCGGCTGGGCACGGTGGCTCATGCCTGAGATCCCAGCACTTTGGGAGGCCGAGACAGGCGG
ATCACAAGGTCAGGAGTTCGAGACCAGCCTGGCCAACATGGCGAAACCCCATCTCTACTAACTACAGGCA
GGTGCCTGTAATCCCAGCTACTCAGGAGGCTGAGGCAGGAGAATAGCTTAAATCCAGGAGGCTGAGGTTG
TGGTGAGCTGAGATCATGCCATTGCACTCCAGCCTGAGCAGCAAGAGTGAAACTCTGTCTCAAAAAAAAA
AAAAAAAAAAAAAAAAGATTTAATGATTGACCTGCTGGATTTTGAACTTGCATGGGGCCTATAGCCTCTT
TCTTTTGGCCAAATTCTCCCTTTTGGAATGAGAGTATTTACCCAATGCCTGCAATTCCCATTATATTTCG
GAAGTCACTAACTTGTTTTGTTGTTGTTGTTGTTGTTGTTTGAGACAGAGTCTTGCTCTGTTGCCCA
GGCTGGAGTGCAATGGCACAATCTCGGCTCACTGCAACCTCTGCCTCCCGGGTTCAAGTGATTCTCCTGC
CTCGGCCTCCCAAGTAGCTGAGATCACAGGCATGCACCACCACCCCCGGCTAATTTTTGTATTTTTAGCA
GAGATGGGGGTTTCACCATGTTGGCCAGGCTAGTCTCCAACTCCTGACTTCAGGTGATCCACCGGCCTTG
GCCTCCCAAAGTGCTGGGATTACAGGCATGAGCCACCGTGCCCAGCCCGAAGTTACTAACTTGTTTTGGA
TTTTACGGGCTCACAGGCAGAAGGGACTTGCCTTGTTTCAGATGAGACTTTGTTCTTTGGGCTTTTGAGT
TAATGCTGGAATGAGTTAGAACTTTGGGGGAACTGTTGGGAAGGCAGATTGTATTTTGAAATGTGAGAAG
GACATGAGATTTGAGAGGGCCCAGTGGGAGAATGGGATAAGGCTTGAGTCTGTGTCCCTGCCCAAATCTG
ATGTCAAAGTATAATCCCCAGTGTTAGGGCCTGGTGGGAGCTGATTGGATCATGGGGGTGTATTTCCCCT

TTGGTGCTGTTCTCATGATAGTGAGTGAGTTACCATGAGATCTGGTTGTTTAAAAGTGTGTAGCACCTCT
CACCTCACTCTATTCCTTCTGCTCTGGCCATGTAAGATGTGCCTGCTTCCCCCTCACCTTCTGCCATGAT
TGTAAGTTTCCTGAGGCTTCCCTAGCCATGCTTCCCATGCAGCCTGTGGAACTGTGAGCCAATTAAACCT
CTTTTCTTTGTAAATTACCTAGTCTGAAGCATTTCTTTACAGAAGTGCAAGAACAGACTAATACATTGAA
CATCTCTTCATGTGCTTATTGGCCATGTGTATATCTTCTTTGTAGAAATACCTATTCATATTTGTTGTCC
CTTTTAAAATTGGGTTGTCTTTTTATTGCTGAGTTGTAAGTGTTCTTTATATTTTCTGGATACTGGACTT
TTATTAAGTGTATAATTTGTAAATATTTTCTCCCAATTTGTGGGTCATCTTTCCACTTTCCTAAAAGTGT
CATTTCAAGCAAAAATTTTAATTTTGATGGAGTTGTGTGTGTGTGTGTGTGTGTGTATGTGTATGTGT
GTCTTTGGTGTCATAGCTGAGAAATTATTGTCAAATCCAGGATCATGAAAGATTTACATCTATATTTTCT
TTTAAGAGTTATAGTTTTGGCCGGGCGTGGTGGCTCATGCCTGTAATTCCAGCACTTTGGGAGGCCAAGG
CAGGTGGAGTTCGAGACCAGCCTGGCCAACATGGTGAAACTCCGTCCCTACTAAAAATACAAAAATTAGC
TGAGCATGGTGGCACACGCCTGTAATCCCAGCTGCTCGTGAGGCTGAGGCAGAAGAATAGCTTGAGCCCG
GGAGACAGAGGTTGCAGTGGGCCAAAATCATGCCACGGCACTCCAGCCTGGCCGACAGACTCTGTCTCAA
AAAAAAAAAAAGATTTATAGTTTTGGCTGGGCGTGGTGGCTCATGCCTATAATCCCAGCATTTGGGGAGG
CCAAGGCAGGTGGATAACTTTAGGCCAGGAGTTTGAGACCAGCCGGGCTGACATAACAAAACCTGATCTC
TACTAAAAGTACAAAACTTAGGCTGGGCACAGTGACTCATGCCTGTAATCCCAGCACTCTGGGAGGCCGA
GATGGGCAGATAATTTGAGGCCAGGCATTGGAGACCAGCCTGGCCAACATGGTAAAACCCTGTCTCTACT
AAAAATACAAAAATCAGCTGGGCGTGGTGGCACGCACCTGTAATTTCAGCTACTCGGGAGGCTGAGGCGG
GAGAATTGCTTGAACCCAGGAGGCAGAGGTGGCAGTGAATTGAGATCATGCCACTACACTTCAGCCCGGG
TGATAGAACGAGACTCTGTCTCAAAATAATAATAATAATAATAATAATAGCTGGACATGGTGGTGCACAC
CTGTAGTCCCAGCTACGTGGAAGGCTGAAGCAGGAGAATTGCTTGAACCCAGAAGGTGGAGGTTGCAGTG
AGCCAAGATTGTGCCACTGCACTCCAGCCTGGGTGACAGAGCAAGACAGGTGTACTCCAGACTGGGTGAC
TGCACCCCAGCCTGGGTGACACTGCACTCCAGCCTGGGTGACAGAGCAACTAACTAACTAACTAACTAAA
ACTACAGTTAGTTTATATATAGTTTTTAGTTAAAACTATAGTTAGTTTGAGCCAGGCGCGGTGGCTCACG
CCTGTAATCCCAGCACTTTGGGAGGCCGAGGCGGGCGGATCACGAGGTCAGGAGATCGAGACCATCCTGG
CTAACAAGGTGAAACCCCGTCTCTACTAAAAAATACAAAAAATTAGGCGGGCGTGGTGTGGTCCCAGCTA
GTCGGGAGGCTGAGGCAGGAGAATCCCTTGAACCCGGGAGGCGGGGCTTGCAGTGAGCCGAGATCGCACC
AATGCACCTCCAGCCTGGGCGGCAGAGCGAGACTCCGTCTCAAAAAAAAAAACAAAAACAAAAACAAAAAA
AAAGCCATAGTCTTTCTAAAACTATAGTTAGTTTATAATTAACTATAGTTTTAGTTATAAAATATAACTA
TAAAGTTATAGTTTTAGCACTTACATTTATGTCTTTGACTTCTTTTGGCAAATTTTTATGTATGATGTGA
GGTAGGAGTCCAGATTCATTGTTTTTCATATAAATATCCAGTTGTCCTTAGCACCTCTGTGGAACTATCT
TGGCATTCTTGCCAAGAATCAATTGACCATAAATGTATGGGTTTATCTTTGGGCACCCAATTCTATTTCA
TTGGTCTGTATGTCTGTCCTTATACCAGCACCACACTGTCTTGATTAATGTAGCTTTGTAGTAAGTTTTG
AAATGGGTAAGTGTGAAAAATTCCAACTTAATTTCATTTTTTTCAAGATCATTCTGGCTATTTTGGGTCC
CTTGCTTTTCCATATGTATTTTAAGATCAGCTTTTCCATGAACATGGAATATTTTTCCATTTATTTAAGT
CTTCTTTAATTTCTTTTTTTTTTTTCCCCGAGATGGCGTCATGCTCTGTCGTCCAGGCTGGAGTGCAGTG
GCACGATCTCGGCTCACTGCAACCTCTGCCTCCTGGGTTCAAGCAATTCTCCTGCCTCAGCCTCCTGAAT
TGCTAGGATTACAGATGCTCACCACCATGCCCAGCTAATTTTTGTATTTTTAGTAGAGACAGGGTTTCAC
CATGTTAGCCAGACTGGTCTTGAACTCCTGACCTTGTGATCCACCCGCCTTGGCCTCCCAAAGTGCTGGG
ATTACAGGCGTGAGCCACCGCGCCTGGCCTTCTTTTTCTTTTTCTTAGAGACAGGGTCTCACTCTGTTAC
CCAGGCTGCAGTGCAGTGGCACAATCATAGTTCAGTGTAATCTTGAATTCCTGGGCTCAAGCAATCCTCC
TGCCTCAGCTTCCCAAGTAGATAGGACTACAGATGCATGCCTCCATGCTTGGCTAATTTTTAATTTTTTT
TTTATATAGATTTGGGGTCTTGCTGTGTTACCCAGGCTGGTCTCAAACTCCTGGCCTCAATCAATCTTAC
TGCCTTGGCCTTCCAAAGCACTGAGATTACAGGCATGCACCACCACACCCAGCCTCTTTAAATTGTTTTA
ACAATGTTTTGTAGTTTTCAGTGTATGTGTGTTACATTTCTTTTGTTAAATTTATTACTAATATTTTATT
CCTTTTATGCATTGTAAATGAAACTGTTTCCATATTTCATTTTTTGATTGTTTATTTTTAGAGAGTAGAA
ATACAATTGATTCGTGTATATCAGTCTTTGTCCTGCAAGCTTGCTGAACTCACTTATTAGCTCTAGGGTT
TTTTTGGTATGTGTGTGTGGTTTCCTTGGGATTTTCTCCATACAAGACTATGAATCTGCAAATATGTGGG
TTTTTAAAAATTTACTATTATTATTATTTTTGAGATGGAGTCATACTCTGTCATCCAGGCTGGAGTGCAG
TGGCACGATCACAGCTCACAACAACTTCTGCCTCCCAGGCTCAAGCAATTCCCCTGCCTCAGCCTCCTGT
AGCTGAGATTACAGGAGTGAACCACCATGCCTGACTAATTTTTGCATTTTTAGTAGAGATGGGGTTTTGC
CATGTTGCCTAGGCTTGTCTCAAACTCCTGGGTTCAGGCTACCCACTTGCCTTGGCCTCCCAAAGTGCTG
GAATTATAGGCGTGAGCCACCACACCCAAATATTGTTGAGTGTTTTTAATCACAAAAGTGTGTTGGATTT
TTTGTCCAATGCTTTTTTTTTTTTGCATCTTACTGAAATAATCATGTGATTTTATCCTCTATAGAATTTG
TTATTGTTAGACTTATTGTATTAGTTGGTATACAGAGAGAGGAGATATTTGATAATGTGCCCTCAGTTGA
CAGGAGAAACAAAGTCATTAATTTTTCCTCTTATAATAAGAATAATATTTGAGAAACTCACACAATATGA
AAAGCTATTCTATTCAGATGTGCACACTACTGTAGCCTATTTCTATTTTGTATTGGTTAGTATGCATCAG
GTCATCTCATAGGTTGGGGCTCTTCTGAGTCTTGCATTTCTCAAAACACTTTTTTTTCTTTTGCTGTATT
TATACCAAGTCACTTTTTGTTTGTTTGTTGGTTGGTTGGTTGGTTGGTTGGTTGGTTGGTTGGTTGGTTT
GAGTCGGAATCTCACTCTGTCGCCGAGGCTGGAGTGCAGTAGAGTGATCTTGGCTCACTGCAACCTCTGC
CTCCCAGGTTCAAGCGATTCTCCTGCCTCAGCCTCCCAAGTAGCTGGGACGACAGGTGCACGCCACTCTG
CCCAGCTAATTTTTGTATTTTTAGTAGAGATGGGGTTTCACCATGTTGGCCAGGCTGGTCTCGAACTCCT
GACCTCAGGCAAGCCACCCACCTCAGACTTTCAAAGTGCTGGGATTACAGGCGTAAACCACTGCGCCCAG
ACTACTTTTTAAAAGAAATTATATAGGAGACTAAAATTGAAAAAAGAAACAAACCTTTACTCAGATTGAG
ATATTAGTTAAACTTAAGGGCCTGAAACAAGGAAAATGGGGTTTGCTTTTTTCTGGTTGTGCAGAGAGTG
TATGAATAAAAAGATCTCACAAAGTTCAAGTGAAAGACTGATTAAAAGAAATTCATCATCCAAATATCTT
CTCAGTGTTAAGCAAGCACATGAAGTTAGCTATAGCTCGACCCTTAACAGCTAATCAGGTAAACTCTTCA
ACTCAGTTTTGAACGTAACATAGTATACTACAGACTTTTTGTTTTTGTCCTCAGAGGTAAAGAGAAACAA
TGGCTATATGGCATACTATGAGGATTAATTTTATATGTCTACTTGACTGGGCCATAGGGTGCCCAATATA
TGGTCAAACATTATTTTAGGTGTTTCTGTGAGAGTGTTTTGGATAATTTTAACATTTAAATTGGTATACT
GAGTAAAGCAGATGATACTCCCTATTGTGAGTAGGCCTCATCCACTGAGTTAAAGGCCTGAATAGAACAA

AAAGATTAACCCTCCCCCAGGTAAGAGCGAATTCTTCCTGCCTGATGGCCTTCAAAATGGGACATCAGCT
CTTTTTCCTGCCTTTGGACTCAAACCATTGGCTCTTCCTGGGTCTTGAGCCTGCTGGCCTTTGGACTGGA
GCTACACTATCAGCTCTCTTGATTTTCAGGCCTTCAAACTTAGACTCAAACTACATTATTGGCTCCCCTG
GGTCTCCCAGATCCCAGCAGATCTTGGGAATTGCCAGCCTTCATAATTGCTGAGGCAGTTCCTTTTTTTT
GAGATGGGATCTTCCTCTGTCACCCACACTGGAGTGTAGTGGTACGATCATGGCTTACTGCAACCTCAAA
CACCTGGGCATAAGTGATGCTCCTGACTCAGCCTCCTGAGTAGCAGGGACCACAGGCACATGCCACCATG
CCCAGCTAATTTTTTAAAAATTTTTTGTAGATACAAGGTCTCACTTTGTTGCCCAGGCTGGTCTTGAACT
GCTGGGCTCAAGCTATCCTTCCACCTCAGCCTCCCAAGGTGCTGGGATTATAGGCATGAGCCACTGTGCC
CAGCCAAAAGTCAGAAGATAATTGAATGGCATCTTAAAGTGCTGAAAGAAAAAATACTGACAACCCAGAA
TCTATACTCAGTGAAATTATCCTTCAAAATTGAAGATGAGGCCGGGCGCGGTGGCTCACGCCTGTAATCC
TAGCACTTTGGGAGGCCGAGGCGGGCGGATCACGAGGTCAGGAGATCGAGATCATCCTGGCTAACATGGT
GAAACCCCGTCAGTACTAAAAATACAAAAAAAATTAGCCGGGCATGGTAACGGGTGCCTGTAGTCCCAGC
TACTCGGGAGGCTGAGGCGGGAGAATGGCGTGAACCCAGGAGGCGGAGCTTGCAGTGAGCCGAGATCGCG
CCACTGCACTCCAGCCTGGGCGAGAGTGAGACTCCGTCTCAAAAAAAAAAAAAAAAAAAAAAAAAAAAAA
AATTGAAGATGAAATAAACATGGTTTCAGAAGAAAAAAAAAGAAATCATTTATTGTCAGAAGAACTACAC
TATTAAGAAACACACCAGGCAATTTTTCAGGATGAAGGAAAATGATCCTTGGTGGCTACAGAGAAATGTA
GGGTAGAATAAGGAGTAAAGAAAGGGTAAATAGAAATTAATACTGACAATTAATTTTTAAAAATCCTATA
CAATTTATAATATATGAAAGAGTAAAACATATCAGTAGTACAAGGGCAAGAAATGGTAAATGGAGTTAAG
CTATCATAAGTGTTTTATTTAGGGAGTATCACAAAAGTATTAAAGTAGAATGTAATAGGCCGGGCGGGGT
AGCTCACACCTGTAATCCGAGTACCTTGGGAGGCTAAGGAGGGCGGATCACTTGAGGTCAAGAGTTCGAG
ATCAGCCTGGCCAACATGGTGAAACCCCACCTCTACTAAAAATACAAAAATTAGCCAGGTGTGGTGGCAC
ACGTCTGTAATCCCAGCTACTTGGGAGGCTGAAGCATGAGAATAGCTTGCACGTGGGAGGCGGAGGTTGC
AGTGAGCCGAGATCCTGTCACTGCACTCCAGCCTGGGCGACAAAGCGAGACTCTCAAAAAAAAAAAAAAA
AAAGCATGTAATAAATCAAATATGCATTATGTAATCACAAAATCCAGCTTAACAACTAAATAATAATTTA
AAAGATATTAAAAACTTAATATGGAAGAAAAATGAAATAAAAAACTTTATTAATCCAAGGCCGGGCGCGG
TGGCTCATGCCTGTAATCCCAGCACTTTGGGAGGCCGAGGCGGGTGGACCACTTGAGGCCAGGAGTTCCA
GACCAGCCTGGCCAACATGATGAAACCCCGTCTCTACTAAAAATACCTGGGCAAAGTAGAGCATGCCTGG
CCGGGCGCAGTGGCTCATGCCTGTAATCCCAGCACTTTGGGAGGCTGAGACGGGTGGATCAGGAGGTCAG
GAGATCGAGACCATCCTGGCCAACATGGTGAAACCCTGTCTCTACTAAAAATACAAGAATTAACTGGGCA
TGGTGGCACATGCCTGTAATTCCAGCTACTCTGGAAGCTGAGGCAGGAGAATTGCTTGAACCAGGGAATC
AGGTTGCAGTGAGCTGAGATCATGCCACTGCATTGCAATCTGGCGACAGAGCGAGATTCTGTCTCAAAAA
AAAAAAAAAAAAAAAATTAGAGCATGCCTATAATCTGAGCTACTCAGGAGGCTGAGACACGAGAATCACT
TGAACCCAGGGCGGCGGAGGTGCAGTGAGCAGCGATCACACCACTGCATTCCAGCCTGGGCGACAGAGTG
AGACTCCCTCTCAAAAAACAAACAAACAAACAAACAAACAAACAAACAAAAACTTTATTAATCCAAATTA
AAATGGTAGAGTAGTAGTAAAGGAACAGAGAATAGATGGTAAAAACAATAAATAACATGATAAACCCGAC
AATTTCAATAATAACTTTAAAGATAGATGGTATTGTAACTGCCCAATGGGTTCACCTTGCCCGCTGCCTA
GACAGAGACGATTTCTCAAGACAGGGGAATTGCAATAGAGAAAGATAAATTCACGCAGAGCTGGCTGTAT
GGGAGACCAGAGTTTTATTATTACTCAAATCAGTATCCACAAGCATTCCGCCTTCAGAATTTTTAAGGAC
AACATGTTGGGTGGGAGGAAGCCAGTGAGCTGGGAGTGCTGATTGGTCAGAGCTGAAATCATAGGGAATG
GAAGCTGTCTTCTTAAGCTGAGTCAATTCCTGGGTGGGGACTGCAAGATCAGATGAGTCAGGTTATCAAT
CTACGTGGTGCCAGCTGACCCATCAAATGCAGGGTCTGCAAAATATCTCAAGCACTGATCTTAGGAGCAG
TTTAGGGAGGGTCAGAATCTTGTAGCCTCCAGCTGCAAGACTCCTAAACCATAATTTCTAATCTTGTGGT
TAATGTTAGTCCTACCAAGGCAATCTAGTCTCCAGGCAAGAAGGAGGTCTGCTTTGGGAAAGGGCTGTCA
TCTTTGTTTTAAACTATAAACTATAAAGTAAGTTTCTCCCAAAGTTAGTTCAGCCTACACCCAGGAATGC
ACAAGGACAGTTTGGAGGTTAGAAACAAGATGGGGTCAGTTAAGTTAGATCTCTTTCACTGTCTCAGGCA
TAATTTTGCACAGGCGGTTTCAGTATAATCATTTCAGTACAAGACAAGATTTAAAAAAAGAAAACTAATG
CTAAGCATTTTTCAAGAAACATACTGTAGGCCGGGTGCAGTGGCTCACGCCTGTAATTCCAGCACCTTGG
GAGGCTGAGGCGGGCGGATCACGAGGTCAGGAGATCGAGACCATCCTGGCTAACATGGTGAAACCCCGTC
TCTACTAAAAACACAAAAAAATTAGCCGGGTGTGGTGGCGGGCACCTGTAGTCCCAGCTACTCAGGAGGC
TGAGGCAGGAGAATGGGTCAACCCAGGAGGCAGAGCTTGCAGTGAGCCAAGATCCTGCCACTGCACTCCA
GCCTGGGTGACAGAGCGAGACTCTGTCTCAAATAAAAAAAAAGAAGGAAACATACTGTAGCCAGACGCCA
CCTATAGTCCCAGATACTTGGGAGGCTGAGGCAGGAGGATAGCTTGGGACCAGTTTGAGACCAGCCTGAG
CAACATAGCAAGACCCTGTCTCCAAAATTTAAAAATGTTTAAAAAGAGATATATTTTACATATAAGAACA
CAGAAAGATGTTATTAAAAATAAAAAAATGACATTTGGGTAATGTGAATATTACCCTAAAGAAAGCTGCA
TCTATGTGGAACTGTTACCGGGAATGGGTCCCAATCTAGACCCCAAGAGAGGGTTCTTGGACCTCACGCA
AGAAAGAATTAGGGGCAAATCCATAAAGTGAAAGCAAGTTTATTGGGAAAGTAAAGGAATAAAGAATGGC
TACTCCATAGGTAGAGTCACAGTATGGGCTGCTTAACTGAGTATACTCAGTTATTTCTTGATTATATGCT
AAACAAGGGGTGGATTATTCATCAGTTTTCTGGAAAAGGGGCAGGCATTTCTCGGAACTGAGGGTTCCTT
CTTTTTTTAGACTGTATAGGGTAACTTCCTGATGTTGCCATGGTATTTATAAACTGTCATGGCCCTAGTG
GGAGAGTCTTTTAGCATGCTAATGCATTATAATTAGTGTATAATGAGCACTGAGGACAACCAGAGGTCAC
CTTTGTCACCATCTTGGTTTTGGTAGGTTTGGGCTATCTTCTTTATCGCATTCTGTTTCATCAGCAGGGT
CTTTGTGGTCTGTATCTTGTGCTGACCTCCTATCTCATCCTGTGACTAAGAATGCCTAAGCTCCTGGGAA
TGCAGCCAGTAGTTCTGAGCTTACTTTACCCAGCCCCTATTCAAGATGGAGTTGCTCTGGTTCTAATGCC
TCTGACAGAACCTCCTGATTGTCACAATATTACCAGTAGCAGCAGGCAGCTATTCACACCCAAATTTCAC
CTTAAAAAGAATGGCTTCAAAATTGACCTCCCCCATGGGAAATATTGCAGGACTTAACACAGGATTGTTT
TTCTCTTCATTTCTCTACGATTTCTTTCTTTCTTTTTTTTTCCTTTTTTCCGAGGTGGAGTTTCTCTCTT
TTTGCCCAGGCTGGAGTGCACTGGTGCAATCTTGGCTCACCACAACCTCTGTCTCCCGGGTTCAAGCAAT
TCTCCTGCCTCAGCCTCCCGAGTAGCTGGGATTACAGGCATGCGCCACCACGCCAGGCTAATTTTGTATT
TTTAGTAGAGACGGTGTTTCTCCATGTTGCAACCTCAGGTGACCCGCCCACCTCGGCCTCCCAAAGTGCT
GGGATTACAGGCGTGAGCCACTGCACCCAGCCTACCATTTCTTTTTGGGACAGGGTCTTGCTGTGTTGCC
CAGGCTGGTTTCTAACTCCTGGGCTCAAGCGATCCACTGGCCTCAGCCTCCTGAAGTGCTGGGATTACAG

GAGTCAGCCACTGCACCAGGCCCATTTCTCTACCATTTCTGATCTCTCTCTAGAAACACTTGGATAACTG
CACAGCTCCTTTCATAAGAAATATATTTAGGGCCGGGTGTGGTGGCTTATGCCTGTAATCTCAGCACTT
TGGGAGGCCGCGGCAGGTGGATCAACCGAGGTCAGGAGTTCAAGACCAGCCTGGCCAAGATGGTGAAACC
CCATCTCCACTAAAAATACAAAAAATTAGTCAGGAGTGGTGGTGCATGCCTGTAATCCCAGCTACTCAGG
AGGCTGAGGCAGGAGAATCACCTGAACCCAGGAGGCGGAGGTTGCAGTGACCCAACATTGCGCCATTGCA
TGCCAGTCTGAGCAACAAGAGTGAAACTTTGTCTCAAAAAACAAATAAACAATGAACAAACAAACAAAA
AATCATTGTTATTCCTCAGAGTAAGAGCAAAGATCATCCCCTGCAGAAGCTTAGGAACTATGCACAGAAC
TTTACAGAACAGGGGCGATGCTTTAACTGAAGGCTGACTACTGACCAGAGAATGGAATTCTGAGAGGGCT
CAAGGAATAAAAGGAAACTAGGCAGGGAAAGGGAAGGCGCCCATCTGAAGCAAACTTCAGCGGCCATCAG
GATATCTTGTGGTGGTCACAAGTTGTAGGCTCTGTTTTGGAAGGTTTGGGTATAGCGCAGGATTCCATT
TGTCTACTTGGCTACACCTCTGCCTGAGGTACACTGTTGCCAGAAAAGAGGGTCCCAATCCAGACCCCAA
GAGCAGGTTACTGGATCTTGCACAGGAAATAATTCAAGGGAAGTCACACAGCACAGAGAAAAAGCAAGTT
CATACAATGTTACTGAGTAAGTTATCGCCAGAAAGCAGGAGGAGGAACACGCCATCCTTGTTAGTGTCTC
TATTTATAAGAAACTTATGAGAAGCTATAATTAAACTTGGAACATGCAGATGTGCTCACTAAAGGTAGGG
GCTATTGGTGTTATAGATGACCATTAATCTTTCAACCTAAGCCTGCTCATTAATGGCATCTTTAATAAAG
TGGGCTACACTCTTAGGACATCTGGACATTCTGCAGGATTGGTGGGAGATGTTCTGTATGGCCACCAATA
TTCTGTAATTATAATTGGTGGTCAGCTTGGGATGTGGCTATTTTCAGACCACAAGCATTAACCTTACAGA
GTGCCTAGCTACTCATTTCAAGGTGGAGTCACTCTGGCCATGTTTTACCAAACCAGAGGTCTGGTAAGGA
GAGGTTCCTCTAACACCATGAGGTCAACGTCACTCAAGTTCCTGGCCAGCCAAACTCTGAAAGCAAGGAG
TCCCAAATTGAGGATCAAGTTCCTCCAGAAATCATTGCTATGGGTGGCAAAGCAGTAGATTCCCTGAAGC
CAATCTCCCACATTGTCTGGAATTTTGGGAGCTTCATTTGCCCAGTTGGCAGTGCCAATGGGGACCCCGC
TGGAAGCCATAGTAGCACCTTTGGGCTCTGCATAGGACTTGCTCAATACACCATATTGGAGTCGTTGGCT
CTTTTTGTTATTTTAAGTTGAAATTTGAAGATTGGCTGAGTTGGTTTCATGATATTGTTGCCTACTGATA
TCTTACACAGAGTACGAGTACATCTGGTTGAAAGAGAAAAGGCAGAGAGAAAAGCAGACTTTTTGGAGTT
GTTGTTCTCAGGCACTAACAGATTCATCCCTTATATGCATATGAATGGACAATAAGATTTCTTGGATATT
TTCATGGCAAAGGTGAGGAGAAATTTTTATTGCTTTTTGAAGAAACATGATTTTTATTACCTTGGGTTAT
TCCAGGAGATAATTGATAAATGTTGAGTAGTTTGTTGGTCTTCTTCTTAAAGGAGGATCAAGAGAAGCAG
TACAGCATGGCAGACTAGAAGCATTTCTGTTTTTTTGTTTTGTTTTGTTTGAGATGAAGTCTCACTCTGT
TGCCGAGGCTGGAGTGCAGTGGAGTGATCTCTGCTCACTGCAAGCTCCGCCTCCTGGGTTCAAGTGATTC
TCCTGCCTCAGCCTCCAAAGTATCTGGGATTACAGGCATGTGCCACCACGCCCGGCTAATTTTTACATTT
CTAGTAGAGACGGGGTTTCACCATGTTAGCCAGGCTGGTCTCAAACTCCTGACCTTAAATGATCCACCCA
CCTCGGCCTCCCAAAGTGCTGGGATTACAGGCATGAGCCACCGCACCTGGCTGAAGGGTCTTCAGTATCA
TCTCTGTGATAGATAAATTGTTTAGTGGGTTATCTACATTGGCCATTGACATCTAGAATTAGGGTATGAG
TTGGGTTTAGAAGAAGGAAATGAGGCTGGTCTCCAATAGACAGTGATTCATATGATAAGCAGAAAGTGTT
ACAGAAGTCTGGTAGAGGAGGATGGGAGACAGATTATTGTCAAGGAGATAGTAAAAGTTTATTTTGAAAT
CCTTAGACTATGCCGGGCTCAGTGGGTCACACCTGTAATCCCAGCACTTTGGGAGGCCGAGGCGGGCGGA
TCACCTGAGGTCAGGAGTTCGAGACCAGCCTGACCAACATGAAGAAACTCGGTCTTTATTAAAAATACAA
AATTAGCCAGGCGTGGTGGTGCATGCCTGTAATCCCAGCTACTTGGGAGGCTGAGGCAGGAGAATCACTT
GAATCTGGGAGGCGGAGGTTGTGGTGAGCCAAGATCACGCCATTGCACTCCTGCCTGGGCAATAAGGGCG
AAACTCCATCTCAAAAAAAAGAAAGAAATCCTTAGACTATAAGTTTGTTATATAATCTGCATGTAAAACA
AGGTCCTATATGACTTAAATAATGTGCAGGGTTCCCTTTAAAAAGTTCAGCAACTACTTTCCTTTTTTTT
TTTTTGAGATGGAGTCTCACTCTGTCACCCAGGCTGGAGTGGGTTGGTGCAATCTTGGCTCACTGAAACC
TCTGCCTCCTGGGCTCAAGCCATCTTCTCACCTCAGCATCCTCGGTAATTTAGTTGGGACTACTGGCGTG
CGCCACCATGCCCGGCTAATTTTCCTGTATTTTGTGGAGAGACGGGGTTTCACCATGTTGCCCAGGCTTG
TCTCAAACTCCTGGGCTCAAGTGATCCTCCTGCCTTGATCTCCCAAAGTGCTAGGATTACAGGCGTGAGC
CACCACACCTGGCCAATGACTTTCAAATTTGTTTAAAGTAATCCCAATCTTTATTTGCCTCTCTCAAGTA
ATTAATGATAACACTTTCTTTAAAAAAAAAATGCTGTCACTAGGCTGGGTGCGGTGGCTCACATCTGTAA
TCCCAGCACTTTGGGAAGCCGAGGCGGGTGGATCACCTGAGGTCAGGAGTTCGAGACCAGCCTGACCAAC
ACGGTGAAACCCTGTCTCTACTAAATACAAAAATTAGCCAGGTATGGTGGTGGGCACCTGTAATTCCAGC
TACTTAGGAGGCTGAGGAAGGAGAATCACTTGAACCCCGGGAGGTGGAGGTTGCATTGAGCCGAGATGGC
ACCATTGCACTCCAGCCTGGGCAACAAGAGCAAAACTGTCTCAAAAAAAAAAAAAAAAAAAAAAACAAAAA
ACAGACGGGGCATGGTGGCTCACACCTGTAATCCCAGCACTTTGGGAGGCAGAGGCAGGTGGATCACCTG
AAGTCAGGAGTTTGAGACCAGCCTGGCCAACATGGCAAAACCCCACCTCTACTAAAAATACAAAAAAATT
AGCTGGGCACGGTGGCAGGTGCCTGTAATCTCATCTACTAGGGAAGCTGAAGCAGGGGAATCGCTTGAAC
CTGGGAGACGGAGGTTGCAGTGAGCTGAGGTTGTGCCATTGCACTCCAGCCTGGGAGACAGAGCAAGACT
CCGTCTCAAAAAAAAAAAAAAAAAAATATGTCACTAATCTCTAAGATCTCTGAATAACTCTCTCAGAATTA
GAGTCCATACAGCTCTGATCTTTTCTTCTTTTATGCTGCTTGTTTTTCCAAGGCTTTTAGTGATGCAAAC
TTATCATTACTTTAACAATTCCAGCTTTCCTTCTATGTCTTGGTTTTACACGACAAGAAGCCCAGAAACT
GAACTTGCTTACTCAGCTCCCGAGGTTGAAGGTGGCAAGAAGGTGGTAAGAATCCTAGACAGGCTAGGCC
TGGTGGCTCACGCCTATAATCCTAACAATTTGGGAGGCCAAGACAGGAGGATCGCTTGAGGCCAGGAGTT
CGAGACTAGCCTGGGGAACATAGTGAGACCCTGTCTCTACAAAAAAAAAAAAGAAAAAATTAGCTGGGTG
TGGTAGTGCACACCTGTGGTCCCAGCTACTCAGGAGGCCAAGTTGGGAGGATTGCTTGAGCCCAGGAGGT
GGAGGCTACAGTGAGCAATGATGGCACCACACTCCAACCTGGGCGACACAGTGAGACTCTGTCTCAAAAC
AAAACAAAACAAAACAAAACAAAGAAGATTTGGTAGAATTCTCCTGTGGGAGTTTGGAGAAAGAAGTAGA
ACATTATTATTGTTTTTTTCCTGTCATATTTCTAATGGAAACAGGATGATTACAAGAGTGCAGGGGAAAG
GTTGGGGAAAAGAAATGTGACTTCTTTCACTTTTACATTATTGAAATTGTTATTTAAATTGTATTCTATA
ACCATAATTAAATCTTCATAAACTTTTCACTTAATGATCTTAGCATTCATTGATGGTCTTTGCCTGAATC
TTATTTCAAAAGGCAAGGCATTTCAAAAATGCTGATTTTTAAAATTTCTATCATTTCTTATACACTTATT
AGCTCACATTTTTCTGTAATGAGTTTACCCTTATCAAGTGGGACTCTTTGGTTAGCTGCTCCTCTAAGCT
AATTTTCTTGTATTCTCAAAGCAGTTTCTCCATACTATCATTTCAATACCTCTTGCTGTTCTAGTTTGCT
GTTTTGAGTATGTCCTTGTCTTACTTATGTGATTGACTTTTTTTTTGAGATGGAGTTTCTCTCTCGTCGC

CCAGGCTGGAGTGCAATGGCACCATCTCTGCTCACTGCAACCTCCGCCTCCCAAGTTCAAGCAATTCTCC
TACCTCAGCTTCCCGAATAACTGGGATTACAGGCACCTGCCACCACACCCAGATAATTTTTGTATTTTTA
GTAGAGACGGGGTTTCACCATGCTGGTCAGGCTGGTCTTGAACTCCTGACCTCAGAGGATCCACCCGCCT
TGGCCCCACAAAGTGCTGGGATTCCAGGCGTGAGCCACAGTGCCTGGCCATGACTAACTCATTCCATTGA
GGGTCTTTTCTCCTGAAGTTTTGTGCTATGACTTGATATTTCAAAAGAAGGGAAATAGATGTCTCAGTAT
TAAATTTCAAACGGGAAGTTTAACCTGTATATTGGCTTATTTAGGGTAAGAGTGAAGCTATCCTGGACAA
GAACTTTGACAGGACAATACTATTCACTCTGAAGGACCAAAAAAATGAGCAGAAAATTTGGGATAAATGTC
AACAAGATTTGAACCCTAAAGAAAAGCAAGCATCGAGTTAGACAGACGTCCATATTCATTCAACTGGGAA
AATAAAACTGCAGTCCCAACATCAGAATTTCCTTGGTCAGTTGGTTATTGCGGGACAGCATTCTTCTGCA
TGACAGTATTGTCTCCTTACCAGCCACAGAGGAGGCTGTGAGAGAGAGGATTTGGGAAATTGGTGCAAAT
GAGAAATCTTGGAAATCTGTAAGTATATAGATATAAAAGTTATTCTTTCCAGTTTGATTCTTTTATGATG
TAGATTTTAATATCAGTCAATTTAGGAAACTCTGTGGCTCTGAATTATAGTTATAATTCTAGTTTTACTA
TTACAGTGAAAGAAGAGAAGAGGCTGTTCATTATTATATTGGAAGTAGTGTAGCATGTTTATTAAGAGTG
CAGAGCCCCAGCATGAAGCCTAGCTCTGCCATTTGCCAGCTGTGTGTGCTCTTGGGCAGACTACTTATCC
TCTCTGTGCCTCATTTTCATTTGTGAAGTAGGGGACGGTGTGTAGTTCCCACCTCACAGAGTGGTTGCAA
GGACCAAATGGGTTAATACATGATAAATGCTTAGTTTAGTGTAAGTTCAATAAATATCAAAATAGTGGTA
TGTTAAAGATAGTGTTTACATGATAACCTAAAATTAATTGCCAGTTTGTTTTAATTTACTGGTCAAGTCT
ATCAAATGATTGAATCAGCATGTTTAAGTGGATATATCTCATTTGTGTCCAGATCATTTTAGTATATTCA
TGACTCCTCACTTTAAAATTCAAATGATAATAGGTACAGTTAGTCCTCCATATCTGTGGATTCAACCAAG
TAAAAATAAAAAAATTGCATCACAACAAGGCATGGTGGCTCACATCTGTAGTCCCAGCACTTTGGGAGGCT
GAGGCGGGTGGACCGCTTGAGGCCAGGAGTTTGAGACCAGCCTGGCCAACATGACAAAAACCCATCTCTA
CTAAAAATACAAAAATCAGCTGGGTGGTGGTGGCTTGCACTTGTAGTCCCAGCTACTCGGGAGGCTGAGG
GATGAGAATTGCTTGAACCCAGGAGGTGGAGGTTGCAATGGGCCGACATCTCACCACTACACTCTAGCCC
GGGCAACAAATCAAGACTGTCTCTTTTTTTTTTTTTTTTGAGACGAAGTCTCGCTCAGTCGCCCAGGCTA
GAGCGCAGTGGCGCAATCTCGGCTCACTGCAAGCTCCGCCTCCCAGGTTCACGCCATTCTCCTGCCTCAG
CCTCCCAAGTAGCTGGGACTACAGGCGCCCACCACCACGCCTGGCTAATTTTTTGTATTTTTAGTAGAGA
CGGGGTTTCACCGTGTTAGCCAGGATGGTCTCGATCTCCTGACCTCGTGATCCGCCCGTCTCGGCCTCCC
AAAGTGCTGGGATTACAAGCGTGAGCCACCGTGCCCGGCCAAGACTGTCTCAAAAAAAAAAAAAAATTGCA
TCTGTACTGAACATGTACAGACATTCTTCCTTTTCATTATTCTCTAAACAACAGAGTACAACTATTTACA
TAACATTTACGTTATATTAGGTATTATAAAAGTCTCCCGAGAGACAGAGGTTGCAGTGAGCCGAGATCGC
GCCATTGCACTCCAGCCCGGGGGACCAGAGCGAGTCTTCCTCTCAAAAAAAAAAAAAAAATTGAGATGAT
TTAAAGTGTACAGGAGGATGTGAATAGGTTAGATACAAGCACAATACCATTTTGTATCAAAGACTTGAGT
ATTCATAAATTTTGGCATCTCTAGGAGGTTCTGACACCAGTCTCCCAGGGACGCTAGGGACGCCTGTATA
TGGCTTAGATTCAGTGTGTTAGTGAAACCTGCTACACAGTAGCCTGTTAGAGTTCCCCATTTTTAAAAA
TACTCTGCTCTTTTAAAATTCATTATACAGCCTTATTTCTCAGTACTGACTAAAATGTCTTATTTTTATA
TATCGAAGCTTTCTATTTATTTTTTAAACCAATGTATACATGTCAAATCCTAAAAATCGCCTGTATTAAT
CTACTTAGTAACTTAATGCCACTCCAATGTGGATATAAATAGAACTTGCACATAGTTTTGAAACTACGTA
GAAAGCATGGAGGCTGGGTGCGTAGGCTCACGCCTGTAATCCCAGCACTTTGGGAGGCTAAGGTGGGCAG
ATCACCTGAATTCAGGAGTTCGAGACCAGCCTGACCAATATGGCAAAACCCCGTCTCTACCAAAAATACA
AAAATTAGCCTGGCATGGTGGCATGCACCTGTAGTGCCAGCTACTTGGGAGGCTGAGACAGGATAATTGC
TTGAACCTGGGAGGCGGAGGTTACCGTGAGCCAACGTGGCACCACTGCACTCCAGCCTGGGTGAAAGAGC
GAGACTCTGTCTTAAGAAAGAAAGAAAGCGGGCGGGGGGGCGGGGGGAAGGGCAAGCAAGCATAGAGCAT
GAGGAAGTTTTTAATGTCTTTTTCTTACAGAGAACTAAAGCCTTTCAGCAGGAAATCCAGATGCTCACTA
AGTGACTAGAGCAGCTGCATCATCTTTAAGAAGAAGGTGCTCAAGAATCATCCCAAGCTGAAGAAAAAAG
TATTGGGAACAAAAAAGACCCTTGAAATGTCTAGAAAGAAAAATTGAGATCAAGGACTTTTTCAAGAGAG
ATTAGACTTGGACAGGAAGAAAGTAAGAATTTCCTGAAGTATAAGCATTCCTTTGATAATGAAAATGATT
GCATTTTATTCATAACTTTAACTTTATCTAATGTTTGAAGCTGTTAATACTGTTAATACTTTTCTCCACA
TTGGGAAAGGGGGGAAATTTGCTACAAACTCTGAAAGCTTCCGATTTTATTTTATTTATTTATTTATATT
TTTTGAGAGAGAGTCTCGCTCTGTCACCAGACTGGAGTGCAGTGACGCTATCTTGGCTCACTGCAACCTC
TGCCTCCTGGGTTCAAGCGATTCTCCTGCCTCAGCCTCCCGAGTAGCTGGGACTACAGGCACGCGCCACC
ATGCCCAGCTAATTTTTGTATTTTTAGTAGAGACGAGGTTTCACCATTTTAGCCAGGATGGTCTCAATCT
CTTGACCTTATGATCCACCTGCCTCAGCCTCCCAAAGTGCTGGGATTACAGGCATGAGCCACTGCCCTGG
CCTCTGATTTTATTTTTAAAAGCCTCTTCTCTCTCCGTATCTCCATGTCTCTTTTGTGTACTTATTTGAT
GTTTGTTGTGAGGGCATCTGTTTACATATATATCTCAATGTACTTTAAGGAGAGGATTAGAAGAAAAGGA
GCTCAAAGGAATAACTCTCTTTTTTTCTTTTTTTTCAGATGGAGTCTCACTCTGTCACCCAGGGTGGAGT
GCAATGGTGTGATCTCGGCTCACTGCAACCTCCGCCTCCCAGGTTCAAGCGATTTTCCTGCCTCAGCCTC
CCAAGTAGCTGGGATTACAGGTGCTCACCACCCGCCCGGCTAACTTTTGTATTTTTAGTAGAGACAAGGT
TTCACCATGTTGGCCAGTCTGGTCTCAAACTCCTGACTGCAGGTGATCTGCCTGCCTTGGCCTTCCAAAG
TGCTGGGATTACATGTGTGAGCCACTGTGCCCGGCCAAAGGAATAACTCTCTAATGGGGAAATTTTAGGA
ATTGTGACAGGCAGATATAATGAGCATTGATGAGGGGCCATTGATGATGTCTCTCAATAATCACTGTATA
AGTCATTCTCTTCTCTACTCTCTGCTTCCCTGAATCTGTAAGGAAAAAGGCAGTCCTAAAAGTTGGATAG
AAATAGGTAGGTTGCAATACAATTTATTTCAGGAGATTCTCTATTTTACTACCTCTTCATAGAATTGCC
TATCATAGCCGGGCACAGTGGCTCACACCTATAATCCTAGCATTTTGGGAGGCTGAGACAGGCGGATCAC
GAGGTCAGGAGATTGAGACCATCCTGGCCAACATGGTGAAACTCTGTCTCTACTAAAAATACAATAATTA
GCTGGATGTGGTGGCACACACCTATAATCCCAGCTACTCTGGAGGCTGAGGCAGGAGAATTGCTTGAACT
CAGGAGGCAGAAATTGCAGTGAGCCAAGGTAGTGCCGCTACATTGCAGCCTGGTGACAGAGCAAGACTCC
ATCTCAAGAAAAGAAAAAAAAAAAAAAAAAAAGAATTGCCTATCATAACCAAATTACGTTATAGTATTTCTA
TAATTGCTATGGTCCAAAGTGGAATCTTGCTCACTCATTTACCATTTACTCATTTAGTCTTTTTTTTTTT
TTTTTTTCTGAGACTGAGTCTCACTCCATCACCCAGGCTGGAGTGCAGTGGCGCAATCTCGGCTCACTGC
AACCTCCACCTCCCAGGTTCCAATGATTCTCCTGCCTCAGCCTCCCGAGTAGCTGGGACTATAGGTGTGT
GCCACCACACCCAGCTAATTTTTGCAGTTTTTAGTAGAGATGCAGGGTTTCACCATGTTGGCCAGGCTGG

TCTTGAACTCCTGACCTCGTTATCTGCCTGCCTCAGCCTCCCAAAGTGCTGGGATTATAGGCATGAGCCA
CTGCGCCCAGCCTTCATTTAGTCTTTTGGCTCATTCATTTGTTTATCCAATATTTATTGAGCATTCAGTT
TTCTTTTCTTTTCTTTTTTGAGACGGAGTTTTGCCCTTGTTGCCTAGGCTGGAGTGCAATGGCGCGATCT
TGGCTCACTGCAATCTCTGCCTCCCGAGCTCAAGCGATTCTCCTGCCTCAGTCTCCTGAGTAGCTGGGAT
TACAGGCATGCGCCACCACACCTGTCTAATTTTGTATTTTTAGTAGTGACAGTGTTTCTCCATGTTGTTC
AGGCTGGTCTCGAACTCCCGACCTCAGATGACCAGCCCACCTTGGCCTCCCAAAGTGCTGGGATTACAGG
TGTGAGCCACCATGCCCGGCCTAATAGTTTTCTTTACTAGAGTTCTTGGGTTTTCTGGATTTCACTGTAT
ATTGTCAAATTGTTTCCTAGGAAATAATGTATTTTTAAAATTTCACTTATTTATTTTATAAATAATTTGA
TTCTAAAGGTGGAACAGTTTGGACCAGCTCATGGGAGAACTGTCTTTTTTTTTTTTTTTTGAGACAGTC
TTGCTCTGCCTCCCAGGCTGGAATGTGGTGTTACCATCACGATTCACTGTAGCCTCAACCTCCTAAGGCT
CAAGTGCTCCTCTTGCCTCAGACTCCCGAGTAGCTGGGACCACAGGTGCACACCACTATGCCCAGCTAAT
TTTTGTAGAAATGGGGTCTTTCCATGTTGCTCAGGCTGGTCTTGAACTCCTTGTGGCTCAAATGATCCGC
CCATCTCTGCCTCCCAAAGTACTGGAATTACAGCCTTTATTTCTTTTAGATTTTCAATTTACTGCCCCTA
AGTTGCAAAATGTTCTCTTAGAATTATTTTTATCTTTGCATTCTGTATCCATTCTGTATGCATATCTATA
TATTCTGTATATTCCTCCTTTCTAATATTGTGTATTTTCACTTTCTCTCTTTCCTTTTTAACCAGGCTTG
CCTGAGGCATCTATTTTATCTTTCCAAAGAACCAGTGGTTCTTTTTGAGACAGGGTCTGGCTCTGTCTAT
TGTCCAGGCTGGAGTGCAGTGGCGTGATTATGGCTCACTGAAGCCTCAACCTTCAGGGCTCCAGTGATCC
TCCTGCCTCAGCCTCCCAGATAGCTGGAACTATAGGTGCACGCCTCCACGCCTGGCTAGCTTTTTGAAGT
TTTTGTAGAGATGAGGTTTCGCCATGTTGCCCAGGCTGGTCTCAAACTGCTGAGCTCAAGTGATTCTCCC
GCCTCGGCCTCCCAAAGTGCTAGTATTACAGGCATGATTCACCGTGCCTGGCCAGTTCTTTTTTTAAAAT
ATACGTTTTATGGCCTGGCACGCTGGCTCACCCTGTAATCCCAGCATTTTGGGAGGCTGAGGTGGGCAGA
TCACTTGAGGTCAGGAATTCGAGACCAGCCTGACCAACGTGGTAAAACCCTGTCTCTACTAAAAATGCAA
AAGTTAACTGGGCATGGTGGTGTGCACCTCTAATCTCAGCTACTTGGGAGGCTGAGGCAGGAGAATCACT
TGAACCAGGGAGGTGGAGGTTGCATTGAGCTGAGATTGTGGCACTGCACTCCAGCCTGGGCAACAGAGCG
AGACTGTCTCAAAAATAAATAAATAAATAAATAAATACACATTTTATTAGTTTATTTTGGTTTATATGTA
ATGAATATATATAGTATGTTTATTAAATCTGCACCCTACTTTCTCTTTTCCCTTCTTAAGTAAATGTGCT
TTTTTTGTCTTTTGTTTTAAATCAGAAAAAGAGTAAGTACTATTGAATGTTCCTCTGTAGCTTGTCCAA
TAGATTTTTATAAGAAATGTTTCTTTTCACTGTGTTCTATGTATTTTGTAATTTTAGTGTTGATTTCCA
TTTTTTGGCTGAAGGTATTCAGAATTTTTGTTTGTTTGTTTTTTGTTTTTGAGACGGAGTTTCACTCTTG
TTGCCAAGGCTGGAGTGAAGTGGTGCAATCTCGGCTCACTGCAACCTCTGCCTCCCAGATTCAAGCAATT
CTCCTGCCTCAGCCTCCCTAGTAGCTGGGATTACAGGTGTGCACCACCATGCCCAGTGAATTTTTGTATT
TTTAGTAGAGGTGGGGTTTCACCACCTTGGCCAGGCTGGTCTCGAATTCCTGACCTCAGGTGATCCCCAT
GCCTCGACCTCCCAAAGTGCTGGGATTACAGGCGTGAGCCACCGCACCCAGCCTAGAATTTTTTTAACCC
TTTATACACACACACACACACACACACACACACACACTTTTCAAAATCAAATATACCAAGAGTCTTTTAT
TGAAAAGGAGCAGCCCTCTTCTGTACCTCTCTTATTTCCCAGAGGGAACTCTTTAACTCTTTTAGCTGTT
TCTGATAGTAACTTCCATTTTCCTAAACAATTTTAAACTGCCTTATCTCGAGTTATCTATATTAGACATG
TTGTTGATTTCCTGTTATATGATAGATGAAATTTCATCTCTCATACCACTTTCCTACCTGCTCCTTTCAT
CTTCCCAATCTGGTTATATTGATATTTTAAGCTAAATGCATAATCAGCATTTACTTTACCGTGATACTAA
ATGTTTACAAAAGCATGAAGTACTATATTCTTGGTACATTTTCTTTCTTGTATTGCATTTTATTTTTCCT
ACAGTTAATACCTTCCTTATATTTTCATACGTTTAATTTTCAGTGTTCATTTATCAAGGTTTTTTTCCTG
CCTAAATCTGTATCAGATGATCCTTTAGTCTTTAAAAATCTCCCATTTTTTCTCTCCCAAAGTCCTTCAT
TCCCTTGCTTCAGTCTGGATTTTACTCTGTGGGCCTGAGCACAGCCATGATGCCATGACTTTCCTTCTCT
AATCTCCTGGTTAGGTTTCATTGTTTGCCGAATCACATTTCTTCCTCTTTTTTGGTTTCCTTTCTTATTT
TACTGGAACACATCCTCCAATGGCTTCCTAAGAAATGGTGCCTTGGAGAGCGACATTTTTTGAGGTCCTT
GTGTGAATGACAATGTCTTTTTTTGTTTGAATCATCATACTCAATTGATAGCTGGGTTTAGACTTTATTT
TCACACACGGACTTCATTGTCTTCTAATCTCTAGGGTTGTTATTGAGGAAAATATGCCATTCTGATTCTT
GTTCCTTAATATGTTATTTCTTGTAATGGATTAAAACATTTACCATAACTTTTTTGTAATAACATTTTAT
AACTAATTTTTTTCTCATAATAAAATTAATTCAGCTGGGCATAGTGGCTCATGTCCGTAATTCCAGCACT
TAGGGAGGCTGAGGTGGGTGGATAGCTGGAACCCAGGAATTTGAGATCAGCCTGGACAACATGGCAACAC
CCCATCTCTACAAAAAATTTAAGAACTAGCCAGGCATGGTGCACACTTGTAGTCCCAGTTACTGGGGAGG
CTTAGGTGGGAGGATGGGTTGAGCACGGGAGGTCGAGGCTGCAGTGTGCTGTGATTGCACCACTGCACTC
CAGCCTGAGCGGCAGGGTGAGACCCTGTCTCAAAAAATTAAAAAATCATGTGTATTAGTGAAGATTTGTA
AAGTAGAAAATAATAGAAATAAAATTGAAATCACCAGTAATCCCACCATTTTGCGATAACTAGTATTAAA
TATAGGTATATTTCCCTCTGATTATTTTCCATGTATATTTTTATCATCATTGAGATGTACATAGTTTTTC
TTAATCCTGCTTTTTTCATTAACTACATCATTGTTAATTTTTCTTAATAAATATTTTTGAAAACTTAATT
TCTAGGAATAATCTATCATATAATAATTTTTCTTTTTTGACATTTGCATTGTTTCAGTTTTTTCTATTA
TGAATAATGTTGTAAAGAATATCTTTGTGGGCCAGGTGCGGTGGCTCATGCCTGTAATCTCAGCAGTTTG
GGAGGCCAAGGTGGGCGGATCACCTGAGGTCAGGAGTTTGCGATCAGCCTGGCCAACATGGTGAAACCCT
GTCTCTACTAAAAATAAAAAAATTAGCCAGGCATGGTGACAAGCGCCTGTAATTCCAGCTACTCGGGAAG
CTGAGGCTGGGGAATCACTTGAACCTAGGAGGCGGAGATTGCATTTAGCCAAGATTATGCCATTGCACTC
CAGCCTGGGCCACAAGAGCGAAACTCTCAGATATTCAAAAAGAATATCTGAATATCTTTATGGCCGGGTG
CAGTGGCTCACCCTTGTAATACCAGCACCTTGGATGAGCAACGCAGGAGGATCACTTGAGCCCAGGAGAT
TGAGGGAAAAAAAAAAAAAAAAAAAAAAAAAAAAAAAAAAGCCCGGGTGTGCACACCCTGTAGTCCCAGCT
ACTCCAGATGTTGAGATGGGAGGATCACTTGAGCCTGGGAGGTCAAGCCTTCAGTGAGCTGTGATAACGC
CACTGCATTCCAGCATGGGCGACAGAGCAAGACCCTAACTTAAAAAATAAAATAAAATAAATAATATCTT
TGTGTGAGTCTTTTTTTTTTTTCCCCGAGACGGAGTTTCGCTCTTTCGCCCAGGCTGGAGTGCAGTGGTGC
AATCTCCGCTCACTGCAGCCTCCGCCTTCCGGTTTCAAGCGATTCTCTTGCCTCAGCCTCCTCAGTAGCT
GGGATTACAGGCACCTGCCACCACGCCCAGCTAATTTTTGTATTTTTAGTAGAGACCGGGTTTCATCATG
TTGGCCATGGTCTCGATCTCCTGACCTCGTGATCTGCCTTCCTCAGCCTCCCAAAATGCTGGGATTACAG
GCTTGAGCCACAGTGCCCGGCCCGTGTGTGAATCTTTATCCACATATTTGATTATTTCTTTATAATACAT
TCCTAGAAAAGTTGAACTAATCTATGCTACTGCTTGGTGCTTATAAAATCTATTTCATTGTACTCTTGGT

```
AGTCCTGAGTCATCACTTTTATTGTCATATTTTATTTTCTTGATTATTTTAATAATGCTTATTTATGGTG
AAAAATATTTTACTTATGGAAGTATTGTTAAGCCTGCAGTGTGTTAGTCTGGAGTGGATGTGGTATTATG
CTAGTGTATAATAACATCTTAAAGCACAATTTTTTACTTCAATACTGTTGATTTCTGCAAAGGAAAACTC
AGGGACTAAGCATTCCCAGATAGACAAGCATAGCAAGAAGTTCAAAAAGCTAGAGAAAGACAACATGCAA
CAAAACAAATGTTATTGAATATTTGGCAGAATTTGCAGATTGCTACTACGCAAAGATTGGAGGAGAAAAT
TCAGAAACTTCAGAAACAGCTCAGTGATTTGAAATTGTCAAATAAAAATATGAAAACTCAGCTGACAAGA
GTAAATGTCCTTAAAGTAAGTAAAGGAAGTGAGGCTTTCAGAAATTCACTAAAGCTTTGGTCTTTTACCA
TTTTAGCAGCATGCTTTTCATTGAAGCTAAAAAAATTAATATTAAAATTATTTTACATACATACAAAAGA
ATATATATTTAAGCATATAGAATAAAATTGGAATTCACCACTCATTTTAAGAAACAAATATTACCAATAC
AATTGAAACCCCCATATATCCATATATCCTCCTCCTTGTATTCTAAGTGTTATTATTACAAATCCCTTGT
TTTTTGTTTTATTATTATTATTATTCTTTTTGAGACAGAGTCTTGCTCTGTTACCCAGACTGGAGTACAGTGG
CGTGATCTTGGCTCACTGCAACCTCTGCCTTCCAGGTTCAAGTAATCCTCCCACCTCAGCCTCCCAAGTA
GCTGGGAATACAGGCGCATGCCACCATGCCCAGTTAATTTTTGTATTTTTAGTAGAAACAGGGTTTCACC
ATGTTGGCCAGGCTGGTCTCAAACTCCCGACCTCAAGTGATCTGCCTGCCTTGGCCTCCCAAAGTGCTGG
GATTACAAGTGTGAGCTACCTCACCCAGTCTGTTTTTGTTTTAGTTTCACTTGTGTCTCTTATTGGGGT
AATAGTTAAAAGTTGTAGTCATTTTGGGGACTCTTCTTTGGACCTTCTCCATATCAAACTTCAGTTATAC
TATTTCAAAAATTATGCCTTAAGCCAAACAGGCACTAAATAACTGATCAACTGATATGCCAGTTTATCAG
CAATATTTCTCTTACTGAAATGCCAATTATCTTCTGTATTTCTGTATTTGATTAATGTAGGGCTTTAAGA
CCTTTGAGGATGCAGAAAACATGTTAAGACTCTTTAAATCCCAAGTGGCCAGTTAATAAAAGTGCTAAGT
AATAGTTATTGATGAGCACGATCATGGAGAAATGTCCTCTTAATTCAGAAATTTTGGAATGTTTTTCTTT
TCCATATATCTCTGTCTTCATAAAAAAAGAAAGAAAAGGAAAAGAAGCAAGAGTTATCATAACTGTTATT
TAGAAGAGATCTAATCCTAGTTATTTCCTTCCTTTCCCCCATCTTATATGCTGTCACAGGACAAAACAAT
TGAAGAGCTCAGGCAATCTTTAGCAAATGTTGAAAGGATGAAAGAGAAGGCAAATGTTGAAACGATGAAA
GAGAAGGCAGTTGTGAAAACAGAAAACTTGAAAACTACATTAGACTCTGCAGAGCAAAAGGCAAGATCAG
ACAAAGAGAAGACCCAGCAGATGTTAGATGCTGTCACTTCTGAGCCCCCAACAGCAAAGAGCGCACCTGA
AGAAGTATCAGGACAAGAACAAGAGGTTTTTTCAAAATAGTAAAATTAAAATTAATTTAGTTGAAGTGAT
AAACACCCACGCCTACTTAGACTGTAACTAACTTGACAAAAGGGAATATTGGCTTATGGAATCATGAGTT
AAACAACCTAACCTCCAGGTGGGCGGAGATACACCTGGGCCCCAGGATCAGCACCTGGAACCTACAAGCC
CTTTCTCATGGTCACTTCTTGGCATCTATGTGTCAGCTCATCTGTCTGACTGCTGGTTGGTTTTCTCCAT
GACAGGAAACATGATCACTGGCAACCATGGAGATTTATATGGAGTTTCTGTGACAGGAGAGAGAATCCCA
AGAAAAGGTCTTATTGACCCAGTTTAGGTCAAGTGCTTATCCCTGCTAAACCCACAGTGGCTAGGGATGG
GATATATGATTATTTTATATACTCTAACAAGTGACCAGGAGTGTAGAGTTCTATGACATCATGTGTCATC
ATGTGAAGCTCAGGGGAAACCATGTGTGTCACTTTCTGTGTCACTGTCTAGGAGAATATAGTAGTGCTTC
TTAACTTGCTTAGATTTTCACTATACTTATAAAGCAAATATTTCGAGAGAATTTTTTAAAGGCCAACTGA
TCATCTGGGGCAATTTTTAAATTATATGTCACTTCTCCATATATTAGTTGCTTATGAAACTTATACCTTA
AGATATGCTTAAAACATAAAGTCATGATATTAGCATTTTCACTTTTTTCTCTCTTTAACTTCTGTGTGTT
CACTTTCTTGATTGTTTCTATTCCTCTCTTTTATTTTTTGAGACAGAGTCTCACTCTGTTGCCCAGGCTG
GAGTGCAGTAGCATGCTCATGGCTCACTGCAGCCTCGACCTCCTGAGCTAAAGCAGTCCTCTCACTGCAG
CCTTCCGAGTAGCTGGGGCTATAGGCGTGCCACCACCACACCTAATTTTTGTATGTTTTGTAGAGACAGG
GTTTCACCATGTTGCCCAGGCTGGTCTCAAACTCCTGGGCTCAAGCAATTCTCCTGCCTTGGCTTCCCAA
AGTGCTGGGATTACAGGTGTGAGCCACCGTGTCTAGTCCCTTATTTTATTTTCAGTCAAATCTGTTTTCC
TTTGGTCACCTTGTAGTTCACTCTTCACTTTTTAGATGATTTAGTGTTTTCTTGCCTGAGTTCAACTCTC
ACATCTAGATATCTTGGACTATTCTGAATTATTACATTTCTGATTCAAAATAAAGTTTTTCCCCCCATTT
TTGCAAATCCTTTAAAAATTGATATTTAATTTTTTTCAGGGGTGTTGTGTCAAATATTTGTCCTGTGTTT
CACGGCTGTGTTTTTTTTTTTTTGTTTTTTGTTTTTTTTTTTTTGAGATGGAGTTTCGCTCTTGTCACCCAG
GCTGGAGTGCAATGGCATGATCTCGGCTCACTGCAACCTCCACCTACTGGGTTCAAGTAATTCTCCTGCC
TCAACCTCCTGAGTAGCTGGGATTACAGGCAGTGCTACCATGCCCGGCTAATTTTTGTATTTTTAGTAGA
GATGGGGTTTCACCATGTTGGCCAGGCTGGTCTTGAACTCCTGACCTCAGGTGATCCAACTTCCTTGGCC
TCCCAAAGTGTTGGGATTACAGGTGTGAGCCACCATGCCCGGCCCATGGCTGTCTTTTGGGAGTATTTTT
TTTTTCATCGCCTGAACAGTTTAGATGATAGTGTCTTTCTATTTTCTTCTTAAAGTAATTTTATGTGAAT
ATAATTTGCCATTTGTCTGTATTCACTTTCAAATTCCTTGAATTGCTCTGGTCTTCAGATGTTTCTACTT
TAGGGTAGCTGGAGGCAGGGCTTACTCACTAGGTTCCTTAGCTCAATACTACCCTCTTCTGTTGGCACAG
TGAGTGCAGTTTCTAAAGTTTACTAGATCAAGCCTTTTTGGGAGTGAGGGTTTATATGATGTCTGATTCT
GTAATACTGTCTCATTTGTATAAACATATTAATTTCCACTGTTTGCTTTTTTCTTTTCCTTTATTACCAA
GCCTCCAAGGAACACAACTACCTCCCTCTCCCCTCAGAAACCTTGCCCTCTACAACTGCCATTTTTGGTC
TCATGTGCTTCCAAGACCCTTGCTTTTCCTTCATTTGTCAGTGTTCTGATCCACCAGATCTCAGATTTGT
TCTTGGTATTTCACCATTTATGATCTGTCTTGTTTCTGGGGGTAAGGTTGTCTGTGTTCTACACCAGTGA
AAATTAGCTGCACCTTCCTCTGTAGCTGCCTCTGCTGGTTTAGAATATTTATTTCCCCACTAACATGCAA
ATTGAAGTTTGTGGTATTCTCTAGTTTTGCTTTAGGCATGATTTATAGGTAGTTTTTATTTGATCTCCGT
GTTGATCACTATGGTTTTTGGAGGATGGGTAGAAAAATGTGTTTTTAGGGGACTGGTATTATCATTCAGC
AAATCAGAAGTCCAAAACGTAATTACCTTATGGATGAAAAATAACAAAATAAGCAGCAATAAAATTAAGT
TTACTCTATAAAAGTGTAAAAGCAAGAAAAAATTTAAATGCAAAGGAAATTTTAAATAGAGTTATTGTAA
TAGAAGAGACCATTTTTCTAGCTTAAAAATATTGTTTGAAAGTAGAATATATTACATTTAATAATGTTTA
ATAAGACTAAATTTCTAGTACCAATTCTTTGTACATAATACCTGGGTGACCCAAACTAATAACATATCTT
GATTTCTGTAATGGTTGTTTGTAGCTTAGTGACTTTCAAGAAACTATTCTCAGCTACTCAGGAGGCTGAG
GTGGAGGTTGCAGTGAGCCAAGATCACTGCACTCCAGCCTGGGCGACAGAGTGAGACTCTGTCTCAAAAA
ATAATAAATGAATAAAATTTAAAATTTAAAATAAAAATGGAAACTGCTCACCTTCCGAGGTAGTTTTAGA
TGTACCCAAGATATCCTCTGTGGGAACAAGTCAGAATCTGGACAGGCCTGTGGGACTCGATGCCTGTTTT
AGAGAGCTCTTCAGCATGGGCGGGGTGAGATTATACTGGACCTTACAGAAGTACCATTTTGGAACAAAAT
AATTATCTTGAATATTCATTCAAGGGATAAATGAGAATCACTTTCCAAATGGCCACAGCCATGATTCCCA
AACTGTGTGCCAAGGCACACTGGTGCACTGTAAGGATCTCAGCATGCCATGGAATGTTTTGATTTTATTT
```

ATATATTTATTGAGATGGAGTCTTGCTGTGTCACCCAGGCTGGAGTGCAGTGACGTAATCTCGGCTCACT
GCAACCTCCGTCTCCCAGGTTCAAGCAATTCTCCTGTCTCAGCCTCCTGAGTAGCTGGGACTACAGGGGC
CTGCCACCACGCCCGGCTAATTTTTGTATTTTTAGTGGAGACGGGGTTTCACCTTGTTGGTCAGGCTGGT
CTCGAACTCCTGACCTCCGGTGATCCACCCACTTCAGCCTCCCAAAGTGTTGTGATTATAGGCATAAGCC
ACCGTGCCCAGCCTAAATATTTTGATTTTAAAGGGAAGCACTGTAATATTTGACATCTGTCAGGAAGGTA
CATGGATACTAGCTTCAACATTACATCACCCTTCATTCTTTTTGATGACATACCTTTGTGATAGAAACTG
CCCAAGGCTTCTCAGGATTTATAAATTTGTTGCCGAGTGAACTTCAGTAGTTAGTGGTATCGCTACCAAA
GAAGCTGTGCTGCAAACTTGGGGAAGGAGGCTCTTTCCCCAGATTCTAGGATCCCTGGCTGCAATGTAAG
AAACTTGCTTATCCTTCCTCTCAATAATATCACCAGCCTAGCAAAAGAGGAAAAGTGAGGGACACCTTGA
CCAGAGCCTCCACTTGCAGCCCAGCCTGCTCAAGCTGTAAGAACCACCTTCTTATTCAGAATTTCCCCAG
AGCCACGGCCCAAGGGTCATCTGCCTGCTGCAGCCTTAGCACACAGGAGCCTGGGCATGAAACAGGCAGA
CCCTCTCCTCCTTCCAGGACACCCTTCTCTCAGGAAATGGAGGCCCTACCAGCTCCTACAGCCAAGCTCT
CCATGAAGGCCAAGGTGTTAAGGTGGGCCAGTTTCTGAAAGAGCCACTTTCTGAGCATATTAAAGAAAAA
TCTCTTGTAAAAACAAAGAGGGCTTAGTGTTAATGCTCCTTTATGAATTGTGTTAGTAGGAACTGATTGT
TCAATCATGGGGCAGTGCAAAACGTTAGCTGTGTTAACTCTGAGCAAACAGGGGAGATCCTTCAAGGACC
TGGAACACTGTTTCCTAGAAAAGCTTTTAATCATGTGTCCAAATCACTGCCACACTCTTCTTTAATGATA
AGAATTGGATTTAGATTTAAGGCTTTAGATAAATGATTCTCAACCTTCAAGATGCTATGAAATGACCTAA
TTAAGGAATTATTTTTTCCTAGGCCTATCCAGAGATTCCAGTTCAGTTTGTGGTATGAGGCTGAAGTATG
GATATTTTTTTCAAAGCTCCTTAAGTATATAAATTGATAAAATTACTTTGGAAGACTGGCAGTGTACGAG
TTTTCTGTTGCTGCTGTAACAAATTATCATAAACTTTGTGGCTAAAACAGTACAAATTTATTATCTTACA
GTTCTAGAGGTCCCATTGGGCTAAAATTAAAGTGTCAACAGGGTGTGTTCCTTCTGGAAAGGGGAAAATC
CATTTGTTTGCCTTTTCCAACTTCTAGAGGTTACCCACATTCTTGCCTCATTGCCTCCTTCCTCCATCTT
TAAAACTAGTAGGAATTGATCAGGCCCATCCAGTCTTTCTCACAGCTACTGTTCTCTGGTTCTTTATCTG
ATTCTACAATTTCTCTGATTCTCCTTCTCTTGCCTCCCTCTTCTCTATTTTTAAGGGTGCTTGTGATTAA
GTTGGGCCCACCTGGACAATCCAGAATGCTCTCCCTATTTTAAGGCCACCTCTTGGCAAACTCTGTAAAC
TTAATTCTCTTTTGCCATGTAACCTAATATACTCATAGGTTCCAGGGATTAGGACAAGGATATTTTGGGG
GACCCATTATTTTGCTTGCTGTAGTTAGCATCTACTAAAATTGAATACATGCATGCCTTATGAAGACGTA
GTCCCACTTCTACATACATGTTAGAAGCAAATTTTTCAGTGCCACAAAATAAAAGAAAATAGCACTCGAA
TATAAATTTTCTCAGCAAGGCAAATTTACTCTTTCAGGAGGGTGCCCCTCGTAGGTCTGGTTGCCACGAG
AGGACGCACAAACAAAGGAAAGCAGGGGGTTTTATTATCTCTAATGCAGCTTGTCCCTGTTACTGCGTCT
TGCCTCCATTGGCTGGAGTTGGACCACACGATCTAAGCTGAACCTGGTTGGCTAACTTGAAAAGTGCAGG
AATGCGGTTTTCAAGTGGGAAGGTGGGAAGATCAATTTTTCTGGGAAAGCTGTTACAGCAGGGAGGGGGT
GATTTCTTGGCTGTCTTGCCTGAGCACAGCAGGATGGGAGGGGCTGATAGATTGGCAGGCAAGATTACTG
TAGACAAAGAACAGAGAAATAAGACTTCAGGACAGACAGTACAAGGAAGTAAAGACCTCTTGGAGAAGAA
TACCTTGTTTGTAACAAAGTGAAACTCTTTGAAGAGGAACTGTCTAAACTACTTGTTTTTAACATATATA
ACAGAAATGTGTACATATTCTTTTTTAAATTTTTAAATTTATTATTTTTTTGGAGACAGAGTTTCGCTC
TTGTTGCCCAGGCTGGAGTGTAATGGCACGATCTTGGCTTACTGCAACCTCTGCCCCCTGGGTTCAAGTG
ATTCTCCTGCCTCAGCCTCCAGAGTAGCTGGTATTACAGGCATGCGCCACCACACCTGGCTTATTTTTTG
TATTTTTAGTAGAGACAGGGTTTCTCCATGCTGGTCCGGCTGATTTCTCGAACTCCCGAACTCAGGTGAT
CTGCCCGCCTCAGCCTCCCAAAGTGCTGGGATTACAGACGTGAGCTACCTCGCCTGGCCAGAAATGTGTG
CATATTCTATACAAAGACATTTACAATATTACTAACGGTGGCATTGTTCATTATTGCCGGAAACTGGAAA
CTACCCAAATGAACAATGGTGGCTTAAGTATGGCAATCAGATCCATTAGTTAAGCATTCGATCTCATTTG
GGGTTGGACAGGGAGAGGTCAACTGGAGTGCTGAATTTTTCTGAGGCCAAACTAGAAAGTAACTCTAGGA
GCTGGGCGTGGTGGCTCATGCCTGTTAATCCCAGCACTTTGGGAGGCCAAGGCGGGCAGATCACCTGAGG
TCGGGAGTTGGAGACCAGCCTGACCAACATGGAGAAACCCCGTCTCTACTAAAAATACAAAATTAGCCAG
GCGTGGTGGCGCATGCCTGTAAATCTCAGCAACCTGGGAAGCTGAGGCAGGAGAATCGCTTGAACCTGGG
AGGCGGAGGTTGCCGTGAGCCGAGATCGTGCTATTGCACTCCAGCTGGGCAACAAGAGTGAAACTCTGTC
TCAAAACAACAACAACAACAACAAAACAACAACAACAACTACTACTCTAGGACCAGGACTGGGAGATGGC
AAATAGGGGAGAGCATGGAGTTCCACTAATAAAATGGTAATACACTAACAGTGGAGAAAGCAATGGGCTT
GTAAGGAGAACTTGGTTCTTGTTGAACATCCGTCACTAATCAGTCTTGCAACCCTTGATCAAGTCTTGTC
ACCTCACTAAACTCGAATTTTCTTTATCTCAAAACTAGAAAGAAATCGTGGCCTGGATTTCTGAATTATG
GGGTTTCAGGCAGCCACAAGTAGGCTGGCAGAAATGTTTTCTGGTCAAATAAAGGAGTCTGTTGCCCCAG
AACAGGAGCCAGGGGCACAGCCAACAGTAAAATTCTGCTTGGGGCCCCATTCCTCAGCTGCAAGGTACTT
GTCTTCAGGTGTGGCAGGCTGAGATCTGCCTCCTTGTTCCCGGCCTATCCCGCTGGCCCCTCCCCTGCA
AGTGTTCGCTTCCATACAGAGGGACCATTAGGGCCTGTACATCGTACTTCAGGTCCCCTCCTGTGGTCCA
ACATTCCCTAGGGGCAAGTGCAACTGTTTATGCGGAGACCACTTTTCCGTGCAGCCCAACTGAAGGTGCA
CGTTCCACCGCAACCTGGTGCTTACAACAGCTCGGGAGGCCGCGCTACCGCGCCTGCGCCCCTCTGAATA
TGGAAGCGCGCGCGAGGTCCTTAAGGGAAAAGGAAGTAAGGGCGGGGACGGAGGGAGACGACTTCAACGT
AGGGAGTTGCTGCTGCTACACTGCCGGCCGGAGAGGACAAGGAAAACGTGGAGGAAGTCGGTGATGACTG
GCTGAAGGGGATGATTGGCGGGTGAAAAGAGCCGGGCCAGAAAGCACCTTTGCATGTGGCTAGAAACCCG
CCTGAAGAGGGGCTGAAACCCACGCCGGAACCCGCCCGATTCGAGCCAATCAGGGAGAGGAGCCGGGTGG
GGGGGCGGACGGGGCGGCCTCGCGGGGGGTGGACGGGGCGGTCTGCGGGGAGGGGGGGCGGTCTGCGGGG
AGGGGGACGGGGCGGCCTCGCGGGAGGGAGGACAGTTTCGCGGGTTCGGGCGGCGAGTCTCCCGGATGCT
CCTCAGCTCTGGGGACGCGGTGCAGAAGTGTGAGGGCGCCCGGCTTCCAGGCAGTAATGGGCGGGTCCCT
GCGCGGGAGCGTGGCGGGCGCTGGACTCTACAGCAGATGTGGAACTGGAGAGCTTGGCGCGCCTTCCGAC
TTTGTCACACACCTGCGCCGCCAGACTGGGGTCGGGCCCCTCCGCGTTCTGCTCTGGAGTGCCTGGGTCT
GGGCCCAGCACCGCGCTTTTAGAATCTCCTCAGCTGAATCTGACGCTCAGCAGTGGGTGAAGCGCAGCCC
CCTGTTTCAGGCCCTGCCGAGCTGGAAGGAGTGTCAGAGCTGGAGCGCGCGTGGCCCCCTCTGTGTTGGG
GTCACCCCGGGGTTGCCAGGGCTCAGGGAGGGTCGTAGTCTGGATTTTGTCACCCGCACGTCCCCACCCC
CCAGCAGGTCTGGGGTTGGAGAATCCACGCGGGCTTCATAAGCTAGATGCCAGTTAACTGTCGAGAGGGG
ACGCTCCCTCCTCGTAGGCGTCCACACTGGAGAAGGAATAAGATGGGCGATTGCCTGGGAAGCCTGACAG

GGCGGCGGCAGCTGGGATGCTGGAGAGGACTGGCCCCTTGAGTTACTGAGTCCGATGAATGTGCTTGCTC
TGCTGGAGGAACCGCGCTCAGGTTACAGTCATCCCAATATGGTTCTGAAGGTGCGTGGTTCAGGTCACTT
AGGACTTGACCAGATACCGGGTTTCTTTTACAAGCCGTTTCTGACGGTGGCCTGTTTCAACTACTGGCAG
AGCTCATGTAAAACAGACTTTTAAAAAAATTTGGGGGCTTTTAGTATTTTTTTCTTATTCCTATATTCT
GAGGATATTTTATAGTAGTCCCACATATGGAATTAGATAATCTCTTTTTTGTTTGATTAACAGTTTTATC
AAGTATAATGTACATACCATAACGTTCACCCATTTTAATGGATTCAATGATTTTTAGCATATTTACAGAG
TGGTGCAACCATCAGCATAATAGAATTAAGGAATCGTGATTTTTTTTTTCTGGTAATTGCTTTTACAGTT
CTCAAAGTTTGCACAAGCGGATATTTTAGAGGTACAGTGTAATATAAGAGCTTCTGAAAATGTCCACTTA
AGTTGTTTTATACCTGAGCAAGTGAAATTAAGAAGGGAATTGAAGCAAATATTCCTGGTAAGTTGTAGGG
AGTGAAACTTTTGTGTCTTGTAATACCAAGTAGATATTGACCATTTCAACTGGTTTTTATGCTGAGGAAA
TGCATAAACCCCATTTTACAGATGATGAAATCGACTTTGAAGGATAAGTTGCCTACAGCTGCATACCTGT
GCCTGGGCTAGGCCCCAAACCCAGATGCTTTATCTCTCAATTTGTTACCCTTGCTACCTCAACAGCTTGG
TTTTCAACCATGGTACTGATGAGTATGAACAGTACAAGCCATTCATTTACTGAGCAAATAATTATTGAGT
GCCACTCTGTGCCAAGAACACTGCTATAGGTGCTAGAGATATTATTGAATCAGATACCGTAGTGAACTGT
TCCTGCCCTCAGCTCATCTTCTGGTGGGGAGGACAATGATCAAGTAAAGAAATATATAGTTTTAGAGATT
CATCTATTTTTTTAATAGGTAAATTAAAAGGGCAAGGAATGGCAGTGGGAGGCAGAATCTGATGAGAAAA
ATCTGAATGAAGAGAGGAAGTTAGGATATAAGAAAGAAAGCAAGGGTTTGATTTGAGCAAGCGCAAAAAT
AGAGTTGTGATTTACTGAATTGAAATAAGGTGATACTGGAAGGACCAGGTTTTGGGGGTACAATCATAAG
TTTGGCTTTAAATGTTTTTAAATACCTTGCCTCTTAGACATCCAAGTGGAGATATGGCATTTAAATTCAT
GAGATTGGATGAGATCCCACCAAAGGAACAGGTTTAGGTGGAGACAACCAAATACCGATGCCTAGGACAC
TGCAGTGTTTAGAATTCAAGGAGATGAGAAGGAAACAGGAGGGAAGATTGAAAAGAAGAGTCCAGTGTGT
TATGAGGAAAACCCCAAGAGCATGCTGCCTTACAAGACAGGTGAAAAATGTGTTCTGTGAAAGAAAGAGT
AATTAACTGTTAAATGTTACAGACTGATCAAATAAAATGAAGACTGAGAATGGCCTGTTTGTAAGGTAAT
AAAAATACATAAAATCTTATGATAGAAATATTTATACATAAAGTTAGTAAGGAAACAGTGTTTACTCCTT
TTTGTAGAAGTGTAAATTTTTACAACCATTTTGAAGGGCAGTTTGATATTATCTACAACTTAAAATTGTG
CTTCCATTGATAATTTCACCTGTGGAAGTTTATCCTACAAAAATATTAATATGTGCACACAAATATGTGT
AAAAGTGTTTATCACAGCTTGTACACATATATATTTATAAATGTGTTGTCCAGGAACAGTGGCTTATGCC
TGTAATCCCAGCACTCTGGGAGGCCGAGGTGGATGGATCACCTGAGGTCAGGAGTTCGAGCCCAGCCTGG
CCAACATGGCGAAACCCCGTCTCTATTAAAAATACACACACACACACACACACACACACACACACACACA
CACACACACACAAATTAGCTGGGCGTGGTGGCGGACGCCTGTAATCCCAGCTACTTGGAAGGCTGAGGCA
GGAGAATCACTTGAACCCGGGAGGTGGAGGTTGCAGTAAGCCGAGATCACGCCACTGTACTTCTAGCCTG
GGTTACAGAGTGAGACTTCATCTCAAAAAAAAAAAAAAAAAAAAAAAAAAGGTGTTTATCACAGCATTGTTT
ACATTTGTAAAAAGGTACAAGTTTTCATCAAGATGGATGCAGTTGTTAAAGGGAAGATATAAATGTGTAG
ATATGGGAGATAGCTGCTATAGACGGAATTGTGTCCCCTGAACTTTCATATGTTGAAGCCCTTACCCTGA
ATGTGGTGGTATTTGGAGGCAGGGCCTTTGGGAGGTAGTTTGATTTAGATGAGGTCACGCAGATGGGGCC
CCCACGATGGGAGTAGTGTCCTTATACAAAGAAGAAGGGAGTCCAGAGCTTTCTTCTGTCAGTCATTTAA
GGACATGGTGAGAAGGCAGCCATCTGTAAATTAGGAAGAGTCCTCACCAGGAACTGAACTGGCTGTCACC
TTGATCTTGGTCTTTCCAGGTTCCACAGCCATGAGATATGAATGTCTGTTTTTAAAGCCACTCAGTCTGT
GGTATTAATATTTTGTTATAGCAGCCCAAGTTAAGACAGATAGCTTTGTTAAATGATAAAGTCAGGTTAT
CTAATAGAATGCATAGTATAACCCCATTTATCTTAATGTATCACAGGAGGCCTTTCTAGTCACACTAACA
AAAGTTACTCCTTTGTGTGCCTTCCCTGATCACTGTTACATTATTCTATGTACAGCACTTATTATCTAAA
ATTATTTCATTAATTTTTATACATGTTTACTGGCTTGTCACAATAGAAGGTAAGCTCTGTAAGGGGTTTG
CCTCTCTTGTTTATATCCCCAGTGCTAGGTATATATTACTTTAGGAAAAACCATTATTTATTAAAAATAT
TTTAGGAAAAAACCCTACACAAACAGTATTCCTGTAGTGGTTTTAAAATAAGACAACAGGCTGGGCGTGG
TAGCTCATGCTTGTAATCCCAGCACTTTGGGTGGCCGAGGCAGGCGGATCACCTGAGGTCAGGAGTTTTG
AGACCAGCTTGGCCAACATGGTGAAACCCCGTCTCTACTAAAAATACAAAAGTTAGCCTGGCCTGGCGTC
ACACGCCTTTAATCTGAGCTACTTGGGAGGCCAAGGCAGGAGAATCACTTGAACCCAGGAGGCAGAAGTT
GCAGTGAGCTGAGATCGCACCATTGCACCGTAGTCTGGGCAACAAGAGCAAATGTCTCAAAAAAATAAAA
TAAGACCACAATTTCTTTGATAGTGTTTCCTTCCAAAGGTGGTGGCTAATTCTCCTCTTCTTGAATGTAG
GCTGGATTTAGTGACTTGCTTCTATGTGTAGAATATGGCCAATGTGGAGGTATGTCAATAGGTCATGAAT
TCCTTTTTGTTCTCTCTCTTCGATCATTCACTCTGAAGTAAAGCAGCTGCCTTGTCATGAGAACATATCA
AACAGTGCTGTGGAAAGGCACATTTGGTGAGAAATAGGCCTACTCCCAACAGCCAGGGAAGAACTGAAGC
CTTCTGTGACATGTGAATGAGCCACCTGAGAAATGTATTTTTCATCCTCAGTCAATCAGTGTCTCAAAAG
AGGCCGTTAGCTGGATCCCTCAACAAAGCCACTTTTGGGTTCCTTTCAGATAATACAGGTTTGCTTTGTA
ATCTACTAGGTTTGGTGGTAGAGTGAGAAGACTGAACACACTCCCCTTTAGGACACATCATAAAGCAAAA
CAAGTATGGCCCAAAGTAGCATACACTTAATGTTCTTTTCTACTAGGATTTACAGAATTCATTGTTGGTA
CAATTTACTCTTTTAAAAAATAATTTTTATGTTGATCAGAATAAAATACGGTATTCCAAGCTATATGTGC
TAACTTGATTTTATTTTAAAAATGTATTGAACACTGGAACACACAGATTTGAAAGATTTGACCTTAATAT
ATATTTATATATAAAATATGATTTTGAAATAATGAACTTTTAAATTTAAAATTATAAATAATTTTTAAAA
TGCCTTCTATTTAGGTAAAGAATCTTCAAAACAAACTTCTCATATGATATGGTTTGTCTGTGTCCCCACC
CAAATCTCATCTTGAATTGTAGCTCCCATAATTCCCACATGTTGTGGAGGGACCCAGTGGAGATAATT
GAATCATGGGGGGTGGTTTCCTCCCTGTTGTTCTCGTCGTAGTGAATAAGTCTCATGGGATGGTTTTATT
AGGGATTTCCCCTCTTGTTTGGCTCTCATTCTACCTTGCCTGTTGCCATGTAAGATGTATGTTTCACCTG
CCATGATTGTGAGGCCTCCCCAGCCATGTGGAACTGTGAGTCCATTAAACTTTTTATTTATAAATTACCC
AGTCTTGGGCATGTCTTTATCAGCAGTGTGAAAATGGACTAATACATCATAAAAGAAATTTCATTGCAAA
AGTTGAAGTCTGAACTAAAAAGCTACAAAGAAAATAATGTTTAATAGCCATCCCAGATAGTGTCCCTGAA
ATACGATGTCAAGGATCTAGAGGAACATATTGTATCTTTAACCAGAATTAAGTCTGAAAAACAAGTATTC
AGAGTCTTAAAAGAGGCAAGCAGGACTTAACGGAACGAATTATAAAACTAAGGTAGAAAATTCTAGTTTA
TTTTTGAAACATGTCTCTCATCATAAGCTCACATATAGCATATGAGCTCCATGCTCCTGATTGATCAGTT
TAATTTCATGGAATTTCACTTATTGCCTGGTATAACATTATTACAATTTTTCATTATAAGACTTGTGATT
ATCAAGGTCAGGATATCAAGACCAACCTGGCTAACACGGTGAAACCCCATCTCTACTAAAAAATACAAAA

AATTAGCTGGGCGTGGTGGTGGGCACCTGTAGTCCCAGCTACTCGGGAGGCTGAGGCAGGACAATGGCGT
GAACCCAGGAGGCAGAGCTTGCAGTGAGCTGAGATCGCGCCACTGCCCTACCCTCCAGCCTGGGCGACAG
AGCGAGACTCTGTCTCAAAAAAAAAAAAAAAAAGATTTGTGATTATCTGGTCAATGTGTGTAGAGAGGAGA
TGTTTGATCATATACGGTACCCTTTTTTTTTTTTTTGAGATGGAGTCTCACTCTGTCCCCCAGGCTGGAG
TGCAGTGGTGCGATCTCCGCTCACTGCAAGCTCCGCCTCCTGGGTTCATGTCATTCTCCTGCCTTAGCCT
CCCGAGTAGCTGGGACTACAGGTGCCCACCAGCACACCTGGCTAATTTTTTGTGTTTTTAGTAGAGATGG
GGTTTCACCGTGTTAGCCAGGATGGTCTCGATCTCCTGACCTCGTGATCCACCCACCTCGGCCTCCCAAA
GTGCTGGGATTACAGGCGTGAGCCACCGTGCCTGGTTACAGTACCCTTTTTGATAGCAGGAGAAAAGATG
GTCATTAATGTATCCTCTTATAATAAGAGTAATATTTAAGAAAGCCACAAAATATGAAAAGCTTTTCTAT
CCAGATTTACATTCTGTTGTAGACCATCTTTATTCTGTTATTTACTGTACGTTAGACCAATTGATACCTT
TCATTTTCCTCTGGGGTTTGCATTTCGCAGATCACTTTTAAAAGGAAAACATAGGAGCCTGAAACAGAAG
TGGGAAACAAATATTTACTCAAACTAAGAGACTAAACTCAGTAGCCAGCAACAAGAGATCAAGGTGTGTG
TGTGTTTTCTGGTTGTGCAGATATTGTCTGAAATAAGATGGCTGAAAAGTTCAAGTGAAAAAGTAATTAA
AAGCAATTCATCAACCATAGCCATAGCTGGATGTATAATAGCTGATCAGGCATAGCAAACTCTTCAGGAT
AATTTCATTTTTAAAAATTTATGTCTTTGTCCTTTTCATCTTCTAAGCACAGTTTCAAATAAGACTACAG
AGTGAGGCTCTAGGGACCATCAGTTTTTGTCTTTAGTGCTAAAATGGTGGCTGAGTGACACACCATGATT
TTTTTTCTCAATATTTCATCATTCTACCAGTGTTGGAAAAGGGAGAGAAGGACTCTCTGAAGGAGACTGT
GCAAAGGATTCTTCTTTTTTTTTTTTTTTTTTGAGATGGAGTCTCACTCTGTTGCCCGGGCTGGAGTGC
AATGGCATGATCTCGGCTCATGCAACCTCCACCTCCCTGGTTCAAGGGATTCTCTTGCCTTAGCCTCTTT
AGTAGCTGGGATTACAGGCGCGCCACCACGCTCGGCTAATTTCTTGTATTTTTAGTAGAGAAAGGATGTC
ACCATGTTGGTCAGGCCAGTCTCGAACTCCTGACCTCGTGATCTGCCCACCTCGGCCTCCGAAAGTGCTG
GGATTACCAGCGTGAGCCACTGGGCCCGGCCCCAAAGGATCTTTTTACACCATGTCTGGTTCCCAGCCCT
TTTTCTATCCTTCCTGTGCAGTGTGGACTGAGTTGACTGAGATATTTAGGCCCAGGACTTCTTGCTTGTT
CTATAGTTATTGAGAAAAGTGTGTCAAAATATCCATCACTGATTAAGGATTTGTCTGTTTATTTAGTTCT
ATCAACATTTATTTTTTAACTTTGAAGCTATTTGCATACAAATTGAGGATTTTTATCTTTCTATTGAATT
GCCCCTTTTATCGTTATGAAATCTCACTTATTTCATGTAATACTTTTTGCCCTATAGTCTAGGTTGTCTG
ATATTAACATAGCTAGATAATATTTCTTAGATTGCATGGTATGTATTTTTCCATTTTTCATTTTCAATCT
TTCTATGTGATTAAAGTATGTCTTTTGTAAACAGCATATAGTTTTGTTTTTTAATCTAGTCTTATAATCT
TTGTCTTTTAATTGGAATGTTTAGGCTATTTACATTAAATTCTGATATTGTTGGATTTAAGTCCACCATA
CTGCTACTTACTGTGTTTTTCTCCTCTGGTCTTTGTTCTTGTAATAATTAGTTTGTTTTTTGTTATTGT
TGATTTTTTTTTTTTTTTGTCAAGATGGAGTCCTCCTCTGTCACCCAGGCTGGAACGCAGTGGTATGATC
TCGGCTAACTGCAACCTCAGCCTGCCAGGTTCAAGCAATTCTTCTGCCTCAGCCTCCCGAGTAGCTGGGA
TTACAGGTGCCTGCTGCCATGATGATTAATTTTATGTGTTAACTTAGCTGGGCTGTGTTGCCCAGATAGT
TGGTTAAACATTATTCTGGATGTTTCTGTGAAGATGTTTTTGGATGAGGTTAACATTTAGATCGGTGGAC
TTTGAGTAAAGCAGATTACCTTTCATAATTTGGGTGGGGCTCATCCAATCAGTTGAACATCTGAAGAGAC
CAAAAGACTGACCTTCTGCAAGCAAAGAAAAAATTCTGCCAACAGACAGCCATTGGACTTGAACTTCAACA
TTGACTCTTCAGTCTATTGGCCCACCCTGCAAATTTTGGACTTGCCAGTAAGTGTCTGAAATCTAGTGAG
GCAATTTCTTTCTTTTTTTTTTTTTTTTTGAGATGGAGTTTCGCTCTTGTTGTCCAGGCTGGAGTGCAGTGG
TGCGATCTCAGCTCACCGTAACCTCTGCCTCCCAGGTTCAAGTGATTCTTCTGCCTCAGCCTCCTGAGTA
GCTGGGATTACAGGCATGTGCCACCACGCCTGGCTACTTTTGTATTTTTAGTAGAGATGGGGTTTCTCCA
TATTGGTCAGGCTGGTCTCAAATTCCCAAACTCAGGTGATCCACCCGCCTTGGCCTCCCAAAGTGCTGGG
ATTACAGGTGTGAGCCACAGTGCCCAGCCTAATTTCTTTCTTTCTTTCTTTCTTTTTTTGAGACAGAGTT
TTGCTCTTTTTGACCAGAAAGGAGTGCAATGTGGCAGGATGTTGGCTCACTGCAACCTCCACCTCCTGGC
CTCTCTAGTAGCTGGGATTACAGGCGCCTGCCACCACGCCCAGCTAATTTTTGTATTTTTAGTAGAGATG
GGGTTTCACCATGTTGGCCAGGCTGGTCTCAAACTCCTGAAATTACGTGATCTGCCCGCCTTGGCCTCCC
AAAGTGCTGGGATTACAGGCGTGAGCCACCATGCCTAGCCGGGTAGTTTATCTTGACTTGACTTCAGGCT
CACCAATCCTTTTGGCTGCAATTCTACGATAGAAAAGGACATAAAAAACTTTAAATTAGCCTTAGAATAA
AGAGATGTTATCATTCCCTAGCAATTAGTATTCAAAGCAAGATCCAAATATGTAATTAGTCATTTATGTA
TCTAAGCTGTTTGTATGTATGATACAAGTTTTCACATACAAATTTCTTCTTTCTTTCTTTCTTTTTTTTT
GATAGAGGCAGGGTTTCACGACATTGCCCAGGCTGGTCTTGAGCTCAAGTGATCCATCTGCCTTGGCCTC
CCAAAGTGCTGAGATTACAGGCATGAGCCACAGTGCCTGGCCCAAATTATTGTAGTTATTTCCAATTCCT
TTCCCCCTTCTCACATCCCAATTAAAGAATTCCACTCAGGAATTGTTGTAGTAGAAGTGCTTTAGTCTGT
GTGCTACGGTTTGGATACTGTTTGTTTGCCAAGTCTCATGTTGGAATTTGATCACTAATGTTGAAGGTGG
AGCCTGGTGGGAAGTGTTTGGGTTGTTAAGGCAGATCCCTTATGAATGGTGTGGTGCCCTTCTAGAGGGA
GTAAGTTCGTTCTCACTCTTGGTTCCCACAAGATCTCGTTGTTGTAAAGATCCTTGTACTTACCCCTCCT
CTCTCTCTTGCCTTCTCTTTCACCATGTGATCTACACACACAGTATCATAAGGCATCTTTCTGATCCTTT
AGTGTTCACTCTCCAGTACCTTTAATATTTGCCTTCAAATTTCTCAAATTTCTTTATTTACTTCCATTTT
TCTCCTACAATAATTGTAGGCGTACTTAAAGTAGAATTACAATATAAATAATATTTTAAAATATCTACAA
CTAATACTAAAGGGGTTACTTTATTTTATTTAAATTTTATTTTTAAATAAGAATTTAAAATATCTGCAAC
TAATATCAGAGCCAAGGGGCTACTTTCTTTGAAATACAAAGAGTCTTTAGAGTCAGACTGTGTATGTTTC
AATCTGGGATCTACCTCTTATATTGTAGGTTTAGACAAATTGCTAAATATTTCTTGTCCCAGTTTTCTCA
TCTACAAAATGGAAAAATTAGCTTCCCTTTGCTGTCTGCCTTGAGTAGAAGCTTCCTGAGGCCCTCATCC
AAAACAGATGTTGGTGCCATGCTTCTAGTACAGTCTGCAGAACTGTGAGCCAAATAAACCTCTTTTCTTT
ATAAATTACTCAGCCTCAAGTATTCCCTTATAGCAACACAAATGGACTGAGATACCGTGTGTGATGTCCT
AATCCTTATAATATTATCCTACTACCCAGGCAGATATTGCTCTCCAAATGTCTTCTTAAAAAGGATGGTT
TCTGAAATGACACCCTCTTGGGACTATTGGAATTACTGAACAGCTGTTTTCATTAGAAATCTTTTTTTTT
TTTTGAGACAGGGTCTTGCTCTGTCGCCCATGCTGGAGTGCAGTGGTGCAATTTCAGCTCACTGCAACCT
CTGCCTCCCAGGTTCAAGTGATTCTCCTGTCTTGGCCTCCTGAGTACCTGGGACTACAGGTGTGCAACAC
CACACCCAGCTAATTTTTGTGTTTTTAGTAGAGATGGGTTTCATTATTTATTTATTTTTTTGAGACGAAG
TCTCGTTGTGTCACCCAAGCTGGAGTGCAGTGGCGTGATCTCGGCTCACTGCAACCTCCACCTCCCAGGT
TCAAGTGATTCTCCTGCCTCAGCCTCCTGAGTAACTGGGACTACAGGTGCACACCACTATGCCTGGCTAA

TTTTTTTTTTTTTTTTTTTTTGTATTTTAGTAGAGACAGGTTTCACCATGTTAGCCAGGCTGGTCTCA
AACTCCTGATCTCAGGAGATCCACCCGCTTTGCCCTTCCAAAGTGCTGGGATTATAGGCTTGAGCCACTG
TGCCCGGCCTTAGAAATATATTTTGACTATACATATATTTTGTTTTATTTATTTTTATTTTTTTGAGAT
GGAGGCTTGCTCTGTTGCCCAGGCTGGAGTGCAGTGGTGTGATCTCAGCTCACTGCAACCTCTGCCTCCT
GGGTTCAAGTGACTCTCCTCCCTCAGCCTCTGAAGTAGCTGGAATTATGGGCACATGCCACCATACCCAG
CTAATTTTTGTGTTTGTATTTGTATTTTTGAGGTGGGGTCTTGCTCTGTCGCCCAGGCTGGAGTGTGTGG
CATTATCTTGGCTCACTGCAACCTCCGCCTCCTGGGTTCAAGCAATTCTCCTGCCTCAGTCTCCCGAGTA
GCTGGGATTACAGGAGCCCGTCACCACACCCGGCTAATTTTTGTATTTTTAGTAGAGATGGGGTTTCACC
ATGTTGGCCAGGCTGGTCTCGAATTCCTGAGCTCAGGTGATTCACCTGCCTCAGCCTCCCAAAGTGCTGG
GATTACAGGCGTTTGCCACTGTGCCTGGCCAACTATATATATATTTTAAAAGGGGACATTTCTTTTTAAT
TTTGGAATGGACATTTGAAAATTGTTTGAATTACTTTAGTCTACTCATATCTTTCAGTCTATTGACACAA
GGTATATCTGGTTTAAAGAGAAAAGGTGGAACAAAAAAAACCCATTCTAGATCAATTGGTAGATGCCAAC
AGATTCACTCCCATATGAATATGAAAGGACAAGGAACCATGAATATTTTCATGATGAAGGTGAGAATAAG
TTTTGATTGATTTTTGAAGAAAAACAATTTTTGTTATCTTGTTTAACTCTAGGAGGTAATCGAGAAATGT
TGAGTTGTTTGTTGGTTCTCTCCCAAAGGGAGGGTAGAAGGAAGCCATGGTTCCTTTATACCGTGGTTGA
CTGGGAGCCTTTATGCCTTTCTGATATATTAAGAGAAAATGCAAGGGGGGCCTAAAGGTCTCTGTGATAC
TGAAGAGAAAGGTATAGGGGTAATAGGGCTGTGAGAAAGCTGAAAGCTGAGATCATGTTACAGAATAAGA
TAGCGGAGTTTCATATTTCTGGTATGGGGCAATTCCTGCTGATGACAAAATCCAGGGTTGTTTTTGGATC
TAGGTGTAGGTGGTTGAAGTAGGGTATAAAGGCAGTCATGTGCTGGTAAACTGGCTCTTGAGAAAAAGCA
CCCAATTTGAGCATTCATTGACTTTTGATACCAACATGTCATTGAGCATAGAATTAGAAAGAGATATGAA
TAATCAACTCTTGGGAGCTGGAATGATCTGGCTTTAACAACCACTTTCTACATCAAAAAAAGTTAATGTT
ATTAATATTAGAATAATAAATAATTAAATAATAAATGAGTGTAGGTGTAGGGCATTGGAATTAAGTACAC
ACATGAATCACAAAGCTGTATTATTGGATCGATCATCTACTGTGACCCCTGAAATCTTGAATTATGGTAT
GAGTTGGTATAGAAGAAGAATGTGAGGCCCCAAATCTTCATTGAGTGAAGGAGGGTTGAGGAGTAGTCAG
TAGAAAAGAATAAAAAGAGAAGATTTTATAGAAGTCTGTTGGGGGTAAAATATTGCTGAGGAAGTAAAAT
AGTACTGAGGAAGTGTTCTTCAAATTCCTTCGACTATAACCACTTTTTAATGTAATCTGTATGTAAAGCA
AGGGTCTACATGATCCAATTTATGTGTTGGCTCCATTTATAAAAGAATATTTCAGTTGTCAAAACTAGTT
GAAAGTACAGTTAATCCTTTAATAATCTGGGGTTAGGGGATATGGCCATCATGCAAAAAAAAAAAAAATC
TGTGTATAATTGTTGACTCCTCCCAAACTTAACTACTAATAACCTGTTGTTGACTGGAAGACTTACCAGT
AATATAAACAGTTGACTAACACATATTTTGTATGTTGTATGTATTATACACTGTATTCTTACAGTAAAGC
TAGAGAAAAGAAAATGTTATTAAGAAAATCATAAAGAAGAAAAAATATATTTACTAATCATTAAGTGGAA
GTGGATCATCATAAAGGTCTTCATTCTCATCGTCTTCACTTTGAGTAGTCTGAGAAGGAGGAAGGAAAGG
AGGGGTTGGTCTTGCTGTCTCCGGGGTAGCAGAAGTAGAAGAAAATCCACGTTATCAGTGGACCCATGCA
ATTCAACTCGGTCTTCAAGGGTCAACTGTAATTCCAATCTTAATTATTTGCCTTAACTAATTTTCTTAAT
AAAAGGTGGAATATTCATAATTTACAATAACACCTTCATTTTCTTAACTTTTCTCACTATATCTCTCACA
TCACATCCTAAACCTTTTTCTCCTGTGCCTAACTCTCCATTCTCTTAAAAAACTCTCCCAGATCCAGTCT
ATGCTGCTCATAATTTCTCTTCCCTTCCTCTTTTTCCTACCTTCTTTCTAATGCAAATTCATCATTTCAT
GAATAATTTTCTCTCCTCTTATTTCCTACTTTTACTCAACAAAAGTCCAGAAACTAAACTTGCTTACTCA
GATCCCAGAGCTGCATAAAAGGACAGGAGATCTTGGATGATGTGTGGGTTGGAAACAGAAGGTATTACAT
TCTTTTGTTAAATAATTGAGGATTTTGCATGTGGTTAAAATGATGTCAGAGCTAGGCAAGGAAACGGGAT
TCTCCTACATTCCTGATAGGAGATTAAATTGGTACAACCCATTTGGAAATGCATTTGTCAATATCTCCTA
AAACCAAAGTGTATCCCTAAAACCAGAATATATCCTACCCTGTGACTCAGCAATTCCACTCCATCAACAG
TGGAATGTAATGAATATGGCTATCAGGTTTCAATATGCTAGTGACATCTGCTACATCTATTAACAGAAGT
CTATAATTTTTTAACCTCTGATCTCTGAAAACTTATTTTATGACTTTATTACTCTACAAACTAAAATGTC
TTACTATTGTGTATCAGATCCACTTCTTTTTAAATTAATTTTTAAATGTCAAGTCTTAATAGTCTTCCTT
TAGCCTCTATTTACTAATTTATTGTCCCCACAATGTCACTCTAAACGTAACTGTTAACTATCAGGAAGTA
TTTCCTTCTTTTTCTATAGAGAACAGAAGATCTTCAGCAGGAAATTCAGATGCTTACTCAGCAAATGGAA
CAGCTGTATCATCTTTATGAACAGCTGTTTGTGAATCATTCCAACTTGAAGAAAAGTATAGGGAACAACA
AAAGATCCTTGAAATACCTGGAAGGAAAAATTGCTTTTAATGATGTTTTAAAAGATTAGACTATGAAAAA
AGACTTTCCTGAATTATAGATGTTATTTTGGGCAATGAAATTAACTATTTATTATTCTAATATTAATAAC
TTTAACTTTATTTGGTGTAGAAAGCTGATAAAAACTATTTATATTTCACTTAACATTGGAAAAGTGAGGG
GGAAAAATCCTTAGAGTTATGCTTCTAATTTTATCAAAAAACATGCCCTTTCCCATATCTTCAGTTTTTT
CACCGTGTACATATTTGACAGATAAAACCATCAATATAATATGGAAAGTTTAGTGTCTTTTATAATCTCT
TCTTGTAAGTTACATAACATCACTTCTGCCATATTCTATCAGTCAAACAGACCAACCTGATACAATGTTG
TTCGAGACTATAAGGGTACCAGGCGGCGCGGTGCAGATCATTGGTGGTCATCTTAAAAGTCTGGCTACCG
CACTCATTTCTTTTACTCACAAACTGAATGATTTGCTTATTCATTCATTTATTCAATACTTATTGAACAA
CCACAGATTTTACAAACATATAGGACTGGCTGGGGGCAGTGGCTCACGCCTGTAATCCCAGCACTTTGGG
AGGCTGAGGTGGGCTGATCACCTGAGGTCGGGAGTTCAAGACCAGCCTGGCCAACATGGAGAAACCCTGT
CTCTACTAAAAACACAAAAATTAGCCAGGTGTAGTGGCTCACATTTGTAATCCCAACTACTTGGGAGGTT
GAAGCAGGAGAATCGATTGAACCTGGGAAGTGGAGGTTGCAGTGAGCTGAGATCGTGCCACTGCACTCCA
GCTTAGGCGACAGAGCAAGACTCCATCTCAAAACAAACAAACAAAATAGGACTTAATGAAGTAAGGTCAA
CAGTAGACCATATAGAGTTTAAAGATAAATATATCATCTCATCTAGCCTCCACCTCTGCCTTTGAATATG
TGTATGGAAATAATACATTGAATGGTTAATCCATGCAAATAAAAATAATCCTTTATTAAGTTTTCTTAAG
ATTGTACAAAACGTGTGCTTGGCCAGGCATGGTGGCTCACACCTGTAATCTCAACACTCTGTGAGGCCGA
GGTGGGATCACTCGAGGTCAGGAGTTTTAAGACCAGCCTGGCCAACATGGTGAAGCTCTGTCTCTACTAA
AAACACAAAAATTACCTGGGCACGGTAGCACATGCCTGTGGTCCCAGCTACCTGGGAGGCTGAGGTGGGA
GAATCATTTGAAACTGGGAGGCAGAGGTTGCAGTGAGCCAAGATTGCACCACTGCACTCCAGCCTGGGCA
ACAGAGTGAGACCCTGTCTCAAAAAACAAACAAAAAACAAAATAACATGTGCCTACCCCAACACTTAAAG
CTATGCTAAACAGTTTAAAGGAAATAATAATTTTCTCTCTGCCCATGTCACCTCAGTAACCAATGTTAAC
CATTCCCATAGTTATGGAAATATGTAAACATATATAAAGGGTAATGGTGTCTTCACAAAACTAAGATCAT
TCTAATAAAAATATTCTGCAACTTCCTCTACTTAGTAGTGCCTCATGGTTGTATCTTAAGTTAAAAGATA

TAGCTCTTCCTTTAATAACTGTATAATATTCTATAGTATGCATGTATCTTAATTTATTCAACCATTTCTC
TTTTGAGGGATGATATAATTATTTCCTTCTTTTGGTCACTACAAATAATGTGAAAATAAGTATCTTTCAA
CTTATATCCTTCCACACTGGTGCTTTTGTTGCTAGGGGATTAATTGACAAATATGAGCTGATAGGGTCAC
AGTGCGTATTTTAAATTCTAATAGCCATTGTCAGATTACTATTTGCAAAAGGATAGAAGCAGTTCATTTA
AGAGTAAATCATTCTCCTTTACATCCAGCTAGCATTGAATGCTGTCATTCTTTTTTGTTGTTAGTTGGGT
AAAAAAAGAAACAAAAAACAAGGTACCTCATTATTATTGTAATTTACATTTTCTTGACTACTAGTGAAGA
TAAGGATCTTTTTTTTTTTTTTTTTTCCTTTCTGTGGAGATAAGGTCTTACTATGTTACCCAGACTGGT
CTCAAACCCCTGGATCAAGCTATCCTCCTTTCTCAGCCTCCCAAAGGGCTGAAATTACAGGTGTGAGTCA
TTGCACTTAGCCAGTAAGCATCCCTCTTCTTTAAAAAAATAATTTCAGGCCAGGTGCAGTGGCACATGCC
TGTAATCCCAGCACTTTGGGAGGTCAAGGTGGGTGGATCACCTGAGGTCAGGAGTTCGAGACCAGCCTGG
CCAAGATGGCAAAACCCTGTCTCTACCAAAAATACAAAAATTAGCTGGGCATGGTGGTGGGTACCTGTAA
TCCCAGCTACTCGGGAGCATGAGGCAGGAGAATGGCTTGAACCCAGGAGGCGGAGGTTGCAGTGAGCTGA
GATCATGCTATTGCACTCCAGCCTGGGTGACAAGAGCAAAACTCTGTCTCAAATAATAATAATAATAATT
TTTATTTTTATTATAGATTAAGGGGTACATGTGCAGGTTTGTTACATGGGCATAATGCGTGATGCTGAGG
TTTGGGTTACGTCACCAGGTAATGAGCTTAGTACCCAATAGGTGATTTTGCATCCCATGCCCCCTCTCTC
CCATGTCTGGTAGTCCCCAGTGTCTATTGTTCCCACCTTTATGTTTATGTGTATTCAATGTTTAGCTCCC
ACTTATAAGTGAGAACATGTGGTATTTGGCTTTCTGTTCTTGTGTTAATCTGCTTAGGATAATGGCTGCC
AGTTCCATCTATGTTGCTGCAAAGGATGTGATCTCATTCTTTTTAATGGCTGGTAAGCATCTTCATATAT
GCCTGTTGACCACTGGGCTTTTCTTTTCTACAAATTGCCTCCTTCTTCCCATAATTTGGATCTTAGGTGC
AGAAGATTGTGCTAATCAAATTTCTTAAATAGTGTCTTGTCATTGGGGACATAATGGTCCATCTCTATTT
AATTTTATTGTTTTTGGTTCCATTCCCCACTTCCATTCCTTATGCCCATAGGTAGCCTCACTTAAATGTG
TTTATGTCTATCATTTTGTTTATGTGATTAAAAAATCATTATTGGGATATTTACATGCCATAAAATTCAC
TCATTTAAAGTCTACAATTCAATGATTTTTAGTAAGTTAATAAAGTTGTGCAAATGCCACCACAATCCAG
GTTTAGAACATTTCCATCACCCAAAAAAGATTTTTTTTTTTTTTGCTTCTAGACAATTAATGCCCTCTT
CCATCACTAGTGCCGGGCAACCACCAATCTGCTTTCTGTGTGTATACATTTTCCTTTTTTTGGACATTTC
ATAGAAATAAATAACTTTAATATGTAGTCTTTTGCATCTAGTTTTTAAAATTAGCATTGTTTTTGAGGTC
CATCTATGTTGTAGCATTCATCAGTATTGTGTTCTTTTTATTATTTAATGGTATTCTATTGTGTGGATAT
GCCACATTAAAAAATAATACTTTATTTTTGGAAGCAATTATAGGGTTACAGAAAAATTGACTATAAAGTA
CAGAGATCCCATAAACTTCCTTCCCCATCTTCACAGTAACAAATTGCATTAGTGTGGTAAATTTGTTACA
ATTGAGTTAACATTAATACATTATTATTATTATTATTATTGAGGCGGAGTTTCGCTCTTGTTACCTAGGC
TGGAGTGCAATGGCATGATCTCAGCTCACTGCAACCTCCGCCTCCTGGGTTCAAAAGATTCTCCTGCCTC
AGCCTCCTGAGTAGCTGGGATTACACACATGCACCACCACACCCGACTAATTTTGTACTTTTTTTAGTAG
AGACAGGATTTCACCATGTTGGTCAGGCTGGTCTTGAACTGCTGACCTCAGGTGATCCGCCTGCCTCAGC
CTCCCAAAGTGTTGGGATTACAGGCATGAGTCACTGCGCCCAGCCTGATACATTATTATTAACTAAAGTC
CGGGGTTTACATTAGGATTCATTCTGTAATGTACATTCTATGGGTTTTGAAAAGTGTATAATTACAAGTA
TCCATCATTACATCATCATACAGAATGGTTTCACTGCCCTAAAAATGTCCTGTGTTCCATCTGTTCATTC
CTTCCTCCTCCTGCAAACCTCTGGCAACCACAACTTTTTTTTTTTGAGATGGATGTCTCGCTATGTTGCC
CAGGCTTATCTCAAACTCCTGGGCTAAAGCAATTCTCCTGCCTTAGCCTCCTGAGTAGCTGGGACTACAG
GTGTATGCCACCATGCCCGGCTTGATCTTTTTACTACCTCCGTAGTTTTGTCTTTTCCAGAATGTCGTGT
ATTTGGAATCATACAGATATAACCTTTTCAGATTGGCTTCTTTCACTTAGTAATATGCATTAAAGTTTTC
TCCATGTCTTTTGGTGGCTTAATAGCTCATTGCTTTTTATTGCAATGTGAATAAAAAGCATTTTTTTTT
GCAAATAATATTCTGTTGTGCAGACTTACTACATTTTAGCTTTCCATTTACCTAATGGTAAATCTTCGTT
GCTTCCAATTTTTGACAATTATAAATAAAGCTGCTATAAGCATTCAAGTGCAGGTTTTTATGTGGACATA
AATTTTCACTTCACCTGGGTAAAAACCAAGGAGTACTATTTCTGAGTCTTATTGTAAGAATATGTTTAGT
TTTGTTAGAAACTGCCAAACTGTTTTACAAAATGGCTGTTCCATTTTGCATTTCCATCAGCAATGAATGA
GAGCTATTGCTGTCACTCTCACATCCTCACCAGCATTTGGTGTTGTCAGTGTTCTGGATTTTAGCCATTT
GAATAGGTGTGTAGTGGTATCTCATCATTGTTTTAATTGCAGTTCCCTAATGACATATGATGTTGAACAT
CTTTTCATATGCTTATTTGCCATCTGTATATCTTCTTTGATGAGAACTTTTGTTCAGAACTTTTGCCATT
TTTAAATTGAGTTCTTTATTTTCTAGTTGTTGAATTTTAAATTTTATTTGTATATTTTGGGATAACAATC
CTTTATCAGATATATCTTTTGCAACAATTATCTCCCAGTCTGTGGCTTGTCTTTTTTATTTTCTTAATAG
TCTCTATCACAGGGCATACTTTTTAGTTTTAATGAAGTCCAACTTGTCAGTTTTTTTTTTCATGAATCTT
GCTTTTCTATTGTATCCAAAAAAATCATCTCTAAACCTAGGTCACTTACATTTTCTCCTACGTTGTCTTCT
AGGAGTTTTATAGTTTTGTACTTTACATTTAGGTCTGTGATGTATTTTGAGTTAGTTTTTGTGAAGGTGG
TATGAGGTCTGTGTCTGGATTCATTTTTTGTTAATGTGGATATGTAGTTGTATGTAGTTGTTCTAGTACC
ATGTGTTGAAAAGACTATCCTTTTCTTGATTGAATTGCCTTGTTCCTTTGTTAAAGATCAGACTTTGGATG
AGTCTATTTCTTTAATTTCTTTCATCCAAGTTTTAAAATAGTCCTCATTTAGACTTTTTTTTTTTTTGAG
ACTGGGTCTCTCTCTTTCACCAGGGCTGGAGGGCTGGAGTGCAGTGATGCAATCACAGCTCACTGCAGCC
TTGACCTCCTGGGCTCAAGTGATCCTCCCATCTCAGCCTCCCTAGTAGCTGGGATTACAGGCACATGCCA
ACCACGCCTGGCTAATTGTATTTTTTGTAGAGATAGGATTGCACCATGTTGCCCAGGCTGGCCTTGAACT
CTTGGGCTTAAGCAATCTGCCTGCCTTGGCCTGCCAAAGTGCTGGGATTACAGGCATGAACCACAACACC
TGGCTAGCTAATTTAAAATTTTTTCTTTTGTAGAGATGGAATCTTGCTGTGTTGACCTGGCTAGTTTCTA
ATTCCTGGCCTCAAATGATCCTCCCACCATGGCCTCCTGGGGTGCTGGGATTACAGATGTGAGCCACCAC
ACCCAGCATATTTTGTTAGATTTATACCTAAGTATTTAACTTGCTTGATAATTTAAATTTTTTTTTTTTT
TTTTTTTTTTTTTTTTTTGAGATGGAGTTTCGTTCTTGTCGCCCAGGCTAGAGTGTGGTGGCACGATCT
TGGCTCACTGCAACTTTTGCATCCCAGATTCAAAGGATGCTCCTGCCTAAGCCTCCCAAGTAGCTGGGAT
TACAGGCATGTGCCACCATGCCTGGCTAATTTTTGTATTTTTAGTAGAGACAGGGTTTTACTATGTTGGT
CAGGCTGGTCTCGAACTCCTAACCTCAAGTGATCCACCTGCCTTGGCCTCCCAAAGTGCTGGGATTACAG
GCATGAACCACCGCACCCGGCCGATACTTTAAATGTTATTGTGCTTTTAATTTCAATTTCTAATTGTTCA
TATTTGGTATATTAGGAAAGCAATTGACTTTGTATATTAACTTTGTATTTTGCAACCTTGCTGTAATTGT
TTATTAGTTCCAGAAATTTTAAAAGTCAATTCTTTGGGATTCTCTACATAGAGAATCATGTAATCTGTGA
ACAAAAACAGTTTCATTTCTTCCTTTTCAATCTGTATTAATTTTCTTTTCTTTTCTTGCCTCATTGCACT

GGCTAGATCTTCTAGCATTGTACTGAATAAGAACAATAAGCATGGATATCCTGTTTTCAATCTTAGAGGG
AAAGCATTCAGTCTTTCACCATTAAATGTAATGTTAAATATAGATTTTTTATAGATGCTTGTTATCAAG
TTGAGAAAGCTCCCCTGTATTCCTGTTTTTCTGAGTTTATTTTTATGAGTGGTGTTGAATTTTGTCATGC
TTTTTCTGTGTCTATTGATATGATCATATGTTTTTCTTTTCTAGCCTGTTAACATAGTGAGTTACATTGA
TTTTTGAAGGTTGAACCACCCTTGCATCTCTGGAATTAAGGCCTGATATTGTTTGGATATTTATGCTACC
CAATTCTCATGGTGAAATGTAATCTCCATTGTTGGAAGTGTGGCCTGGTGAGAGGTGTTTGGGTTATGGG
GGCAGATCCCTCATGGCTTGGTGCTGTCCTCACGATAGTGAGTGAGTTCTCACGAGATCTGGTTAATTTA
AAAGTGTGTGGCTCCCTCCCTGTCTCTCTATCTTGCTTCTGCTCTAGTTATGTGATATGCTGTCAGGTGC
TGGGCTCCCCCTTCACCTTCTGCCATGATTGTGAGCTTCCTGAGGCCTCACTGGAAGCTGAGCAGATGCC
CCGCACCATGCTTCCTGTACAGCCTGTAGAACTATGAGACAATTAAACCTATTTTCTTTGTAAATTATCC
AGTCTCAAGTATTTTTTGTTTGTTTGTGTTGTGAGATAGGGTCTCACTCTGTCGCCTAGGCTGTAGTGCA
GTGGTGCGACCTGGGCCCACTGCAACCTCTGCCTCTGGGTTCAAGTGGTTCTCCCACCTCAGCCTCCTGA
GTAGCTGGAACTACAGGTGTGTGCCACCACACCCGGCTAATTTTTGTATTTTTTGGTAGACATGGGGTTT
CACCATGTTGGTCAGGTTGGTCTTGAACTCCTGACCTCAAGTGATCAGCCTGCCTTGGCCTCCCAAAGTG
CTGGGATTACCAGCATGAGCCACCACAGTTGGCCTCAAGTATTTCTTTATAGCAATGAAAGAATGGCCAA
ATACAACCCCACTTTATCATGGTATATAATTCCTTGTATGTATTGCTGAATTTGATTTGATAATATTTTG
TTAAGGATTTTTGTATATATTCATGTGGTATATTAGTCTGTAGTTATTTTATTTTATTTTTATTTTTTGA
GATGGAGTCTTAGTCCATTGCCCAGGCTGGAGTGCAGTCGTGGGATCTGGGCTCCCTGTAACTTCCACCT
TCTGGGTTCAAGTGATTCTCTTGCCTCAGCCTACAAAGTAGCTGGTACCACAGGTGCGTGCCACCATGCC
TGACTAATTTTTGTATTTTTAGTAGAGACAGGGTTTCACCATGTTGGCCAGGCTGGTCTCAAACTCCTGA
CCTCAAGTGATCCACCCACCTTGGCCTCCCAAAGTGCTGGGATTACAGGCAAGAGCCACCGTGCCTGGCC
ACAGTTATATTTTTTTGGATTGTCTTTGTTTGGTTTTTATATCAGGGTAATATTAGTTTCATAAAATGAA
TTTAGAAGTATTCTCTGTGTCTATTTTTTGGAAGATATTGTGTAGGATTAGTGTTAACTCTTCTTTTAAG
ATTTGATAGAATTCTCCAGTGAGACCATCCGGATATGGAGATTTCTGTTATGGGAAGTTTTAAAATTATA
AATTCTGGCTGGGCACTGTGGCTCATGCAGTAATCCCAGCACGTTGGGAGGCTGAGGCAGGAGGATCACT
TGAGCCCAGGAGTTTGAGACCAGCCTGGGCAATAGAGTGAGACCCTGTCTCTACAGAAAAAAAAAAAAAA
TTAGCTGGGCATGGTGGCATGTGCCTATAGTCTTAGCTACTCGAGAAGCTGAGGTGGGAAGATGTCTTGA
GCCTAGGAGTTCAAAGCTACAATGAGCTATGATCATGCTGCTGCACTCCAGCCTGGGTGACAGTGAGACA
CTGCCTCTAAAAAATAAAAAAGTAAAAATAAATTATAAATTCAATCTCTTTAATAGTTAAGGGCAATTAA
GATTATCTGCTTAAGGCCAGGCGTGGTGGCACATGCCTGTAATCCCAGCACTCTGGGAGGCTGAGGCGGG
TGGATCACGAGGTCAAGAGATGGAGACCATCCTGGCCAACATGGTGAAACACTCTCTCTACTAAAAATAC
AAAAATTAGCTGGGCGTGGTGGCACGCACCTGTAGTTCTAGCTACTCAGGAGGCTGAGGAAGGAGAATTG
CTTGAACCTGGGAGGCAGAGGTTGCAGTGAGCTGAGATCATGCCACTGCACTCCAGCCTGTCAACAGAGC
AAGACTCCATCTCAAAAAAAAAAAAAAATACAAAAAATACAAAAAATTAGCCAGGTGTGGTGGTGCGTGCC
TGTAGTCCCAGCTACTCAGGAGGCTGAGACAGGAGAATCGCTTGAACCTGGGAGGCAGAGGTTGCAGTGA
GTCAAGATGGCGCCACTGCACTCCAGCCTGGGCAACAGAGCGAGACTCTGTCTCAAAAAAATAAATAAAT
AAAACATTAAAAAAAGATAACCTACTTAATATTGGATGATTGTAGTAGTTTGTGTTTTTCAAAGAATTGG
TTCATTTAATGTAAATTGTCCAGTTTATGTGTGTAGAGTTGTTTATAATAATTCCTTATTATTTTTTAGA
CATCTGTATAGTCTGTAGTAATAGACCTTGCATTCTGAATACTGGTAACTAGCGTCTTCTCTCTCTCTCC
TTTTTTTTTTTTTTTTTTTTTTGAGACAGACTCTCGCTCTGTTGCCCAAGCTGGAGTGCAGTGGTGCGA
TCTTGGCTTACCACAACCTCCACCTCCCAGGTTCAAGTGATTTTCCTGCCTCAGCCTCCCGAGTAGCTGG
GACTACAGGCACACACCACCATGCCCAGCTAATTTTTGTATTTTTAGTAGAGATGGGGTTTCACTATGTT
GCCAGGCTGGTCTTGAACTCCTAACCTTGAGATCTGCCCGCCTTGGCCTCCCAGAGTGCTGGGATTACAG
GCATGAGCCACCGCGTCCATCCAGTCTTCTCTCATTTGTGCTTTGTTAGTCTTGATAGAAGTTTGTCAAT
TTTATTAATTTTTCTTTTTTTTTTTTTTTTTTTTTTTTTTGAGACGGAGTCTTGCTCTGTTACCCAGGCCA
GAGTGCAGTAGTGTGATCTCGGCTCACTGCAACCTCCGCCTCCCAGGTTCAAGTGATTCTCCTGCATCAG
CCTCCCGAGTAGCTGGAACTACAGGCTTGCACCACCAGGCCCAGCTAATTTTTGTATTTTTAGTAGAGAT
GGAGTTTCGCCATGTTGGCCAGGCTGGTCTTGAACTCCTGACCTCAGGTGATCTGCCTGCCTCAGGCTCT
CAAAGTGCTGGGATTACAGGTGTGAGCCACCGTGCCCAGCCGATTTTATTAATTTTTCAAAAGAACCAGT
TCTTTGTTTCATTGGTTTTTCTATTTTTTTCCTGTTTTACATTTAATCAATTTTGTTCTTATTTTTATTA
TTTCCTTCCTTCTGCTTGCTTTGGATTTATTTTGTTCTTATTTTCCTAGGTTCTTGGTGTGGGAGCATAG
ATTATTAATTTGAGATCTTCCCTCTTTTCTAATACACACATTTAGTGCTATAAATTTCCCTCTTGGTGGT
GCTTTAGCTGTGTCCCTCAAGTGTTGATATGTTTTATTTTCATTTTCATTCAGTTCCATGTATTTTTAAA
ATTTCCCTTGACCTATGTTTTATTTAGGAGTACTTGTTTCATTTCCATGTGATTGGAGATTTTCCTGTTA
TCTGTTATTGGTTTCTAGTTTGATTCCACTGTGGTCAGAAATCACATTCTATACGATTTCAATTCTTGTA
AATATTTTGATGTTTGTTTTAATGCTCAGGATATGGTCTATCTTACTATTTCTTGCATAGACCCTCAAAA
GGTTGTGTAGCCTGCTCTTGTAGGGTGGAGTATTCTACAAATGTCAATTGGATTTTGTTGATGCTGGTGT
GGTTGAGTTTTTCTATGTTCGTGCTGATTATCTATCTCATTCTATCAACTGAGAGAGGAGCTGAATCCTC
CAACAATAGTGGATTTTTCTCTTTCTTCTTTCTTTCTTTCTTTCTTTTTTTTTTTTTGAGACAGAGTCTC
CCTGTGTTGCCCTGGCTGGAGTGAAGTGGCGAGATCTCCACTCACTGCAAGCTCCACCTCCTGGGTTCAT
GCCATTCTCCTACCTCAGCCTCCCGAGTAGCTGGGACTACAGGCACCCGCCACCACGCCCGGCTAATTTT
TTTTGTATTTTTGGTAGAGGTGGGGTGCCAGGATGGTCTCGATCTCCTGACCTTGTGATCCACCCGCCTC
AGCCTTCCAAAGTGTTGGGATTACAGGCGTGAGCCACCGCGCCTGGCCTCTTCTTTCTTTTTTCTTTTCT
TTCTTTCTTTCTCTTTCTCTCTCTCTTTCCTTTTCTTTTCTTTTTTTTTTTTTTTTGACAGAGCCTCACT
GTTGCCCCAGGCTGGAGTGCAGTGGCCTGATCTCGGCTCACTGGAACCTCCGCCTCCCAGGTTCAAGTGA
TTCTCTTGCCTCAGCCTCCAGAGTAGCTGAGACTACAGGTGTGCACCACCACATCTGGCTGATTTTTGTA
TTTTTTATTAGAGATGGGGTTTTGCCATGTTGGCCAGGCTGCTTTCAATCTCCTGACCTCAGGTGATACA
CCCGCCTTGGCCTCCCAAAATGCTGGGATTATAGGCATGAGCTATCATGCCTGACCTTTTTTCTTTCATT
TCTATCAGTTTTTGCTTCACATATCTTATAACTTTGTTGTTTGGGGGCATTTAAGATTACTGTGTCTTCT
TGGTTGATTGATCCTTTTGTTATTATATAATGTCCCTCCCTGTGTCTGGTAATTTTATTTGCTCTGAAGT
CTACTTTGTTTGACACTTTCCTTTAATATTTGCATAACATATTTTTTCCATCCTCTTACTGTCAAATTCC

TTATATTTTTATTTGAAGAGTTTCTTATAGATACCATATAGTTAAACATCTTTTAAATCCCCTCTGCTAA
CTCTGTCTTTTAACTGGGGTATTTATTTTTATTTATTTTTTTCTTTTTGTGATGGAGTCTCACTCTGTTC
CCCAGGCTGTAGTGTAGTGATGCTCACTTGGCTCACTGCAACCTCTGCCTCCCGGGTTCAAGTGATTCTC
CTGCCTTGGCCTCCCAAGTAGCTGGAATTGCAGATGTGCACCACCATGCCTGGATAATTTTTTTGTATTT
TTAGTAGAGACTGGCCAGGCTGGTCTTGAACTTTTGACTGTATGGGAACAGACACACAACTCTCCCAAAT
AAGCACAACAAAGAGACACAGAAGCAGTCCAAGCCTCTGATAAACTCTCCCATCCTGAATCCTTAAAAAT
GCTTAGTCTGTAAGAGGATGTGCCTCTGACCTAACTCAGCCAGACGCCCCTCTCAGGTTTGTTTTTTCTA
AAATAAACCTGTCTTGACTGGCAAGCCACCTTTCTTTTCTCTCCTCTTTCTTTAATTCCTACACTGACTT
CAAGTGATCTGCTTGCTTCGGCCTCCCAAAGTGCTGGGATTACAGGTGTGAGACACTGCGCCCGGCCTAA
CTGGTGTATCTAGACCATTTACATTTAATGTAATTATTGCTATATTAGGGCTTAAGTCTTCCTTTTCATT
TTGTTTTCTCTGTTTTTTAAATTTCTGTTTTCTTTTTCCTAATTTCATGCTTGTTCCTGAAACATTTTTT
AGAATTCCATTTTGAATTATTTATAGTTTTTGATGATAAACATATATATTTGGTATAGCTTTTTTAGTGG
TTGCTCCAGGTATTACATTTTGTATATATGACTTAATACAGTGTATTGATGTCATTTTACCAGTTTGAGT
AAAGTATAGAACTCTTAGCTTCCATTATGTCTCTACTTTTCCCTGTTTATATAATTATCTTAGCTATTTC
CTCTTCATACATTTAGAACCACATCATACAGTGTTATAGTTTTTGCTTTAACCATCAAACATATTTTAGA
AAACTCAAGAGAAGGAAAGCCTATTGTATTTACCCACAGTTTTGCTCATTATATTTTCTGTCTCCTGATG
TTCCAAGATTCCTTCATTTTTAAAAATCATTTTCTTTCTGTTTGGAGAACTTCATTATTTAGTAAGTCTT
TTTGTTTTTGTTTTTGTTTTTTTTTAGAGATGGGGTATTGCTGTCACCTAGGCTGGAGTGCAGTAGTGTG
ATCATAGCTCACTGCAGCCTTGAACTCTTGAGCTCAAGCAATCCCCCTGCTCAGCCTACCAAATAGCTGG
TACTACAGGCATGCACCACCATGCCTGGCTAATTTTTTTTTTTTTTTTTTTCTGAGATGGAGTCTCCCT
CTGTCACCCAGGCTGGAGTGCAATGGCGTGATCTCAGCTCACTGCAACCTCTGCCTCCCAGGTTCAAGCA
ATTATTCTCTCATCTCTGCCTCCTGAGTAGCTGGGACTACAGGCACACACCACCACACCTGGCTCATTTT
TGTATTTTTAGTAGAGACAGGGTATCACCATGTTGGCCAGGCTGGTCTCAAACTCCTGACCTCTAGTGAT
CCGCCTGCCTCAGCCTCCCAAAGTGCTGGGATTACAGGCGTGAACCACCATCCCCAGTGTGTTGTAGGCT
TTTAAAATGTAAAGCAAAATTGTTCTACCAGCAGTGAATCAAACAGTAGGTTTTGAAACGTCAAGAAGCC
CAAACACAAATTTAAGTTAGAGTTTTGTAAAGTAATATAAGTTCTCCTTTAAATGCATTTTAAAATATTA
ATAATTTTCTTTAGTATTGCTTAACCCCCTGTAAGTCACTAGGGCTCCATAATTATTTTGGAACCAACTC
CTAAGTTAATATTCTTTCACTGTAATTTCAGCATCCTTAAATCTTCTAAGCACAGCTATAAGTTGAAATG
ATTTTAGAGAACTGTGAGTAAAAATCTAATATGATAAAATGGCTCCATTTTGCGGGGAAGGATGTACTGG
TAATTGACAGAAAATGACCAGGAACATGGAAATAGGAGTAGGTCAGACAGATTGAATTGTTAAGTATTTT
GAATATACTATAAATGAGATATAAATGATATTTTGAAATCAATATGCAATTTTTGTTGTATCTAATAAGG
ACTTTTAAGGATACAGTCAAGAAGGAGAGATGCAATATTACTGTGTTTAGCCTTACTAAAGCAAAGGAAA
GTACTGTACGTAAAAGTTCTCTGGCGCGGTGGCTCATGCCTGTAATCCCAGCACTTTGGGAGGCCGAGGC
GGGCAGATCACGAGGTCAGGAGTTCCAGACCAGCCTGGCCAACATAATGAAACCTCGTCTCTACTAAAAA
TACAAAAATTAGTTGGGCGTGGTGGTGTGCACCTGTAATTCCAGCTGCTTGGGAGGCAGAGGCAGGAGAA
TTGCTTGAAACCGGAAGGCAGAGGTTGCAGTGAGCCAAGATCGTACTACTGCACTCCAGCCTGGGCAACA
AGAGAGAAACTCCGTCTAAAAAAAAAAAAAAAAAGTTCTCCGGCATTTTTTGAAAAAGGCAAACTGCACTC
ATAAAATTTTACCTTTGGAACAGAATCTTTATAGTTACATAATCAATGGAAAGAACAGATTTGATGACAA
TATTGAGCTTATGAATTAATCAAATTTGAAGCTGCTCTACACCCAGAATTATTATTATTATTATTATTAT
TATTATTATTTTTGAGACGACGTCTTACTTTGTCTCACTTTGTCGCCCAGGCTGGAATGCAGTGGCGCG
ATCTTGGCTCACTGCAACCTCCGCCTCCCAGATTCAAGCGATTCTCCTGCCTCAGCCTTCCGAGTAGCTG
GGATTACAGGCACCTGCCAGCGTGCTCGGCTAAGTTTTGTATTTTTAGTAGAGACGAGCTTTCTTTTTTT
TAAGACGGAGTCTCGCTCTGTCGCCCAGGCTGCAGTACAGTGGCGTGATCTCGGCTCACTGCAAACTCTG
CTTCCCGGGTTCACGCCATTCTCCTGTCTCAGCCTCCCGAGTAGCTGGGACTACAGGCGCCCGCCACCAT
GCCCGGCTAATTTTTTGTATTTTTATTAGAGACGGCGTTTTGCCGTGTTAGCCAGGATGGTCTCGATCTC
CTGACCTTGTGATCCGCCCGCCTCAGCCTCCCAAAGTGCTGGGATTACAGGCGTGAGCCACCGCGCCTGG
CCAGAGACGAGCTTTCACCATGTTAGTCAAGCTGTCCTCGAACTCCTGGCCTCAAGCCATCCACCCACCT
CGGCCTCTCAAAGTGCTGGGATTACAGGTGTGAGCTACCATGCCCAGTTTATACCCAGTCTTGTTAAGTG
AGATGTTACATCTCCCTCTGTTTAGTTCACTTGACGCAAGATTCTCTATTTTTTTTTTTTTTTTTTTGAG
ATGGAGTTTCACTCTTGTTGCCCAGGGTTGTAGTGGCACAATCTTGGCTCATTGCAACCTCTGCCTCCCA
GGTTCGAGCAATTCTCCTGCCTCAGCCTCCAGAGTAGCTGGAATTACAGGCGCCTGCCACCAATACAATA
CTTTTTTGTATTTTTAGTAGAGATAGGGTTTCACTATGTTGGCCAGGCTGGTCTCAAACTCCTGATCTCA
GGTGATCCACCCACCTCGGCCTCCCAAAGTGTTGAGATTATAGGCATAAGCCACTGCACCCGGCCTAAGA
TTCTCTATTACTTGAGAATAAAACAACCTGTTAAAATATTATACCACAGTGTGCTTGGCCTATGTAACAT
CTGCTTAGATAACATACTCTCTTAAGCAGTAAATGAGTATGAGTTACAGGGGCTCTCCTTTTGTTCTTTA
GGGACTCTAGAAATGCCAGATAATTCCACTTTTGTGGTGACAGAAGAATCTGGCAATAATAGCTACCGTT
TACTGAACAACAACTGCACATTAAGCACTGTGTCATATGCTTTAGGTATGTTATTTGATCCTCACCAAAT
GCCTAGGTATTATTCCTCTTTTCTTTTCTTTTCATTTTCTTTTCTTTCTTTTCTCTTTTCTTTTTTATTT
TCTTTCTTTTTAACAAAGAAAGAAACTGAGGGGGCTGGGTGTGGTGGCTCAGGTGTGTAGTCCCAGCATT
TTGGGAAGCTGAGGTTGGAGGATCACTTAAGGTCAAGAATTTGAGGTTACAATGAGCTATGCTAGCACCA
CTGCACTCCAGCCTGGGTGACAGGTGAGACTCTGTCTCTAAAAAATAAATAAATTTACATCTGTTCAAAA
GATAAATGACCTTTTAAACAAACAACATGTAGTATAAAGTTTATGACATACAATCATAAAAAATAATTAA
TAAAAAAAACAGCCAATGTGACCTGATATTTATAGAACACTCTTAACAATAGCAGAATACACATTTTTAA
AAGTACCTGTAGAACATTTATCAAAATAGGCCATACTATTTTTCTCAATAAATTTAAAATTATTTCTGTC
ATAAAATATACTTTCTGGCCACAATATAATTAAATTAGAAATCAATAAAAAGGATATCTAGAAAATCTCC
AAATGTTTGGAAAATAAAACTTCTATATCACACATTAGTTTCAAAAAAAGAAATTGGAAAGTGTTTTGAA
CTGTCTGAAAATTAAAACACAAGATAATAAAACTTGTGAGATACAATAAAATAGTGCTAGAGGGAGTCTT
GTAGCACTAAATGCCTATATTAGAAAATAGGGGCCCGGCGCGGTGTCTCATGCCTATAATCCTAGCACTT
TGGGAGGCCGAGGCAGGTGATGGCTTGAGCTCAGGAGTTCAAGACCAACCTGGGCAACATGGTGAGACCG
CCTCTCTACAAAAAATACAAAAATTAGCTGGGCAGGGTGTCATGCACTTGTGGTCTCCGCTCCTCAGGAG
GCTGAGGTGGGAGGGTGGCTTGAGCCTGGGAGGTTGAGGCTGCACTGAGGCATGTTCATGCCACTGCACT

CCAGTCTGTGTGACAAAGCAAGACCCCGTCTCAACAACAACAACAAAAACAACAAACAAACAAACAAAAA
ACGAAATTAGAAAAAGAGTAAGTTAAACACAGAATAAAATGAAGACAGGAAATAATTAAGATTGGAGCAG
AAACTTATGAAATAGAAAACAAAAATAGCAGGAAATCAATAAAGCCTAAAGCTGGTTCTTTGAGAAGATC
AATAAAATTAATAAATCCCTAGGCCGGGCATGGTGGCTCACGCCTGTAATCCCAGCATTTTGGAGGCCG
AGGCGGGTGGATCACGAGGTCAGAAGGTGAGACCAACCTGGCTAACACAGTGTAACCCAGTCTCTACCAA
AAATACAAAAAAATTAGCCGGGCGTGGTGGTGGGCGCCTGTAGTCCCACCTACTCAGGAGGCTGAGGCAG
GAGAATGGCGTGAACCCAGGAGGCGGAGATTGCAGTGAGCTGAGATCATGCCACTGCACTCCAGCCTGGG
CGACAGAATGAGACTCTGTCTCAAAAATAAACAAAACAAAACAAAACAAAAAACAGGTTAAAAGACCGGT
GTGGTGGCTCATGCCTGTAATTCCAGCACTTTGGAAGGCTGAGGTGGGCGGATCACGAGGTCAGGAGTTC
GAGACCACCCTGACCAACATAGTGAAACCCCATCTCTACTAAAAATACAAAAAAAATTAGCTGGGCATGG
TGGCACATGCCTGTAATCCCAGGTACTCAGGAGGCTGAGGCAGGAGGATCACTTGAACCCAGGAGGCAGA
GGTTGCAGTGAGCCGAGATCGTGCCACTGCACTCCAGCCTGGGTGACAGAGCAAGACTCTGTCTTAAAAT
AAATAAATAAATAAATAAATAAATTAAATTAAATTAATAAACCTCTAGCCAGACTGAACAGAAAAAAAGT
GAAAGGAAACACAAATTGCAAATATCAGGAATGAAGGAGATAACCTACAGATTCTACAGCTATTAAAATA
ATAATTAGAGAATATTATGAAAAACTTTTTAACAAAAAATTCAACATATATAAAATGGACAAACCCCTTG
AAAAAAACCAAATTACCAAAAATTGTACAAGAAGAGCTGACCTGAGTAGTCCTATATCTATTTTTTAAAA
TTGAATTTGTAGTTTAAAACCTTCCTACAAGGAAAACTCCAAGCCCAGATGGCTTCAGTGGTGAATTATA
CCAAATGATTAAGGAGAAATAACAGCAGTTCTCTACCACCTCTTTCAGAAAATGGAAGCCAATGGAATAC
TTCCCAATTCATCCTAGGATAACAGCATTACCCTGATACCAAAACCTGACAAAGACATTCTTAGAAAACT
ACAGATCAGTAGTCTTCAGGAACACAGGTGCAAAAATTCTCAAGGAAATTTTAGCAAATCCAACCTAACA
ATATGTAAAAAGGACAATGCATTAAGACCAACCGGAGTTTATTTCAGGCATATAAGTCTTCATTTCAAAG
CCCAATCAATATAATTCACTACATTAACATAAAATTAAACCATATGATTACCCCAACAGATCCACCAAAA
GTGTTTGACAAAATCTAACATCCGTTCCTAATAAAAACTCAGCAAACTAGGTATAGGGGCCCTTTGTTTG
TCTTTTTCTGGTTTCCAAGTCCTTGAAACAAAATCCAACTATGTCCAAATGCCATGAAGGTTTGTGTTGC
TGCTGATGTCAGAGATAAACATTACTTTTAAGGACAGGACGGAGTGGAGTAGTAGAAGCATTTAGATGAG
AAAAAAGACAAATTAACTTGTTTAATTCTTCTTAAGAGCCAAAATGCAGGTGTTTCTTGCACAATGTAGT
ATTCTTTTTCTTTTTACTTTCTTTTTTTTTTTCTTTTTTTTTGAGATGGAGTTTCGCTCTTGTCACCCAG
GCTGGAGTGCAATGGCGGATCTCAGCTCACTTCTGCCTCCCGGGTTCAAGTGATTCTCCTACCTCAGCCT
CCCGAGTAGCTGGTATTACAGGCATGCGCCACCATGCCCAGCTAATTTTTGTATTTTTACTAGGGACGGG
GTTTCACCATGTTGGTCAGGATGATCTCAATCTCTTGACCTTGTGATCCGCCTGCCTCGGCCTCCCAAAG
TGCTGGGATTACAGGCGTGAGCCACCGTGCCCGGCCTATTTTTCTGTAGTCCCATTTTCTTGCTTCAGAG
TTATTCAGGAGTTAGCACGGTACTACAATTGCTATGCACAGAAGCTGAGGAACATTTGGTAGTGTTAAAT
ACCTAACATTGACTTAAATCTGTACATAGGTAGTTCTAGATATACTATGCTTCTTTACTGCATCAACCAG
ATGGACATTAAATGGTAGAATTATGACTAATTTGTATAAAGCATTTTATATAGTATATATATATTTTATTTA
TTTATTTATTTATTGAGACAGAGTCTCGCTGTGTTGCCCAGGCTGGAGTGCAGTGGTGCGATCTTGGCTC
ACTGCAAGCTCCGCTGCCCTGGTTCACACCATTCTCCTGCCTCAGCCTCCCAAGTAGCTGAGACTACAGG
TGTCCGCTACCACGCCCGCCTAATTTTTTTGTATTTTTAGTAGAGATGGGGTTTCACTGTGTTAGCCAGG
ATGGTCTCGATCTCCTGACCTCGTGATCCGCCCGCCTTGGCCTCCCAAAGTGCTGGGATTACAGGCGTGA
GCCACTGCGCCCGGCCTAGTATAATAATTTTTAAAATTAGCTTTAAATATTTTTGAGTTAAAATCTTGAT
ATTTTAAAATGTTGCCCATTAATTAATTTTTTTTTTTTTTTTTTTGAGACGGAGTCTCGCTCTGTCGCC
CAGGCTGGAGTGCAGTGGCACGATCTCGGCTCAGTGCAAGCTCTGCCTCCTGGGTTCACGCCATTCTCCT
GCCTCAGCCTCCAGAGTAGCTGGGACTACAGGCGCCCGCCACCACGCCCGGCTAATTTTTTTGTATTTTT
AGTAGAGACGGGGTTTCACCGTGTTAGCCAGGTTGGTCTCGATCTCCTGACCTTGTGATCCACCCACCTC
AGCCTCCCAAAGAGCTGGGATTACAGGCGTGAGCCACCACGCCTGGCCGCCTATTAATTTTTATAAGCAG
TTTGCTTTTAATATTTTAGAAGAAAATAGCTCTTTGAATACATTTAAAACCAGTTTTAACTTTTTAAATT
TTAATACTTTATTTATTTATTTATTGTTTGTTTGTTTGTTTGACAGAATGTCTCGCTCTGTTGCCCAGGC
TAGAGTGCAGTGGAACAATCACAGCTCACTGCAGCCTCAAACTCCTGGGCTCAAGCCATCCTCCCACCTC
AGCCTCCCAAGTAGCTAGGACTAGAGGCATGAGTCACCACACCCAGCTAATTTTTAAAAGATTTTTTTTT
TGCAGAGACATGGTCTCACTATGTTGCCCAGGCTGATCTCAAACTCCTGACTTCAAGTGATCCTCCTGCT
TCAGCCTCCCAAAGCGTTGGAGGTTACAGGCATCAGCTACTATGCGCAGGTTTTAATTTACTTTTGAATA
AGTATGTGAAATTAAATAATTCAAACTTAAAGCTGTTGGAACTTTATTCTGAGCCTTGAGAGGTGTGTGG
CTGTGCAGCCTGAGTCACATGGCATGCAGCTGCAACTTTTGCCTTGTTTTTCCTTTAGATAATTAAGAAC
AAACAGCACCAAAGACCCCCACAGATCATTACCCCTCCTTATAGAGTAATAAAGTATTCTTTCTTGGAAT
TTAGCAATCTGTAACCAATCAAATTGCTGTGGCATATGCACTAGTCTTGTATGAAAAGAGTCTTGCTCTG
TCGCCCAGGCTGCAGGGCAGTGGCAGTCATAGCTCACTGCAGCCTCGAACCTGCCGGGCTCAGGTGATCC
TCCCACCTCAGCCCTCTGAGTAGCTAGGACTACAGGCATGCACCACTGTGCCCAGCTAAATGTATTTTTT
GTAGAGATGGAGTTTTGCCATGTTGCTCAGCCTGTTTTTGAACTGGGCTCAAGCAATCCTCCCATCTCAG
CCTTCCAAAGTGCTGGGATTACAGGCGTGAGCCACCATGCCCGGCCAAAACCAACTAATATTAACAGTAT
TTTGTGTGTCTCTCTAAATATATCCTATGTGAATGTATGTATGTATTCTTTCTTTTGCCTTTATAAACAA
ATGATAGTATATTTTTCATAACGTTCTGCACTCTGATTTTCTTCTCAATGTATCTTGGCAGTCTTTCTCA
GTATATAGTGACTTTTCTCATTTTTTTATCTTTATACCTCAATATCTGGCACATAGTAAGCAAATCATAA
ATGCTGAGTGAATGAAATATTAAATGAATAAAAAGGAAATTTTTGTGCTGCTATTGGAAATTAGCTCTCT
ATATATTTCAACATGTTACACATATACAATGATCTAAAAACTTGTCTTACTCTTTCCTATCCACTAGAGG
GAGACATCAACCTGTTGTGGAAAAGAATGATCACTTAAAGTCTTTAGAAATTCTGAACCAACTCTCTAGC
AGGTGATCCTTGTTAGAATTTGAGCCCTTAACGCTATCCAGGACTGGAGGTTGAAGGACGATAGAGGGA
GCAGGAGGAGAATGCACATGGATTAAGGAGCGAGAACACAGGTGAACTTCAGCTTTTTTGCTAACAGTCA
GACAAACTACTGACCCTGACTCAGTGATGTGCTAGTAAACCAGCTCTTTAAAAAAAAAAAAAAAAAGCCCT
AGATTGCTGATTTGTATGTAATGTTTATGAATTTCAGTAGAGAAAAAGACAATATTCAAACTGAGCCATG
CACCCAAAACAAGAGAACAGCCAAGAAGTGTTCACTTCTATCAGTGCCCTGGGTTGTTTGAAAAAAGAAG
CCGACCTGAGCACCTGTGAGCTCCCTTCTGGCGAGGAGAAATCTGGAGTGTAGTTATTCCACCATGGCCA
AATTCAAGCCACTCGGGGTTTAATCACCGAATTGCAAATTCCTTGAACATTTAACAGTAGGCTCTCTTGG

CTGGGCGCGGTGGCTCATGCCTGTAATCCCAGCAATTTGGGAGGCCATGGCAGGAGGATTACCTGAGGTC
GGGAGTTGGAGACCAGCCTGGCCAACATAGTGAAACCCCATTTCTACTAAAAATACAAAAAATTAGCTGG
GCGTGGTGGCAGGTGCCTGTGGTCCCAGCTACTCGGGAGGCTGAGGCAGGAGAATCGCTTGAACCCAGGA
GGCGGAGGTTGCAGTGAGCCGAGATTGTGCCACTGCACTCCAGCCTGGGCGACAACAGTGAAACTCCATC
TCAAAAAAACAAAACAACAATAACAACAACAGTAGGCTCTCTTGAGCCAGCCTGAGCAGGCTCTTGCATG
CTGCTGAAGCTTGTCGGGTCTTAGTTACTTTTCCTGTAAAGTGGGGATGATAAATCTGCTCATTATGTAG
ATTCTATTACATAGAGGACACATAAGTTCTTTGAATGCTTAAAGCAATGTTTCCTAAACTTCTTTGGTCA
TGAAATCACCCAGTGGCTTGTGTAAAATAAACATTCCCAGGACCTGCCCTAGAGCACCTGGGTTAGAACA
TTTTGGGGGAGGGGGCTGGGAATCTGTATTTTAAATAAGCAACCCAGGTGAGGCCGGGCGCGGTGCCTCA
CACCTGTAATCCCAGCACTTTGGGAGGCCGAGGCGGGTGGATCACGAGATCAAGAGATTGAGACCATCCT
GGCTAACACGGTGAAATTCCATCTCTACTAAAAATACAAAAGAATTAGCCGGGCATGGTGGCAGGAGCCT
GTAGTCCCAGCTATTTGGGAGGCCGAGGCAGGAGAATGGCATGAACCCGGGAGACAGAGCTTGCAGTGAG
CCGAGATTGCGCCACTGCACTCCAGCCTGGGCGACAGAGCGAGACTGTCTCAAAAAATAAATAAATAAAT
AAATAAATAAATAAATAAATAAATAAATAAAAATAAAAAATAAAAAAGTGACCCAGGTGACTCTTATGAC
CCTGTGAAATGGGAGAAACACTGCTGCAAATTACTCTTATAATTGGGTCAGGTGTCAGGGGTCTTTCTCT
AACTTCACAATTGGGCCTGCTTGAAGAGATGTGTGCAGAGTTCCACAACACACTCCAGGCAGGCATTTAA
TCCGTTCACTGTCTTCTCTACCCTCAGAGCCCAAACTTCCCAAAGAGGAAAACCTGCTCCTTGCCATCTC
TTAGGCCAAGGCTTCTGTACACCTGGGAAGTCCTTCAATCTGAGGATCTCTGGGTTGTTTTCAAGCTACT
ATTTATTGAGAATTTACAAAGTGTCAGGCACGTTACAGCAATTTGTCATTTCTATGAAATAGCTTCTTGT
GCTATTCCCATTTTACAGAGAAAAATCAAAGAAGTTGGGAAAATGTCGAAGGGCACACAACTAGGAAGTG
TTTGTGCTGAAAACCCACCCTAGGCCCAAGCCTTGGAACTCCAAGCCTGGGTTCCATCCCTGCACTGGGC
AATTCTGATCTATGTGCGCTAGTTTCCTTGTGTTCTCTGTTCTCTCCATAGAAATCCTGGGCTCTCTTCT
CCCAGCCACAAGGTTAGGTTGAAAAACAGAGCAGATGGAGGTAGTTTGTAGCCTACAGGTGCCCTGAATG
AAGCTTCCACAGTGCTAAAGTGGAAGAACGAGGGACTCCAAGGGAAGGATTCAAGGCTGGGCCCATGCAC
CTGTGTAATTCAGAAGAGACCCCAGAGGAGATCAGCGCCCTCTAATTAGCCCTGGTAAGGAGCTCTGGGA
GTTACTGTAACTCTCTCAGAAGAACCCAAACATGCGGGAACGTGACTTCTTACCTTCTGAAAGTCCACAA
AATTCCTGATTGCCACCATTAATTTGTCACTTATCATTTGCAACAGGCATTGTAGGTTGTCTTATGCATT
TGTCTTCTCCCTTCAGCTAGTGTATAAAGTCTTAGGGAGACCAGCAGTTCAGAGAGAATGGGCTTTGGTG
TGAAACAGATCTGGTTTGAACCCTCTGCTACTTACTAGCTGTTGGGCAAGTTCCTTAAATTCTCTGAGTC
TTAATCTTCTCATCTGTAAAATGGAGACATAAGGAGTACCCACCTCATTGGATTGTTTAAGGATAAAAT
TAAATAGTGCAGGCAAAGGATTTACAAGCAACTGCTGAATGAATGGTAGTTATAGCCTCCTCCTCATCAT
CTGTGAGCAAACACCCTCATATTTCCTTGTGTCTCAGGTAGACACTTAAGGTATTGCAAGCATTAAGGGA
GCATTGTCACAAAGAGATAAATGCATGAGGGCAAGATGCAGTCTCAAAGAAGAGTGTTTTATGAAAGAAT
AAATGTAATGCTGAGTGTCAGAAAAAAATTTTTTTTTTAAAGATGAGGTATCTATCACCCAGGCTGAAG
TGCAGTGGTGTGATCTTAGCTCACTGAAGCCTCAACCTCCCAGGCTCAAGTGATCCTCCAGCCTCAGCCT
CCCGAGTAGCTGGGACTACAGGTGCCACCACACCTGGTTAATTGTTGTATTTTTTGTAGAGATGGGTTTT
CGCCATGTTGTCCAGGCTGGTCTTGAACTCCTGGGCTCGAGCGATCCTCTCATCTTGGCCTCCCAAAGTG
CTGGGATTGCAGGCATGAGCCACCACACCCAGCCTGTCAGAAAAATTTTAAGGTGAAAATAACTAAAGAA
GTTGTTAAGAATTTTCTCCCTTGAGTGGTATTTTAGACTGAGATGAGGGAGGGTAGAGGTAGGATGAGAA
GGAAGGGATGGGGTCCGGTTGAAAGGCCTGTGAGATAGTAGCAGTGCAATATGGCAGATGTTGACAGCCT
CAGTGCTAGGAACACAGAAACTGAATCTCTTGCAAGGAGGCAGGTGTGCATCTGTATGGAAGTCAGATGA
CCTGTGTTCCTATGAGTGCAAATCTGGAAAACACCCTCAAGTTTCCTTGTCAGCAAATTGGTGATAAAAT
CAACATTGTAGGGTTGGTGTGAACATGCAGCATGATGTGGCCATGCAAGTTCTTTGTTAACTAGAAGCCA
GTGTCATGCCAGGACAGCAGTCCTCCTAGTAAGCTGTGGCTGGTGGCGTGGTAGAATACGTGGAGCAGGC
TGAGGAAGCACTTGACTTGACTATGAGCAGAACCATTAAGAAGCTAGTTAGCTAAACTGCCTGGACAGTA
GAAAAATAATATGTGAGGATGTAAAAGGAAGAGAAACAATGTGAGGGGAGAGGAGAATGCAGAGATCCTG
GCCCATGGAACAGCATTGGTGATCCTTAAGTAGCTGCATGAACTACTTGGAGAAGTTCATTTTCTGTTTA
TAATTCCCAGCAAAGGAGAGGACTGAATAAGAGAGAAGAAAACGATTCCTTTCTCTGGTTAGGTTCATCA
GATCAAACGGTGACATATGTGAAAGAAGCACGCTCTGTGCACAAAAAATCAAGTCTGTATTTTTATAAAA
GCCATTTCTGGGCTGGGCGCGGTGGCTGACGCCTGTAATCCCAGCACTTTGGGAGGCGGAGGCGGGTGGA
TCAGGAGGCCAGGAGATCGAGACCATCCTGGCTACCACGGTGAAACCCTGTCTCTACTAAAAAAATACAA
AAAAATTAGCCGGGTGTGGTGGTGGGTGCCTGTAGTCTCAGCTACTTGGGGGGCTGAGGCGGAAGATTGT
GCCACTGCACTCTAGCCTGGGCGACAGAGCGAGACTCCGTCTCAAAAAAAAAAAAAAAAAAAGCTATTTCT
GTAATGAGCATCACTGGAGAGTTAGTTGCTATGGGTCTAAAGGACAATATGAGGCAGTTATAGTAACTTT
CCATGATATGAACAAAGAAATTGAAAATGTTAGATACATTTACAAGAAGATGTAGAAAAAACTTTAGTCA
AAATTTTTGAAATATTTTTTGAAATATTAAACTATGAAATCAGACAGTCTTATCTATGGTCTCAAGCCAT
GTCTGTCTGTACCTTTTTTTTTTTTATCTCATTTCAGGGAATATTACACTGGCTGACTTATTAATATCTT
CTGAGCCAGAAAATGTAAGGAAGCTGCATTTTCAGAATTGCATTTGAGTCATTTGTGAAATTGCATATTA
CAATTTGCCGCCATTTCTAACAGTCCTATAACTTTTTTTTTTTTTTTCTTAACTGGGTGTTCACATTCA
TGCCAATGACCTCTAGGGGCTAGTTTCTCTTCTAGCTCAAGAGAATTGCTGCAGAGTTGGAAGTAAGGAC
AAAAATGTGTATGCTTCATGTTTGATTTCAAATGCATAGAAAATTAGAAACTTAAGGTATGCAAGGGATT
TGTGTGGAATTTAAGTACCTTTGAGGGGCAGTGGACAGGACAAAAAGTTATTTTTTACCTGTTTGTTTAC
AAATAGCAAAGATCAAGACTGAAACACATGAGTGTGATTTAGAAAGAGTTGGCTGCAGGTGCTGCTTGCT
CAGGTGGTTCATTTAAACTGCAGGTCAGAGCAACCTTGTCTCATGGTCCTGGTGCCCAGGTATCAGGTTG
GGTCTGTCTTGCTGCTTATGTCCTTGTTACCCTCTGAGGGCCCCAGTCCAACGCAGATCAATAAAGAATA
AGTTACATAAATATGCTCATAGGTGGTCATTCCTAGACAAGAAATTGACAACATTTCATTCAACAGTATC
TGGGCTCTACAGGACAGACATGCCTCCATTTATGCAACAAATAAGAACAGCATCTCATGACAGTGGAGAA
AACATGGGATGTGCAGGTAGGTAGGTAAAGTTGGGTGGAAACTTTCACCCTACCAAATGCACATGGTGA
CTTTATAAAATAAATGTTAGCTCTCTGAGCCTCAGTTTTCCCATCTGTAAAATAGACAGTCCCAGGGAAT
TTTCAAGGATTAAATGAAATAAAAGTGAATCAACCTATGCAAGCCTGCCTACTGTGGTGTCCAGGCTAGA
AAAATGCTCAATAAATATTAGGTTTGTTTTTATTTCTACAAAAGATGTGATCCTAAAGAGCTCTATCCAA

ATTCAAGTTTCAAATGTCAAATCACATTTTGTGAACTTTATGTTCAGTTGAGATGATCTCTGACATATTA
ATTAGTAATCCTATCTTTTTCATTCATCACCACCAAAAAAAGGTGTTATTGCACGTTCAATTAATCTTTC
CCCTTTATTAATTCCATAAGTGTAGGGTTTTATCTCTCAGATTCTCTTAAAACAGACCAATTTATACCCA
CATAATATAAATAAGCTTGTTCCTATAACACTCTGGAGCAGATAACTATCCCAGAACCCAAATCCTCCTA
CTTGGCTTCAAGCTCAGAGAATAAAGCAACAATCCAAAGGCACCCTTTGGCATGACACCCTTCTAGACAT
CTGTAGCATTCCTCCTTTCCCTCCACTTTTCCTATTAGCTTTTGCTTTCTTGCCTTTTACAGGGTTTTGT
TTTGCCTCTTGGTAGTTTCTTTCCTACGGAAAATTCTCCCTCTGATCTTTCCAAGTCAAAGGCTTCAGCA
AACATTTGTTGAACGCGTGGATTGTGCTAGGTGGGTGTTATGGACCATGGAGAATGCTAGAGATGTAAGA
CATGCGCTGTCCAATCGCAGCGCAGGTTGTGTTGACAGGTAAGATGAGGGCTGTAGGGGAGCCAATGTGC
ACGTTCCACTGGGCTAATGTGCTCTTCACCTTATTTAGGCTCTTGGCTTTGGGATGTGTAAGACTTTGCT
AGACAGAGAAGGGGTGGGGTGAGAAGATGAGGAAGGTGCACCTTTTATGGAGAGGCTTTCCTTCCTCTTC
ACAGCAAACCATACCTGTACTACATTGACTTCCTTTGCTTTCCCAGGTGACATCTAGCTCATGCTGCAAG
CTCATCTTGTTAATCATAAATGCTAGTAAGTTAATATTACCCATCATATATAACATGACTTAATTTTAAC
AATTCAATGCTTTATCCCCAAAAGATGACTTAATGGTGACAATTTCAATCCCCATTGTAGGATATTTTGG
AGACAGGCAGTCCTTTCAATGTCATATGTGGGTGCTTCCTTAGGCAGGTCAGGGGTGAGGTGGAAATGAG
GCTGGGACCCTGCTCACTTATATAGCAGGCATCGTTCTCAATACCAGGCTTCAGGGGGCTTTTTGGTCTA
GCCATTGGTATGAACTGCCTCAAGAATAATCCCTTCATCATTGTGGTCACAATTCAGGTAGAATTGGAAT
AATCACCCTCTCCACTCTGCATTAAACCAGGCAAAGTTTCCATCTCTGGGTACCATTGTCTTTCTTGATG
GACAGGGTGAGTCAGAAGGAAACTTACTCACTCCCATTCATTTTCTGCTTATTATTTCCTGCAGTGAGGT
TTCCTTGTATAATAAACAGCTTCTGTGGGTGTTTGAGCTGCTCTGAAAAGAGAACATGCTGTTCCTGTGT
GTAGAATGCCTTCTGAAGGAAGCATCACAGTGAACACAGAGCAGAAGCTTGGCACACAGGTGGCAGAAGT
TTGTCTGCAGTGTTCTGCATAGAGCAGAGAGTCAAGCCATTTTCATTCTGATTGATTGGAGGCATGGTAT
GGAGGTAAATGGGTCCTTGGCCTCTCTCCTGGATTCAAGTCCTTCTTAGCCACTGATAGGTCATGTGACC
ATAGGGAGGTTGTTTAACCTTCCTGAACATTCATTTTCTCAAGTATAAAATGGGGGTAATAGAATTTGCC
TTATAGGCTTGCGTATAAAATAAGAATTATTGAGAGAAAGCGGGGCATAAATGTCCAATAAGCGGTAGCT
GTCTATGAAGCCACTGTTGTTACTGGGTTCCTTTCTCACTAGGTGGCTTCAGGTAGCTGACAGAAGCTCT
GTGAGCCTCAATTTCCTCACTGGAAAAGTGGAGTCAATATCTCACTGAGCTGGTGTGAGGATTAAATGAG
ATGCTGTGCAGGTGCTTAGCACAGCGTCAGGTATGATGTTAATATTGATAGATGCATTTTCTTCACCCTC
ACCTATCTTTTTCTGCCTGTTGGCTTATGGTTGAAATTCCTTCATGACGGTTTCCATTTCCAGAGATATC
TTGTTAACAAGTATATACCACCAAATGAAGCTGATTTTTTTTTTTTTTTTTTTTTTGAGACAGAGTCTC
GCTCTGTCGCCCAGGCTGGAATGCAGTGGCGCGATCTTGGCTCACTGCAACCTCCGCCTCCCATGTTCAA
GCGATTCTCCTGCCTCAGCCTCCTGAGTAGCTGGGATTACTGGCATGTGCCACCACGTCCAGCCAATTTT
TGTATTTTTAGTAGAGACGAGGTTTCACCATGTTGGTCAGGCTGGTCTCAAACTCCTGACCTCGTGATCC
ACCTGCCTCGGCCTCCCAAAGTGCTGAGATTATAGGTGTGAGCCACCATGCCTGGCCATGAAGCTGATTT
TTTTAAACCATCATTTAACATTTTCTCCATAAGGTGGCAAGGAGGAAGAGCATATGGGGACTGGGTACTT
TGAGAGACCCCAGGACAGGAGACAGGGAGGCTGAGATTGGCATGTTGTCTGCTGCAGTTATTTGCCAGCG
ACACACTCTTCCCGTCCAAACTAACTTCTCTGCCTCAAGGACAGGGAGACTCTGCCTTTCAACCTGAGAG
AAACCAGGACTCTCAGCTTTAATGAAAATTGGACTTAGGGTGGGGCAGTGGAGACTTTTCACAGCTATTG
TTTAGCTGATGAAGCAGATGCTTCTCCATCTTTGGAGCCTGTCTTCATTACCTGTGGACCTCATCTTTAT
CAACCCAGAGCACACTTGCGTCTCTCTATTTTGGCTAAACACCAAACAGCTGAGGCTGGTACTGTAAAAC
TTTCCCTCCAAATGCCCCCCCTCGTCTTCCTCTATTAGAGATCTGGATCACAACCCTCAAAAACCATGTC
CCTTATGCCACCTGAGTAGATGGTTTGATGATTAATTAGGCACAGATGTGACACTGGGGGGTTCTCACAA
TGGCCTGTGGGTCACATGCTACTTTCCTTTTCATTTTCATCAGCAACAGCTGCCTTAAAGCCAGTTAAGA
CTGTGGTCCTAGTCTCGCACCCTGGGGCTCCTGCTGGGGTGGGTGAGGGGAACACCCCATTAAGCTGGGG
GAACTGGGGCTGCCACCAGGGGGCGCGAGGGGCCTTCGCCCGAGAAGAGGGGTGGGCAGGTGCCTCCAGC
GGAGAAGGGCGCCGTGGCCGGAGGCACAGGTCTCCCCGGTGCCACTTCAAGTGAGTTCGAGGAAGTACCT
GGGATCTTTGATCTAACGCGAAAGGCCTTCCCAGTGACCTCTTGAGAGCTGAGAACCCACTCCCTCCACC
TCTAGTCCACGGCTTTGCCACTCCAGGGCCCGAGGTTACGTTTGCTGCTGGGGATTTGACAAACCCAAAG
CCTCTCTGGTTTCACCACTGGCTCCTTAGAATCAGACATCTGTTCTGAATGACACTTATGTGAGTCAGGG
GCTGAGGACGTGATCCTCGAAGTGTGGTCCCCAGACTGGCTGTATCAGTGTCGGCATCCCCCAGGACCTG
GTTGGAAATGCATATTCTCAGGCCCTACTCCAGACCTCTTAAATCTGAGACTGGGGCTGCGGGGAGCGCC
ATCTGTGCGCCACTATCCTTGTGGGTGGACCAGGAGTCGGTTCGAGGGTGCTCCCACTTAGAGGTCACGC
GCGGCGTCGGGCGTTCCTGAGACCGTCGGGCTCCCTGGCTCGGTCACGTGGGCTCAGGCACTACTCCCCT
CTACCCTCCTCTCGGTCTTTAAAAGGAAGAAGGGGCTTATCGTTAAGTCGCTTGTGATCTTTTCAGTTTC
TCCAGCTGCTGGCTTTTTGGACACCCACTCCCCCGCCAGGAGGCAGTTGCAAGCGCGGAGGCTGCGAGAA
ATAACTGCCTCTTGAAACTTGCAGGGCGAAGAGCAGGCGGCGAGCGCTGGGCCGGGGAGGGACCACCCGA
GCTGCGACGGGCTCTGGGGCTGCGGGGCAGGGCTGGCGCCCGGAGCCTGAGCTGCAGGAGGTGCGCTCGC
TTTCCTCAACAGGTGGCGGCGGGGCGCGCGCCGGGAGACCCCCCCTAATGCGGGAAAAGCACGTGTCCGC
ATTTTAGAGAAGGCAAGGCCGGTGTGTTTATCTGCAAGGTAAGCGCCCCTTCGCTCGAGGTGTGGTTTAA
TTGTCTCATTTTGTTTGAAATCCTGCGGTGAGAAACCAGTCGTGTTGAGAACAATAAAAGACCAAAAAAC
GATCACCAAAACCAACTGTCCTGAAAGCTACTGGAAAGTTGGAAAATGCATGCTTTGATTAAATGTCTTC
ATTCAAGACACTGGCAAGTTAACTTATTTAGTTTGTGCCGTGAGCTCTGGGTTGATTGTGCTAATATGAA
TAACTGAAAAACATTTTATTTCCCTATGGTTTTCCTCGATGGACTTCCCCACTATGGGTGAAATGACAAT
GGAGTTGAATACACTTTCTGATTGAACTTTGAGGGCCTGGGAAGATGTACACGTCTCAGGCAAGATGATA
GGGGTTTTAAAATGTATTAATTGGCATTCCTTAGCCATGTCAGCAAGCTGCGTTCCTCCTTTCCTGGGCA
GACCAAGCTAAGCTCTAACTGGTCTCCTTTATTTGCTGAAGAGGAGTCCAACAACTGCCCTCTAACACCC
TGCGTGTTATTCTTATTGGAAGGACAATATTAAGTCAAGTGAATGTCATTTTTGTGAAAAAACTTTGAGT
GGACTTCTATTTAGGAAGATAAGGTTGATTTAATTTTACTCGCTGTTTAAAAAGCAGGATTGTGTTTTGG
TGTGGTAGGCAACATTTTGGAGGACAGACTTTGCCTTATTTTGTTATATTTCTAGTATTTACATGGGCAT
TCCATTAGAAAGTTTTACTTTTGCTCTAAGTTTCGTAACTCGGTGTCTAGTGAGGGGAAACATGTTTGTA
ATTTAAAAAGTGAACATGTGAAAGGAAAGGCTTTTCTGAGAGTGTTGTAAAACAAATGTAACGTGACTAT

GAAAAGAACATGATTAACATCTTTGACTCCTATTTTTTCTGAAGAAAATGTATTTTGATATGAGTTCTAG
AAGAAGGAAACTATAAGGATCTGTTCATCAACAGGCATTAGAGTATACACCGTAGGATTGCATTTTACGT
TCAAGCATTTTTTTAGATGAATTTCTGAAACATTCTTATTTTAAAAGCCATCAGATGCTTGTTAACACTT
AAGTCTTGCTCAAGACATAGAAGTTTCTGAAATCAATTAACATGTTTAGGACACATTTCGTAGTGTTCTG
AGGGATGTGAATAAATCTAATCACAGTTTACATTTCTTAATGTATTTATAATTCAGAAAAGGTAGAATTT
AGTAGTAAATTCAACTCATAACCATATAATTAACATTTAATAGATATTGATATGTTCACTTTTAAGAATA
AGAAGGAAATTTTCTATAAGTGTATGTTGAACACATAATAATTCAAAATTCATGTGATAATTTTAGGTGA
TGCTTTGAGTCGTTTTATAGAATATAAATATGGATAAAATATAAAATACTGAAGGCTGAACTCAAAGTGT
TTAATGATAAGTTTTTGATAATACATCTAGAAACCTTGAGAATTGTATGCTTGAACGTTAGATTTCATAA
TTCAGTGTCTAGCACATTGTTTTATATGCAATAGCACTTTAAAAAAATTAGGCTACAGCAGTATAATTTA
CATACAGTAAAATTTAGCCTCTGTAAATGTACCTCTATGAATTCTGACAGATGCACAGTCATGTAACCAG
CACCGCACACATGACACAGAACAGTTCCATTACCCCAAAAGTCCCCTTTGTACCTCTACCTACCCCACTG
CCCCTGAAAATCACTGATCAAAACTACATAATGATTATGTGGTTTTGCTCTTTAGTACGTTTTTACTTAG
ACATATTTTCCTTTACTTCTTTTGAAAGAAAAACCTGTTTTTCCCTTTTTATAGGATGAGTCAGTTTGTG
CTATTTTTAATTCTAGTACCTTGGGATAAATCAAGGCAAAGACAATGCTATTTGCAAATGGGAAACTTGA
GACTTGGACTAAGTGTTAAATTCATATAGGGCTAATAGATTTAGTTCTTAGCAGATTTAGATTCTATTGT
GGTTTAAGCCTTTGGTTATGGCATATATCATTAGTTATCCTGAATTGAAATACAAGGCCATTAAAAGTTA
TTTATATCATATTAATAGAATGCATCATTCTTTTATAATCTTTGAATTTTAAAACTTCTTTATTAAAAAA
AAAACTACTTTTCATTATACCTGAGATTAAGAAAGCTACCTGAAATTGCATATTATCAAATAGTGAGAAG
CAAAACAGGGATTGAAAATGACAAATTGAAGACATTTAAAATGCAGAGTGATTACAATTGCTGAAGGTAA
AATATTTATCTTCATAGGGGCTTAGGTCTGTGTCCAACTTATTTGTAGATGTCAGGATTTTTAAATTTCT
GTGCTCATGTCTTGAAGTCTAGATTTTCCTGCAGGGTGGAGATGTATAACCTTTTGTAAACTAATATTTT
TCACTGTTTAACACAGTATTCAATTCAGTATACAGTTAGGAGCCTGTTATTGGTAGGTACTGCTAACATA
TATATATATAAAATTGATGTCTTTTTCCTTTTTCCTTTGTTCTATGAAAAACAGCCTGTATTTTAAATAT
GTAACTTACCTTGCATACCCAGTTACAGTGGTAGTAACTAGGATATGCAGAGTGGCAAGTTTATGAGGAG
CTAGCAAACTGGATAGTTGGCCTTCCTAGCTGGAATTATGACAGGTCTTGAAAATGAAGGGCTTTTAGTG
GAGAATCTTTGTGTGGGTGTACTTGAGAGAGGGCAGGAGAGTTAGGGTGACCTAGAAAGATAGATTGCTG
GACTTGTATATGTTTCCTCAAAGCCAGACTGCAGCATTTTGTTAGTAAATTGTTGTGTGTTCTACTGTCA
AACCCAGGCCTGGAAGGGGAGTTGAGTGCATTCAGCCTAACTTCTGGATTGGCTGTGTCATCTTGAATCC
CTTCACTCGGAATTCTCTCTGACCCTGTCCCAAATGAATATTTGAATTTGGTCCAGTTCCTACAGAGCAT
GGTCTGTGGCTGTTGTTGGTGTTAGGGAAGAGCAGAAACTTGCTGTTGAGAGAGAAGACACTTGAGAAGA
CTGATGAACTCTCTCCCACCCCTGCCTTCGAGGCTTGGTCCTCCTACCCTATTCAAACCCTTGAAACTCT
TTCCTATCCAACTAAATAAGCGCCAATTGGTTACTAGGAGAATTAGCTTTTCCTCATTTTAGAAGGAAAC
AGGGTTTCCTTATGTACATGTTCTTAAGAATTACATGCAAATCAGTTATTAATGATGAGTTCTCTGGTGA
TTTTGGAGTGTTTTATCTTCCTAATATTAAATTAATTGAGGGCCTTAATATTTTGTTTTGAAAGAATATA
TTTAAAAAGGCTGGGTGTGGTGGCTCACGCCTGTAATCTCAGCACTTTGGGAGGCCTAGGTGGCTGGATC
ACTTGAGGGCAGGAGTTCAAGACCAGCCTGGCCAAATAATGAAACCTTGTCTCTGTTAAGAATACAAAAA
ATTAGCTGGCCATGGTGGCTCAAGCCTGTAGTCCCAGCTACTCAGGAGGCTGAGGCATGAGAATTGCTTG
AACCTGGGAGGCCGAGTTTACAGTGAGCCGCGATCATGCCACTGCATTCCAGCCTGGGCAACAAAGCAAG
ACTCTATCTCTAAATAAATAAATAAATAAATAAATAAGAATACATTTAAAGATAATAATTGGCCAGGTGT
GGTGGTTCATGCCTGTGATCACAGCACTTTGGGAGGCCGAGGTGGGAGGATTGCTTGAGGCAAGGAGTTC
AAGATCAATCTGGGCAACACAGTGAGACCCTATCTCTACAAAAATTTAAAAATCAGCTGGGCATGATGGT
GCATGCCTTTAGTCCCAGCTACTTGGGGGGCTGAGTTTGGAGGATCCCTTGAGCCCAGGAGATCAAGGCT
GCAGTAGGCCATGATCTTGCCACTACACTCTAGCCTGAGTTACAGAGCTAGAGTATAACCCCCACCCCCC
AAAAAAGCTAATAATTGTCAAACAGCTACTTATGCACATCAAGGATGCTTGTTGCTTAAGAAATCTTTTT
AAATCTTTTCCATGAAATTCCTTCTAGTTGCTGCTTTGTGAGCGTGAATTTTTTACTTCTGCAGGACACA
CAAATGTGGAGCATTTGAACTGAATGCTTGGGAAAGTGTGATGGGCAGGTGGAAGAAGAATAGGGATGAG
GACTTATCCTCTATTCTTATCCTCCTAGACTTATCCTCCTAGTCTGCAAGCTTGAGAATATGGCATCAGG
AATATGTGGCATTTTGTCCACACACACAGTGTTGGCAGGCTACCAGCAGCCCAGCTATCTGGACTAGGGG
TGATGGATTTCTGTGGACAGAAGTCAAAAAGTAAAATTAGGAGGCAAAAATCTTCAGGGTGGCCATAAAG
ACATTGTAACTTGTCTGGAAATTCCAACCAACACTAAATGTGTATCCAGTGATATACCAATAGACTGGCT
TCATCTTCTTGGATGTGTAATAATACCTTACAGAATGCTTTCTTTTTTTTTTCTTTTTCTTTTTCTTTA
TTTTTTTTGAAATGAAGTTTTGCTCTTGTTGCCCAGGCTGGAGTGTAATGGCACAATCTCAGCTCACTGC
AACCTCCACCTCCCAGGTTCAAGCGATTGTCCTGCCTCATCCTCCCGAGTAGCTGGGATTACAGGCATGT
GCCACCATGCCCGGCTAATTTTGTATTTTTAGTAGAGACGGGGTTTCTCCATGTTGGTTAGGCTGGTCTC
AAACTCCCGACCTCAGGTGATCTGCCCACCTTGGCCTCCCAAAGTGCTGGGGTTACAGGCGTGAGCCACT
GCGCCCGGCCTCAGAATCCTTTCACAGACATCATCTCATTTCACCCTCAGAGCACCGTGAAAAGGTACAG
CACCAAATAGGTACCTGATTCTACTGAAGAAGATGTGGCAGCTCAGGGAGTTTGTGGATTTGTCTAAGAT
TGCCTGGCTTTCAGGCAGAGCTGGGGCTAGAATGAATGTTCTGCTCTATCCATTGATAGAATATACATAA
GAACAGGCTTGATGGTGGCTGACCTTTTTTTTTTTTTTTTTTTGAGACAGAGTTTTGCTCTTGTCACCT
AGGTTGGAGTGCAGTGGCGTGATCTCGGCTCACCGCAACCTCCACCTCCTGGGTTCAAGCGATTCTCCTG
CCTCAGCCTTCTGAGTAGCTGGGTTTACAGGCAAGCGCTGCCACACCCGGCTAATTTTGTATTTTTAGTA
GAGACTGGGTTTCTCCATGTTGGCCAGGCTGGTCCCGAACTCCTGATTTCAGGTGATCTGCCCACCTTGG
CCTCTCAAAGTGCTGGGATTACAGGCATGAGCCACCCGCGCCCGGGTGACTGATTTCTTATTAACTAGAT
TTACAGGTGCTTTGATAAAAACCAGTCTAGTCTTGGCTGGCACGGTGGCTCATGCCTGTAATCCCAGCAC
TTTGGGAGCCCAAGGCGGGCGGGTCACGAGGTCAAGAGATCAAGACCATCCTGGCTAACATGGTGAAACC
CCGTCTCTACTAAAAAATAGAAAAAATTAGCTGGGCATGGTGGCGGGCACCTGTAGTCCCAGCTACTTGA
GAGGCTGAGGCAGGAGAATGGCTGAACCCGGGAGGTGGAGCTTGCAGTGAGCCAAGATTGCACCACTGCA
CTCCAGCCTGGGCAACAGAGCAAGACTCCATCTCAAAAAAAAAAAAAAAAAAAGTGTAGTCTTTTTGGAGT
GTTTTTCTGCCATTTCTAGGGCCAAACTTTTTCTTGTCCATGAATCATTGTCAAAATTGGGAATTTTAAA
TACTACTTTTTTCTTTTAATTCAAAAGCCATAGTATGTTTCCCAGCCAGTACATTAGAACACCATGCACG

ATCCCATGTGTACAAAAAGCTTTCTGGCTGAATTCAGATGTGACCTGAGAGGGCCAAATACAGGGGTGTG
TGCTGGGAGAGAGAGAGAGGTCTCTGGACAGAAAACAAAGCCTGTTCACCACCCAGGATATGGACCAACT
ATTTTAGGTTATGGTGACTAAAGAAAATTGACATGCAAATAAATGAATAATTCTTAGAATCAGGATGTCT
GGGTACTGGTTCTTTGGTTGGCCAGGTGAAATTCCATGCCAGGCCCAACAATTAAACTCTTTAGAGACAA
TTTTTTCCTGTTGTACCAGAACATTGTACTGAGGCCATGTTTGAACATTCAATCGATGTGTTGGGAAAAC
TCTGCCCTACAATGTTAAAGAAATTAAATCTTTTGGGGAGTCTTTCCTTTGACCAGTTTATATCTCTGTT
TTAGAGGAGGGCTTCTCAACCAGAATGGGTTTGTTGACTTATTTTTACAGACCTCTGGTAGAAAGGAGGT
CTTTTTTTGCTACCTGTTCTCCTGTCTCAGAGAACTATTACAATGGTGTAAGTTCATCATTTCTTCCCCT
TATTATGGCTCTGCTTAGGAAGAAAAACTCTTTGCATTGGCTACCAAGTACCTAACTATTCAAGATGCCA
CTGACAAAGAGTTAATCTGTGAATCATGTGAATCTGATATATCTGAAATATATCCAAACAAAAAGCACCT
AGCCTTTTAATGACTCTCCAGAAGTCAGTTCTCTAACTTTAATTATCATCCTTCTGGGGATATGTGGAAA
TTCTACAGAAGTTGATTGGTGATATGTTGAGATGTGAGATCTGTATTTTCTAAGCAAAGTTGCCATGCAC
CTGATTGATTGGCTAGGTGTATCCTGGCATTTGTCATTTGTTGGTGGGGTCTGATAGTTGGTTTCACCAC
TGCTGGGTACCCAGAGTCATCACATCCATAGAGACAGAATGTAGGCTGGTGGTTGCCAGGGGCTGGGGA
AGGGAGGAGTGGGGAATTTGTTTAACAGAGAGTTTTAGTTTTGCAAGATGAAATGAGTTCTAGAGATTGG
TTGCACAATAATGTGAATATCCTTAACACTACTGAACTTTATACTTAGAAATGGCTAAGATGGTAAGTTT
TATGTTACATGTATTTTAACACAATTAAAAAAGAAAAAAAAAAAAACAACTTCAGGCCAGGCACGGTGAC
TCACACCTGTAATCCCAGCACTTTGGGAGGCTAAGGCGGGCAGATCACTTGAGGTCAGGAGTTCAAGACC
AGCCTGGCCAACATGGTGAAACCCCATCTCTACTAAAAATACAAAAATTAGCCTGGCCTAATTGTGCATG
CTTATAATCCCAGCTAATTGTGAGGCTGAGGCAGGGGAATCGCCTCAAACCCTGGAGGTGGAGGTTGCAA
TGAGCCGAGATCACACCACTGCACTCTCCAGCCTGGGTGACAGAGTGAGATTTCATTTCAAAACAAAAAA
CCACTTTAGAAACTGCTAGTTTTGGCAATAGTTATCACTATATGTTTTATCCTGCATATTTTCTGTTAAG
AATAAGGAATTGTTTATGTTGATCAGGAATCTAAGTAATTAAAATACAAAATTCTGGCTGGTGGCTCTCG
CTTGTAATCCCAGCACTTTGGGAGGCCAAGGCGGGTGGATCATTTGAGGTCGGAAGTTCAAGACCAGGCT
GGTCAACATGGTGAAACCCCATCTCTACTAAAAGTACAAAAAATTAGCTGGGCATGGTGGTAGGCACCTG
TAATCCCAGCTACTAGGGAGGCTGAGGCAGGAGAAGCACTTGAAGTCAAGAGGCGGAGGTTGCAGTGAGC
CAAGATTGTACCACTGCACTCCAGCCTGGGTGACACAGCGAAACTCCATGTAAAAAAAAAATGAAATATA
AAATTCCATACTCATTATTAATTACATATAGTATTAAAATAAAACCCAAACACCAAACCTTCCTTGATCC
TATATCCTTCTCCAGCTACCATTCTCTCTCCTCTCCTTGGTCCAAATTTTTGATTTACAATGTTGGTTGG
AAGTGGTACCACTTTGGTGTTAGTTCCTTATCATTTACCTGGTCTGTCCTGCCTCTTCCTGGTACATTA
GCTCCCTGAAGGCAGGGTGTATGTCCCAGAACTCCTTGAAGTCCCTTTTCTCAGCATACTACCATGCCTA
CTGCAGCACCCCCCATCTTTAATGTCCTTGACTTGGTGAAATATTACATTTTGAACACATTTCCTCACTT
CCTTATGACAAATATTGATTGAGTTTCAGTGCAAGGTGAGTAAGAAATGGTACTTGCTTTCAAGGAGCTA
AAAATCTGAATTTCCTTTTTTTTTTCTTTTTCTTTTTCTTTTTTTTTTTTTTTTGAGACAGAGTCTCACT
CTGTCACCTGGGCTGGAGTGCAGTGGCACGATCTCAGCTTAATGCAGCCTCCGCCTCCCAGATTCAGTGA
TTCTCATGTCTTAGCCTCTCGAGTAGCTGGGACTACAGGCATGCACCACCACGCCTGGCTAACTTTTGTA
TTTTTAGTGAAGATGGTGTTTCACCATCTTGGCCAGGCTGGCCTCAAACTCTTGACCTCATGTGATCCAC
CCACCTCGGCCTCCCAAAGTGCTGAGATTACAGGCATTGACTTTACTTCTTACTCTCCTATGCACCTCTA
TCATTTTGAAGAAGGGTTCAAGGTAGTTCTGATAAGCAGGATTAGGTTTGTATGTAAGTGATTAAAGGGG
TGCTATGAGCAAAAAAAGTGTGAAGGTATAACAAGCCAACCACCTCACAATGCAGTTTGCATGTTTCTTA
ATGGACATAGCAGGTTTTCTGTAAGAAAACAGCAGGAGATTCGTGTGGAATGATGGGTTGAGGCAACATA
GTGGCATCCCTTGAATGCTCGAAGAATGTGACTTAGAGTTTGGTGGGAAGCAGAGAGCTGGGTTTTAAGA
ACATGAATCTGACAACTCTATGGATCTGGAGGAGAAGCTAACTGGGGACGAGGAGCAGTAAGAAGCCTGT
TACAGATGCACTGATAAGAAGTAATGAGAGCTGGCCGGGCACAGTGGCTCACGCCTGTAATCCCAGCACT
TTGGGAGGCCGAGGCGGGCAAATCACAAGGTCAGGATTTCAAGACGAGCCTGGCCAACATGGTGAAACGC
CGTCTCTACTAAAAATACAAAAAGTTAGCTGGGCGTGGTGGCGGGCGCCTATAATCCCAGCTACTCGGGA
TGCTGAGGCAGAAGAATCGCTTGAACCTGGAAGGTGGAGGTTGCAGTGAGCCGAGATTGCGCCACTGCAC
TCCAGCCTGGGTGACAGTGCGAGACTCCGTCTCAAAAAAAAAAAAAAAAAAGTAATGCGATAATGAGAGCT
TACTTCAAGATGGCAGCAAAAGACAGTGGAAAAAAGGCATTGGGAAAAAAAGCCAATGTGCCTTGATGAG
TAAAGTTAACTGAGTCAAGGGGAGAAGTCAAAGGTAACTATGATGGGCTTTTTCTATTAACACAAATAGG
AAATGAGTGGTTTTGGGAAAGAAAGTGATGAATTACCCCTCAGATATTGTATTAATTGTCTATTACTGTG
GCCGGGCATGGTAGCTCATGCCTGTAATCCCAGCACTTTGGGAGGCCGAAACAGGCAGATCACTTGAGGT
CAGGAGTTCGAGACCAGCCTGGCCAACACGGTGAAACCCTGTCTCTACTAAAAATACAAAAATTAGTGTG
GTGGTGTATGCCTGTAATCCCAGCTACTCAGGAGGCTGAGACATGATAATTGCTTGAACCTGGGAGGCAG
AGATTGCAGTGAGCTGATATGGCGCCATTGCACTCCAGCCTAGGCAACAAGAGTGAAACTCCATCTCAAA
AAAAAAGATTTGCCTGTAATCAGCCAGCACCCCCAGCCTTGTGCTCACTTTACATACAAAAATTCTGTTT
TTTAGAGCATAAATTGAAGGGCACATTCAAAACTGATACGTAGGCCAGGCATGGTGACTTATGCCTGTAA
TCCCAGCACTTTGGGAGACCGAGGCAGGTGGATCACTCGAGATCAGGAGTTTGAGACCAGCCTGGCCAAC
GTGGTGAAACCCCATCCCTACTAAAAAATACAACAAATTAGCCAGTCACAGTGGTGCGCACCCATAGTCT
CAGCTACTCGTGAGGCTGAGGCAGGAGAATCACTAGAACCTGGGAGGCAGGAGGTTGCAGTGAGCCGAGA
TCATGCCACTGCACTCCAGCCTGGGTGACAGAGTGAGACCTTGTCTCAAAAACAAAGACAAAACCAAAAC
AAAACAAAACTGAGAAGCAACAGATTGATAAGTGACACAGTTACACTGGTCAGTCTCTTCAGCTAATACC
CATTGTTTTTTATTATTGGAGATTCATAATGTGTTTTCTTTCTTTTAAAAACTTTTTTCGGAAATGGTAA
TTTCTCTCTTTTTTTTTTTTTTTTTTTTTTTGAGACAGGGTCTCACTCTATCACCCAGGCTGGAGCGC
GGTGGCACAATCTCTGCTCACTACAACCTCTGCCTCCTGGGCTTGAGCAATCACACCTCAGCCTCTTGAG
TAGCTGGGACAACAGGCACATGCCACCATTCCTGGCTAATTTTTAGTAGAGACGGGGTTTCACCATGTTG
CCCAGGCTGGTCTCGAACTCCTGACCTCAAGTAATCTGCCCACCTCAGCCTCCCAAAGTATTGGGATTAC
AGGCGTGAGCCACTACGCTTGGCCTCATAGCGTATTTTAATATTGGTTGAGACTAGCCTTGCTCATTGAT
CTTCTCTTAGCGTTTACTTGGTTATTCTTGCTTATTTTTCCATAAGAACTTTCATTTTTATTTAATCCTG
TGTTTTTTGGTTTTAAAGACTATTTTATAATAAATTTTCGTGATTAAACTCTTGTGCTTAAACTCTTGAT
TAAACAAACAAGCAATGAAGAGATGAATGAAGCAGAAAATGTGAGTTTCATGCCTCACATTCCCACTCCT

CTGAGGTTAATATTTTCATGTATATTTTTCAGGATGTATTTGTAATCTCATACAAACGTATGTATTTTTT
TAATGAAAATATTTAAATTTTCATAGTTAACAGCTGTAGCTCTAACTTGGCAATATCTTCTGTGTTTCTT
TACAGCCATTATACTTGCCCACGAATCTTTGAGAACATTATAATGACCTTTGTGCCTCTTCTTGCAAGGT
GTTTTCTCAGCTGTTATCTCAAGACATGGATATAAAAAACTCACCATCTAGCCTTAATTCTCCTTCCTCC
TACAACTGCAGTCAATCCATCTTACCCCTGGAGCACGGCTCCATATACATACCTTCCTCCTATGTAGACA
GCCACCATGAATATCCAGCCATGACATTCTATAGCCCTGCTGTGATGAATTACAGCATTCCCAGCAATGT
CACTAACTTGGAAGGTGGGCCTGGTCGGCAGACCACAAGCCCAAATGTGTTGTGGCCAACACCTGGGCAC
CTTTCTCCTTTAGTGGTCCATCGCCAGTTATCACATCTGTATGCGGAACCTCAAAAGAGTCCCTGGTGTG
AAGCAAGATCGCTAGAACACACCTTACCTGTAAACAGGTAAGTCCAGTCTTCATTCTGAATTATAGTTGC
TAGCCATTTCTCAAATCACTTTATGGTTGAGTGAGAAGGAAATAATATGTTAGACAAGGTCTTTATTGTA
TTAATTACATAGTTTACTTACAGCACCCAAAACACAGGATGCCCTGTTCTATTCTGATATTTTAGTTCTC
ATTAAAAACTGGTATGTGTACATCAGTGTTGTGGGGAGAATTTGCTATCATGACTATTGTCTTTATACAG
TAAATACTGAACTTAAGTCACTCCTTTTCTTTTTTTGAGACAGGGTCTCGCTCTGTCACTCAGACTGGAG
TATAATGGCACGATTGCGGCTCACTGCAACCTTCACCTCCTGGGTTCAAGCAATTCTCGTGCCTTAGTCT
CCCGAGTAGCTGGGATTACAGGCGCGTGCCACCACGCCCAGCTCATTTTTTAAATTTTTAGTAGAGACAG
GGTTTCACCATGTTGGCTAGGCTGGTCTTGAACTCCTGACCTCAAATGATCCACCTGCCTTGGCCTCCCA
AAGTGCTGGGATTACAGACGTGATGAACACTGTGCCTGGTCTGAACTTAAGTCACTCTTAATGGAGTTAT
TTGGATTTGAAAAATGAATTTTTACTTTACTTTCAGTTTCAAAGTCTTCTTATAGTGAAACCACAATTTA
ATGTTCATGACAAATTGTTTCCAGGATAAAAGTAACTGTGATAGTATTACAACTTAAATGAAATTCTAGA
CATGCGAAGCATGAAAAGATAGATGATTGGTATAAGCTTTTTAACCATGAACTAAAATAATAACATTATA
TAAAGATTGGTGGAAACTATTGAAGTTTAGGCTTCAGTTGACATTCCCTGAAGTTAAAAAGGATATGTGT
ACTCTTTAAATGCAAGGTAACATAATGGATTATTTCCATCTAATTATTAATATTTCTAATGATAATCATA
GGTATGAAGGGAATGGATAGTATAATGAGAAAGGAGAGGGGGAGATAAAAATCTAAAAGTACTAAGGGCA
TGTTGGATATTGAAATTCACTACTTTCAAATATTATCATAAAACTTTGAGACAGTAACATTGCACCATTA
TTTTTCTTCTTTTAAAAACATTTTACTCATTGGTAAAGAGAATATAAACATTGTGGATAACTTTTTTAAA
GTAATGGTTTGTTTTTTTTTTCTCCTTCCTCCTTTAAAGGAAGACATATTTTGTTTCTGAGCATGAATTA
TAATCAAAGTTCTGCTAATTTTTGGGCAAATTAATCCATTATATAATTACCTTCATTTATAAATCAATAA
TACCTTTACCATTCCCTTTCCAAAAGAACCATGCCTGGCAACATCAGGAACTAGCCAGATGTGTTTTGGA
GGCTGCCTGGGGATCCCTTGTTAGACTTTTCGTTCCTTTATGAACCTCTTGCCTGTGGTCCAGCATTGAG
CCTCTGCTTCCTTCCAAGCCTTTCCAGGCCAGGCACTTGCTTGTTCTCTCTCTTCTCTTCTCTCTTCTTT
TTTCTCTCTCCCTTTCTCTTCTCTTCCCCCTTTTTCTTGTCTCACATTCATCTCAAGGTAACTTAAAGTC
CATTTGTTATTCCTCTTAAAGTTATTTTTATTTTATTTTTTTGAGATGGAGTCTCACTCTGTTGCCCAGG
CTGGAGTGCAGTGGCACAGTCTTGGCTCACTGCAACCTCTGCCTCCCGGGTTCAAGCAATCTCCTGCTTC
ATCCTCCAAAGTAGCTGGGATTACAGGTGTGCACCACCATGTCTGGCTAATTTTTGTATTTTTAGTAGAG
ATAGGGTTTCACCTTGTTGGCCAAGCTGGTCTCGAACTTCTGGCCTCAGGTGATACGCCCACCTTGGCTC
CCCAATGTGCTAGGATTACAGGCATGAACCATTGCGCCCAACCTGAAAGTTATTTTAAATCTAGACCTTT
ATCTGAAATTGCAGAGTGTGAGATGTTTGTTCTCCATTTAAATGGGAACTTCAAATGTCTGAAGGGCTGC
TTAGCAATGCTGTTGGGAATGACTGATGTTTGGAAGTGGTTGAATGCCTTCACACCCATCCATGCAGCAT
TCGTGAACTCTAGTAACTACAGAAGACCAATGCATATCCTGCCTGTGGTTCAGACCTGTGGGTAAGATTT
GATCTGGCCACTCCTTTCATTACACTTAGAGATGTAGCTCCCACCCCATGGCTATGACTGGTCTTCGGCA
GTGACAAATGCTCATCAGCATCACGTGGATGGGCATAAACTCACCTACCCACTTTCAAACATTAGTCATT
CCCCACAGCGTGGCTCTTTGTAGATATGATATCAGTATCAAAAGCTTTGCTGTATCAGATTTCCGGGAAT
ATATTTACCAGGAACCCTGGAGGAAAAAGAGATTAAATTAGGCAATGTTCATGCTATTTTTTTTTCCTAG
AAAGCCCTTCCTTTCCCTTTTATGCTCTGTTCAATGGATATTTTCTTTGCTCCCTAGAGAGACACTGAAA
AGGAAGGTTAGTGGGAACCGTTGCGCCAGCCCTGTTACTGGTCCAGGTTCAAAGAGGGATGCTCACTTCT
GCGCTGTCTGCAGCGATTACGCATCGGGATATCACTATGGAGTCTGGTCGTGTGAAGGATGTAAGGCCTT
TTTTAAAAGAAGCATTCAAGGTACAAGAGAATTGTTAACTGCTTCTTTAGTTTCCTACTTTTGATTTCAA
ACAATTTTGCAGAGATGACTTGGCAGAAATGTCACTACTGGCCTGTTTGGCACACAAAGTATTTGATGAG
CAGTTCAGAGGATCATGTGTGTTTGGAAGTGGGTTGGGTGGTGGGGTGGAATTGCAGATTTCTACCCCAG
AACCCCAAGATTATACAGCCAACTCGAATGGGTCTTACCCCTCGTTCACCCACATGGGTGTTGGATAGAA
GACATCGAGTTACAACCTTGTGAAGATGTCTCTTGGAAAAAATGTGCTCACAAGGAGTTGCAAAGATTGT
TTCTTTCTTTTACTTAAATTTAATATATAGCATGCTTAACAGTCATGATGGTGGGCTGGCTCCTGAGGAA
GAAAGAATAAACACATTTTTTGGAAATGGTCAGAAATCAGGAATTCAGCTACAGTGGACTTTGAGAATTG
ATCTAGACACATTTCTTCCCCTAGGCTAGGAGGGTCTCAGTTCACAATCCCCTTGTTTTCTGGGCTGTGT
TTAGATTATTTCCCTAACTTTCTCTAAACGCCTTCTGGATTTTTTTTTTTAAATCAACTTGTTGATGAAA
AGAATCAAACTCTGTAAAATATTTGAAGAGATTTATTCTGAGCCAAATATGAGTGACAAATGGCCTGTGA
CATAGCCCTCAGGAGATCTGAGAACATGTGCCCAAGGTGGTCAGGCCACAACTTGGTCTTATACATTTTA
GGGAGACATAAGGCATTAATCAATGCATGTAAGATGTACATTGATTCAGCCTGAAAAGGCAGGACACCTG
AAAGCAGGGGCTTCCAAGTCACAGGCAGTTCAAAGATTTTCTGATTGGCAATTGATTGAAAGAATTATTA
TCAGTAGGAAGCAATGATTGGGTTACAATAAGGGATTGTGGAGACCAAGGTTTTATCATGCAGATGAAGC
CTCCAGGTAGCAGGCTTCAGAGAGAATAGATTGTAAATATTTCTTAGGGGTCTTAAAGGGTCTGTTCTAT
CAGTGATTCCAAAAGGGGAGGGAGGGTATAATGAACCATGTCTGTCTCCCTTGTTCCATCATGGCCTAAA
CTTATTTTTCAGGTTAACTTTGTAATGCCCTTGGCCAAGAGGAGGGACCCATTCAGATGGTTGAGGGGCC
TTAGAATTTTATTTTTTGGTTTATAAACTTCAAGTTGTGCACCCCTGATTTCAAGGCTGGTCAGCTCATC
TCCCTGCATGTGTCTTTGCTACACTCCTTCTCTCGTACCAGCCCTGATTTGCTGAAGTCACTTTCTTGCT
TACTCTTGTTTTCTCTATTTGCCCCATAACCTGTCCCTCAACTGCTCCCTCCCAGGCAACACCCTATGTT
TCCATCTGAAAGCTCCCTTCCTTTTTCTATCAAAGCCCCAATGCTTTGTTCTTTGCCAGTTAAGAAAAGC
AACGTTGAGAGAATTCATAGTGTGTAAATGGCAAATAGCAATTTACTAAATTAACTCACCCATTGATAAC
TCTAAGAGGATGTTTTACCTTAAGCAGAGAAATACTGATAGAATCCAGGATATGGTGAGGAGTGAAATGT
TGGTAGTCACCTTCCTACCTGTCCCCTGAAATTCACCCTGTATGAATGGCAGCCTCTTTGTCCTGGATTT
TATAATTACTAGCTCTGCGACTTCACCTCCTAGCCTGTTTCCTCCTCTGTGAAATGGAGATACTCATAGG

GATTTCTAAAGATGAAATAAGGTTGATTATATGAAAACATATTCAGTGCTCAAATATTTTATTTGTGAC
AATCTTAACAGTAGATTATAAGGCCAAGTCCATTTCCTGGCTATATGATAAGAACAATATTGATTTTCTG
AAATTCTGAACTGAATTCTTGATACGATGACTATTTTGTATCTTGCTGAGTTTCTAGGATTTTACCCCTT
AAGAACGTTTGGACCTATTACTACTAACCATATCTTTTAAAAAGAGATCCTTCTTTTTTTTTTTTTGCTTT
TGGGGAAACATTGGTCTGCTTGAAACATCTTTGACCCCTGAGACTACAGCTAATAACAATTGAAAGTAAA
TTTCCTTTGCTTCTCTATGTTGTTTCTTCCTTCCTGCTGCATCAGACAGGAATGTCAAATTCTAAATGTG
CAAAGAGGAAAGAGTTAAAGCTGTTACAGTTGTACAGTTGTAGTGCCTAAATGATCCTTTCTTTGCATGC
TTCCTGTCTTTGATATAAGTGCATTACAGTAACTGAAAGTGGCCACTTATTTTTAAAATTGTCTCAAATA
GGCCAGGATGGTACAGTATTGAGAAATTCCTTGCATGTAACTTTTTTTTTTTTTTTTTTTTTTTTGGAGA
TGGAGTCTCATTCTGTCACCCAGGCTGGAGTGCAGTGGCACAATCTCGGCTCACTGCAAGCTCTGCCTCC
CAGATTCACACCATTCTCCTGCCTCAGACTCCCAAGTAGCTGGGATTACAGGAGCTGGCCACCACACCCT
GCTAATTTTTGTATTTTTAGTAGAGACAGGGTTTCGGCATGTTAGCCAGGATGGTCTCGATCTCCTGAC
CTTGTGATCCGCCCGCCTCGGCCTCCCAAAGTGCTGGGATTACAGGTGTGAGCCACCGCACCTGGCCCAT
TCTTATGTTTTTTATAATTTTAAACTTGTCTTGCTAACTTGATTTATAAGCTAATTGACCATATCTTAGT
CATGTACCTGTCCCCTTCACTGTACAAATGCACTGGAAGCTGTGTTGTGCTTGCTTTTCCATTGATACTT
TGTTGGCTTCTTCACACAATGAGTTGCCATCAGAGTGATAAGTGCTGTTGTTTCTCTACTGGGTTATGGA
GCACAGAGGAAGGAGGACATAGGGAGAAGGACCTCATCACTTCATCTGGTCCAGATGACAGCATGGCTTA
TTTTTTGAGCTTATCCTTTACTTTTTGTTCTCTTTCCTATTGGTGTTCATTTAACAAATATTTATTGAGC
ATTGTACCAGGCTCTACGGATGCAGTGGTGAACAAGACAATAGATTATAGATTCCATGAGGGCAAGGATT
TTTGTCCATTTTGTTCACTAGTGGCACTTACCAATTCCTTGAATATGATTTTTCAAAATTAATTGGGCTT
ATACACAGAGTTCTGTATCATTTTTCACTTAATATTGTCGTATAAGCATTTCTGTTGTTAAATTTCCAGA
GACCCTTTTCACAACTGCACAACTGTGTAATATTCTATCTTATGATCAGATTTAATTTATTTAACTCTTT
ATTATTGAAGGCCCTATCAATTATTTTCATTGTTTTAATGCTATGGTTACTTTATTTGTTCATGAAGTTT
TGAAAAAAATAAGTTTCTCTGGATATGTTTTTAGAACAAATCTGTGGGGTCAGAGTGCATTAATGTTTAA
AGTTCTTGACAGATGTTTTCAAGTGTTCAAGTCTTAAGAAGGTTGTACAGACTTGCTCTTTTACCAGCAG
TGTGAGTGTCGCTTTTTCCAACCTCTTGGTAGCATTGACTCTTATCAAAAAGAAAAAAACCTTGCTACAT
TGATACGTGATGTATAGTATCTTTTGGTTTCAATTTGCTTCTCTTTATTAGTGAGGTAAATGTTTTCTCA
TAAATCTATCTGCCATTTGTATTTTCTCTTTTATCTTCTTTATTCAGAGATTTTGCCCGTTTTTATATTG
GGTTCTGGCATTTGCTTGATAAATTTATTGTGTGCTTTATATATTAACCTATTATTACATGTATGACAAA
TATTTTTTCCACTTGACTCTGATTTTGATATGCAGAAATAGTTAATCTTTAAATAGTCAAATATTACCAA
CTTTGATAGTTTTGTGTATAGTTTTTAAGCCTAAAAAAAGTCCTTTCATACCCAGGCATTATATAAACTT
TTGCGCATATTTTGTTATTTAATAGTTTGTTTTTACATTTTATTATTTAATTCAAAAGAAATTTATTTTG
GCATACTGAATGAAATAACCAAATGTATTTATCTCTCGTTAATTTTCTCCACATCATTTTACTTAATAAA
TCCATTCATTTTTCATTGATTTAAAATATGGGAGCCAATTTTTAAAAGTTGAGTTTGAGATATAATATGC
ATACAATAAAATTTACCTATTTTCATTACTGGTAATAGTAAGTACATAGAAAACCACAGAATAATATAAC
ACTGTTAATTGTGGTTTGTAACCTCATATTTTGAGTAGAAAGTCTAAAGGAAGAACCAATGAAAAACAAT
AACTACAACTTTTTTTTTCTTTTTTTTTGAGACAGAGTCTCACTCTGTCATCCAGGCTGGAGTGTAATGG
TGCAATCTCGGCTCACTGAAACCTCCGACTCCCAGGTTCAAGGGATTCTCCTGCCTCAGCCTCCCAAGTA
GCTGGGATTACAGACACCCACCACCACGCCTGGCTAATTTTTGTATTTTTAGTAGAGATGGGGTTTCACC
ATATTGGCCAGGCTGGTCTCGAACTCCTGACCTCAGGAGATCAGCCCACCTCAGACACATGTAGATTGAA
AATAAAGGGATGGAAAAATATTTCATGCAAATGGAAACCAAAAAAGAGCAGGAGTGGCTATACTTAGACC
AGACCAAATAGAGTTCAAGACAAAAACTATAAAAAGAGACAAAAAAGGTCACTAATAATAAAGATGTCAA
TTCAGCAAGAGAATATAACAATTGTAAATATGTCTGGAGCACACAGATATATAAAGCAAATATTATTAGA
GCTAAAGAGAGAGACAGACTGATATGGTAATAGCTGGACACTTTAACACTCCACTTTCAGCATCGAACAG
ATCATCCAGACACAAAATCAACAAAGAAATGTCAGATTTAATCTGCACTAAAGACCAAATGGACCTAATA
GATATTTACAGAATATTTCATCCAGTGGCTGCAACATACACATTCTTTTCCTCAGCACATGGATCATTCT
GAAGGATATACCATATATTAGGCCACAAGACAAGTGTTAAAACATTCAAAAAAACTGGAATCAAATCAAG
CACCTTCTTTGACCACAATGGAATAAAACTAGAAATCAATAAAGAATTTTGGAAACTATACAAACATGGA
AATTAAACCATATACTCCTGAACAACCAGTGTGTCAATGAAGAAATTAAGAAGGAAATTAAAAATTTCTT
GAAACAAATGGTAATGGAAACAACATACCAAAACCTATAGGATACAGTGAAAGCAGTACTAAGAGGAAAG
TTTATAGCTTAAGTGCCTACATCTAAAAAGTAGAAAATCTTGAAGTAAACAACTTAATGATGTATCTTAA
AGAACTAGAAAAGCAAGAGCAAGCCAAACCCAAAATTAATAGAAGAAAAGAAATATTCATAAAAAGATCA
AAGCAGAAATAAATGAAATTGAAACCAAGAAAACAACACAAAAGATTGACAAAATATGAAGGTTTTTTTG
AGAAAATAAACCTGACAGATCTTTAGCCAGACTAATTTTTTTAAAAAAAAGATAGAAGAGTCGAATAAAA
TCAGATGAAAAAGGAGATGTTACAACTGATACCGCAGAAATCTAAAGGATCATTATAGGCTATTATAAGC
AACTATATGATAATAATTTGGAAAACCTAGAAGAAATGGATAAATTCCTAGACCACATACATACTGTTAA
GATTGAACTATGAAGAAATCCGAAACCTGAACATACCAGTAACAAGTAACAAGATTGAAGCTGTTATAAA
AAGCCTCCCAGCAAGCTGGGCACAATGGCTCATACCTATAATCCCAGCACTTTGGGAAGCCAAGGCAGGA
GGATCACCTTAACCCAGGAGTTCAAGATTAGCCTGGACAACACACAGAGATCCCTATCTCTACAAAAAAA
AAAAAAATTACAAATTAGCCAGGTGTGGTGGTATGCATCTGTAGTCCCAGCTCTTCAGGAGGCTGAGGTG
GGAGGATAGCTTGGGACCGGGAAGTCAAGACTGTGGTAAGACAAGATTGCACCACTGCATTCTAGCCTGG
GTGATGGAGTGTGATCAGGTCTCAAAAAAAAAAAAAAAAAAGTCTCTCAGCAAAGAAAAGCCAGGACTGAT
GGCTTCATCCAGAATTTTACCAAACATTTAAAGAAGAACTAATGCCAATCCTATTCAAACAATTCTGAAA
AATAGAGAAGGAGGAGGGAATAATTTCAAAATCATTCCGTGAGACCAGTATTACCGTGATACCAGAACCA
AAGAAACATCAAAAGAATATGACAGACCAATATCCCCAATGAATATTGATGTAAAAATCCTCAATAAAAT
ACAAACCAAATGCAACAACACGTTAAAAAGATTATTCATCATAACCAGGTGGAATTTATCCCAGGGATGC
AAGGATGGTTCAACATATGCAAATTAATTTGATGCACCATATCGACAGAATGAAGGTGGAAAACCATATA
ATTTCAATTGATGCTGAAAAGGCATTTGATAAAATTCAACATCCCTTCATGATAAAAACCCTTAAAAAAC
TGGGTATAGACAGAATATACCTCAGCCCAATAACAGACATATAACAGACCCACAGCTAGTATCACACTTA
ATGGAGAAAAACTGAAAGCCTTTCCTCTATATGGAACATGACGAGGATGCCCACTTTCACCACTGTTATT
CAACATAGTACTGGAAGTCCTAGCTAGAGCAATCAGAAAAGAGAAATAAAGGGCATCTAAATTGGAAAGG

AAGAAGTCTAATTATCCTAGTTTGCTGATGATCTTATATTTGGAAAAATTGAAAAATTCCACCAAAAAAC
TATTAGATCTAATAAATTCAGTAAAGTTGCAGGATCAGTAGCATTTCTATATGCCAACAGCAAACAATCT
GAAAAAAAAATCTAAAGTGATCTCATTTACAGTAGCTACAAATAAAATACCTGGGAATTAACCAAATAAG
TGAAAGTTCTCTACAATGAAAACTATAAAACACTGGTGAAAGAAATTGAAGAGGACAAAAAAAATGGAAA
GATATTCCATGTTCATGGAATGGAGGAATTAATATGTCCATACTACCCAAAGCAATCTACAGATTCAGTG
CAATTTTATCAAAATACCAATGATATTTTCACAGAAATAGAAAAAACAACCCTAAAATTTGTATGGAACC
ACAAAAGATCCAGAATAACCAAAGCTATTCTGAGCAAAAATATCAAAACTGTGGAAGAATCACATTACCT
GACTATAAATTATACCATAGAGCTATAGCAACCAAAACAACGTGGTACTAGCCTAAAACAGACATAGGGA
TCAATGGAACAGAATAGAGAACCCAGAAACAAATCCATACATCTACAGTTAACTCATTTTTGAAAATAGT
CTCTTCAATAAATGGTGCTGGGAAAACTGGATATCCATGTACAGAAGAATAAAACTAGATCCCTATCTCT
CACCATATACAAAAATCAAGTCCAGATGGATCAGTGACTTAAATCTAAGGCCTCAAACTATGAAACTACT
AAAAGAAAACACGGGGAAACTCTCCAGGACATTGGGTGGGGCAAATATTTCTTGAGTAATAATACCACAC
AAGCACAGGCAACCAAAGTAAAAGTGGACAAATGGAATCACATCAAGTTAAAAAACTGCTTGCATGGCAA
AGGAACAATCAATGAAGTGAAGAGACAACACACAGAATGGGAGAAAATATCTGCAAACATCTGACAAGGT
ATTAACAATCAGAATATAGAAGGAGCTCAAACAACTCTACAAAAAAACTTAAAAATCCAATTTAAAAATG
GGCAAAAGAGCTGAGTAAACATTTCTCAAAAGAAGATGTACAAATGGCAAATGGGTATATGAAAAGGAGT
TCAACATCATTAATTATCAGAGAAATGCAAATCAAAACTACAATGAGATACCATCTTACCCCAAAGTAGC
TTATATCCAAAAGATGGGCAATAACAAATGCTAGTGAGGATGTAGAGAAAAGGGAACCCTGGTATACTGT
TGGTCAGATTGTAAATTAGTACAACTACTATGGAGAACAGTTTGAAGTTTCCTCAAAAAACTACAAATAG
AGCTACCATATGATCCAGCAATCCCACTGCTGGGTATGCACCCAAAAGAAAGGAAATCAGTATATCGAAG
AGATGTCTGCAGTCCCATGTTTGTTGCAGCGCTGTTCACAATAGCCAAGATTTGGAAGCAACCTAAGTGT
CCATCCACAGGTGAATATAGATAAAGAAAATGTGGAACATATACACCACTATTCGGCCATAAAATGAATG
AGATCCTGTCACTTGCAACAACACAGATGCAACTGGAGGTCATGTTAAGTGAAATAACCAGACACACAAA
GACAAACCTCCCATGTTCTCACTTATTTGTGGGAGCTAAAAATAAAAACAATTGCAGTGCCTCATGCCTG
TAATCCTAGCACTTTGGGAGGTCGAGGCAGGCAGATTGCCTGAGCTCAGGAGTTCGAGACCAGCTTGGGC
AACACGGTGAAACCCTGTCTCTACTAAAATACAAAAAATTAGCTGGGTGTGGCGGCATGCGCCTGTAGTC
CCAGCTACTCGGGAGGCTGAGGCAGGAGAATTGCTTGAACCCGGGAGGTGGAGGTTGCAGTGAGTCGAGA
TCATGCCACTGAACTCCAGCCTGGGTGACAGAGAGAGACTCCGTCTCCAAAAAAGAAAAAGAAAGAAAAC
AATTGAACTTGTGGGGATAAAGTAGCAGGTTGGTTGCCAGAGGCTAGGAAGGGTAGTGGGAGTGGGGAAA
GTGGGAGTCCCAGCTACATGGGAGGCTGAGATGGGAGGATTGCTTAAGCTCAGGAGGTGGAGGTTGCAGT
GAGTTGAGATCACACCACTGCAACTCCAGCCTGGGCAACAGAGGGAGACCCTGTCTCGGAAAAAAAAAAA
GATGATAAATCAAAGTATTTTAATAAAATTGGGCCATACTAGAGATGTTATTGTTTGAAATCAAATATAT
GAAGTATAGTTAATAATATAAGTGTAATAGAAGAAAAGGAGCCTTAGAAAGCTTGAAAAACATCGTTGTA
CTTCATATACATCTTCTTTGCTTACATTATAATGGACAATGCTGCAACAAACATGGAAGTGCAGATATCT
CTTTGCAACATGAGAGATTCATGTAGATCTAAGAGACTGTGAAGACTGTTTCAATATTGGAGTTACAATT
AGCTTTTTAATTACCTCTTCTGGCCAGCTGTGGTGGCTCACGCCTGTAATCCCAGCACTTTGGGAGACCA
AGGCGGGTGGATCACCTGAGGTCAGGAATTCGAGACCAGACTGGCCAACACGGCCAAACCCCGTCTCTAC
TAAAAATACAAAAATTAGCTGGGCGTGGTGGTGGGTGCCTGAATCCCAGCTATTTGGGAGGCTGAGGCAG
GAGTATCACTTGAACCCGGGGGGCAGAGGTTGCAGTGAGTCGAGATCGTGCCACTGCGCTCTAACCTAGG
CAACAGAGGAAGGTTCTGTCTCAAAAAAAAAAAAATTACCTTTTCATTGTTTGCTAATGTGTAGAATTCT
GCATGTAACATGTCCAGTTTAAAGAATGATTATAGAGCAAATCCCTGTGTAACCAGCGCTCAAACAATGA
AATAGAATATAATGGCAGCCCAGAATCCCTTTGGGTGGTCCCTCCTGCCACACCTACTTCCCTCCCTGCA
GAGGTGGGACAGTCCTCCTTTCTGCCTTCCTTGCTGTGTATGGTTTTACCACCTACACGTGCATCCCTAA
ACGATGCAGGTTGATTTTCTCTGTTTTTGAACTTTATGTGTTCATGTCTTCTACATATATTTTGTGACTT
TTTTCTTTTATGACTTGCTCATTTCATTTATCATTGAGATTCATTTATTCTCCGCACTGAAATTCTGGTT
CATTATAGGCTTAATGTAAGATGTTGAGGCCATATTGTTTATTAGAAAGGCACTAAAATGCCCTATTCAC
TTTCACTTTTGCTTCTCATCTATTTTATTATAATTTCTATTTCTTAACCCTTTCTCAAACCCATGTAGCT
GTCCTCATCCTCCCTACCAACACCCCATCCAGACATCTCTCATTTGCACAACTACAGCAGGCTGTCATCT
GGTCTCCTGGCCTCATCAGTTTTGCTGCCTCTGATTGGTTCTTCGTACTGCATCTGAAATAATTTTTGAA
ATATAAATATTCTTAGCTCTTCCTTGCATAAGAGAATTAAAAGTACCATTGTCTTAGAGATTGCTATATA
ACTAACAAGTTCAAACTCTTAGGATTTTACTACAATGGGCCTTATTTTCTGTACTTCTGTGTCTTTGAGT
TGTTTAGAGTAGCTCTACTTCATAAACTTGGTTCTGGGCTTTTGTGGGAGGTCAGGTCTGTTCCACATGT
CCCCACGTTCTTCTTGGACCAGTGGCTACCTCACAGGAGCTCAAGAGGCCAAGCCAAACTGTTGGAGCAG
CACATCTATTGATATATCATTGGCTATAAAAAGTCCTGTGGTCAAGCCCAACATCAACTGGTAGGGAAGT
GTTTGCTCTCTGCGCACTCTAGTACACTGCAGGGTCGCAAGGCTGAGGGAGAGAATGAAGAATTGAGAAC
GGTAATCCACCACAACTCTTGTCAATAGCAGTACTTTCTGTCATTATTTAGATTGCTAATTTCTTTATTT
GTTCCTTTTGTTATTTTATTTGACTATGAATTCCCATAAAAATATTGTATTAAACCCGAAAGAGGGATAT
ATGTAAAAGAATATAAGAAGTTGAATTTGATGACTTGATTTACAACTCTTGAGTTCTGTGACTTGGAGCA
AATCAATTTAATGTTAGTCTTATTTTCCACATCCAAAGGATATATTTTTATATCTCTCTTTTGAGAATTC
TAAGAATATGCAGAGAATAACATATTAGTAAAAAACCAGGATATTGAAATGTTCCTAGGTCTCCTTTACT
CATTAACAAGGTGACAATGTAGCTTGACTTTGGCTTTGTACCTGTACTGGTCATTAAGAAGATGTCCCCT
ATCTCTCAGCTGGAAAGTGTTATCAGTGTTGTTGACCAGGAAGAGATTTAACTAAGAGATCATAGCAATA
ATCTTTTTTTCCCTCCCACTCTGCTATAGGACATAATGATTATATTTGTCCAGCTACAAATCAGTGTACA
ATCGATAAAAACCGGCGCAAGAGCTGCCAGGCCTGCCGACTTCGGAAGTGTTACGAAGTGGGAATGGTGA
AGTGTGGTGAGTGCTTGCTTCCCTTCTTATTGAATATGGGCCTTGCTAAAAGCCCTGTCCTCTGAGGAAC
TGGGGACAGGTAGCCGGGAAAAGAGAAGATTTGGGACATAGTAATTAAGTATTTGCGTGTTGTCACATTG
GAGGGGGCATTGACTTATCCACAGTAACTGCAGAGGACAGAGCTGGGGTGAATGGGAACAGATTATGGGA
GGCAGATTTTGGCCCCAGGTAGAGAAGAGCTTTCTAGAGTTCAAGTGGTCTGACCACAGAATAGGCCACC
AGATGGGTTAGGGGACTTCTAGCCACTGGAATCCTCAAACAGGGCTGGGTGGCCGTCTGTCTGTGATCTT
GAAAAGTCCAGTTCTAAGGATGAAGTCGTGGTAAATGTCCATGGTTAAAACTCGTGACAAAAAAGTAGGA
TATCTTGTGGGTTACTGGGGTAGCCATGGGGAGGCTCACACCTATCCCCTCGTCTAGCTTTCTAGAAGTA

GAAAAATATGTAGGAGTCAGAAACATAATGGAACTATGAAAAGTACATACAGCATAGATTTTGTTCTATG
ACAGTCATAGGTGTATACATATGTGTATTTAACATATTCACATACATATATTCACATGTATTTTGTACAC
TCACATACATTCGCATATATTTTATGCACAAAGAAAAGTGAGCACTTTGGTATATAACTGACAAAGATGC
CAACACCCAGCTCTCTCCACCTGGCTAGATTTTGGTTCACTTGTCTGTACTCACTTGCTTGTTTATATGT
ACTCAGAGCAGTTCTGCCTGCACTTATTCTTCTGCTAGCCAGTATTTTACCTGTGGTTAATTGTAATTTC
TCTGTGTAATTATTTGAAAATTTAAAACAAAAATCCATCACTTTACTCTCTGACAATTTCTTTTTTTTTT
TTTTTTTGAGATGGAGTCTCGCTCTGTCACCCAGACTGGAGTGCAGTGGCCCATTCTCAGCCCACTACAA
GCTCTGCCTCCCGGGTTCACATCATTCTCCTGCCTCAGCCTCCCAAGTAGCTGGGACTACAGGCACCCAC
CACCACGCCTGGCTAATTTTTTTTTTTTTTGTATTTTTAGTAGAGATGGGGTTTCATCATGTTAGCCAGG
ATGGTCTCGATCTCCTGACCTCGTGATCTGCCTGCCTTGGCCTCCCAGAGTGCTGGGATTACAGGTGTGA
GCCACTGTACCCAGCCCTCCCTGACAATTTCTTAGTAGCTTTGCCTTGTGAGCATTCTCTGCCCTTTTCT
TTTCTCTGTGTATGTAACAGATTAGAACCCTCAGCTATTATAGTTCAGTTACAGCAGAAGTTCTCTTCAT
CTGATCATGCTTCTCTGGCTTCCTAGAGTCACTGATGATCTTCATTTCCTCTGTAGAACATCCTGCCAGT
GCCCATAGCCTCACAGCGTGTATTATTGGTTATTCTCTCAAACACCTAAACATTTCCATTCCCACCGCTT
CACATTATCCTTGTCAGAAACCGGTGGGCTTCTTTTCAAACCTGTTTCTACTCACTGTAATTGTTACATT
ATAAAATTTAATTAAAATTTACTCAAACATATTATGAATAGGAAAAGACAAGTTTGGTTTTTTTCTGTGA
AAGTTTAGTTAAGGCCGGGTGCGGTGGCTCACGCCTGTAATCCCAGCACTTTGGGAGGCCAAGGCATGCA
AATCATGAGGTCAAGAGATCAAGACCATCCTGGTCAACAGGGTGAAACCTTGTCTCCACTAAAAATACAA
AAATTAGCCGGGCGTGGTGGCATGTGCCTGTAGTCCCAGCTACTTGGGAGGCTGAGGAAGGAGAATAGTT
TGAACCTGGGAGGTGGAGCTTGCAGTGAGCCGAGATCGCGCCACTACACTCCAGCCTGGTGACAGAGTGA
GACTCTGTCTGGGGGCGGGGGGAGGAGGAAGTTTAGTTGAAAGTTTTGAATAAAATCTTAAAGGACTAAT
AGCTATTGAGATAGGTATGGGTGAGACTGGGGGAAAAAAACCCATAAACCTTGGGAGATCCTGAATTCAG
AATTCTTTAGAAGTATCTAGGTTCTTGCTCTGTTTTTGTTTTAAAGAGGCTGAAACTGAAAATCCAGAGA
TAATATCTTATGTGTATGTTTATGCAGAAAAGTGACTTTGTCTAATTGGCCCAGATGCTTAAAGAGAAAG
CCTTGGCACTCTGACAAAAGATTGCAAATAAATGTTTTAAGTTTTAAGTTAAACTATTTTAAAGTGAGTA
TGTGTGTGTGTTTAAAAAATGATTTCCAAGTTAGTCTTAAGAATGCTTTTATTATACTAGGATCCGTTGC
ACAGCTATTGCCCTCATGGCTCAAGGCAGTGTATGCAGGGAAGAGCATGGAGGTTGGATCCCATAGAGTC
TATGTTTCATTTTCGTTTCATCACTTCCTGCTGACTGTAACTGTGCTCAAACTACTGAATCACCTCTTTG
GCCCTTGGTTTTCATGTCTCTGAACAGAGATATCTGCTTCACTTGGTTTTGTGAACAATAAGTATGAAAA
CATATATGAAGACTTAGCACAATATCTGACACTCAATTTTAGTTTTCCTTCCATTCTCTCTCCTTCCCTG
AAAAACTCATATGAGCTTTGATACAACACTGTTTCATGAGACAGAGTACAGAGGGATAGTTAAAGAAGCT
TTCATAGAAAAGGGAATGAGAGAAAGGTTGTTGTATTTAGCCAGAAAGTCTAAGAAAAGACTGTATTCTC
TTTGGAGATTATGGAAGAAATGAGATGGGTTGTTGCACATATACAATGGGATATTTTGCCCTTCACTGAC
CATAGAGAAAGATCATTAGAGATGAACTTTCTTAACTCTGTCTCTCTCCTTTCCCATCACTCTTCTTATC
TGCCTTCCCCAAAACCCTCTATGCATGCTTTTTCTTCTATCAGGTTTGGAGGACTAGAGATTCTACCTGC
TTGTTGGATCCTCCTGCACCATCCTGCTTCTTTTATTTTGAAACCATGTAGTCTGTTATCACCCTTTTCT
TCTGAATTTCTGATCTTGTCTTTTCTACTGAAGTATGGATGTGGTCATATAATGGTAGGACAACACCCAC
CTAGACTAACTTTATGGATGAAACTTCATTATAAGGATATACTGAAATGTAAGGAGCCAGGAAATCCCTC
TGAATAGCCATGTATTTGGCCTATATCCCCATATTGGGACAATAGCTCAACATATTTTGGGTGCCATATC
TTTATATACCTGCTGTATACTCTTCTGTGAAAGGGATTTGATAGGTGGGTAGTATAAAATAGTGGTTAAA
AGCACCAGCTCTGGATTTAGGCTACTGCTTGGGTTTAGATCCTGCTTCTGCTATTTTCTAGCTGTGCCAT
CTTAGACAAGTTATTTGAGCTTATGTTTGGTTCCTCTTCTGTACATTGGAGACAGTAATAGTTCCTGTAC
TGTAGGGTAGCTGTCAGGACATGTGCAATATGCAATGCCTGGTGCATAGAAGCTTCCAGTAGACATTAGC
TGCCATTTAGTGTCATTTATCACTACGATCATCATCATCTTTGGCTGGGGCTATTTACCACTGCCTAATA
TGGAGCACTCGATTTGGTGGAGCTGCTCATTAAGCTCACTCAGAGGCAGCTGCCTAGGTTACAGTGTCAA
AGCCACAACACTAGAAACATCCTTGATAGAAAAATGAGCTCCTTGTCAAGGGCTTTATTGAGTCTAGAAC
CCCCAGAATTCACTACAGGACCTAGAATGTTAGACTTTGTCAGTGAAAATTTGTCAAGTAAATTTGAACG
TATGAATTCAAAATCTCTCACTTTGGGTATGTAAAGGGTATATAAATCTGTTTTGTAAATTCCTTATCCT
TATATACTCTATACTCTACAAAAGAGAAATGTATGATCAGAAAGGTGCTTTTTTTTTTTTCTTTTTTTTT
TTTTGAGACAGGGTATCACTCTGCTGCAGCCCAGGCTGGAGTGCAGTGGTGCAATCTTGGCTTACTGCAA
CTTTTACCTCCTCGGGCTCAATTGATTCTCCCACCTCAGCCTCCCGAGTAGCTGGGACTACAGGTGTGTG
CACCACCATGCCTGGCTAATTTTTGTATTTTTTGTAGAGACAGGATTTCACTATGTTGCCCAGGCTAGTC
TTCAACTCCTGGGCTCAAGTGATCCCCTTGCCTCAGCCTCTCAAAGTGCTGGGGGATTACAGGCATGAGC
CACCTTGCCTAGCAGAAAGGTGCTTTTTAAAACTATACATTTTGCAGCAAACCGCCATGGCATGTGCATA
CCTATGTAACAAACCTGCATGTTCTGCACATGTATCCCAGAACCTAAAGTATATTAAAAAAATTAAGAAA
AACATACATTTTGCTCCATTTTATCCTGGGTGTATAATTGACCTTAGCATTCTGCTTGATTACTAATAAA
ATGAATTGTATTTTAGGCCTTTAATTCTTTTAGCAGTAAATTTGGTTCAAATTTTCTGAATAAATAGAGC
CCTTTCTTCTACTATAACTAGTCAATGTTAAGAGGAAATTCTGACAAATTTTCCTGGGAGCCAATAATTT
AAATTTGCTCACATTTTCTAACTAATATTTATTTTTAAAAATGTAAACAATTGATTTAGTGAATAAACAT
AATGATGGGTGTATAAAACCAAGCATTTTGCAGATTTCAACTTTTAGGGTTTCTTTTTTTAAGGGAAATT
CATATAAAAGTTATAACCATGCTAATGACATCCTTACTTACAACATGTCTTTCTTAATTTCCATTTTACA
TTTTTTGTCTTTAACCGATGAAAACTTATAAAGATGTTGGTGCTCAAATGTATAGGGATTTGGAAGTTAT
ATTTTTGTTGTTGATTTCCATTTTTCTTATCGTCAGAGAATATGATCTGAATAATACCTATTTTAAGATT
TTCTTCATTGCCTAGCATGTGATAATTTTTGCAAAATATCTATGGCCTTTGTAGATCAAGCTTGTTAATT
ATGTGGTTCAAATATTCTGCATTCTGACTTTTTGCTCTTTCAGCTGTTGAGAGAGAGATTTAAATAGCCC
GTTATAATACTGCATCTGTCAGTTTCTCTTTTTCTTTCAGTTACTTTTTGTATTGTGTTTGGAGGCTGTG
TTTTATTGTTTGTCTATTTATTTATTTATTTATTTATTTTTTCAACCCAAGTCTTGCTCTGTCACCCAGG
CTGGAGTGCATGGCACGGTCTCGGTTCACTGTGCCTCCTGGGTTTGTGCGACTCTCCTGCCTCAGCCTCT
TGAGTAGCTGGGACTACAGGAATGCACCACCATGCCTGGGTAATTTTTGTATTTGTAGTAGAGATGGGGT
TTTTCCATTTTGGCCAGGCTGGTCTCAAACTCCTGACCTCAGGTGATCCGCCCACCTTGGCCTCCCAAAT
TGCTGGGATTACAGGCATGAGCCAGCGCACCTGGCCTTTGTTGTTTTGAAGTATATGAGTTTAGAATTAT

TTATCTTTTTAAAATATTCTAGCGATGAGTCTCCTTATCTATAATAATAATTTTTGCCTTAAAGTTTATT
TGTCTGGTATCAATAGAGTAATGTCAATTTATTTGGTTAATTTTGCCTGTTAAATATTTTTCTATCTGTC
TACTTTGTTTTTCTATATGTTAGGTATATCTCTTACACCTAATCTATGTCTAGATTTAAAAATATGTATA
ATTTCAGAGTCACTCTTAAATGGTCAATTTGGTATTTTTTGTTTATTGTGATAACTGATATTTGGGTTCA
TTTCTATCATCTTATTTTTTGATTTAAAAAATTTTATTATGTATTTTCTACTTCTTCCCTTTTAGGAGTT
GATCACATTTTTATGTTTTCTTTTTCTTCTTTTGCTAGTTTAAAAGTCATACATTCTGTTTCAATTCCCT
TTTATCTTTTGAGACAGAGTCTCGCTGTGTCACCCAGGCTGGAGTGCAGTGGTGTGATCTTGGCTCACTG
CAGCCTCTGCCTCCCAGGTTCAAGTGATTCTCCTGCCTCACCTTCCTAAACAGCTAGGATTACAGGCATT
TGCCACCATGCCCAGCTAATTTTTGTATTATTAGTAGAGATGGGGTTTCACCATGCTGCCCAGGTTGGTC
TTGAACTCCTGGCCTCAAGTGATCCGTCCCCTCCCGCCCCACCCGCCGAAACCACCTTTGGCCTCCTAAA
GTTCTGGGATTACAAGTGTGAGCCACCATGTTTGGCCATGTTTCAATTCCTTTAATGACGTTTATGTTTT
GTAACGTGTTCTTGATTAATTTGAGAATTTAAGCTTCTATCTTCCCAAAAAAGAATCTTAGAAATTCTAA
CCAAAATCATTCCTCTCTGATTTTGCATGTTATTGTTTGTTATTTTGGTTCCACCTTGTTTCTATATCAC
TAAAACTTAATTCTTGGGCCGGATGTGGTGGCTTATGCCTGTAATCCCAGCACTTTCAGAGGCCAAGGCA
GGAGGATCACTTGAGCCCAGGAATTCGAGACCAGCCTGGGCAACATGGTGAGACCCTGTCTTTACAAAAA
ATACAAAAATTAGTCAGATGTGGTGGTGCACACTTGTAGTCCCAGCTATCCAGGAGGCTGAGGTGGGAGG
ATCTCTTGAGCCTGGGAGGTTGAGGCTGCAGTGAGCTGTGATCATGACTGTACCACCATACTTCAGCCTG
GGTGACAGAGACCTTGTCTCTTAAAAAAAAAAAAAAAAAAAGTAAATCCAAAGAACAAGCATATAAATCAA
CTTTGCTAGTAATTAAAACATACAAAGTAAAGCGAGATGGTTTAGTTAGATTAGCAAACATTAAAAATGA
TTTTTAATGCCCAATGGGTTCTGAGAAAACAGTCAAACTATTGAGGACTGGGTAACATAGTAAGACCCTA
GTTCTACAAAAAAATTTAAAAGTTAGCTGGGCATGGTGGCATATTCCTGTAGTCCCAGCTACTCAGGAGG
CTGAGGCAGGAGGATTGCTTGAGTCCAGGAGATGAAGGCTGCAGTGAGCTATGATTGCATCATTACACTC
CAGCTTGGGCAACAGAGCAGGACTCTGTCTCAAAAATACAATTAAAATAGTGTAGATACTACAATCTAAT
TTTGTGTATAAAGGCTGGGTGCAGTGGCTCACGCCTGTAATCCCAGCACTTTGGGAGGCCAAGATGGGCA
GATCACTTGAGAATCAGGAATTTGAGAGCAGCCTGGCCAACATGGTGAAATCACATCTCTACTAAAAATA
TAAAAATTAGCCAGGCATGGTGGCGGGCTCCTGTAATCCCAGCTACTTGGGAGGCTAAGGCAGGAGAATC
GCTTGAACCCGGGAGGCTGAAGTTGCAGTGAGCCAAGAATGTGCCACTGAACTGCAGCCTGGGTGACAGA
GTGAGACTCCGTCTCAAAAAATAAATAAATAATTTTGTGTATAAAACGTGGAAAAATATGGTGGCAGGCAC
CCATAGTCCTAGCTACTCGGGAGGCTGAGGCAGGAGAATGGCGTGAACCCGGTAGGCGGAGCTTGCAGTG
AGCCGAGATCACACCACTGCACTCCAGTCTAGGCCACAGAGCAAGGCTCCGTCTCAAAAAAAAAAAAAAA
AAGAAAAAAGAAAAATAAAAGCATTAAAAAGACTGAAAGAGTTTATGCCAAAATTTATTCTCTTCTATAT
TTTTCAGATTTTTTCACTTAATTTGTTATTTGAAATATACTTGTTTTGTGTAAGTATAAGGAAATATATA
CATATGCACACATGCATATAAACATTTTAAGAATGTGTTATAATAAAAGTATATTATTTGATACCTTTGG
AAATATCCCCATTTTTCTACCTGAAGAAAATTCCTAATTTCATGGTTTGGAAACAGGTTTATGAGCACTC
TTTATAGAGAAACGGTGTTAGTATCTATAGATGACCTGGAAATGGAGACCTAAAAAGTTTCTGAAAAGTT
ATGTCGTTGGTTTTGCTAGTACGGTCACGACCATAGTAATCTTTGGTACGTGCCCCACAGGCTCCAGAAA
ATAAAAGTCAAGCTGCTTTTGCTTGACTGCGGTTTTACCCTGGCAATTCGAATGACTCTGCTTTCCTCTT
CAGGCTCCCGGAGAGAGAGATGTGGGTACCGCCTTGTGCGGAGACAGAGAAGTGCCGACGAGCAGCTGCA
CTGTGCCGGCAAGGCCAAGAGAAGTGGCGGCCACGCGCCCCGAGTGCGGGAGCTGCTGCTGGACGCCCTG
AGCCCCGAGCAGCTAGTGCTCACCCTCCTGGAGGCTGAGCCGCCCCATGTGCTGATCAGCCGCCCCAGTG
CGCCCTTCACCGAGGCCTCCATGATGATGTCCCTGACCAAGTTGGCCGACAAGGAGTTGGTACACATGAT
CAGCTGGGCCAAGAAGATTCCCGGTAGGGCTTTCTGGCTATCAGTTTTCCATGTACTTGTAGAAAGGCCG
GCCGCTAATATTTAAGGGGCAAGAGTACAAAGTAGAGGTCCATGAGCTGTGCCTAGATATTTAACAGGTC
CTCAGCTGGATTTGTAACTTTTAAGTGCAATATGTTCCTTCCTTCTGTCTTGGCATACCTACCTTCAACA
AGGCCGTGTTCTGATTTAGAATTCTGAGACTCTTCTGAGTTCTGTACCCAACATGGTAGTGCAGAAAGAG
TTGTGCGTGGCCCAGCCATTTCTATTCTTGACTGCCTTCTTTTCCCATGGCTAGATGCATCCCATACCAC
CTTGCACAAACCCTATCCTGTGTGTCCACATCTGCTACAGACACTCACCTGTTGGCCACCTCTCATGCCT
AGAGGTGGTCTGGGAGGATGGACCCAGGGAACCTACCTAGGCTCTGGAATTGGGCTTGGGGTCATTTGGG
CAAGAATCCTAGAGTCCTGGAACCTGGAACGTGGTTAAAATGATAGACTCCACATTGACCCATTTCTTGG
CTGTGGATTCCTCACCTTGAAAGGAGGGGTGGGGTAGAGTACAGTATGACTAGTTTGAAAGTGAAAGGTT
TGTCAGATGCTAAATAGAATTTTGTAAATTATTGTTCCAGTAGAGAATCAATATTATGTACATAAATGAA
TATGTATGGACAAACAGAGTAAATCAGTGGTTGAAGTTACACGAATCATCAATGGGCCCATAAACCTGGA
ATGCCATCAAGTTAAAAATGAGCTTAGTTACTCATGAGTTGTCACTTGGAACCTGCGTTTTCCATCCTCC
AAAGTGATCACTTCTCTCAAGCCCATTTGTAATATATATCTGAAGTGCTGTATGATGCTAAAATTACCAG
CTAATTATCATTTGACTTGGTGTTTCTGTGGAGGAGTGAATCTAGGATTCTAACCTAGAGTGGCAACACC
CCACGATCCCCCTGTGACAGCTTCTCCATGCTGTTCTTTACAGTCCTTGAAGAAATGAAGTCTCTTATAA
GTTCTGAGCCACTGGGGGCATTCCCATGGCCTGGAGGGCAGCGACTGCACTGGGCAAGCTGTAAAGATGA
GGAGGGGTGAGAAGCTGGGGGAAGAGAAGTTTTGGGTAAAGAGCCTGGGGAACTGAGGCCTATGGTGACA
GTATCATTTGGGGACTTTTGTTGGCCTGGGCCCATTTCTTCTGAGCTTCCTGAGGATTTTTGGTTTCTAG
TTGTATTTTGTTTTGTCTAGCATCTTCACCTTTGCCAGAATTATTTTATTTTCTCTGCTTTTTCCCAGGG
GAGGCAATACTGATGCACTTTCCTCTAGTTTTTGCTTTAAATGTATTCCAAACACGATTTTGCAGGACCA
CACATGGAGAGCAGTGGTGAAATTAATTATTGCTGAAAGCTGTGCACCTTCTTTGTGCCATAAGAAATCT
GAACTCTTAAACTGCATTATTCCTTATTCAAGCCTGGTGTTTTGAAAAGTTTTCAGGAAACGTAGACATA
ATCTGAAGGCGTGATTTTTTTTCTCCTCTCTTAGCTGGCATAGTCATTGTCCAAACCAAAAAATATATAT
TAAAATATCATCTAGCCTTGATCTTGTTGAATATCTACAAGATTAAGAACCGTGATCTCTCTTGGGTAGG
CTTATTGTCAATCACTATGGGTGAGACTGGGAAGGTATATACACATTAGGAACCTAAACTGAGCAAAGCA
TGTGGATTTAGAAAGTATTTATCCATCTTTACATTCATAACACCATTACATTCTCCTTGAGGCAGATTTG
CGTTATAATTGTTCAAAGACTTGAACCATGTGTGTTCTCTCTGCTGTAGTTTCCTCATCTGTAAAACAAG
AATGATAAGAGATCCTGCCTATAAGACATTCTCAGAGATAGGCATTGTTACCCCCATTTTCCTATAAGAA
AAACAAAGACTTAATGGGAGATTAAGTGAACAGCTAGAAAGAGGCTGAGCTGGGGTTCGAACCAGAGTCC
ATTTCACTCCAAGGCGGTGTCTTTTGTTATCATATTTATATTACATGGCCCTCTCTTTTTATCATGGCTT

GTGAAGGAAGCCCCGGTGTTCTCTGCTTTGCTTTTGAAGTGCTTCCCTCCCCAGAGATTACCTGTTTGCA
AACAGTACTGTGACCAACATGGGTTATTAGGTTGTCAGGACCTGCTTCGTTATTATATTTGCTCTTTATT
TATTTATTTATTTATTTATTTTTGAGACAGGGTCTCGCTCTGTTGCCCAGGCTGGAGTGCAGTGGCGTGA
TCTCAGCTCACTACAGCCTCGACCTCCTGGGCTCAGGCGATCATCCCACTTCAGCCTCCAGAGTATCTGG
GACTACAGGCACCTGCCACCATGACCAGATAATTTTCTGTAGAGATGGGGTTTCTCCATGTTGGCCAGGC
TGGTCTCAAACTCCTGGGTGCAGGCAATCCACCCACCTTGACCTCCCAAAGTGCTGGGATTACAGGTGTG
CTTGGCTATATTTGCTGTTTAGGATAGAATCACCCAGAAACAGTGCTTCTACCCAGAAGAAGGATCTTAA
CACTGGATAGGAAATTTTAATCAATCAGAGAAATCCTTGCAGTTGAGGCCTTGGTTTTCTGTGAGGGCTG
GCACTGCTCTCTGCAAGCCTCCAACCCCAACCTCCACCTACCCCATCCCCCACCTACCCCATCCCCCACC
CCTTCTGATCCCAGTCAAGGATTGGGTCAGACAGGCAGGTCTTCTGACTGGCAGCCAAGCATCAACATTC
TCAGTAGTGCAGAGGAATTATCAGGACACAGCTAACAAAGATCAGTTCTGAGCCGAGGTCGTAGTGCTTG
ACAAACTCTAAATGAAGTATATTTGTCTCTAGAAGGGGTCCAAGACTGGAAACTAAGTTGCGCAGCTTAA
CTTCAAAGTTTTCTTCCTTTAATGAGCAGTTAATCACATCTATAAAATATCAACTCCCTAATGGTTTGTG
TTTTCTTAGTGTTTTAACACTTGCCATTCTGTCTCTACACACACAGGGAGCTGAGGAGGAGGGGTGGGGG
TGTCTCACCGCCTCTTGCTTTCCCCAGGCTTTGTGGAGCTCAGCCTGTTCGACCAAGTGCGGCTCTTGGA
GAGCTGTTGGATGGAGGTGTTAATGATGGGGCTGATGTGGCGCTCAATTGACCACCCCGGCAAGCTCATC
TTTGCTCCAGATCTTGTTCTGGACAGGTGAGAAAAAATACATTGTGTTTCTTCTCTGACTTGTTTGAGTA
AGGTGCTTAGTGAGTGGGAACAAAGTCCTGGGTGCTGCAATTAAAATCTCACACTTGCAGGGCAGAGGAT
GATAGCATCATCAGCTCCTTCACTGGGTCAAGAACCAGAGAAGGAGAGAGTTGGGTCCAAGGATTCAGGG
TCCTGTGACTCATTTTTAATCTGTGGTGCAGCAGCATTTACAGGCCAGCGCTTTAATAGGGGACTGTATC
CCGTAGGTATGTGGCCACTATGTGTATAAGTCGACACAGATTTTTCTCCATTAAAAATTCCATTTTCAGG
TTATAATCTTAAGTTGTCCTGCTGTTTTTTGTACCTATAGTGACCAATTATATCTGGAGCTTTCTGGACA
GGTGATAAAATTCTTAGAAATGTGCCAAGTTTATTTTCACATGCTTTAACTCACTCTTTTGTTTTTTTTT
GTTTTGTTTTGTTTTGTTTTTTGTTTTTTTTCTGAGATGGAGTCTCTCTCTGTTGCTCAGGCTGGAGTGC
AGAGGTGCAATCTTGGCTCACTGCAACCTCCGCCTACCGGATTCAAGTGATCCTGCTGCCTCAGCCTCTC
AAGTAGTTGGGATCACAGGTGTCCACCACCATGCCAGGCTAATTTTTCTATTTTTAGTAGAGAAGTGGTT
TCACCATGTTGGCCAGGCTGGTCTTGAACTCCTGACCTCAGGCGATCTGCCCACCTCAGCTTCCCAAAGC
GCTGGGATTACAGGCGTGAGCCACCATGCCCGATCTGCTTTAACACATTCTAATGCATGTACTATATAGC
ATTTTTGGCAATAGCGGTGGAAGGAAGGGTTACTAAAACTATATGAAACTTAACAGAAAATGGGACATGA
TGCTGTATCTTGGTTGTGTTTGATTTTCTTTTAAAGATGACACAGAAAAGGAAACAATTTTTAATTGACT
TAGGTGAACTGTTTATGGAGGGAAAGCTGGACTGTATAAAAATACTCAAGCTTTTTAGCAGGAAAGTAGA
ACACCCTCTTGGTGTAAATTCGAGCAGTTCGAAATCTTCTTGGAAATTGATTTCCACATCTCTTTTATGG
AAAAAGTGCTAGGTTGAATGTTCAGCCACATCTGACTCTGCATAGCGTGGGAGGATGCCTAGTGTCTACC
CCAACTCTTGCATTATAATCCTGTTACCACTTTAGATCATCAGAAGACCCTGTGTTACACAGATGAAGAG
TGATGCCCCAAGGTATCAGTCCCCATTCTGCCTTTTGTCATGGTTGACAATGTTATTAAAAGAGCACTGT
TCTGCATAATGGTGTTTTGATAGAGAACAGATCCTCTGAGAAGAGCTGGAGGACTGATGTGACTTGAACA
GGAGCAAGCCCAGGTGGTAAACCATGGAGGGAGGCTCTGGAAGACCAGAGAAGTTCAGGGCACAAGACCC
TTCAGTAACAAACAAAATAGTTAACCTATTGGCTTGTATGTGCTTGGCAGCACCTTATGCATTTAACTTA
TGTCAACACATTTAATCTTCACAATCTTCCTGCCCCCTTTGAGGGAGTAGGATCCATTATTATCTCTATC
ATTCAGATATTGGAAATGGGAGATTGAGAAACCTGCTTACAGGTAGGATAATAGGTGGTGGAGCTGGACT
TGGGGGGTTGCCAAATGGCAAACTAACTCTCTACTTTATTCTACCTGTTGTTATGGGTGACAATGTTGAC
AAAGAGCACATTCTGCAGAACAGAGATGTTTTGGTAGAGAACAGCCCTGTTTTACTTGTAACACACTGCA
GAAACCCACTCTCCCCACTGTCATCTCAGGGTACCATGTCGCAAGGCAGGCTGAAAAGCCAAGCACCTAG
CCAAGCCATTGCTCTCATTCATTCATTGTATTCTGCTTGGTGTTTTAACTGGGGCCAAATATACATATGT
ATAAATATACACATATAATTTTCCTTGAAGTTAGTCCTAGGAACACATTCCATCCCTTGACAAATAATTT
GCAGACTTTAGGATTATTTTATCTTTTGTCTTGATTTCTAAATTGATGCCAAATTTAGTGTTTATTTTTG
GTGACTATTTCATTCCTGGTTTTTAGTACAATTAACTCTCCACTCTCCCATTTCTCTGTATGCGTTCTTT
AATTCCTGTAATTGTGTGTATACATTACTATAAGTGGACACAAATCCTGGAAAAATATTAGGCCTACCTT
TTAGTTAATAGAAGAAAAGTTATTTTTCTTACAAATTATTTCTAATAGACTTACACTGCCTTTATAACTT
AAGTGAAAGTATTATGTTGTAAAACATAAATCTAGTATATTTGATTGAGTATAGAAGAGGAATTCTTGGG
AATTGTAAATGCATTCATGTTGAGCAGGCATTTTTTTTTTTTTTTGGAATGACTACTGGTGTTTATTTGT
TGTTGCAATTTCTAGTAGTTTTTGTTTGTTTGTTTTTTGTTTTTGAGATGGAGTCTCGCTCTGTCACCCA
GGCTGGAATACGATGGCATGATCTCAGCTCACTGCAATCTCCGCCTCCCAAGCTCAAGTGATTCTTGTGC
CTCAGCCTCCTGAGTAGGTGGGATTACAGGCATGTGCCACTACGGCTGGCCAATTTTTGTATTTTTTTTT
TTTTTTTAGTGGAGACGGGGTTTTACCATGTTGGCCAAGCTGGTCTCGAGGTCCTGACTTCAAGTGATCC
CCCAGCCTCAGCCTCCCAAATTGTTGGGATTACAGACGTGAGTCACCACGCCCAGCCTACAGTCTCTAGT
ATTTTTAACACATTAACTTTCTGAAGTCTGGAACTTGAAGTCTAAGATAGTTCAGTTACTTAGTCCTCTC
TTATACAAATGAATATACTTTTATGTAATAGGTATATTTGTAGAGGAGTTGCTCATTCAAAAAGTCAGGA
GTCATGCTCCATAAAGACTTCTATTACGACTCTTTTTTGCAAAGTGAAGGGAATCTTCACACCATTTGAA
AATAACTGTCTTCTGCTGGATTGTCCTAGCAGAGCTTCTTCAAGTGGTAATATGGCTGAATAAACAGTGA
ATACAACTAACAGTTGCCCATTTGTGGATACTGAAACTATAATTTCTGTTTCCCTTTATTCTTGTTGAGG
TGTCCACAACAAGAAAACTTGTGTCTACTGAGGATGAGAGGAAAATCTCATTACTTCAGCTTATTTCTAA
GCATTTAGTTTTTCTTTTACTAACCACTAAATTCATCATAAATTCACGTGAAGATCTAAAGAACCTGACT
GTCTAATTGCTCAAAAAAAAGTCACATATGCAAAGACATTTTTGTGTCCTTAGTATCAACAGGCAACTGA
CTAATGTTAAATTATTAGTCAGAGGAAGTTTGTATCTGGCTTGGATCCCATTGTGGACATTTGCAGATAG
GTCCGTGAAATTGTATATGTATAAATGTCTTGAGTTTACATTCACATTAGTTATTTGTATGCTAAATTCC
TTCAAGATAACCACCGAATTTTCAATTCCCAATTCTAAGCCTTAAACACTCCCTGCCATTGCCATACACA
CAGAGGTAAACCATGGTCTGTACCCAGGTGTGTGCTGCGAGCAGAGATATATATATATATATACACACAC
ATACATACACACACACACACACACACACACACACACACACACACACACACACACACACACAAATAGTGTA
CCCCTAAGGGAGGCCCACTCATTCAACATTTTGTTGTTGTATTAAACAATATTCTTCTTTAGGCCAGGCA
CGGTGGCTCACGCCTGTAATCCCAGCACTTGGGGAGACTGAGATGGGTGGATCACCTGAGGTCAGGAGTT

CGAGACAAGCCTGAGCAACATGATGAAACCCCTTCTTTACTAAAAATACAAAAATTAGCTGGGTGTGGTG
GCAGGCGCCTGTAATCCCAGCTACTTGGGAAGCTGAGGCAGGAGAATTGCTTGAACCCAGGAAGTGGAGG
TTGCAGTGAGCCAAGATCACGTCATTGCACTCCAGCTGGGCGACAGAGCAAGACTCCATCTTAAAAAAA
ATAAAAAATAAAAAGCAATATTCTTATTTTATAAAGAGTGATTATTGGCCGGGCTCGGTTGCTCACACCT
GTAGTCCCAGCACTTTGGGAGGCTGAGGTGAGTGGATCACTTGAGGTCAGGAGTTCAAGACCAGCCTGGC
CAACATGGTGAAACCCCTTCTCTACTAAAAATGCAAAAATTAGCCAGGCATAGTGGTGTGTGCCTGTAAT
CCCAGCTACATGGGAGGCTGAGGCAGGAGAATCACTTGAACCTAGGAGGAGGAGGTTGCAGAGAGCAGAG
ATCATGCCACTGCACTCCAGTCTGGGCATCGGGGTGAGACCCTGTCTCAAAAAAAAAAAGTGATTGTCAA
GTAATAAATTTGATATGGTTTGGCTCTGTGTCCCCAGCAAATCTCATCTGAAATTGTAATCTCCACGTGT
CAAGGGAGGGATCTGGTGGGAGTGATTGGATCATGGGGATGGTTTCCCCCATGCTGTTCTCATGAGAGTG
AGTGAGTTCTCACAGGAGCTTATGCTTTAAAAGTGTTTGGCAGCTCCCGGCTGTCTTGCTCAGTCACTCG
CTCTCCTGCCTCCATGTAAGATGTGCCTTGGTTTCCCTTTGCTCTCTGCCATGATTGTAAGTTTCCTGAG
GCCTCCCCAGCCATGCAGAACTGTGAGTCAGTTAAACCTTTTTTCTTCATAGATTACCCAGTCTCAGATA
GTGCTTTATAGCAATGTGAAAATGGACTAATACAAAGATATTCCATGTTATTACTGATTTTATTTAGTAG
TTTATGGACAGATAGTGTGCAAAAATAAATTTCCTGAGTAGGTCAGTTTGGTTGATACATTGTTTCAATA
TTTTAACATTCAAATCATATGCCCTGTTTTTGTTTTTGTTTTTTTTTTTTAGAGACGGTCCCGCTCTGT
GGCCCAGGCTGGAGTGCAGTGGTGCCATCACGGCTCACTGCAACCTTGGGCTCCTGGCCTCAAGTGATCT
TTTGCTTCAGCCCCCTGAGGAACTGGGACTATAGGTGTATGCTACCATGCCTGGTTTATTATTATTTTGT
AGAGACAAGGTCTTGCTACATCGCCCAGGCTGGTCTAGAACTCTTGGCCTCAAGTGATCCTCCCACTTTG
GCCTCCCCAAAGCACGAGGATTACAGACATGGGCCACTTTACCCAGCCAGCCCTGTCTTTAATTCAACTC
TTTTAACCCTGTCCTAATTTCTTACTCATAATTCAGTTTCAATCTAAAATTATAAAATAAATAAAATAGA
TGTCATTAATTTAGAGTCTTTACTAACTTTGTTCTGTGTAACTCATCTGAAAGACCTTTACTGGGCTGTC
ATTTACGATGTCTTATACTTTATTGCCTCTTCATTTCTCATTTATTTTGTTGAAATGTATTTGGTTTCTG
CAGACTGTGGAGTGAATAAAAATATTCTAACTTTGCCACCCCTTGAATGAAATGGTTGACTGTCACACCT
GCTTAAAAAGAAAGCAATCAGACCTAGTTCTTTAGACTTTGTTTAGAAATTAACTTTCTCCATGAGTTAT
GTATGGTCTGATTACTGTGAGGGACAGCCTTTATCAGGGTTTAAAATACCTCAGTATGCCAACCCTCCTC
CCATTTTTGGAACATAAATTTGCAGTGAAAATGGCATATATTTTAATGAGGAAATGATACCAATTTCAAT
ATTGAGGAACTAAGGCACAGGTACTTCTGGAAAATAGGATTGATTTCAGGTGGGTTCCCTTACCATACCA
CTTGGGGAGGGGTGTGTGTGAGTGTGTGTGTGTGTGTATGTATTGTGCATGTGTGTATAATCCCACAT
CAGCACAGAAGAATAAAGAGATAATCAAATATCAATGCAGGAGTTGGTGGGTTTTTTTGTTTTTTTTTTT
TTTTGCCCCATAGAGATATTTTCAAACTAGCTTTCCTTAGTATCAAATGTCCCCAAGTCCAACAGTTACA
ATTTCCAATAATTAATTGTCCGCAGGCAAGGTGATTCAGGTGTTTTTTGTGTTATCTCTGTGCAGGGCTT
GTGTTGTCCTTACTGGATGCCTGCATCAGGTTGCCTGGGAGAGCCTAGAGCTGGGGAGGTGGAAAGATGA
GGCTTCCTGTAGATTTGGCACTCTTTGCCCAGTGCTCTGGATTCTCTAAGACGGCCTTTTCCTATGAGTG
ACTTCCAGGGGGCACTGGTGTTTTGTCACTTAACCTGTGTACTTATAGAAAATTGCAGGTGTTTACAGAA
TTTATGATTTAGTAAATTTAGTAACTTAGTAATGCTCATATACCAAAGTGAGCAATTTGCATGCTTGTAG
CTCTGTGTGAGCGAGTCTGGGTGGGAGAGTGTGAGTGCTTCGGAATGCAGGATCCCGGTGAGTGCCATGT
ACGGCAGGTAATGGGAAAGACTTCTGCAGGACTGGTGTATCCAGTGGTGTCAGAGGCTCTTCCCTGAAAT
ACTGCCATCGCTGGAAATGCCCTGAGTTCGGGGAAGGAGGAGGGGAGCAGCCAGCTCTTTGAAGACCTCA
AGGCCCCTTCAGGGGCTGCTAGAGACTAAAAATGGAACTCGCATAAACCCACTGCCCTTTCTGTGTGCTG
CAGGCTTTTGGGAGCAAAGGGTGGTTTTGTGACAAAATCATCTAACTGCTTGTCAAGGACTTCCAATAAC
CCTGTGACTGACAATAATAGAGTGTTTTGGGGGAGCAGTGAGGTGGAATAATGTGTGTCTGGCTGGAGTG
AATAGAAGCTGGTATTTTCCAGATAAAGTTCAAGTAATTTACTTCCAAAGTATATTTAAACATTTATTTC
TACAAGGAGTGCTCCAAAGAATTTTGATTAGATGGCTCAAAGTTTAAAGATAATCCTTGCTTGAAGATAA
TCCTTGGCAAGTCAAAAATTTTTCCCCACCTCCATGTATACCTTCTTTTCCTGATTCTAATCCATCTTCT
CTAATTGCGATTTCTTTCTCATAGTCAGCTTTTTCAAATTACAGGTAAATGTCTTAGTTGCTACACAAGT
TTCTAAGTGACCACCAGGAAGTGAGAGTTAAGCCCTAGATATGGAGTTTTATTCTTGGGATATTTGCTTC
TGTGACACACGGTCTTCCTCATTAATACTTCCCGATGGGAACATGAAGTGTCTCATTTTGAAATACGTGT
CATATCTGGGGCTGGTTGACTGATATGGTTTTGATTGAAAACAATCAATAGGAGTGGTATTGCTGTAAGA
AAACATTTGGTGAAAATGTAGAAGGAAAATATTCCAATGCACATTTTTGCCTAAATAATATTTATTCATA
TATTTACTTCAGGGATTTATAGGAAATGGCCTATCTTCTTTATATGAAGACAATTCTAGTAATTTCATAT
TGCTGGGTGTGGTCTCATTAACACCCTGTTGTAGTTAAAATGATATTATCAGATGAACATGTTACAAGAT
GAAACTTGAGATTAAAAATAAAACATTCCTTATTGTTTTTTTGATGGTTTCCTGAAGCTATGTTCCTTAA
ATTTCCAAACGAACTTTTGTAGGGATGAGGGGAAATGCGTAGAAGGAATTCTGGAAATCTTTGACATGCT
CCTGGCAACTACTTCAAGGTTTCGAGAGTTAAAACTCCAACACAAAGAATATCTCTGTGTCAAGGCCATG
ATCCTGCTCAATTCCAGTAAGTAATCACACAGCTGGGCCATGTTTTATCGGGGAGAGATGCTGTTTCTAC
AACTAGCGTGATATTAAGAAGAATGTTGAACTTCTATTTTATTTGAAAGGGTAAAATGGTTTCCTTTTGG
ACTTCGTTTTTATTTTGATAGCGATTTAAACTGTAGGTAACTTTTGGTAACTTGGACATAAATTACTCAT
TAAGTGAATGACTGGCAATCAATTTAAAAGTAGCTCAAGCCACTTGCTGGAAAAGAAAAAAAAAAGGAACT
TTAAATTGTTTATCTTTTAAACTTTTTTCAGTGCTCACACAGACACTTTACATGGTTGGCATGCATTTAT
ACTTATGTCTGGGGTCCTCCTTTTTTACAGATTCATTCGTTCAGTAAAGATACAATCCTACCCTCAAATG
GCTCATAGTTTAGGCAGGGAGAGAGAGAAAACAAATCATTAAAAATAATGATTTCTGTGCTATGATAAAG
TCTACACAAAATACTACGGGAAAATAGGAGGAGAGATGCTGGAGTTGTTGCAGAAGGGAATGATTGAACA
AATCTTCAGGAAAGAGCAGAGGGAAGTAGGTATGACTTTAAAATGCAGTGCTGAAGATTAGAAACTGCTG
CCCAGGCTTTGGGCAGCTTAGAAGAGGTTCAGGCAGGGGAGTGTCATGCACAGATATGCGATATAGAAAG
GTCACTCTGGCTTCCATGTGGAGGACTAGAAAGGGCAGAGACTGAAGCCGGGGGCCCATTAGAGGCAATG
AGAGCCTGAACTGACATTATGGCGTGAGGTCAGGGAGCAAAGGACTTGACTTGAAGGAAAAGTGGGAGGT
AGAGGAGGGAAATAAGGTGTCTAGGATATGCAGATGGTTTCGTTTTGTTGGTTTTATCTTATATAAATAT
CTGATTATTGTTAATAAACATTCAAATGAGAAAAACATACAAGGAAGAAAATAAAATCATCAGGAATACC
TGCCCTCAAAATAACCACCATAACTTTGGTGACCATTCCTTTCTTTCTTTTTTTTTTTCTTTTTTTTTT
TTTTTTGAGACAGGATCTTGCTCTGCTGCCCAGGCTGGAGGGCAGTGGCATGATCATAGCTCACTGTAAC

CTAGTACTGAGCTCAAGTGATCCTCCCACCTTGGCCTCACAAGTAGCTTGGAATACAGGTGCATACCACC
AGACCTGGTTAATTAAAACAATTTTTTTTTGTAGAGACAGAATCTTGCTGTGTTGCCAGAGGTGGCCTTG
AACTCCTGGCCTCAAGCAGTCCTCCCACCTCAGCCTCCCAAAGTTCTGGAATTTACAAGCGTGAGCCACT
GTGCACAGTCTGTATCTTGTTTTTCACTTTTCTTTTTGAGACAGGGTGTCACTCTGTTGCCCAGGCTGG
AATGCAGTGGCACGATCATGGTTTACTGCAGTTCCGACCTCCTGGGCTCAAGTGATTCTCCCACCTCAGC
CACCTGAGTAGCTGAGACCACAAGCACCTGCCACCACACCCGAATAATTTTTGTATTTTTTGTAGAGGTG
AGGTATCCCTGTGTTGGCCAAGCTGGTCTCAAACTCCTGTATTTTTGTTTTTCTTTTCAAAATGCTGTGA
AACCATTCTGGGTCAACTAGGAGAGATCTAACACAATCTTTGATATGAGGGCATTATACTAAATTGTTCA
ACCATTTCTCTGTTATTAAATATCCAGTTCCTCTTCCTTTTTAACCATTATAAACATTACTGCAATAAAT
AGAGATGTGTTATTTTGTATGAATTTCTAAGTTTCTGGATGGTTGTCAAGACTGGTCATTTCACGATCTA
CCTGGTGTCTAAGCCAGCCGCTCTAGCAGATATTGATGGCTTTGCTTAGCCATTTACTCTTGTCGAGCCT
TTAGGTTATTGACTTTTTTTCTTCCTCAAACACTGTATATCCAGGTTTTAATGTTCACCTGAAGACTTAC
AGATATCTCTATTTAGACAACATATTGGGCCTTATTTATCCAATCTTAGAGTTCGATACTTGAAACAACA
GGGATATATCAGATCATATTATACTACGGTCTTTAAATCAGCCAAAGTAGCAGTTCCTGAAGCCAAGATT
CAATGCAGAATTCACTGTGGTCACATGTTTCCAGCTGCCTCTTGATCTGGGGCCAGCTGACCTTCATACG
TGTCTTCTCTCACAGACTCTTGGATATTGGCACTAGTTTTTTTGTTTGTTTGTTTGTTTTGAGACAGAGC
CTCACTCTGTTGACCAGGCTGGAGTGTTAAGGATAGTTACTTTTGCAAAATATAACAAAAATGAATTATG
AGAAAAATAAAAGTGTAAAATACAAGTCCTAGTTTATAATATTATTAGTTATCACATTCAACTGATTTAA
AATTACTCTGTCGATTGCTAAAAATGTTCCTAAATGCTTACACTCAATTTCTACCCATCTCTTTGTAAAT
GGGCAACAGACCATACATTAGCTCTGGAGAGAGCACAGGATACTGTCCAAGAGTTGCTTGGATCTAGGGT
GGAGGGTGGGGTTAGCCCCTGAAGAACTGGGTGAGGGAGAATGAAGAAGGAATCTGAAGGCCATGTGAAG
GTACAGAGACCTGGAAGACAACCTTTGAGCATTTCCTAGTTAAGTCTCAATCTGGCCTTACCTGCCTAAC
AGGTCATTTCCCCTGCACCCAACACACCCTTCCCTGTTTATTGTTACCATTCACCTTTTACAGAATAACA
TGAGGGCCCAGCTTATACTGATGATTATGTTGATGTGCATATAAGGAAAGTCCAGCCAGGTGTGTTTTTT
TTTTTTTTTTTTTTTTTTTTTTTGACAGAGTCTTCCTGTGTTGGCCAGGCTAGAGTGGAGTGCAGTGGT
GGAATCTTGGCTCACTGAAACCTCCGCCTCCCAGGTTCAAGTGATTCTCAAGCGATGCCTCAGCATCCCA
AGTAGCTGGGATTACAGGTGCATGCCACCATGCCTGGCTAATTTTTGTATTTTTAGTAGAGATGATATAT
TAGTCTGTTCTCACACTATTATGAAGAAATACCTGAGACTGGGTAATTTATAAAGGAAAGAGATTTAATT
GACTCACAGTTCAGTATGGCTGGGGAGGCCTCAGGAGACTTACAATAATGGCGGAAAGTGAAGAGGAAGC
AAGATACCTTCTTCACAAGGTGCCAGGAAGGAGAAGTCCCAAGCAAAGGCAGAAGAGCCCCTTATATAAC
CATCACATCTTGGGAGAGCTCACTCACTGTCATGAGAACAGCATGGGGGAAACTGCCCCCATGATTCAAT
TACCTCCACCTGGTCTCTCTCTTGACACATGGGGATTATGGAGATTACAATTCAAGATGAGATTTGGGTG
GGGACACAAAGCCTAACCATGTCAGACAGGGTTTCACCATGTTGTCCAGGCTGGTCTTGAACTCCTGGCT
TCGAGTGATCTGCCCACCTTGGCCTCCCAAAGTGCCGTGATTACAGGTGTGAGCCACCACATCCGGCCCA
CCAGCCAGGATATTTGAAATTGATCATGGAATAAGATCAACCCTTTCTGACCTTTTCCAAACCACCTACC
AACATTACCTCACATAGGTGCTGCCATTTCTGTCAAAGGGAGGATCTGCTTGAAGAGTACCTTCCCATCT
TGGCAATGGAAGATCATCAAATGCCAGATGATGGGGCTTCTCTCACTTTCAGAAATAATTTAGATCTCTT
TTCTGTGCAGGAAAGTGCTTCTCGGAAAGCACTGTTTGCTTGTTGTTACAACACTTTACAGTATAAAGCC
TTCTGTTTGGCAAGGCTCCTTATAGGCATTTTAGCCTCCCAGACATCATATTGTGTTGTTGTCAAAGCTA
GACGCAGCATCTGTGCAAATGGGAAAGATGAAGGCTACAGCATTCCCCTGCAGCATGACAGAACTGCCAC
ATTGAGATAATTACAGAAGGCGAGGGAGACATGTGATGTAATTACCACTTGTGGCAGTAAACGAGTAAAA
TTTGTTTACTGTAAATCCAAGTTTAAGAAATCTTTTTTTTTTTTTTTTTTTTTTTTTTGACAGAGTCTTG
CCCTGTCGCCCAGGCTGGAGTGCAATGGTGCGATCTTGGCTCACTGCAACCTCTACCTCCTGGCTTAAAA
CAGTTCTCCTGCCTCAGCCTCCTGAGTAGCTGGGATTACAGGCACCCACCACCACGCCTGGCTAATTTTT
GTATTTTTAGTAGAGATGGGGTTTCACCATGTTGGCCAGGCTGGTCTCGAACTCCTGACCTCGTGATCCG
CTTGCCTCGGCCTCCCAAAGTGCTGGGCCCTCGCCTGGCCAGAGATCTTCTTTTAAGGAAGTTCCTTTCT
TGGTAGTCATAACAATTGTCAAAATAAATTGATCCTGTTCAGCATTGCTATGGCGAAAATGGGACAATTT
TCACTGCTAGGTTAAGTGAGTCTTTTCTATGCTAGGTTTTAAGGATTTGTAAGTACAGGCTTTTTTCTTC
TGGATTATTTGTGGTATTTAAATTTAAAAAAAAATAGGGATGGAATCTGCCTCCCCGCCTTAAAATTTAA
AACCCTGACAGAATATATAAAACAGATATTGGACATTGGACAACAGTGATCCCCAGGAGGAGGGACACAA
ACGAGGAGAGCCCTTTGATTGTCCAGTTTACTGCCTGGAGCCAGTTTCCAGGTTGCAAAGCAGGGATGGG
TGTGTTAGGTTTCTCCAGAGAAACAGAACCAATAGGATGGATAGGTAGGTAGGCAGATAAATGAGAGGGG
ATTTATTATGAAAACTGACTTGAACAATTATGAAGGCTGAGAAGTCACATGATATGCGTCTGCATGCTAG
TGAACCAGGGAAGCCAGTAGCATGGCTCAGTGTAAATGGAAAGACCTGAGAACTAGGGAGCTGGTGGTGT
AACCCTCAGTTTGAGATTGAAGGCCTGAGAAACTGGGAGGCCACTGGTGTGAGTCCCAGGGTCTGGAGGC
TGGAGAACCTGGAGTTCTGATGTCCAAGGGCAGGAGAAAATGGGTGTTCCAGCTCCGAGAGAGAGAATTC
TCTTCCTCTGCCATTTCGTTCTATCTGGGCACTCAGCCAATTGGACGGTGCCTGCCAACATTGGCTAAGG
GCAGATCTTCCTTACTTAGTCCACTGTTCTTTCTTTTTTTTTTTTTTTGAGATGAAGTCTTGCTTTGTTA
CTCAGGCTGGAGTGCAGTGGTGCCATCTTGGCTCACTGCAACCTCCACCTTCTGGGTTCAAGCGATTCTC
CTGCCTCAGCTTCCAGAGTAGCTGAGATTACAGGCATCTGCCACCACGCCTGGCTAATTTTTTGTATTTT
TAGTAGAGATGGGGTTTCACCACATTAGACAGGCTGGTCTCGAACTCCTGACCTCAAGTGATCCACCCAC
TTTGGCCTCCGAAAGTGCAGGGATTACAGGTGTGAGCCACTGTGCCTGGCCTTAGTCCACTGACTCTAAT
GCCAGTCTCTTCCTGGAACACTCTCACAGACATACCCAGAAATAATGCTTTATCTGCTATCTGGGTATCC
CTTTATCCAGTCAAGTTGACACCTAAGACTAACCATCACAAAGGGTAACCCAAATAGACACCAGTGGTCT
CCCTTGGTAGCAAGGCAGCTAGGACTTGGAGGGGAGAGTACTGAGTGGGAAAGAGCTGCACAAAGAATTT
TGGAGATCTATGGAGAGTCCTCTTCAAGTCTTCAGCTGAGTGCTAATCTGCCCATGCTTATGAGGATACC
AAGGACAGGGAAAGAACCATCAGAAAGGAGCGGGCGAAACAATCCCTAGAGTTCACACAGGGCCAGGAAC
AGTTCACATTCTCACCAGCCAGTGGGAAAAACCTTGCAGTTCACTGGGTATTGGGCACTTCTCAGCCTTC
CTATAGTATTCAGAAGGGTATTGCCTCAGTAGTGGGCCTAGACTAAAAGCCATTATGATCCTACCAAACA
AAAAAGCAAGCCTGGAGGATCAAACAATTGCTAAGTGATTTAACTGCATCCCAGCACAAAGCTCAAGAGT
AGAGACACATCCCATTTCATTACATGTTGCTTTATTGTGCATCACAGATACTGCATGTTTTTACAAATCG

AAGGTTTGTGGCAATGCTGCATTGAACAAGTCTGTTAGTACCATTTTTCCAACAGCATGTGCTCACTTT
ATGTCTGTGTCAAATTTTGATAACACTTTGCAATATTTCTAACTTTTTCATTATATCTATTACAGTGATC
TGTAATCAGTGATTTTTGATGTTACTATTGTAATTGTTTTGGGGTGCCACAAACTATGCCCATATAAGCT
GGCAAACTTAACCTATAAATTTGTGTGTTCTGACTGCTCCACCAACTGGTGGCCCCACCACCATCTGGAA
TTCTGGGAGAATTCTACCATGCATTTGAGGAAGGAATAATACCAAGTGATATGGTTTGGCTCTGTGTCCC
CACCCAAATCTCATCTTGTAGTGCCCATAATTCCCACATGTTGTGGGAGGGACCTGGTGGGAGATGATTG
AATCATGGGAGCAGGTCTTTACTGTGCTGTTCTCATGATAGTGAATAAATCTCACGAGATTTGATGGTTA
TATAAAAATGGGAGTTTCCCTGCACAAGCCCTCTTCTCTTGTCTGCCGCCACATGAGATGTGCCTTTCAC
CTTCTGCCATGATTGTGAGGCTTCCCCAGCCATGTGGAACTGTAAGTCCAATAAACCTTTCTTTTGTATA
TTGCCCAGTCTTGGGTATGTCTATCAGCAGTGTGAAAATGGACTAATACACCAAGTTTACACATACTCTT
ACAGAAAATTGAACAGCATGGAATGTTTTCCAATTCATTCTGTGAGGCCAGCATTACTCTGATAGAACAC
TCAGACTAACACACTAGAAGAAAAGAAGACAACAGACCAATTTCCCTCATGCATGTATAAGCAAAAGTTC
TCTAAATTTTTTTTTTTTTGGTAACTAGAATCCAAAACTGTATTAAAAGAATAGCACATCATGAACAAGC
AGAATTTTTGGGAATACAAGGTTTCTTTAACATTTGAAAATCAATCAAAATTCATATTAACAGAATAATA
ATGAAAAACCATATGATTTTATATATATATATATTTTTTTTTTGTTTGTTTGTTTGTTTTGTTTTTTTTT
GTTTTTTTTTTTTGAGACAGTCTCACTCTCCGCCCAGGCTGGAGTGCATTGGTGCTATCTCAGGGCTCAC
CGCAACCTCTGCCTGCTGGGTTCAATCAATTCTGTCTCAACCTCCTGAGTAGCTGGGATTATAGGTGCCT
GCCACCATGCCTAGCTAATTTTTGTGTTTTTAGTAGAGATGAGGTTTCACCATGTTGGCCAGGATGGTCT
CAAACTGCTGACCTCAGGTGATCCACCCGCCTTGGCCTCCCAAAGTGCTAGGATTACAGGTGTGAGCCAC
TGCACCTAGCCATGATTATCTTAATAGATGCACACAGCATTTGACAAAATCCAACATCCACTCCTGCTAA
AAACACTGTACAAACAAGGAATAGAAGGAAACTTCCTCAATCCATTAAAGGGCACCTATGAAAATCCTAC
ATTTAATATTATACTTAATCACAATCAGGAACAAGGCAAGTATGTCCACTGTCCTTAATTCTATTCAACA
TTTTACTGTAAGTTCTACCCAGTGCATTAAGGCAAGAAAAGAGGTAAAAGGCATCAATATTGGAAAGGTA
GAAGTGAAAGTCTTTATTTAAAAACATGAGAATCTATGTAGAAAGTCCTAAGGAGTCTAAAAAATGTGAA
TTTAGCAAGTTTGTAAGGTGTAAGGGCAATATATATAAATCAATTGTATTTCTGTGTGGCACCAGTGAGC
AATTGGAAATTGAAATGAAAAACCACTACCATTTACAATAGCATCAAACATTGTGAAACCTTGGGAATAA
ACTTGCAAAAGACATGAAACCTGCACACTAAACACTGCAAAATATAGCTGAAGGAAATTAAAGAAATCCT
GAATAAATGGAGAGAGATGTTAATGGATCATAAGATTCAGTATTGTTTTCAATCTATAGATTCAAACTGA
TAAAAATCCCAGGAGGCTTTTTGGTAGAAATTGATAAGCTGATTCTTAAAATCATGTGAAAATGCAATGG
ACATAGAATAGTCAAAACAACTTTGAAAAAGAACAAACTGGGAGGACTTACACTACCTGATTTAGAAGAT
AATGTGGTATTGATGTCAACAGAAACAAATAGATCAATGGAACAGAGAGTCCAGAAATAATCTATACAAC
TACAGATGTTCCTCAATTTATGATGGGGTGATTTCCCAAAAAACCCATCTTAAGTTGAAAATATTGCTAG
TCAAAAATATACTTAACACACCTAACCTACTGAACATCATAGCTTAGCCTAGCCTATCTTTTTTTTTTTT
TTTTTTTTTTTTTGAGACGGAGTCTCGCTCTGTGGCCCAGGCGGGAGTGCAGTGGCGCAATCTCGGCTCA
CTGCAAGCTCCGCCTCCAGGGTTCACGCCATTCTCCTGCCTCAGCCTCCCCAGTAGCTGGGACTACAGGC
GCCCACCATCACGCCCGGCTAATTTTTTTTGTATTTTTAGTAGAGACGGGGTTTCACCGTGTTAGCCAGG
ATGGTCTCGATCTCCTGATCTCGTGATCCGCCCGCCTCGGCCTCCCAAAGTGCTGGGATTACAAGCGTGA
GCCACCGCGCCCGGCCAGCCTAGCCTATCTTAAATGTGTTCAGAATACTTACATTACCCTGCAGTTGGGC
AAAATCATCTAATATAAAGCCTATTTTATAATACAGTAATGAACATTTCATGTAATTTATGGAATACTGA
AAGTTACTGTACTGAAAAACGAAAAAACACAATGGTTGTATGTGTACTGGAAGTACAGTTTCTACTGAAT
GCAAAAACTTGCAGCTGAGTGTGTTCATTATCTTGGTTGTGGTGATGGCTCCACCATGTATATGTATGTC
AAAGTACATCAAATCGTACACGCAAAATATGTGCAGGTTATTGCATGTCAGGTATACCTGGATGAATCTG
TAAACAATGTAATGAAAGCAAAACAAAAAGATTAAGAGAGCAAAGTTTGTAGGCTAAATGGAAAAGAAAT
ACCACCAAGCGGGGAACCAAATCACAGGGTGGAGGCCCTGGAGGATAAGGGTCAGGAGAGGAGAAATGGG
GGTAGGTCTCTTAAGTCAAAAGGCTGCGAACTTCTCTATTCCATGTTAGGATAGCAGAGTTTCCAAGCGC
TGCATTTGGTTGCTGCTAGATGGCCTTGCCAGGCTAGATAAGCATTGGGCTGTCTGACGATGGTCTCCTG
CATAGTTTGGTCTCCTGTTTTCCTGTGTATGTGACATGCTTAAGTTAGGATTATGTCACTCAATCACATC
TGCAGTGGTACAGCACGCTAGCTGGCCAGGTCGCGGTTTGTCAGTAGTCATGTTTTAAAAGCTGCCCATT
TCTGGGTTATGCATATCTACTAATAATGGCTATAATATGGAATGGAAATTAACTGTGTCATCCAGCTAAA
TTTCAGCTCAGTTTCTGGTATGTATATTAATGACTTCTAAATACTAAGGATGTCAAAATGATTTAGATAT
AATGCTTTTGGTCTAGAATGGGATATATACTCAAATAGTTAATCAAAGGTCTGATCCATGGTGGGCTTAA
GTGGAGAGGCACATATTTCTCTCTTGGGGAGGCAAGGGAAAGGACCACAACATTCTAACTCTCTCAGCCA
ATCCTCTTCCACTATGCATATATAGGTTGTGTGGTACTTGGAATTCCTGTATCATACTTAGCCTTTGATA
TGGCTCTTGAGAGTAAGAGACAACAGAAAAATGTTGCATTTAACAACCTGTTACAATGCTTGTTAGAGTG
TTTTTATAAACTCTAAGGTGTTATGCAAGTGTCATAGTTAATAAAATAGCCTACCCAACACCCAACAGAC
AGACTGGCCATCTTGCCACCCAAATCCTCCCTTGGATAGAATTAGAGGGGGTATGGAATTTAGGAATTAG
AGTGTAATTAATTACATTGATTATCCATAGTCTTTAAAATATTTTAAATTAGAAACAAGTCTATTTAAAC
AGTTTTAAGATTTACAAAGGATGAAACTTTTCATTAAATGAAAGAAATAGAGGGGTTAAGCCAGGAAATC
CTATTTTACATTAAGAAAATTATTAAGAGACACTGGCTTAAACCCTAGTTCCCTCTGAGTTTATAGGGAG
AGTTCCCATGGAGTGGGTGGGTGGAGAAGACAAAGACATAGATGGATGCTGATGAGGAAAGATGCGGGGG
TCCTTTTCTGTTGACCAAGAACACTGGGGCAAAGCACAGTTGAACAGCAGCCTGCAGCCTCACACCATGG
CACCTTTTGAGTCCCATCTGCCCTCATGTGCTGGGGGCAGGAGGTGGTGACAGAGGGCGTGGGTCATGGC
CAGAGGTTCCTTTCCTCAAAGCAAACAAGCAAACGCCACATACGGCTCCCCAAAGCCAGGACTTCTTCCC
TTTGGTCAGTATTCTGGGACTTCTATTAGCACATTAGATTTTTCTCATTTATTTGCCTTCAGTCAAGGAA
AGCTTATGTTTTCATCCTTTGAACAAATCAGACGTGGCAAATCTTGAAGGAGAGGTGGCTGTCCCCCACC
ACTGTGCTGCTCAGAATGTCACCAGGTGGGCTGGTGAGAGGAGCACACAGCTGTTCCCAGCTGATAAAGG
GGAGAGAAGATTGTGTCCTTGATTTTATTTCACTTTCTTTGGTATGTGTGAGGCATGGTGCCAAGATCTT
GGTTTTTTTTGTTTTTTTTTTTTAAACTATACTTCTTCCGTTTCATCAAAAGTAATTTAATTTTGTTTTA
CAGTGAATCCTAACTGATGTTTTTACTTTTGGGGGATGGAGAGGGTGCTATATTTTTGTGGTTTTCTGTG
CCTGACTGGGCAGAGCTTTGGATCTTGTCCCTTGCCCCATGCTGCCCAGGGCCTGCCACTTAGCAAGTAC
TCTGTAGATATGTATTTGATGAGCAAGGGCCTGAGCATGGATGTCTGAGGTGCAGGCACGCACTGCTGAC

TGGAGAGCCAGGCAGCAGCATGGGTATTCTTCAGCACAGTTCTTTTCTGGGAGGGTATTTCTTTTCTATG
TGATCAATGAGAACAGGAGTCTCCAGGATAATTTTATGTAAGTCAGTCTTTTTGTATATACACTGCCCCC
CTACCCCACCATATGTAAAATGGATTTCGCATATGCCTTTCCACAACTGCAGTGCCTCACCTCCCCAAAC
CGCTGTGGCTGATGGACTCTGGGCCCCAGGTGGAGCTGTGCTGCCCCTACAGCCTGCAGAAGGCCCAGGG
TCTGGCCTTGGCAATGACTGTGGTTCGTGAAGTGGGTAACACAATGACACATACGTGTTCTCTGAGGGGA
AACTTCGTTGCACACAGCCCAGGGAATTTATGTTATTGTAACTTTGGTTCTGAGGCGTTCTTTTATTATT
ATTATTACTATTATTTTTAGTAACAGCTTTATTGTGATATAATTCATTTACCATATAATTTATCCATATT
AAGTATACAGTTCAATGTTTTTAGTTTATTCACGGTATGTGGTGCAACCATCACCACCATCAATTTTAGA
ACATTTTCATCACCTGAAAAGAAACCCCATGCTTCTTAGCCATCATTTCCCACTCCCTATCCCACCCACA
GCCCTAGGCAACCACTAATTTGCTTTTCTGACTCTATGGATTTGCCTATTCTAGACATTTTATTATAAAT
GGAATCATACAACATGTGGTCCTTTGTGTCTGGCTTATTTTGCTTAGCCTGATGTTTTCAAGGTTCATCT
GTATCAGTACCTCATTCCTTTTCGTAGCTGAATACTATTCCACTGTATGGATAGACCACATTTTGTTGAG
CCATTCGTCAGTTAGTGGACATTCCACTTTTAGGCTGAGTTATGCTGCTATGAACATTTGTTTATAATCT
GAGGATTTGTTTTTATATTTTCAATCTTTGTCACTTTGAACTGAGACATGTACAGGCACACAATTTTGGC
TCCTTTTGGAATTCCCAGACATAGTATTGCTTGATGGCAGCGGAAGTCCATGGAGCACATGTCATGCAGC
TGAACACACTACGGGGTAGTTAAAAGGAAGTACTTGTTTATGCAGATGGGGTTAATTTTAGGGAAAGTAA
GCTTGAAATAATTTTCTCTGTACTTTTGATAATTTTCTGTGTGTACCTAAAACATACATTAGCATGCATA
TTTACCATTTCAAATATGATGTGTGTTTGGCTAAAAAAAATAAGGGTCTGGCCGGGCACAGTGGCTCACG
CTTGTAATCCCAGCACTTTGGGAGGCTGAGGCAGGCGGATTGCGAGGTCAGGAGTTTGAGACCAGCCTGG
CCAGCATGGTGAAACACTGTCTCTACTGAAAATACAAAAAATTTGCTGGGCATGGTGGCGCATGCCTGTA
ATCCCAGCTACTAAGGAGGCTGAGGCAGGAGAATTGCTTGAAACCGGGAGGCGGAGGTTGCAGTGAGCTG
AGATTGTACCACTGCACTCCAGGCTGGGTGACAGAGTGAGACTCTGTCTCAAGAAAAGAAAAAAAAAAAA
AGGTCTGTGCCCTCAAAGCACTCATGTCCAGTCTTGCTGAGGGCAGAAGGGTGGCTGTGGGGTGTGTGTG
GGGACAAGGCAGACATCCAGCATGTGGGGCAACATGGTGTCTCTGCTGAGGATGAACAGGGCACTGTCAG
AGTATCAGGGGACACCTCAGACCAGACTTAGGGTGGGATGGTAGGGAGGTTGGGGGAAGCTTCCAGAAGG
AATTTCTGACCAGGTTGGAATCTACAGGAGGAATGGGTATAAATGAGCAAAAGAATCAGGGTAGAGAAAG
AGGAAGGAGAGAGTTTCCAAGCAGCAAGTTGAGCATGTTCGGAGCACCACACATTCAGGGAGTTGAGAGG
GGGACTCAAGGCGAGGTGTGGTGGGAACTGCAGATGAGAGAAGCGGGGAGGGCCCTGGTACCTCTGATAG
CTGCACCAGGTGGTTTGGACTCTATCCTATGAGCTGGGAAGTCATTAAACGGAGCCCCATGAGCAGATCT
GCTTTTTGGCCTCTCAGAAGGGGACACACGGGGCCAAGGGTGGGGTCTTGTTTCCCCTGCGGTGGGAGGG
CAAGTCATCTCTGGGGCGACAGTGGGAGGTTTGAGGCTGTGGGGGGATTCTGGAAGAACCAATGTGGAGA
ACAAAGTGAGCACAGGGATTGGAGAAGCAGCTTCAGGGCTATTGAAAAGATGAATATTTTAAATTCGTAT
CATCAGACATTATGGAGGTCCCTAGGGATGTGGCAAAGCACTACACTTACGTAATTGTGCTTCAGAATGT
CCCTTGCCTTACCTGAGTTAAACTTAGTTGAATTGAGCTGCCTTAATTGAACTGAAAGTGCCAATAAAAA
TAGAGAACAAAAACTGCCAAAACAAATTCTGTGGTTGCTGGAGCACCAGCCATCATCAGTCTCATGACAG
CCAAGACTCAGCAGCTCCCTGGTTGATTTCACATATTTATTCTTGCTTTGAAATGGAAAGCCTGGAAGAG
AAGCTAATTATTAAAGGGAATCAAGGAGTCAGGCAGGGGTCGGGGGGAGGAGATTTATCTGAGCTGTTAC
TTTGCTGCCATTGGGATGCCACAGTATCTCAATCCTAGAGTTGGAGGGGAGTTAAACACAGGGCAGGGCA
GGATGGGGGAGGCAGCCTACCCAGGACGTGGCTGTGGGGACCTAAGCAGATGTGTTCCTGCATGCGTTGC
TCAGTGAGGAACTGAGGCTCAGAGAGCTCCAGATGGTGGCTAGAAAGTAGGTCTGTCTGACTCCAAATCA
GTGGTCTTCCTGCCCCAGCCAGGTGCCACTCAAGCGAGATGCAGAGGTGGTAGCAGGGGCCCTGCCATGG
CTGGCTGCGGCACGTGGTACACACAAGGAGGTGGCAGAGGAGGCTTCATCACATTGGCCATTCCTTTGTT
TATTAAACTCCCTTTAGATGGGGAGCCCTCCGTGGGGCTAAAAGTAGAATTAATCTCACCTTCTGACCAT
CTCTGTATCTGTTGCTGCAGATGAGAAACACCACGTAATGATTTCGGGAGACTAGATATACTCGCCACGG
CAAGGCCACAATTATGGGCCTGGTGGACACTTCAGGTGGCAATTTAGTCTGTCTGCATTAGGCCAGGCTT
CTCTTCTAGCTCTGTGACGGGGCTGGCTCTCAGGGAAGATCCCCTGGGGGAGGTAAGACCATGCTTATAA
GCTCCTGCCACACATGCAGCTGTCAAAGCAACCCAGATCACCTCGGAGCAGGCGCACGGAACAGCTGAGC
ACACGACTTCTGCTCCTTTGCTCAGAGCAATGACTTCTGGCTTTTATTCTTTGTCCAGGTATGTACCCTC
TGGTCACAGCGACCCAGGATGCTGACAGCAGCCGGAAGCTGGCTCACTTGCTGAACGCCGTGACCGATGC
TTTGGTTTGGGTGATTGCCAAGAGCGGCATCTCCTCCCAGCAGCAATCCATGCGCCTGGCTAACCTCCTG
ATGCTCCTGTCCCACGTCAGGCATGCGAGGTACGCGCCCTAAGGAGCTGCTCTGCTTGGGCTTGGGATGG
GATTATGTGCTCCACGGAGGGTGAAGTGATTTGGGAAAAGTGTCTGCAAGTTAAGGAAAATGAATGCCTG
AAAGGGAATGGGGAATTTGTCAGTTCACACACCTGTAAGCAAAGATGGGCACAGAGTGGGCATGGAAGGA
ATGTCATGTGGTATCTTACAGGCTCTGCATGGCAGCCAGTGGTGGCTCATGGGTTTTTCAATTGCTGGGG
TTTATAGCCTGTTTATGGAGTCCTAAAAGGGGCAGTTCCTCCCCTAACACGAACTGCCACCCCTGTTTAC
ACCACCCAGGGCTGAGGCCCTGAGGCCACTTTTTGTGGAGAGGCTAAGACCCGCTCCCCTAGATGGCCCC
TCGAGCTGGTGATGCGAAGAAGTGCACAAATGCTTCCCTAAGAGTTGTTCTTTCGGTGGCATCAGGAAAT
TAAGGATAAGACTTAAGAGAAGTGGTGGACCCAGCAGATTTAGGAAGGCAGGGCTGTAGGTAGGGCATGT
TTCTGATCAGGAAACGTAATTGTGTGTGCTGATGAAGAGGGTGTGCAGTGGTGGCTACTGTTGGTACAAT
GATGCTCAGTGCTTGGTGTCACCCACGATGAGGGTAGCCTTGCCCTGGAGCTGGAGGAGGGGAGGGGAGG
GTGGAAGGTAATTAACTGGTCACTGAGGAGGCAAGTCTAGAGGCTGTGGAGAAGGACAATATACACCTCG
AGAATCTTAAGTGAGATGAAGACCTCTGCCTTTCCCCTTTAATGATTGCTCAGCACATAGCCATTTGCAG
AACAGATCCTGTGTTTGTAGATTCCTTCATTGTGAATTTATCTGCTTGCTAAAATTTATTTGTAACCCCA
AAATCAATATTTGTGGTGTTTTTGAGGTCATGAACAGAGTGGCAGAAATTTTGAGTTGCCCTTTATGTAC
AGTCCCAGCTGAGATGGAACAAGCAGCTGCTCTCATACTGTCAACAAGTGTCCTTTACTTGGTCTACTTA
GTGCCATGGTTTTACATTTTTGTGCTTTTGGTGACTTCACTGTTTAAAATGCCCCCCTGGTGTGGTGCTG
AAGACCTGTCTAGTGTTCCTCGGTGTGAAAAAGCTGTGATGTGCCTTATGGAGAAAGTATGTGTTAAGCT
TTGCTCGGGTGTGAGTTATAGTGCTGCTGGCCATGAGTTCAATGTTAATGAGTCAATGGTATTTATCACA
TAAGGCATCTTTAGAAAGAAACACACATAAAACAAGGTTTTGTATTGATCAGCTGATGAAGATGTGGCCA
GAGGCTTGCAGGAACCTAACCCTGTATTTCCCCTATGAGTGAGGATTCAGTGTTCACAGTGACTTTACGG
AACATAATTACCGCAAACAATGAGGATTGATTGTCCTATGTGTCAGGCCATTGTAGGTGTGTGGTGGGAC

ACAGAGGCTGACAAGACATCGTCCTTGCCCTTGAGCCTAAATTATCAGGGGAGCTGGATGCACGAGCCA
TGGATAAATGGGCTGGGGAAGAGTGGGTTTAGGGGTGGGGTAGACTGGCTCTGAGCAAAGAGAGCCGGG
GAAGGCTTCGGGGTTCCTGTGGCTGCCTCGGAGGAGGGAATCTCAGCACCTTTTTGTCCCCATAGTAACA
AGGGCATGGAACATCTGCTCAACATGAAGTGCAAAAATGTGGTCCCAGTGTATGACCTGCTGCTGGAGAT
GCTGAATGCCCACGTGCTTCGCGGGTGCAAGTCCTCCATCACGGGGTCCGAGTGCAGCCCGGCAGAGGAC
AGTAAAAGCAAAGAGGGCTCCCAGAACCCACAGTCTCAGTGACGCCTGGCCCTGAGGTGAACTGGCCCAC
AGAGGTCACAGGCTGAAGCGTGAACTCCAGTGTGTCAGGAGCCTGGGCTTCATCTTTCTGCTGTGTGGTC
CCTCATTTGGTGATGGCAGGCTTGGTCATGTACCATCCTTCCCTCCACCTTCCCAACTCTCAGGAGTCGG
TGTGAGGAAGCCATAGTTTCCCTTGTTAGCAGAGGGCACATTTGAATGCAGCGTTTCCACACTCAATGGC
CTCATAGGATCTCAGTGTGGTCTTTCTTACTTTCCTTCTTCCTTCCTCCCCTTTGTGAAACATCTTAAAG
GTTTTGGAATGAATGGTGGAAATCTGACTTGGAAGGGCTGCGAATCAGAAAGGGGAGAGGAAGTGACACG
CTTACAGAAGTGGGCTAACCCTTCTTGTGTGGCACACACTACCCTTCCCTCTGAGAGTTGACCTTTGCTG
TTTTCCGGACCACTCCATTGTAAGATTGAAAACCCCTGTGGCAATTGCGTACTTACCTCCCAGGCCTGTG
GGGACTGATCATATCATATGATGCTTATTCTGTCAAAGGCCAGAGGGACTGTGGTTAAGCTGGGATGTGA
GTCATGTTCTCTCCCTGACCTTGCTGCCAGCTGCACACAGATTTGTCCCTCTCGATTTGTATTCACAGAG
CCTGCCAATAATTTGGGGTATGTGTGTATGAGCGTGTGATCATTTTCATGCAGGACTGTGGGAGATACAA
ATCTCGCTGCTTCTGGAGCTGCTCTTCCTTAAACCTGTTGTCCCATGGGGCCAGCGTGGGTGCTGGAGAA
AGGCCGTGTTTGCAGGAATGGGGTTCTCTCCTGTGGGTGTGGGTGACAGCCACAGTGTTTCCCTGGGGCA
ATGTGGATGCAGTTTCCATCTTGTACAACCTCATAAGTAGCAGCCACAATTGCCCCATCAGTCACCACAA
GTAGTCAGGGATACTTTGGGCTGTGGATGTGTGCAGTGTGCTGTTTTATGGATGGATGAGTAGCTATGCA
CCCCAGTGTGTCAGCTCTGGGGCCACACTGTATAGCCTTGATGAGTACGCCCCTTGAACAAGACCCAGTT
TGTGAACTCTCCTTAAAGAGAAATATTTAGGGATAATTATTTATAGCAAGAAAGAATTCTTTTACACTTG
AGAGCTCTTTTAAAAATATTTTCTTATTGGAAAATTTATATGGTGGGCAGGGTGAAAAAGAAACAGTAAA
AATATTAGTTCTTATTCCAAGTGGAACATAAATAGGACATGAAGAAGGGCACCTCTGAAATGACAACTTT
AACTCACCTTTTAAAAGATGTGAAATTTCCAGTTTTGGATACACGGTGAATATGTAAAATGAGTAACAGC
ATACTATGGAAGCCAGCAATTAAATAATCATGTTTCATTATTGCAGTAACGTTTTAAACAATTACCTTGT
GATATGATATTAAATATATTTTCTTTTTGAAAATATGTTCACTTTGGGTAGCACATCCTGTATTTACTAA
GTCATTAGGAAGACTGCATTCAGTGTTACCAAGACTGGTTTTTGCTAGTAAGACCTCGAATAATCCATAA
TTTTGATATTGGTGCAATTTTACTATAAGTTGAGCTTAGCTGTTTCAGAAATGCTTGGACAAGTACCTAG
AGAACACACTGATGTCTGTGTTCTGAGGCAGTCTGAAGTTATTCTTAGAGACTCAGTTACAGCTTTAGTA
AGATTTAGTACAGGCAGGATAAGCTTGGTTTCATAGGAACCAGGGAACCAGTGTTAGTGTCAGCTTCTTT
CCTCCTGGTCAGCCTAGAATCCCCCACTCCCAATAGAGGGGTTTGGAAGCTGGAGAGTAGGAAGTAAGAG
GCAAAGAAGGCAGCCTTCAGCAACTCATTATCTGCCAGTGAAATTCTATTAAATGTATTTTTAAAAGAGA
TTACCAGGTAACAAAAACATAAAAAACCAAAACAAGGCCAGATGTGGTGGCTCACGCCTGTAATCCCAGC
ACTTTGGGAGGCCGAGGTGGGCGAACCACTTGAGCCCATGAGTTTGACTCCAGGCTGGGCAACATGGAAA
CCCTGTCCTACAAAAGATACAAAAATTAGCCAGGCGTGGTGGTGCAGGCCTGTAGTTCCAGCTACCTGGG
AGGCTGAGGTGGGAGGATCACCTGAGCCTGGGGAGATCAAGGCTGCAGTCCATTGCACTCCAGCCTGGGT
GACAGAGGGAGACCCTGTCTCAAAAAAAAAAAAAAAAAAAAATTGCCACGAAATATATATATATATATAT
ATAATTTTTTTTTTTTGAGAGTAGATCTTAAGACAGAGATCACTTCTACTCCTGGGAGTGAACTGGCAAT
GGCAATCCCTTTAGAGCCTCGAGTGGGCAGTATCAGGAGCGCCGCACAGTGAGTTTCCAGCTGAGCTATT
CTCACCGAATCTCGCTCTGTTCTCACAGCACCCCTCTGTCAGGCCTGTCTCATAGTGACTGCCCACCAGG
ACTGACTACAAAAGACTTGACCCTAAAATAGTCTTGAAGGGATTTTTCTCAAAAAATTAAGGCGGGAACA
CAAGACAAAGCTGTCAGCCTAGTCACAAATCTGAAGACTCAACTGCATTAAAAATAGTGCAAAATCGGCA
GGAGCTGTACAGTGCGAGTCTTGGTCTGGAATACTCCCCCTGCTAACTCAGCTGGAAGGGCAACTATCTT
AGATTTCAGTAAGGAAGAAAAATCAGTTACCAATACTTGGCAGAGCCATATTATATATCCATATATATTT
ATGTATATAAGTGGAATTGAAGCAATTCTAGAATTTTCTAGCATGTGAAAGCAGGGTTTAGTTCTTATTT
ACGTCTGCTAAGGGACTTTTCAAATTCAAAGTGAACCTTCTGTTTATAGGCCTATTTTGAAACAAAGTAT
CCTCACTTAATAAGATTTGACACCTTTTTTTTTTTTTTTTGAGACAGGGTCTGACTCCTGTTGCTCAGG
CTAGAGTGCAGTGGCGCCATCATGGCTCACTGCAGCCTCGACCTCCTGGGCTCAAGCGATCCTCCCACCA
CAGTGCCCCATCCCACCCCATTCCCGCCCTCGCCGAGTAGCTGGGGTGCACACCACCACTCCTGGCTAAT
TCTTTTAATATTTGTAGAGATGGGGTTTTACTATGCTCCCCAGGCTGGTCCTGAACTCCTGGGCTCCAGC
GATCTGCCTGCCAAGGCCTCCCAAAGTGCTGAGATTACAGGCATGAGCCACTGTGCCCAGCCCCGCCACA
TTTTTTTTTAAGTTGCTGAAAATCTTTTAAAAAGATAAAAACACATTATTTAGTATCTAAAGATAATATC
TGTGCCAGACACAGTTCTCAGTGCCTCAGACATTCACATTTAATCCTTATTATAATAACTGCTATTTCCT
TATTTTCTGGTTGTGGAACTAGACACGGTCTAAGCAAACTTGCTGAAGGTCACGTGGGGAGTAGGTGATT
GAGCTGAACACAGGCAGTCCAAGTCCAGTGCTGACAGTGACCATGCACTTCAAACAGTTTAAAAATTTAA
AGAAAAATATTTTAAAACTGCAGAATCTATCAGGTGCAACCTGACATGCACGGCTGCTGTGATTTAAATG
GGGCCCCCTTGTGATACCCCCTTACCTCCCACCACAATGTCCAGAACACCCCTACAGACACAGTAAGTTT
GTAAACCTCTCACATCAAAGTTCAACTCCACCTTTCATATCTGTGTAAATTAAAGCCCACGGGGGCAAAT
TCACCTATTCAAGGTCATAAAACTACTCATGGCAAAGCTTGGACTGGCACGCAAGTCTTCTGCTTGCCTA
GCGGGCCAGTATTGCTCCTGCCCCAGGACTTGCTTCTGTGAGAATCTGCTTTGTGAGCTGAGTCGCAGCA
GAATGGAGGGGCGGTGAAGTTAGGGTTGTCTTCTGCTGTACCTTTAGATCCCATCTCCTCAGCTTAGATG
GGTCTGCATGAGCCTTTACACAACAGCAGCAATGACAGATGGAAAAATAAGATGCATAATCTGTTATTCC
CATTGTCCCATCTCAGGTTCATGAGCTCTAGTGGGTACTGTGATCACCTCCTGTCTGTGACTGCTTTCCC
CAAACACGTGGAATATGTTCCTTGGAAGTGTACTCATGTAAAATTCACATCTTTTAGGCACTGCTGCTTC
CCTGTGGAGTGTGATATACTACAGTGTGAAAACACGTGCCACTTATTCTTTATAGCTCTCAAACTTGCTG
GAATTTTGGCTCCAGTGGCAGCTCTTAAGATGTGCATTGTCTGTGATGTATGATCGTAGTGCCATTTTTG
TTGCTTTGGAGTCAGGGAGGTTTTTTGTTTGTTTGTTTGTTTGTTTTTTAATTCCGAGGATCCTATTCAC
TTGTAGGGCCAGCCACTGGTAAACTGGTGGTGGGTTTCCTCTATGGGAAGCACATAAGGAGTGGTGATAC
CAGCCGCGAACAGTTCCTGTTAACTGTACAATGGATGTTTTTGCATTTGTTTCCTCTGTTGGGTGTCTAA
ATGCCTTAACTGTTGGTCCTATACCTTTTGTCATTCAATGTGTACTTCAGAGCCTGTTGGTTGGCTATAA

TTTGCCATTTTCTCAGACGAATGCTTTGTATCATTACACTAATTTGTTGACTTCATTTGCAGGCTTTACA
TTTGGGCCTTGTAGAAATGAATGTTTGCTGCTCTGTGAAAGCAGATTTTGAGACCTGCTTTCCCTTCCTC
CAGGGAGTGTTTTCCTTACTGTGTCCCTTTAATGTCTATGGCACTGTCGTAGAGAGTTTAACATGATATA
AATAAAGTGTTTCATTATTTTGGCTTTAAAAATGTATTTGTTGGGGTTGAGTGTAAGAACTTACAGTAA
TTAGGCTAAGTAGTGTCTACATTCTATTCTGAATTCTTATTGTGGGGTTAGAGAGTCCTTTGAGAATTTG
ATGAAAACCAGGGCTAGTCTTCCTGGGAAAGGGCACCTGAACACAAATGCTTGAGTACAATTTCAGAAGA
GTTAAGAAGCTCTGCTTTAATGTATCTTCTTAAAAAGAACAATTTCATCTTTAGTCAGCTAATCTCACAC
TTGTGATTGATTTATGACCACAGGTCCTGTGTATACAAGTAAAATGCAGCTCACAAAAGTCCTGGTATCC
AGTGCATCGATTATTTGGATAGATTTTCTGTAATCATTCTGAGTTTGATTAGAATTATATCCTTTACAGA
TGGGGAGAAAAGCAATTCATTCATTTGAAGTTATCTTAGTGCCAAGAGTCATGTGAAAATGTCCCTTGCA
TGTGGGCAATGAAAGATTTGCAGACGATATAAAACCCAGACTACCTCATAAAAGAGTTTTGGGAATACAC
TGAGCTTTGAGTGAAAGAAGCTGCAGTGGCCTCCCTGGAGATGGGGAGCAAACCAGCTTAAAGGCCCTTA
TCCTGAGGAAGAGACAAAAATTGACATGCACAATATTAAGCTTTGAAATGCAGACCACACTTCCTTTCAC
TGCAACTTTGACTTGTCCCGCATCTCTACTTAAGGGCAGAAAAGGCCTCTCAAACACTCACCTCATTTGG
AATGAAGATGGAGACTCTTTTGCCTGAAGCAACGATGGAGCAGTGACCCTCTAATCAACTCGGTGGCCTA
AAGAAAAATCTTGGGTAACATTTTCACTTCAGTTTCCCTCTGGGATCATTGTAATCCATGAAAAAAATAA
TTTTAAAGAAAGAGTTAAAATACTTTGAAGTTAGTTATGTGGTTAAAAACCACCTTCCTTTCTATTATCA
ATCCAACAATTTGATAACTGTAAACGCTAAAGTGAAGACGGATTCTCTTCAGATGGTCTCCTTAACTGCC
CAGGGCTTGCAGATGTCTCACCCATGAGGGGCACCAATGTAGAAAGCTGAGGCTTCATCTACTGATGAGC
TTCACTGGTTTCCCCTGAGGTTTGTGCTTTGGCAGAGAAGGGGAGGAGGGGACTGGGATTGTGTGGTCAG
CTGTGCCTGCCAACAGATGCAGGTTAGGAACTGTGTTCAGTATCTTCCAATAAGAAAGGGGAAATGCCGA
TGCCTATCCTCTTTGTTTAGGTAGAAAGTAAAATGCTACTGGACTTAAATGGGCAACAAGGGGCTTTGCC
TGTTCATTTGCCATGGAGAGGGCTGGGAATCCAGGTGCGGTGGCTCACACCTGTAATCCCAACACTTTGG
GAGGCCGAGGTGGGCAGATCAGTTGAGGTCAGGAGTTTGAAACCAGCCTGGCCAACATGGCGAAACCCCG
TCTCTATTAAAAATATAATAATTAGCCAGGCATGGTGGTGTGTGCTTGTAATCCCAGCTACTCAGGAGGC
TGAGGCATGAGAATGGCTTGAACCTGGAAGGCAAAGGTTGCAGTGAGCCGAGATTGGGCCACCGCACTCC
AGCCTGGGTGACTGACAGAGTGAGACTCTGTCAAAAAAAAGAGTAGAGTAAACTGGGTATAAGATCCTTC
CCTTTGCGTCCACCTCTCATGCCATGCTGCCTTTGCCATTCCCTACAATAGCTGAGGGTCACACGCTGAA
TAATTTAATTTACACATACACGAGGGTCCAGAGCTAAGTTAATTCTGTAAATAAGACTTAGAATAAAAGG
CCCTCTCCAAATATTTTAAAAATAATAATTTTTGTTTTTTGGAAGATTAAGCATACCACTGAACTGCTTT
GTTACAGAATTCAGTACAACAGAAGTCTGGCTAATTTTGTTTTTTAATGAGAAACATCTGAGTTGTACAT
ATCACAAACAGCTTCAAGTTTCTGTACCAACCCCCCGCCCCCACCCCCGCCGTGGCCAAACAGTTAAAAC
CCAAAGCAAAGCATCACTTTGGATGTGAAAAAGTCTTAGAAAATTAACTTACAAAAACATCCCTATCAAG
TCGGTAGTTTGGCATTTACTTTACATTAGTCAAAAGCTCCAGCTAAAATCTAATTTTTTTAAAAAAAAAT
CGAAGTTTACATTATTCATACAGATTGGGCATTGTTAAAAAATATGCACAAATAACCACATCCATGCAAT
ACAATTTCTTTAAAAATTTAAAGCAATATAAAAGAGCAGAGCTAGGTACTGAACAGAACATTTTGGTGTA
TAACCGGCAGCTCAAAATTGCCAGCTGATTGGAGTAAAACTGATTCTAAGCGTATTAAATATGATTGATT
GTTTCCATCAGCTAAGGGTGCCTATGAGTTTCTGAACCATTTCTAGGGTGGAATGTCCTCGCTTGCTTCT
ATAATATATGTGATGGACACCACTGCTCATTGACCATACCTACATTATAATAATGCTGTTTTACAAACAA
ACCAGAATTCACAAAGTGCTTGGCTCTTCAGGAAACTGACATTTCCAGAGATCCCTAAACTAATCAACTA
GTTCTGCCAAAATACCCGGGGCACCTGCCACACAGGTTCCCTGCTCCTGGGGAGGAACACAATCTGAAAG
CTGCCCTGGGCTCCAGGGAGCCCGTGCTGGGTAAGCCCAGAAGAAGTCTGCACAGGTCCCGGGACCTTGC
CAACACTAAGTCACTCAGATTGGTCTGGGGCCACGTGCTGGGCACCCTTGGCAATCAGGCAGGTGGTGTA
GCACTGTGGCCAGCTATGCCCTCTATGTGGGGGGTGGCCCATTGGTGTACCTCAGCATGGGGTAAAAGGA
CCGGGCAAAGTTGTTGGCCCTGAGTGCAGCTGTAGTCTTCTTCGGAGGAGGGCAGCAGGCAGGCCAGGAGC
AGCAGCAGCAGGAGGAGCAGCTGCAGGGGTAGGGCTGCCCGGACCACCCCTTGAGAGGAAGGAGCGCTGTG
GCCGTGTGCTGCCGGGGACCCTGCCAACAGAGGAGGTTGAGAGCTGATTGGGAGGCTCCACAGGCACAAC
CCACTCTATTACCTAAGCCCCTGCTTATGTAAGTAAGAAATCCAAGACCTGAGATTTAAATAGGGCCAAC
AGTTGGGGTTCAGTTTCAGAGGAGAAAACCAGCCCTTTCCAGACAAAAGAAAACCAGATTTTTGCAAGGA
CCTTGATAGTGGCATTGGCAAGACTGAGTCAGTGGGAGTGTGGAGCAGGGGAACGCACTGCTGTCACGGT
AAAGCCCCGTTACCTGCTCTCTGTCTCCTCCTCGCCTTCTGTAGTTCTCACTGCTCTGAACTGCTGGGTA
AAGAAACTCCAGTTAGTAAGTTGAAGACAGTTTAGTCCTATCAATGATAAAAAAAAAAAAAATCCTCCCT
TAAATTATATACCACCTTTATGTTGTGTTACAGCCAAACTTTGGAGACTAGAGTAATACAATTGAGATTA
AACGTCACCTGAAGTAGGAAATAATTAGGTTAATCTACTCAGTTTCAGGGTCAAGTGTGTTGAAGTTTTT
AATGGCAAAATCAGGGAACCCCTTTAGCGACACTATAAGAGCTCTCATTCACAACCTACTGTGATCCCAA
AGAAGAGTGACTAGAGGCAGACTGTAAGCCTCTCTATGGGTCAGCAGAGACCTGTGCTGTCCTGAAATGG
CTAATGGGCTCTTGGAATCCCAAGCTTCCCTCATCTTAGTGACTTTAAAAAATAACCAGTGAGGTTCTCA
CAGAAGGAAGGGGCTTCTTACCTTTGCTCGGGGAGCTGGCACGGATGTTGCAGGAGGCTGGTCCCCCGAG
TCTACCTCGTCGAAGCTGGGCAGGGGTGAGGCTGGGTTCTGAAATTCAGACCCCAAAGGTTGAGCACAGA
AATGTGTTTCATGCATATTCTTCATGATATAGCTCACCCTCCCCTACCTTAAATCAATCTTTTTTTGTTT
TGTTTTGTTTTAGACAGTCTCACTGTGTCACCCAGGCTGGAGTGCAGTGGCACAATCACAGGTCACTGCA
GCCTCAACCTCCCAAACTCAATCCTTCTACCTCAGCCTCCTGAGTAGCTGGAACTATAGGCATGCACCAC
CACACCTGGTTTTGTATTTTTTTTTTTTTTTTTTTTTGCAGAGACGGGATTTCACCATGTTGCCCAGGCT
GGTCTCAAACTCCTGGACTTAAGTGATCCACCTGCCTTGGCCTCCCCAAGTGCTGGGATTATAGGCATTA
GCCACTGTGCCCAGCCTTAAATCTTTCCTGAAGGGGCTCTTCTATTGCTCTCACTCCCAACAACAACAGA
CTTTTTCGGACAAAAAGGAATGTAAACAAGGAAAAGCCAACCCATATTAAAAACCAACCCATAGCACAGA
GCTGGGGAGACTGAGTTTAGCAGCAGCAGTTTGAGTAGATGGTGAGCTCATCACAGGTCGGTGATGAGAT
CATGTGGCCATCAAGAGAGTCTAGTTTTGGCTGCTTAGGAGAAAACAGACCTGCCCTAAGTCTGGTGAGG
CCACAGTCTGGGTATTCCCTTTGTTTTGAGTTGGATCCCATTTTAAAGTAGGCCAGCTATGGTGGCTCAT
GCCTGTAATGCCAGAACTTTGCATTGCTTGAGGTCAGGAGTTCAAGACCAGCCTGGGCAGCATGGCAAGA
ACCCTTCTCTACAAAAAATACAAAAATTAGCCACTTCCTTTAAAAAAAGTTTAAAAATTGTCATCCCGCC

ACTCCCTTTTAAAAATGACAAAACAGATTCAAAGAGCTCATGCAGCTCTTTAAGTCCACACAGCTAGAAA
AAGGGCACGACATGAGGCCCCACTCGGACCACCTGGCCCTTGCTTCTGGCCTCTGTCTTAGAGCATTGCT
ACAACACTGCTGTCCTGTCTGCATGTAATACGGCAATCTTTACAGTTAAAGCTACAAGTAGACTCACCT
GGGTTCCCTGCAAGGCCATTAAATCTTGGGACACTTGCTCCCGTAACTGTTTGAGTTTCTTCTCAATAAC
ATGCACCTTTTCTTCAGCTTCAATACAGTCTTCTCCATGTCCCTTAATGAGAAGGCTGTTTGAAATCTCC
TGTAACATGTCCACTTGAGGTTGACGTTCTACCAGCTCCTTTTCCAGTTGCTGAAAACAGATAAAGTGTG
TGAAACAGTGACCTGTCCAAAGGGAAGCGAGTGTGGACACAGGAGGTTTTCTCAGTACCAGAAAAATTC
CAGAATGAATGATGGGTAGTACTCAACTCGAGAATCCTCTATTTCTCATATCTGCCTGTGTCCTCCAGCC
CAGCACTATTTAGATAGCAAGTGTATTATGCCCTGCCCCTATTTTAATTTCTTTTCACTCTGAAGACAA
TTGTGATGCTGGAGAAATTAGAAGAAAGAAGTGAGGCAAGTGGTGTGGGAAGACCAGGTCCCTCATCCAC
CACGGAAGGAAGTAAAGGGAAACTCTAAAGTCAATCAACCGAGAAACAGCAGCGTAACCATAGAGGTTCA
TACCAGGCAAACGGGCTTTAATTGTTAAGGGTGGTTATCTTGCTTGCAATATGGCCACTAGACACATGTG
GCTATTCATTTATTTATTTTTTTGAGGTGGAGTCTCACTCTGTCGCCCAGGGTGGAGTACAGTGGCACGA
TCTGGGCTCACTGCAACCTCCGCCTCCTGGGTTCAAGCGATTCTCGTGCCTCAGCCTCCCAGGTAGCTGG
GATTACAGGCGCCTGCCACCATGCCCAGCTAATTTTTCTTGTATTTTTATTTTATTTTGTATTTTTAGTA
GAGACAGGGTTTCACCATGTTGGCCAGACTGGTCTTGAACTCCTGACCTCAGGCGATCCGCCCGTCTCAG
GCTCCCAAAGTGCTGGGAGCCACCGTGCCCGGCCTACATGTGGCTATTTAAATTAACTAAAATTAAAAAT
TCAGTTTCAGTCATAATAGCCACATTTCAGGTGCTTTAAGCCACATGAGGTTATTAGACAGTGCAGACAC
AGGTCATCTCTATCACTTCAGAAAGTTCTACTGGACGCCACTGCTTTGCTTTGCAAACATTTTAGGAAGC
TGTATTTTTAAACAATGGCTAGCACTCTGATTAAAATTTAAAATATTTAAACCACATACAGATTTATGGA
TGAAAATGTCACCTTGAGCACCAGTGAGAATACAGAAATCTCATCTTGGTGTGTTAGTGACAAATACACC
AGGACACGACTCTCCTCCAAGAAGAAAGATTTTTCCATAGTGGATACAGAAAACCCATTCAGCTCATCAC
AGGTGTGAAGCAAATGAGCACCATATTTCTCCCCAATGAGCAGGATTCACGAGAGAAAAATACTTCCACT
CAAATGGCCTTAAGTTCCTCAGGATATCGAGAGCACCTATGTCCTCAGTTCTGTGGACTGTGGCTCTCCA
TTCCTGCAAGTCATTTGGCTTCAGAACTACAAAGGGCAGCTCGGTAAACACCAACTGGAGGAACACTAGG
GCTGAACTCGTGCATTTACAGGCAAACACCACTGGCACAGTTCCTGAAATACTAGGCGAGGCTACCTGAG
TGTGCTGCCTCTCTGGGGCTGACAGAGGCTGGTGGCAGTACAGAGCCCTTGGGAGGAAACTTACCATTAG
TTCCCTCCGACACTCTAGGAGAGCCCGGGGGTCTGCCTTTGGATCGGTGACATGAGCCTTCTGCCTCCGG
TTCTTGGCACTCGCTAACCACAGCAGCAGATTTTGACTCAACTGGTGGAAGTCCTTAAAAAACAACACAT
CAGAGCGCGGCCGTGTCTTAGAGCCCTGGAAGAGGGTGTGCCAGGAACATGGCTTACTGCTTCCAATCCA
TCACAGTCATTTGCTTTTCTGGCCTTACCCACTGAATACGAGGACCAGCTTTAAACTAAATGCCAGGGCC
CCAAAATGAGGAAGAGGAAAGAAGGAAGACACTCAGCACAGTGCCAGGAGGCCGCGAATAAAAGTGCCAC
TATGAAGGTAGGGCTTTGGGATGCCCAGCTGATTTTATATATGAAGGCCACACGCATTCCTCAGCCAATC
TGCTGGGTTCTCTGCTGGGTTCCAGTGGCAGAGGGAAACAACCCAACAGGACAGGCTGGGGTGGGCTCAC
GTTCCCTGAGACACAGCCAGAGCTAGGCAGTGGTGCAGAGCTCACACCCGCTGTGCATTTACTGTGTCAG
GTACTGGGCTAGGATTATACATACTGCCTCATTTACTCCTAAAAAGAACCTTTTTAAGGTTCTTTCTAAA
AAGAAAATGGGAATGATTCCCATTTTCAGATGAGAACACTGAGGTCTAGGAGGTTCAATGCTTTGCTCAA
AGTCACATGGCTATTAAGCAGTAACTGCTCCTCTGCTTCAAGGCCAGGTCTCTTAATCACTCTGGCAAAA
GGACAAAAAGAGGAGTTGTGGGGTGGCATCTCTAACCTACAGGTCGCCTGCAGGAACCCTGACTCCAGGA
GTGGCTCTGGGCCTGGGCAACAGAGACGAGACCTGGGACAGGGAGTAGGTCTCTGAGATGGCCGGTGAGC
CTCTGTGGAAACAAATGGTAAAGCACATGTTTCCTGACACCAGCCACATTTGGCTGCACGGAAGCAGCCT
GATGATGATAAAAATATCTGCTGCTCCTACCACGTGGGCCTGGGTACCGGCTCTGGGAGGCGGGCTGCTG
AGTCAGCGTACCTGGCACTGCATGAGCGACTGTCGTAAGCCCCCTCTCCAGCTGTCCACTGCGCCCTGTG
CTGCTTCCCAGAGCAGGCTCAGCTGGCGGAGTCTACTTTGGAGCTCTGTGGATTCGGGGCTCTCGGTTTG
CAGAAATTCCTTGCTGCTCACGTTGACAGAGACCACTAATGCCTTGTAAGTGTCAAAGGCTTTCAGTATC
TCCTACCAGAGAGAGAAAAGATGAGGTTAGGAGCTCTGAAAGTAGGGAGGAGGGGCTCATTTTGAACCTC
AGTAGGGAACAAATTTTCCACACACTTTTCCAAGCTGCGGCCACAGAAATGAGAGTGACCTCGCCTGGGA
CTGGCTGGAAAGCATCAGGTGAGGGAGCTGCCTTAAGGTCTGTGAACTTGGCCAACAGGGCCCCAAAGTA
GAGGCCTGCTGGAGGGAGGAGACCCTGCTGACCTCTACAGGCCCCGCTCTGCAACTGGCTTAATGTTTCT
GGACCGACTAAAGGTCTTCCAGATAAAGTATATGTGGTTATTCTGCATTTGCTCCTAGAAATGCCAGAAA
TGTTATTCCTTAGGAGGAATGGTAACCCCTAATATATTAACACAGATAGTAAAATAAAAGTACAAATATG
AAAGGTACCTGGATCCTCCAAAACCCCTGCCCTGGGTCTCAGGCTACTGCTCATGGCACCCTTAAAGCGC
AGGGCTCAAACTGTCCCTTTGCAGCTCCCTGGGCTAGTTCCAGTGGGGTCAGGACTTATGTAAGTGACAC
ATCCTAATTGCATAAAAGGGTAATGAGGTCAGGCCACGGGATTCATCAGTAGGTGAGCCGGTCCTTTCCC
AAGCCCTTTCAAGGAAGATTCCACCACTAGTCTTTCGTGTAACTGTGCAGCATACAGTTTGGAAGAGTGG
TTTTACACTGCCTGACAGTGTCCACTAGCACCTCCAGAAAAGTCTAGAAATGCCTCGGATGTCAGATTTT
TCCATCTCTGGAGATCTGAGCCACACCTCCCCAGTACTCTGGGATCAGGATCATTTGCAGATACTCTTCC
ATGTGAAAACAAAAATCTGCATCTATGTCCTTGCCAACTATGGAACTGAAATGGAAGAGAGTGACCTCTA
CATACACCATCTGCAAGCTGCGCCTATGCCACGAATACATGGGATCTGCTCGTCCAGCATAGCAATGCGT
TCACATGCACATTCTGAATCCCTCTTCCCCACCACACCTCTAACTCACCTGCAGTCTCTTCACTCTCAGT
TCTATTTCCTGGATATCAGAGGGAGGCTTTGCCATCTTTAACATTTCCAGCTCTGCTTCAGTTTTTTTCA
GCCAAGTAGTGATGGCGCTGATATCAGAGTTCAGCTGTTGCAAATTTTGTTTTATTTTGAGCTTATTGTG
AAGCTCCTGTGCTTGAATCATCTCCCATCTGTCGAAGGCACCTGGAATTAAAAAATCGCCAATTAAAAAA
AGCAATAATGCAACAGATTTCTCTGCCTCCAGCTAATTAGGGGTCAGGGTGGTTAAAAAAAAAAAAAAAA
AAAACAAAAAAACTGTAGGGGATTCCCCTGACAGAAGGGTCTGGTTTTGGGAGTTCTCTCTTCTCCTGGA
ATGTGGAATAGCACATGATCTGAGGCGTACACTCCCACAGAGGCTGGAATGAAGTGGAAGGTCTATGTGC
TACAGTTTCAAGCTCAACAGTTCAGTTCCTGCTGAATTTTTTCAGTTTTCTCCTTTGGTCCACAAATGAC
CAGGTCGATGCTGTCAGCTTTAGATTTAGTTGAGTAATTACTTTTATAATTACTGGGCTGGTCGAATGAA
GAGACACTTGAGATAACACTGATCATCATCCTCAAGTCTGATCTTTACACACAAATATAGAAAGTGAAAA
CCTGCACTTCCTCAGGAGGCTTATTTTACCAACATTTAAAGAATAGTTTTCAAATTACACTGAACAGCCT
AGGAATTTGTTCGTGAATGCCAATCGCTGATTTAAAAATAACATTGGTTGTTGTAGGGTAAGTCCCCCAG

TTCTGGCGAATCGTATAGTTGGTTAATATCTAATGAATGTTCTCTTGAGCAAGGACTTAAATACCATACT
CTGCCTCTCTGGACGACTGCCAGTTACAGGCAGTACCTGACTGCTGCTCTGTGATACCGGCCAGTCCCCC
GTCTTCCTGCTGTGGGTTGCCATTCAGGACTCGCGGGCCTTCTTTGCCACCATCCGTGCCTGGAGGTAAT
AGTAGCTTTCCCTAGAATGAGCCAGTTTTTAAGTTACCATCTGTAGATATGAAGGATATCTGAAGAACAA
CTGGATTCATTTCATATTAACAGTGAAGAAATGAGATGGGCCCCTTTCCTTTGAAGGGTATCTTGCTAGG
AATACAGTGGTGCTTTAGTGTCTAGGTAGCATTTATAAGCTGGCAAAGCTGATGGCAGAAATAAAGCCTC
AGCTAAGGCCCAGGGAGAGGGAAGCAGATGAGATGTCAGTGATGGGAAGAAAAGGGTCTGTTTCAATTGG
CATGCTTCCAAACACCCCTCAAATGATCCACACGAAACAAATCAGAACAATTTGTTGAGCTTACCAGACG
GTTACTGCGTTAGCACTTTGAATTTTCATAGTGTTTTACAGAATTTTAGTTATCCCTGTCACTCTGTAGA
GGTGGTTGGCATCATTATCACAGAATCAGAAATGCACAGAGGATGAATCTGCCTCCCAGGGGCATTCGTT
ACCAAGTGTTTATCTTTCACCGCACATACTGACTCTTCTGTTATCACACAGCCGATTGGGCTGTTATCTC
GGGCCTCTCCAAAAATAAATGTGTCCCTTTTAGAAAAGCCCTGCTTTCTTTGTCTTTCTTCTGTCTGTAT
GGCCTATTTGTGCAGAATGAAAATAATAAAAAAAAAACCTTCAGATTTGTGGTGATACATCTGGCTTCAG
ACACAACAAAAGGGTTGAGATTTTGAAACCGGCCAGGTGAGGAACACAGGCGTCATCACAGGAAGGGATA
GCCAAGCCACATGAGCCAAGGATGTAAAGCAGAGGTCAGGGACTGCGGTCTTTCCCCTGTCTTATTATTC
TTTTTAAAAATGACACCTGCTTGTTAAGCAAGAGGAAGTGTTTCTGAATTGGACACAAACAGCCCATTAT
CAGCTGACTTGGATTTGAGCATGCAAAGGCAGAATCTCCTCCAATGATGTAACAATATTCTCTCCTTAAT
TTCTCTCGCTGCTGCCCTAGGCTGCCCTCCCAGGAGCTGCCTAGCCAGAGCATGCCAAGAACTCAAGGCA
GCTGAGGGAAATGTAACTAAGAAGAAACAGCCATTGCTATAAACAACAAACCAATACAGGAATAATAATC
ACGACCAATACAGGAATAATAATCACGACCATTACTTCTGAGGACCTTCTTTTACCTTTATACACAATAA
TCTTAACAACTACTAGGTGAAATAGCTTTAGCCTCAGGTGAGAAAGGCTTACAGAAGCAAGGCGAAGTGC
CTCAGGTACCATGGCAATGGATTGGCAGGGCTAGGAATCAAATCCGTGTCCACTGCAGCACACCATCAAT
GATTTTTTGGAATAGGATGTATGGACAAAAGGTTAACATAACAAAGGCTTGAAGGTTGGATGCAGTGGAC
CATGCCTGTAATCCCAGCGCTTTGGGAGGCTGAGGCAGGTGGATCACTTGAGGTCAGGAGTTCAAGACCA
GCCTGGCCAACATGGTGAAACCCCCATCTCTACTAAAAATACAAAAATTAGCCAGGCATGGTGGTGCACA
CCTGTAATCGCAGCTACTTGGGAGGCTGAGGCAGGAAAATCACTTGAACCCAGGAGGCAGAGATTGCAGT
AAGTCAAGATCGTGCCAGTGCACTCCAGCCTGGGTGACAGAATGAGACTCCGTCTCCACAACAACAACAA
AAAGACAAAGGCTTGAGAGCTCAGGAGCAGTCAGGAAAGCCAGCACCTTGCTTGCTCACTATTTGCACAG
ACACCTGACTCGACAGTAATAATGACTGTTACACCACACCAACATACAGAAAGATGGTTTTTGGCCAGAA
CCTATCTCTAAGTCTAATCGGTTTTGCCGGGGTTCTAATGAAGTATGGACAGCTCAACAGAGACACTGTC
ACCATAAGAAAACCAACTCAAAATATGCCTGGGGAATGAATACACGCAGTTTACACCAAAATCTCTCTCT
CTTGCAAATGTAAGTATGACTCACAGACATAGGCTGTACTCCCAGTGAAGTTAAGACTTACATAGGGTGG
TTTATAAGGGGTGCTGGACGCAGGGGGAACAGGTGGAACATTCCTGTCACCTTCCATTTGCTTGTAGTGA
TGCTCGGGACAGGAAGGGCTGTCGGGAACATGCCACGAGTGGCCATCCGAAATGGATTTACCTGAAACGA
AAGACAGCAAGCGACAGTCTATTCTCTCCTACTGAACGGGTCACGGGTGACATGGCATCAGGTTACAGTA
TGAAAATGAGTTCTGCAGCTTTCCTTGCAAAGCATGCATGTTTGCAAAATGTCAGTATGTCCCAGAAGAG
AATGAGATGAGTCATGCAACTCAGCAACACTGTGCCTTCACTAGATGGGTACACAACGGAGCACGACCAA
CATGATTTGCTGTGGGATGAGTGGCGTTTTGGAGCCAGGGTCTCGAGTGGTAGGGACACTGAGTGGCAAG
GCCGGGTCTGGGGACCAAGATGGCAGAAGGCCTCTCAGGAGTGAGGGGAAGAGTGAACATCAAGATGGAC
TTGGGAACCAAAAGGCTCCTCAGGGCTCTCCCCGACCCACCATGGCAGATAGGGATGGGGCTAAGGATGA
GGATTAGAGCTGCAAATCAAGGAAAGGAAGGTTTTTCCCTCCTGTGGCAAATCATCAGCACCCTTTACC
GCCCCAACCCCCCACCCCTTTCCACCAGGGGATCCCAGTAAAGCAAGGAAACAGTTCCAAACCAAGCCAC
CATGAAGAAAGCTTGGCCCATGCCAAAGGACTTCAGTTAGATGGAGAAAAAAATCATCAAAACAGGCACC
ATGAAAAATTCCCTCTGCACAGGCCTGAAGGGAGGAGAGGGGGTTGGCATCGAGACGGCTCTGGCTTGGA
TGGGGTTTTGTAAGGAGCACGCAGTTATGGGTGAGTACGGCAGTGTAAATACACCATGACACAAGGACCA
AGGCGCATGGTGTCCACAGAAGGCAGAGGTAGACACGACATGGGAGCGAGGTTGAGGATGCAGTGTGCGC
CACAGGATGCTGCCATGTTGACACATGCATGGGCGGGGGCCTACCAGAAGACGCTTTCAAAGTTTTTGTG
GTCATTTTAAGATATGCCTCAGGATTTTCAGGGATTTCTACATCTGAAAAAGAACAATGTCATTTGCCTC
ACTGGAGGTGCCTGAAGATTAATGCCCAAGTATTAACACACAGTAGAAACATTGTCAGCTGGAAGGAGAA
AACTACCCTTTATTTTTTTAATTAAAAGGATTTTGAAAACCAGAAAGATTTTTTTTTCCAGCCAACTCCT
GACTGTCCAAAGCAGGACACTGGGTATCAAAGGGAGAAGCTCAGTCTGCAGACACTCTGAGAAACTCAAC
TGAAAGGGAGGGTAGGCACAGTGGCTCATGTCTGCAATCTCAGTACTTTGGGAGGCTGAGGCGGGAGGAC
TTCTTGAGCCCAGGAGTTCAAGACCAGCTCTGGCAACATAGCAAGACCTTGTTTCTACAAAAAATTTAAA
AACTAGCTGGGTGTGGTGGCGTGTACCTATAGTCCCAGCTACTCAGGAGGCTGAGGTGGAAGGATTGCTT
GAGCCCTGGAGGTTGAGGCTGCAATGAGCCGTGGTCGCACCACTGCACCTCAGCCTGGGTGACAGTGTGA
GACCCTGTATCAAAAAAAAATCACTGATGAGTCTCCCAGACAGCCAGAGCCATCACTGAGTAACCTTAGT
GTCTGAATGTGAATTTCATTTTTTTTCCCCCTTTCATTCCACCTGTGATGAGAGTGAGCCAATTCTCAGG
TAAGTTAAGAGATGGGCAGGATAGAGCACAGGAAACCACAGAAGTCAGGGTCGGCCACAAGATGGACTCT
TGGTCATTGAGAGCTGGCCGTGTTGCTAAGGGGCTAAAAACATAGCCAAACGGGTCACTTTCCAGGGTGC
TGGGAACCCAGCTGTTACCTGACAGTGCGCTGTAGTATGGGCCCTCCTCGTCCTCTTCGTGAGAGGAGGA
GCCCCCCACGTCGCCTGTGTGGTCCCACTCCAGGGGGATGGAGTCCACGCTGACAGGGGTCTCGCAGCCA
GACCGCTCGTGCCCTGGGGCCACTAGATGACACAGGGACTGAGGAGATGACGGTTCCTCGCTCTCTCCCC
GTTTACGCCAAGAATCAGTCTGGATTTCTCTGGGGTCTTCCATGTCTGTTTCATTCTCAGAGGCCTCCTT
TTCATCTTCCAAGCCCTAAACCACAGTATCCAGTTGTTAGAATTAATCAACTCATAGGCTTCTGCAATTA
GAAGAGCATGAGAAGTCTGCCTATCTAGCAGTTTCCAAAAATAACTGCCAATAGTATTTCTAAGGCAGCT
TTAAAAAGATCAGGTTCCCAGGTCCTGTTTCTGGTTATTCCAGTTTAGACAATCTGGAGTGGGGCCTAAA
ATCTGTTATTTTCCCAAACCTCCAGCTATTTTTTCTTAGGAAAAAAAAGCTGAAGTTTGATAATCTAAGT
TAAACAACTTTATCTAGGAGATAAGGAAATGGTGGCCAAAGTTTCATTGATGGTTAATGGCAGGTTCCTC
CAAGAATCAGACTATTTTTGAAAAGGACATTTGAATGTTCTGGGTAAGACTCAAACTTCAACCAGATGCA
CCAGGTTCTTTCTTTCTTATCCTCCAACTTAATTGCTCAGTGTCTGTATTCTGCTTGTGTCATAACGTCT
CTTTCAGTCTAAGAAAAATGACTCTAAGTGGCTGTACTTAAAAATGAGAAATTGTGGGGTAATTTTTGAG

GCTGTGTCTGATGAAATAACTACATTTGAATGTGGCCAGTTGGAGACACAAAAAAAGAAAGAGTGGCCAG
TCGTATCGGTCAATGGTTGTCATTCAAGCTTCAGGCACACAAAGGCAGTACGCTTTGAACAGTGGCCTTA
ACTCCACCTGAACTTCCCAAAAGGGCCTTTCGTCTGGGGAAACATCAAAGTTGCTTTTGAAACTCTTGTG
TTTTCTCTTCCAAGGTGAGAACAAAGCATCAGAAAGGCACAAATACTAAAAGCTTCCAGCCTCTAAGAAA
GAGGGAAGGGCAAATACATTCCTAAGTTACTAATGTAATAAAAGCCAGAAGAGTTCTTCAAGAATTCTAG
GGGTAGTGACGCATGCCAGACAAGCCCAGCCCTGAGGAATACTTAAAAGCGACTCGTGGAGCATGCGCCT
CAGAAGTGCCATGCTTTCCACTGGGGAATGGGAACTTGTAAGTTACTGTGGCTCTATATTAATAAAAGTG
GAAATTAAAATGTTTTGATATAGCCCTTTCTTTTCAACCAAAAAATAAACCATAATTAACCATTATAAGA
CAGGTCCCCTAATTCTTTAAAAATTTGGTCTCACGTAAACTCTGAGCAGCCCAGGTGCCATTTCTAGGCA
GCAGTGCCCGTACCGGAGTGCAGGAGGTGAGCCGCCGGTGGAACCGGGAGACCCTTCCAAACACCTCCTG
GCAGTAGCGGTGGAGTTCCTCCAGCTCATCCTCAATCAGCACAGCATCCAGGGGCTCGCTCTTCTGAATC
AGCTGCTCCCCAAACACAATGAGCTGATCAATCTTGTTGGTATTTAATGTAATTTCCTGTTGGAAGCCCT
GTTGAGAGAGGAGAAAGAAAGGATTTCAAAGAAAGTTACCCTGAGCTTCCACTGCCTGTTTCTTCTAACA
GGGCCATAGAAAAGCATCCAAATGTCATTATTGTTGTTTTCCTTCACCTACTACTCTAGCTTTAGTTTTT
AACTAAGTGACAATGACATTTTAAGAATTTTAAGTGATTGTCTATATTCCCCCTCACGGGCACTGGCTTT
TCCAATTAAAATAATTCTAAAAGTTTGACACGGGTGGACATTTACTGTTATTAGGTGTGAGAGAAAGAAC
TTGCCATGGCAAAACTTGTTGGGAACAGAACATTTCCCATAATAAGCCACGAATGGGCATTTGCTTTTGC
TGACACAATAATATTCACTGGTGCTGTTATACTAGGGAAGGCAAATTTCCATTTCTCAACCTCTTCCAAA
ATCTGGCCAAGGAGAGAATTACAGTGAGATTAGCCTGTCATACAGATATCAGAAACAATGGGAGAGCGGA
CCTCTGTTCTTGGCCCCACTGGTGACACCCATACTCCTGGACCGTAAAGAACAGTATCCTTGCACGTGAT
AATCTGGTAGTACACAGGTGGGATGTAGCCTGGCTGCTTTAAGAATTCTGAAATTTGCTCTCAGAGTATC
GTGTGAAATTTGCACTTGGCCAGCTCTCCCACGCAAAGGTGTGTTCTTTTGAGAAGAGCTAGGGAAGCAG
CAGCCCTCACATTCAGTTGGCGCATCTTGTCATCGGCGTCACTCTCTGAGAAGTGCTCCACGTTGGTCAG
CTGCAGGTCCATCTCTGTGAGCCACACCAGAATGCTCTCCCTGGTGCCCTCAAATTCTTCCCTCTGGTTG
GTGAAATGCTGCAAAAGTGGGGAGGAAATCACATTTCTACTGACCACGGAACAAGAGTTCAGACAGACAG
CAAGGCCACCTTCGGCCACAAGAAAAGGGTACCCAGAATACTCAGGGAGAAATCTGCCTCTAGGGTACCC
AGAAAGCCCCAGAAGCACTATGTTGTTCAGAGGCTGGGGTCTGGTTCTGGCTTTGTGAGACCAAACAAGC
CCCCTCAACTTCTCTGAGCCCCAGCTTCTACGCTGGCAAGTCGGGGAGAGAGTGGGAATGTTGATTATGG
TCTCTGAGGTCCTTAAGCATTTGAAATTCTAAAATTCTCTAGTCCAAATCAGTGATTTTCCTCTGTCCTT
TGAAGAGCCCCCTGAGGGGCCAGGCCAGGCCTTCTGCCTGTTTTACACATTGGCCTTCTGCAGCTTTTGC
TTGACGGAAGGATTTAGTAGCTTCAAGATGGAAAAGCCTTGATATCAGGATTGAGGCCAGCCTGGTGCCC
CCTTCTGCCTTCACTGATAGAATTCTGAATGTGTCTTCCCAGAGAAAGAAGACTCAGAGCAGTTGTATCA
TCTCCAATTAAGGATGCCTCTCAGGTTACTGCTTCACAGATAGGCAGCTGATGTTCAGATCAGTATAGCT
TCAGTGCCAAACGAAGGCAGATTAGCCACAGCCAGATCGGCAGGAGATAATTAATGCAAGAGGCCGGGCA
TGGTGGCTCACACCCACGATCCCAGCACTTTGGGAGGCCAAGGTGGAAGATTACTTGAGGCCAGGAGTTT
GAGACCAGCCTGGGCAACATAGTGAGACCCCATTTCCACAAAAATTAAAATCAGCCAGGCACAGTGATGC
ACGCCGGTAATCCTAGTTACTCAGGAGGCTGAGGCAGGAGGATCCCTTGAGCCTAGGAGTTTGAGGCTGC
AGTGAGCTATGATCTCACCACTGCACTCCAGCCTGGGCAACAGAGTGAGACCCTGTCAAGAAAGAAGAAA
GAGAGAAGAGAGAGAAAGAAAGACGGAGAGACAGGAAAGGAGAGAGAGACAGGAAGGGAGAGAGAGACAG
AAAGAAATGCAAGGGAGTTGTCTAGGTTACTAGAAAAGCCAATGTCTTCCTGAGAAGGAGGGAGGGGGAG
AGAGAGAGAAAAGAAAGGAAGAAAAGAAAGAAAGCCCAGATTTACATCTTTCTAGAATGGGTTCAACCAT
GCTCTGCCCTGAGAACAGACGCAGAAATTAAAATTGTGTCCTGTAGTCCCTGCCTGTGACAGTCCTTTCA
GTTTATAACTGGATTCACACAGGTTTACACAGCACATCTTCTGAATGACAGAAATCTAAGGTGAATATTT
ACCTTCAAAAACCAAACCTTTGTGTGCTCTGAAATTCAGAGAATAATCACAGTCCCCAACCCCCCAGTGC
AGACAGGGGCTCTTGCATTCACGTGCCTTGTCCATCCTCCTCAGTGCGAGAGCTGGGGGGGGTCCCATAA
AAACAGACAGATGGGCAAAGCGGGGCTCCTTCCAGGGGCCCACGTGTTGCCTTTTCCAGACCCAGCGAAG
CGGCGCCCTGGACTCTGAGCTAACATGCACACCACCACGGGTTACAGAAGTTGTAAAAAGAGCTGTGCGT
TGGTAACGCAAATCTCATCAACAGGCCCTGCCTAAGAAGCCCCACATGCAAATCCCCCTTTTAAAAAACG
AACGTTGGCAGCTTTGGGCTTCTTTGTGTTGGAGGACTGTTAAAACAGCTCAGGCCTGAAGTGAAACCTT
CTACCTGCTGCTTTGTGCCACAAGCCTGCCATTGCGTATCGTGCGTTATGTCTCCTGGAAAATCTACACC
CGAGCCAGGTGCAGAGGAGCTCACCCTGAGTCTCCGCAGGACGGCTGTGACCCGCCTCTGAAGGTTGTCC
CAGCGCTGGTTGCCCTCGTGGACCATCTGCTTCAGCCTGCTGGCCGTGTCTGTGCGGTTCTCCCGGGCCA
GCCGCCGGTACTGCTTGTTGATGAGCTCCAGCTGAGTGAGCCGCTCATGAATCTGCCGCTGAAAGGCCTG
CATCACATGGGAGGGGTCAGAGCCAAAGCATGCAGAGTGCCAGGACGCCCTCCTTCCCTTCTACATCCCA
AGCGACCTGCTGCCAGGGGTTCATCCCCAAACTGCAATGGCAGCAGAGGGCCTAATTCACCAGTCCTGAT
GCCAGCTACAGAACAGGCTTTCAAGTTCATTACATAGCAGCTGGAGTACATCAGCAATGTCTTGCAAAGC
TGTCTCAGCAGCTGGGGGCAGGCTGTGGTTTAGGCAGCCCTTGCCAGAGGTGAGGGGAAGCTGGCTACTT
AGAGGAAGTCATTTCAGCAGCCCCCAGGCTCGCTGCAGGCTTGGTTATGATCAGGAGACCGGGATGGAGA
AGGTGTTTACCTCAAACCTCTTCAGTTCCTCTTTGGCACTCGTGTACAACACCTCTGAGGAATTTGGGCA
GGCTGCCGTCCTCTCAGCTGACTTGAGCCAGTCCTCAAAGCGAGAATAGTCGTCTAAAAACTTCTGCCAC
AGGCGCCACGTCTCCTCGATTCTGATGGGAGCAAAGCAACTTAACACAAGCCATCCCCTCCAAGCCTGTG
CTTTTGCACTTCTTTTATCCCCTGACACCCGCACGGTTTAGTGGGGAGACCCTGTTACCCCTTCTGGGA
AATAAGAGGGACGCCACTTCTTGTCTGTGCTCCTCCTGCCTGGGAGCGCCAAGCAGCTCAGAGCTCCTGC
TTCACAGAGGTTAAAAAACCAGGAGACAGGGCTGCCTCCACTACTGCCCAGCTAGGTCAACGGAAGCACA
GCGGCCAGTCCACAGCCACACCCCACACAGGACAGCTGGGGAGAGACATTACTCCGGTTACATTTTTCTT
GAATAAATCCTTTGATAAGCGTTGGGCCTTCTCTGCCAATACCTGGCGCATTTCTAAGTGAAATGAACAG
AATAGTTACTGTGAATGAGGTCAGAAGGGTGTATTGAGTTCGGCTGACCACGCTGAAGGCATTTGGGGGA
GCTTAGTTCTTACTTCATGCGCCGCTCCATGGACATGGCACAAATGTTCCTCCAGCGTCTGTCCAGGCTC
CTGGTGGTCTGCTGGATCGAGTCACACTCGGTCTCATTTGCACAGGCATCGGAGTCGTGCAGTAGGACGT
CACAGATGTTAAACACGGACTCCACCCCTGCGCTGTGTTGTTCAATATCTCGCTGTAGATCCTGTGATTA
CAACAGAGTAAGAAACCTCTTGAGATGTTGGTGGCAGCAGGAGGGTCAGCATCAAAGGACCTCCGTTCCT

CCCTCCCTTCTCCCAGCTCAGGGGATACTTCCCTGGGTGGATTTCCACCATGAACTTGGCAGTACACATG
GAATCCCTCTCATCTTTGTGCTACCCTTGTGCTGTCAGCACCTGACACAAAGTTTAAACACTGGAAACAT
CTAGGACTTATGCGCTGAACCATGTGAGGGGTGCCACGGTGATGGGTGTCCTCTACGCACTGACAGGTGG
CGCCATTACTGTTGAGAGCCCATCGCCCCACAGACTTCGGGTATGCATGGGATCTACTCCATACCACCCA
ACCCCAAAGGGCTCCAGTTTAGACTTGGTTTCAGGGAGGTCTTTAGAAACTGAGTCTCTTCAGCAGGAAC
TCTCAATCTTTTATCAGCTACCGAACTCTTCAAACACACACCAAATTGTGCATGCAGCAGTGTGGATGCC
CACAGCTTCCCCGTGAGCCCATTCAAGGGCTTCATGAGCCCAAGGGAGAAATTCTGGCAGACAGACCTTG
CCTCCCCAACTGATAAAGTCCAGCCAAAGCTGTGGTGGCTTGGAGAGAGGTGGGGTCTCTGGAGTCTTGT
CCTTTGATGATGATAGTGATGCAGTTCCCCAATTTGGGAAAAATAACATTTATGAAGAGAAAATGCATGG
TCATAGGAAAAAACTGGAAAACCTCTTCACGAATAAACATGGCATTTTTAGTCATCATCAGATAATATTT
CTGCTGTACCCCATGGGTGGGCTGCGGGGAGTGAGAGAGATAAGGAACCTGTTTTGCCATTCTGGAAGAG
TTAGGCATCCCTGATGTCCAAATTGTGTGACAAGTGACATGAGACCACAGCATTAATTTTAATATCCAAA
TTACATTGTGAGAAAGCAAACACTAAGTCAAATTCTATCTTAATTATTTGATAATATACCAATTTCTAAA
ATCTACACTACTTTAACCACTATTAACTAGACTAAATCCAGTTCCCAGGACTCAACAAATTTCAGTTAAT
AAGAGGACTGTACTATAAATGGTAGCTGTCACCATCTACAGAAAGGCAATATAAGCTTCATTCCAGGTCA
CTTTCATATTTAAATAACTTGAGATTACTACTATATTACTAGATGGACCACTATTTTCATACTCTCTTT
TTTTTTTTTTTGAGACAAGGGTTTCACTCTGTTATAGTGGTGCGATCTTGGCTCACGGAAACCTCTACC
TCCGGGCTCAAGTGATCCTCCCACATCAGCCTCCCAAGCAGCTGGCCACCATACTCAGCTAATTTTTTGT
ATTTTTGGTAGAGATGGGGTTTACCATGTTGTCCAGGCTGGCCTCAAACTTCTGAGCTCAAGTGATCCA
CCCTCCTTGGCCTCCCAAAGTGCTGGGATTACAGGGGTGAGCCACCACGCCCAGCCCCTATTCTCTTACT
TTTCTTCATATAAATACACAATTCCGATCATTGAGTGTTTAGGTTGATATAAGAAAATAAAATGCTAACC
CGCCAACTGAATTTTAAATCAGGCAGTTCCTAACACTGATCCCGAGTACAAATGAACACCACCAGGTTAT
ATTCAGAAGAGATGTGTTTTCCACTTGGCCACCCTGTGTGCACTGTGAAGAATGTGCAGGGTGATTTCTT
TAAAGCTCTGCAGTGTGGGTAGAATGCCTGATATGCTCGAATGGTGGGAGTCTCCCTGGAGTCAATTTGA
GGACTAACTTTAAAGTTATTACATCTAAATAAAATTCCAGTTTTAAGAACTCTTACCGGTTCACAGAACT
GTCATGGGCCCTTCTAAAATTAGAAGATACATATCCCATGTAAATACTAAAATAATAAATTAGGAACCCT
AATACTGGTATTAAAATAAATAATACTAATCATTAATAACTGAAAAATGCCCATGACCTCATCTGGCTCC
AGGTGGGTAAGGTCTAGTTGAAAAGCCGAGAGAAGTTCTAGTTTATGGACAATATGAATGCTCTGTATTT
TAATAAACTCTGCAATTATCCTACATTATTTATTCAGCTTACATTGAATCAAATGGCTAAAGAAAACTGA
TTAATATTTAGGGTAAATGGCCGTAAGAAATGAACTCTACAATAATTTATAAAAGACCATCAACATCTTG
GTTAAAAAAAAAAAAAGCCCAAACATTTTCAAAACTTTTCAAAAAACATTTTCAAAAAATTTTTAAAAACC
ATGTAAAACACCACACAATGGCCTACTAGTTACCTTGTACAAAAAAAAAATAAATAAAGTGATAGACTAC
ATTTTAAAATGCAGACCATTTAAGTGCTAGACAAGAACATTTTGCAAGCTGAAATAATCCTACCGCTAGT
AACCACGGAGACCTAAGTCTGCACAAGAATCAGGTTTTAGAAACTGTCCAAACCTAGAGAAAAAGTGGAT
TTAAGAAACAACATAAAACAATGAGAAAGACTTTTGCCAACAGTTCTAACAGGCTCCTGTTCATTTCGTT
TTTCTGCCCCTGGGCAGGTGACACATAACCCTGAGGTTGGGGAGGAACTTGGGGGCCAGGGGGTACAGAG
CAAGAGGAGAAGGGGAGACATGAAACTGGAGAAGAGAATGCAGCCAGAAGAATGAGAATAAAAAGGAACC
AAAAACAGAAGGTAAGGGTGGCTGAGGAGAAGAAAAACAGGCTGAAAAGACAGAAAATCATATAGCGTGA
AGCCCCCAGTGCCAGCTCCTGAATGTGTCTGTGGGAGGGGCTTGGGTAGCAAGTGGGACAGGATGGTATT
GGGATGGTTCAGGGGGTTTGAGGTGAAGCTCAACTGGCCCACGGCAGGGGCTATTAATTAGCCAGTGGAA
GGGTAACTAACAACAACTCCAAGCCACCATCTGGCACCCCACAGAGAAACAAGCAACCAACCAATGAACA
AACTAGGACAGGGATCTTAAAGATTCAATGAAAGTGGTTCGTGATTTAAGTGTCACAAAATTGCCACTAC
TTCCTGTGCATTTTAAAGATGATATATTCCGTAGGAATAACCCCCATTACCTTATACTTAAAGGTGTTCT
ATATAAGAAAGGTGAAACAGAAAGGACTCCTATAGGGTCTGACCCCTCCCCAACCAGGTATATTACAGTG
AGGATCCGGGGACATCATGGCTCTTAGCTACTTTTGGGGGCTGAGGGCTTTTGCAGAAGGCAATACTAGG
TGATGCCATGTTTTTAGGTCTTATTTTTGGAAGCAATTAATTTATTATATTTAGTTTGAAAAGTAAACAT
AGGTAAGGTGGTTGTTTTTTTAACCCAGACCAAAAATGGTCACTAGGTAAGGTTTTAAAAAGTGGCCCAT
ACATAATTCTTTTGTGTGACACATTTGTTTCCAGTGTTTTGGATGGGGTACTTAAGGTCTGAGTTTAGCA
TAATATAAACACACTGTAACTTATTCTTTTTAACAAAAATACTGAAAGTATCCTGAGATCATCTGTGGTA
GGCAGAATAATGACAATGACACCCCCCAACCCCCCAACAAAGACATCCAGATCCTAATCCTGGAATCTGT
GAATATGTTAGATTACACGGCAAAGGAGAATTACGGTTGCTAATCAGCTGACCTTGAAATAGGGAGATTA
TCCTGGATTATCAGGGTGGGCCCACTGTAATCCTAAGGGTCCTTAACAGCAGAAGAGGAGTCAGCTAGAG
GGAGATGTGACTAGGAAGACAGACACAGAGAGATGCAATGTTGACGGCGTTGAAGGCAGAAGAAGGCGCA
TGTGAGCCAAGCAATGTGGGTGGCCTCTAAAAACCAGGAAAAGCAAAAAAATGGATTCTCCCCAGAGCTT
CCAGAAAGGAGCGTAATCCTGATGACACCCTGATCTTAGCCCAGTGAGATCCATTTCAGATCTCTAACCT
CCAGATATATAGTAAATTTGCGTTTTTAAGCTGCTAAATCTGTAATTTGTTACAGCAGTAGTAGAAAACT
AACACAGCATTTAACTTCTTTACAATAATGGTAGTCCTGAACACCAATTCCATTAATTTTTTTTTTTAA
GTAACCAAGGGATAGAAATGTCACTAAGGTGATGCTGAATTCTATAAAGACAGAATTTTCAAATCAACCA
GATTGAAATTATGTGCCATTGTAGGATGGGAAGAAATAAGGCTAAGAGAATAGCAGTGGCTCCAAACTGT
ATGCTTTTGGGAACAAATTCTCTGCAATTTAATGTTCTGTCACACTTCGGATTTATAAAAAATTAACACA
CAATCAACAGCCCCTGCAAAATTTAGCCAGCCATTCTTTAAGGGGAAAGATACTGACAGCTTCCATATAA
TCTACCTGAAAAAACTCACCACTCAGGGTAAATTGTTATTTGCAAGGCCTTGCCTTTTCACAGTCTGTTC
AAAGACATTCATCCTAGTGGATCACACTTGTAAGTAAAACTGATGTGTTCAGTAGCTGTGACTCCAATGA
GAGACGCATTAAAATCTCTGTAATGTCCATTAAAATTCCATAATACTTATATCAATATTCTTTTCTGCAC
AAAGCAAAGACAGAGCCTAGATGACCTCCATGAAAAAGACATGCTTAAAGTTCCAAGGCTAAGTGGAAAA
ACCAGTATTTTTAATTTGTAGCATTACTAAATCATATCACTTTGAAAGCCAGATAACAGGTATCTTTTAA
ACAGTAATTGTAATAGCACTTAGAAAAGTCAAGAGCAGGGAGGGCCAGGCATGGTGGCGCCTGCCTGCAG
TGCCATCTACTCAGGAGGCTGGGGTGGAGGATCACTTGAGCCCAGAAGTTAAAGACCAGCCGGGGCAAT
ATAGTGAGACTCCATCTCTTAAAAAAATGTCAACAGTAGTATCAAATATTAAATCTGGTGAAAAAGGTTC
ACCCCCAATCCGGTCTCCAAGCACCTGTGGTATGTGGTGTGTGGTGGAGGCTTAACATGAAGAAAACAGA
TTCAAGTCTGAGAATCATACTGCTTCTATGGTTGAAACAGAATCTGCCCATAGGTCTGAGAAAAACAGGT

GAACAAAAGCTAAAGAAAGAATAAGATAAACTTAGCTATTTAAAAAAAAAGTAAAGACATATCCAGGCAT
TACAAGTGAGAATGAGCATGTGGCCATGAGACCAGGGAAGGCAGGAAAGTGGATTCGATAAACCAGTGAC
ATCAAAGAGCACCTGTCAGGTGGGTACAATGAGAAACACTGGCAGAACTCAGCAGCTTTCAAACTGCCCA
ATTTCCAGGGTTGGCTCAGAGCATGCATATCTGATAACAAAAATGCACAGAGCATTGCAGCTCTTAAGAG
GCTTCCTAAACTATTGGTCCAAGCATGTTCCTTATCACACCTTTTCTTGTTTTAATTTTTTAAAAAAGCT
GTACCAGACACACAGAATATAATCCCATAAAAACCTTCCTTGGTTAGAAAAGTTGCTTTTCTTTCAATTC
ATTGCCTTTCAAAACTATATTAACAAAACACAACAAAGATCAGTTAAAAAAAGACATAATTAAAAAAATC
TCATTAACCACCAAGATTAAGGTTTGCATCTTAAACAGTATTCACACAGTTTCACAAAAAGCTACATGAA
TGTGGGAGGGAGCACTCAAGAGACAGATATAAGAACATGGAAAGGTGGTCAGTTTTCTCTGGAAAAAGCA
AACCAATGTTATGGAATGTGAGCACGTGAAAACACATAGATATACGGGGAAGGCCTCAGTCAGTGCATAT
CGCGGACACCGTACTCTTGCAAGAGCTCATTTCTGATTGTCCCACCTGCTGCTCAGCGAGCCTCTTCTGG
ATCTCTTGATCATCGCAGACATCATAAACAACAGGCTTGGAAAGCTCAGACTCAATTCGAGCCAACCAGG
TGCGAAGGTTGCTCATGTTTTTGTCCAACTGCTGAATAAAAGCAAAGGTCTCCTTCAGCTTCTTCACCCT
ACACATATTTGCAGAAAAACAAAACGAAACAAAAAAAAACCAGTGATGGAAAACAAAAGCCCAATACTTA
GTGGTGGAAGAATGTGCCAGTAAGAGCATTGCAGGGTAAAAAAGAATCTATTTTGCTTTGATTTTATATC
AGAACAACTCTCATGTCACCAGATACGAGTTCTCAGAGAATATGTGAAGCTTTGCAAGGCTGTTGCCTCT
GTTGATTTTCAAAAGGACTGAGAGTTAATCCACCCATGCAAATGGAAGTCCTATCATTCCCAGAGTGAGA
GCCCCTGAGACCCAGTTCATCTTCCTGGGGCTCCAGAGGTGAGAAGATATGCCATTTTTTCCTAAGTGAA
AATAACCACTCCTGACTTCTGCCCAGTTTCTGCCGTGGGTATGCCTGAGACTGCAGCAGCCGGTGATCTA
CCCTGGGAGATTAAAGATGTTACACGCCTGGTTCACTTGGTGGTATTTGGTCCACAAGGCCTCTCATGGG
ACCCTCCTCTCTGAGTAAGCAGAGAACATGTGCCAAGCCCTACCGCTTCAGTATGAGGGGTTCACCCAGC
CGTATACATTGAACCAGCCCATGCGGGTAGATTATGGGGCATCTCTGTCCGTCTAAAAGGGAGGGGGCAA
AGGAAATCTGCACGCAAGCGCAGTTCTAAATGTGATCTCCCTCGCCAGTCTGCCTCAGCTCCCATCCGGC
CCAACTCGGCGTGGAGCAGATTTGAAAGCACACGCATGGCATGAGTACAACTTGGCGTGCACGTCCACAT
GCTGTCAAGGGGACGTGATGTAGCTGTTGGGGGAAAACAATCTTTTTCTGACATATATACTAAAATAAAA
TGCTCCAATAAACCGCTTTCCTTAAAGTCCTAAAGCAGAGCGAGGTGAGCCAGGATCTGTCCTGGCGTTC
TGTGGGATTTGTAGTTAATTTCAGACATTTAAAAGTAATGGCTCCAATGGAAAGTTCCCACTTATCAATA
CTTACGTTGGGAGATGCTGTCAGAACTGCACCCCATAGCTGGGAGCACTAGAGAGATAAATGGGTGCACT
GACCCTAACTCTCAGGAAGCATTGTGCTCCATGCCACCATCACCTCTTACTTGACCGAACAACCTCCTCT
CAGCCCCCTAGACTTCCTGCCCACCTTTGGTTCTGTAGCCAAAGTGTAAGTAAGTTCTAGAAGGCAAGTC
TGATCCACGCTCAAAGCCTTCAATAGTCCCTGCCCTACCCTGAAAAACCGGTTCAGCCCCTTGATCTCTG
TACCTCAAGCATTCAGGGGCCACTCTGCCTCTAACCTTGCACTCTCTCAGACACTGTGCACCCACCAGGA
CAGGGAGTGCCATGGCCAGGCTGCAGCCGGCCAGTTTCCGCCGCACTCACAGCACCTCCCACAGGGCCTG
GTGGGCAGGAAGCTCTCCACAAATGCTTGGTGAATGGACAAATACGGACAGGCACTTCCATGGGACTGAC
TTCTAGTTCCATTACCAGCTACTTTTAAGATTTAGTGAAAGTCCTTTCACCTCAGCCCCCTTATTTCAAG
TACACCCGCAAAGCTGCTTAAGCTTCAGGGAAGTGGTAGCATCGGGTGAGGTGAGGGCCGGAACTCCAGA
GGCAAGCAGACCTGGGCCCAAGTTCCATTCTCCCATCTAAGAGCTCTGCACCCTGCAATGTACCTAACCG
CTGACTCTGAGTTTCTTCATGATCTGTAAAATTATCCACCTTGCAGGTGGCGGTGAGCTTGAAATAAGAG
GCTGCATGTAAAGTCAGCTGCACAGAGTGAATGCTGGACCACATGATGCTACAATCACGCTTTATTTACA
AGGCATTGGACCTCACAAAGTTCTTTCATCAGTGTTTTATTCTCAAGGGCAAGCTTGGAAGAAGGACATG
TGGTCTGGAGGTGGAAGAACACAGACTCTGTGGTCAGGGCCTGGGTTTGCGTCCTGGCCATGTTTAATGC
CATCTATAAAATGGTGTTAACAGTAGTACCTTCCTTCACTGGGTAGCTGAGGGGACTGAATGAGATATAA
CATGTGAAAGGCAGAATGCCTCGGAGATAAATGCCCAGCAACTTACAGTTGTGATAAGTTTCAAGGAGCC
ATGTTTTCCAAATTACATTCTTACTGCAAACACCACAAGGATACGTTCCCTTCAAAGCCACAGATGATTT
ATTAAAAAGAAAGTAACAGAATCCAGGACCAGGCCTGGATACAGCTGTAACCTAGATCCTGCCTTCATTC
CTATGGCTTCAGAGGTACACCCTCCTCACCCCAGTATCTTGCCACCTTGATTGCCCTGGTTCCAAAAAGA
ACACTCCAGACAACTACCAGGGTAGCTGAGAACCCCTGGCACTGTGGGACAAGGAGTCCTCCAGGCAGTT
CCTGAGGGACTGCCCTCCTGGAAGGCTCTGCTGGAGAAGAGGCCCAGCCACGAGAGCTTCCCGGGGGTGG
GGGAAGGGCTCAGGCTCGTGACCTCTGCACAGCTCTCCTGCCCTCCCCACTTCTCCCTCTTCCCAGAATG
AAATCTCCCACGGCCTTCATCTAGCCCCTGACCCTATTCCACCCTAAGAATCTCAGCCTCTTTCTTATTT
TGAAAAGAAGAGGGCTAGAATCCAAGTATTTATTTATATATATTTTTCTTTTTCCTTGTTTCCTCTCTTC
TAACTTAAAGCAATTAACACACCGGAAGAATTCAACTGGTTAAATGAAAGGAGCTAACTAGCAACACAAC
AGCCTGGGTACAGATCCACAGGACTGTGGTGATCTTGAACTGTTAACCCTGGGGGTTAGGTGTGCAACAC
GCAGAGGGGGTATGGAGAAGGTGGGGAATAATTTGCTTGGTTTCCCCAGGGCTGTGGTATCCAAAATGG
GGTGCTCAGAACAAACCAATGGGGTGTAGGAATAAAATATGAGACTGTCTACTGTCATCCCATTCTTTTA
AAATTTCTACAATGTGTATGCTTTAAAATTATAAACTTAATTATTAAAATAAAACATCTATATCCCACGC
TGATGGCCACATGTGCTAGGCCTGTTGTGCTCCATGTTAGCAACTCATGTACTTTTTTTTTTTTTTTTTT
TTTTTGAGACAGAGTCTCTATCGCCTACGCTGGAGTGCAGTGCTGCGACATGGGCTCGCTGCAACCTCCG
CCTCCCAGGTTCAAGTGATTCTCCTGCCTCAGACTCCTGAGTAGCTGGGATTACAGGCACCTGCCACCAT
GCTCAGCTAATTTTTGTATTTTTACTAGAGACAGGGTTTCCCCATGTTGGCCAGGCTGGTCTCGAACTCC
TGACCTCAAGTGATCCACCTGCCTCAACCTCCCAAAGCGCTAGGATTACAGGCATCATTTCCTCTTCATA
ACAATGCTAGGAGATAGGTAGTATTATTATCCCTACTTGACAGATGAGGAAACCGAGGCACAGAGAGTAA
AGAGCTTGCCCAAGTCACATGGTCAATAGCGGAAGCAGGATTCTAACCTGGGTAGTCTGGTCTGGAGCTG
CTGTTCTTAAGCACTACCCATCCTCTCACATAATCCCACACACACTAACATGCACATACTGGAGATACAG
GATCATTTTGCTGCAGTCAGAGAACATGACCAGAAGTCTGGACTCATAGCTCAGGATACACTGAGGGGTA
GGAGCTGATATAGTAGATGCTACAACCTGGGCTCTTAGCAGGTGCCTGGGGAGGAGGCTGGAAGGCTCAA
TACATGCTGCCCACGTTTCCCCTCCATGATTTCTTTCAGTAAACACTTAACCATTTGCCTTGTCTTGGA
TCCTGCACAGACCCTGAGGATTCAGAGATAGCTGGAAGATAGGACTTCTTCCCAGAGAGGTCATCACCTA
ATTTAGATGTAATGTTGACACTGTAATACAACATAGGAGTTGCTCAATAATAGCTGTTGAAGGAGTAAAT
GATGTTCACTCATACCTTCCAATTTGTCTGATTTGTCTTCTTCATAAAGAGGTGGCCAAATTAGATTTTT
AAAGAAAAGAGGTAAAGACCAGAGCATATCAGAGCCCTTCTGCCACAAAGCAGTGTGCTGCCAGCCTAGG

AGCCACTCGTGCTCCTCAGCCCTGGTTTCACACAGGGCCAATGAAGCAGTGACGGACATTCACATCACAG
GCATACTTAGTGCAAGTTAAAGAGGGGGGGAAGGTGGGAGGGAAGGAAAAGAAGGTCACCAAGTGACAAA
GCACTCATCCAGCCAGGATTTAGCCGGTATATCCCAAACTCCATCCAGAGGCCTAATACCTCCAAATGCC
TGGGAATCTAAATGTTGTTCCTCTGATCATCAGGTAACAACTTACCCTGGGACTCATCAGGTGCACTGCT
GAGCGTGTATCGTTCTGTTCTGTACAGACACTGTAATCTAATTATCACCTGTCCCAGGTCAGGAAGTATT
TGTCTTTTGCCAACCCAGGCAACTGACCTCCACATTGTTGGGCCTTGTTAACACTACTCTTGAAAAATTT
AAAATCTCAAGTTAATATCTGGAAATGAGAAAACCTATTCAGAAACCAGACTGCTGGCACACAGAAGCAA
CCACAACACTGCCTGACATCAACCACCTGAGCGCTTTGCTGCCGTGGCCACCATCTCTGCACTTGCCCAG
GTTTTGACCCAGGTGCTCTTAACATTTCTCACATAGACATTTCAACAAATAACCTTTCTCCAGGAAAAAG
CAGCATGATTTCCTGAATTAAATTCCAGTTATGAGAATCAGAAAAACAAAATTTTTAGGTACAAAAGCGA
AGTCTTCCACCTGCATAGGCTCTTTATTGGGAGACCTGAACAAAAGCAAAATGTTTTCTATGAAACCAAA
CAAAAGAATTATGCCTAAGAGCCGCTTTAAATTAGAAGAGTTCTTTTGCAGTGATTATGGGTAAAAATGC
AGAAAACAATCAAGGCAAATAAAGTTTTTCTTTTAACTAGCAATGGATGAGAATATAACATTGATGAACA
CTGCTCTCCTTCCAAACAAACAAAATCAAGTCAGGTTAGCAACATTCTATATACCAAGCCTAAGCCTTAA
CAATGTATGATGAAGGCTTTACATGTCAAATTTATACATATGGAATAATTTACCATTTAGTCCTATCCTC
TGTGCTCAGGAGTCTACAGTTAAATTATAAAAGCCCTAAATCAGTCTAAGTGAACAAAAAAATTCCTATG
CCTAATTTAAAAAATACTAAGGAAAACTGAGATGGTTCAAGTATCTGAATTTGTACTGAAATAAACAAAT
AGTCAAACCTGCGGGCAGCTGTCAGTTGCAAAAAACACTGTACAAATCCTGTACAATTGTATCTTTTCAC
ATGACTAAACATCCTTATGGCAAAATAATGCATTACTCCAAGATCCTGAAGCCCTGATTTAGGGGCAGAG
GCATTACAATACACGTCTGAGCTCATTGCCTCTTTAAAGCATTTTTGTCACCAGAGGACTTCCATTTTCC
ACACGGCATAATCACTCCTCTGCCCTGCTTGTCAGAGGCAGACTGCAGACACCACACGCATGCTGACGCT
GGGAAAGAACCCATCCCCCGATGGCTGAGCACAAACACTCCGCAGCCACCATCTCATCGGTGATTTCTAT
TGTAACCAAAGCGACACAGCCAGAGAGCAAGACACAAGGGACAGCAGCTGGCGCCTCGGCCCAATGCAGA
GCTGATGACGAAAATGGCACTTACTGTTGATGAGAAAAAATCATTCCTTATGTTTAAGCGAAAGCTCCAA
GTTCCCGGCTGCACCTCCACCTCCCAGGGCCGAGGCAGCCCCTCCCCCTGCCCAGCGTGCCCTCTTCACT
GGTTCAGCATCTTGCACAGAGGCGGACGCAGCCCTCTCCAAGGCTCCTTGTGAGCACGGCTGGCTGGCTC
GCAGGCACAGGGCAATGCCAGCGGGAAGGAAGACACCTTCTCCCCTGCTAACTGCAATTTTTAATCTCAG
TTTTCTTCCTTCCAGTAAACAAATATCTCCAGCTTTTTCCTCACACACACAGTCTTTGTTCTGACGCTAC
AGGATTGCAACGCTGGGGGAAGAAAGTCACACTGTTATCTTGGCTATGGGTTATTTATGAAGTGCTATAA
ACAGAGAGAAGAAACATTTAGATTTGGGGCATGCAAAAGAGGATTTCTGTCCTCCTCAAATTAAATTTCT
CTGTTTCAGGTTTAAAAGAAACAGCAAAATCTGAAGCCCCTGAGTCCAATAGGAATGCCTTCCTCTTGTC
CTCTTAAAGAAGAAATATCCCTGTGGGGGTTTTCTGCTCTGCCCTTTTGGTCCTGAACATCCTGGTTTAG
GAGGGTCATTTAGTTTATCTGCTTTGTGCAAAAAAATTCTATTTTGCAGTATAAAGGGAATTTATTGCAG
AGGAAGAAATTCTGTAATTTTCCTTGCTAGCTCCTCCCAGGGTTTACCATAATGTGTCTGAAAATTCCTC
CTTATTTATAGCCTCAGTTTCTTCGGACAATCCTGAGTGGCAGTGCTTGGTTTGTGTCTAGTCTACCTTA
GACTCATTCCCAGCCTTATTCTGAGACTTGATATCATTTTTCAGGAGTCCCTAAAGACCAACATTTAGTC
ATTATTATATCCCCACCTTGAAACGTAGCAAACACGTGCTATACCAGTGGAATCAGAAGTGCAGATCTGG
CAATAGTTCTCCCAAAATGCTGCATCTAACTCAGGCCCACGTGGTTGGCTGTTCCTGCAACCTGCTGAAC
GTGAACCTCTGAGGCTCAGTACACTGGACCTGCCTGATGCTGGCCATCAGGCCGCTTGCTCATTATCCTC
TTTCCTTTGGGGAGCTCCCCAACCCTCAGGAAGGCATTTCTGCAGGGTCTGGGAACAGCGGCCACCCATT
CTAGAGGCAGAAGGATCAGGCTGATGGGAAGGAAAATGGAAGTGAGGAGCCTCACATCTGGCTCTCCCTG
TGCTAAAATAATCCCTAAATCCTTCCAGTCCCACTGGATCAGGCAACCTGCTAAGACCAACGCAAGTCAA
CTTCGTGACTAGCAGCATTGTTTGGTGTTCCAGAAAACCTTGAGAAAATACAGATAAAAGGAGAGCAATG
AAAAGCTTTATCAGTTTAAAAAGGCACACGTATTCCTGCCCATTCTGCAAGGCATGGAAAACAATCTTAA
CACACAACTGCCACGGTCGTAACTTCTGAGTTTAACGGTAACATTTTAATTGCCACTACTATAAAGTAGG
TGAGCTTTTCAGGTTGGTAGGCAAAATTTAGAAGTTATGCTTGGTTTAAAAAGTTCCTTTTATGGATTTG
ATATTTCTGATAGTGAGAGCAATTCAGTGTAAACAGGAAGGAGCTAATCTTCAAGGTCATACGGTACTAG
GAAAGTCCCTCCTTGTCAGTGGCTTAATAAGGACGACAGGCCTTGCTAGTGGTGCTACCATCAGAGAGAA
ATTCAGGAGAGAACATAAAATTGATGACATTTGTTCATGACATGTTATAACATGACATCTTCCATAATGA
ACATTTAGAAAGTACAGATAAGCAAAAAGAAAATTACAATCATTTTCATTAAAATGATTCCAACCAAGAG
AAAAACCAATGTAAACTTTCTGGGAGGGTATGCTTTTCCACTTCGCTGTCCAACCTGTATCAGATACTGA
ACGCTTTCATCAGATTATTCACACATGCTGCTAGAAAGAGTCTTTAAAGAGTTCCTCACCCTGATCCCAA
GTCTCTAAAAGAATTCATCAAGATGTGCAACCTGCCAGAGGGACTCACTGAAGACACAGCCCCACCTGTG
TCTACAGAGCTCTGGTTCATAGGACAAGCAGAGTTCTCTCATTAAGGAAATGGGGAGGGAGTTCTGGGAA
ACAAAAGTAGATGAATTTTTAAGGAGTTCAACTACTGGGTTTTTAAAAATAAGGGGAGGCATAGGTGAGA
TCAGGTGGCAGGTCAACTCCTTCTCTGGCATCAGTCCTATTGAGGGGATGAGATCCAAGGACCGTCTTTT
CAGAGCTTTGGCCCGTGCTGGCTGTGAACGTTAACCTTGCATCTTTCTGTCTATCACCCAACAATTTGTA
TCTCAACTGTTCTTAGGTAATCCAGATTCCTCCAAAACAGAGGAACACACATATTGGCAGTTCTGAAGGA
CACCTTCTGTAATTTAGTTGTCTGTCTTGCATTCAGAAGTTTTGCTGAGTCACTTTTCAAAGACGTTATC
AAAGGCTGGGTGCAGGTGGCTCATGCCTGTAATTCCAGCACTTTGGGAGGCAGAGGTGGGAGGATAACTT
GAGCCCAGGAGCTCAAGACCAGCTTGGGCAATATGGTGAAACCCCATCTCTACAAAAAACAAACAACAAA
AGCAAACAACTATCCGGGCATGGTGGTGTGTGCTTGTAGTCCCAGCTACCTGGGAGGCTGAGGTAGGAGA
ATTGTTTGAGCCTGAAAGGTAGAGGCTGCAGTGAGCTGTGACTGTGCCACTGTATTCCAGCCTGGGCCAT
ACAGCCAGACCTTGTCTCAAAAAAAAAAAAGAAGAAAAGAGGAGGGAGAGGGGCTAATAGACACAGATAAA
AAAAGTTTAACTCTTCCTTTAATTTGACAAATGAACGTAGTAGCATATAATATTTCTTGTCATCAAATCA
ACTTGGGTTCTACATAGTTACAATCACCAAACATATATATAGTGCTTTAAATGACCTGTGTTGATGAAAT
TACCTGCATGTTTCATAAGAGTGTAGATGTCACCACTGTAAGAAGCTGCCTGAGGGCCCATGAGGACTTT
TAAAAGCTCCCAGAGCAACAAGGAGGGACAGCCAATCACAGGCCTCTTTATACCCACACCAGGGCCCAAG
TAATCTTATGTGCACATTCCTGTCCCGGGCAGAATTCCCATTGTCCTTGGCTAAATTATTTACCTTCTCT
GAGCTGCAGTTTCCCTCTCCGTAAAATGAAGAATCACACTGACTTTGCAGTGTTGTTTTAAGAATTCAAA
TGAAATAATCTATGTGAGGAGCCTGGCACTTAAAAAATAAGCAATGTTGGTTTCCTCTCCTATCTATCCA

ACAATGGAGGCTACCACCTGAAATGATCAGAAATCTAATGTGGTTTTTAAGGAAGCCTATCCTAAATCCC
ATTTTTTCCTCCAGTGAATTAAAACTGATTTATTGAGGCCTTGGACTTCTGAAAACCATTCTTAACCTTG
AAGTTAGTTTTATAGTTAAGATCTTGCAGTAACAAGGCCGGGTACCTATGTAGGATCACCTTCCAATCTT
TTTTTTTTTTGAGACGGAGTTCGCTCTGTCACCCAGGTTGGAGAGCAGTGGTGTGATCAAGGCTCATTGC
AACCTCCACCTCCCAGGTTCAAGTCATTCTCCTGCCTCAGCCTCCTGAGTAGCTGGGACTACAGGTGCGC
ACCACCACGCCCAGGTAGTTTTTGTATTTTTGGTAGAGATGGGGTTTCGCCATGTAAGCCAGGCTGGTCT
CAAACTCCCGACTGCAGGTGATCCACTGGCTTCAGCCTCCCAAAGTGCTGGGATTACAGGCATGAGCCGC
TATGCCTGGCCGATCTTATTTTTAACAAGAGCTGCTGTTCCCTGCCCACAGGGCCAAAGCAGAATACTGT
GGGAAGGATGGAAGAGGCTACATGGTGTCCTGGATCCTGTGGGCAAATGAAGCCATCAGGGCATCCCGCA
GAGCAGGTTCTTGTCGCCACTGTTCAAATGTAAAGTTTGCAGCCTGTGCTTCCAACCCTTCCCTTCCTTT
GTACAAGGCCCAGGGTGAAGTCAGCATCAGGGATTCTATGTAAGGCTGATTCTATGTAAGGCTGATTATG
ACAGGTCCAAGTTTGCTGCCTCAACCCACAGATTCACCTGAACAATAAACTCAGCTAAGAGCTTCTTAGA
TTCTAGCTGTCTGTCTCAGCCTGGCCCTTGCTTTAAAATAAGAAAAATGATTCCCTCCCAAATTCCTTAG
TGCTGAAGGGATTAGCACTCAGCACGTACTGCTCATTTCAGTGTTTCAAATGAGAGGGTCTGGGCTGTCA
GGGAAGTGACACTGCCTAAGTTGAAATCCTGGTTACGTCACATGCTGGCTATGTAACTGTGGGTAAGCTG
CTTAGCTTCAGTCCTCAGTTTCCTTCTTGGTATGTAAAATGGGACAATGGTATCTACTTTACAGAATCAC
AGTGAAGTTTAAGTGAAATCACACATAAAAGGCATATTGTTAAGAATATAGGCAGCTGGCAATATATTTG
CTATTATTTCAACTCCTTTTCCCCCAGCTGTTCTTTCCAAAAAGATCAATAAAATTTTACCCACTGTTTT
ATCTCTTTCCCACCAAAAGGTTGGCTGAAGACAGGCAAAGAGTGAGCGAGGAAAGCAAATAGCCTGTTAA
ACTCCAAAGTGATACAAGCAGAGCATGAACGATTAAAAATGGACTGTCATTCTAACCTTCAGGAAACATT
AGCTAGATCTTGATCCTGTATGATCCATGAATGGGTTTGATGCCATCATACCCTCGACTAGTGCCAAGGG
CCCGAGAAGACTTAGGCTATAAAGGCGACCACAAAGACACAATTTATCCCACAGAAATTATCTTATTCTT
AACGAATGCACTGAAACATTTACTCATTTCAACAAACATCTGACGCGCTATTCTAAGCTCTGAGAATTAG
GTAGTCCAGTTGCAGGCCTCACTAGGGAAAGACCTCTCATCACTAGACATAACCAACAGAATCATCTTCC
ACTCAATAAACACACGACCTAAGAGTCTTCTCATGGAAAAGTAATGAAAACAACCACTCCATAAATGCTG
GCTCATATGTGCTGGCCCCATACCAAAGGCATGACACATATCCTCACAGCAGACAGCACCAGCGGCCTCT
GATGTAAGCCAATTAGACCCATTTTACAGATTTAGCAACTGAGGCCTAGAAAGGTTAAATCACATACTCA
AGTTTCCACAGTGAATAAGTGGGAAAGTCAAGAATGGTTCAAAACTTGTGCTCTTAATCCTTACTTAGGT
TTCCATCATGCATTTCTGTAGGTTTGTTTTTTTTCCCCCAACTGGCTGTGGAGAGAAGTTGAATTTGGGC
CAGTCTATGTTGCCAGCCAAATCCCCCTAATATTTGTCTTCAGCAAACCCTCCACTGCTAAGGAACCAGG
CATGACTCAGATATTTTTTCAGAAGGCCAAGTATTTAGCAGAGATTTAAAGTCTTCTAAGATTTAGCCCC
AGCCCATCTTTCTAGCTCATCTCCTATGCTTGGGGCCAGTGGGGCTTCTCATCACTTCCTGAACGGCTTC
GATGCTGCTCTATTCTGTACCTGTTTGCTCTCAATGTATGTGTCTCTCTCTCTGCCACCAGTAACCGCAA
TCCCTCATTCAGGACCATCTGGGAACGCAGCCCCTCTGTAAGGCTCTTCCTAATCCCAGGAAGATGGGAT
CTGAGCTCTCAAACCACTTGGTTTTACAGATGCTCAGATACCTACTCCCACTAATGTAACTGACTCAACT
TACTTCCTGCCTGTAATTCTCATAGCATTTAGCTCAGTGCCTCTGTTGATTGACTCAGGTTCACTTGTGG
TTTCCAGTAAACAATGAGGTAAAGAAGATGCCAAACTTAATAATTTAAATTATTAAATTTAAATAATAAT
TTAAATAATAAATTTAATTTAAATAATAAATTTAAATAATAAGATAAAAGTATCTTACTTTTATCACCTC
CCAATTCTTTATTCACCTTATAGGTTCTCCTGTATATTCCAAATTCTATGTGTTGTTCAAAACATCTGAG
CACACTGCTATGGAAAGGACCCGTGTGGCCAGTGGAAGCACAGCTGCACAAGTGGTCCCAAGGCCAAGTG
ACGGTTCGCTGTATGCCACGTGGCCACTGAAAAACATCCACCTGGAGTTTGTCTTTAGAGAGGGAATTT
GAAGACATTTAAAAATTTTGGGCATCATCATCATTTTGGGAGGAGAGATAAAATTATCAGCGCTATTTCT
GATAAGATTGCACTGGCCAATATAGCTTTGATTTGTGGTCCTTTGATTTAGGACTGGGCTGCGCCCAAAT
CCACATCCTAGGACAAGACACCCATGGGAGACCTGGCACTCTGAGCCCACACACTTTAAGAGTAGACTCC
TGCCCCTGCCTTGAGTGCAAGTAGTGGGGCAGTCATGGGCCCCCAGCATCCAGAAGCCAGGCCTGTGCCC
TTACCTGATCTGCCATACTGAGGCAGGAGCAACGGGCATGGCTCCACTGTGGGGACACACAAATGCTAAC
ACAGAGGCAGAATTTCTAAACAATACCCCCTCCCAAGGATCCCTTTCCAAATCAGTTTCCAACTCTTCAT
TAAAACTACTCTAATTCATGTAAAGTTGTAAGCTAAAGAAAAAATATTAAGGTGGGATATACTAGCATAT
AATTCTTTTTGTAACACTGAAAGAATTTCCACTCATTTTTATCAAACTTTGCCTTAATCTGTAAACTTAT
AAAATTGCTGGATCATCTTAGAGGAAGACTGGGTTCAGTTTACTAGATCTGTAAAGTAATTACTGTTCCT
GGAGAGTAATCATTTTTAGCCCATTTCTTACCTTGATCCGATGACATCAAAAAGATGTTGCCAACGATCG
TTAATTTTGTTGAGCTTGTCATCGATCTCAGCTGCTCTTGATTTGTTGCTGGCCTTGATCAACTGGTCAC
CCATCTGCTTTAACTGTAACTTGTTTTCACTAAACAAGTTTATTTCTTCCATGCAGTCCTGGCAAAGGCA
CCAAAACATAAAGCCTGGCTAATTAGCCCAAACTCATTTCTTCTCCAGCCACAGACATAGAGTTACCTCT
TGAAATTAAAAAAAAAAAAAAAAATTGGCCAGGCATAGTGGCTCATACCAATAATCCCAGCAGTTTGGGA
AGCCGAGGCAAGAGGATCACTCTAGTCCAGGAGTTCAAGACTAGCCTGTGCAACACAGCAAGACCCCACT
TCTAAAAACACTAGCAAGGTATGCTGGCACATGTCTGTAGTCCCAGCTACTCAGGTGGCTGAGGTGGGAG
GACCCCTTGAGCCAAGAAGGTTGAGGCTGCAGTGAGCTATGATCTCGCCACTGCACTCCAGCACAGTGAG
ACACTGTCTCAAAACCTCATACCTTCTAATGAAGCTAACTTTTCAGTGAGCAGCTAAAAAGTCAGGCAAC
GCGCATCAGGCAAAAGCAAAATATGTAAGGCAATAATTATTTTTAATAGTTATTTAATTCAAAAGCCCTC
TGTTTCCTCTCACAGATTTCTTCTAACCTACGTGGGAGCTGAGGACAACTGAGCATAACTAATTAGGCTG
CTATCAGTTACAGTTTTCCAGAGGTTTGACTGGGTGGTGTTTTAGGTGACTACAGCAAGAATGTTATTAC
TTTTCCCTGTGGAGACCACTGATCATTTCAAAATTATGAGCCTCACTGCTGTTGGCCTCTCCCCTTTAAC
AAGGGGAGCTTCTTTTTTTTTTTTGAGATGGAATTTTTGCTCTGTTGCCCAGGCTGGTGTGCAATGGCAC
CATCTCGGCTCACTGCAACCTCCACCTCCCAGGTTCAAGCAATCCTCCTGCCTCAGCCTCCCAAGTAGCT
GGGATTACAGGTGCCCACCACCACACCAGGCTAATTTTTGTATTTTTAGTAGAGACGAGGTTTCACCATG
TCAGCCAGGCTGGTCTTGAACTCTTGACCTCAGGTGATCCACCCGCCTTGGCCTCCCAAAGTGCTAGGAT
TACAGCAATGAGCCACCACGCCAGGCCAAGGGGAGCTTCTTAATAACAACTAGAGAAACCCTAACTCACT
TGGGGTATCAGCTGACATGTAAGGATATGTAAGCCCCTTCCCTGGTGAAACTTTCTAATGGAGAGAAAGC
AACTCTCCTCGGTACCATGCCCACTGACAATGGTCTCACACTCCCATCTCTCTGGAACCTCCTCTCTTCC
AACTGTTCTCTCAAAAGGATCGAAAATAGTGAAGTCCCTTCAAATTTCTAAAATGCTACTGGAAACACCC

GTAACATTGCCCCTGTTTGGGCTTAGGAGTGAGGAGGGCCGACAATTCCATGGTAGTCATAACTACATCC
ACCTGGGTGTCCTCCCTTACCTTCTGTAACTTTTCAATCATTTCTTCAATACTAATGTCCGCTGTCTGTA
GAACTTTGTTTTCCATCTGCACCAGCCAGGCACACAACTCTTTATTTTTTTCATTGAATACAACCCATGT
ATTGAGTCTGTCTTCAATCTCCTGTTTACGTATGGCCACCTGCAAATGAAAATACATTTGGCAGCTGAGT
ATAGCCAGGAAGGAAAGCACCCCCTTCTCTCCCTCAAAAAAACTGAGTTTCATTCATTTTAATCAGTAGC
TCTCCGCACTCAACCTTGTCTGGTTTTGCCTCTTCTAAACCTAGGGTTTAGCATCAACAGAAGTTCCTTA
CACCTGTGATAAATGTCATAAAAAATAACAAAATAAATACTGTACCTGAAATGTAGCTGATTGGAAGGAT
TGTTTTTATCCAATACTCGTGTGTTACTATCTGGTTATAGTAAAAATTAGAAACAGGAAAGGCTAGATGA
AGATATAACCCAAATCCTTGCCCTTATAACAACGAATCAAATCCTTATACCAACATAAGGACAATGTCCT
ATTTAACTTAAAAACTATTAATCCAGATAGAATGTCAATCAAACATTTATAATGCAAATGGACCAGGAAA
ACTACAGCCGTTTAAATGTCCTTAGTGTTATGCTTCAAAACAAAGCAAAACCAAAAACAATGTACATCAC
TCATTTAACCCACTTGCCCGTTATGCACTGGATTTTGGATGGAAACCATAAAAGTATCATCAACAGCTGG
TCTGCAGCAAGCAGGCTGACCCCAAAATACCCAATACCCCATTATGCATAAGTAACCCCTAAACTGACAT
CAGCTAAGGGTCCTCCTCCTTAAAGGTTTAAATTTCACTAAATATAAATTTAAATAATGCAAATCAGCCT
AACTAGATGTACAAAAGTATTCCCAGGTTTTAAGAATCTTCAGAATCTTAGCGTTAAAAGGGGTGGCTAA
GAGTTCTTTTGGTAAAGTTTTGACACCCCACTATATGGACCAGGAAACCAAGGGTGAATTCTCTGAGATT
TTCCTGCTGTGTATAAAGAAACCTCTGCTCTTTTCGGAGGAGAAAATACTGAATGCTTATATATCCTAGC
CAGCCAAACGTGTTAAAAAGGCTTGAAAAACTATCCTAGAAAAACAAGTGTTGTGTTTCCATTCCTCGGG
GCATCTGTTTATCTTTTAAAAATCCTGGCATTTTGCACATTGTCATTCTGATTGATTTCATAATAGTAAC
AATTAGGAACATCTGGGCCCCAGTCTTCCTGTCTACCTTAACTTTCAGAACACTTTTCATATATTCTAAA
CATTTTCTTTTGTATAAAAATTGAAAAGTTCTAAAAGAACATTTAAAATTAGGGTACATTGTGAATATTA
AATACTAAAATCAAGGAGAACGTGTCTGAATTTCAACTTTTTAAATACATCTCTTAATTCACAAAAATGA
GATTAAGGAATTTATTTTCGTTGGAATTCTCTGTTCTTAAAACAAAGATCTTTAAGACTATTTGAACCCC
TTAATTCAATACTGATCCTGTCACAAGCCTATACCGTGTAATACTCTATTAATACAATCCCATTCTTAAT
AAGTTGAAGTGATCCATTGAGACAACATAGCAGTTGATCATTTCTCTTACAGGATTTTAGAAACCAGCTA
CTTGAAATAAACATCAGGTTCCTGTGAATGCAGAGTACTCATATGAAATGCTCCCATGCCTGGTGGGCAT
GAAGTAAGACTCCTGCTGTTAGGCCCAGAAGAGACTCCCCAGTAAAGGACCTCTTCACTGGGTCCAGCTT
CTGATACACTGATTAGGACTTGCCACCTACACAAGCCAGAGAGCAGTCTACACATCTGATCAGAATTGCA
ATTTCTGTCTCCACTTAAAGTGACTTTTTAAAAAAGCTCATTAAAAGCGTGCAAAGTTCTAGCATTTAGT
GCTGGAGAAACAAAAGGGTCAAATCTGTTAAACCTGTTGCTGCCTTCTAAAGGAGCAGCGGCCGGGCCAG
GGGTCCCACTGAAAAGGGCCTCCGGTTCAATGAAATTAAGCTCCTTTCTACTTTGTCTGGCCTTCAGAGA
CATTTCAATCCACTCCCAAACAGCCGTGCCCTGCAGTGAGCTGACTTACCCTTAAGCAGAGGTCCTCCCA
TTGTCTGTGCAAATGCTCTATTTGCTCCTTCAAAACCATCACATCTTCCACGAGAACGTGCCGGGTTAAG
TCCGCCTTCATAGTTTGAAGTTCTTTCAAGTTCTGAGTCCAGCTAGCCAAAGACTGTTCTAGTTCCTGCA
TTTAATCACAAGAAGGGGGTAAAAAGCCTTCAACTCAAGCGGCTGTTGTTTCCAAACCTGTAGGCTAATC
CTTTGATTAGACTCTGGGGGAGGGGAGGCCAGGAGAGAGGGAGGGACCTTCTGAATGGGAAACAGCCCAA
GACGAGCGCCTGCAGTTGTGGTTGGCCAGTTCTCCACCACCTTCTTATCAAAGGAAAACTCTGTTCTACC
TTTATTTTCATTTCCTCAGGTAGCTCTGATTTTGATAGAATTTATTCTATTTTAAAGTCACATAGGTCTT
CATTTAGAGGAAAGTGTATTTGGAGTCTAATAATCTTTACACACACACACACATGCACACATACAATTTT
TAATCCTGAAACTACATTTCAGATAAAGTGTGATTTTCCATTTAAAAAAACCCTAAGAAATGCATTGCTG
CTATTGTGGCAATCACGTAACAGCAACAACTTCTGTTCACAGGGAATTATTTTTGGTTAACTTTTGAAAA
TAATGAGTAAGTATAACGGAAGAAAAAATAAACTTTTCTAATTGGCAAAGATTAGTTAGCAGATATTTTT
CTGGCCATGGAAACATCTATCTTTTAAAATGCAGCATTGGCTGGGCTCAGTGGCTCACACCTGTAATCCC
AGCACTTTGGAAGCCCAAGGTGGACGGATCACCTGAGGTCAGGAGTTCAAGACCAGCCTGGCCAACATGA
TGAAACCCCATCTCTACTAAAAATACAAAAATTAGCTGGGTGCGGTGGCGCGCGCCTGTAATCCTAGCTA
CTTGGGAGGCTGAGGCAGGAGAATTGCTTGAACCCAGGAGGCGGAGGTTGCAGTGAGACAAGATCGCACC
ACTGCATTCTAGCCTGGCTGACAGAGTGAGACTCCACCTCAAAAAAAAAAAAAAAAAAAAGAAAAAGAAAA
AGAAAAAGAAAAAAAAAAGAAGCATCTGTCAAATTGAAACCTTCTGAAATCTAGGATTTACTCAAGAGAT
TTACTTTCACAGCAGGGAAGGTAAAAGGAAACAACCAGAACACTCAAGAGTCTACCAGATTTTTATTGTG
CTTACAATTCTTCATGACTTGGCACATTTTAAGGGTCTTCACTCCTATCTGTCAAATGAAATCTGAAATA
AGATACTATGCCTTTTTAATTTTTATTTTTTTTTAAGAGACAGGGTCTCACCCTGTTTCCCATGCTAGA
CTACAGTGGCATGATCATGGCTTACTGCAGCCTCGACTGACCTCTTGGGCTCAAGTGATCCTCATGCTTC
AGCCTCCAGAGTAGCTGAGACTATAGGCACGCACCACCACAACTGGCTAATTTTTATATCTTTTTGTAGA
GATGGAAGTCTCACCATTTTGCCCAGGCTGGTCTCAAACTCCCCAGCTCAAGTGATCCCCTTGCCTCAGC
CCCCTGAAGTGTGGGGATGACAAGGGCGAGCCACCATGCCCTGCTGATACTATGCCTAAAATCAGGGATA
AGTGTGAAAGGCCCTAACAATATGTTAATTCTGATTGATTTTCAGAGTTCTAAAAGCTACACTGGCATGA
TTTCATAACTTACCAACAAGAATTTATGTTTAATAAAATGGCCCAGAGAATTCTTTTTAAAGGTTGCATG
AAGATTGAGGAATTAACACCTTTCTCAGAAGATAAATCATTAGGTATTTAACATTTTTATTACCTACTTT
TGGTCTCACGATTGGTTCCAGTAGATGACAGCAGATTCCACAGTGGAACACTTTGGAAAGCTACATAACA
TAAAGGGGGCCACCTGCCAGCTGAGGTGTACCACTTACTGACTTGAAATTGGAGATCTGGAAACCTCTGA
GCTTCAAACAGAGTTTCCCAGTCAGGTGGCAGGAAGCTCAGCCTGTCCAGTGCCCTGCTCAGAGGTGCTG
GCTCGGCCACCGAGTTATGCCCGGCCAGGTTTCAATCAGTTTGGTTTGAATACTTACAATATTGACAATC
GGAAAGTGTACAGTCACTGGATAAGGTTGAGACTCCTGTTTTACTCTCACTGCCCTGCCCTTTTCCCCTC
TAACACTCACCATGTTCATACACATACACACACACACACACACACACACACACACACACCCCTATGCATA
CAGTGTGGCTCTCTGGCAGACTGGACCATTAGCTCCACACATGGCAGGGACCATGACAACACTGCTCACG
GATTCAGTGCCCAGAACCTGCCATGGTGCTGCTGCACAGCAAGTTTTCAGATACCAAAATGTACGGCTGA
AAGGAAAGCAATTTGGCTGTATGTCTCGAGAGCTTTAAAATGTTCATAAAGACTAAATGAAAAAAGCAGG
GAGTCAAACAATATATAGAATGAGGTCTCTTGTGGAAGTTTACTAGAGCTGACGATCAGTTTGTATAAAA
ATGTCAACAATCATGCCTGTCTTTAAATTAAATTGCTCCCTCTCCCTCTCCCCCTCCCCTCCCCCTCCCC
ACCCCCTCCCTCTCCCTTCTTTCCACGTCTCCCTCTGATGCCGAGCCCCCTCTCCCTTCTTTCCACGGTC
TCCCTCTGATGCTGAGCCAAAGCTGGACTGTACTGCTGCCATCTGGCCTCACTGCAACCTCCCTGCCTGA

TTCTCCTGCCTCAGCCTGCCGAGTGCCTGGGATTGCAGGCGCACGCCACCACGTCTGTCTGGTTTTCGTA
TTTTTTTGGTGGAGACGGAGTTTCGCTGTGTTGGCCAGGCTGGTCTCCAGCTCCTAACCACGAGTGATCT
GCCAGCCTCGGCCTCCCGAGGTGCCGGGATTGCAGACGGAGTCTCGTTCACTCAGTGCTCAATGTTGCCC
AGGCTGGAGTGCAGTGGCGTGATCTCGGCTCGCTACAACCTCCACCTCCCAGCCGCCTGCCTTGGCCTCC
CAAAGTGCCGAGACTGCAGCCTCTGCCCGGCCGCCACCCTGTCTGGGAAGTGAGGAGCGTCTCTGCCTGG
CCGCCCATCGTCTGGGATGTGAGGAGCCCCTCTGCCTGGCTGCCCAGTCTGGGAAGTGAGGAGCGCCTCT
TCCTGGCTGCCATCCCGTCTAGGAAGTGAGGAGCATCTCTGCCCGGCCGCCCATCGTCTGAGATGTGGGG
AGCGCCTCTGCCCTGCCGCCCCGTCTGGGATGGAGGAGCGCCTCTGCCCGGCCGCCACCCTGTCTGGGA
GGTGAGGGGAGTCTCTGCCCGGCCGCCCCGTCTGAGAAGTGAGGAGCCCCTCCGCCCGGCAGCTGCCACG
TCCGGGAAGTGAGGAGCGTCTCTGCCCGGCAGTCGCCCCGTCCGAGAAGTGAGGAGCCCCTCCGCCCGGC
AGCCGCCCCGTCCGAGAAGTGAGGAGCCCCTCCGCCCGGCAGCCGCCCCGTCCGGGAAGTGAGGAGCGTC
TCCGCCCAGCAGCCGCCCCGTCCGGGAGGGAGGCGGGGGCAGCCCCCGCCTGGCCAGTCGCCCCGTCCGG
GAGGGAGGTGGGGGGGGCCTCTGCCCGGCCGCCCCTTCTGGGAAGTGAGGAGCCCCTCTGCCCAGCCGTC
ACCCCGTCTAGGAGGTGTACCCAACAGCTCATTAAGAACGGGCCATGATGACTATGGCGGTTTTGTCAAA
TAGAAAAGGGGGAAATGTGGGGAAAAGATAGAGAAATCAAATTGTTGCTGTGTCTGTGTAGAAAGAAGTA
GACATAGGAGACTCCATTTTGTTCTGTACTAAGAAAAATTCTGCCTTGGGATGCTGTTAATCTATGACCT
TACCCCCAACCCCATGCTCTCTGAAACATGTGCTGTGTCCACTCAGGATTAAATGGATTAAGGGCGGTGC
AAGATGTGCTTTGTTAAACAGATGCTTGAAGGCAGCATGCTCGTTAAGAGTCATCACCACTCCCTAATCT
CAAGTACCCAGGGACACAAACACTGAGGAAGGCCGCAGGGTCCTCTGCCTAGGAAAACCAGAGACCTTTG
TTCACTTGTTTATCTGCTGACCTTCCCTCCACTATTGTCCTATGACCGTGCCAAATCCCCCTCTGCGAGA
AACACCCAAGAATGATCAATATAAATAAATAAACAAATAAATAAAAATAAAAATAAAAAATAAATAAATA
AATTAAATTGCCCCAGACTTGCAACCAAACTGTCAAAGAGATAAGTTTCCACCATCTTCATTCAACCAGA
TAAATTATCTATACCACAAGAATACCTGAAAATTTCCAATTTTTTACGTAACATGGGATGTAAAATTTCA
AGTTGTTTGGCTGCGAAAAGCGGTGTGTTGCACAGGATTTGACTGGACTCTGCAGTATCAGGACAGCATC
TAAGCCTTGCCTGTGGACTCAATTACCAGTGGAACTGTCAAGTCCCATTTCTCTGTACTACCATTTGGGT
AAAGGAGGACCAAAAAAGAACGGGTATATAAATAAAATTTGACCTGCATATGCATACTCTATCTTTGGAA
GAAAATACAACAAACTTGTAACATTGATTGCTTCTGTGGAGAGGAACTGATAAGAGAAAAATTTTACTTA
TACAAAAATTATTTAAAAACCAAACTGTTCCAAGGACTCAATCTTTGGACAAGTGTTATGAAACACAGAT
GTCCATTGTAGCAATTTTCATAATAGTGAAGTTAGAATATATGTAAAACATATATGTAAGGAAATTATTC
CATTCCTCAACGTGGCTGTAGTGGGAATATAATTTTTCTTTTTTATCTTTTATCTTTTTCTTTTTGCAGC
TGTGCTTAGAAGGGAATATAATTTTATGAGGAGGAAAGTCAAGCTCAAATTGGTCAAGTGGCTAGCGTAT
TTCCCCCAGGTGAATCAGGGATGAAACACACTGACCTGGACAAGCTTTGGGTTACTTGGGATCTTTTCAG
AATATGGTCACGGGTTGAACGAACTCAATGCTTTTTGCCTTTCCCTGATTACTTTCCACTGATAAATAGG
ATGCTGAGACCGTGAAAGCTGAAAAGATCCCACTGGAAACTGAGAAGTGTGATACTTGAGAAAAATTATG
GCTGCTCAAGGGTTTACATTTCATGTTCTGCACAGGTTTCTAGACCTTATGGAAGGAAACTCTGTGTTTC
AGCTGAGAGCATGACTCCAAATTATTTCCGTTGTTACCAAAGTCTTGCTCTAAGCCTAATGAGGTAGGGA
TGATAAAAACTTTGAAAATTTGGCATAGAAATCTTGTTAACCTAATAAAGCCACTGACTGACACATCACC
ACCAAATATCACATTTAACAGTGAAATGTTAGAATCATTTTCTTCTAAAATCAACAATGGAAGACTCAGC
TATTAATACTTCTGCTTAACAATGTTCTGAAGGTATTGACCCGTGTAGGAAAAATAGGAAAAAAAAAAGT
ATATTAAAAAGAAGAAACAAACAAAAATAACCTTGTCATTATTGACAGATGATGATGGTCTCATAGACAC
CCAAAAAAATACATAAACGAATTATTGGAATTAACATAAGAGTTTAACAAGATGGTTAAACATAAATATG
CAAAGACCAATTACATTTCTAGGCATCAGCAATAATCAGTTAGGAAATATAATTAGAAAAAGGCAGTATT
TTCAATAGCTTCAAAAATATTGCACCAAGAAATAAATCTAACAAAAGATATATCTTTTGTGATTAGGAAA
ATTATAACAAGAATAAGCCAGGTGTGGTGGCTCAGGCCTGTAATCCCAGCACTTTGGGAGGCCAAAGCAG
GTGGATCACCTGAGGTTGGGAGTTAGAGACCAGCCTGGCCAACATGGTGAAACCCCGTCTCTACTAAAAA
TACAAAAATTAGCTGGGCGTGGTGGCGGGTGCCTATAATCCCAGCTACTTGGGAGGCTGAGGCAGGGGAA
TCCCTTGAACCCGGAGGCAGAGGTTTCAGTGAGCCAAGATCGTGCCACTGCACGCCAGCCTGGGTGACAA
GAACGAAGCTCCATCTCAAAAAAAAAAAAAAAAAGTTATAAACCATTAGTGAAAACAACTAAATAATATGA
CCAAAGGGAAATATATACCACAGTCATGAGCATGAGCAGGAATACTAAAAATAATTATCCAAGTTAATCT
AAAATTCAATGCAATTCAATTAAAACTCTTATCAGAACTTTTCATGGTTTAACAAGCTGTTCCTCAAAGT
TACGGAAGATCAAAGACCCAGGGACATCCAAAGTAATGTGAGAGAACAAGGTGTGGGTATACATCACACC
TGAAATAAAGATGTGTTACAATAAAGTGCAGTAATCAAGACAGTTTGATATTAAAGCTGACATACACAGA
CCAGTGGAACAGAGAACTGAGAAACAAATCCTGCGTTTATGGAAATTTGGTATTTGACATTAGACAATAA
ATAGGCACCAAGACAACTGGCTATCCATACGAATAAAATTAGAAAATGGATCTCTGCCTTAAAACGTATG
CAAAAATCAATTCCTCAATGAATAAAGATGTGAATGTGAAAATCAAAAACTAAAAACTTTTTGAAGAGAA
TGTAAGCACGTATTTTATGACTTTAGTATGAAGATTTTGCAAAGGAAGCGGAAAATACAAATCATATAGG
AAAATACTGACCAATTCATCCACATTAACAAAATATCTTTTGTTCAGCCAGCAATACCAAGGAAAACGCA
GAAAAACAGGCTCTCAGATGGGAAAAGACATTTGCAATGTATATACTCAGTAGAAGAGGAATATTTAGAA
TAAATAAGCAGCTCCTTCAACTCAATAAGAAAAAGACAAATAGCCCAATGGAAAAAAATCAGTAAAAGGC
ACAAATAGGCAATTCACAAAAGGGCAAATATGAAAAAAATGTGCAACTGACTAATAAACTATAAAGAGAT
ACTATCTCACAGCTGCTGGATTAGCAAAAGTTTAAAAAAAAATCTGACAATACCAAGTGACTACAGAAGG
GATATATAAATTGTTGTATATTCTTATAATGCATACTATACAGCAGTGAGAATGAATGTGCATTAGGTGC
CAACATCTATGACTCCAAATCACAATGAGGGAAAAAAGTTACATTGTAGGCCAGGCGCTGTGGCTCACGC
CTGTAATCCCAGCACTTTGGGAGGCCGAGGCAGGTGGATCGCTTGAGGCCCCAGGAGTTCAAGACCAGCC
TGGCCAACGTGGCGAAACACCATCTCTACTAAAAATACAAAAAAATTAGCCAGGCCTGATGGCACATGCC
TGTAATCCCAGCTACTTGGGAGGCTGAGGCACGAGAATTGCTGGAACCCGAATGGTGGAGGTTACAGTGA
GCCAAGATTGCGCCACTGTATTCCAGCCTGGGTGACAGAAGGAGACTCTGTCTTAAAAAAAGAAAAAAAA
ATTACATTATATATAGTACTGCTTATATAAAGTTTTAAAATTTATGTATTTTGTTTACTTTTTAGAGACA
GTCTTACTCTGTCATCTAGGGTGGAGCATAGTGGTGCATTCATGAGTCACTGTATCCTCGACCTACTGGG
CTCAAAGGATCCTCCCACCTCAGCCTCCCCAGTGGCTAGGATCACAGTCAAGTGCCACCACATCCAGCTA
ATTAAAAAAAATTTTTTGCTGTACATATGGGGATCTCACTTTGTTGCTCAGGCTACTTTCAAACTGCTGG

ACTCAAGGGATCCTCCCGCTGCAGCCTCCCAAAGTGCTGGGATTATAGTTGTGAGCCACCATGCCTAGCC
ATATAACGTTTAAAAACAGAAAGCAATTCTACATCTCATTGACAGCAGGCTGGGCGCCTGCTGTCACTTT
GGGAGGCCAAGGCAGGAGAATTGCTTGAGCCCAGGAGTTGGAGACCAGTCTGGGCAACATGGCAAAACCC
TGTCTCTACAAAAAATAGAAAAATTAGCCGGGCATGGCGGTGCATGCCTGTACTCTGGGCTACTCGGGGG
GGCTGAGGTAGGAGGATCGCTTGAGCTTGGAAGTTGGAGGTTGTAGTGAGCTGAGACTGTGCCACTGCAC
TCTAGCCTGGAAGACAGAGCCAGACCCTGTCTCTTAAAAACAAACGAACAAACAACACTGACACCTACAA
ACACATGTATTAAAATTATTAGGACATGTGTAAGAATGATGAACACCAAATCCAGGGTTACTGACACCTC
TAAGGAGAAGTTAGATCATACAGGACACTTGAACTGTGTGTATACTTTTTAATTTTTTAGCTAGGTGATG
GTGTCATGGCAGTTTGTCATATTATTTGTTATGCCTTTTAGCACATCAGACATTTTTACAACAAAGAAAA
AAGATGTAGGGAGAAAGACACTAATTTCTGGCCTAATTTGAAGTATAACACTATTCATTTCTTCCTAATT
TTTTCAATTTGATCCCCGAAAGTCACTGAAGGAAGAAAAAAATTAAAATACCACTCCAACAGTCTCTCAA
TGTCTTTTAAACATCAAAGCTGCAGACAGAAAAGAGATGCAGGGAGTTGCTGACCTGGGAATTTTCCTGG
CCCCAATTCCTATCCATAAGTTTGCCTTGTCTCCAGCAAAGGCCTAAAATATCCAGGAAGTTTTGCTAGT
GTGGTATTCATTAGGAAGAATATATAGTTTGGATGGTTTTATAAAAATGCTATACTGGAGCAAACTCCAA
CCTACTGGCTTTCAAAAATGAATTCTTTAGTCATATTTTACTCTTGTTTCAAAGAAGAGGACATTTGATA
AGGGAACAGCTTTTACAGGAATCTCAGAGGCCACATCTTATATTACAGAGGAGGAGCAGACAGAAAGAAG
ACCTGAAGGAGAAAACCCCTAAGATCCTAAGAAGTGAGTTTTTGCAAAAGTCTTTCTCGTCTTCAAACAA
CAATCGTAAAAAGCATCAATTCTAATTCCTTAAGAGACGAGCATGTTATGTTAGACAGATCGGGAAAATA
TTTTCTGATTGAAAATGAAAACTCAGTTTCAATACAGAAAGAGGCAAAGAAGCACTTCAAAGTACTCAGA
AAACAGCTAAGTGATTATCTTGGCCACTTGTTTGGATTTCAATACCTTAATCAGCTCTTTTTCGTTATGG
AGGTCCTCGTGAAGCTCTGGAAGAGGATCTTCACTTTGTGCCTTTAAAACTTGCAGCCTGCTTTTCAACT
CCTTGATTTTCTTTTCACACTGGTCCCAGGTCTATTTGAAAACAAGATTAAAACTGGTAAGTATTTTGCT
CTTTAGAATGAATTGTAGAAATAGAATAGCTCATTTAATCCACATAATCTTTCTATTAAGTTTGTTTTTA
ATAAATCACACAGACACCCAGTTCCCTGTCTTAAGCAGACTATGGTCTCCAAAAGCAGAAGGAACACCAA
TATGACTCGACCCTCCTTGCAGCTTTACCTGTGGCTCATTTCAACCACCAGGCTAGGCTTTGCTTGAAAA
TAGTTCTTCCGGGCTGGGCATGGTGGCTCAAGCCTGTAATCCCAGCACTTTGGGAGGCTGAGGCGGGTGG
ATCACCTGAGGTCAGGAGTTTGAGACCAGCCTGGCCAACATGGCGAAACTCCGTCTCCACTAAAAATACA
AAAATTAGCTGGGTGTGGTGGTATGTGCCTGTAATCCCAGCTACTTGGGAGGCTGAGACAGGAGAATTGC
TTGAACCTGGGAGGTGGAGGCTGCAGTGAGCCAAGATTGCACCACTGCACTCCAGCCTGGGTGACAGAGC
AAGACTCCATCTTAAAATAAATAAATAAATAAATAAATAAATAAATAAAAATAAAAAAGTTCTTCCTCTC
TCCCCAATCCCTCTCATCTAACCAATGTGATTTCTACTTTAATTTTGGAAAAGTTCACACCTAAAAGGCT
ACTGTACGGAGTAACTGTTAGCATTGACAGTCTTTGGTATATGCTATGACAGCACCACAGAACACAAGCA
CTCAGCCACCTTCCTTGTCTTCTTTTCCACCGTCACCCCTCTCCTCTGCTGGCTGTCTTCTCCTTTCTAC
AGCCTGGCTTTAGTGACCTTTTCACATTCAACCTTCACTTTCCACTTCTCACCACTGTGCTGACTACCAC
CTTCTGCTTAAAGCACTTTCCTGTTTACAAAGCATTTTCAACTTTATTAACTCATTGTAATTATAATAAC
CTTAGGAGATAGACAAGGAAAGTATTATCATATTTAAAACAAGTATTATCATATTTAAAATGGGAAAACT
AAGGCTCAGAGAAAAATGACTAGCCCGTGGATCTGGGGTTAAAAGCCAAGTCAAGGGTCAACCATCTCTT
TTCTTCAAATTTTAACTGTTGAACAAAATAGGTGCCTGCATTTTCAACTATAGGGTATTTATATTCGATT
CATTAGGATAAACTTCTTTCCTGAAGTTACTAAAACTATACAAACCTACAATGAAACACTATTATTCAGT
ACAGCTGATACCTAAACATACTTGGGTTGGCCTCAGTCTATGGTAACCTCTCACTGAAGGGAGGCCACTT
GTGTAGCAATATTAACTATCTGGAACTCAACTCAAAAGAAAGCAAAGGAGAAGCAAAACCATGAGTTCTT
CAAACTGTTATTTGCAATTATCATTATGCTTCACAAACATGGCAGATGCTTAACAAATGTTTGCTAGTTA
ATGAATTCCATATAGTCCATATATCAAATAAAATTCAGATACTTTATTCACAGGAGAAATTTTCAAGCCC
TAACTCAGCATATATTTACTCTTAATTCAGAAAAATATGTCTGGTAAGTTTGGTTATCTAGTTTTGGCAC
ACACGACAGACTAGAGAGAGTGGGCTATAAGAAGTAAGTGAGCTTGGAGAAAGACAAAGTAAAAATAGAC
AGTTTGACATTAAGAGGAGAGAAAGAAAAATGATAAAAACCATATCAGAACTCAAAGAGCACAGTAGTTC
AGGGAGGGCCACAGGTTCAAAGTAATTCAGAGGCCTTGAGAACAACTTGGTATCTTAGCATAACAAAACA
ATAATGATTTTCCTAACAGTGACTCAAAATATAACACTGTAGTTCTTAAAGGTATAATCATACATTATTT
GGAAAATTCACTTATATGGAAAAGTGCATTCTCTGATGATAGCAGAAAAATGAAGTGTTTCTGTCTGTTC
CATACATGGAACATTAGTTTTATGTATTGAACTTTCATTGAATATGTTTCCTGTTTCATAAAAGTAAGTA
TCTTAATAGAATCTCAAGTATTTAAATACTAAACATTGAGCTCTTGCAATGCTATATCATCATTTCACAT
TAAGTAACTGGCATGACTTACAGATTACAGCTTGAGTTGGAAACTCATGATACTATAGTTTCCTAAAACC
ATTTCCATTTTCACACCACAAATGAAAATCTATGTACTGAATTTGAATATCATGAATGGAAAAGTAAGTG
GTGAGTTTACCTCTACAGTGCTCTGGAACTGCTTAATCATCTCTGCCAGCTGGGGCTCCATGTCTTTCCA
GCTGTCCTGAAGTTGACTGATTCTCCTACCCACAGACTCTTTAGTTTTCAGGTCAGTTGTGAGCAGTAAC
TTTTCTCCAGCTTCCAAGGTTAGGGCACAGGTAGTTCGCCTCCTTTGAAAATGAATTTCTTTATTCTAAG
AAAAAAAAGAGAAGTAATTTGCTTAGGTTTCTGATGTGTTCAAAATGTGATTGTGTGTGCCTGTGTATAT
TTCCTTCAGAGCTTTTCTTAAGAGTTAAACTAGATATAAATTAGACAAATTGGGTCAGAATGTACATACA
CACACACATCAAAAGCTAATGTTTTACACTGAGTAGATAAGCATACCACTAAGTGAGGTGTTCTTAAAAT
AATTTCCAAAGATTGGTGAGATAAGATTCTCAGTGTAATGATTAGCAGCACAGAGAAATAAAAAAATATA
CATCATAGAATAATAGCCTGCAAGGTAAATGGATCTAAGAGTATTAAGAAAGTGAATGGAGTAACAGACC
TGAAATCAAGTAACAGACCTTATATTACGCTAAACAAATGTAAAAGGAAAGAACCGCGAGAAAGGGTAAAA
TACAAAAAATATACATTTCTTAAGCTTTTTATGAGCACATAAACATGTACATTGATGTGTGCCCCAAAGG
CGCAGCTTTAAAAAATTTCATCCGAATATCATGTAGGCTTTCTGAAAATTAAAAACAATTTAAAAACAAT
AGTTTAGACCCGAAGTGATGGCTCATGCCTGTAATCCCAGCACTTTGGGAGGCCAAGACAGGCAGATCA
GTTGAGCTCAGGGGTTCGAGACCAGCCTGGCCAACATGGAGAAACCCTGACTCTACTAAAAATACAAAAA
TTAGCCAGGCATGGTGGTGGATGCCTGTAATTCCAGCTACTTGGGAGGCTGAGTCCCAAGAATCACTTTA
ACCTGGGAGGCAGAGATTGCAGTGAGCCAAGATCACACCACTGCACTCCAGCCTGGGTGACAGAGTGACG
CTTTGTCTCAAGGAAAAAAAAAAAAAAAAAATTTAAGAGACAAGGTCTTGTTTATTTTTATTTTTTTCTAT
ATTTTAGTGGCGGTGTTACAGCTCCGTGACTGCTCCTGCAGAGCAGGGCCGCTCCGCAGGCAGTGTGCAG
AGAGTAGCGAAGGTCCTGTTTTTTAAGAGATGCGCCACCACACCTGGCTACATGGGCGTTCTTTAAAGAG

ATTGAAACTAGGTATTTATAATACAAAAATAAAGTAAAAACTTTAAAATTGATCCATACTCCCAAAGGCA
TTTGGTTTTAGAGGAAAAATTAAATAGTTTTTGTCTGTTCTAAATATGTTTTCCTGGCTGGGCATTCTGG
TGAGTGCCTGTGGTCCCAGCTACTCGGGTGGCCGAGGTAGCCTCACCAGAAGTTTGAGGTTACAGTGAGC
TATGATCACGCCACTGCACTCCAGCCTGGGAGACAGAGTGAGTACCTATCTCTAAAAAAATAAGTAAATA
AATAAATAATACATAAATATTATTTCCTTCACCTTGAAATTTCTTGAAGGAGACAAAGTGTGGGCATTTT
TCCAAAATGGGAGCTGATAAACATCAACAGAGCATCACTAATTTACAAAGGCATTTCTGAGAAGCCTGAA
GATCACCCATACCCAAAGGAGGAAAGCCAAATGCACCCTCAGGAGCAGCACACAAATAAGAGAAACAGCA
ACTGGACCACAGGCACTCCACGTGCATCTCTCCAACATATTGTGCTGCGCAAATGAGCCACTCGTATTAG
ACCTGCTCCTCCCTTAGTCTTCCCTAACTCTGTCAACAGCACACTATTCACCAAGATGCTTGAGCTTCAA
CCCAGAGTCGTCCTTCATCTAGCTTTTCCTTTACCAGACTCACAAACCGACACTCCAAAATACGGTGTTT
TGACACGCTGAACTGAAGAAGTCTCAGGGTCTCTCTACCCTAACGCACTGCGTCTCCTACAGAAGCTGAA
GTCCTTTATCTGCCTAAGACCCGGACTCACCAAGGAGAATGATTGTTTTTTCTTTCCCTCCCTGTTACCT
CATTATCTTATTGCAGAAAAGAAGACCCAGATGTAACCACACCCAAATAGGCTCTTTCAAGATGACTGCC
TCCAGCGATCACTGAAATTCCAAAGATAACCTTTTTTTTTTTTCCAGACAGGTCTTGCTCTGTTACCCA
GGCTGGAGTGCAGTGGTGTGACCATGGCTCGTTGCAGCCTCAACCTCCCGGGCTCAAGTGTGACCCTCCT
GCCTCAGCCTCCTGAGCAGCTGGGAGTACAGGCGTGCACCACCACACCTGGCTAAATTTTGAATTTTTTT
GTAGAGACAGGGGTCTCACTATGTTGTACACAGGCTGGTCTCAAACTGGGCTCAAGGGATCCTCCCACCT
CGGCCTCCCAAAGTGTTGGGATTTCAGCCAATTCTCATCAAACTGTGGCACCTCTGTCCCCTCCTCTCAA
ACTCATGTGGACACATATGATAGCCTTCATTGTTAGAGTGTGGCAGAAGCGATATATGTGACTTCTGAGG
TTGGGTTTATAGGGCAATACAGCTTGTTCTCGGGATAAGAATCTTTGAAACCATTGGGGTACCATATAAG
AAGTCTGGCCACTGGAAGCCCTCACGTGGTAACACAACAGAGAATGATGCCCAAGGAGAGGAGCTCCACT
GTCCCAGCTCCTTGCTGCTCCAGTTGTTCCAGCCTAAGCATCAGTCATGTGAGTGAGCTTCAGATGACAC
CAGCCCCAGCCACCATCTGACTGCAACTGCCTGAGAGACCCCAAGCAGGAACCACCAACTCCTGTCAACC
CCAAGAATGACGAGACAGAATGATGAGTGTCATTATGCAGCGATAGGTAAGTGAGATGTTAGGATTCCTA
CTTTTCCTTTAGCTCCCCTACAATCAGGAACAGCCAGAGTGATCTTTAAAAAATATGGGGCTGGGCACAG
TGGCTCACGCCTGTAATCCCAGCACTTTGGGAAGCTGAGGTGGGTGGATCACCTGAGGTCAGGAGTTCGA
GACCAGCCTGGCCAACAGGGTGAAACCTTGTCTCTACTAAAAACACAAAAATTAGCTGGGCATGGTGGCG
GGCGCCTGTAATCCCAGCTACTTGGGAGGCTGAGACACGAGAATTGCTTCAACCTGGGAGGCAGAGGTTG
CAGTGAGCCAAGATCGCAACACTGCACTCCAGCCTGGGCGACAGAGTGAGACTCCGTCCCAAAAAAAAGA
AAAACAAGCAAACAGTGTCATGCTGCCCTCTCCCTCAGCTGAAATGCTTCAAAGGCTCCCTGGTTCCAGC
CAGACCAGGTAATCCAGCTGCCACACCCAACCTGCAAAACACTCCTCCCTACCCGCCTTTCTAGTTCACC
TCCTGCCACTACTGCCTTGCCAGCTCTGCGCCAGTCACACTGGCCTTTTTGCCGTTCCTCTGTGCTGAGC
TTGTTCTCATCTTGGGGACTTGGAGTAAGCCTCTCCTTCAGTCTGAAAGGCTCTTTCCTTAGATCTTGCA
TGGCTGGCTCCTTCTCATCATTCAGTCCCAGGTTAAATGTCACATGGCCAGAGACAACCCAATCTAAAGG
AGCCACACATCCCCATCTCTACTGGCCCTGTTTAATGATCTACGTAAGTCTTATTACAATCTGATATTT
TATTATTTATTAATTTATCTGATTAATTATTCTGGTTTACTACTTTGTCTGCCCTTATGAGAGCGAAGGT
CTTCTCTCCATCCACAGAATACACCCAGCACTTAGGACAGTGATTGGCACAGAGAAGGTACTCAATTAAT
ATGCGATGATTGCATAATGAGTGAGGGCTGTACAGGATTTCAGGAGGGTGGTGTTTGTTGAGAGGCTTCT
CTAAGGTGGAGAGTAGCTCTACAGCTCCATGGGACATGCCAACCACCTATGCTAATCCTGTGCTCATCAG
GCAAGTTTCTTTTGGAAAGCTTTGTTGGCTGAATGAATTTGCCCCTTTATTTTTATTTTTTTTAAATCAG
TTTTTAAAATTTTGTGAGTGCATGAGGTTTTTAAATATAGGCATGCAATGTCCAATAAGCACATCATGGA
GAACGGGGTTTCCATCCCCTCAAGCATTTATCCTTTGAGTTACAAATAATCCAATTACACTCCTTAAGTT
ATTTAAAAATATATAATTAAATTATTATCGACTATAGTCACCCTACTGTGCTATCAAATAGTAGGTCTTA
TTCATTCTATTTTTTTTGTACCCATTGAATTTGCCCTTCAAGAGTAAACAATGCCATCACTGTACATTAC
TACACTAATGGTCAATTTATACATTAGTCAGTGGCTTAAGAATCTGGGTGGTTTGAGTCTGTTGCCCTAA
ACCTCCCCCAATTTATTCACCCATCTCCACTCCATGCCTCCTCTCATGGCCCAAGAGAACCCTAGTATTT
CTGGATGAATGGGTAATATCGGGTTTCCAACCCCACAATGCTAGGGACTGGGCTGTGGGGGGTGGTGACT
GCACCTTGCTGGCCTCACACTGCAGAGAGCCCACTTGGATCACATCATCATCAAAAACATTAAACCAAAG
GTGAATGAACATCTTGCAAACAATGACCACCCTGTGGTTCTCACACTGCTACGATGCATACACTACCTTC
AGCTCATGGATCAGACTTCTGGTTTGGTAGAGGCTGAAGCGCTCCTGGCCCTTCACTGCAGATAGCAGGT
GGCTGGTGTCAGTGAGGAAGCGAAACAAGTTCTCCACAGAAGTAGTGAAATCTTGCCACTGCCTCACCAG
CCCATCAACGTCACCCTTCCTCTGCCGAACACCCTGGACAGCATTCTGCCACCGATCCGTCAGCTTTGAG
AATTCTGTAATAAATTCTGGTCTGGGGAAAAACAAATGGTTATAGAATCCAGACATCGACATGTAGAAAA
AATAACTATCAGTGGGTAATAGCAGCTCAGATTCAGTTTTTATAAGTACAATTTACATGAAAAAAATCCC
AACTTCTAAACACCTGAGTGCTATTCAATTTAAACATGATTAAGGCTTTGGGAAGGGCAGCATGCAGACT
GAGTTTAGCAGAAGGTATCTGCACGTAACCTGGTATTTTGCCAGCATGCATAACCATTCCCTTAAACAAA
CTGAAGCTGTTTTAATATACATTAGGCCAAACGTGGAAAGGAAAACTAGAAACTGGATCAAAGGGAAACA
GATGAACAGGCAGGTACTTTGTAACACTATGGATTACTTGAGTGTACTTTACATAATTTTAGCAATAAAG
AGCATGCTTTATTGCAGCTACTCAACAGTTCTTTTCTGGATAAATAATATCCTTCACACGAGAAATAAGG
CCTCTTGTTTATTATGGGAAAGTCATGTTTTTCTGTACAGATCAAATAGAAATTAGCTTATCATCCTGGA
ACTGGCTTGCATTTACTGCTTCAGAGCTAGGGAGAAAAGGGCTTTACATTTCTTAGTTATGCTGAAAGAA
GATTCAGAGGTGTATGGGTGGTGATGTGGAAGAAAAATCATACCCATTAGGACATTTAGAGAAGTATTTA
AATGGCCAGGCCATTTCCAGGCTATCTGCCATGTGTACAGCTGCATGAGCAGACTCACTCAGCATTAGCA
GACTGGCCAAAGGTGCTCTGTTCAGCCTGATTGGCACTGCCCAGTGACCCTAAGCCCACATATGTAGCAT
GGAGAGAAAGCCCTTCTTTCAGACTTATAGGATTTAGCTACCTACTGGGAACATTAGGAATAATCATTTT
TTAGAAATTATTTTTTAAGTCGCAAAACATCATGAGGATGATGGTAGAGAAGGAAACAGTACAGAAGAAT
CATTTGGGGGCACAAACTTAGTTAACTATACTTGAGAAGTGGGCATTTTCCAAAGCTTCTGGGCTGCTAA
CCCCATCCACCTACCATACGGAAAAGGTGTCTGTCACAGATGTTTTTATGGTCACCCAGCAAGATCTAGT
CCCACTACATAGTTAGAAGCCTGGTCCTATGGTGATCTGTCAACCAACAGGGCACAGGGCACCAACATGG
TCAAGGTTCACATGGTGGAAAGCCTGCCCTGACTGAATGCATTACCTTCCATCCGCCCCACAACCTTCATG
AGGCCCAGACAGCTCACCTGTTCTCTATTTCTGTTGTGTCCAGGAGTTGTAAGGACTGGGTGACATAGGA

ATCAGCAATTGTCTGGTTTATAGAAACTTCAGCTTCTAACATCTGTATATGAGTCCAAGCAGAAAATATC
AGCTAGTAAAATTCATTTTATGAATCTCGGAACCTACATTTCCTATTAAAATCTAAGCTTACAAAGGATA
TGAGGGATAATTAATTTTCATATTATTTGAACCTACTGCAAAAAATGTTCAACTATCATATCAACATCAC
CTACGAATATATTCTTAAAAGCAAACAGGTCTAATAATAATTACATCTAATACCCATTTGTTGGGCATTT
ACGATTTGGTAGGCACTGTAAAACATGCATTGTCTCATTTATTTCTCAGCCTTAGGATTTAAGCACTATT
ATTACATCCATTTGAAGAGGAGGAATCTAAGGTATAAAGAGGTTCAGTAACTTACTTAAGGCCACTCAGC
TTTTTGGCAGGGGTGATTTCATTTTAATTGGATGATCTTAATGTAGCAATGTAGACTTCAATCAGTTACA
TTAAAAAGTTGCAGTGAAGTAATTCTGCACACTTTTGAAATGTGTCCTTTGTAATCCCAGCACTTTGGGA
GGCCGAGGCAGGCGGATCACTTGAGGTCAGAAGTTCGAGACCAGCCTGGCCAACATGGTGAACCCCATCT
CTACTAAAAATACAAAAATTAGCCAGGTGCAGTGGCACATGCCTATAGTCCCAGCTACTCGGAAGGGTAA
GGCACGAGAATTGCTTGAGCCTGGGGGGTGGAAGTTTCAGTGAGCCGAGATTGCGCCACTGCACTCCAGC
CTGGGTGACAGAGGAAGACTCTGTCTCCCCCCACCAAAAAAAGCAGGATCTGCCTATAACCACCAGGAGT
ATTTTCAAATACATGTCAGCATAAGCACTGAGGAAACTCCTGTGAAATTATTAACGCTACAGTTATAATT
ATACCAGGTGCTTTAATACTATGGAGAATTATTGAGTGAAAATACAAACATGAGTCGAAGTATTTTATTA
TACTCTTGATAGAATGGTATAATGTTTGCATTTTGTGGAAGCAAAGTTGTACTAGAAGCTTCCATGTACT
GCAGAAAATCTAGGAGTCCTCTCCCTAATAAAATAGAGCAGTAAATGTTGAAATTTATGAAACGTACAAG
AATTTTACAAATGACCAATTGACAACTGAATTTGCTTAAAGGTATACATTCTGTGTTTAGGGACTGATAG
GTACACTCCCTGTGTTTTATTTAAAGCTATCTTTCCCTGACTCCTGCCCCAGATGAGCGGTTCAAGGGTG
GCAGAGAACACAGGTTTACCTTATAGGTTTTCTGCTGCTCCAGGAGCTCAGGAAGGCTGTTAGCCACATC
CACTTTGAGTGCTTCTTCTATCTTCTCCAAAAGTTGGATCCACTTTTCACAGCAATAAAGAAACTTTTCA
TTCAATCCAATTCCCTGAAGCTCACTACAAAGGTTTAAAACAAAACACACCCATGTTAACAATGCCATTC
CCGAGCTGAAGCCGTTAATTTTACCTTAATTGAAACAACGACAGAGAAGGGATGTTCTAACCTGCAGCGC
TCCAGTGCCGTGGCCGTGGCCCGAATCCATTGCCGGTTCATATTTTGTAACGTCTTCACAGCTACGTCAC
TAAGTGGGAGCTTGAGGCTCACTTCATTCAAATGTTCAATATCAGGTGATTGGGCTGTCAGTGCCAGCAC
ATGATTCTATTTTTAAAAAATTGAAGTACAGGTTTTTGGATGCCAATAAGATATCTAGATGACAAAAAAC
CCTCCTTACCTCAAAGATAAAGGAAAACTGGGGCCTGAACAGGCAAATGACTTGCCCACAGTCAAACAGC
TTGCTAATGTTAGAGTGGGACCTGAATTCAGCTATCTCAATGCTGTGCCTTCTAGAATACCAACCTGCAA
CACGGCCAGCACCCAAACAGCCCAGGAAATAGAAAGTTATCTCAGATTTTGTCACCGAAGAATACAGAAA
ATAGGCTTTTTTATTTTTTATTTTTCGGAATGGAGTCTCATTCTGTCGCCCAGGCTGGACTGCAGTATCA
TGATCTCGGCTCACTGCAACCTCCGCCTCCTGGGTTCAAACGATTCTCCTGCTTCAGCCTCCCAAGTAGG
TGGAATTACAAGTGCCTGCCACCACACCTGGCTAATTTTTGTATTTTTAGTTTCACCATGTTGGCCAGCT
GGTCTAAAACTCTGACCTTGGATGATCCACCTGCCTCGGCCTCCCAAAGTGCTGGGATTACAGGCGTGAG
CCACTGCACCCAGCCTAACATGCTTTTTAAAAAAGGACCAATTCTGGGCTTTTAAGTCCCATTTAGTCTG
CCAATAACCTGGCCTTCAACAAACAGGTCAAGCACAGAGTGATGAAAATTTGATTCTTAAAATAACTCTA
GCAGAGCAAGGGACTTAAACACCCATATTTTGATAGAACATGACATTGCAAGAAAGCAAACTTATCAAAA
TTTCATTTTTAAAAAGATATTCCAGCGACAGCTTCTAAGCTGACAAGCAAACATCCTTAACAATATTGAA
GTTACCACTACAGAACTCTGCTGTAATATTCTAGGTCAGGATAAGCAAACTTTTTCTGTAAAAGGGCAGA
TCATAAATATTTTAGGCATTTGTGGGCCATATGGTCTCTGTAGCAACTAGTCAACTCTGCCCTTGTAGCG
TGAAAACTATAATAGACAATATGTAAATGAAAGGGCATGGCTGTGTTCCATCAAAATTTTATTTAAAAAA
AAATCAGTGATGGACAGTGCACCACAGTTTGTTGACTGCTGATCTAAGTTATGAATATTGATTCCTAGGA
GAGTTACAAGACCAGATCTAATTCTTTCAGTCATTTATGTTTACTAAACTAAACTTACGAAGGTAAAGAA
AAATGCATAATAGAATTTTTTTTATATTAAACTAACCAGAAAAATTCAATTAATCACAACAGCCAATTTC
TAGATTATTTCAGTTCACTGACGGTAATTATGAAAAAACATCTACTACAAATTACTCTGACGTATTACTA
AAAGAGATCCCTATGTCATCCTACTTTTTCTAGGCCTGAGGGAAAATAGGACAGTAATGAATGGCATAAA
AATGACTGTGCTCAAGGGTGAGTTAGGCCAGGCGCAGTGGCTCAGGCCTGTAATCCCAGCACTTTGGGAG
GCCGAGGCAGGCGGATCACCTGACGTCAAGAGTTCAAGACCAGCTTGGCCAATATGGTAAAACTTCATCT
CTACTAAAAAATACAAAAATTAGCCGGACATGGTGGCACATGTCTGTAGTCCCAGCTACTTGGGAGGCTG
AGGCAGGAGAATGGCTTGAACCCGGGAGGTGGAGGTTGCAGTGAGCCGAGATCGTGCCACTGCACTCCAG
CCTGGGTGACAGAGCGAGAGTCCGTCTCAAAAAAAAAAAAATAAGAGTGAGTTAGGATGCAAGCATTCCAT
AAGTTCACAGTAATCAGCTTATTTTTTTTAACCTTATGGTGAGTCTAAGCCCTTAGAAAAGACAAATATT
GGCAATACCAGGAATGAGTCAGGATTTTCTTTTTCCTGTTGGTGAAGTCTATCCAAATTCTCTTCTTCAT
GCATAATAAGACCTTTTAAAGATTCCAGCCGGACTCCAAAATCCTTAAACTGTGAGAGAACAAACTAGAA
CAAGAGAAATTTTCATTAGAAACTATTTTCATGTACATATAAAACAGAATTAAACACAGGCTTGGGAGCT
GCTAAAAATTCAAGATGTTTTTGGCTAGGCACGGTGGCTCATGGCTGTAATCCCAGCACTTTGGGAGGCC
GAGGTGGGAAGATTGCTTGAGCCCAGGAGTTCAAGACCAGCCTGAGCAACATAGGCAGACTCCATCTCTG
CAAAAAATAAAAAATTAGCTGGGCATAGTGGTGTGAGCCTGTGGTCCCAGCTTTTTGGGAGGCTGAGGCA
GGAGGATCAACTGAACCTGGGAGGTCAAGGCTGCAGTAAGCTGTAATTATGCCACTGCACGCCAGCCTGG
GTGACAGAATAAGACCCTGTCTCCCTGTCTCAAACAAACAAACAAACAAACAAAAAAAAACAAAAAATAA
AAAAAAGTAAATTCAAGTTGTTTTCAACACCCAGAAGTTCACTATTATCTCAAGAATCATAGATAAATAT
TCAGAAGCCCCCTGATTTTTCACTCGTGCCTTTGAGCCTTCCCAAATGGACAGATCACCCGCCTGAGGAG
ACCACATAGAGAGTCAGTGAGCACTCCGTTCTCTCAGTCCCACTAGTTAAATGTGCTTTTTTGTTTGTTT
GTTTTCCTGCTGGTACTGAGATGTGATACTGCAACTCCATGGCCTTCTGTGTAGCTTGTTGACAGCTCCT
GCACTAAAGGCTTTATAAAAAGTGAATGAAGGCTGAGAGCAGTGGCTCATGCTTGTAATCCCAGCACTTT
GGGAGGCCAAGGTGGGTAGATCACTTGAGGCCAGGAGTTCAAGACCAGCCTGGCCAATGTGGCGAAACCC
CATCTCTACTAATTATACAAAAATTAGCCGGCCAGACACAGTGGCTCACGTCTGTAATCCCAGCATTTTG
GGAGGCCAAGGCAGGTGGATCACGAGGTCAGGAGATTGAGACCATCCTGGCTAACATGGTGAAACCCTGT
CTCTACTAAAAATACAAAAAAATTAGCCAGGCATGGTGGCAGGCACCTGTAGTCCCAGCTACTCGGGAGG
CTGAGGCAGGAGAATGGCATAAACCCAGGAGGCGGAGCTTGCAGTGAGCTGAGATCACACCACTGTACTC
CAGCCTGGGCGACAGAACGAGACATCTCAAAATAAATAAATAAATAAATAAATAAATAAATAAATAAATA
AGCAAGCCAGGCGTGGTGGTGGGTGCCTGTAGTCCCAGCTATCCGGGAGGCTGAGGCAGGAGAATCGCTT
GAACCCGGGAGGTGGAGGTTGCAGTGAGCCAAGATTATGCCACTGCACTCTAGCCTGGGTGTCAGGTCAA

GAGTCTGTCTCAAAATAAAAAAAAGTGAATGAAGACACGAAGATATGACAAATCATCATGCTTTAAGCAG
CTACTTCTATGGCTCAATTACTTGACTCAGAAATCCAAATAACTGTGAGATCTGAACAATGTATGCAATA
TAATACATATATGACTTCTAGAACTAACATCTTCAATAAGGAAGAAATGATTGCTTAAGATCTGCCCATG
TGATTGAAGCTAGAATCGTATACATTTGGGAGCAGCTTCAGTCTGTAATTTTGCTAAGGAGCAGCCCGTA
AAGCACTACTGCTTCAAAGGATACAAGGGATTGAGGATGGAATGCAAATGTCTAAGACTAAAACTTGAAT
GGAAAGAAAAGATGAACCTCAAATTCATTTGCTTTCACAAGCAGCATCTTTTCCAAATAAGCAGCCCTCT
GGAGAGAGTGCAGGGGGCCCGGGAGGAGCATGTGGGTGCTGGACTCTGCGGGTTGTGGGAGTCGATCCAG
GACACTGGAATTTTGGAGAAAGGCTTCTTTTGTTTTCTGCACATCATGCTGCAGCTCCTGCAGAAGAAAA
AGGGATGGCAAACACCTCTTCCTCCTTTCAAACCACAATTCCCTACCCGCTGCTGCTCCATCAAAATCTA
GGAGAATATTTGCCCTGAAAACGTAGGCATGATCTTTTGTTATTATTTATTTTAAATAGCTGAAAAGGCT
GGGCTTTCTTGAAATGATGTATATCACTGGCGCTTTTCCGAAATTTGTCAGTTCAAAACTAAAAGTGACC
ACTGACTAATAGAGTCGAGGCTTCTAGTGTATAGAAACTGGAGACAACCTGAGTACTCATGTACTTTATA
TTTCAGTTGTCAAACAGTTTAGGTATCTGCTTTCATGCTGTTTCAAGAATCAATGCAACTCTGACCCCTG
CCTGAGACTTTCTGATATAAATGGATTCACGTGCAGAAACTATAGAATTTTATTAATCAGGCTGATTTTA
AGGCTATTCTGGAAATATTGTGTACATAAAATTTGTTTTTTTATTTTTAAATTATCAGCTCAGGTAGAAG
TTAATCAGATGTACAGAGCATTATCTGTTGGATTCTCACCTAATTAAATTGGTTGCCACGTTTTGATTTG
ACCTACAGTAGCAGAAGATACAAAATGCATCTGTTCACTCAGTTCAGAACTAAAGAGTATTCACTTTCTG
AGCGTTCATTAACAATAATAGAAAAAACACCATAGAGGAAACTAAGCAAGTCTTTAATGTAGTCTGAAAT
TTACTATACCCACAGAAAAGGCCTAGCAACATGGCACCAAGTCCATGATTACTGCTAAAACAAGAGATAC
AACATGTATTATTCTTACAGGGTCACACTCAGTTGAGACACTTGCTTTTACTTCAGATTTCATATGAAGC
TTTTGCCTTAGAGATGTAACACTAGAGAGAAAGCACAGACTTGGAACGAGGTGATATCGAGTCCCCCTGA
TCCAGCTATTTGCTGCCTAGACGTCACCTCTGAGCCACCACCTGGTCCTCCCAGCCTTGCCTATGTCCTA
CATGGCAAGTTCACAGCACCTGTCCTGACTACTCTGTCCCTGTGGTCTGTCTGGTCCCCAGGTCATGGCT
GTCCCTTACCCCATCTGTTGGGCTGACTTGGCCTTGGTTTTCCAAATGGGCTTTGTACCCACCTTTATGT
CCTGCAGGGCTGGGGGCAGGATCTCTGCCAGGTTGTTTCCAGACATGCTGATGTTTGCGAGCTGTTGAAA
CTTTGCTTCCTGCTGCTTCAGCCTTGCGGCAGCTTCACCATGAGCATTGCTATAGGCCTTCCAGAGCTGG
AGCAGACTCTGGGCCTTCTGCAACTGGTCTGCAATGGCTTGGTTCACCTGAGTCCACCTGTCAGTGCAAC
GCAAATAACATAACCCTCATTCTCTCCTTTCTCTTGTAGCGAAAGTACAATGCACACACTCTACTGGTAA
GTTACTAGCAGATGGATCATTAAGAAGACACTGTTAAATGGTTTTTAAAATTAGTGGCATCACCATTATA
GAAACCATTATATAAAAATAAATCCAAATTAGGCTATTTACTTGACTTTATAATATTGCACAAAAACTAC
AAAATGTATGATTGGCAACAAATACCTATGATGTTATGAATGTTTCACTCTCTTTTTTTAAGAGAGGGGA
GTGATGAAGGGAGCTCAAACTTTTTTTTTTTTTTTTTTGTAGAGACAGGGCCTTGATATGTTGCCCAGGA
TGGTCTCAAACTCTGCAGCTCAAGTAATCCTCCAACCTCAAGCAATCCTCCTGCCTCAGCCTCCCAAAGT
GTTGGGATTATAGGTGTGAGCCATGGTGCGCCCCGCCTATGAATGTCTCTTTGGCAAAGATGGAGAAAAC
ACTGAACTGTATGCCTGATAAAATGACTCCACATGAAGAGGCTCCCAGTTTATAGAGATATGCTATCTTT
AAACAGGTTTTAACTTTGTATTTATATCAAATAAAATTTATTATCTGTTTACACAAATGTTCCTTACATA
GAAGTGGAAATAAAGGAAATTGTTTTATTATTCCATATACAGACTCTAGTATCTTGCCTTTCTTCCCTAC
TTTTTTTTTTTTTCTGAAACAGGGTCTTGCTCTGTTGCCCAGGCTGGAGTGCAGTGGTGCAATCTCAGCT
CACTGTAGCCTTGACCTCCTGGGCTTAAGTGATCCTCCCATCTCAGCCCCCACAAGTAGCTAGGACCACA
GGTGCATGCCACCACGCCTGGCTAATTTTTGTTTTTTTGTAGAGATGGGGTTTCACCATGCTACCCAGGC
TGGTCTTGAACTCCTGGACTCAAGTGATCTACCCACCTCGGCCTCCCAAAGTGCTGGGATTACAGGCATG
AGCCACTATGCCTGGCCCATTTAACTTTTAAAAAATATTTTCCCCACGTTAGTAATAAAAGAAAATAAGT
AAACCTCATTTTAAGTGGCTGTACAAATGGTCTGTGGGTTTTTTTTTCTTTGTTTCCTTAGTTTAATTGC
TAAATTCCTTAGTTTAATTCCTGTTTAGTATGGATAGTTAAGATATTTGTAATTTTTGCTATTATGATAA
TGCTCAGATACAGTTTTATTCAAAAGGCTTTTTTTCTGTATTTCAAGATATTAGTCTTAGACTAGATTTC
TGGGAGAATTACAGAGTCAAAGAATATAAAGATGTAAATATTTGTAAGGCTTTGGGAATAAATGGTCAAT
CTCCTTTCTGAAAGCATTATATTTACATTCTAACATGAAATACATGAGAATGTTTGCTCCACAATATCCT
CAACAATATCCTCGACCCTGCTGATTAAAGAATCAAAGGTGGAAAATAGCACACTGCTTTACTTTTATGC
ATTTCAAAAATCTTATCAGAACTGTCTTTTAAAATAAGATTTTCCCTAATTATAAATACAACATATATTC
ACTGTCAAAAAGCAAACAAAATCCCTCCAGATATTTTTCTTTTTATCTATCTATCCTACCTACTTACCAA
TCCATGAGGAAGTTAAAAAATGCTTGACATCTCATTTATCTAGAGGTAACTACTATTAGCATTTTAGTGT
TCTTCTCTTCAGTCTTTTTGTTATGCATGTTTTTCAACATGCCTTCCAACATATTCTTGTGCCAACAAGT
GAATGTGTACGTGCAGCGTAACAACTGAGTTCCTTTACCAACAGACTGCCCTGCCATACGTTTTGACGGT
AGCCCTGATATTGTATGTGGAGTCAGATGCATTTGCAGGTTCCTCTTAGTCTGTCTCCTCCCCGTCTTCC
AATAAAGACTGGATCAAGAGCTAAGGGCACCACTGCAGGGTATATAATTTGGGGTCCCTTGTTCATTACT
TGTTCGAAGTTGATTTACAAGAGAGGCTGAAACTGCATACAGGAATAATCAGGAAGGACACTTAAGATAG
CATAACTCTTCATCCCTATCTCTAATCAATTGGTTGGAGGCCAACTTTTATATCCCACTCATCAAAATAA
AAGCCCTGCAATTAACTAGGGCCACACTCCTTAAAGGGAGCTTTCATATCCCACCATAAGTAGTTCATCA
AAGAATTCCTTCCAAACCCACAAATGCCCTCCGCAACAGATACTCTAACATCCCCTTTCTTCCACCTTAT
AATGTTTCCAGTGATGTTTGAACACCCCCTGCAGGATGCCCATCTGGCCCACTCCTTTGTCTGTTTCTGC
CTCTGACTTTGGTGTTTCCGAGATCGAACTTGACATTTGGTCTATACTGTCTGTAAGTGAGTACACTGGG
GTTGTTATTAGGCCATTTCTAGACTAATTATACCAAACACTTGTACAAGGGATGTCACAGCCCTCATGAC
ATAGAATCTTACATAGACTAGATTCATCAAAGCAGAAGAGACCAGAACAGTAGGAAACCAGTCATCTCAG
AGGAGGAAGAAGACTTTACAATGCCTATGCCCCCTCATTCTTCACAAGTCATTAAGATAAAGATATCTAT
CATTCAAATTATATCTGAAAGCATACCTTTTATGAGTATTTTGGCATTTCTCTTCGATTATTTCAGCAAC
AGAGGGGCAGAGACCTTTGAGTTTGCCGATAACCTCCTGGAGTTTCTCCCAACTCCCTTCACTGCTCTCA
GCTTCATCTTGCAGAGACTAAGAGACACAAACAAGAAATTTAAGTTTCAGAATGGCCTGGCTACTTCCAA
AGAAGGTGGCAGCTTCTCAACACTTGCTACTATGTAGCAATAACACTCAAATCTTACAGCTCTGATAAAC
TATTAGGAATGTGAAGAAAACAATGGAGAAGGCATTCTTTATTTGAGGCTGAACTTTTAAGTACTAAGTA
ATATAAAGTACTTAGCACTTAGGCATACTGAAAAAAAAAAAGGCCACTCAAAAACCAAAACCTTAAATTGT
GAAATAATATGGACATGGAAAATAAAGGAAGATTCAACATTTTCAACTCAAAATTCAAACATTTTACAAT

GTTTTACTGATTTGGCTCATGTGACTTATTTTGGAATTTCCAGTTATTCTTTTGAAACTGCTATTTAACA
TGCTTTGTGCTTCTCTGTGGGAGGGCACAAACACAGTTATGCCCGTTACTGTGCTTCCTCCCATTTGTAA
TTTCCTGCCAATAATGCACCATGCCAAGCTCTGGTTAATTTACCTGAAGGTTCTCCACCTGGCATCTCAA
GGTCTCCAATGATAACACCACAGGCTTGCTGTGTTCCATGCAGTACCAGAATCGGATTGTCATCATATTC
ACTTCATCATAGAGTTGATCATAAATCTTCCACTCCTGTAAAACTGACTGCATGGAGGTTTTGAGCTGAT
TGACCTAGACAAAAAGTGGAAACGTACTGATTTAGAAAATCACTGAGAAGACATGCTCTCCAACAGATCT
ACCATTGTGTCCAATTTAGGCATTTCAATTTGAGAGTATTGAAGGATCACCAGTGATTAACTGAAGGTGG
AAAGGGTAGGTCAATGCATAAGAACATATCAGAGAAGGCTGTTTTATAATGAGTGAATGAAAAAGAGCCC
AAAGATCAGAAGGATCAGCACTGAAGGAGTTCAGACTAGGAAGAGACAGCCCAGGGAAAGAACACTGGGT
GAGTATTAGAATTTGTGAGTGCAAGGTTCAGTTATATTCTATTAGCTTTCTGACCTTGGGCAACTTATTG
GACCCTAGAGTCAGTTTCCTCATCCACAAAACAGAGATAATAATTGAAAACACAAATAAAATAGTGTCTG
TGAAAATGCTCTGACAACAGCACAACATTATAAATGTAAGATGTTACCTGGCACTTAAGTCTGATTATTA
CTACAGAGCAAGCACCAATTGGAGAGGAACATGCTCTACCAAAATGATGGGCAAGTGCAAAGCAGGAGGC
AAGCAATGGTGAATGTATTTTGTCCACTGGTATGTTCTGATAATGATGAAAAAAGTCCAAGCATTCTGTT
GCATATCCAAAATGATCTCAGATACAATCAAGAGTATGTAAAGAAAACTTACAAATCAATATTAAAGACA
GATAAACTAACTAAAAACTGGGCAAAGGAAGTGACTAAACATTTCCCCAAAGAACATATATAATGGTCAA
TAAACATATGAAAAGACACTGAACATATACAGTCATTAAGGAAACCTAAATCAAAACCACAATGAGATAT
TATTTCACATCCACTTTGATGGCCATAATCAAAAAGTCAGATAATAATGTGTTGGTGACGATGTGGAAAA
ACTGGAATCCTCATACATTGCTGGTGGGAATGTAAAATGGTACAGTCACTGTGGAAAACAGCTAGATAGT
TCCTCAAAAAATTAAATAGAGTTGCCATATGACCTAACAATTGTACTCTTATACACACAAGAGAATTAAA
AGCGTATGTTCACATAAAAACCTGACACAAATGTTCATAGCAGCACGATTCATGAGAGCCTAAAAATGGA
AACAACCCACATGTTCATCAACTGATGGAGAGGTAAACTAAATATGGTATATCCATACAATGGAATATTA
GCCATAAAAATAAATGAAGTACTGTAAATACTACAACACCGATGATCTTGAAAACATTATGCTTAGTGAA
GGAAGCCAGACCCAAAAGGCTATATAGCATATGATTCTATTTATATAAAACGTCCAGAATAGGTAAATCC
ATAAGAAGGTAGACTAGTGGCTGCCAGGGACTGGAGAAGGGGAAAAGTGGGGAGTGACTGCCAATGGGTA
TGGAGGTTTCTTTTTGAGGTAATGAAAATGTTCTGTAATGAGATAGTGGTGATGGCTGTGTATCTCTGTT
AATATACTAAACATCACTGAACTATACCTTAGAAGGTGAATTTTATGGTATGTGAATTATATCTCAATTT
TTAAAAAGGATCTGGGTTGAAATGGAATGTGATCACTATAGTGGCTCCACAGGCCATCTTTATGGGTAGT
GTGATGTGAGTTTTGGGTACAATCACACAGCTCTGCACTCAGACCCTGTTTTCTGTTTAATAACTACAAG
GAATGCTGGCACATCCACAGTGACAGGGAGGCTCCTCAATCTCTGCCCCAAACAGGGCTGGATAAAAAAC
CAAAGTGGGACGCTAAAATGTGAGTCTCATGTTGGCAACTATGTGGACTGAATGTCTTTACAAGGGCAGG
ATGGCTAAGGAAAAGAAACCAAGTTATTTAGTTAAGAAAATAAAGAAGGCGGCCAGGTGTGGTGGCTCAC
GCCTGTAATCCCAGCACTTTGGGAGGCCAAGGTGGTTGGATCACCTAAGGTCAGGAGTTCAAGACCAGCC
TGGTCAACATGGTGAAACCCTGTCTCTACTAATAATACAAAAATTAGCCGGGAGTGGTGGCACACGCCTG
TAATCCCAGCTACTAGGGAGGCTGAGGCAGGAGAATCTTTTGAACCTGGAAGGTGGAAGTTGCAGTGAGC
TGAGATCATGCCACTGCCCTCCAGCCTGGGCAACAAGAGCAAAACTCTGTCTCCACAAAAAAAAAAAAGG
AAAGAAAAAAGAAAATAAAGAAGAAAGGCAAGGAAGGAATTCCTCATCGATGTACATTTTTGCTAGAAAT
GATCTCACATCTATCTGGGTGGCAGGGATAATTCTGGCACAAAGTACCGCATCATCCCAGAGCCCATATA
TACATGTCAACACAAGAACTGCCATGGCTCATGTTGCACAAGGCCTTTGCAGCTTCCACAGATAAAGGTG
GTGGAACTTCTAGCACCTTAAAGGCCTTCTGGCCTTATAATAAAGCTTCATGGAAAAGACACAGTACATG
AGGTTTGAGGGAAAGGATGAGAAAATCATCAAGTAAAATTCACTATACTAAAAACAAGCGGGAGGAATAT
TTTCAAAATGTTCCAACTGGGGTCATCAGCAGGGCAGCATTTATTGAGCATTGTATAGGCATCAGTATTA
AGATAGAAATAAATGACTAGGTGTTATCATCCCCATTTTATAGACCAGAAAATCGAGGCTTAGAGAGGTT
AAGTAACCTGACCGAAGATACAGATCAAAAATGGTGCCGCCAGGATCCTTATTTAGGCAGAAACTGCAAA
GCCCTTGCTCTTAAACACTAGGTTGTATTGACTCTTGTTTACCCCTGGGCTCAAGTAATCCTCCCATCTC
GGCCTCCCGAATAGCTGGGATTACAGGTGCATGCCACCACATCCGGCTAACTTTATTTACTTTTTGTGGA
GATGGGATCTCACTCTGTTGCACAGGCTGTTCTTGAACTCCTGGCCTCAAGCGATCCTCCTACCTCAGCC
ACCCAAAGTGCTGACATTACAGGTTTGAGCCACTGGGCCAGGCCTACATTGACTCTTGACAGCTTATAGA
TGGATGATCTGTGCCTCACGCCTTCTGCGTTTTTTTTTTTTTTACTTTATTGAAATATAATTCATGTACC
ATACGATTCATCTATTTAAAATGTGTAATCTCCATAATCAATTTTAGAACATTTTCATGACTCTGAAAAG
AAACTGCATAACTATTAGCAGTCACTCCTCGTTCTCCCCAGCCACTAATCTGCCTTCTGTCTTTATAGAA
TTGTCCATTCTGGTTATTCCACGTAAACAGAATCAAACAATATGTGACCTTTTGTGACTGGCGTCTTTCA
CTCACCATAATGTTTCCAAGATCATCAGTGTTGTAGTATATATATATATATGTATGTACTACTTCATTCC
TTTTGTATGGATAGACCACGTTTTCTTTATACATTCATTAGTAGATGGACAGTTGGGTTGTTTACACTTT
CTGGCTATCATGAATCATGCTATGAATATTCACGTATAAGTTTTTGGCGTGGACACGTTTTCATTTCTCT
TGGGCTATCTATGGAGGAGTAGAACTGCTAAGTTGCATGGTAACTTTATGTTTAACCATTTGAGGAACTG
CCAGACTCTTTTCCAGCTCCATGGAACCCGTCCAGCAGTTTGTGAGGGTTACGTCTCCACATCCACATTA
ACACTTGATACTGTCTGTCTTTTTGTTACAGCTATCCTAGTGGGTGGCAAGTGGTACTTCTTTGTGGTGT
TGATTTTCATTTCCTTGATGGTTAATGACATGGAATATCTTTTCAATGCACTTTTCGGCCATTTGTATTG
TCTTCTTCACAGAAATGTTTATTCAGATCATTTGTCTTTTTTTTTTTTTTTTTTGAGACAGGGTCTCA
CTGTGTTGCCCAGGCTGGAGTGCAGTGGCATAGTCTTGCCTTACTGCTCCTTCCACCTCCCAGGCTCAGG
TGATCCTCGTGCCTCAGCCTCCTAAGTAGCTGGACTACAGGCACACACCACCACACCCAGCTAATTTTTT
CTATTTTTGGTAGAGATAGGGTTTTGCCATGTTGGCCAGGCTGGTCTTAAACTGCTGAATTCAAGCGATC
TGCCCACCTTGGCCTCCCAAAGTGCTGGGATTACAGGCGTGAGCCACTGAGCCTGGCTTGTATCCATTTT
TTCCATTTGGTCATTTTTCCTTTTATTATCAAGTTGTGATAAATCTTCATATATTCTAGGTGTAAGTCCC
TTATCAAATATATGATTTATAAATACTTTTTTTAACAATTTGTGGTTTGCCTTTACTTTTTTGATGCTGT
GCTTTAAAACATCAAGGTGTTTAGTTTTGATGAAGTCCAATGTATCTATTTTTTTCTTTGATAGCTTACG
ATTTTGGTGTCATTCTAGGTAACCCCTGCCTAATCCATGAAGTCATGAAGATTTACACCTGTGTTTTCTT
CTAAGTTTTATACTTTTAGCTCTAATACTTGTGTCTTTTTTTTTTTTTTTAATACAAATGGGGGTCTTGC
TATGTTGCCCAGGCTGGTCTTGAATTCCTTGCCTCAAATGATCTCCCACCTCAGTCTCCCAAAGTGTTGG
GATTACAGGCATAAGCCACCATGTCTGGCCTGCATTTATGTCTTTGATCTATTTTAATTTTTGTATATTG

TATGAATGCAGAGGTCTAACTTCATTATTTTACATGTGGATACATGGTTGTCCCAGCACCATTTTTCAAG
AAAGTGTTTTCCCTCATTAAATTGTCTGAGGATCCTTGTTGAAAATCAATTGACTACAAATGTGAGGGCT
TATTTCTGGACTCTCAATTCCATTCCAAGTATATATATGTCTATCCTTATGACAGTACTATCTGCATGTT
TTCACATGCATTATTTCATTTAATTTTCTCTTTATATTTTTATTATATTGTAATTATCTGTTTACATGTG
TTTCTTCCACTAGCCTATGAGTTCTTTGAGGGTAGGATTCATTTATTTTCTTGTTTACCTTTGTAACCCT
GGCAGTGAGCACAGTACCTCACACAATGTATGCTTAACAAATGACTGAATAAGCTCATCTCTATTTTTCT
GCTACATTCCTGGGGGAATGAGGACTGAGGAATGAGGCTGAGTGTTGCCTATGGATTTCATGCAGGTTAT
TCCCTATTCCCTCTTGGTACAAATGGTTGAAAGTAGATTTTAGTAGGTGACAACCCACAATGAAGGTTCT
CTAGGAAACATGGACATATCTATAATTGATGGTATAGATTATACCATTGATAGATTATACCAATTGATTG
GTATAATTGGTTAGTATTTTTAGTTCTCTTCTTCCTCTGTTGTGGGAAAATGTCAAGGTTGCAATGTCTAGAG
ATGCCTGAGCTCGCTCTCTTTTGGTGCTCTCCTCCTGGAAGGGGTAAAATGCTGACATTGACATGCCTTT
TGTAAGATTATTAGATGTCTTGCACCCTTTCTTCCTTTATACTCTCTCTTCAACACCATGTAGTGTTTCT
TCCAAACTTTAGAGTCCTCCTGGAGCTGACTATGCTCCTAGCTCATAGAGGCTACATGATACAGGATCAC
TTCCTCCCTGAGGCATCTCCCTGTACATGGAGACACTGCTTCATCACTGTTTCTGTATATCTTGCCAGGA
AACAATGCCAGATACTCTGTTGGGTTTGGGGTATGGAGATATTTATGTCTGAGTGAGTACATTAGACAAA
ACAAAGATAACCAAGTGGATTTGCAGCCTGTCAATGACGTTGGAATTGGTGGCTTTGCCTCTAATTATTG
AGTGCATAAAATGGGACTTGAAATGCTTCTAATTTACTTCAATTTTCTCAGCAACTTTTCAGTGTTTGG
TATAGAGAGTCTCCATGAGTAAAGGACGAAAACAACTACAACGACAAATAAGGTAAAAGAATATGTGAAG
AGAAATAGCACATTTCAAATGAATTCTAGTACCTGAGTGAGAACACTGCTTCTCTTTTGAAATAACTCAT
CAATTCGGGATGCTGTATCTTCTAACAATGGCACTGCCCCACTCTCCAAAGTCAGATAACTTTGTTTCAA
CTCATCTAGTGCTTTGGATTTAATTGCAAGTTGATTTTCTATATCCTGGAAGAGTAAGAGGAAAAGGTTT
TCAATGCACAATATTACAAAACAATTAATAAGGTGTCAGAGACAGGAGTTCACTCTTTTCAAGTAAAAAT
GTCATTAGATTATATAATTAAATAGCATTACATCAAAGAAATTTAAATCATAATACTCTTAGTTCAATTA
CATATGACACAACTCTGTATTTTAGGAGAATCTAGGCAACACGTCTGAACCATCATGGCAGAGCAGAAAG
GATGCTGGTCCGAGATCTGGTCCCCATTCCACGTCTGCCCTGCACTGGCTGTTTGACCAGGCATAAGTCA
TCGAACCTTTCAGTCTCCATTTTCTCATTTGGAAAAAGTGATGATACCCACAGCATGTGTGCCAAGCTAA
GAACTCAAATAAAATCACGAGCAAGAAGGTGCCTTTAAACCATATAGCATCATATAAATGACAGACGATA
TAACTGTTGGTAGTTCAGTAATAACTTTAATCATTTTCTACCTCTTAGTTTATTAATTCACTCATAAGAG
GCACCCTGACCTGGTCTACTCTTTATAGATACATTTTTAAAAACCTACAGGATCCCTCTACTACAAAGGA
CACCATGGGGCCAGCAGTCTGAAAACAGAGATGAATGAGGCCAGCAGCAATGGTGCCACTCTACTCAGAG
GAAGGACGGTCGGAGCTGCTTATTTGTCCTTCTCAGGATTGCAGTTGAAATCCAACTTGGAAAAAGTTTA
AACTTTTTAAAAATTATTAAAGCATTACATGCTCATTACAAAGAAACTGGAAAACACAAGAGATCTTTGG
CATTCAGAGGGATTCATTTTGAATTCCCCTCAAGTCTCCCAATTCACAAATTTGGGACGCGCTTCTGCAT
ACTTTCTTTAGCATTACATTCCCATCCAGATGCATGTGTTCTGAATGCATGGCCTCAAGATAACGACCCT
TAGCTCATGTTCTATTTCTCTCTTGAAAATTGCTTTGCATAAGGATCCCAGCTTTTTTTATTTTTATTTT
TTGAAAATTGCTTTGCCTAAGGATCCCAGCCTTTTTTTTTTTTTTTTGAAAATTGCTTTGCCTAAGGATC
CCAGCTTTTTTTTTGAAAATTGCTTTGCCTAAGGATCCCAGCTTTTTTTTTTTTTTTTTTTTTTTTTTAA
ATCCTTTGTAAGAATCACTGCATGGTCCATAAGGAAAGAGAAACATGAGTGCCTCGTGGGCATGGGGTAG
CTGAGCAGGTGGCTTGTACCCTGGGAGGGACAAGCTCCCTTGTGCTAGCCTCACAGAGGAGCACTGAAAT
CCAGTCCCGCAAAACTGCCAGATTACCACGTGAGGAGCCCTCAGGTCACTCTTGGAAGGTGGAAATCACA
AACTCTAAACCAATGAATGTCAGGGGTCTTCTGGACTGGAAAGTAGAAAAAGGGAAAAAAATCTGTTCCA
TAAGAAACTGATAGCTAGGTTTGGGAGTAAGAACGGATGATGAGAGAATGGAGCTGGAGGAATCTTCCAC
TGTATGACCCTCTATGCTTTTAGAATTTAGAGCCACATGAATATATAGCGTATGAACAGAAAACCTCTCA
CTGTCGTAACAATCCACCCATACTAACATGTGGGTGAATTTATGAAATATTATTCTTCTGGACTGGTTAC
AAAGGCACCCAGGAAACAAAACGACTTCTCTGAAATAGCCTTTGCCAATGAGATTTAGTCAGCTGCTACC
TCTGTCCATCTCTGCCACCCTAACTCGCTCCCTCACACCCTGACAGCCTTATTTATTAGCATGTTTCTTT
TATCATAGGTTTAACTTTTTTCATCTGCAAAGTTATAAATGAAAACACTTTAATATTAAATCACTTTCCT
TCTTTGAATTTATAAAACAGTCTCTCCTAAAGGCTTGACTAACTAGATTTCTAAAAACACTTATTTACTA
ATAAGCTGTCATAATTCCCCTATAATGTAAAGAAAACTGGTAAGAAATGACTACAAAGCAGACAAAAGGA
AGTAACAACACACACACACACACACACCCTTCAAAAATGGCAGCATAAACAACAGCCATGCCGGGCACAG
TGGCTCACGCCTGTAATCCCAGCACTTTGGGAGGCCAAGGCAGGTGGATCACTTGAGCCCAGGAGTTTGA
CACCAGCCTGGGAAACATGACAAAACTCTGCCGTTACAAAAAAATACAAAAGTTAGCTGGGTGTGGTGGC
ACACGCCTACAGTCCCAGCTACTTGAGAGGCTGAGGCGGGAGGATCCTTTTTTTTTTTTTTTTTTTTTTT
TTTTTTTGAGAGAGAATCTTGCTCTGTCACCCATGCTGCAGTAGGCATGATCTCGGCTCACTGAAAACTC
CGCCTCCGGGATTCAAGTCATTTTCCTGCCTCAGTCTCCCAAGTAGCTGAGGCTACAGGCATGTGCCACC
ATGCCCAGCTAATTTTGAGCCACCGCGCCCAGAGTGGGAGGATCTCTTAAGCCTAGGAGCTCAAGGCTGA
AGTGAGTTATGATTGCAACACTGCACTCCAGCCTGGGTGACAGAGTGAGACCCTGTATCAAAAAAAAAAA
AAAAAAAAAAAGAAAAGAAAAAAAAAAAGCCATGGCAATAGCAGCACACGAACAACCACACACGGTGGGT
TGCTCGTTTCTTTTGCTCTGCAGAATAATACGGATTTAGCCCAGTAGTCCTGTCATCTGACCTTGCTTCA
CTGAGGCCTAACAGTACCCTTCAAGTTTCCCAACTCCCACTTCACCGGCAAATTAATTTGTCTTACTTTA
ACTTCCAATTTGCTACACATAAATCAGGGTGGAATTAAAAATAATCTTTTGCTAATTATGGAGATTCAGT
AGAATTTGCAAGTCCTATTTTTCCATTCTGTGAGAACCAGCATTAAATATTTTTAAAATATCTAAATTCC
TCTGACTTTATCACGAACATACTTCTTTAAGAAGCTGTGCTTGCTTATAGTATAGAGGCATCAAACTTGA
GGGATTAATAATCTCATCTCAAACCTCCCCACTCTATTCAACTATACAATTTTCCTTGATAATTATAATA
TGTCAAACGTGGCCTTTTTCCAGTCATCAATGGCTTTTAGAAGCCCTTCGGAATATTTCAATCCTAATGT
CTTCATGCTTCATCAACTCCAGTCCTTAACTTTTCTAGAGTAAAGCCACTTTAGCAAGCTTACCTGAACT
GAAGCATTCTGCCCTGGGATAAGTCATTAAAGTATACATCAATCATTTTCATCATTTTCTTTTCTTTTTT
TCTTTCTGTTTTGTTTTTTTAGAGATGGGGTCTTATCCAGGATGGAGTGCAGTGGCATGATCATGGCTTA
CTGCTTGAACCTTGAACTCCTGGCTCAAGTGATCCTCCTGCCTCAGCTCCCGAGTAGCTAGGATTACAGG
TGTGCAACACTATGCCCAGATAACTTTTTTTTTTTTGGTAGAGACTGGGTCTTATGTTGCCCTGGCTGGT
TTTGAACTCCTGGCCTCAAGTGATCCTTCTGCCTTAGCCTCCCAAATTTCTGGGATTACAGGTGTGAGCA

ACTGCACCTGGCCTCATTTTAGTTCTTGTATGCAAAGAATAGTGGAAAAAAAAAAAAAAAAAGAGAAATT
AACATTTATAGAAAAGCAGCCTTTTAGGTCTATTAATAGATATATTCAGGCAACTATTAAGCACCTATGA
ATTTCACAGGCAGTGACAGGTATAACAGGCATGCTGATGTGCCAGCCTGCCTTGAGAATCCCACAATCTG
GTAGACGACAGACCCGTGGACAGATGAGCCCAGTACAGTCTCTGACACATGATGCTACATGGGGTGCTAG
GGAAGCCTGTTTTATTTATTTGCTTCCATCTTGGCCTTGTTTATGGCCTTTTACAAAGAGGCATCCAAGC
AGCAGCATAAAAAATTAAAATAGGAAGAAATGAGCTAATGGAAATGTGGGAGTAGGTAGGAAGGCACAGT
CAGTGGGCACGTGGTGAGGGAGGGGGTCAGGGTGCTTTGATTGAGTTCTGACAAACATAGAGGAGAACCT
GTGTGTGGATGGTGGGGGCGAGGGGAGGGAAGTAGAAATAATTCTGCAATCAGCTGCAAATGTAATGGCA
CAGAGGCAAATGGGGACTGACGAGGGATGATGCCGGCCAGGCATGTCTGTAAATTTCTTTTAAAGCCCCT
TGTCTCAGTCAACACTAGTCATTTTTCTAATGAGCAGAGCAAATGTGAGAAATGGTTTTCTATTGGTAAA
ATTAATGGATTATTATTGTTATTAGAGATGGGGTCTTGCTTTGTCACCCAGGCTGAACTACAGTGGCATG
ATCATAGTTTACTGTCACCTTGAATTCCTGGGCTCAAAGGATATTCTTCCCTTAGCCTCTTGAGTAGCTG
GGACTACAGGCATGCACCACCATGCCCGGCTAATTTTTAAATAGTTTTTTGTAGAGACGGGGTCTCACCG
TCTTGCTCAGGCTGGTCTCGAGCTCCTGGACTCAAGCAATTCTCCCACCTCAGCCTCCCAAAGTGCTGGG
ATTATACACATGAGCCACTGCGCCCGGCCTTAATGGCTTATTAAATAACATAATGAGTATTAGAAATGGG
TTCTCACTAGTAAATTTCATGTACTCAAGATCCATGGATTGGCTAAACTACCGTAGATATAATTTCCACC
CCTACTTGAACGGCTATAAGAACTGGGCATAGCCTGTTGCCTTCAACTAGTGCAATAATCCCTAAGGTAA
GTCCTTATGTGGTTTTTGTATCCAGTTTAAACTCCAAGGATTCTGGTTGCCTAATGTTGGCCATAGAAAT
AATGGACTCTTGCTTCTGGAATATTACTATGTCTGCCTTTCATGCAAAGCGGTGGTTGGTGTGCTAAAGA
GGGCAGAGAGGCTTTGCTGAACTTAGTTATATAAACTATTTTTAGTGCTTGCTTGCTAATCTATGTTTCT
ACAGATGGTGGCATTGTGTCTGGAATTTATTTTATTTACAGCTTGGTAGTGAGGTTGTGGGAAGAATAGC
TAAACTTAATCCATTTCGACCTTGTTCCGTGGCTACCATTATCTATCAAAAAGAGAAACAACTGTGTAAG
ACTCACTTGACTTAGGTCTATTTGCAACTCTTTGTAGGTGAGGGACCAGAATGTCATTCTAAAACATGTG
AACTTCATTCTGTGGTCCATCTGGAGCCACTGGAGGATTTTCCAGTGGAGAGTGTTGTGACCCTTTGCAT
TTCAGAAATATCCCTCTGCAGCAATGTGGAGAATGAATCAGAAGGAAATGAGGGAGGAGGCTGGCAAGTG
GGCTGGAAGCAGCTGCATGAGACAGGCCTGCACTGAGGGTGGTCTGAAGGAAGCCGGCCTGACCGAGACA
GACTGGCCAGACAGTAAGGAGTAAGTCAAGAGCACCTAATGAGAAACTGTATGTAGCGACACGCATGAAA
ACACCTCCTGGGCTCTGGAAAGAACCACCTACTAGGGGACAGGCCAGCACCAGGCTGCGGAATGTAGGCT
TCCAGTAAGGAAGCACATGACTCCAAGGTGGCTGTCAGAAGGCTAAAGTGGAGATGGCTCATTGGGAGGT
GGGAACAGTATACGAGCAGGTGAAAAGGGCCGCTTACGGTGGTGCTGCTGCTCACATTTATGTCCAGTGC
TATCCCGTGACCTCCTCAGTAGAAATGGGGTCCGGCCAGACTTTCCAGTCCTGACAGTGACTATTGTAAG
GCCGTCACGCAGGAAGTGCAGAAACAGCACAGCGTGTGCCGCCTGCCGTGATGGCGATGGCAGAGGTCCT
CTGAATGGGCAGCAGCCACAAGGGCAGTGCTAAAGCAGGATCAGTGTGCAAAGACTGAGTGATGCGGCAA
AGCATAGCTGAACCACGGACAACACCCTCAAGCCCAAATGTGATTCAGCAGAGGTTCCAAGGGACAAGTG
AACTTTTTAAAGCATAATACACAATAGGTAGAAGAAAATCATTTTCCTCGAAAAAACACAGAATGAAATG
CTAAAAATAATGAAACCTTTAGAGTAATTTTGTAACATTAGGCAAAATGATTAAACAAATGGAAAATTGG
AAAGCATTTAAATCAAAATTCCCTTTGAACATTTTTCCCCAAGAGTACTACTCAAACCTCTTAAGAGCAG
CAATACTGTAACGGTGAAAGTACATTCTTCTGTTTATCATAAAAAACGGCACTTTGCAATTTTGTAAAAC
CCATGGGTCATTATCTAATTGACATAAGAAAATAAGTAAATAGAGGGGAGCTGGAAGAGAGTTTCCACAA
ACTACAGCAACTTATCCTCGGGGCAAGAGAGGTGACCGAATCACCCCAGCTCGCGGGTTGGGTGGGATGC
TGTTCCCCTCCTCACCTGACAGTCCAGGAGCAGCTTCTGCACTGAGATCACACTTTCAGGTTTTTGTAAA
GTTTTCAGTCTCTCTTCTTGTGCTTCCAGCCAGTTGTTCAAGATCTGTATTTTATTTTCACTCTCAGTGA
TACTTTCTAGAAGTTGTTCTAAATGTTGTATCTAAGTGAATGTAAAGATTACAAAAAATGTTAAAATGTA
TGTTTTAAAAGGTAAATGCCATGACGTTATTTTTTAAAAAACAATTTTGCTTCTTTTCAAATTTCTAATA
TTTCATGTAATAAGATGCTCTGATAACTTTTGAATAAAGATTCAAAAATCAGAAAACAGAGTTAAAGCTC
CTCTTAGGAAAAAAATATCATATTTAAGGTGAAAGCTAATCTGCTGAGAAAGGTAGCTGTTGTGGAGTTT
CAGATGTATACAAAATAAAATGTTCCCAACATTCGATATTTTTTCATTGTGTCATCTATTAATATATGTA
AAGTATAAGACAAATTTCTTTCCTCAGACTTTCTGCATTAGAGTTGCTTAAAATTTCTACCAATATCAAT
AAAAAATAATTTATCAATTCAATAAAATAATCATTGTCTTTAATGTCTGTGATTCTCATTCATAATAAAT
TTTTTATTAGGTCATAATCATAATATACACACATTTTTATATTCTTTTTTACATACATTATAACTACTGT
GTCATGACATAATTTTTTTTTTTTTTTTTTTGAGACGGAGTCTCGCTCTGTCACCCAGGCTGGAGTGCAA
TGGTGCAATCTCGGCTCACTGCAACCTCCACCTCCCGGGTTCAAGCAATCCTCCTGCCTCAGCCTCCCTA
GTAGCAGGGATTACAGGCACGTGCCGCCATGCCCAGCTAATTTCTGTATTTTTAGTAGGTCAAGAAAACA
CCTGACCTTGTGATCTGCCCGCCTCGGCCTCCCAAAGTGCTGGGATTACAGGCATAAGCCACCACGCCCA
GCCTGTCATGACATAATTTTAAAAGGCTGCCCGGCCAGGCGTGGTGGCTCTTACCTGTAATCCCAGCATT
TTGGGAGGCAGAGGTGGGTGTATCACTGGAGGTCAGGAGTTCGAGACCATCCTGACCAACATGGTGAAAC
CCTGACTCTACTAAAAATACAAAAATTAGCTAGGCGTGGCGGCAGGCATGTGTAATATCAGCTATTTGGG
AGGCTGAGGCAGGAGAATTGCATGAATCTGGGAGGTGGAAGTTGCAGTGAGCCGAGATCGCGCCACTGCA
CTCCAGCCTGGGGAACAGGGCGAGACTCTGTCTCAAAAAAAAAAAAAAAAAAAAAGCTGCCCCAATGTTT
CATCAAATTAATACAGTATAATTCGATGAACTATTCCCCTAGAGTGAGAATTAAGGCATGGTACATTTTC
ACAGCTGTAAACGATGCTGAATTGAACACTCTGTGCACATCATTTACTTTTTTGAAGGACTATCTACTTA
AATGTGTAAGAGGTGACTTGCTTGGTTAAGTGATAAGATTATTATTACGGTTCTTTACATTTTCCAAATG
CTTTCCAAGAAAGTACTTAAGCCATTATCAGCAATGTATGAACGTGACAGCTTTGGGTTTTTGTCCTTAT
CTGATTAATTTTTTTTCTAATTAAGTGCATTATGTTACACAGTGTTTATTTTGAGTATCTGCTAATGATA
TCTTTCCATGTTTATTTGCTAACTATAATTTCCTCTTTTGTGAATTGTCTGTTCATGTCCTTTGTCCATT
CATGTACTTGTATCTTAATTGTGTAAATCCATTTGTATGCATTCTCTACACAGTAAACACACCAATTATC
ATCATGATTATATGTAAAGTATTTTTTCAGGAATAAGTTTTCCGAATCTTTTCAAGAGTCATGGAGTGAA
AAATCTACCAAAAAGCCAAGTGCATTTTTCTTTCTTTTTATAACCTTTTCAAAGCTGAAATAGCTTTGCC
CCTTTTGAACATCTGCTTTCATAGAAAATGTAAAATCTCTGATCATTTAGGAGTCTGACATAATACTTGA
CATGTTCCTAAATAAAATTCCTCATCTTCACTTGCCTAGCTCAATTTCCCACTAAGAAATCTCAAATATA
AGAACTATTTTTATATTCTCTTATAGGTACCAATGGAGAATGCTAAAACATAGGATTTATAAAAGGGCTA

TAGTTGAGATGATTATTAGGCTTAATAATCAGTCAACTAATTGAACGTCTTTTTGATTTTTCAGAAAGT
GTGTTTCATAAAGGTCAAACCACACATCCAGTTGTGACGCAGGAACACACCTTTCTATTCAGCATTCCAT
GTACACGGTGCCACTGGCGGTTCATCTCCCCCAGGTGCTCTGCAAACTCCGTTCTTTCATAGCGCTTGCT
TTCTACATCACAGGTGCTTAGCTGAAGTAATGACTGGTTAACGAAGTCAACTATCCACTGTTTATAGTCC
ATTTCCATTCTAAACTCCTAAAATAAGCAAAGTTAAACACCAAAGCAGTCATGAATGTTGGTCAGATCAA
ATGGATTTCCCTTTATGTGCTCGAGGGGGCACCAAGCTCCCGTCCATTAATCAAGGGGCACCTGTCAGGA
GTTCTGTTCTACCCTCCCCAACCTACACCAGGAGTTGGCTTTATTGGAGTAGGGATTCTTTTGGGGAATT
ACACAGAGATGCACTGCTTTCAAATAGGCTGAAAAGTCAAAGGGGCACTATGTATGGCAGTTGCTATCAT
CTGAACCCTGACCACGACCCAGGATATGACAAAGCTTCCTGGGGGAGGCTGCCTGTCAGCTGTGCTGGAA
TTCTGGGCCATCCTGAGGGCTCACGGAAACAACCAGATGGGAAATAGGAAGTAAAGTCTCTTTCAGAAAA
CCCAGGACACCTTAAGGAACTCTGTCATTTAGGCAGCTTCCCTGTTCCTTCGGGGATAGTTAAGGCCTCT
CAGGTGGCTTTAGAAAGTTTGGGTGGCTTTAAGTTGTACAGCAATCCTAAACCCACCCAGGGCCAACAAC
ATTTCTGCCAAACCTGTCACTTACTGATTTTATCTCTGCAAGTTCTAGCACCTCTTTTGGAGACACCCGG
GGGTGACAGTCATGTGGTATGTGCTAGGTTGCTAGAGCCTGTGAGAATATACACGTGTAGACTTTTCGAA
GATTTTACTACACACTGAAGTTAGGATGTGATGGTACATAAAAACAAAATTCTCTGCTAATATCTTGCTT
GGTGATTAAGCCATTCATCTTCTGCCTACCAGAAGCTAGTTCCATCAGCCTGCATGGTCTTAAAGCAATG
ACCACACTTGTCACTCATCTTTGTATTCCCAGTGGCCAGCATAGTGCTGAGCACACAATACACGTTTGCA
TGTGGCTCATGAAATGTTAATTAAATCTACTTGAAATTAAATATCACAGAGAAGGCCACATTTATATCTA
TTTGTAGAAGGATCTCAATATTTTCTTACTCATTCTCTTACTCAAAGAACATTTCATTAACACCTGTTAG
AGGAAGGCAGGTATTGGGATAGGCGTGCTATATTTTAGCAAGGTGAAGGATGGCCCCTGGTCTCGAGAAG
CTCAGTCAAGGTGGGGAGACAGGCAAATAAACCAATAATTATAATAATGCATGATAGGAGCTACTAATAG
CATCATGGAGACATCTAATCCAGGAAAGTCACCTAGTCTGGCTGGGAGAGTCAGGGGTGGATTTGCAAAC
AAGGACAACTCGAGCTGACTATGGAAGATGACTAAGAGGACGTATACAGTTAAACGTGGGCCCTGGCATT
CCAGGTAGAGGGTGCAGCATGTACACAGGATGATAAGGGAGAGCACCAAGAACAGTTAAGGAATCAAAAT
CACTCTGTCAGGCAGAGTCTGTGGTTATTGGGGGTGGTGGGATGGGGATAAAAAGGTGAGACCACAGTCT
GTTAAAAGCTTGCTTGGATTGTCCTGTGGTGATGGGGGCTGGCAAAAGGAATTTAAGTGGAACAAAAGCA
AGTCTACTAACATCTCTCCAGAATCATCCACCACCCCAGTTTCCTACCCCTAGAATTAGTTTTTGAAAT
TATATCCTATGTGTCCCTTTGTCCAGCATTACCCCTCTGATTAGCCTTCTTGTTTCAATGAAAAGACTTC
TGCTCCTTTTGCATAATTACCTTGTGCTTCTGAAGAAGATGTTTAACTTGAGATGCAGAACTTGGTGAAT
GCACGGAGTCTTCATCTGAAGTTTGATGCTCCACATTGTTCATCCAGCTAATCATTTCTGTGATTGCTTT
ACGAGACGGCAATTTCTCCATTTGAAGCTGTAAGAACAAAATGATTTCCATTTAATTGCCTGCAGTTAAC
AAAATGAATCAGAGCATCACTAAAGATGATATCTGGTTTGATAAAAGGTCTTGCTATATAATTATGCAGG
TTACTCAAAAAAAAAACAAACCCAGCATTCAAACTTAGAATAAGCGACCCCAAAACAATGACAATGACCT
TCACATAAACTAACACAGTGGCAAAGATAAACTGAGAAATAAAGTAATTAAGCCTGATTTCTCTCTTAAG
AAAAATCCCATTGGAGGAGGGTCCAGTAATTAAGACTTATATTCAGTGGTGCCAGAGAAAAATAGGTAGT
GTCAATGAAAATTATTGAGTCAGAGAAATAATTTTAAAAGAGTTATGAGCTAACAAGTGAATGCTAATTC
AAATGCTGAGGCTCTAAAGACTTACCTGGTGAAGTTTTTCTTGAATATCTGGAAGTTGAGTTATGAGCAT
TGTCCATTTTTGTTCAAACTGTGCTAAAGAAGCTCTCAGTGTAGCTGTATCAGTTTCTTTCAGGTGAAGA
AGCTGGTTCCCGATACTGATAACGGCAGTCTTCAAGGAGGATTTTTCATCAACTTCTTTTGAAAACTCCT
AAAGGAGAGTTTTAAAATTTAGAAACTTAAAATTTAAATATAGCAGAAAGTAAGAGTCGGAATAACTGGC
TAGAGTCAACAAATAAACATAGTAAATATACGAATGTGTATACACACACACACACACCCCTTTTTCCT
ACTGTTGGGCATTACATACACGATGGGGAACAAAAGAGATGGAATGCATACCCCTCAAGAAGCTTATCAC
CCAGTGGGTTAACATTTTTAAAAATAAGTCATTATTTAAATGGGGTAAGTTTTACAATAAACTATGGAAC
CCAACACAAAGTGCACATTAAATGAATTACTTGCAACAAGTTTGTAATTAAAATGTTTAAATCTTTCCTA
TGTAGAAATTCTTTCAAGTATGTTGAAAAAATTTACATTTTAATAGCAAAGTTAGTAATCATAGCTACGA
AGTATGAAAAATAAAAAAAAAACAGGAAAAGTCTAACAGAAAAGACTACGTTTCATAAATGCATTGACCA
ATAATCATTTTGTAATTATATTACAAGAGTAATACATTTTTATTTCCCCCAAAATTTGGGGGATATTTTT
GAATTTTTTTCCAAAAAACACCTCAAAACAATGGAACAAAAGCTTTTTAGTAGAAATATCAATTTTGTTT
ACAATAATTTAAAACTATGCATTTATTAATGTTAACATTTATAAGTTAATAACCTTATAAAGTTGTTTTT
GGGTCTTGTATTTTTTGTATTTGTAAAACATGACCTATGTCAGTGCAAGTTTTTTGAGACTGAGTTTCAC
TCTTGATGCCCAGGCTGGAGTGCAATGGCGCCATCTCAGCTCATTGCAACCTCCACCCACCGCGGTTCAA
GTGATTCTCCTGCCTCAGCCTCCCGAGGAGCTGGGATTACAGGCATGCACCACCATGCTCGGCTAATTCT
GTATTTTTAGTAGAGACAGGGTTTCTCCATGTTTGTCAGGCTGGTATCGAAATCCCGATCTCAGCTGATC
CACTGCCTCAGCCTCCCAAAGTGCTGGGATTACAGGCGTGAGCCACTGCACCTGGCGCAAGTTTTAAATT
CAGATATATTTTATGGGGTCAATTAAAAACATATTTTATTATAAACGAATGAACAGTATAAACAGTTCTA
GGTTTGAAGAACACAGCTGCCATTCGCCCAAGTCTTACCCCTTATCCACAAATAAATACGAAGACTATCA
CATCAACCCTGATGCTTTTTCCTTGATATTTATTTCTGACCAGTAATTAACTGAACATATGCTATTACAA
CTTACAAAAAAATTGTTGATGTTGCTTCTGATTGTATCCAAGTCCTGAGACACATTGAGGGACTGTTCTT
TCCAGTAATTCAGAGTATGCTGGGAAGATTCCAACCACTTGGTTAACTGATCCGAATCTCTGTTATAACT
AACAGGAGCAAAGTGAGAGAGAAGGCAGATTAGAAACATATTCTGATAATGATATGCATCACCAGCAAAT
TTTCTTATTTTATTGTATGTCCTCCTATGTTGATCAGTCCTAACATTCAGAATATCATGACGTTAATAAG
GATTATATCATGTTTTATACCATGATGCTCCTGGCATTTTCTAGGACTCTCTTCATTACAGCTCAGCAAG
AACAGTGAGGATTTTAGGCCAGATGTGGTGGCTCATGCCTGTAATCCCAGCACTTTGGGAGGCCGAAAAA
GGTGGATTGCCTGAGGTCAGGAGTTCGAGACCAGCCTGAAAAACATGGTAAAACCCTGTCTCTACTAAAA
AATACAGAAAATACCCAGGCATGGTGGCAGGCGCCTGTAGTCCCAGCTACTCAGGAGGCTGAGGCAGGAG
AATCGCCTGAACCCAAGAGGTGGAGGTTGCAGTGAGCCGAGATTGCGCCACTGTACTCCAGCCTGGGCGA
CAGAGCAAGACTCTGTCTCAAATAAAAAAAAAAATAATAATAATAATGAGGAAGTCTAAAGCATTCTTTA
TTTCTTATTACAGCTACACAAAAGTATACCCAATGAAGGAACAGAGATTTTTATCCATCAAATGTCTTCT
ATAAATTTGTTTATATTAAAAATATAGGTCAGGCACAGTGGCTCACTTCTGTAATCCCAGCACTTTGGGG
TAACAAGGTGGGAGGATGGCTTGAGCCCAGGAATTTGAGACCAGCCTGGGCAACATGGAAAAACCCCATT
TCTACAAAAAATACAAAAATTAGCAGGGCGTGGTGGCATGTGCTGTGGTTCCAGGTACTTGGGAGGCTGA

GGTGGGAAGATTACTTGAGCCCAGGAGGTCAAGGCTGCAGTGAGCCACGATCACGCCACTGCACTCCAGC
CTGGGTGACACAGTGAGACCCTGTCTCAAAAAATAAATAAAATTACATACACACACACACACACACACAC
ACACACACACACCATACATACACACACACACACACACACACACACAACCAGCATTTGTATAAGCTGTATA
ACAACAAACTGCTGCTGGCTGAACACCCAACGTATTTGCCCGAGGTAGTGAAAATATTCAAACAATATTC
TGCCCTTCTTGTAACTTTTAAACTGCCTTAGATTAAGATGCAGGGATGAGAATGATGTTTAAATGTTCTA
TGTTCTCCTCCTTCCTCACACGGTTCAAGATTATACCAACTAAGCACAACAAATTCTCCAAAGAACTCAA
AAGCCTATTTCAAACTATTCTGTTAGCTAAAATCATTTAATTTTTTAATTTTAAAACTTTTGGAAAGAG
CAATATCATGGTATAAAGGTAACCTATATATTATTTTATAACATAATTCCTAGCTTCTATAGAAATGTGT
AAACTAGCTGGGTGCAGTGGCTTACACCTGTAATCCCAGCACTTTGGGAAGCTGAGGCAGGAGGACTGCT
TGAGGCTAGGAGCTTGAGACCACCCTGGGCAACAATGTGAGACCCCATCTCTACAAAAAATTTTATAAAA
TTAGCCATGCACGGTGGCCTATGCCTGTAGTCACACCAACTTGGGAGGCTGAGGCAGGAGGATCGCTTGA
GTCCAGGAGTTCAAGGTTGCAGTGAGCTATGATAGTGCTGCTGCACTCCATGCACTCCAGCCTGGGTGAC
AGTGCAAGACCTTGCCTCCTTAAAAACAAAAAAGAAAAGAAAAGAAAAGAAAAGAAAAAACGATCACAGC
AAACTGATTACATGTTATACTGTGTCTAGCAAACCATCAGAGATTCTACATCGCGTTTAGCCCAGAAGAG
GGACCCAACTGCTTTAGACTGCCCAAGAAAAAACAGCATAAGGTGGGTTGCAGGTAAAATTTAGTTGACT
ACAGAATCCCCGAGGTCTTTCTTCACAGCACAATATGAAGCCAATCCACCCCCAAAAAGGCTGACCTGAG
CAGATGCTTGAGAAGAGCTTGCAGCCTGTGGAGCTCATGGTCAATTTTCTTGTTCAGGGACAACCACTGC
TCTTCCAGTTTTGCGATCTGGCCCTCTAATTCAGGACAGCTCACAGACGCCACCAACTGTTTGCCTTCGT
TCAGAGTTTGGTAAAGCCGGGCGTGTTTTCCACCAATGTTTCTTTTTATTTGCTAATAAAAAGTAAAGTC
ATAGAATGAATTATTTAGAAAATAAAGTCTGCCAAGCTATTCACAAATACTGCATTTAAAACTGACATTT
GTGTCCACTGATAAAACAGTAACACTTTCCCAACATTCAAGACTATATAGTCTGACTGGATGCATGATTA
ATGGTTTATTGGTTACCTTTCATGATAGGTGTCCAATCTTGCATTTCTAGAGCACAGATTCAACTTTGTA
GACTTACTGGCTGGATGCAGTGGCTCATACCTGTAATCCCAGCACTTTGGGAGGCTGAGGCAGGCAGATC
ACCTGAGGTCTGCAGTTCGAGACCAGGCTGACCAACATGGTGAAACCTCCTCTCTACTAAAAATACAAAA
AATTAGCTAGGTGTGGTGGCGCATGCCTGTAATCCCAGCTACTTGGGAGGCTGAGGCGGGACTTGGTGGC
GCACACCTGTAATCCCAGCTAGCCAGGAGGCTGAGGCAGGAGAATTGCTGGAACCCAGGAGGTAGAGGCT
GCAGTGAGCTGAGATTGTGCCACTGCACTCCAGCCTGAGCGACAGAGCGAGACTGTGTCAAAACAAAACA
AAACAAAACAAACCAACCAACCAACCCAAATCAACTTTATAGACTTATTGCATACAAACAAAAAACAAGC
TGGCAGTCATTAGGCCATGCTGAGCTCACAGATAGGTTTTGTGTGACCTTAAGATCAGTTTGAAAAATCA
GGAAATCTTACCTAATAATCAGGATTGCCAGTGTCTGTGGGAAAACTGGAAGACCTAGCAATTGTTGGTC
TGCATCTCATGTGGCAAAGGGCGGCTGTAACTGAGCAGCAGCTGCTGGCTCTAGGAGAGCCTACTCCCTC
TCCTTTTCCCTTGGCTCAGTCCCCACCACCCCTCTGATTGCAGAGCCAGTAGGGTTTCCTTATTTCTATT
CTGCCCCCGAAAGCACTTCAGATGGTGACTTAGATATGAAGAGGATAAATAAAATAGTATTTCTCTATTA
TCCATGAGATGCGAATACTAGGCAGAAAAATTCATTTCCAGGGTCTTCTACTGAATATAAAGATTCAGTA
GAGAGAAAGGAAGAAAACTTTAGAAAAATAAATTAAAACAGCGTATCATTAATCCAACTTCACGGAAAGA
AAAATGAAATTCTTTGAAGAGAAGTCTGTCTAAAGGTAATTATCTAACACAGCTGGATTCAGCTAATGCC
ATTTATCCTGACACCTGTTTAATCTTAAAAAATAAATTATTAACAAAACAGAAGGTTTGCTATTTTCAAA
TTAAGTTAAGCCTTTTAAATCATTACCAAAAAATTCCACGTCCATAGCCCTTTCCACCACTCCCATTTGT
AATCCCCTCCCCCCCGTGTCTGAGCATCTGTATTAAAAGAAAAAAAAATCAGTCTAATTTTCTAAGTGAA
GTGCTAGATTCTTCACCTTTAAAACATCTCTGAAAAGTCTTAATTCACCCCCCAATTTTTTTTTTTTTTT
TTTTTTTTTGAGATGAAGTCTCGCTCTGTCACCCAGGCTGGAGTACAGTGGCGCTATCTCAGCTCACTGC
AGCCTCCGACTCCCGGGTTCCAGCGATTCTCCTGCCTAAGTCTCCCAAGTAGCTGGGATTATAGGCACGT
GCCACCACACCCAGCTAATTTTTGTATTTTTAGTAGAGATGGGGTTTACCATATTGGCTAGGCTGGTCT
CAAACTCCTGACCTCAGGTTATCCACCCACCTCGGCCTCCTAAGGTGCTAGGATTACAGGCATGAGCCAC
CACGCCCAGCCTAATTCACCGATTGTATGCATGGGATACAGTCTGTGCACGAGTAACTAGGCTGAGCCAG
CATTTGAACACAGGTTTGTTGACTTCAAAGGCCAGACAACTGACTCCTAGGTTCCATGCCCCACAGACGA
CGGCTGATCAAGATGACAACATCTGTCAGACTCACACAAACCTTTCCTTGATTCTGAACTGAGAATGGCC
TATGAAGTCCATATGTGAGATGGGCTTTACAGGATATGTCTTCTTTAGTCTGGCAAATTTATTTAAAAGT
CTTAGAACAATTTTTTTCTTTTTAATATTTCAAATGTAATAGAATCACACATTTTAACAGATATGGTCAC
TTTTGGAGAAAACAATCACACTCATATTAGGTTGGCTAATATTAGACTGTTGCTTAAAATAATAAGCCTT
AAAATACTGTTCTCATCTGCATTCTTTCAGCTGTTTAGATGATACCTTCTGTATCCCTAGACTAACAAAG
AGCTAAACAGTACTCTCATCACCCCCACTCCCACCCACCCCAGAGGACTCAGATTTACCTTAGAGTTAGG
CTCAATATAATTAATAAGGCGGCAATGAGACCAACTGTAGCTTTCCAGGCATCTAGGGAGTATAAATACA
GTGTCCCAGCCTCTGGAAAATGTTCCTTATAGAGGTTAAAATACCTCCATGGAAAAGAGAACCCTGGAAT
TATTTCCTGCTTTCATTTTCCAACTAGTTCATTCAGGCAATAAATGTGCTTTTGAGGTTTTAAAGTTGAT
ATTTCATAACTGCCTCTAGCCGCACAACTCAGATTCTGACGGCATATATCCTAAAGTTAAAACTAGGAAT
TTTAAGTTCCTGGTGAGAAGACTTAAAACTTGTTTTTATCTTGTTGGTCATGTTCTCAATGTCACTTGAA
AACTATTTTGAGGTTTTATCTTTTCTTTCGCACCAAAATTAGAGACACAGAGACAGATGATAACAACGCA
AAAAGTTACACAAAAAAGTTTAAAAGTTTGAGGGTTTTTGTTTTTTTGTTTTGAGATGGAGTCTCGCTCT
GTCACCCAGGCTGGAGCGCAATGGCATGATCTTGGCTCACTGCAACCTCCACCTCCCAGGTTTAAGCAAT
TCTCCTGCCTCAGCCTCCCAAGTAACTGGGATTACAGGCACATGCCGCCATGCCCAGCTAATTTTTTTTT
TTTTTTTGTATTTTAGTAGAGACAGGGTTTCACCATTTTGCCCAGGCTGGTCTCAAACTCCTGAGCCCAG
GCAATCCACCTGCCTTGGCCTCCCAAAGTGCTAGGATTACAGGTGTGAGCCATCGTGTCCGGCCTGAGAT
GTTTTTATAATGCTGGTGACAGGTAAGATTATTGTCTGTCTTATGGGCTACGTCTAGTCAGGACTTCACT
GTAGGAATAAAACGAAATATATGTTTAGAGGCCGAAGGCTGACAAAGTTCTTTCCATTCTTCAGCTCATT
TCCATACTAGTAGCTCACTGGCATTCACTTCCAGAGACAGGTAGAATTGGCTCGATTATCTGCATTCCAC
AGATAAAGAAATTGAGGCTTAGGGACAGCAAGGTCACAGAAGTGATAAGTGATGGAGCCACGACTCAAGC
AAGGTCCTCTCCCCCAAGCCAGACATGTGGTTATGCTAAGGAGTTCACATTCAAATCTGTAGTCTCCCTG
AATACATTCAACAGTGAGTTGTATGATGAACATTTTGTTTCAATTCAAACCTTCCAAATCAAGCCACTTA
GTCAAAACAAATGTAAAACACAAAGTGCTATGGACACGCCTTTGATAACTTAAATGGAAGACAAATACCT
GGTAAAATGAAATCCTTTCCACTAATCTTTCCTCTGTTTCTTCCACCAAACTCACAGAGGGCAATGTAGA

TATAAGAATTTCCAGGTCCTTTTCAAGAGATGCATAGTTTTCATCAAATTCTTCCCATTTCTAGAGAATC
AAGGACATAAAATTAGTGGAAGCCCTTTACCAGATTGGTTCCAGATAACAACATAATTAATCACAAAACA
AAAATGAACACCAAGACCATACAAAATTAAAGCACAGATTCCAGGTGTGTTCGAGAGACGTAACCCCACC
CTGGTAAGCGCTCAGCATCTAATGGAAAAGAATTCCATCACCTTTGAGGACAAGGTTTAAAAAGAATCTG
AGTTGGCATTTAGTGTTTTATGCTTGTCTTGTCAAACTGGGTAACATGACTAAAGGAGTAATACAATGAA
GTTAAAATGATACTCTTAGCAACTCCGTAGAGACCTTGGAGCCACAAGAGAGCCTTTCTCTTATTAGGAA
AGGGAAAGAGCTAACTTTTAGACCCTTACTCAACAGAAGCTATTAGGCTGCTCCTGCTCTCCAAGCCCAC
GCCCAAGCCCACCAAACCCCCATGCCACTTGCAGCATAGGTCTGCTCAAGGTGTCTTTGAGGAGTATAGG
CTTACACTTCATCAGGGGAGGACAACTGCCTTAGCCCTAGTCTTGTCATCTTTTAGCTTGCCCCGTTTCC
ATGGATGCCCACCCCGAGGACCCCAACACACCACAGAGCTGAGTTATTGACTCCAAACATTGTCTGTTAG
GAAAAGAACCACCTCACTCTTTTCCATATCTATTCACATAGTGGCTCACTTGGCTTTTATAGAACACTCA
CTGGGTCCATGGAGTCTTTTTTAAAAAATACCATGACATATTATAAATATCAACTTGACACACTAACTAG
AAAATAAATTTTGTTAGCAAAAAAAATAACACCATATTACACTATCAAGTTAAACATTTCCTTCCTTTTT
TCTTTTTTTTTTGAGACAGAGTCTCGCTCTGTCGCCCAGGCTGGAGTGCAGTGGTGCAATCTAGGCTCA
CTGCAAGGTCTGCCTCCCGGGTTCACGCCATTCTCCTGCCTCAGCCTCCTGAGTAGCTGGGACTACAGGC
GCCCACCACCACGCCCAGCTAATTTTTTTTTTGTATTTTTAGTAGAGACGGGGTTTCACTGTGTTAGCCA
GGATGGTCTCGATCTCCTGACCTCGTGATCTGCCCCCCTCCGCCTCCCAAAGTGCTGGGATTACAGGCGT
GAGCCACTGCGCCCGGCCTCCTTCCTATTTTATTTCCTTTAAGTACTAACATTGGCTATGAAAGGTGTGA
GGGGAATGCCTCAAAACTGAGAAGGAGCTTTATGCATGCTTATTTTTTTCTTTGAGTTTAGACAAGATTG
TCATCCATTTTAGGACATCTGGGCCTGTTCTCTTGAAGAAGTACAGTTTTTAAACCAATAACTGTTTCAC
CCAAATGATCTCATTCAAGGTCTCAAAGTGCTTATCGTTTTGCTTATTCATACATGAACCTAAAAGGCAG
AGAGACGCAGTACCATCCCCAATCTATGTATGAGAAATCCCAGCCAACTTTTCCTTCAGGGAGCGGCCTC
AGAACCTGAGCAGGGGTCCACATTCCTCACTGTCAGGCTTCCATTTAACTATAGCTTAATGATAACTAGA
TACTTCTTCTCAACACCTGGGGTGGTGATGGAAAATCAGCAATTCCCAGCTTCAGTACAACGTTTACATA
ACCCAAATACCTGCAACAAACTCTGCAGCTTCATACCACATTGGCGTGACTTTTCTTCTAGTATTTTAAC
TTCTGTTACTTGTTCTGCCCAAAATGTCTCTCTGTTTTGCAATAAAGAAGGAAGTATTTTGGCAGAGTAT
GCTTGGATCAACAACATGTCAGCAACAAGCTTCTGGAAAAAAACCTATGAGATGGAGAAAGTTTTAATAT
TTACTTTGAAATTGTGAAAACTCTTAAAAACCAAGTTACTTCAACTTTATATCCAGTTATTTTTGTTTTA
AATCCAAAATCCCAGGACATCCGTGTAGAGTCAAATTGACCAGCCTGGCCAAGATGGCAATACAAAAATT
AGCTAGGCATGGTGGTGAATGCCCGTAATCCCAGTCATTTGAGAGACTGAGGCAGGAGAATCATTTGAAC
CCGGGAGGCGGAGGTTGCAGTGAGCCGAGATTGTGCCACTGGACTCCAGCCTAGGTGACAGAGCAAGACT
CCCTCTCAAAAAGGAAAAAAAAACAAAAAACAAAAAAACTCAGTCTTTGAACACTAGTGGAACTTCAACA
AATTATAAAGTATTACCCTTAGGTGTTATTTTCCACTAAATAATCCATTTTAAATGACAAACATTTTTGT
CAATTTCAATTTCCAGATAGATCTTTCTAAATCAGTTGTTTTGAGTCTAAATGCTACAAAAAGATAGATG
CCAGCTAGGTGTGGTGGCACACATCTATAGTCCCAGCTACTCAGGAGGCTGAAGTGAGAGGATTGTTTGA
GACCAGGATCTCGAGGCTACAATGAGCTATGATTACACCACTGCACTCCAGCCTGGAATACAGAGTGAGA
CCGTGTCTCTTAAAAAAACAAAAACAAAAACAAAAACAAACAAACAAAAAACAGATGTCACTGTGGCTGA
TGAATTTCAAGACAAGTTGGATGGACAGATGTGCAAACTCAAGCAACCCACATATTCGAAAGACAGGTCT
CCTTAACCCTGGCTTTAACTTCTACTCAAGAGAATGACTAAATAAAGGGAATTTGCTGCTTTATAGGAAT
CCTGGACATAAAGCTTCCTGTATTTGTATTTGAACTTCAAGAACCTTTCAAGAGGAAGGCTTTATTTCAC
ATGGTTCTTCTCCATTTACAGTTGTCTGGAGGGATCCCTCCATATTATGTGAATCCCTTCTCCTAAGCCT
TGAAAAGGACATATACATAGAGACGTTTATAAAAGCATCTAGCAAGGGGCCTAGCACACTGCAGATAATC
AATATTATTTTCTCCTCTTCCCCTCCATCCTTCATACAATATTTACCTTTCAATTTTTCTTAGACTAAGC
TCTACCTTCCAAATGCTAGACCATAAGCTTACCTCAGGTAGGAACCGTCCTACACATTTTTAATTATCAG
CACCTAGATTACTCTTTATCTTTAGTTGGTGATCAAGAAGTTTTTGTTTAATGAAATGAATTTTAAAAAT
CAAAGGATTTACTATAGTCTTATACTACATAATAACACACTTTCCTTTTGATTCTAGTTCTCAGGAAAGC
CTTTTCTTCTTTTTTTTTTTTTTTTGAGATAGAGTCTTGCTGTGTCGCCAGGCTGGAGTGCAGGGGCGTG
ATCTCAGCTTACTGCAACCTCCGCCTCCTGAGTTTAAGCAATTCTCCTGCCTCAGCCTCCCAGGTAGCTG
GGATTACAGGTGCCTGCCACCATACCCAGCTAATTTTTGTATTTTTGGTAGAGACAGGGTTTCACCATGT
TGGCCAGGCTGGTCTCGAACTCCTGACCTCAGGTGATCCACCCGCCTCAGCCTCCCAAAGTGCTGGGATT
ACAAGCATAAGCCACTGCGCATGGCCAGGAAAGCCTTTTCTAACTTTCCTAAGTCACCTTCTGCTATTAA
ATGCTCTCATAGAATGTATCCTCATTTTAATTTTAAATTTGTTTGAAGACTTGTTGATAAATATCTATCT
TCTCAATCAGGTGAAAGCTCTGTGAATGTAAGGAACTGTGTCTGTTTTTACTCATAACCCAAATTCCTAG
CATGTACCAGGGTTCCTGGTACACATTAAGCATTCTAATAGATGTTTATTAAAAGAATGAATAGCTTAAA
TTTCAACAAAGAAGAAAAATGGATCCTTTCTGTTCACATTCAGAAATACCTTAAGATTTTAGTCTATGAA
GGGGTCACCCGACCCATGTGTCTGTCTCACCTTGTGATTTTCTATTTGAGCCTGTAACGCCACTTTACTT
TTGGTTTGTTTTAAGTGGCCATGAGCAAGCTTTTCCTTCCCAATCTTCACCAGTTCCACCATGCCTTGCA
ACAAAGCATCTTGCTGGCTCTCAGTGACGAAAGGGCTGCTGAGTTCTGTGTACCTGGCTCTTAGCATTCC
CCACATACTGTCAAGTACATCCTGAAAAGAGAAGAGCAGGTGCACACATGCATTTTCATCCAACCGGGGC
AATAACTGAAAGACAAATCTAAACTCTGCTGGTGGAAGAAAAGGATCTGGCTCCTCACAATCACAGTGCT
GAGTCAATGTTTTCTGCTCAGGCATACCTCTAATTTGTAAACCTCCTGGAGTAAAGCATAAGGTAAATGA
AGCCTCTCCCCTTCATCTCTTAGTTTGGCCACTCGGCTCTCGGCGTTCTCCAGCTCCACTGTATATGCAT
CTGCTTTCTAAGTGAGAGACAATACAAGAAAAGAAAACCCTTCAGTAAGTCAGAGAAGTACACATAGTTA
TCTAAAAAGAATTAAATAGTACAGAAAGGGATGAAGGGAAAAGCAAAAATCCCAGCTCCCGCTCCCTCAC
CTCCTGCTCTCCTTAACAATCTTGCCAGAGGTCCCAAGTTCCTAACATGCTCCATACCAGTAGGGGTAGA
CATGCATATCCCTAAACTCAATGAACTGCACCACAGCATTCTGTCCTGCGGTTAGCATTCCTCACTCACC
AGCTCTTCAGCATCTCTTCACATTGGTATACACATATCTAGCTCCTTCGAAACAGACACACAGCATGCTA
TTGTAAGGGTGTACCCTGCTTTTGTTATCAGTCAGCTCTCAATGGACTTTTGGGCTATATACAGTTTTTA
ATTCAAGCAGAGCTGCTGGGTCCATCCTTAAATATTTATGACTTATTTATTTATTTATTTAGAGACAAAA
GTCTGGCTCTGTCACCCAAGCTGGAGTGCAGTGGCACAATCTCAGTTCACTGCAACCTCCGCCCCCCAAG
CTCAAGCAATTATCACACCTCAGCCTCCGGAGTAGGTGGGACTACAGCCGTGTGCCACTGCACCTGGCTA

ATTTTTGTATTTTCGATAGAGATGGGGTTTGCCATGCTGGCCAGGCTGGTCTTAAATTCCTGGCTTCAAG
TGATCCACCTGCCTCAGTCTCCCAAGGTGCTGGGATTACAGGCGTGAGCCACCAACCTGGCCAAAATATT
TATCTTTATGCACTTGTCTTATATCCTTAGGAGGAGTACAAGTTCAGCACTTCAAACAGTGCTGGAACAT
AGTGGATCCTCAATTAATATTTGCTAAATACATGAAGTCAAATTATTGCTGGAAGAGAGAGTATTCATGT
TTAAAATTCTGATATACAGACAAAGGATCCCCAGGGCTCCCCTGGCAAGAGGATGAGGGTCTCATTTTCC
AATACCCTTACCAACACTGGACATACACATTTTGTCATGGTTGATAAGTGAAAATGGCCTCCTTTTGTTT
TAATACATTGTGCTTCAGAAAATTAGGAGATGTTTTAAAAAGTCAACATAAATAGTTCTCATTTTTTAT
TTATTTACTTAAGCCTTGCTGCTGCTCACAAAGGAAAGTAGTTCAGAAGCACGGCTTATATGCAAAGCTC
TGTGGTTCAAAGTTAAGTCAGTCTGAATTATTTTGACTTGATTACCTGAAGCTGTTCAGCAACACTCTGC
CCACTGATTTCATTCAAAGACTGTTGTAAAGATGTCTTACTCTTAATGAGCTGATGATATAATCTCTTTA
TTTCATTCTGTAAGATAAATGTCGGAAACTGAGCAATCTCATTTAGGCCTTCATTATCTTTTTTTATATT
TAGTTGGTTTTTATAATTTTTGTGACACTAGAAATTTCAAACAAATACAAAAATAGAGAAATCCCCATTT
TATCATCATTAAACTTCAACAATTATTGATTCATGGCTGACCTTCTTCCCTCTACATCCTCCCTCCAGCT
CTCAACTGTACCTAATCTCCTTTCCTTCAGGCTATTTTGAAGCAAATCCCAGGTCTCAAGTCATTTCATC
AGTATACGTTTCAGTATATATTTCTAAAAGATAAAGATCCTTCTCTTTACTCCAACATACTCCTCCCCTG
CCATCAATAATAATTCCTTAATATGATTTAACTATCCAGACAGAATTCACATATCCCTAATTGCCTATAA
TTTTTCTTTTTGATTTGTTTCAATGATGATCCAAATGAGGTCCACATGTCATGATGGATAAATACATCTT
AGATCTCTCTTAACCTGCAGAATCCCTGACCACTTTTTTTGTTTCTTGAATGTGTGTATGTGAAAAAATG
GGTCATTTGTTCAGTACAGTTTCCCACAGGCTGGATTTGGCAGACTGCACTCCCAGTGTGCTGTTTAACC
TGTTCTTCTTTTCTTGTGTCTGTTTTACTTGGATTCTAGCAGCTTGGTCAGATTCAGGCTTGATTTTTAT
GGGCAAGCCTCATTCATAAATAGTATTGGGTTTCATTTCTTTTTCATTAGATAATTTTAGTAGCTTCCTA
ACTCTTCTACCTGCCTGGAGTCTCTGCCTCTCCAATTCACTTTAGACAACTGCTGGAGGAATCTACCTGA
AACATACACGGATTGTCATTCCTTAGCTCAAAAACCTTAATGGCTCCCTCTAGCTAGAAAAACAAAAACA
AATGCCTCCCCCGCCCCACCATTTTAATTGTTAAATGGCTAAATGTAATACAAGAAATGAAACATTATTT
TAGCTCATCCTAACAAATTCTTACTCAAGACTCTACTTTTTTTATTTTTTATTTTTTTACTTTTTTCTTT
TTTTGAGATGGGATCTATGTTGCCCAGGCTGGTCTTGAACTCCTGGGCTCAAGCAATCCACCTACCTAGG
CCTCCCAAAGTGCTGGGATTACAGGCATGAGCTACTACGCTCGGTCAAGACTTTAAAGGGCTTCACCTTT
TTTTTTTTGAGATGGAGTCTTGCTCTGCCGCTCAGGCTGGAGTGCAGTCGTGTGATCTCAGCTCACTGCA
ACTTCTGCCTCCCAGGTTCAAGCAATTCTCCTGCCTCAGCCTCCCAGGTAGCTGGGATTACAGGCACACA
CCACCATGTCCGGCTAATTTTTGTATTTTTAGTAGAGATGGGGTTTCACCATGTTGGCCAGGATGGTCTC
AATCTCCTGACCTCAGGTGATCCGCCTGCCTTGGCCTCTCCCAAAGTGCTAGGATTACAGGCGTGAGCCA
CTGCACTCGGCCAGGGCTTCACTTTCAAATGATCTCCAACCATGAGCAACAAACAGAAGAGTCTCATCAT
TTCCCTTAGCAATTCTTATTAACAAATGTCACCAGGAATAGGAATAGGCATTAGGGGTTCATGCTGTAAC
TTAAAACAGTGCCAAAATAGGCTGTGTGCTCGGAATCATACCTGGTAACTGCGGTTGTAATCGAGGCCAG
CTTTCAGGGACTTGCTTCTACAGACAGCTGCAGCCTGAGTGTGCTCCAGGCAGACTTGAAGGTTGTCAAA
ACATTCAAGGAGCAAGTTGGTGTTCTCGCCAGGCCAAGTCATGGCTTTCAAAAGATCACCCTTCTTGTCA
CTTAGCGCTAAATAAAGTTTCTTCAACTCAAGAGCCAGCGTCTGGAGTGGAGAGGAAGGAAGACAATGAA
TGAGCTCTGACCTCAAGAGGCTTCCACGTGGGCTTAACTCACGGGGCTGCTGTAATGGCCAACACATGGG
CTCGTGAGAAGTGCCCTACCTCGTAGTGCACCTGCTGGCCAGAACCATCCTCCCTGTAAAGTCTGGGCAT
CTCCAGCATCTCCTCCACACTGCTGAGGCACTGACTGAGGGTCAGGAATAGTTCAAACAATTTTTTATCC
AAATTGATATATGCTTCTTCTGTCATATTTTCCTGAATCAAGAGGAAAAAAGAAAAAGAAAATTAAGATA
CCTTTGCCTTCCTAGACCTATATTTTGCCTAGTTTCCATTATAGTTTATGATTTATGTTATGCTTCTTTT
GTAATAAGTTGCTTCAAACGCTTTGTGAACTAGGTAGCAGAACAAATAAATAAACTTACGATGTTAAACT
TGGAGAAAAATGAGTTTAAGAAGCTCAACGTTAGGTAGTTATTTGAGTACTGCATGGAACTAAAAGGTAA
ATCATGAGATGAAGGATCCCTTAGCAGGGCGATCCAGGTGAAAGTGTGGTCCCAGATAAATTACACTGTC
TCCTTTACCACTGTTTCCCACCCTCCACATTCTAATGTAGGAGAAAGCGGTTAATGAAATCAAGTATAGC
TGGGAGAAGGAAAAGAAGTCACAAAAGAGAAGCTTGAAGGGGTTGATTACAAAGAGGAGGTACAGTGTCT
TAAAAACAGGAGCAGGCTGCAGAGGAGGGGGAAAGTGTCATTTATGAGCCGATTGTGAGAATCAAGGCTT
AGGTGTATGACTCCAAGCACGTCCCCAGTGTCATGCATTGCGCCTGGTGAGTCTGGGAGCCACAGATCTG
TTTTAGCATAAGCTGCTGGGGCCACCTCTTTTTCTTTACCCACAGTTACCCTGAATTCTTGAACAGTTAT
AAGTAGTTTAGGAGCATGCCATAGCTAGTCATCACTCCAACTTGGGCCCTGTCTCCTACTATCTTCTCTG
ATAGACACCTCACATAACCTAGCATTAATTACCTCAGTATTAAGTCTGCTCAGGGTTGAAAACCATGCCT
ATACTCCCTCCCTACTCTCCTCTTCACCCTTCCAATCCCAGATCACCACTGCAGACGGCACTCATCAATC
ATGATCCTCTTTCCTGCTGATCCTGGACTCAGAATCCTTTGCACACAGTCCCTAGGGAACCACTACAAAA
TATATTAGAGTTGGCAAGCAAGATCAATTCAATTTGCAATCCTAGGACCCATTCCATTATGTTTCCTTTT
ACTTGTTCAGTGACGACAATTATGACCAAGTCACAATGATGATATCTCCTTTGTTTATGTTATTACAATG
AGGAAAACACATTGTGTGCAGCTTCTACCTGTGTCTGAAGGTTACTTGCTTCTTGGCGCAGGTCTTCAAG
TTGGGTGGTATAGGTTTTCAGTTCTTCAGTTGTTGGGTATCTAAAGTTATACATAGTCACGCTGGGTAGA
ATACCCATATTTGTGGAAACCTATTTGACAAAGGAAAACCCTATTACTGACAGTTTTAGACCCTGCTGAT
GTTAATTAATTTATTTTTTTATTTTCGAGATGGAGTCTTGCTCTGTCGCCCAGGCTGGAGTGCAGTGGCA
TGATCTCCTCTCACTGAAACCTCTGTCTCCCATGTTCAAGAGATTCTCCTACCTCAGCCTCCCGAGTAGC
TGGGATAACAGGTGCCTGCCACCATGCCCGGCTAATTTTTGTATTTTTAGTAGCGACGGGGCTTTGCCAT
GTTAGCTAGGCTATTCTTGAACTCGTGACCTCAGGTGATCCACCTGCCTCAGCCTCCCAAAGTGCTGGGA
TTACAGGCATGAGCCAACATGTCCAGCCTGCTGATATTAATTTAAATAGAAAAAGATGCCTTAGCATGCT
GTCTTCTGAGCCACTTTCTTGGTGAACATTTTTGTCTATCTTGCCATTTATAAGAAAAAACAATTAAGTT
TTAATATTTTGGACAGCTTTGAAAAGTCATGACTAGTTATATTTAGATACTTGAGGTTTCATTTAGATAT
CAAAATGAGAGGAAAGGCTGGGCTTAGTGGCTTATGCCTATAATCCTAGTACTTTGCAAGTAGAGGTGGG
AGGATTCCTAGAGGCCAGGAGTGCAAGGGAGTTCAAGACCAGCCTGTACAACATAACAAGATACATTCTC
TGCAAAAAAAAAAAAAAAAAATTATACAAAAATTTTAAAGTAGCTGGTCATGGTGCTGCACACCTGTAG
TCCTAGCTACTCGGAAGGCTGAGGCAGGAGATCGTTTGAGCCCAGGAGTTCAAAGCTATAATGAGTTTTG
GTCATGCCACTGCACTCCACCCTGGGTAACAGCGAGAACCCGTCTCTTTTTTTGAGACGGAGTCTCGCTG

TTGTCACCAGGGCTGGAGTGCAATGGCACAATCTCAGCTCACTGCAACCTCTGCCACCTGGGTTCCAGCA
ATTTTCCTGCCTCAGCCTCCCAAGTAGCTGAGATTACAGGTGCCCACCACCACGGCCAGCTAATTTTCGT
ATTTTTAGTAGAGATGGGGTTTCACCATGTTGACTAGGCTGGTCTTGAACTCCTGACCTCAGGTGATCCA
CACGCCTCAGGCTCCTGAAGTGCTGGGATTATAGGCGTGAGCCACTGCACCTAGCTGAGACCCTGTCTCT
TAAAAAAAAAAAAAAAAGGTGGTGTGTGTGTGTGTGTGAAATCATTAATCTTTCAGTTTAGTAATAAC
AACATTCACGCTACAGGGCTAGCTGCTTATTTACCAGTTTACTTTTGACACAGCCAACTATTAGAATAGA
ATTCAAGTCTCTTCTAAGGGATGGGTTTGCATCTTGATTTGTTATTGAAAAGCTAAATAAGTACTGAAAA
TGAGCTGTGATTTCAGAAGGGTGAATGATTCAGAATTAGCTCCTTTCTCAAACTGGAAAGCTGACAAATA
AAATGAAACAGGGTGAGGTGGTAGATGACTCTGCTTGGGGAAAGAACTAATAATGAGTGGAGTTCTCCTG
TTTGCAAGAGACCTATGTACACGTTACAGTGTAATATGGAGAAACCAAGGTTAAGGGCCAACTGATGAGT
TTGATTGAACTTTAATTGGTCAAATAAGGTCCTTAGCGGGAAAGAGGACAGCTGAGAAGTCCTATCAGAC
TGGGAAATTGGGAAATCACGGGTAACCTTTGCCCAGGCAATGTGAGTATGTGGTGGAAGGCAGAAGCCTG
CCTTGTGCGCAGTGGGGCTGTTTTGCTCACCTGCTCCCTGTCTGGAGAGAGACAGTAGTGACTGACACAG
CAAGCCAGCCTGATAGAGCCTGTGACGGCAGTGATAAGGAGGGCCAATCACAGGGAACACCGATTGGCCA
GTGCCATCGGCACAGGCGTTGGCACATGGTAGATTCCAAAGAATTTTCTGATGAATGAATGACACTCATT
GTAGCGCTGTATAGTTTTTAAAGTGTTTTTTTTTTTTTGAGACGCAGTTTCACTCTCGTTGCCCTGGCT
GGAGTGCAATGGCGCGATCTCAGCTCACCATAACCTCCGCCTCCCAGGTTCAAGCAATTCTCCTGCCTCA
GCCTCCTGAGTAGCTGGGATTACAGGCATGCACCACCACGGCCAGCTAATTTTGTATTTTTAGTAGAGAC
AGGGTTTCTCCATGTTGAGGCTGGTCTTGAACTCCTGACCTCAGGTGATCCACCTGCCTCAGCCTCCCAA
AGTGCTGGGATTACAGGCGTGAGCCACCGCGCCTGGCCAAGTGTTTCTTAAAATACATATTCATTCCTTT
ATTCATTCAACAAACAGTAACTGAGAGTCTGTGATGTCCTAGGTACGGTGCTTGGCACTCAAATGCAAAC
CAGGCAGACATGATCTGTCTTTCTTCCCCATCTAATGGGGAATACAGACTATAAACAAACAGGCGGATAG
TTGTTATAAATAACAGCTCTGATGAGGGAAGCCCTGGGTGCTACAGAAGCACAAAGGAAGGGTTCCTAAT
GCAGGTTTCCAAGATCAAGAAAATGTATCAGCCAAGTAAAAAACTCACTTGGCAACTTTGCTTTCTGGAG
AATATACATGTTTATTTAATGAATGCTTGTTGGATTTTCAAAGATAAACAGGCTATTTGCACCATGTAGA
TACAGACTGACCTGAGGCTCCACAAGCTGAGGGAGTGGGAGCTTTATTTTTGATGAGAGTTCATGATGCA
GATATTGCCACTTATCTCCATTTTGGCCCTGGGGTGACAAGATCGAGTCTGGAACGTCATTTTCAGGGCT
GGATGCCTGGTTGCTTTTGAAGAAGAACAAAAGGTGAAGAGAATAATCAACACTAAACATTTTGTATTAC
ATTCACAGTTCTATGAGCAATTTTTAAAAGAAACACTCTTAATTCTCCCAGTCATAAAACCACTGAATGA
CCAACTCTATTTTTAAATGTTTTACCTTGCAGATGATTCCTGAGTTGTATCGTTATCATGTTGGCAATAC
TGGGGCCACATTTTCTTAGCATTAAATTCTATGAATTTGATGAAATCTTTCTGTTCCATTGGTTTTAACT
CCAGAACCTGTAATTGAATGAGATTCAAATGGTCCAATCCATCAAGCTTTTCGATTAGTACCCACTAGTT
TCCTCTGCTGAGATAAATCTAATTTTGAGCCAGTTCCTAAATCATTAATTACTATTTCTCTTTCTTGCAT
TCCTGTTCTTGTAAACTCTCACTTCCCAAAAACCTATTTAAAATATTCACACAATAACTGTTATTTAAAC
CGCATACATGGAAAATCATCAAAGACATACAAACACATTTTGAAAAGACAGGCAAAGCAGAGTCGCAACT
ACAGAAGTTCACCCTGAAGACAGCTGATATAAGATGTAAGTTAATAAAGGAGCAAAGTTATGGTGTCCCC
AGTGTTAGCAGCTGAAAGCAAAGCAGATGCTATGGTAAATGCTGAAAACTCTCAGAGTTTCTGCACACAC
ACAAACACCCACATGCCACACTTTGCAGAAATTCCATATAGAAAGCTTTTTTTTGTTTGTTTGTTTTTGT
TTTTGGAGACATGGTCTCACGCTATCACCCCAGGTTAGAGTAGAGTGGTGTGATCTTAGCTCGCTGCAAC
CTCTGCCTCCTGGATTCAAGTGATTCTTGTGCCTCAGCCTCCTGAGTAGCTGGGATTACAGGCTTGCACC
ACCATGCCTGGCTCATTTTTTTGTATTTTTAGTAGAGCTAGGGTTTCACCATGTTGTCCAGGCTGGTTTC
GAACTCCTGACCTCAAATGATCTGCCTGCCTCAGCCTCCCAAAGTGCTGGGATTACAGGCATGAGCTACT
GTGCCTGGCCTTTTTTTTGGTTTTTGAAACAGGGTCTCGCTATGTTGCCCAGGCTGGCCTCGAACACCTG
GCCACAGGTGATCCTCCCACCTCAGCCTCCCAAGTAGCTAGGACTGTAGGTTTGCACCACCTTGCCTGGT
TAAAAAGTTATATTCTAGTCCCTACAACTGTTGGGGGCTAGAATTACCTGTTGCTGCTGGAAATCTTTTT
GTCTGCTGAATTGTGGCCTTTCAGTTACAATGGATTCCAATTCAGAAAGGTTAACTGGTTGGAGAGCTTC
TTGATGCTCTGGCTCTGAGGATTTCTTTAGAATGGTAGGATGCTGCAAAACATTTCATAATGGCAGGCTA
TTTATTTTTAAAAATAAACTCCACTTTATCTCAATTCTAATAATGGGACTACATAGAAAAATTTTACATG
AAATAAATGATGGTATTTTGTTATTTGCTATAATTATATACTATAATTTTTTGTTTTTGTTTTTTGAGAT
GGAGTTTCGCACTTGTTGCCCAGGCTGGAGTGCAAGGGCATGATCTTGGCTCACTGCAACCTCCACCTCT
TGGGTTCAAGGGATTCTCCTGCCTCAGCCCCCCAAGTAGCTGTGATTGCAGTTGTGCCCACCACACCCAG
CTAATTTTTGTATTTTTAGTGGAGACGGGGTTTCACCATGTTGGCCAGACTGGTCTCAAACTCCTGACCT
CAGGTGATCTGCCTGCCTCAGCCTCCCAAAGGGCTGGGATTACAGGCGTGAGCCACCACACCCAGCCTAC
TATGATTTAATGTACCTATTTCATAACAACTTCAAAAACTACTACATTTGGTGAAGTGATCATCTTACTT
CTTCAAGCTAATTCATCCAATGAATTACTAAAAGCAAGAAAATGTATTGCCTTTTTTCTTAAAAACAAAT
ACCAAATAAAAAAGTACCAAAAAGAGAAACAGTATTATAAATTCAAATTTCCCCTATGGCTAAAATACAT
TTTTTTTAAAAAGAGAGAACATATTAGGATGAAAGGGGAACCATATGGCCTATGTATCTGCAGCCAGTCT
TATTTCTGTGAACATAAATCTCTAAGTAGGAACCACTCATAAGCACATGCAAATCTTTTATAGTAAGATC
TACTCATAAGATGCACATTTGCATTTATAAACACAGAGTGCTTTTAAAAATCATGAGAACACTTTATATG
ATACTTTGATTATATATATATAAATACTTGCAAATGAATAACAAAGTATCCTGGAAACAGGTTTATGTTTCT
GATGTCAAATTTTAGTCACATCTATGAAAGCTTTGTTTTCCAGTCAATTAGAGTCACAAAATTCCTTTAT
AATACATCCTTCTTTTACGAAGAAGCCTTACACTAGACCTCACTGCCAACAAGAACACTCAGCTACATTA
AACCAACACAAACCAAACCACCGCCATCACCAACAACAACCTAGACAGGAAAACTGCAAAGTAGAATGAA
ATAAAAATAACAAGCCAGTGTACTCATCTATGGTGTTAATGTGTGAAATTCTTTCACACTTAGTACAGTT
TCTCTGTAGCTGGTTCATCACTTCCAACCAGAGTTCTCTTCTGGCAGGTCTGCCACATATGTGTATCAAG
ATGAATGTCCATAGATAGTCATTTTTTACCTGATCTTCACTGTGCTTCTCCTGAAGCATCATCTGGACTT
TTTCTAAATTGCACTTCACTGTTTTCAGTTTCAGGGAAAGCGCTTCAGCCTCATGTTGAGTGGCTCCATT
ATCTCCCAGGCCCTGATCTTTGCAAGTCTCTAACAGAAAGGCAACCTTGTGCTCAATCTCTGTTAGCATA
GCCTAGGAAATAAAAGCATTTAATTATTCATAATGTTGTTCTTGAAGAAGTATTGTGCCTGCAAACAAGT
TAAGACTTACTCTTTTTACTTAAGTGTATACAAGAAGTCCCAGAAACACAGGATGGAAGAAACCCTGGAA
AAACAAAAACTTCCACAGAATTCTTGTACTTTTCAGTAGGGATGCAACCAAACCAATCCCAATTACACAT

```
GTCACTCTGTAAAATAATTTAAGTAAATGACTCTATAGTCGCCTTACAAAACATAGCAGAATGTATCCAG
CAGAGGATAGTGGTTAAGAACACAGATCTTGGAACTAGACTATCTGGTTTCAGATCCCAGTCCTACCACT
TAGTAGATGTGTAAACACAGGCACCTTACTTTAGAGGAGTGTGCCTCTAGTAGTCTGTAAAATGAAGATA
ATAACCGAACTCACCTCCTAAGGTCATTATCAGGAGTGAATGAATTAAATCCATGTACTTTGGCCAGTGC
TTGATACATCTGTGCTTAAAAAGTGCAGATATTCTTATTTCCCCCTACCTTCCTAATCTTTTTTTTTTT
TTTTTTCTGAGACGGAGTCTCACTCTGTTGCCCAGGATAGAGTGCAGTGGTGTGATCTCGGCTCACTGCA
ACCTCCACCTCCCAGGTTCAAGTAATTCTCCTGCCTCAGCCTCCCGAGTAGCTGGGATTACAAGAGTGCG
CCACCACGCCCAGCTAATTTTTGTATTTTTAGTAGAGATGGCGTTTCGCCATTTTGGCCAGGCTGGTCTC
AAACTCCTGACCTCGTGATCTGCCCACCTAGGCCTCCCAAAGTGCTGGGATTACAGGCATGAACCACCAT
GCCTCGCCTACCTTCCTAATCTTTTATGTTGCAATCCAAGTGTGGAGTAGGAATTTAAAAAAGAATTCCA
CGTAACTGTTTGAAAATTATTTCCCTTGCTCTTTTCCTTCTCTTTCTCAAGACAAATAAGCCTCCAAACT
CTCACAACACCATAGAAGAAATAATTTGGAACCTGAAATATTTAGTTATTGATACAACCGGCCAATTCAC
ACAAATCTAAAAATATATCAGCTGGATGAAGTAAGTTTCCCAGTAAGTCTCGGTCATTGTATTCCTGCTC
AACAGATCAAGTTTGCCCTCTCCTGGGGCTCAGCAGCCTGCTCGGTCATGCCAGCTGGCTGGGCACTCAC
GTCAGCAGCAACAGACAAACTCACATTCCAGCACCATGATCATTTGTACTAAAACTCGGTGCGTGACTAA
GAACAAGTTCCATTCATTGAGCGAATTTAAGGAATTAAAAATTTTCCTTAAGGACGAACTCTATTCTTAA
AACAAAATTGCAAATAATTTATCCTATAACTCCTTCATCCAAGCAAGCTGTAACAGGCCCCTTTATCTAT
GCTTTTACTTTCTGTGGTTTCAGTTACCTGCAGTCAATCAGGGCTCAAAAATATTAAATGGAAAATTCCA
GAAATAAATAATTCATACATTTTAAATTTTGCACCACCTGAGTAGCGTGATAAAATTGCACACCATCCTG
CTCCATCCCGCCCAGGATGTGAATCATCCCTTTGTCCAGCATATTCATACTCCAGCACTCGGCTCATTAG
TTACTTAGTAGAGGTTGAGTATACCTAATCTGAAAATCCAAAATCCCAAAATGCTCCAAAACCTGAAACT
TTTTATGCACCATGCCAGAAGTGGAAAATTCCACACCCAACCTCATGTGATGGGTCACAGTTGAACTCTG
TTTCATGTATAAAATTATTAAAGTTATTATATAAAATAACCTTCAGGATATGTATATGAGGTATAGATAA
AACATAAATTGAGGCCTAGCATGGTGGCTCATACCTGTAATCCCAGCACTTCGGGAGGCTGAGGCAGGAG
GCTCACTTGAGGCCAGGAGTTTGAGACCAGCCTGGGCAACACAGTGAGACCCTGAGTCTACAAAAAATAA
AATTAGCCAGGCATGGTGGTGTACGCCTGTAGTCCCAGCTATTCCGGAGACTGGGGCAGGAGGATTGCCT
GAGCCCGTCAGGTCAAGGCTGCAGTGAGCCATGATCATGCTACTGCACTCCAGCCTGGGTAACAGAGCAA
GACCCTGTTAACTCTAATATAAATAAAGAAATTAATTAATTAATTTAGTGTTTAGACTTGGGTCCTCTCT
CTAAGATATCTCATTATGTATTTGCAAATATTCCAAAATCCCTCCCAAAAAACCAAATGCAAAATACTTC
TAGTTCCAAGCATTTGGGGATAAGGGATACTCACTCTGTAGCCATCTCAGTTGTCAGATCGAAAAAACAT
AATACACACAGAGTTTGGTACTATCCACGGTTTCAGGCATCCATTGGGGGTCTTGTAACACAACCCCCAC
AGACAAAGGTGGGACTACTCTACTTATGTCCTCTATAGATTCTTCTAAGTTTAAACAATATGTACCCATA
GACTGTACAGTGGCTATAAACAAAATGTAGCATAATTTTATGCTCTGTTTTTCCCACTTAACTATTACAT
ACTTTTTCATCTGTCTCCACACGTTTCATGATTTTCATTTTAACAGCTACAAGTTGATATCCCATGATTC
ACTTACCAATTTCCCTCTTGTTACCCCTTTGTTTCTAGTTCTTCACTTTTGTAATCAATGCTTCTATAAT
TATTTTTCTCATTTGGGATTATTTTCAGAAGGTAAATTAAAAGTAATGGTACTGGCCGGGCACGGTGGCT
CATGCCTGTAATCTCGGCACTTTGGGAGGCCAAGGCAGGTGGATCACCTGAGGTCAGGAGTTCGAGATCA
CCCTGGCCAACATGGGGAAACCGTTTCTACTAAAAATACAAAAATTAGCCAGATGCTGTGGTGCATGCCT
GTAATCCCAGCTACTTGGGAGGCTGAGGCAGGAGAATCACTTGAACCCAGGAGGCAGAAGTTGCAGTGTG
CCGAGACTGTGCCACTGCACTCCAGCCTGGGTGAGAGCGAGACTTCACCTCAAAAAAAAAGTAATGGTAC
TTTTAACTCAAAGAAGATGAACAGCTTATATGTTGACAACTGACCTCCCAAAACATTGAGCCAATTAGAT
AGAACTACCAGACATTAGAGTATCTATTTTTCCAGAATGATATTTTTTTAATGTAATGTGACAGCTGTTT
TAATTTATGTCTTTAATAATCAAAATTAAACAATTCTCAAATATTACATTACTAAGCATAATCCTCCCTC
CCTCCCTCCCTCCCTTCTTTCCTTTCTCTTTCTTTTTTTTGACAGTGTCTTACTCTCTTGCCCAGGCTGG
AATGCAGTGGTGCAATCATAGCTCACTGCAGCCTTGAATTCTTGGGCTTAAGAGATATTAGTGCCTCAGC
CTCCCAGGTAGCTGGGACTACAGATACACACCACCATGCCCAGCTAGTTTATTTTTTAATTTTTTTTTAA
ATTATTTTGTAGAGACAAGGTGTAACTATGTTGCCCAGGCTGGTCTCAAACTCCTGGCCTCAAGCAATCC
ACCCGCCTTGGCCTCCCAAAGTGCTGGGATTACAGGCGTGAGCCACCACTCCTGGTCCATAATCTTCACT
GAACTGTTTGCTCCTGTCCTTTGGCCATTTTTCCACTGGAATTTTGTGTTTTTACAGACCACTTTAAGGT
TTTTATATGTTTCAATAATAACTTTATTGTGTTATGTTATATAAATGAGCCAAAGATGCCTTTGTATGTT
GGCCCCATGTGGTTTTTCTTCAAAGCAGGTCAGAAGCAGTAAGTTCAAAAAGTGCCAGCACCAGACTCAA
ATTTTTACACATTTGACGGCTTTAAATGCAGCCCAAATAAGCATATTTTAATCCATTTAGAGCCTGTCTG
CTTTGCATACCCCTGAAAACTGCACCCAACATCTGCCAGCCACGGATAAGACTAACCCTGGGCTATAAAA
AAATCCCAAGCCTCTGCTGCCCTTCGGCGCTCTCTGACCCAGAGACCCTCCACTGTGCTGAGACATCGCT
AGACACATAAGTTCCCTCTCCGTTTCTCCTCTCCCCTGGGAGTTCCCTTGCCTTCCTCCCCCTCTGGGTG
GTGGCCTGACCCCCAGTCTATGCCTTAGCCTCTGGAAGGTCTCCTGCAGTAAAGAGCTTCCCTGTCTCTC
ACGATCATAATCTTGCCAAAATGCTGCCCAAATAAAGCTTGTTGGGTGCAACTGCCACCTGGTAGTCATG
TCTTTTCCTTGAGCAGCCTGGAAATCCTTGAACTCACTACAAGTGGCAATGAAGATGGGATTCTGGTGAT
AATCAACGAGTTGGCATAGGGTCTACCCAGTCAGTAGATAATCAGTTGGCAAATCAATCCTGAATGGCCT
TAAGTGGGTGGGACTCAAAATCTGGACTGCCTCGAGTTGAGTTTAGCATAGCATTGCTCTGTGCTGTATG
ACGCTCTATGGCATTCACAGGCTCCCCTGGGCCTCATCAGCCAGGCCAAGCGGCAGTGCCAGTATCTGAG
TGAACCTATCCCTTTAGAACTGACTTTTGGGCTGGGCATGATAGCTCACGCCTGTAATCCAGCACTTTGG
GAGGCTGACTTGGGTGGATCGCTTGAGCCCAGGAGTTCGAGACCAGCCTGGGCAATATAGTGAGACCTCT
CATCTCTACAAAAAAATACAAAAAGTAGCCGGGTGTGGTGGTGCAGGGCTGTAGTCCCAGCTACCCAGGA
AGCTGAGGTGGGAGGATCACCTGAGCCCAGGAAGTCGAGGCTGCAATGAGCTATGATTGCTCCACTGCAC
TCCAGCTTGGGTGACAGGGTGAGACCCCGAAAAAAAAAAAAAAGAACTGACTTTTGAGATCAGAGGTGCC
GAGATGCACAGAAAAGGAGGCTGGCCTGTCTGTCTGGTTCCTGGATGTTGTTAAGACTATGGGCTTACAT
AGAAGGGGAGAATGCACAACTGTGGATCAAAGGCAGGCTTCCCACAACAACATAACAGGCTACAGCAGGA
AACGCTCCCTGTGGCAGGGCTAGTGATATGCGAACTCTGAGACAAGAGGATGTCTTCATCCTGGCAGACA
AGCCCATATGATAAAGACAAGTCTGGTCTCCTAAGTGCAGCTGGGAGAGAGGCCTTTGCAAGCAGCTCGC
GTGCCCCTGCTCTTGTGACACTCGATTATGCTGTTGCAATGTCATCATTCTAGCCTCTCCCTGGAGGGAT
```

TAGAAACCCCAACCTTCGGGCTGAGCCGGCAAGCTTTACTCAGAGCGACTAGCGGCAAGGAAGTTTATAT
CCCTGCCCCTCCCAAGCAAAACCCAGGGCATTCCTAGTAAAATGGTTGCAAAGCCCTTTTATGCTGTATC
TTCAATTTTGCAAATTAATACTTTTGGTTTCATTTATGATGAATGAATATTCTAATTACTTACTAAAATT
GAATAAAATAATAGCATTTACTGAGCACTTGTTATATACTTTATATACCTATTTAATCCTGACAAAAATC
CTATGAGATAACTTTATATCCTATGACACTGCTTTAAATACCTTATTTAAATCCTGCGACACTACTTTAA
ATACCTTATTTAATCCTGACAAAAATCCTATAAGATAACCTACTATATAAGGAAAATGAGGCTGAGAAGT
TCACTTCCCGAAGTTCACAGCTAATGTGACAGAGCTGGATTTAGACTCCTAGATTCTGAACACTACTGTC
CCCTCAAATAAGATAGTTCCATAAAGCATTTCAAAGAATTACCCTGAGAACTAAAAGCTGAGGCCAAGAT
AAATGTAAGGGTCAGAGTAACAGAAAGAAAAACAGTGTTGCTTTAAGAGAAATTCACCCAATCTTGGCAG
ATGATTGGTGGAGAGGCAAACCATGAACTCTGACTTCTCAGTCTTACCTGGCACCCTACCAGCTGCTGTT
CCAGCACCTGCTGCATGTCTGCGTTTAATGTTTCCGGCTCAACTGCCACGTTGGCTTGTTGCAGCCACAG
CTCCAGCTCGGCCACCTGGGTCTTGCAGGCATGCAGGACTTCTGTGGGCTCCGGCCTAGTTTTCTCCACC
CTGGGCTCCAAACCTCCTTGCGCGTCAGAAGAGTCCAGAGTGTCAGCCTCAATAGGAGGTGTGGTGCCCT
AAGAGAAATCCAAAGATAAGCCAGGGAGTCCAAAGTTTTCAGACTTGGGCCTGCAAAGACCTGGGAACCT
GCAACATTTCCCCAGTTAAAAGAAACAAAATCAGGACAGAAGAAGGAAGAAAGAAAAGAGAAATGCACCT
CCACACTCATAGCAACAATCACGTGACCTGGTGCCACAGGTTTCCAAGCAGCCGATCTGCGAGTAAGCAG
GTACAGTATTCCCGGGCACAGAGGACGCAAACAGGCTCACAGTTCACTACCCGGTGAGCCCCAGGAGACA
GGTGAGAATGTGAGTGACAGGGTGTGTGTGTGTCCGAAACATTTAAGGGAATTGGCCAGTGTTTAGCGTT
ACGTGACACATGATTAAGCAATGCTTACATTGCTGCACACTCTATTCCAACAGAAAAACAAAACAAAACA
GAACACGATCTTTACCTCCCAGCAGGGATACAATAAAATATACCACATAATTTTAACTTGACATCTTCTC
AAATAGTTAGATTATAAAAATTTTAGCTTTTTAAAAACATACATGGTATTACTTATCTAAATTTTTCCCT
AATAAAAACAGCTTGAGTCAAGTAATGAACTTCAGTGGGGTAACCTGGAAACTTTTTTCCTATTCCTCAG
AAGGAATCCCTAAAATACCTTCCTTCCCCTTCTGCATACTCGAATATGATTGAGTTAAGGACTAGATGCT
CACAGTATAAAGAAAGTGTGGTGTGTTCTTTTTACATTGAAATAACTGGGTTGTTTATCAACTGATTGGA
AAATTTTCTCCCAGATACCAAATGAAAGTATTCCAGTAATTATATATTAGATATGTTCAACCTGGAGGCA
AAAGATAATTGGATAGAGAGATGTATTTACCTCCCACTGTATTATCTATCCTTCCTCAGAATATGGAAAA
AGTAGTATCGATACTTCTAGAGAAATTCCTTTAGGAATAAGGATTTGTGTTTTGCTGTATAAACCTTTTG
CTCTCAAAAAATATTTTATTGATTATGATAAAATACAATGTTTTCTATAAGAGTTTGTTAACGTGTTAGC
ATCTAATAATAAAATGTAATTCTAGCCAAGTGACAAACTTTGAATGGGAATCGATTGCAAATATATACCC
TAACTCAAATGCACATTCTTCAATGTTTACGGAATTTTGTTTAGACATAGAACTTTCAGTGTAAAAGAGC
GAACAAAATTGGTAGGTGGTAACAAACACGTGTCAGGCATGAGAATGCTGTTCATTTTCATGCACACTGA
TGAGTATTATGAAAGCTGGTCTGGCACAAGTGTCTTGGGTTGTACTTTTTACCTTTCACCATCTATTATC
TTCACATACATGTGCTGTTTTCTGCCAAAATGCCATTTCTTCCCTGCCTTCATTAATCTATTATTATAAT
TTTCTTCAAGAATCTTGAAAACCTTCTCAAGGAAACTTTTCCTTGTGTTGTGCTTTTTCTGAACTTCATA
TATAGTCAAGTCTATGCTTGGATTCAACTGTTTTAATTTTCTTTTTTAATCCTGACCTTTTTTTTTCTTC
TTGGGAAGAGTTTCCCTCTGTCACCCAGGCTGGAGTACAGTGGCATGATCTCGGCTCACTGCAACCTCCG
CCTCCCAGGTTCAAGTGATTCTCCTGTCTTGGCCTCCCAAGGAACTGGGATTACAAGCACACACCACCAT
ACCTGGCTAATTTTGTATTTTTAGTAGAGGCAGGGTTTTGTCATGTTGGCCAGGCTGGTCTTGAACTCCT
GGCCTCAAGTGATCCACCCGCCTAGACCTCCCAAAGTGCTGGGATTACAGGCATAAGCCACAGCGCCTGG
CCCTGATTTTTTTTTAAAAAAAGCAACAGTTGTGTGATTTTGCTTCCAGACTTCCAGATATCAATTTCTA
GTCATCTGATTAATTCCCTTCTAGTTTTCAGATATTGCTATATCTAGTTTTCAGATATTGCTACAGACAA
AGATTTTGGAATTCCCTTTCCTTTTTTTGCCACTTGAGAGAACAATCTATTAATATTAATTAATCTAAGA
CAATCTATTAATATTAATCTGTAATCACAGATTTACCACCTGCCTTCATTATTTATTCAAAAATTTTATT
TGAGCACCTGTTATATGCCACGCACATTTTTTTTTTTTTGAGATGGGGTCTTGCCATGTTGCCCAAGTGG
GTCTCTAACTTCTGGGCTCAGGTGATCCTCCTGCCTCGGCCTCTCAAAGTGCTGGGATTACAGGCATGAG
CCACCACACCCAGCCCTCCACACACTTTTTTTAATGACAGTATTGAGTTTCTCTGCTTTCTCATGAACTC
ACCAAATTAATGAGGAAATAAGCAAGCTGCATGACTAATCTGGGTTTTTTTTGCTAGTTATTTGAACCTG
AAAAGAATCCAAAGGGGAAGAGAAGACAAAAAGAATATTTCCAACCATACAGCTTCAAGAGCTGAGGGTG
GCCTGAGGAACCCACTAGAGATCAGTTCACCCACCTCTTTTTAAAGTCTAAGAAATCCAAGTGCACAGAA
TGTTCAATCAGCCCACATGCCTCCCTTTTTACCATGTTGCTTCTGAGAAGCACCCAAGTTACTAACCCAA
GGTCACACAGCTCTGTGATCTTTTAATTCAGAGTTCCCTTGTTTTTTACACAGTAGCATCCCTGTAAAAT
ACCTTCTCTATATGATAGCCCCAAATTCTAAAAGCAAAACTTATTTAAATGGATGTTTTATAATTGTACA
CTTTGGCGGGGGGGGGGGGGTGTAAAAAGTATTACTATAAGTATTTCTTATTAAATAAATATGTCTTCTC
TAAAGCATAACTGTAAATTAATAATAGCTAGCCTTTATTGGGCTCTTACCATGAGCAGGCACTGTATGGT
CACACAACTAGTAAACAGAATCAAAAGCAATTCCTGCTTTCACTACACTTTGGAATCTACAAGTCCACAT
TCTTGATATAATTTCACCAACCTTTTAGTATCCAAGTTAACTTTTCAGTTGGTGAATCACATTGCTTCAC
TTCTGCATCAACACAACACTGATCTAAGTAATCAGTGAAGTAATCAGTAATCAGTAAAAAAAACTGCAGT
TAAAATGCAAGTTGATTTTCTGGCTATTGCTACATTTCATGCCAAAATAGCAAACCTTTACATTTTCTCC
TTAATATTTCAGTCAATTCTACAAATACCTGCATATCTCCCCCACTGCTTATACCTGCATATCTCCCCCA
CTGCTTATGAAATGTAAAACTGCATACCTAAAGTACAGTACCTAACTGCACATGAATAAATGAAAAGCAT
GCCCCTAGAATGGCATGGTGGTGGTTTACTCTGAGGTCATGCCTAGCTTGATTTCACATTTTCACATTTT
TCCATACTAAATATTTATCCTTGGTTGTAATACGGGTCAAGAATGACTCAGAATTTTACTAAAAATTATG
CAATTATCATTTGGTCAATACACTTAACCTCTGAAACAAAAGGTTTGTTGAGGCTGATAGAAGGCTGATG
ACATTGGCTGCCTGGTTTCTGCAAAGTCCCCACTTTCCTTCTCATTAGTGATGTGCTGTGCCAATGAGAC
AGAAATCACTAAAAGGCAGGAAGACAGTCACCAAGAGGTATGGAACTTGGAGCCAGTAAAGGTGTCCCTG
AATAATCAGAAGTGGACAAATTCCTCCTGTAGTAAAGGGTAACATCTATTTTTCCTGCTCCAAGAATTCC
TCCCCAGCAAAAGTTCTGAGTTAAGAAGAAAATACAAATACACACATACATAAATTAGTTCAAAAGAGAG
TCACTGGAGCCTAATAGTTCAAAGCTCAGGTTTTAAACTCAGAGTCAGAAAGATCTGGGTTTGAATCCTA
GCTTTGCCACTTACTAGCTAAATGACCTTGGGCATCTTACTTCTCTGAGCCTCAGTTTCTCCATCTGTAA
AGTGGGGTAACAGTAATATTTATCTCATAGAGCTGTTGTTAATGATTAAAAGAGATAGTATATGTAAAAT
CCCAGTACCTGGCCCATATTAAATGTTCAGTAAGTATTTTGTTATCCTCCTTTTTCTTCCTCCTTCTCTT

TATTGTCATCATTATCTAGTATCCACATGGCCAGGGAAAAGACCCTAGAGGTTATCCACACCAGCAGAAA
CAATATTAAGCAGAATGGCTACTGTAGCTAAAACACCATTGAAGCTACATCTGATTTTTAATTAGATGTC
AAAAATAACATTACGGTGGGCAGATGGTTTGAGACCAGGAGTTCGAGACCAGCCTGGGCAACATGGCAGA
ACTGTGTGTCTGAAAAAATACAAAAATTAGCCAGGCGTGATGGTGTGTGCCTGTGGTCCTAGCCATCCGG
GAGGCTAAGGTGGGAGGATCACCTGAGCCCAGGAGGTTGAGGCTCCAGTGAGCCATGATTGTGGCCACTG
CACTCCAGCCTGGGTGAAGAGTGAGACCATGTCCCCAGAACAAAACCCAGATTAATTCTGAACAGCAAAA
AAACATACTGACTAGGTCAGCAACTTCCTTAGACCTAAGCATTGCCACTGGGTGTAAACCTCTGACATTT
GTCCACCTTCCTAGACATATATTGTTAAGAGAGACAGAGAATGAAAGGGAGGGAAAGAAAGAAGAGAAAG
GAGTAACAATTTGAGAACTAAGAGATATTTTTGTAAGACTAGACAAAAGATTGGGAGAAAAAAACATAAA
TAGAACTCAGTATAAAAGAAGAAAAGAGATGCAATAATTAAACAATAAAAACAGCAAAAACATGCCAATA
TCTTTTATAGGAGCTATTTGATGAGACCCTTGGAGCTTTAGGTCCAGCTAAACACCAAAATTAACTTGGG
AAATAGTACCCATCCCCCACACCCTGCTGTAAGGCCTTATTGAGAACAACTGAGGTACAAGATTCCAAAT
TAGGAAGCCAGATTAGAATATTCTGGGTTTGATTCCTTATTCCTCCATTCACAAGCCATATATATATATA
TACATTTTTTTAAAAGACAGAGTCTTGCTCAATCGCCCAGGCAGGCTGGAGTGCAGTGGCGCAATCTTGG
CTCACTGAAATCTCCTCCTCCCAGGTTCAAGCGATTCTCCTGTCTCAGCCTCTTGAGTAGTTGGGATTAC
AGGCATGTGCCACCACGCCCGGCTAATTTTTGTATTTTTAGTAGAGACGGGGTTTCACCAGCCTGTTGGT
CAGGCTGGTCTCAAACTCCTGACATCAGGTGATCCACCTGCATTGGCCTCCCAAAGTGCTGTGATTATAG
GCTTGAGCCACCATGCCTGGCCCACTAACTATATTTTTACTCCCTGAATTTTGATTTCTTAATTTGTAAA
CATATGGTAGGTATGAACCTACCTTATACAGTCTGAGGGTTAAACAGATAACTATAAATGCCTTTTATGT
AACAGGCTATTAATCAATATTAACCCTTCTCTACTTTCTTTGCCCCCATAAGTTCTATCTACAGATTAAA
GAAGTAGTCATCAACAGAAAGACTATTTCATGATGACAAATGGTAAATGAGTGAAAAGCGTCTAATTCTC
TATGCCATGCCTATTTTCTTTGTAAATATCTGATGACAAGTCTTCCAGTTCTACAGCTTGACAGCACATA
TCTTCATATGTTAAAGTTCACAAGGAACACTTAGCTTGACGTACAAGGTATTGCAGGACACAGAACACTG
GTCATCTCTAGGTGCTAGTCCAGCTATCTGAGCAGTTTACTTATTACCAACCAGGACTTACCTCTTCTGT
TTGGTTGGGCCTTAGGGAACATTCTGGGCCTTGCTCAGTGTTTAGTGAGTCTGGTGTGAGGATTTGTGCC
ATGGAATTATCAGAGGTGCTTATTTTCCCATATGCTTCCTGTAAAGAAAAGAATCAGAGCTCCAGAAAGG
GTCCTGCCCTGGTGCCACATGAATTCTTCTTTCTGCGCATGCTCATTTTACAAACTACCTGCTTGCAAAA
AAGTCAGATATGGAGAAGTCAGATACGATTAGAAAAAAGTTTGTTCATTAGGGAAAAAATCAGCTTCCCC
AAGACTGTCTTTATTTGAAAGACTTGCATTCTCCACACTTCTCTTCTTAATGAGCACATAAACAATCTAG
AGAATTACGTACTTAAGTAAATTCTTCCAGAAGTATGCTTTGTCTTGTTGAAGTATTCTTTAAAAGTATG
TCCTTATGAAAATTTAAATTACATGGCCAGGTGTGATGTCTCACACCTATAATCCCAGCACTTTGGAAGA
CCAAGGCAGAAGAATTGCTTGTGCTCAGGAGTTTGAGACCAGCCTGAGCAACATGGTAAGACCCTGTCTC
TATCAAAATAATTAATCAATTAATTATATGATAAAGGCCACATTTCAAAGAGTGGGAAAAGGTGAATTT
ATTCCATTTAGGAACAACTACCAAGGCATTTTATGAAAAATATAAGTAGAATTCTTGTATTACTCCTAAC
AATAAATTCTAGTTATGAAAAATATAACTAGAATCCTTGTATCACCCCTAACAATAAATTCTCATTGTAT
TCTCAAAGTTATGCCATAAAAATTCTAGGTGTGGGGAAGCATGACAAGAAAGGAAAATAATATTAGTATT
GACTACATAAAAAAATAAAATAATATGCACCACAAAAGATACCATAATCTAAGTTAAAGAGAAATGACAG
ACTGGGATAACTATTACACATAGTGTTAATATTTTTTTTGAGACGGAGTCTCGCTCTGTCGCCCAGGCT
GGAGGGCAGTGGCACGATCTCGGCTCACCACAAGCTCCGCCTCCTGGGTTCACGCCCTTCTCCTGCCTCA
GCCTCCCGAGTAGCTGGGACTACAGGCACCCGCCACCACGCCCAGCTAATTTTTTGTATTTTTAGTAGAG
ATGGGGTTTCACCGTTTTAGCCAGGATGATCTTGATCTCCTGACCTCGTGATCCACTCGCCTCGGCCTCC
CAAAGTGCTGGGATTACAGGCGTGAGCCACCATGCCCGGCCAATATTCTTAATATATTAATTACTCTATA
AATAATAAGGAAAACATCAACCCCTACATAGAAAAACAGTCAAATGGTAGGAACAAGCAAGTCGCAAAAG
AAGAGTTACAAAAGCCAATAGGCATCTAAAGAGATATTCAACATTCTTAGAACATAAATTAATTTAAACC
ACTGGCTAAGTTTGGCTAAGACTGACAATATCAAAAATCAGCTTGTGTGTTGGTTGGGGGGGGGGTCTG
GAAATGCAATTCCATGTATACCTAGGAGAAATATTGTTGGTATAGCCTTTCTTTTTCTTTCTTTCTTTTT
TTTTTTTTGAGACAGGGCCTCACTCTGTCACCAGGCTGTGGTGCAGTGGTGCAATCTTAGCTTCACTGC
AACCTTCATCTCCCAGGCTCAAGTGATCCTCCCACCTCAATCTCTGGGACTATAGGCATGCACCACCACG
ACCGGCTAATTTTGTATTTTTTACAGAGACAGGGTTTCACTATGTTGCCCAGGCTGGTCTTGAACTCCTG
AGCTCAAGCTGTCCGCCCACCTCAGCCTCCCAAAGTGCTAGGATTACAGGCATGAGACAACTGCACCTAG
CCTGGTATAACCTTTCTAGAAGGCAGTTTGAAAATGTGTGTCACATTTTAAATGGATATATACTTTGATT
CAGCAATCCTTCTTTTAAGATTAACCAAAGTTAAGCAATGGGAAAATGACATGTACACAAAGAATTAACA
CAACGTGACAGAAAGCATGTGGATATTATAATCAACCAACCTTGATTGCTCTACTTGCAAGTTGTATGAT
CTTGGACAAATTAACCTGAACTCTCTGAAACCTCAGTTACTTCACCTTTAAAATGGGAATAAAACCTATC
TTACCTATGCTTGCAATTAAGTGACATATATAAGGCATTTAGCATTTCCTAACAAAATGTTAGTGTCTTT
TCAGCTTCTACTGAAAACAGTGACTGTTATCAGAAAGGTATAAACCAAGAATTAAAGGTAGAGATTAGAT
AAAATTAGAAAGGTAGGCGGGGACCAGGAAAATCTGGAATGTCACGCTAAGTTTGCATTTTCTTCAGTAG
ATAATCAAACTCCATGAAGAATTTTAGGCTGAGGTTTCGCATGATTGGTTTTAGGAAAAGTCATCAGTAT
TTTATAAGATGTATTAGGAAAAACAATTGGAGACTGTAAACCAATTAGAGGGCTACTCCAAAAGTCCAGG
GAAGTAATAAGAATTGCTTGAAATAAGACGATGGCAAAAATAATGGGAGGAGAGGCTGTACACAGTGAAT
GGACATCATTGGCCACTGACAGGATGTGACAGGTGAGAGAAATGAGGCACCTAGTAGAACTCCAAAGTTT
ATCTCTGAGAAAATAGTGGCACCAACAGCAGACACTGAGAAATTAGTAAGAGGAGCAAGCTTTGAAGGAA
AGGTGGTAAAATAGGTTTGAGTTGGAGAAACTCCATCCCAAAAAAGTCTATCACGAGGATAGAAATGTGG
AATAGATTTATAGATTTAAGAGAAAAGCCAAGACTAGAGATTTAGTTTGGTAATCACTGGCATAGAGGTG
ACCACAAGCTCTCAGAGGAAATAAAATTGCCCTGAAAGAAAACAGAGAGGCCGGGCGCAGTGGCTCACAC
CTGTAATCCCAGCACTTTGGGAGGCCAAGGCAGGTGGATCATCTGAGGTCAGGAGTTCAAGACTAGCCTG
GCCAACATGGCAAAACTCTGTCTCTACTAAAAACAAAAAAAATGAGCCAGGCATGGTGGCGGGCACCTGT
AATCCCAGCTGCTCGGGAGGCTGAAGCAGGAGAATCGCTTGAACCCAGGAGGCAGAGGTTGCAGTGAGCT
GAGATCGCACCACTGCACTCCAGCCTGGGCGACAGATCGAGACTCTGTCTCAAAAAAAAAAAAAAAAAAA
AAGAGAAAACAGGGAGAAGGAAGAGGACAGAACATTGGGGGAATGCCTACCATCACAGACGAAAGAGAAA
GAGGGGCAAGAAAAGGAGATGGAGGAGGGACTAGAGGTAGAAGGGACAGGGAAGAACAGAATTAAGAAAG

TTAAAGGAACACCGCAGTTAAAGAAGGAAGAGGTGGTCACTCCCAGAGAGGTCAATAAGGATTAGGACTA
ATAAAAGGGTATTGAATTTGTACTCCAGAAGTCAATGGCAGTTTAAGCATAGCCAGAGGCTGAAACAAGA
TTACAAAAGGGGCCGAGGGAGTAGAACACCAAGGAAAGACCTTCAGTAGCAAATGAAAGACGAAGTGTAG
TAATTGACATGGGAAGCAGGATCCAGAAATTCAGTTCATTAAAGTACCATACTGAGCTGAGTATAGGATA
TAAACGATAAGCTTCTTTCCACTCATGAAATCGTATCAGGTGTATTCATAAAAATGTGCTAAGTCATAAT
TGAGGTTCAGAATCCTATTGGAAAACAGGGAAAGAGACAGCAATTTCCTTTGCAGGATGTCAGGAGGTTT
CTTGGAGCAGGGGAAGTTGAGATGGGTCTTTGTGGATGGAAGGAAGTCTACAGAGAGGCATGGAGAAAG
GGCATCCCAGGGACCAAAGCCTTCTGTGGAGCTACTGAAGATGCAGGCTGGTTCTGGAACTATCTCTCTG
TTTGAAGTAGTGGGGCCACAAGGAAGAGAACATGTTAGGGAGGGGAAGCCTGAGTACTGAGGTAGAGAAG
GAAGGAACCTAGCCAGAGGCAGAGACTGACAAGGCAGGTATAGGCAGAGAATGGCGCCAATGATTAAGGA
AAGAGTTGGCCTGAGAGCAGGGGGAGGGGTCAGCCCTGGACAGGAGGCAGGAGTGAGAGGTTTATGGATC
ACGAGGATGCAGAGATCTTCCGGGAGCAAAGGAAGCACGTAGTTTTCACATAGCCTTACAATGATTTTCT
AAAGTGAGACCATTTGAGAGACTGGAAAATATTTAGAATGTCATAAGGAGTAAAAAGACTTAGCGCATCT
AATTTATCTTACATACTACTTTGTTCCACAAAAAAAAAAAAAAAAAGATTATGGAGAGACCCTCCACCCAA
AACTCCCAAAAGAGTGGCATGTTAATTTACATGCTTGGTAAAACAGTGCAGTGAAGCTTTTAGCTGCTC
CTTTGAGGTATCTGTTTGGTCAGTTTGGATTTTCACATATATGGAGTTTTCCTCAAAAAAAGTACTCTCC
TGTTATTAAGTACACAATAGAAATAGAACCAAGCAGGTGCTCATTAAGGCTGTCTTTGCATTTGTGCAAA
GGTAATGTGAGAAGCTTTCAAAGATTCACGGTAGCCAAGATAGAGAAGCAACCGAAGTGTCCATCAACTG
ATGAATGGAGAAAGAACATGTGGCATATATACACAACAGAGTACTAGCCAGCCTTCAAAAAGAAGGAGGT
TCTGTCATTTGTGACAATATGGATGAACCGGAAGACATTATGTTAAATGAAATAAGCCAGGCACAGAATG
ATAAATACTGTATGATCTCACTTACATGTGTAATCTAAAAAATATGGACTGCATAGAAGCAGAGAATAGG
ATGGTGGTTACCAGGGCTGTTGGGGGCTGAGAGAGGGCCTGGGGAGATGTTGGTCAAAGGACACAAAATT
TCAGTTGAACAGCAGGAATAAGTTCAAGAGAATCTATGTATAACATGGCAATTATAGTTAATAATAATGT
ATTGTATACTTAAAAGTTGCTAAGCGACTAGATTTTAGGTGTTCTAATTACTGAAAAGATGACAAATATG
TGAGGTAATGCATATGTTAATTAGCTTGATACAGCCATTTCCAACGTATACACATTTCAAAACATGTTGT
ATACCATAAATATATACAATGGTTGTCAGCTAAAAAAAAAAAAAAAAAAAAAAAAAAAATTCAGCCCATGCA
GGTTCCCTCCCTAAGCATTCCTTTAAACAAAATAGTTCTTTACTATCCTTATTTTTATTCCTGTCTGAGC
TACAAATGGGCATTTTAAAGGTTTAGGCAGTGCTTGCTGAAAACCAAACAAAGGAAAGAGGGAAGAGAGG
AAGCAAAGCTAACATAGAAAGTCAGGCAACATGGCGAAACCCCGTCTCTACTACAAATACAAAAATTAGC
TGGGCGTGGTGACGTGTGCCTGTAATCCCAGCTACTTGGGAGGCTGAAGCAGGAGAATTGCTTGAACCTA
AGAGGCGGAGGTTGCAGTGAGCTGAGATCATACGACTGCACTCCAGTCTGGGCGACAGAGCGAGTCCGTC
TCAGGGGTGTAGGGAAAGAAAGTCGTGCAGAAAGAGATCCCTGCTCCCCCCTGGGCCCTCGTAACCCCTA
AGCGTGGCTGATACGCCCAGCATTACCTGAACAATTGTTCCAGAGGATGAGGAAGCTCTGTCTTCTTCCA
TGTCCTTGTCATGCTTCCAAAGTGAAGACCAAGACTGAGGCGATGGCTCTGCCTTCTCATCTCCATTCTA
TCACAGTAAACGATTGGTTAGCAAAGGGAAGAGCTTCCCTTACTGTCATAACCGGTGCCCTACTCACTCA
CGTCTTTTATACCAGACTCAACTTATCAGGCAGTGTAACCACAGCCCTTTATTGCAGTCCTCCCCCATTT
TTTTATCTGTATTTTTTTACTAACTATATCATGTTTACAAATGTGGCTGCTCTTCCTAAAGCCTAGAAA
ATACTTTTAAAAGTAGGGGCTCGGCTCACGTCACACAACGGAAATCTTTAAAATGGTGCTTTTAGGAATT
TAATCTGCTTTGGTAAATGTAACCTTAAATGGTATCTTTGAGGCCAGGCACTGTGACTCACACCCATAAA
CCCAGCCCTTTGGGAGGCTGAAGTGGGAGGATCACTTGAGGCCAGGAGTTGGAGGTTGCAGTGAGAACCA
CTGCACTCTAGCCTAGGCAACAGAGTGAGATCCCATCTCTAAATAAATATTTAAAAATACGTAAAAGTTA
GAAAAATTAAAATGCTATCTTTAAAATTACAGCCACGAGTATAAGAAAAAATGTTCAACCTCACTAATCA
CCAGGGAAATGCAAATTAAAACCACAGTGAGATACTACTTTACACCTGTTAGAATGGCTTATATAAAAAA
GATAAAAATGACAAGTGGTCATGAGGATGTGGAGACAACAGAACCCCTGAATACTGTCGGTGGAATGTA
AATTGGTACAGTATCAAAGTTCCTCAAAAAACTAAAAATAGAACCAGCAATCCCACTACTGAGTACATAT
CCAAAGGAAAAAACTCAGTATGTCAAAGAGATGTCTGCACTCCCATGTTCAATGCAGCACTGTTCACAAC
AACCAAGATACGGAATTAACCTAAGTGTCCACCAACAAATGAATGGATAAAGAAAATGTGGTTATATACA
CATACTGAAATACTATCTGGCCTTAAAAAATAAGGAAATTCTGTCATTTGCAACAACATGGGTAAATTAG
AGGATCTTCTGTTAAGTGAAATAATCCAGGCACAGAAGGACACATACCACATCATCTCCCTTTAATGTGG
AATGTAAAAAAAAAAAACTCATAGAAGCAGAAAATAAAACAATGGTTACCAGCGACCAGGGATTACAAAA
ATGTCTGTCAAAGGACATTAAAAAAAGGGCACAGGAGGAATAAGTTCAAGGGATCTTTTGTATATCATGG
TGACTATAGTTAATATATGTTTGAAAATCATGAAGAGAGTAGATTTTAAGTTTTCTCATTACAAAAAAAA
ATGGTATGTGAGGTAACATGTATGTTAATTAGCTCAATTTAGCCATTCCACAATGCATATATACATGTAC
TGTATCAAAACATCATACATGTCATAAATATATATATATATATATATATATATATATATATATATATTTT
TTTTTTTTTTTTTTGAGACAGTTTTGCTCTTGTCACCCAGGCTGGAGTGCAACAGCGTGATCTCGGCTCA
CTGCAACCTCTGCCTCCTGGGTTCAAGCAATTCTCCTGCCTCAGCCTCCCAAGTAGCTGGGACTACAGGA
ACCTGCCACCACACCTGGCAAATTTTTTGAATGCATACAATTTTTACTTGTCAATTTTTTTAAAAAAATC
ACAGCTTGATGTTCCCCTTCATGTGTCCATGTGTTCTCATTGTTCAATTCCCACCTATGAGTGAGAATAT
GCGGTGTTTGGTTTTTTGTTCTTGCGATAGTTTACTGAGAATGATGATTTTCAATTTCATCCATGTCCCT
ACAAAGGACATGAACTCATCATTTTTTATGGCTGCATAGTATTCCATGGTGTATATGTGCCACATTTTCT
TAATCCAGTCTATCATTGTTGGACATTTGGGTTGGTTCCAAGTCTTTGCTATTGTGAATAATGCCGCAGT
AAACATATGTGTGCATGTGTCTTTATAGCAGCATGATTTATAGTCCTTTGGGTATATACCCAGTAATGGG
ATGGCTGGGTCAAATGGTATTTCTAGTTCTAGATCATCACACTCTGGGGAGTGTTGTGGGTTAGGGGGAG
GGGGCAGGGCTAGCATTGGGAGATATACCTAATGCTAGATGACGAGTTAGTGGGTACGGTGCACCAGCAT
GGCACATGTATGCATATGTAACTAACCTGCACATTGTGCACATGTACCCTAAAACTTAAAGTATAATAAT
AATTAAAAAAAAAGAAAAAAAAATCACAGCTTGATGAACATGTACTTTTTTGTTGCTGTCAAAGACAAACA
ACACTATAAACATCAGCTCAGAAGGAAATACATGTCTCAAATTAACATCGTACTGAAGTCACTCTTTTTG
GCCCCTGGTCCCTCCATTATTTTCGTAGTTCTCTCTGCCATGAAGGGGTATAATCAGATTGCAAAGTTGT
TTGATGGTCACAGAGCACACAGTAAAGTTGTACTCTTCCTTGTCACAGTTCCACCATGTCCCAGCGACAC
ACTCTAGGACAAGAGGTCTGCTCTGTGTGAGAGTGGAGCTATTTAACCATCTATAAAATGAGCCCAAAAA
GTGTCTGGTGGTTACATGTAAGTCACAAAAATTGTAAGTTGCTTCAATTTTCTTCCTTTTGTCTTAAGAC

CCATTGCAACTTATTTTTCAAGTATGAAATGGAAACTGACGTCAGAAAAGACAACTGAAAATGTCTCAT
TCAACCAGTTATAATCAAGTAGTACAAATTCTTAGTATTACTTGCTAACACAACTCTTCATGTCATTGGA
AATACTGTTTTAGAGCAAAAGAGTAATTGAAATGCGGAAAAATACAGTTCTAAAAATGAGACCAGGAGTG
CCAAACAGCATGCTCTCAAAACTTCAGAGAAAGTCCTCAGAAATCAGGATACTACAGAGAACTTCTTCAC
CTTCTCCCGTATGCCAACAAGAGTGTCTGAATTACATTCATCTCACTCTTACACAGTGAAGTAGGTTTCC
ATACACTTAAACATTAATAACATAAGAGAACTACTTCAATCATACTTTTAAAATATCAACATTAATTTTA
AAAATTCTTAGGTTTCCATTCACTTTAAGATCTTTTCATTGACTTCTTTTAGAGATCTGGTTCTAACAAA
CTTTAACAAGAAAATCATTTCCCTTACATCGCTCTTCACGGAACTTTCTTCCACCTCTTCCTCGACTGCT
GCCAGGTAAGACATGGAGCCTCTTCTGTTCAACTGAAAGGCACAGCACAAGAATACCTGCAGTCTGCTTG
CCAGTCAACATCACCAAGATCCCAGTCCAGCTGCATTTTTATGTAGCTAATTTTTTACTTACTTTATCCA
AGATGCCCACCCCCACAAGAAGCCTGTCTCCTGGTCCGTTCAGCTCCTCCAGCCAGATATCCGGAGTCAG
TCAAACCTTAGGTCTTGTTATTTTCATGGCCCCCTGTGCCCCTTCATAAACGATTAAAGAATGTGATTCA
TTGATGTGAATGCAGAGAAGACTTAGGCACTGGGCCCTTCTTGAGTCTGCAAAGGGCTGACTTTTCTGTA
CGAAGATACTTCAAAGGGAGGCTTGATCCACCTGCCTGTGAAATTTTATAAGCATGTCCTAAAGTAATTC
AGGTGTTAAGAATTCTGGGTGGAGTCCAGAACAGGCACACCCTGAGGATTTATATTCACTAGTAAACAAC
CTCAGGTTGAGTATTTCCACTTTAAAAAATTCCTTTACTACAGGCCATAGACATAGATGCCACAGGTCGT
TCAGGTGGAAAACACTACCCATTAATGCTCTTGTGGAGTGTGGGGCCAGCATTAACCTAAAGTCATACCC
ACCTTCCGCTCAGAAGCATCCCTCTCTGCCACTCCACCTTCCTCTGATGTTACAGCTGGCAGCCTATCTC
TTTCTACTCCTTCTTGTTCTTGCTTCAAATGCTGGTGAAGGTTTAGTACGGTGGCCTTCAAGTCCACCAA
CAGGTCTTCTTTTCTCTGGTTCAAACTCAGAATCTGTTTCTCCATACGTTCGATTTCTCCCTGTGTAGAA
AGAGTGTTTGCATAGGTTTGAGAAGTCTGAGGCCTCTGCAGGCCCAGAGCAGCCTGCTTCCTTTGGTACA
AGGGCTGAAGATTTTTCTTTGCTATTTGGTTTACAAAGCCAGAAGCTAGTCTCTGGTACGGTATAGCTCC
TTTCCATCCTGGATACAATTCCAAAGGTCCTGTGTAGGGTTTATAAGCTATAGGATGCCTCAGCCTTACC
AGAGACCTTGTGAATCAGAATCTCTGCGGGTTGAGCCAAAGCATGGAAACTTGTAACATGCTCCACACGT
GACTGTGGTGTGCGGCCAGGGTTGGGAGCTACCGCTCTAGTGGCCAGCTACAGGACTGAGAGAACCAGGA
TCCACGGGGCAGGGCCCCGGAGTCTGCACACTAACCAACACTGCATAAGTGCCTTATGCAGACTTTCCAT
TGTGTCCCAAAGCATATTAAAAATGCATGTCCCCAGGAGACATGTTCCCATGTCTCTCCAGGAAATTCTT
AAGCAGACTAACATTTGGGAACCACTGAGAGAAAATGAAGACAGAAATCTCATTCTTTTATTATCATCTT
TGAAGGCTTCTTTGGTATTACTAAATTCATTTACTTTTTTTTTAAGCAGAGTCTATCCTGCTCAATCATT
TACTTTTTCTACAGTAAAATCTTCCTACTAAATAGGAATAGGTAAACAAATAAAGGTACCATGTAGTATA
TCTTATTATGGGAATGATGGACAGATGATCTCAAGCTTCGTGATGTTACTTTTAACATTTATATTATTGA
TATGTGCAGATCAAATTTCTTATTCATGGCAGATATGCAGATGCCCACTGTATGTCTGAGATGACTATAG
GATTATAGATTCTTAGCTTTGGAAGAAACAGCAGGTGACAAATACACTAACATCCTCCTCTCTAGCACCT
CTGAGAGATGTCATTCAACTTGCCTGAGCTCCTGAAGTGAGTACTGCATCAGAAGCAGCCTGCTCCTTTT
TAGAAAACCTTCATGTGTTTGAAATTTGTTCCTAATATATTCCTTAGACCCCTATTCTTTCCTTGTTATG
TCTTCCTTTCTTGCTGTCAGTTCATCCATCCACCCATCCTACAGATAGTCATAGAAGCAATAATTTTCTT
ACAAAACAGAGAAACGTAATCTGTCTCCACCTGCAAGAGAGAGTTCTAAAGGCCAGAGAAAGAAGGTGAT
TTGTCCAAAGCTGCAACTAGCACACAGCAGAGCACAGGCCTGGGCTTTCTCCTGGCTGTACTGCACACAT
TTCTATGCCAATACCCCTATTCTGTCTGAAGTCAAAATTTCTGTGATTGCTTTTGGGAAATAACAACTGT
TTGACTTAAATCTGAGTTGGCTGCATTTTGTGTTCCACTTTCAATAAACACTAAACTTCAGAGGTACACT
GCCTCCTGACAAGAGCAATACTACAGCCACTAGGATAACACAAACAGAGTAGAGGCACAGTCCTACATGG
AGCAGCTGCTCTCAAAGCAGCATCTGCAGACCCCTGGCCACAGTCCATGAGGTCCAGATCATTTTCATAA
TACTAAAATGTTATTTGCCTTTTACACCATACTGACATTTGCACTGATGGCATGAAAGCAATGGTGGGTA
AAACTACCGGCACCTAATATGAATCAAGGCAGGAACACCAAGTATATTCGTTGTTACTGGGTTCTTCACT
TTGATGTATTTATAGTAAAAAAAATTCCATTTTCCTTAAGAATGTCCTTGATAAAAATATGTGTCTTAGT
TTATTTGTGCTGCCGTAACAGAATATCTGTGACTGGGTAACTTATAAAGAACAGAAATTTATTTCTCACA
GTTCTGGAGACTGGGAAGTCCAGGATCAAAGTATTGGTACGTTTGGTGTCTGGTGAGGGCTGTTCTCTGT
TTCCAAGATGGCGCATTGAAGACTACATCTTCCTAAAGGGAGATTTGTCGTGTTCTCACACGGCACAAAG
CAGAAGGGCAAAAATGGGTGGACTCCCTCCCTCAAGCCCTTTTCTGAGGGCACCTAATCCCATTCATGAG
GGAAGAGCCCTCATGACTCAATCACCTCCCAAAGGCCACACCTCCCGATACTGCTGTGTTGGTGATTAAG
TTTCAACATGAACAAAAATGTTGGGGGGAGGGGAGGCAACATTTTTTGGGAGGAAAAAACATTCAAACCA
CAGCAGTATGTATTTTTAGTATTCTTTGTGAAAAAATGGAAAGTATGCATATGGCACTTCTGCTGCATAC
CAAGGGCCAATGGTTGAGAAAAGCACTTATGCTACTGTTTGAGTTGTAAGCTGAACTATCCTTTTTATTC
ACAGAACACTATTTTTACGTGAAAAAAGCCAGCTGATAACTGTATTGCTTTCCTTAAATACTAAAAGATT
TTTCTGAAGAGATAAGTGTTAATATTAACAACTATGATTTAAAGAATATTAGACAATGTGTCAACATTTG
GAAGATCGGCCTAACTCAGCTAATCAGGATTATCCAAGTGATCGAGCGTGATGTATAAAATCATGCATTG
TTAGAAGATCCATTCGAAGTACAAAGTAGGCCAGTAAATTTTAATGTAAAAACGTATAAAGTTCATTGAC
ATGGGTTTAGATTCCGTTTTACAATTAATACATACTTTGCACTTGTTGGGTTTTAGTATAGTTTCAAAGA
AAAATGTCCACAATTATTCAAAAGGACTATTAAAATATTCCTCCATCTTCCAAGTGCATGTCTTTGAGAG
GCTGGATTGTCTTCCTATACTTAAAACAAAACTACATGCTTCAGCAGATCAAATGCAGAAACATTTGCAG
CACCCACATCTGTCCATTAGGTGGGTGCAAAAGTAATCGCGGTTTTTGTCATTACTTTTAATGGTAAAAA
CTGGAATTACTTTTGCACTGACCTAATATTAAGCCAGATATTAAAGAGATTACAAATACATAAAACAATG
TCACTCTTCTCATTACTATTTGTTTTAGAAAATATAACTACTTTAAAAAAATGTTACTTCTACTACAGCC
TGGGTAACACAGTGAGACCTCATCTCTAAAAAAAAGAAAATAAAAATAGTTATTCCTATTAATATGTAGT
GGGTTTATTATTGTTGCTTAAAAACTAAATGAATGTTTTTACATTTCTGAGTTTTAATTTAGTTATCAAT
GGATATAATTCATATAAACAAAAGCTCTCTGGGGTCCTTGATTTTTTAGCATAAGGGGAAATCTAATATT
TTTACAATACTGAGTCTTCATTACTGAGTGGGAATTATTGATCCACCATTTAACAGCTGTGTCATCTTGC
ACTCTCCTGTACTTCACTGTAGATGTCAAATCACTTGCCCCAGGTCTCACAGCTGGCGAGTAGTGTAATC
TTCTTTTGAGTACCATATTAATTGCTTGCCTGTATCAATTTGATGGCAAGAAAAAAAAGCAGCTCTCTAT
TACCCTTAGCATACAATCACGTTTTTTTGTTGTTGTTGTTTTTTATTATAGAAATGCTACTTCAAAAACA
AAGACTGAAAAAACCTAGCAACAGATGGTTAACATGCAAACCATTGTAACTGAATCCACAGGACACTGTT

TTTTTATTTTTATTTTTTTAATTTTTTTGAGACGGAGTCTCACTCTGTCACCCAGGCTGGAGTGCAGT
GGCGCGATCTCGGCTCACTGCAAGCTCTGCCTCCCAGGTTCACTCCATTCTCCTGCCTCAGCCTCCCGAC
TAGCTGGGACTACAGGCGCCCACCAACACACCCAGCTAATTTTTTTGTATTTTTAGTAGAGACAGGGTT
TCACCGTGTTAGCCAGGATGGTCTCGATCTCCTGACCTTGTGATCTGCCCGCCTCGGCCTCCCAAAGTGC
TGGGATTACAGGCGTGAGCCACCGCGCCCGGCCCACAGGACACTGTTAATTCTGACATATGGCAATATGT
CAGTATGGCAATACTGCTTAGAATATGGAATTCTTCATTACAATAGTATTCAGGGTCTTCACTGCTGAAG
CCCAGCCTGCCTACACTGCCTGACTCTATCCCAGAAAGTCAGGTTGTCCAAATATCCTGTGTGTTATATC
AGGTTCTTTGGTACCAGAGCAAATTCACATCAAAATGCTTCAAGCTGAGGCCATGGGCACTTAAAAAGCC
CTCCATTAAAGAAGGAGATGCGGCAGCCCTGGCTCAGTTTCTGGGATTAGGACTGCCCAGGCTACAAACA
GATAAGGCTTCTCTTGATCAAACATCAGGGGCTATAATTTTGTCACTTTTTAGTAATGATAATTATATAA
TCATCTATTTTATGAAATAGGGATGGAAAGTAAACACACACAGAAATACCTTCAATTGTTACAGAGAAAC
AGGTGTTACACTGCACCACTAGAAAGGCTCCTAGACACCAAAGGCTTAGTAAGTATTAAATAAATGCACT
GATGGACAAATGAAACATACCTTTATGAATGAAAGAAACATACCTGTAGTTGTGGCAGCTTGTCAGCTTG
GTCTGGTGACATATGTTCAAGGGAGAACTGAGCTGAATAATTATTTAAGATCTGTTTCAAATTTTCTATT
TCTTCATCCCATTCATTGGTCTGTTTTATGACTACCTATAAAATAACCCCCACAAAAAAGAATCTTTGTC
ATAATCTAAGCAGATTAATGGACTATTTTCATTGTCTAGCCCCATGGAAGTTTTAATCACTCACAGCAAA
TATGCACCCATTGAGATTTCAATAGGACGTGGTAGCCTAAACAGAGAGAAGAATGTTTGCAAAGCTGACA
CCTGATCTTCTTGCTCTACTAGATGCCAGGGCACCTTGGGCAGTGCTTAAAGTACAAGTCTCACTGGACA
CACCTTTGCTCTTAAGTATTTCTGGTCCAGTGGGTTTATTCTGGAAAGCATTTTATGGCGTGTTAACATA
AAGTTGCTAACTTTTGAGAAGTTACTGACAAGTCACATACACCATTTTAATACATATTCCATGGCCGGGG
GAGCGGGGGGGCTTTCCGCATAGAAAGGTGACATAACAATTCAGACTGAACAGAGCATGTGAGGTCAGTG
ATGATGGGTTTTCCCGGTCCAGACTCATCTTCACCTGGTACCCCTTGGGATCAGTGATGTGTGTTTTACG
AGTAAGAGGCTGAGGGTTCAAGAACAGTCTAAATTTGCAGAATAAGAACTAACCAGAACAATACCTGGCA
TCTAGTGCTAGGGGAGCAGGAAAGCTCAGACCTATCTGTGGACTAAATAATATGATTAAGCACGATGAAA
AACAAAGAAACAGACTTCAAAAGAAAAACTAGATACTTCTTTGGTATGCTACATAATGAAGCAAAATGCC
TTTTAAAACTACAAAGTTTCTAGCCAACACGAAATTCTTCCTTGTATTTTCTTTAATATTTAACTATAAT
TTTAGCCATAGGCTGGAAATGAATAACTATGTTCACTGTGCACATCTGTTCCCCAGCCCTCAATAATGAA
CTACATCCCGTTCTCTCCACAAAAGGAATTTGTCTTATTTTCTACAACGAGGGTACTTACAATATCTAAA
GTAGAAATCAAAGGAAATGTACCATATTCTAATGATTGTCTTCACCACTGTCTTCCTTAGCTTTGAAATA
TATGAGGGGACATCTGATTGCCACCAGCACAATGAGATGGAAAATTTGAGCAGCATAGTTTGATACCTAA
CTTGGCACAAAACAGAACTGCCTCTTCTATTTCACCCATTTCGTCTGTGAAGAAGCCACTTGAAAGCATA
GTTAGGACCGTGGCTTTCTTTTTCTGACCAGGAGACTAATAAAGCACAAAAGGATGAAAATAATGGATCA
AATTTTATATTTTTTTCTCTTTATATTATTACAAGGTAGTACATTGAGTGCTAGATCTTTTTTCTCTCTG
TAGGTGTTACAGAATGACATCAGTTGACCAGCAGCCAGACCAGAGAAACTGAGTTAAGACTCAAACCAGA
GATTACAGTCTCCTCAAACCTTAGGAGAACAGAGTGGCCACCAAAATGTGCATGAAATTTAAGAGGGAAA
AACATATAGTCATTTTTCTTCTTACAACCAGAAGGCGGTCATGAAAAATGAAAAATAACCCTTACAGTGA
CCCATCTAATCAGGAAAGGCAGCATGCAGGAGGTTGACGGAGACGGTTGGAAGTCTGTGCAGACTTTCTG
CAACTTTCTGTTCTTGTGGGAGTGATTATTGATCCAGGAATACAAACTAAAGATTATTCCTAACTAATGA
TGATTCCTGATGGAGAGTAGTGATTTAACAAAACCCAACCACCACCACCACCACCACAACACAAAACCCC
TCTGGGGAGAAGATGAAGAATATCAGCTCTCAATATGCAGAAATGACACCAGGAGTTTAGAAACTCAAAT
TCTTGTTCCATGTGTACATAAATTAACCTCTACACAAGTTAACTCTGTGGTCTTTCAGCAAGTCACTTAA
CCCTGATGCCAATTTCCTTATCTGTAAAAATAAAGATAAAGTGCCTACTCTACCTACATCACGTTTGGTA
ATGAGAAAATCAATAGGAGAGTCACTGAGATGAACACAGAGATTACTATGGTGATGATTACTTTACAGAT
CTGTTGGCCTCAGAGGCTGCAAATGCCTTGTTCAGGTTTGACTCTCTTCCCACAGCATTTTGCCCATGTA
GGTCAACAACTGTGGAATGAAATTAAATAGACCATAACTATGCTTTAATGTCTTAAAGGATAAGAACTGA
GAAAAATAACCTTAGCTCCATTTGAGCATGAAGATATGCTTTTATATCAAATGCCACCTCCTACAATAAT
AGGATAATAATGAATTTCAATTAGAAGTGAAAACCAAACCAGCTTTTGGTGAACATTTTCATCCAGTAAG
TTGGATGTCATCAGAAACTGCTTACCTTTAATAACTCATTTTGTTCTTGAGTCACATTTTCCAATAGTTT
TATATCTTGTAAAAGCTGATTTGTCCGCTGAAACACAGGCAGAGGTTTCATTCCTGTTTGGGGCAACCTC
AGTTCCACTTGGTAAGACACTATCTCAGCAATGGTTTTCTTCATGGGACGTATATTTTCAAGTATGACCT
TAATTATATAAGAGGAGCATGTTACAGAAATGAAAAGACAATGGCCACTGTTAAATTTAATTATTCAAAA
TTAAAATACAGTATAGTTTTTATAGTTTGCATTTTTAAAATAATTTCTTAGCTCAGATTGAAAAGAATTA
TTATATCACTCATGATCCGGGAGTTGAAAGTCTCAGGAAAGAATAACTGGGGCAAGAGTAACCTACCAAT
ACTAAATTACGCATTTGGACAACTTTTTCTTCCTTTTCTCCCTCCACTTTCTGTGTAGAACTGGCGTTCT
GCTGTGTATATTGTCACTAGGCAGTGAGCAATGTAAGGGCAGGTACTGCCTCTCACTTTCGTAGCAACTA
CACCTAGCACAGGACTTCCCGTATAGTAGGCCCTCAAAAGTGCTTATTGACTTGAACAGAACTGTGCTGC
ATGAGTCCCAGGAGTATAATTATATTTGCTTTAATAACATCTGATCCATAGAAATCTGGATTTATGTAA
CCAATACATTAGAAGAGATTACTCACCGTACTAAGTCATATCTCATATAATATCATTTCATTTAATCCTC
ACAACCCCTCGAGAGGTAAGTATCCTAACCTCCATTTCACAGGTGAGGAAATTGGGCTCACAGAAGTTAG
AAGATCCAGGTAAGCTTAGTCTGTAAGAGGCAGAGCTGGGAACAGAATCCAGGCCTCCCTAGTCCTAAAC
CACATGCTCTCAATCACTAGGCTGAGCAGGGGATCAACATTTGCCTGCTGTTTAGTCATGTCCCAGCTCC
TCTGTCAGGGGCTCTATTTACATTACAATTGGCCAATGTAATCTCCTCAGTACCAGTGCACGGATATGAA
AGAGAATCCAAAAACCATTAATTACTCAGTCATGCAGCCAGTGAGCAGTCTAGCTGGGGCTGGAACCCAG
TTCAGCCTGAATTAGGTGCTCAAGCCCTTGAGTTTGATTTAAATGAAAAAATAACCTATAGGAAAATTAT
CTTTACATAGGTGGTACTACAACTACGATTTAAATATACAGTTATAGTTATTCCCATCAATTTCCCAACC
TTATTTTGCTATTACTCTGGTAAGACTAAATGCTTTTTTAAATCACATTATATTATATTTTGAAAAAGAC
ATAATAAGTATCATAAGAAAATACTTTAAATAATAATCTATGCTTACCTCCCCATGTTTGAGATGTTCTT
CAGGTGAAAAATCAAATATTTCTTTTGATAATAGGATAGTTTTGATTTTTGAAACTCTTTTTTCCATTGA
TTTTACTTCAGATTCAATAGCAACCACATCCTAGAATTTCAGAAGAACACACTGATGCAATATATATATTGT
ATATTAATCATCTATAAAACAGTTTATTGGCATTAATTTTATTCTCTTATTTAGCCAAATAATGTCTGCC
ATCTATACCTCTGAAAAACTAACCAAGCACTATAGATAAATAAATAATGTTCACCATTTTCTTTCCTTTT

TTTTTTTTTTTTTTTTTTTTTTTCCTGAGACGGAGTTTCGCTCTTGTTGCCCAGGCTGGAGTGCAATGTC
GCGATCTCTGCTCACTGTAACCTCCGCCTCCCAGGTTCAAGCGATTCTCCTGCCTCAGCCTCCTGAATAG
CTGGGATTACAGGCACGTGCCACCATGCCCAGTTAATTTTTATATTTTTAGTAGAGACGGAGTTTCGCCA
TGTTGGCCAGGCTGGTCTCCAACTCCTGACCGCAGGTGATCCACCCGCCTCGGCCTCCCAAAGTGCTGGG
ATTACAGGTGTGAGCCATCGTTCCTGGCCAGGGACCAACAAAACTTTATAAGAAAATGAAGCAGTATGTA
CAATAGCTGTTTATAGTGATATCTTCAAATTATGAGGAAAAGTTAAATTACATGGACATTATTCTGTGCA
CCTACTATTTAAGAAGGTATATAGAATTATACAATGTATTTTAGGGTAATTTTCATCAAACATTATAGAA
GCATTTAAAAATTTTGAAATGAGCTTCAGTAACCAAAAATAATTACTTTAACACTTACTATTCCCTGAAG
ATACATGAGTGTGGTGTAGGGAATGTAACTGAGTAACAAATGTAAATAATGAAGAACTTTAATTGCCTCT
ACTATGTGACTCTATCTTTAAATAAATGCTTCTGATGTTTCAAGCCAAAATAAAAATCCAGAGGCTGGCA
AATAACAACCCCTCAATAAATATTTGCTATTGGTAAATAAAGACTTGGGACTACCTGTTTTACACTTGTT
TTTAATTCCTTTTTGTGGAGAAGGGGGTCTTACTGTAGTACCCAGGCAGGTCTCAAACTCCTGTGCTCAC
ATTATCCTTCTGCCTCTGCCTCCGTAAATGCTGGGATTACAGGCGTGAGCCACCGTGCTGGGCACCACGC
CCAGCCAGAACTATCTCTTTTAATTCCCTCTTTCCTATCCAGCATTTAAAAATCAGTAGTATTTCTCTTT
GACAAAGAGAAAACACTGAGCTTATTTTATCGGGATTCTTTACTCTTTAAAACAGACCACTTCTGGATTG
AAAATAAGGAGATGCTTTTTGTTATAGTTACACTACAGGTTGCAAAGTAAAGTAAAATATAATTCCACAA
ATGAGAACATACATGACATTTTACCAGATCAATGTGTCTTCACATTGATTAGTTGTATAGTGCTTGGTTA
GTAGTATAACTCTAATTTATTTGACAGAATCCTGCTCTGTCACCCAGGCTGGAGTGCAGTGGCGCAATCT
TGGCTCACTGCAACCTCTGCCTCCCAGGTTCAAGCGATTCTCCTGCCTCAGCCTTCCAAGTTGCTGGGAT
TACAGGTGTGCACCACGATGCCCAGCTAAATTTTGTATTTTTAGTAGAGACAGGGTTTCACCATGTTGGC
CAGGCTTGTCTTGAACTCCTGACCTCAAGTGATCCACCCGCCTTGGCCTCCCAAAGTGCTGGAATTATAG
GGATGAGCCACCATTGCCCAGCCTCTAATTTAATCCTGAATGATTAAATGAATGGTGCAAACTTACATCA
GCCATTCGCTGAATCTGTGGAAGGCTTTCCATTATTTTTTGTTGTAAAGCTGTTACTTGATTACTTAACT
CTTGTATGGATTGGGTTAATTCATCTGTTTCAAAAATTATTGACAGGTCTTCTAGATCCATAAAGATTGA
ATGTAAAAGATTGTGCTTCTGTTCTGAATCTTCCAAAGCCATCTAGATAAACACAGAATGGGAAAAATAG
AGAGAAACATCAAGATCCTGATATAAGCTGATTAATATTTAAATCAGAGAAAATTGAAAGTTATCTCAAC
ATTTTAAACTAGTCATTTCTAGTTCGATAATGAAAACAGAACACCCTCTATTGTCAATGACAGTGAAAGA
CTTCAGAGTATCTACCTGTATAACTGTAACATAATAAGAAACATAAATATTTGGTCTTGGTCCACTTCTA
AAACACTTGGAATCCTTTAATAATAGGGGAGAGAGAAGTGTCTTTTATTATACATAATAAGCCCTTTCAT
ACATGTAATAACTTTCAAATTTAAGATGTCAAAATAGCTCAGCCACCTAATGAAAATGTTCAGCTTGATA
ATGTACTCTTCAGGTAATTCCATAAAAAATAACTGATAGGAGAAAGAACATTCACTTACACAACTAGAAT
TTCAGTCACAAGTCACTAAAACTAAGTGGGTTATTCAGAATTTTATATTAATCTTATTCAAAATCCTTAT
AGGAGAAAACTTTTAGGAAAACAAAACTTAAAACCAATGCTTTTTTTTTTTTTTTTTTTTTTTTACCAA
TTATCACTGACAACAGCATCAAAAACCATAAAATACTTAGGAATAAATTTAACAGTATACATGCAAGAAA
TGTATACTGGGCCGGGTGTGGTGGCTCCTGCCTATAATTCCAGCACTTTGGGAGGCTGAGGTGGGTGGAT
CACCTGAGGTCAGGAGTTCGAGACCAGCCTGGCCAACATGGCAAAACCCTGTCTCTACTAAAAATACAAA
AATTAGCCAGGTGTGGTGGCGGAAGCCTGTAATCCCAGCTACTCAGGAGGCTGAGGCAGGAGAATCGCTT
GAACCCAGGAGGCGGAGGCTGCAGTGAGCCATTATTGCACCCCTGCACTCCAGCCTGGGTGACAGAGCAA
GACACCATCTCAAAAAAAAAAAAAAAAAAAAAAAAGACCTGCATACTGAAAATCACAAAACATTGTTGAGAA
AAATTAAATCCCTAGAGAAATAAAGAGATATACCATGTTCCTGGATTGAATAGTCACTATGGTTGAGATG
TTAATTCTCTTCCAAATTGATCTACAAATCTAATGCAATCCCACTCAAAATTCCCACAGACCTTTATTTA
GAAATTAACAAGCAGATTCTAAGATTTATATCGAAATACAAAGGCCTTGATTTAGCCAAAACAAATCTGA
AAAAGGACAAAGTTGTAGAATTGATGCTACCTGATTTCAAGACTTACTGTAAAGCTATAGTAATGAAGAC
TGTCATATTGGTGAAAGTATAGACATATAAATTAATTGAACAGAAGGGAGAGCCCAGAAATAGATGCACA
TGTATAAGGTCAATTGATTTCCAACAAAGTGCCGAAGTAATTTAATGGTGATTGTTATCAATAAATGATG
CAGAAACAATTGGATATCCCCATGGAAAAAAAGAACTTTGATCCTTCAATCACACCTTATGCAACAATTA
ACATGAAATGAATCATAGATCTAAGAGAGTAAGAGTTAAAACTATCAAGTTACTGGAAGAAAACACAGGA
AGAAATCTTTGTAACCCTGGGTTAGGTAAGGATTTCTTAGAATGCAACACAAAAGAATAATCCATAAAAG
AAAATATTGATACATTGGACCTCATCAAATTAATAACATTTGCTCTCTGAAAGACAGTGTTAAAAGAATG
AAAAGACAAGCCGCAGACTGGAAGAAAATATTTGTAAATGACATATATGTCAAAAGAATGGTTTTCAGAA
TATTTTACAAAAAACTTACAACTCAACAAGAAGACAATGCAATTTTTTAAATGGGCAAAAAAAATTGAAC
AGATACTTCACAAAGGAAGTGTACAAATGACCAATAAAGACATAAATAAATGCTCAAAATTATTAGTCAT
TAGAGAAAACCTGTTTAAACCACAATGAAATACCACTGCAAGTCACTAAAATGGCTAAAATTTAAAAGGC
AGACAATATTAAGCGCTGTTGAAAATATGAAGCAATTAGAACTGATGTTGCTGGTGGGAAAGAAAAATGA
TACAGCCATTTTGGAAAACAATTTCTCAGTTTATTATTTATTTAAACACATCGTAAAAGTCAGAGATCCT
ACTTTTAGGTATTTATTCATTGAAATAAAATGAAAACATTTGTCTACACAAAGATTTATATATAAACATT
CACAGCAGCTTTGCTCATAATAGCCTATGGTAGCAGCCTCTAAGGTAGCCCTGAATGACCCCTACCTCCT
GGTATTCATACCCTTATATCAGCTTCCTTGAATGCAGGCCAGACTTACTAATTTAATTCTAATAAAATGT
GGCAGAAATGATGAGATGTCACTTCCAAGGTTAGATTACAAAGACTGTGGCCCAGCCTGGGCAACAAAGT
GAAACCTTTTTGCAAAAATTTAGAAATTAGCCAGGCATGGTTGTGTGCGCCTGTAGTCCCAACTACCTGG
GAGGCTAAGGTGGGAGGAACATTTGAACTCAGAAGGTGGAGGCTGCAGTGAGCCGACATTGTGCCACTGC
ACTCCAGCCTGGGTGACAGAGCAAGACCCTGTCTCTAAAAGAAAAAAAAAAAAATGTGGCTTCTGTCTTGA
CAGCTCTCTCTCACTCTCTTGGAGATTGTTTATGCTGAGGGAAGCCAGCTGCCATGGTGTGAGGCAGACT
CCTGGAGGAGCCCACATGTCTGTAAGTAGAAGCAGATCTTTTGAGGCCTGTCAACAGCCACGGGAATGAG
CTTGGAAGCAGATCCCACCTCCTCCCTCACACAAGTCGAGCCTTCAGATGAGCCTGCAGCCTTTGTCGAC
ACCTTGACTGCATTCTCATGAGAGACCTTGAGCCAGAGATACTTAGCTAAGCCATGCCCATGGACTCCTG
ACCCACAGAAACTGTGATAATAAGTTTGTTGTTTCAAGCTGCTAACTTATGGAGTAATATGTTACACAAA
AATAGCTAATATATAGCTCAAAACTGGAAGCAACCCAAATATCTATTAACTGGTAGATAAACAAACTACT
CATTTCCAAACTTATTTCCAAAACTGGAACACTACTTGGCAATCAAATAATTAACTATGCATTAAGTGTA
ACAACCTGGATGAATCTCAAAGGCATTATGTTAAGTGAAACAAGTGAGCCACGTAAGACTACATACTGTT
TGATTCCCTCTATATGATATTCTAGAAAAGGCAAAACTATAGTAATAGGAAACAGTGAGTGATCACCTAG

GGTTGAAGACAGGTGAAAGGGGATTGACTGCAAAGAGGCAGGAGGAAACGTCTTGGGAGATGGAGATGTT
CCTTATATTGATGGCGGTGGTGGTTACACAACTGCACTTTTATCAAAACTTACCTAACTGCTACTTAAAA
TAGGTGTATTAATATTTTTACTGTATGTAAATTATACCTCAATAAATTTGATTTAAAAAACAGGCCGGGT
GTGGTGGCTCACGCCTGTACTCCCAGCACTTTGGGAGGTCGAGGTGGGCAGATCAGCTGAGGTCAGGAGT
TCAAGACCAGCCTGGCCAACATGGTGAAATCCTGTCTCTACTAAAAATACAAAATAAGGTCAGCGTGGTG
GCACACGCCTGTAATCTCAGCTACTGGGGAAGCTGAGGCAGAAGAATCACTTGAACCTGGGAGGTGGAGG
TTGCGGTGAGCCAAGATCGCACCATTGCACTCCAGGCTGGGCAAAAAGAGTGAAACTCCGTCTCAAAAAA
AAAAAAAAATTAGTTTTCTATTTTTATAATGTCATTTTATGAATGTATGTTTCAGTTATTCTTACAACAG
TAGTATTTGTGGAATTATCTTTAGGTTACAAAGACCTGTTTTAACAAATGCAATCCAGGTAGAAGGGTAT
AGTGCAATTAAAACAAACATTTAAAGCTTAGTTGAGAGTTCTGACACTTCTTTAAAAGTCAATATAAAAA
CTAATACCTGAATATGCTAGAAAATGGAAAAGGGCATCCTAAAAGTAAGATTATTGCACAAATGAGGATT
TCACATAGGACTAGTTATTTGGGACTTACTTCCCAGGAGGAGATTAGGACACATCGGGACACATAGAAAT
AAACCCGAGCCTTCCTTGTCCCTACTTCCTTTCCTCAGTTCTAGCTCAGAAAGAAAGTCTAGCAATTTAG
AATGTCCTGAAGTTTGAGAGATGCTTTTACATTTTTACATGTGTATCAGTAGAAGGTAGCAAAATCCCAG
CTGCTTTTGCCTGAGCTCACTTTTGTACAGTTTTTTTTTTTAACTCATAATAAGCATTTGAAGGAAAAAA
AAAAAGCATCATTCCTCTCTCTTGTCTTGGTAAAGTCCTCAAAAATAGTGAATCAGGGAGGTGATAAAGA
GTTTAAAAATGACAAACTTTGGGGATGTGGAAAGTTAATCCAAGTGGGGGAAGGCAAAAAAAAATCACAAG
CAAGGGGAAGAAAAGAAAAAAAAAATGGGTAGAAATGCAGCATCTTTACAACTGTTACCGTAAGAAAAAAA
TATGCCAACGATTCTCAAACGTCAGGGAGGTCTGAGGTCAGCAGCTCACTTAGGAACACACTGTGCCATT
CCAAAGATAAAAAAAGGAGCTGAATCACCTTGGAAGTCTGATTCTGTAAACACTGTTACCAAATAAGCTT
TTCTCTAAGGGATTCCTTCTCATGGCAGAATAAGAGAAGGGGAACACACCTGCGCAATGCAACTTCCCTA
GTACTCAGCATCCGGAAGATGTTTTGCAGCCGAGGCCTCAAGTGGGAAAACACTTTCATTTGTTTTGACT
TTGTAAGCCAGCATGGACACGTGGGGCATGTGTGGAGTACCAGCAAGGACAGGAAATTTGGAATCATGGT
GTGTTAGAAGTGGAAGGAACCATGGGTTCGTTTTCTATTGCTGTGTAACTAATTACCACAAACTTAATGG
CTTAAAACAAAACAAAGTTATCTCACAGTGTCCAAGGGTAAGGAGTCCAGGCATAGCTGAGGTGAGTCCT
CCTTACAGGGAGCCACAAGGATGCAGTCCGGTGCCATCTGGAGCTTGGGGTTCTCTTTGAAGATCATTCA
GGTTGTTGGCAAAATTCAGCTGTAGGACTGGGTTCCCTGTTTCCTTGCTGGCTCTCATTGACTCTCAGCT
TCTAGAAAAAGCCTTTGGGCCCTAGCTCCATGGCCCTCTGACAATATAGCCGCTTTCTCAAGAAGAATCT
CTCTGCACTCTGCTGCAGGCTGAGTAGCCCTTATCTGAAATGCTTGAGACCAGAAGCATTTCAGATTTTG
GACTTTTTCAAATTTTGGAATGTAAGTATTATACTTACCGGTGGAGCATTCCAAATCCCAAAATCCCATA
TTAGAGAGCCTTATAATCACGTTAATCAAGTACTTATGGGAGTGACTACCCCATTACCTTAATCATATAA
CGTAACCTAGTCAATGAAGGGACTATCCCATCATATTCATATTCCTGCCCACATTCAAGTATTATTCTTT
CAGGTCATATACACCAGAGGATGGGAATATTGGGGGGCATCTTAGAATTCTAACAACCAAAACCATCAGC
ACTATCCTATGCACATTCTTTTTTTTTTTTTGAGACGGAGTCTTGCTTTGTCGCCCAGGCTGGAGTGCAGT
GGTGCGATCTCGGCTCACTGCAAGCTCCGCCTCCTGGGTTCACGCCATTCTCCTGCCTCAGCCTCCCGAG
TAGCTGGGACTACAGGCGCCCGCCACCGTGCCCAGCTAATTTTTTGTATTTTTAGTAGAGACAGGGTTTC
ACCGTGTTAGCCAGGATGGTCTCGATCTCCTAACCTTGTGATCCGCCCACATTCTTATTTCATGGGAGA
AACTGAGGTCCATAGAAGATATACTAAATTATCCAAAAAGTCATAAAGTAGTTATCAGGACAGTAAGAGC
TGAATCCTGGTCTCCAAAATCCATGTCTACTGCTTGCCACTCTCTCAAGCTTCCTTCTGCCACTGACATG
GTTAGCGGTAAGGTTGTATTTCAGGAAAGGAGGAAAAAAGCACCAAGACAATCAGCTAAGCCACGAATCT
TTATGTAGATGCTATGAGTGGCAGAAAACCTGGAAGAACACTTACCTGCACAGTGCTAGCATGGTGACTC
AGTGTCCTCAAAGAGTCATAGTCAGCAGGATTGGCCAGCAAATGACTGGTATTTTCTATCCAAGCCTCAG
TGCTCTTCAGAAGGTCACTATATTCCTCCATCTTAACTGTGGCCTGGGAAAGAGATGCAGGACCAAACTT
AGTCAGATGCCTTTTACTGGAGCTGAATGACTCCTAGATGAAGAGTCAATAGCTGTTAGTCAGGGGTGTG
TCAGGCCTTGCAGATGTCTGCTCCCCATGGCTGGGGCTACTTATTCACCTGCTCTAGGCTATGACACTTC
TGACTTTTAAGACTAACTCTGACCATAGGTGGAAAGGATTTAATCAGTTCTACTCCAACGTTATGGGCCT
CAGCAAAGTTCTGGGTTAGCCTTGCAAGTATTCTGGTTCTCATTTTATGCTTCATTTTAAAAACTGGACT
GTACTTTGTCCTCCTGTTCAGGACCTTGCCCTACAGTTCTTCTAAGACTAGGATGCTGCCTCACTCTTGC
TAAATCACAGACACAACTCAGCCAACCACAGCTCCTATTTGGAAGGAGGGTAGAGAGGGTATCTTTTCCC
CGAATGACAGTCTTTCTCATTGTTGTCTCCCTTACTAGACTCCTGAGACCACCTGCCCTAAATTCCCATT
ACTGGTCTTTATCCACCTGTTGGGGAGCCTGGACTTCCCAACAGTTTGCCTGGCTCTTGCTGTGGTCAAC
TTCTGGATTCTTGGTTCTGTCTGCCCAATCAGACTTCCTGCCTGCACTAGCATTGAAATCTGTCTCCTCA
GCACCCACACAAGCCTACCATGGCCCCAGCTTCAAGTCCAAAACTGATAATTCAACAGAAACTGACTGTT
TCTGAATATATTGTTTTGCTTTAACACCATCTCAATACCACCACATGATATGAAGCTATTACGAGTCACA
GCCATACCTTATTCAACTGTGAGGTTCTACACTCTGCTCTCTGTGATACTTGCTGATACTGCTGGAAAGG
AATCATCAAGTTATCCATCCATTCTTGAGCCTGTCCTGGGTCCTGTTCAACAATGTCCTGAACTTCAGAA
TCCAGCTCATTTAGTTTGGAATGCCATAGATCTAACTCGTCCCACATTTTCTGGAGAAGGAAATCGTAAG
TCAACTTGAATGAAGAGGTCATAGTTTATGGAGGCAATGCCTGGTTTTCACACAGTATTTACATTTATAA
ATGCTACTAAAACATCACAGAAACAACATCACATGAACAGTTGTTAATTTATACCCAGCAATTTGTGATC
TAAACTGAAAAACACTTTTCCTGAGCTCTCCTAACTACAACTGTATTCATTTCACTACAAATTAGCTGTA
GGGGAACAGAAAGACCTGGACATTTTTAGAGATGACTGACACAAACAAGGTCAATATAGCCCTCATCTCT
CAAGAGTGACAAGCAAAACATTCTGTTTAAAAAGGGCTTGGGGAAAGACTTGAACCTATTTACACTAGTT
CATACACACACACGCACGCGCGCACACACACACACACACGCTCTATTAATCTACAAAATAATTTCAAG
TGAAAAAATAAAACAAAGAAAAATATCTGGGCTGGGTGCAGTGGCTCACACAATTTTGGAGGCCAAGGTG
TGTGGGCTGCTTGAGGCCAGGAGTTCAAGACCAGCCTGGACAACACAGGGAAACACCGTCTCTACAAAAC
TTAGCCAGGTGTAGTGGCGCACACCTGCAGTCTCATCTACTTGGGAGACTGAGGTGGGAGGATCAATTGA
GCCAGGGAGGTCAAGGCTGAAGTGAGTTTTGATCACACCACTGCACTCCAGCTTGGGTGACAGGGTGAGA
CCCTATCTCAAAAATTTAAAAAAAGAAAAGAAAATTATCTGCTGACTTGGGATGAATGCAGAGGCAGAAA
GCTCTAGAAACATGTATTAGGAGCAACTGCTTTTGACTCAAGAAACCAATAGGTTGGATTCAAATCTGAA
CTTCGCTGGGCAGAGGAAAATTTCAAAGGTAAAATATTCAATTCTTAATGTTTGCTTAAGAACATTTTTT
TCCCTATCTTGAGGACTAGGAAAATCTAACTTGTTAAATTAGGTTCCTCTGCTTAAGATTTGTCCAATAG

TGAGCCATACTCTGACCTATTTTAAAAGCCCCAAATTATTAAAACATTTCCTTAAGACATAGATTAGAAC
AAGAATCCTTTCCCTATGCTGGAGTTTACTTGCGAATTAAGAAGGAGAATAGTGTTTATGTACAGTTTTG
CCTAAGATTTTATTTTGTAAGATATTTTACAAGGGAAATAAATTTGGAATTTTTATTTTTATTTAACCTT
TGCAGTCTAAAAAAGAGCTTTAATATTTTTCATATTCTATTGAATGATTTTTAGTATCAGTATCCCCAAG
ATAAGATCCTTACTTTCCTTTACTTGTGAAAATGCTAGTTCACAATCACAGGCTCTCAGAAGTTTGGGTA
TATGCCCACCATGGAAAAACAGAATTATTTTTTTGAGACAGAGTCTCACTCTGTCACCCACACTGGAGTG
CAGTGACATGATCTCGGCTCATTGCAACCTCCATCTCCTGGGTTCAAGTGATTTTCGTGCCTCAGCCTCC
CGAGTAGCTAGAATTGCAGTCTTGTGCCACCACACCCAGCTAATATTTGTATTTTTAGTAGAGATGGGGT
TTTGCCATGTTGGCCAGGCTGGTCTCAAACTCCTAGGCTCAAGTGATCATCCCACCTTGGCCTCCCAAAG
TGCTGGGATTACAGGCGTGGGTCACCGCACCTGGCCAAGAGAATAATTTTTAAATGCAACTTTCCCTATC
AAGCCTCTCTAGGTGATGCCCCTGTGGATTTGGTTTACAATTTCTGTGCTTCAGATTAATTCAAAGAACT
CACCCTGTGGTGACTGATGAACAAGGCAGGAGTGGGTCAGAAGTACCAAATGCTGAAGGGAGTTAAAGGA
GGATTTTACCTTTTGAATTTCTTGAGCTTTCTCAATATTTTTGCTTTTCTGCTGCAACATCTTTTCAACA
TTATGAAGCCCATTGTTAATTTCTTCTATTTTTCTCCTCATTGCATATGATGGTGAGCTTTTTAAGACTT
CATTGCTAATCTGTGAAAGAGACAAAGACGCATTTGGCTTAGAGAGGTTGTCTGCACTTTATTCATAGGT
TCGAACAACAAAAGTGGTAGTCACTCTGTTTTAACTTGTAAAAATTTTTAAGGGCTGGGGGAAGAAATT
CTGGCAAATGCATTAATGAGAAGGTGGATAGGAAGACTAATAAATGGCAGGTGTGTTTACTTCACCTTTT
AAATCTCATCTTAAATAAAATAAAAATTGGTTTTTTATTTGTACTGTAATACATGTATTGTAACATGTAT
TACAGATATATGCTGTGTTGGGCAAAATTACTGAGTGGATTGTGTGAAACATTTCCATATGGATCAAATG
ATATAAATGAATTCCTGGGGGATAAATTATTTTTATACAATCTTTCCATTTTATGAGAATCTATCTGCAT
AGATCTGTTTTCAGTAAAACCAAACTTACTCTCAAGCTGACTTTTTTAAAAAAATGTAATTCCAATCATA
GTATTCATTTGGGTGAAACAACCTTCTAAAATTGCCATTTCTTGAGGATGCACAGAGCTTAATTATTCTC
TGTGTAACCATTTGTAGATGTTTTCCCAGCCATCAGAAACTTAGCTACTGAACAGCGTAATTTTTTTTTA
TCTAAACGATTCTCTTAAAAAGAAACAAAAAAAAACCTTGAGCTAGGAAAGATAATAAATGAATGTTGAAT
GTATCACTTTCCAAATACCTGACTGATGTGTGTTCTTGTTTTGCTATTTGATAAGGCTTTCTCCAAGCAG
CTACTAAATAACCAAATAATACTTTATGCTTTTGTATAATCCTTTGTTTTGTAAATTAAAAAAAAATAAC
TCTATCTGTATAACCATTGAGACTAAAATCATCCTGTGCAGACAGTATACAGATGCTGAAACTGTAACAC
AGACTAAATGACTTGCTACAGTCATATGTCAAGGAAGTAGCTGAACTTGTCCCAAGAAGCGCCCAAGTCC
CTAGATTGAGTCCCAGGCTCTATTCACAATATCAGGCCTTGATACTTTTATATCATGTCTTTATTCCCCA
GACCATACTGCAGTCAATATTATTAGAAAAAAAAAAAATCCCACTTTGGTTCCATATTAGCTTTTCATGGC
TGGCTGTGTCACAAATTACCACAAGAAAAGTTTTCTGATATTTTGAGCACTTATTCTCCTGGCAGAAATG
TATACCATTGAGATACATTAGGACAGATCATGATTTAGGAAACATATGTAGCCATTTGAATTATACACAA
TGTTACTATGTCTGTCCCCCGGGATCCTTGAACTTCCTTTAGCTGTATCACACAATAAAAATTAGTTGCT
GTTTGTTACAAATATAGAGGGTCATAGCGGAAATTTTCTACCTTGAATTTGAACGACTGATTTTGATTAT
TAATTTACTCTGCTAGGGATTTTCATAAGTATTCATGAGCATAACATTTAGTTTCTCTCAAAATATTTAG
TATTTTCCTGAAATAAAATCAATAGTAACGAGATCCTTGAGAAAGTACGAAATAGGTTTTCTTGTGTGTT
AACTAAAAAAGATTTGTTATAAATATACGTTAAGAGTTTACATATTTTTTACATGTGAGATTTTCCTGAG
AAATCTGTCATAGAATTAATGACATATTCTAGCAACTAAGTTTGAAATCTGAATTTTTTGTGTTTAAGAT
CTATTTTATTTATCAAGTTGTAAGTATTCTAGACAAAAAAAAAAAAAAAAATCCTTCTGTGGATACCAGA
CCAAACAGAATTTTCTTCTGTTTGATATGGGCTGTCTTTCTACAATCTAATCAAAATATCTTGCTAAGCT
CCTATGTTTCTAGTATTATAAAATATTTTCCACCTTTTCTTTAAATCTGGACTTTCAGGTATAAAGATTT
GCTCAGGTACTTTTCATGAGAATTCTGTTAACATCATCGTTAGACAGACACTACATACTAAGTGCTATTC
CTAGTGAGTTGTGAAATTTGTATTCTTATTGCCTTAGTTGTAATGTCAAAATGTTTCAAAGAATGTATTT
TAAAGCAAAGTATTAACATCCAAAATGTTCAAGTGGTTGTACAGTGGTTGTACAAAAGCAAACAAAACCA
GTAAAAAATATTATATAACTGTATTATAAAATGCAAGAGAAGAATAAGCATTTTGACAATTAAATACATA
TAAATCATCTAATTCTGTTATCTTATGTCACATATTTAGAGCATCTTTATCTTAGCATTCAATAGACACG
ATGGTCACTTAACTCTTAAAAGAAGTTATAGCTGAAATCCTGGCAAATGGAATTTGACATTAAATGATAT
TTTCCTCTTGATAGTCATTCAGCTCCGTAAATAATAACAGTAGTACAGACATTATTATTACCTTCTCATC
TATGTCTTCTAAAGCTTTTCTGCATTCTTCCACCTGGGATTCAATCTCTGCAGGGACTATGGTGTACATT
TCGGAATACTTGATTCGCAGTTTTTCCATAATATTCTCAAAAGTTAGTTTCCCTTTCTTAAGGATGCTTT
GAAGCTCCTAAAAGCATTAAGAGAGTTGCAATACTCACGAGACTGGGGGAAAAGTTTAATTCTAAAAAGT
GAAAGCAGCCTTCCAGCACATCCTTATGATTTAAAGGAGTGCAGTTTGCATGACAAAACCCCACTAGTGA
TACAAGCTGATTAAGCCCCAGAGACACTCAGTTTAGTCAGATGATGCTTTCTAATTTGTAAGAATTAAAC
TTGATATCTCTTCATAGTGTCACACCATTATCTAGAAAAGACATTACAACACCCCCTGCTTCTAAAGTAC
CTTTAGGATTTAATTGTATCTCCATTGCAGTCCTGATCTAAAAAGCTGCAAGCAGCAAAAAAAAAAAAAA
AAAAGTTTCAAAGAAGTTTTTTGTTGTTGTTTTAACGTGTTGCTATTTCTACTTCTTCCTCCATTATCAT
CACAATGATTTAAGGCCACTAAAAGCCCCACACTTGGAGCAGAAGTGTCTACTTTCATGTAATTAGACAG
CCCTGCAGAGCTCAACTGCTTTCAAAAGGGAAGGTTCCAGTTCCATACAAAGAATGTAGGTTTTTAGGAG
ATAAAAGAAACCTGAACAAATAGTCTATTGGTTGTGGCCTAGAAACCAAATCTGATCTACCTTCTCCTGC
AGTAATTATAAAGGAGAAACTCATTTGTATGGGAAAGTTTCCCAAAGATCAAGTGGAAAAATACTTCTTG
ACTTGACTGTGGCTTTTTTGTTGTTTGTTTTGTTTTTACAGTAGCTGTTCAGTAGCATTATTTGTGTTCA
TGGATTGAGTCACTGTACTGAAGAATGATTACAATTTTAAATGACTCTGTAATGTGTCATTGTTTTCCTT
TTCTTAATCCTCAGCAGAGGACAAATCTAGAGAGAGAAAGTTAGAGAACAATGCCATTCAAAGATGGGGT
TTAATAAGTAAGTGTCATCCCGTTTTATCTACACCTAGTCCAGGAGTACAGGCTTTCATTCAGAGGTACA
CTTAGAAGGCTTCCCCATGAAGACTGCTTCTTTACTTTCCAATATAATAACCAAAAGTTCTGTTTAGACA
GCATGTGACTTTTTTTTTTTTTGAGATGGAGCCAGGCTGGATTGCAGCGGCACGATCTCGGCTTACTACA
ACCACCACCTACTGGGTCCAAGTGATTCTCCTGCCTCAGCATCCCAGTAGCTGGGATTATAGGCACACGC
TACCATGCCTGGCTAATTTTTGTATTTTTAGTAGAGACGGAGTTTCCCCATGTTGGCCAGGCTGGTCTTG
ACCTCCTGACCCCAAGTGATCTGCCTGCCTGGACCTCTCAAAGTGCTGGGATTATAGGTGTGAGCCACCA
TGTCCGGCCAACACGTGACTTTTGAATAAACTTCCAAACATACTTTTGGGCTGTCACTATTGGACTGGAA
TGAAAGAGGAGATTCTTCTGAAGAAATGAGATTCCAGATGACCTGTAGGGTGTACATAGACCCTGTCAGA

GACAAGGCGCCATGTCCTACTAAAGGAGTAATGTAACATACTACTTAAGAGTGGTCTGAGGCCCTTGTTC
ACCAAACACACTGGAAACATAGTTGAAAGAAGGCTGCTTGGTCCAGACTGGCCTACCTTCCAGCCTTGTT
TCAACTCTGTTCTCTGCTCTCCAGCCACACTGATCTTCTCCCTTGGTTCTGCCCATACCATGCCACAGGG
CCTTTGCCTATGCCTCTCTCTCTCTCCCCAGACCGCTCCCCCAAACCCAGCCACTGAGTTATCTCTACCC
CAAGGACTTTGGATACAAGACTGTGGGCCTGTACCTGCCACATTCACTAATTCATTCCTCACTTACCTCA
AATTGTTCTGACTTTTCTGGGTGATCCTGGAATGCCATATTTTGGAATGAAGTTGTGGTCTGTTGAAAGA
AATTCTTCAAAGCAATTATCTCTTTTGTGAAGGAATGTCTTTCTTGGATTTCAGTCTGCACCAATTCTTT
ATTTTTCTGAACTTTCTGAAGAAGCCTAAAAGAGAACGTCAAAATATAATTGTTTCTTTATCCTGCTCTT
CTATGAATAAAATGAAACAGTTTTATTGCAACAATTAATGAAATGCCTGAATAGCTACTAAAGGATGGTT
ATTTCCTCTAAGAAAAAAAGTAACAATTTTCAATAATGGATGTACCACATATAAAAACAGGTACAAAATC
TACCACTTAATCAAAAACCTCTCCAAATCTTTCGCCTCAAATACTCTCTTTTCACACTTTACATTGTAAC
TGACATTTCTGTCCTCTCTTTTTCTCCACGTAATCCTTGAGCTCACATGAAAATGACTTAGAGGTGTGAA
TGGAATCACAGGTGGGCTCTTGGGGACAGACAATCCCACTGGGCTTCTTCTCTTAAGCTGACCCATTTTG
CTATGGATGCAGCAAATATCAGAAGAGGCACTGAAGTGGGTAAAATCTTTCCTGAGGGTTATTTGGTAAG
TATCTATGATATTGTGATATAATAAATATATACTTGATCTCTGCTGTAGTTCCTGAGACAGAGCTCTTAA
TACCCTTGTAGATAGGAGTGCTAGCTAGGAGAGTCTTTTGTTCTAATACTTGATTTTTGACCAGTTCCTG
ACACAGAGCTCCTAAGCCCTTTGTAATTTCCTGAGTGATAGGAGCATCTTTAGTTCTAAGAAGGCAACTC
TAGGTGGGATCCTGAGTAGCCTCAGGATGAGGGCTGGTTGCCAGGGGAACCAACTATGTGATTAAAAGGT
TGGAACTTTCAGTACCACCCCTACCTCCAACACACACCCCCAACCTCTGGGGGAGGGGACAGAAGCTGAA
GGTTGAGTTGATCGCCAATGGCCAATTACATAATCAATCATGACTACATAATGAAGTCTCCATAAAAAAA
CCCAAAAGACAGGGCTCAGAGAGCTTCTGGATTGCTGAAAGCCTGGGGGTTCCACCACCTAGAGAGAGCA
GGGAAGCCCCAGGCCCCTTCCTATACCATGCCTTAGGCACCTCTTCCATCTGGCTGTTTATCTGTATCCT
TCATTATATCCTTTATTAATAAACTGGTAAACATGAGTAAAGTGTTTTCTTGAGTTCTGTGAGCCACTCT
AGCAAATTAATTGAACCCAAGAAAGGTATCAAAGGATCCCTTGATTTATAGCCTATCAGCCAGAAGTGTA
CCAGCGGGGCGCAGTGGCTCACGCCTGTAATCCCAGCACTGTGGGAGGCCGAGGCGGGCAGATGACCTGA
AGTCAGGCGTTCGAGACCACCCTGGGCAACATGGTGAAACCCCTCCTCTACTAAAAATACAAAGAATTAG
CCGGGTGTGGTGGCACATGCGTGTAATCCCAGCTACTCAGGAGGCTGAGGCAGGAGAATCGCTTGAACTC
AGGAAGCCGAGTTTGCAGTGAGCCGAGATCATGCTATTGTACTCCAGCCTAGGCGACAGAGCAAGACTCT
GTCTCAAAAAAAAAAAAAAGGAGAAGTATAGGTAGCAACCTACTACTGATGATTGGCATCTGAAGTAGAGG
TCCTCTTGTGGGATGGATTGAGCCCCCAGCCTGTGTGATCTGATGCTGTCTCCGGGTGGATAGTGTGAGA
AATGAATTGGTGTCTGCTGGAGAACTGCCTGATGTGTGGGGAACCCCCATAACCAACATGGTGTCAGAAG
TGCTTTGTTGCATGGTGTGTAAGGGTAGAGAGAAAAAACAAGTTTGCTTTTTCTTCAGAGCACCTCTAGC
CATAAAACTACTATATTCTTTGACCCAGTGATTCTACTTCTCACTATCTTTCTCAATGAATTAGTCACAG
ATGAAAATATAGATTCTGGCATAAGAATATTCACTGCAGTGTTGTTATGAAAATTAAAAAAAAGTAATTT
AAAGATTCCTTATTAGGGGCTTGGTTTAACACATTATGGCATATCTTCATGGTAGAATATTATACAGCTA
GTTACATTTTTTATTTTTATTTTTTGAGATGGACGTTTCAGGCTGGAGTGCAATGGCATGATCTCAACTC
ACTGCAACCTCTACCTCTTGGGTTCAAGTGATTCTCTTCCCTCAGCCTCCTGAGTAGCTGGGATTATAGG
CGTGCGCCACCATGCCCGGCTAATTTTTTGTATTTTTAGTAGAGACGGGGTTTTACCATGTTGACCAGGC
CAGTCTCGAACTCCTGACCTCAGGTGATCCATCCACCTTGGCCTCCCAAAGTGCTGGGATTACAGGCGTG
AGCCACCATGCCCGGCCACAGCTAGTTACATTTTAAAAGAACATTTAATGGCATAGGAAGACAAACATGA
TTTGCTGGTAAATTACTCAGCAGAATACAAAACAGTACAAGTATTTTGATCTCTATTTATTTAAAAACAA
AATCATAGTAAAAAAGGAGAAAAAATGATTGGCAGTGGTTATTGCTGAGTGGTGACATTAAGGTAGATTT
TTATATTAATTTTTGTAATTTTCACATTTTCTGAATTTCCTTTTTTTTGAGACAGAGTCTCACTCTGTCA
CCCAGGCTGGAGTGCAGTGGCACGATCTCGGCTCACTGCAAGCTCTGCCTTCTGGGTTCACGCCATTCTC
CTGCCTCAGCCTCCCGAGTAGCTGGGACTACAAGCTCCTGCCACCACACCCGGCTGATTTTTTGTATTTT
TAGTAGAGACGGGGTTTCACCACGTTAGCCAGGATGGTCTTGATCTCCTGACCTCGTGATCTGCCCGCCT
CAGCCTCCCAAAGTGCTGGGATTACAGGAGTGAGCCACCGCGCTCGGCCTGAATTTCCTATAATGAATAT
GCATTACTAAACTAGAAAAAGGGCAAAAACAAACAAACAAACAAAAAACCCACAAATGATAAAAAAGGAA
ATTGGAAGGACATTCACCCTCATTAATACCAGGATGGAAAATGTGTGCTTAATTATAGTTACTAATCTGT
TCCATCCCTTTTTATACCTATCAGTGTTGTCTCACCTCAATTCTATTGTATCATTTGCCATTATTCTATA
CTTTTAGATTTTCTAAATTTTGAGCCATAATTGTCAAGCACATGTCCTTAATAGTTTTTCATAAATCTTA
CTTGTTGCATCGTTCTTTCATAGAAGTAATTTCTTGAAATGCTGGAACAGTTTCCACAGCCCCTGAGCTT
TCAGGAACATTCTGGATACTTCTGATGCGCTGAAGAAGTAGAGTCAGTAACAGCTGTTGCTTCTCCACGT
TCTCTCCATATTGGCATAAACAGTCTAGCAGCTCAGAGAGTTCCTCTGTGGTGGCTGCCTCTTTTGTTTT
GGAAATTTCAGGGAGTTCTTCCTGAAGATTATCTAAAATAATTGCCTCTCGTTCAATCTAATTCAAAAAA
CAAAAAGAACTAAAATAAGTAAAATATACAATTACATTTCAGGACCTGAAGTAGCCATAATTTTTGTATG
CTCTCTCTTCAAAGGGTTCCTAGTGCCATATCCTAGTCTGTTTTCCTATAGCTGGGAATATTAATCCTCT
GCTATCAGAATCCCATAATGCCCAGCTATTGCTCATGTAGATGTGTGACTGAAATGGAGTACTGCTGTGG
TGGGCTGAAGGAAATGCTGTTGAATATCTTCATAAATAATGTATTTCTCCTTCAGATTTCAGATGGATAA
AGCAACATTTCTCCTGAGATAAGCACATGAGCTCCACCAAACTGCTTTCACTAAGTGTAAGAGGTTGGGC
AACTATTGGATATGGAAAATTTTTCTGCTGGTCTCTTTTCTTTCACTTCCAATCCCTGTATGCTAAAAAA
GTAAGGCCAGCAGGTTCTCATTACCCTGACACACAACAAAGGTAAAGCAGCCAGAATTACCAAACCAGTG
AAGTATTTATCAATAGTGGTGTACACAGAACTCAGAAATACATAACCTATTACATCACATATCTAGAAAC
TGGGAGTTCCACCAGCCCTGAACTCAACTAAGATGTAGAAAAAAGTCTCAAAGGCCCCTGAATCAGGTCA
TTCTTACGCCTCCCCTCGAATCCCCTGGCCCACCCCTCGGCTGCAGTACTCATTTATCAAATCCTGCCTC
AGTGATGGTTAACTCTCCTGCTCCACGTTCAAACTCATTCATGGATCTTGCAGTCATGACATTACAGGAT
ATCACTCCAGTCATCTATGTTTATGATATCATGCTAACTGAAATGGTGAGGACCTGAATGTCCAGTCAGA
CATGCCAGAGGCTGAGAAACAAAGCCTGTGAAAATTCAGGAGCCCCAGTATCAGGGGTCTAGTGGCCTGG
GGCATGCCAGGACTTCTCCTCTAAGATAAAGGTCAAGTTGTTCAATCTTACAACTCTACCACTAAAAAAG
AGACACAGCACTGAACGGACCTTTTGGGGTCTAGGAGGCAGTATATGCTATCCTTGGGATTACTGCTCAG
ATGCATTTATCAGAATGCTGCCAATGTCGAGAGGGGCCTGGGGAAAAAGCACCGCAGCAGGGTTGGGCTG

TGGTATAAGCTGCCCTGCTGTTTGGGCTGTATGACCCAGTTGGGTACCCAATAACTAGAATACACGGATG
CAGATGTAGACTGGCCACTGTCCAAGAGACCTAGGTGTGCGCAATGGGTGCTTCTCATCACCTCAAACCT
AAATTCAGTTGAATTAGAAGTCCTAGTTCTTTGCCAGACAGCTACACTTACACCAGGAAATGAGATAAGG
GTTCCATTGTATCATTTTCTGTCCCCCTGCTGGAAACTAGCATGCAAATAAAGAAATTGTTACATAGATG
GGGGAATTGTACATCTAGGGTTTCCAATGTGCATCAGGGTTGAAAAAACTGTGTCTGTAATCCAGGATTT
AATGGGGCACCTCTTGGTGCTTACACACCAGAAACTGGCAGATTTGACTTGATAATAACCAGAAATGGGC
AGCTGTAGCAAGCACAATCCAGTAAGAGTAAAAAGAATAAAGGCTCAGACCTTTCCTGTTTCGGCTCCCC
TCATCTCCCACTCCTGTTCCCTGGGATCACTTTCCAAAATAAACTACCATTTGCAAGCCTCAGTCCCAAG
CTCTGGTGTCCACTGTGAAGTTGGTAAGTGATTGAGAAGGGGGAATACAAGAGGGAGAACAATCTCTTTT
TTTTTTTTTTTTTTTTTGAGACGGAGTCTCTCTCTGTCACCCAGGCTGGAGTGCAGTGGCATGATCTCGG
CTCACTGTAACCTCCCACGCCCTAGGTTCAAGCAATCCTCTGCCTCAGCCTCCGGAGCAGCGGGGATTAC
AGGCACCTGCCACCATGCCTGGCTATTTTTTTTGTATTTTTAGTAGAGACAGGGTTTCACCATCTTGGCC
AGGCTGATCTTGAACTCCTGACCTCGTGATCCACCTGTCTAGGCCACCCAAAGTGCTGGGATTACAGGCG
TGAGCCACTGCTCCTGGCCACAATTTTTATTAGGACAATAATTTTACCCCAAAGCCAGGCAATTCTTCAA
CTTGGGAATGAATAAACAAACTGAATTCACCCACCCAAAGCAATACTACTCAGGAATAAAGAGAAATGAA
CTACTAATACAAGCAGCAGCCAGAATTTCAAGTGCATTATGCTTAGTGAAAAAAAGTAAACTCAAAAGGC
CACAAACTGTAAGGAGTCCATGGATATGACATTCTGGAAATGGAAATACTATGAGAACAGAAACAGATTA
ATGGTTCCAGGGGCTGGAGGTTATGGAAGGCACTGACCACAAAGAGGAACGAGGGAAACTTCTAGGGTGA
CAGAATTGTCTTAAACCTTGATTTTGCTGGTGATCATGTGACCGTGTGCACTTGTCAGAACAACATATTT
TACACTAAAAAGTGTGAAGACAGCCCTAGCATCAGTAAAATAGTTGTCAAAAAGCCTGTGCATTCACTTT
TCCACCTAGAATAGGCTTTGCAATACCTTGATGATTTTCCTTAGACATGGGATCCTAATCAAATTGGTTA
TAAAACTTTCAGGTTCACGGTCAATTGTAAAGTCCGGTCTAGAGAGGGAGAAGGACCCATAGTTGCATCA
TAAGCAAATCCAATGAAGGAGACCAAAAAACCCAGAACCAGCAGAAAGAGACCCAACAAAGAAATGACT
GTTGGTGCAAGTGGAAGAAGCCGGCCTCACATCTCCAATTATCTTTGACAATGTGACGTTCTTCTAGCAC
ATTATGATCATTGAAGCATAAAATGATGATTCTGAATAACACAAGTGAATAGTTATAGTAAAGAGATTCT
GTTTAAGAAAACAGGGAGGTAAAATTTTAGGGGGACACAAGTTCTATCAAAATTTAAATTTAGTTTTTAA
TTTGTAAACTTACAAACAGGCATTTAATTTTTAAAAAAGTCTGCTAATATAAACTTTATTTCATAAACAC
TGGATTATTATGTTACTATAGATGACAGGTTTAAAGCAGAAATTCACTTTGTCATATATAAAAGCACCAA
TCATGCTAACAGAAGCTTACATGTATGGGCTGTTAGATGATATACTTTTTATTGAATGGATAAAAGCTAC
ACTAAAATCTTATATCAATTTGATGTATGTAAATATCATGTAAGTTGACAGATTAATGACTAAGCACCAG
CGTCTAAGTTTGAATCCTCTTCTACCCCTTGTGAATTTGAGCAAGTTACTCAGTCTCACTGTGTCTCACT
TTCCTCATCTACAAAGTAAGGATAATAAAAATATCCTCACAGAATTCTTGAATAGTGCTCTGAACTATCC
TGTCACACAATAATTGCTCAATTTAGTAGTTGTTTTTATTATTGTTATTACAGGGAAGCATTTTTTTTTT
GCTTGTGCTACTCTTTGAAAAATATTTTGTTAGCAGATTTTGTCAAATGCTTATGTGAATAATTAGAAAG
TTCTATATGAATGGAGTCTGAATTAATAACACATAATTGTAAATGGGTATATAGCAATAATGTGATAAAA
TAAAAGGAGCAAAATCTTAGAATTAGCCCAGACCTGAATTTGAATAAGAGATGTCCCTCAACAAATATTT
ACTAAGTGCCCACTAAGCGCAGGGCCCTAGCCAGGTTCCAAGGTTACAGCAGTGAGCAGGACAGCCCCAG
CCCCAGCCTACAGGGGTTTACAGCTTAATCAATCTCTACCTGGGGACCTTGTGCCACTACTCAATCTATC
AGTGCTTCAGTTTCCCCATCGATAAAATGGTGATAAAATTTACTTCCCAGGGACAATGCAAAGATTCAGT
GAGAACAGGTGTGAACTGCCTTCTCAGCACAGCATAGTAACTCAATAAATGGTACCACTATGGACAGGCA
AGCACTGGTGCCAGCAGCCCCAACCAAAAGTGTAATTTACAAAGTTTATTTTAACATTTCAAGAGACTAT
TCACTAGTCAGGCCTCACCAGGACCACTGACATAAAATTCATTTTTAAGGATAATAGTTATAAGCAAGAT
AATACAATAGTGCTAAGCATTTCATCCTAAGATAATTTTACGTTGTGTTTTTGTTTGTTTGTTTTTGAGA
CAGTGTCTCACTCTGTTGCCCAGGCTGGAATGCTAGAATACAGTGGCATGATCATGGCTCACTGCAGTCT
TGACCTCTCATCAAGAGATCCTCCCACCTCAGCCTCCCAAGAAGCTGGGACTACAGGCATGTGCCACCAT
GCCCAGATTTTTTTTATTTTTTGTAGAGATGGGGTTCACTCCATTGCCTGGGCTGTTCTAGAACTCCTG
GGCTCAAGCGATTCTCCTGTCTCAGCCTCCCAAAGTGCTGGGATTACATAGGTGAACCACTGCACCCGGC
TATCTTTAACTTTCTAAATTAATTTTCTTTCTAAATATAGTTCATACCTAAATCCTGAACCAAGGTTAAA
TTAACATTTGTGATTGATATATATCATGCAGGTTTTGAGACTATTTTCAAAAAGAACATCATAACCTCAT
ATATTTTTAGGTCCACATTTAACAATTACAGTTAATTTCCATAGTTGAAAATTATAGATAATTTCAAAAT
TATTTGGTGATTACACATATTACCTAATTCTAAACCTTTAGTATAATGTAGAGACAGTTATTTCTGAGAG
GGGTTATTTTCACAATAAAGATTGTAAAACTCAAACCAGCTAGTAGTCACTTATTAATAAGAATTATCTG
CTATCAATAAAGGCACTACTATAAAATAATCTGAATAAGTTCTTGCAGGTTATCTTAATAAGGCCTGACA
TCTATAAACATTTATGTATCATGTATAAGTGATGTGCACAAATGGTATAGGCTAAGGACTCGTTTTATAG
AAAAACAAGGTGAAAGTAATAAAACAATTTAAATAACATGTTAGAAACTACATGGTTTGTTGAAAATGAA
GCACTCACTTCTTCACTGACAAATTTCCATTCCTGCTTCAGTTCTTCGCACCACATCTCCCACTCTTTAG
CAGCTTCCAGCAAACTCAGCCATTTCTCCCACAGAGCCGACACAATCTTGAGCAAACATATGCCATCATT
TTCTGTGCACCTGAGTCTCAAGAGTCTAAGGATCTGTCGTAGTTTCATTAACTCTTCTTTGGTTGATATA
AGATTTGACACCAAGGCCTTAAGAAAGAAAAGAAAAAAAATAAGAGGGACATACTATTACGGTTTTCCTG
AAACTTACTAACTCTTTTAAATCCTGAACAATTAATTATTTCAATCTTCCATAAGTATTGCATGATCCAC
CTCTTATCCTTTTAGAAGTCAATTTAGACCAGATGAGAATTATCTATGTATTATTGTATTCTGCATGAAT
TTGGGATTACAGGGACAAATAATGACCCATAAACCATTTTTTTCCAAGAAAGAACATACTTTCAAAAGCA
AATATTTGCCAGACGCAGTGGCTCATGCCTGTGATCCCAGCACTTTGGGAGGCCAAGGTGGGTGGATCAT
GAGATCAGGAGATCGAGACCATCCTGGCCAACATGTTGAAACCCTATCTCTATTAAAAACACAAAATTTA
GCTGGGCATGGTGGCATGCGCCTGTAGTCCCAGCTACTCAGGAGGCTGAAGCAGGAGAATTGACTGAACC
TGGGAGGCACAGGTTGCAGGGTTGCAGTGAGCTGAAATTGTGCCACTCACTGCACTCCAGCCTGGGCAAC
AGAGTGAGACTCCGTATAAAAAAAAAAAAAAAAAGTCTATAAGTGGCTGGGCACAGTGGCTCATGCAGCA
CTTTGGGAGACTGAGGCAGGAGGATTGCTTGAGGCTAGGAATTCAAGACATAGCAAGGCAACATAGCAAG
ACCCTGTCTCTACAAAAAATTAAAAAATTAACCAGGCATGGTGGTGTATGCCTGTAGCCCCAGCTACTCA
GCGGGCTGGGATGGGAGGATCCCTTGAGGCCAGGAGCTCAAGGCTGTGATAAGCCATGATTGCACCATTG
TACTCCAGCCTGGGTGACAGAACAAGACCCTGTCTTATTTAAAAAAAAAAAAAAAAAAAAAAAAAATCTAA

AAGTACAACAGCCCTCATTATCTGGGTTTCTCCTTTCAAGGTTTCAGTTACTTGTGATTAACAACGGTCC
AAAAATACTAAAAAATTCCAGAAGGAAAAAATGTGTAAGATTTATTTGTATAAAATGTATGTTTTATTTG
TATATAAATATATAAGTGCTATTCTGACTAGTGTGATGAAATCTCAAGCCATCTCTCTCCATCCCACCTG
GGATACGAATCTTCCCTTTGTCCAGCACATCATGCTGTATATGTTCCCCACCTACGCGTCATTTGGTAGC
CTTCTTGGTGATCAGATCAACTGTTGTGGTATCAAATGCTTGTGCTCCAGATGAATAGTAGCCCAACGCT
ACCTCACCATGGCTATATCATTTCATTTCATCACTTCATTTCATTACCTCACTTCATTTCATCACCTCAC
TTCATTTCATCACCCAGGCATTGTATAGTCTCATGTCATTACAAGAAGGGTGAAAACAGTACAATGACAT
ATTTTGAGAGAAAGAGACCACATTCACCCAACTTTTATTACAGCATATTGTTATAATTTCTCTGTTATTG
TTGTTGACCTCTGACTGCACTTTAATTTATAAATTAAACTTTATCATAGGCGTGTACAGGAAAAAAATTA
TATACATAGAGTTCAGTGTTATTCACAGTCTCAAGCATCCACTGGGTGTCTTGGAACATATCCCCTGTGG
ATAAAGGGGGACTACTGTACATTTTGTTATTTTTAAGTCTCACATTTTACTAAGTAGTTCCTTTGCACAA
TACTTCCTATATCAACCACCAACACAATATTGAAAGGTTTTTCTTGGTTCGCTTTTGTTTTTGGGGAATG
TTAACTACAGATGATTTAGAAAGTCCTCATCCAAATCCTAATAACATAATACCACAGATTCTAACAGATA
AAAATAAGTAAAAGCTCAAATTGCTTTGTAACAGTCTAAGAAGTAACCAGAATTCAGAGCTTATGACAGT
TGCAGTAAGCGATCAGTGGACAACAAGGCTCTGTCACTGATCCAGCAGTATCCCTCAAAGTCACATGAGA
GGTGATGCTTTAGAAAAGCCATCAGTGAGGACAGGATGCTATTGGGGGATGACTGTCTGTGAACCTGATT
AATTAAATCTCTCAGTACCACTGCTTCATTTCCTTCCTTCTGGCTTTTTAAGCTTCAATATATTACATAA
GGCCAGGCGCAGTGGCTCGCGCCTATAATCCCAGCACTTTGAAAGGCCGAGGCTGGAGGATGGCTTGAAG
TCAGGAGTTCAAGAGCAGCCTGGTCAACATTGTGAAACCCCGTCTCTACTAAAAATACAAAAATCAGCTG
GGCATGGTGGCGGGCACTGTAATCCCAGCTACTCAGGAGGCCGAGGCAGGAGAATCAAATCACTTGAAGC
CGGGAGGTAGAAGCTGCAGTGAGCCAAGACTGCATGACTGCACTCCAGCCTGGGCAAGACTGTGTCTCAA
ATATATATAAAACATTACTCTCTGGCTTTCGATTTGAGGAATATTCATGGATATTTAACTCACTGTGAAG
ATTTCTACGCGTCTTAACAGGACCACATTCTCTGCTGCCTCTGCCAGTTTGTTCTGCAATTTTTTGCACA
CAGACTTACTGGCTAATTGCCAATACTATTACCTTGCTCTGTTCCAAGCGCTCTAAAGCTTCTCTGTAAG
ACAGTGGCAACGAGGACATGGACTGTCCAAGAACTGTCTCCATTTTGCTGAGGTTAGTGTAAATATCCTC
TTCCATTTTTCTATAGCATTTGTAATTCTCAAGATACCTAGTGAGTCACAGTTAGAAAAAAAGTGGTATT
AAATTTTATTTAACACAATAAATTCAAAATTTCCCAGAATAAATATTCCACACTTAATTTTTAAGAAAAG
ATATGACAACTTTCGTTTTTGCTAGGCAATGCATTTTAAAATGTTTTCCAAGAAGTTTTTATTCCCAAAG
GGACCTGCATATGGGTTTAAATGCAAACTTGAAAAGGAAGCAAGGGCCGTCCTCTAAAATGAAGATTTTT
TTTTTTTAAAGTTCACTTCAGTAAAATGAAAACTGCATTCTCAAACACACTGATGAGCTGTAAATTGGTA
CAATTCTTGTGGAAAACCACTTAGTCTTAAAACTATTCCCATCTTTGACCCATTAATGCAGCTTCTGCAA
TTTACCTTAAGAACTGTATCCTAAACATATAGAGCTTATCCTAAATCTTTTGCACAGTAAAACATCTTTA
CTCACTAGACTATTAATTAAAACATCACACATTGGAATACCCTTATCTAACAAAGGTATGATTAAGAAAT
TAAAACAATTCATCGTATACAATATTATAGAGTAATTACATTACTTTTAGAAAGTATTTGTTACAATCAA
GAAAAGAACTGTTATAAAATTTTAAAATAAAGCTGGATATTTGATATTTTATATATAGCATATATATTTT
AAAACACTAAAATTATGCATACAAAAACAGACACAGCCTAAATCCCCCATTGAATGTAACTAAAAACTCT
ATATCAAATTATTCTTAAAAAACAACTCTTAAAACGCATGAATAAATTGACAAGGAATTAGGGAGTCAAA
CTGTAAAATGGAAATATACAGAAATAGGCAAAGTTGTAGGACCAGTTTTTTGCCTTGAGGGCACTTGAGT
TTCAATTTTCTTTGATTCCTACTGAAAGGTGGGGGACAGACCATAAAGCTGGGAGCCAATCCCAGGATGG
GTGTCTAATAGAAAACTCCCTCTGCAAGAATATTTGTAACACATATAACTATAAAGGACCACTCTCTAAA
ATATAGAATTC

| Exon | Reference Position | SNP | AA change | Frequency in Liverpool – Blood | Frequency in Liverpool - Tumor | number of individuals with change in heterozygosity [1] | number of individuals with a loss of heterozygosity [2] | In which populations observed populations [3] |
|---|---|---|---|---|---|---|---|---|
| Exon –7 | 49671 | A to G<br>ATTCCTATATTCT | None | 0/92<br>0% | 0/96<br>0% | 0 | 0 | 3 (C, S) |
| Intron –7 | 49904 | C to A<br>GTCCCACATATGG | None | 0/92<br>0% | 0/96<br>0% | 0 | 0 | 3 (C, S) |
| Intron –7 * | 49934 | A to G<br>ATGTACATACCAT | None | 0/92<br>0% | 0/94<br>0% | 0 | 0 | 3 (C) |
| Intron –7 | 49994 | A to T<br>CCCTTGAGTTACT | None | 90/92<br>98% | 94/96<br>98% | 0 | 0 | 2 |
| Exon –5 | 83980 | G to A<br>CTGGAGGTTGAAG | None | 0/42<br>0% | 0/52<br>0% | 0 | 0 | 3 (S) |
| Intron –5 | 85938 | G to A<br>CTCTCCGTAGAAA | None | 26/88<br>30% | 27/94<br>29% | 4 | 1 | 2, 3 (N, C, I, A) |
| Exon –2 | 89837 | C to T<br>TTCCTACGGAAAA | None | 16/96<br>17% | 13/88<br>15% | 7 | 1 | 2, 3 (C, I, A, S) |
| Exon –2 * | 89889 | T to C<br>CATTTGTTGAACG | None | 1/94<br>1% | 0/92<br>0% | 1 | 0 | 2 |
| Intron –2 * | 90090 | T to C<br>CTTTGCTAGACAG | None | 1/94<br>1% | 0/94<br>0% | 1 | 0 | 2 |
| Intron 3 | 126711 | A to G<br>AAGTCAAGCTGCT | None | 0/96<br>0% | 2/96<br>2% | 2 | 0 | 2 |
| Exon 5 | 130189 | G to A<br>CCAAGTGCGGCTC | Val to Glu | 2/96<br>2% | 1/96<br>1% | 1 | 0 | 1,2,3 (C), 4(As), public variation |
| Intron 7 | 154138 | G to A<br>AGAGCCGGGGAA<br>G | None | 3/93<br>3% | 3/96<br>3% | 2 | 0 | 2 |
| Intron 7 | 154202 | A to G<br>GTCCCCATAGTAA | None | 3/96<br>3% | 2/96<br>2% | 1 | 0 | 2, 3 (C, A, S), 4 (As) |
| Exon 8 | 154431 | G to A<br>GTCACAGGCTGAA | 3' UTR | 32/96<br>33% | 35/96<br>36% | 2 | 2 | 1, 2, 3 (N,I,A), 4 (all) |
| Exon 9 | 160052 | A to G<br>ACTTCAATTTCCC | 3' UTR | 38/96<br>40% | 35/96<br>36% | 4 | 1 | 1, 2, 3 (N, I, A, S), 4 (all) |
| Exon 9 | 160089 | A to G<br>AAAAATAATTTTA | 3' UTR | 14/96<br>15% | 16/96<br>17% | 4 | 3 | 1, 2, 3 (N,I,A,S) |
| Exon 9 | 160165 | A to G<br>CAATCCAACAATT | 3' UTR | 9/96<br>9% | 8/96<br>8% | 1 | 0 | 1, 2, 3 (A), 4 (all) |

| Exon | Reference Position | SNP | AA change | Frequency in Liverpool – Blood | Frequency in Liverpool - Tumor | number of individuals with change in heterozygosity [1] | number of individuals with a loss of heterozygosity [2] | In which populations observed populations [3] |
|---|---|---|---|---|---|---|---|---|
| Exon 9 | 160376 | C to G<br>GCTGTGCCTGCCA | 3' UTR | 10/96<br>10% | 9/96<br>9% | 1 | 0 | 1, 2, 3 (N,C,A) |
| Exon 9 | 160602 | G to C<br>AGATCAGTTGAGG | 3' UTR | 1/96<br>1% | 1/96<br>1% | 0 | 0 | 2 |
| Exon 10 * | 303073 | T to C<br>CTATAGTAATAGG | 3' UTR | 0/74<br>0% | 0/94<br>0% | 0 | 0 | 3(A) |
| Exon 10 | 302972 | G to T<br>CTGGATGAATCTC | 3' UTR | 6/76<br>8% | 6/92<br>7% | 1 | 0 | 2,3(N,I,A,S) |
| Exon 10 | 302848 | A to G<br>AACTGGAAGCAAC | 3' UTR | 5/72<br>7% | 7/78<br>9% | 1 | 0 | 2, 3(N) |
| Exon 10 | 302689 | T to C<br>CTTGACTGCATTC | 3' UTR | 9/86<br>10% | 11/94<br>12% | 3 | 0 | 2,3(all) |
| Exon 10 | 302671 | C to T<br>TGCAGCCTTTGTC | 3' UTR | 0/86<br>0% | 0/94<br>0% | 0 | 0 | 3(A) |
| Exon 10 | 302556 | A to G<br>GCCCACATGTCTG | Met to Val | 14/84<br>17% | 14/94<br>15% | 3 | 0 | 2,3(all) |

* SNP's observed in 48 breast cancer patients. Genomic DNA was isolated from blood (B; 96 chromosomes) and matched tumor tissue (T; 96 chromosomes).

1. For some heterozygosity calculations, individuals 47 and 48 were excluded because it is believed that the blood or the tumor sample was switched. These excluded cases were when both individuals showed a change in heterozygosity.

2. Loss of heterozygosity calculation includes any case where a heterozygous blood genotype became a homozygous genotype of the minor allele in the same individual's tumor sample. A change from a homozygous genotype of the major allele in the blood sample into a homozygous genotype of the minor allele in the tumor sample would also be counted 3. Populations analyzed:
   1- cDNA (prostate, Clontech)
   2- 2-Liverpool clinical
   3- 3- Coriell (N, North Europ.; C, Chinese; I, Indo-Pak; A, Afric-Amer; S, SW Native Amer)
   4- 4-CEPH family (Ca, Caucasian, Af, Afric-Amer, As, Asian)

| Exon | Contig64 Position | SNP | Coriell Frequency/20 chromosomes | | | | | Frequency in Liverpool | |
|---|---|---|---|---|---|---|---|---|---|
| | | | N. Eur | Chi | In-Pk | Af-Am | SW-NA | Blood | Tumor |
| Intron 3 | 126711 | AAG | 0 | 0 | 0 | 0 | 0 | 0 | 2.1% |
| 5 | 130189 | TAC | 0 | 16.6% | 0 | 0 | 0 | 2.3% | 1.1% |
| Intron 7 | 154202 | CGT | 0 | 27.4% | 0 | 7.2% | 12.3% | 3.5% | 2.2% |
| 8 | 154431 | AAG | 26.4% | 0 | 28.2% | 47.6% | 0 | 31.9% | 36.5% |
| 9 | 160052 | AGT | 27.6% | 0 | 45.4% | 23.25% | 35.6% | 39.6% | 36.5% |
| 9 | 160089 | TGA | 13.2% | 0 | 14% | 14.4% | 28.4% | 14.6% | 16.7% |
| 9 | 160165 | CGA | 0 | 0 | 0 | 10.4% | 0 | 9.4% | 8.3% |
| 9 | 160376 | GGC | 10% | 16.7% | 0 | 27.8 | 0 | 10.4% | 9.4% |

FIGURE 2(b)

| Exon | Reference Number | SNP | Coriell Frequency | | | | | Frequency in Liverpool | |
|---|---|---|---|---|---|---|---|---|---|
| | | | N. Eur | Chi | In-Pak | Af. Amer | SW NA | Blood | Tumor |
| Exon -7 | 49671 | TAT | 0/18<br>0% | 1/20<br>5% | 0/20<br>0% | 0/20<br>0% | 3/20<br>15% | 0/92<br>0% | 0/96<br>0% |
| Intron -6 | 49904 | ACA | 0/18<br>0% | 1/20<br>5% | 0/20<br>0% | 0/20<br>0% | 3/20<br>15% | 0/92<br>0% | 0/96<br>0% |
| Intron -6 | 49934 | CAT | 0/18<br>0% | 1/20<br>5% | 0/20<br>0% | 0/20<br>0% | 0/20<br>0% | 0/92<br>0% | 0/94<br>0% |
| Intron -6 | 49994 | GAG | 18/18<br>100% | 20/20<br>100% | 20/20<br>100% | 20/20<br>100% | 20/20<br>100% | 90/92<br>98% | 94/96<br>98% |
| Exon -5 | 83980 | GGT | 0/20<br>0% | 0/20<br>0% | 0/20<br>0% | 0/20<br>0% | 5/20<br>25% | 0/42<br>0% | 0/52<br>0% |
| Intron -4 | 85938 | CGT | 6/20<br>30% | 3/20<br>15% | 5/20<br>25% | 9/20<br>45% | 0/20<br>0% | 26/88<br>30% | 27/94<br>29% |
| Exon -2 | 89837 | ACG | 0/20<br>0% | 1/20<br>5% | 1/20<br>5% | 2/20<br>10% | 3/20<br>15% | 16/96<br>17% | 13/88<br>15% |
| Exon -2 | 89889 | GTT | 0/20<br>0% | 0/20<br>0% | 0/20<br>0% | 0/20<br>0% | 0/20<br>0% | 1/94<br>1% | 0/92<br>0% |
| Intron -1 | 90090 | CTA | 0/20<br>0% | 0/20<br>0% | 0/20<br>0% | 0/20<br>0% | 0/20<br>0% | 1/94<br>1% | 0/94<br>0% |
| Exon 9 | 160165 | CAA | 0/18<br>0% | 0/11<br>0% | 0/18<br>0% | 1/14<br>7% | 0/12<br>0% | 9/96<br>9% | 8/96<br>8% |
| Exon 9 | 160376 | GCC | 2/18<br>11% | 2/12<br>17% | 0/18<br>0% | 5/18<br>28% | 0/16<br>0% | 10/96<br>10% | 9/96<br>9% |
| Exon 9 | 160602 | AGT | 0/18<br>0% | 0/20<br>0% | 0/20<br>0% | 0/20<br>0% | 0/14<br>0% | 1/96<br>1% | 1/96<br>1% |
| Exon 10 | 303073 | GTA | 0/18<br>0% | 0/18<br>0% | 0/20<br>0% | 1/20<br>5% | 0/18<br>0% | 0/74<br>0% | 0/94<br>0% |
| Exon 10 | 302972 | TGA | 1/18<br>6% | 0/18<br>0% | 2/20<br>10% | 1/20<br>5% | 3/20<br>15% | 6/76<br>8% | 6/92<br>7% |
| Exon 10 | 302848 | GAA | 2/18<br>11% | 0/20<br>0% | 0/20<br>0% | 0/20<br>0% | 0/20<br>0% | 5/72<br>7% | 7/78<br>9% |
| Exon 10 | 302689 | CTG | 3/18<br>17% | 3/20<br>15% | 3/20<br>15% | 9/20<br>45% | 3/20<br>15% | 9/86<br>10% | 11/94<br>12% |
| Exon 10 | 302671 | CCT | 0/18<br>0% | 0/20<br>0% | 0/20<br>0% | 3/20<br>15% | 0/20<br>0% | 0/86<br>0% | 0/94<br>0% |
| Exon 10 | 302556 | CAT | 3/18<br>17% | 5/20<br>25% | 4/20<br>20% | 8/20<br>40% | 3/20<br>15% | 14/84<br>17% | 14/94<br>15% |

FIGURE 2(c)

| Contig64 position | Exon | SNP | Caucasian | Af-Am | Asian |
|---|---|---|---|---|---|
| 130189 | 5 | G to A<br>CCAAGTGCGGCTC | 0 | 0 | 37.5% |
| 152603 (only seen in CEPH) | Intron 7 | T to C<br>ATGGGATTATGTG | 0 | 37.5% | 0 |
| 154202 | Intron 7 | A to G<br>GTCCCCATAGTAA | 0 | 0 | 37.5% |
| 154431 | 8 | G to A<br>GTCACAGGCTGAA | 12.5% | 12.5% | 12.5% |
| 160052 | 9 | A to G<br>ACTTCAATTTCCC | 37.5% | 12.5% | 37.5% |
| 160165 | 9 | A to G<br>CAATCCAACAATT | 25.0% | 25.0% | 12.5% |

FIGURE 2(d)

| | | | |
|---|---|---|---|
| Exon –7 Forward | ER2-1F | M13f TGTAAAACGACGGCCAGT | CACGCGGGCTTCATAAGCTAGAT |
| Exon –7 Reverse | ER2-2R | M13r CAGGAAACAGCTATGACC | GGTTGCACCACTCTGTAAATATGCTAAA |
| Exon –5 Forward | ER2-3F | M13f TGTAAAACGACGGCCAGT | GGCACATAGTAAGCAAATCATAAATGCTGA |
| Exon –5 Reverse | ER2-3R | M13r CAGGAAACAGCTATGACC | AACCCAGGGCACTGATAGAAGTGAA |
| Exon –4 Forward | ER2-4F | M13f TGTAAAACGACGGCCAGT | GTCGAAGGGCACACAACTAGGAAG |
| Exon –4 Reverse | ER2-4R | M13r CAGGAAACAGCTATGACC | GACAAATTAATGGTGGCAATCAGGA |
| Exon –2 Forward | ER2-6F | M13f TGTAAAACGACGGCCAGT | CTTCCTCATCTTCTCACCCCACC |
| Exon –2 Reverse | ER2-6R | M13r CAGGAAACAGCTATGACC | TTCCTCCTTTCCCTCCACTTTTCC |
| Exon4 Forward | ESR2ix4f35755 | M13f TGTAAAACGACGGCCAGT | CTGGAAATGGAGACCTAAAAAGTTTCTGAA |
| Exon4 Reverse | ESR2ix4r36210 | M13r CAGGAAACAGCTATGACC | GATCATGTGTACCAACTCCTTGTCG |
| Exon5 Forward | ESR2ix5f39066 | M13f TGTAAAACGACGGCCAGT | GGTCGTAGTGCTTGACAAACTCTAAATGAA |
| Exon5 Reverse | ESR2ix5r39580 | M13r CAGGAAACAGCTATGACC | ATGATGCTATCATCCTCTGCCCTG |
| Exon8 Forward | ESR2ix8f63153 | M13f TGTAAAACGACGGCCAGT | GTGGGACACAGAGGCTGACAAGAC |
| Exon8 Reverse | ESR2ix8r63651 | M13r CAGGAAACAGCTATGACC | GGGACCACACAGCAGAAAGATGAA |
| Exon 9 Forward | 2ix9f69194 | | TAACATTTTCACTTCAGTTTCCCTCTGG |
| Exon Reverse | 2ix9r69643 | | GTCCAGTAGCATTTTACTTTCTACCTAAACAAAG |
| Exon 9 Forward | 2ix9f69494 | | GAGAAGGGGAGGAGGGGACTGGGATTG |
| Exon 9 Reverse | 2ix9r70066 | | TGTAGGGAATGGCAAAGGCAGCATGGC |
| Exon 10 Forward | ER2_10f_146946 | | GACAGCTCTCTCTCACTCTCTTGGAGAT |
| Exon 10 Reverse | ER2_10r_147971 | | CTTCTGCCTCAGCTTCCCCAGTA |

FIGURE 2(e)

| | | |
|---|---|---|
| Exon 10 | ER2_10sf1 | AGCTCTCTCTCACTCTCTTG |
| Exon 10 | ER2_10sf2 | CAAACTACTCATTTCCAAAC |
| Exon 10 | ER2_10sf3 | TACACAACTGCACTTTTATC |
| Exon 10 | ER2_10r_147971 | GACAGCTCTCTCTCACTCTCTTGGAGAT |
| Exon 10 | ER2_10sr1 | GTAGCAGTTAGGTAAGTTTTGA |

FIGURE 2(f)

cDNA Sequence for the Estrogen Receptor Beta (GenBank ACCESSION AF051427.1 GI:2970563) (SEQ ID NO:2)

```
tttcagtttc tccagctgct ggctttttgg acacccactc cccgccagg aggcagttgc 61
aagcgcggag gctgcgagaa ataactgcct cttgaaactt gcagggcgaa gagcaggcgg 121
cgagcgctgg gccggggagg gaccacccga gctgcgacgg gctctggggc tgcggggcag 181
ggctggcgcc cggagcctga gctgcaggag gtgcgctcgc tttcctcaac aggtggcggc 241
ggggcgcgcg ccgggagacc ccccctaatg cgggaaaagc acgtgtccgc attttagaga 301
aggcaaggcc ggtgtgttta tctgcaagcc attatacttg cccacgaatc tttgagaaca 361
ttataatgac ctttgtgcct cttcttgcaa ggtgttttct cagctgttat ctcaagacat 421
ggatataaaa aactcaccat ctagccttaa ttctccttcc tcctacaact gcagtcaatc 481
catcttaccc ctggagcacg gctccatata catacttcc tcctatgtag acagccacca 541
tgaatatcca gccatgacat tctatagccc tgctgtgatg aattacagca ttcccagcaa 601
tgtcactaac ttggaaggtg ggcctggtcg gcagaccaca agcccaaatg tgttgtggcc 661
aacacctggg cacctttctc ctttagtggt ccatcgccag ttatcacatc tgtatgcgga 721
acctcaaaag agtccctggt gtgaagcaag atcgctagaa cacaccttac ctgtaaacag 781
agagacactg aaaaggaagg ttagtgggaa ccgttgcgcc agccctgtta ctggtccagg 841
ttcaaagagg gatgctcact tctgcgctgt ctgcagcgat tacgcatcgg gatatcacta 901
tggagtctgg tcgtgtgaag gatgtaaggc ctttttaaa agaagcattc aaggacataa 961
tgattatatt tgtccagcta caaatcagtg tacaatcgat aaaaaccggc gcaagagctg 1021
ccaggcctgc cgacttcgga agtgttacga agtgggaatg gtgaagtgtg gctcccggag 1081
agagagatgt gggtaccgcc ttgtgcggag acagagaagt gccgacgagc agctgcactg 1141
tgccggcaag gccaagagaa gtggcggcca cgcgccccga gtgcgggagc tgctgctgga 1201
cgccctgagc cccgagcagc tagtgctcac cctcctggag gctgagccgc cccatgtgct 1261
gatcagccgc cccagtgcgc ccttcaccga ggcctccatg atgatgtccc tgaccaagtt 1321
ggccgacaag gagttggtac acatgatcag ctgggccaag aagattcccg gctttgtgga 1381
gctcagcctg ttcgaccaag tgcggctctt ggagagctgt tggatggagg tgttaatgat 1441
ggggctgatg tggcgctcaa ttgaccaccc cggcaagctc atctttgctc cagatcttgt 1501
tctggacagg gatgagggga aatgcgtaga aggaattctg gaaatctttg acatgctcct 1561
ggcaactact tcaaggtttc gagagttaaa actccaacac aaagaatatc tctgtgtcaa 1621
ggccatgatc ctgctcaatt ccagtatgta ccctctggtc acagcgaccc aggatgctga 1681
cagcagccgg aagctggctc acttgctgaa cgccgtgacc gatgctttgg tttgggtgat 1741
tgccaagagc ggcatctcct cccagcagca atccatgcgc ctggctaacc tcctgatgct 1801
cctgtcccac gtcaggcatg cgagtaacaa gggcatggaa catctgctca acatgaagtg 1861
caaaaatgtg gtcccagtgt atgacctgct gctggagatg ctgaatgccc acgtgcttcg 1921
cgggtgcaag tcctccatca cggggtccga gtgcagcccg gcagaggaca gtaaaagcaa 1981
agagggctcc cagaacccac agtctcagtg a
```

FIGURE 3

Amino Acid Sequence for the Estrogen Receptor Beta (GenBank ACCESSION AAC05985) (SEQ ID NO:3)

```
1   mdiknspssl nspssyncsq silplehgsi yipssyvdsh heypamtfys pavmnysips
61  nvtnleggpg rqttspnvlw ptpghlsplv vhrqlshlya epqkspwcea rslehtlpvn
121 retlkrkvsg nrcaspvtgp gskrdahfca vcsdyasgyh ygvwscegck affkrsiqgh
181 ndyicpatnq ctidknrrks cqacrlrkcy evgmvkcgsr rercgyrlvr rqrsadeqlh
241 cagkakrsgg haprvrelll dalspeqlvl tlleaepphv lisrpsapft easmmmsltk
301 ladkelvhmi swakkipgfv elslfdqvrl lescwmevlm mglmwrsidh pgklifapdl
361 vldrdegkcv egileifdml lattsrfrel klqhkeylcv kamillnssm yplvtatqda
421 dssrklahll navtdalvwv iaksgissqq qsmrlanllm llshvrhasn kgmehllnmk
481 cknvvpvydl llemlnahvl rgckssitgs ecspaedsks kegsqnpqsq
```

FIGURE 4

Estrogen Receptor Beta

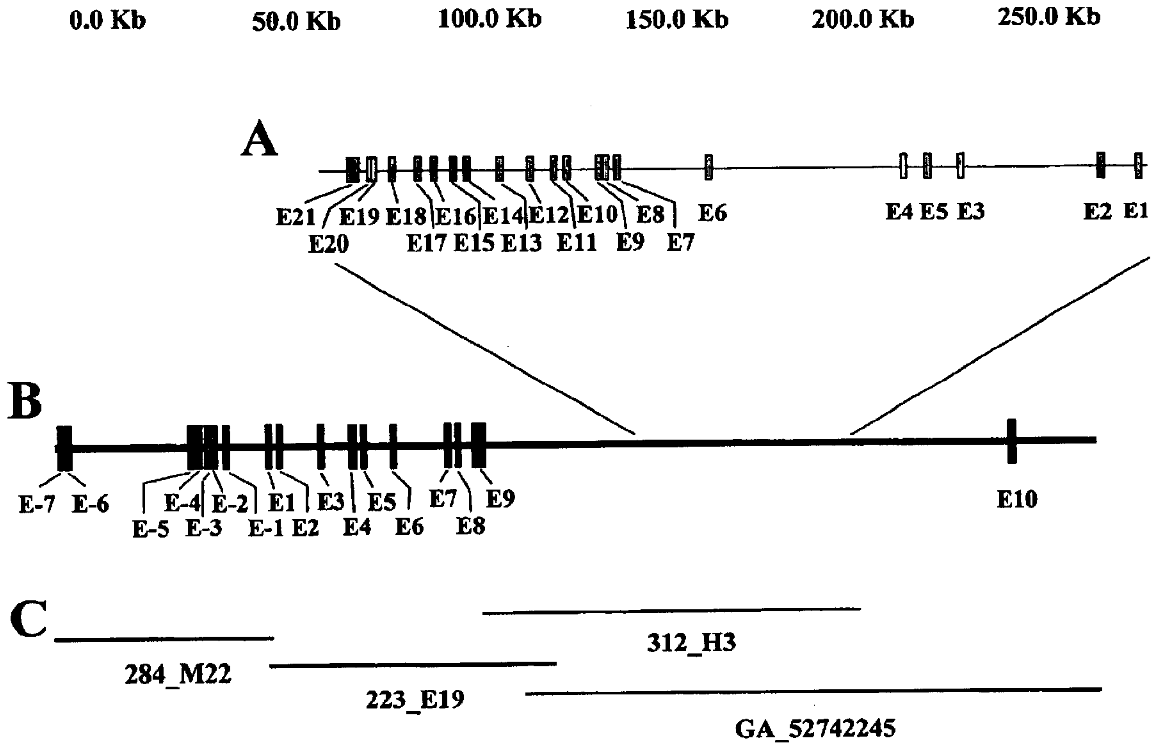

(A) Complete structure of the human synaptic nuclei expressed gene 2 (syne-2) contained within intron 9 of ERβ. Exons are represented by filled boxes and introns by horizontal lines. Note that the gene is on the opposite strand as ERβ. (B) Complete structure of the human estrogen receptor beta (ERβ). Exons are represented by filled boxes and introns by horizontal lines. (C) Order and names of contigs used to complete the genomic sequence. GA numbers represent Celera contig numbers. Research genetics BAC clones are represented by standard plate and well numbering.

ESR2 Genomic Structure

| Splice Variant | | | AF051428 | | AF051427 | | AF060555 | | | | AB006589 | | | | AB006590 | | | | HSRNAERB | |
|---|---|---|---|---|---|---|---|---|---|---|---|---|---|---|---|---|---|---|---|---|
| length (bp) | | | 2041 | | 2011 | | 2745 | | | | 3593 | | | | 1740 | | | | 1560 | |
| CDS | | | 419-1906 | | 419-2011 | | 471-2012 | | | | 1276-2763 | | | | 99-1691 | | | | 19-1452 | |
| | BAC | | cDNA | | cDNA | | cDNA | | BAC | | cDNA | | BAC | | cDNA | | BAC | BAC | cDNA | |
| | start | end | start | end | start | end | start | end | start | end | start | end | start | end | start | end | start | end | start | end |
| Exon(s)? | ? | ? | | | | | | | | | 1 | 1185 | | | | | | | | |
| x-1 | 2320 | 2647 | 1 | 328 | 1 | 328 | 1 | 380 | | | | | | | | | | | | |
| x1 | 13605 | 14056 | 329 | 780 | 329 | 780 | 381 | 832 | | | 1186 | 1637 | | | 9 | 460 | 13838 | 14056 | 3 | 221 |
| x2 | 16527 | 16699 | 781 | 953 | 781 | 953 | 833 | 1005 | | | 1638 | 1810 | | | 461 | 633 | | | 222 | 394 |
| x3 | 27769 | 27885 | 954 | 1070 | 954 | 1070 | 1006 | 1122 | | | 1811 | 1927 | | | 634 | 750 | | | 395 | 511 |
| x4 | 35933 | 36232 | 1071 | 1370 | 1071 | 1370 | 1123 | 1422 | | | 1928 | 2227 | | | 751 | 1050 | | | 512 | 811 |
| x5 | 39317 | 39455 | 1371 | 1509 | 1371 | 1509 | 1423 | 1561 | | | 2228 | 2366 | | | 1051 | 1189 | | | 812 | 950 |
| x6 | 47012 | 47145 | 1510 | 1643 | 1510 | 1643 | 1562 | 1695 | | | 2367 | 2500 | | | 1190 | 1323 | | | 951 | 1084 |
| x7 | 61538 | 61718 | 1644 | 1824 | 1644 | 1824 | 1696 | 1876 | | | 2501 | 2681 | | | 1324 | 1504 | | | 1085 | 1265 |
| x8 | 63365 | 63551 | | | 1825 | 2011 | | | | | | | 63365 | 63600 | 1505 | 1740 | 63365 | 63659 | 1266 | 1560 |
| x9 | 69074 | 69274 | 1825 | 2026 | | | | | 69074 | 69986 | 2682 | 3593 | | | | | | | | |
| Exon(s)? | ? | ? | | | | | 1877-2745 | | | | | | | | | | | | | |

ESR2 Genomic Structure

| Splice Varient | | | AF074598 | | | | AF 074599 | | | | AF061054 | | | | AF 061055 | |
|---|---|---|---|---|---|---|---|---|---|---|---|---|---|---|---|---|
| length (bp) | | | 306 | | | | 1215 | | | | 659 | | | | 372 | |
| CDS | | | 1-255 | | | | 1-1148 | | | | 1-222 | | | | 1-372 | |
| | BAC | | cDNA | | BAC | | cDNA | | BAC | | cDNA | | BAC | | cDNA | |
| | start | end | start | end | start | end | start | end | start | end | start | end | start | end | start | end |
| Exon(s)? | | | | | | | | | | | | | | | | |
| x-1 | | | | | | | | | | | | | | | | |
| x1 | | | | | 13867 | | 1 | 190 | | | | | | | | |
| x2 | | | | | | | 191 | 363 | | | | | | | | |
| x3 | | | | | | | 364 | 480 | | | | | | | | |
| x4 | 36154 | | 1 | 79 | | | 481 | 780 | | | | | | | | |
| x5 | | | 80 | 218 | | | | | | | | | | | | |
| x6 | | | | | | | | | | | | | | | | |
| x7 | | 61625 | 219 | 306 | | | 781 | 961 | | | 2 | 182 | | 61828 | 2 | 292 |
| x8 | | | | | | 63618 | 962 | 1215 | | | | | | | | |
| x9 | | | | | | | | | 68759 | 69235 | 183 | 659 | 69103 | 69182 | 293 | 372 |
| Exon(s)? | | | | | | | | | | | | | | | | |

| | | exon -7 49904 | | exon -7 49934 | | exon -7 49994 | | exon -7 49671 | | exon -7 83980 | | exon -5 85938 | | exon -4 89837 | | exon -2 89889 | |
|---|---|---|---|---|---|---|---|---|---|---|---|---|---|---|---|---|---|
| | | T | C | C | A | G | A | A | T | G | A | A | G | G | A | A | G |
| total | total | 0.96 | 0.041 | 0.96 | 0.04 | 0.99 | 0.01 | 1 | 0 | 0.95 | 0.05 | 0.77 | 0.23 | 0.93 | 0.07 | 1 | 0 |
| N.Eur | N. Eur | 1 | 0 | 1 | 0 | 1 | 0 | 1 | 0 | 1 | 0 | 0.7 | 0.3 | 1 | 0 | 1 | 0 |
| a01 | GM03715 | n/a | n/a | n/a | n/a | n/a | n/a | n/a | n/a | 2 | 0 | 0 | 2 | 2 | 0 | 2 | 0 |
| a02 | GM06816 | 2 | 0 | 2 | 0 | 2 | 0 | 2 | 0 | 2 | 0 | 2 | 0 | 2 | 0 | 2 | 0 |
| a03 | GM10923 | 2 | 0 | 2 | 0 | 2 | 0 | 2 | 0 | 2 | 0 | 2 | 0 | 2 | 0 | 2 | 0 |
| a04 | GM10924 | 2 | 0 | 2 | 0 | 2 | 0 | 2 | 0 | 2 | 0 | 1 | 1 | 2 | 0 | 2 | 0 |
| a05 | GM11814 | 2 | 0 | 2 | 0 | 2 | 0 | 2 | 0 | 2 | 0 | 2 | 0 | 2 | 0 | 2 | 0 |
| a06 | GM12136 | 2 | 0 | 2 | 0 | 2 | 0 | 2 | 0 | 2 | 0 | 1 | 1 | 2 | 0 | 2 | 0 |
| a07 | GM12137 | 2 | 0 | 2 | 0 | 2 | 0 | 2 | 0 | 2 | 0 | 2 | 0 | 2 | 0 | 2 | 0 |
| a08 | GM12547 | 2 | 0 | 2 | 0 | 2 | 0 | 2 | 0 | 2 | 0 | 1 | 1 | 2 | 0 | 2 | 0 |
| a09 | GM12548 | 2 | 0 | 2 | 0 | 2 | 0 | 2 | 0 | 2 | 0 | 1 | 1 | 2 | 0 | 2 | 0 |
| a10 | GM14667 | 2 | 0 | 2 | 0 | 2 | 0 | 2 | 0 | 2 | 0 | 2 | 0 | 2 | 0 | 2 | 0 |
| Chi | Chi | 0.95 | 0.05 | 0.95 | 0.05 | 0.95 | 0.05 | 1 | 0 | 1 | 0 | 0.85 | 0.15 | 0.95 | 0.05 | 1 | 0 |
| b01 | GM00576 | 2 | 0 | 2 | 0 | 2 | 0 | 2 | 0 | 2 | 0 | 2 | 0 | 2 | 0 | 2 | 0 |
| b02 | GM03433 | 2 | 0 | 2 | 0 | 2 | 0 | 2 | 0 | 2 | 0 | 1 | 1 | 2 | 0 | 2 | 0 |
| b03 | GM06090 | 2 | 0 | 2 | 0 | 2 | 0 | 2 | 0 | 2 | 0 | 2 | 0 | 2 | 0 | 2 | 0 |
| b04 | GM07426 | 2 | 0 | 2 | 0 | 2 | 0 | 2 | 0 | 2 | 0 | 2 | 0 | 2 | 0 | 2 | 0 |
| b05 | GM09820 | 2 | 0 | 2 | 0 | 2 | 0 | 2 | 0 | 2 | 0 | 2 | 0 | 1 | 1 | 2 | 0 |
| b06 | GM11321 | 1 | 1 | 1 | 1 | 2 | 0 | 2 | 0 | 2 | 0 | 1 | 1 | 2 | 0 | 2 | 0 |
| b07 | GM11322 | 2 | 0 | 2 | 0 | 2 | 0 | 2 | 0 | 2 | 0 | 2 | 0 | 2 | 0 | 2 | 0 |
| b08 | GM11323 | 2 | 0 | 2 | 0 | 1 | 1 | 2 | 0 | 2 | 0 | 2 | 0 | 2 | 0 | 2 | 0 |
| b09 | GM11324 | 2 | 0 | 2 | 0 | 2 | 0 | 2 | 0 | 2 | 0 | 2 | 0 | 2 | 0 | 2 | 0 |
| b10 | GM11325 | 2 | 0 | 2 | 0 | 2 | 0 | 2 | 0 | 2 | 0 | 1 | 1 | 2 | 0 | 2 | 0 |
| In Pak | In. Pak | 1 | 0 | 1 | 0 | 1 | 0 | 1 | 0 | 1 | 0 | 0.75 | 0.25 | 0.95 | 0.05 | 1 | 0 |
| c01 | GM01032 | 2 | 0 | 2 | 0 | 2 | 0 | 2 | 0 | 2 | 0 | 2 | 0 | 2 | 0 | 2 | 0 |
| c02 | GM01225 | 2 | 0 | 2 | 0 | 2 | 0 | 2 | 0 | 2 | 0 | 1 | 1 | 2 | 0 | 2 | 0 |
| c03 | GM04300 | 2 | 0 | 2 | 0 | 2 | 0 | 2 | 0 | 2 | 0 | 0 | 2 | 2 | 0 | 2 | 0 |
| c04 | GM07895 | 2 | 0 | 2 | 0 | 2 | 0 | 2 | 0 | 2 | 0 | 2 | 0 | 2 | 0 | 2 | 0 |
| c05 | GM10176 | 2 | 0 | 2 | 0 | 2 | 0 | 2 | 0 | 2 | 0 | 1 | 1 | 2 | 0 | 2 | 0 |
| c06 | GM10666 | 2 | 0 | 2 | 0 | 2 | 0 | 2 | 0 | 2 | 0 | 2 | 0 | 2 | 0 | 2 | 0 |
| c07 | GM10667 | 2 | 0 | 2 | 0 | 2 | 0 | 2 | 0 | 2 | 0 | 1 | 1 | 2 | 0 | 2 | 0 |
| c08 | GM11213 | 2 | 0 | 2 | 0 | 2 | 0 | 2 | 0 | 2 | 0 | 2 | 0 | 1 | 1 | 2 | 0 |
| c09 | GM11860 | 2 | 0 | 2 | 0 | 2 | 0 | 2 | 0 | 2 | 0 | 2 | 0 | 2 | 0 | 2 | 0 |
| c10 | GM14611 | 2 | 0 | 2 | 0 | 2 | 0 | 2 | 0 | 2 | 0 | 2 | 0 | 2 | 0 | 2 | 0 |
| Af. Amer | Af. Amer | 1 | 0 | 1 | 0 | 1 | 0 | 1 | 0 | 1 | 0 | 0.55 | 0.45 | 0.9 | 0.1 | 1 | 0 |
| d01 | GM14660 | 2 | 0 | 2 | 0 | 2 | 0 | 2 | 0 | 2 | 0 | 1 | 1 | 1 | 1 | 2 | 0 |
| d02 | GM14661 | 2 | 0 | 2 | 0 | 2 | 0 | 2 | 0 | 2 | 0 | 2 | 0 | 1 | 1 | 2 | 0 |
| d03 | GM14663 | 2 | 0 | 2 | 0 | 2 | 0 | 2 | 0 | 2 | 0 | 1 | 1 | 2 | 0 | 2 | 0 |
| d04 | GM14665 | 2 | 0 | 2 | 0 | 2 | 0 | 2 | 0 | 2 | 0 | 1 | 1 | 2 | 0 | 2 | 0 |
| d05 | GM14672 | 2 | 0 | 2 | 0 | 2 | 0 | 2 | 0 | 2 | 0 | 2 | 0 | 2 | 0 | 2 | 0 |
| d06 | GM14682 | 2 | 0 | 2 | 0 | 2 | 0 | 2 | 0 | 2 | 0 | 0 | 2 | 2 | 0 | 2 | 0 |
| d07 | GM14683 | 2 | 0 | 2 | 0 | 2 | 0 | 2 | 0 | 2 | 0 | 1 | 1 | 2 | 0 | 2 | 0 |
| d08 | GM14696 | 2 | 0 | 2 | 0 | 2 | 0 | 2 | 0 | 2 | 0 | 1 | 1 | 2 | 0 | 2 | 0 |
| d09 | GM14698 | 2 | 0 | 2 | 0 | 2 | 0 | 2 | 0 | 2 | 0 | 1 | 1 | 2 | 0 | 2 | 0 |
| d10 | GM14700 | 2 | 0 | 2 | 0 | 2 | 0 | 2 | 0 | 2 | 0 | 1 | 1 | 2 | 0 | 2 | 0 |
| Nat. Amer | SW Amer. Ind | 0.85 | 0.15 | 0.85 | 0.15 | 1 | 0 | 1 | 0 | 0.75 | 0.25 | 1 | 0 | 0.85 | 0.15 | 1 | 0 |
| e01 | GM12060 | 2 | 0 | 2 | 0 | 2 | 0 | 2 | 0 | 1 | 1 | 2 | 0 | 2 | 0 | 2 | 0 |
| e02 | GM12061 | 2 | 0 | 2 | 0 | 2 | 0 | 2 | 0 | 1 | 1 | 2 | 0 | 2 | 0 | 2 | 0 |
| e03 | GM12062 | 2 | 0 | 2 | 0 | 2 | 0 | 2 | 0 | 2 | 0 | 2 | 0 | 2 | 0 | 2 | 0 |
| e04 | GM12063 | 2 | 0 | 2 | 0 | 2 | 0 | 2 | 0 | 2 | 0 | 2 | 0 | 1 | 1 | 2 | 0 |
| e05 | GM12064 | 2 | 0 | 2 | 0 | 2 | 0 | 2 | 0 | 2 | 0 | 2 | 0 | 1 | 1 | 2 | 0 |
| e06 | GM14308 | 1 | 1 | 1 | 1 | 2 | 0 | 2 | 0 | 1 | 1 | 2 | 0 | 2 | 0 | 2 | 0 |
| e07 | GM14309 | 2 | 0 | 2 | 0 | 2 | 0 | 2 | 0 | 2 | 0 | 2 | 0 | 2 | 0 | 2 | 0 |
| e08 | GM12310 | 1 | 1 | 1 | 1 | 2 | 0 | 2 | 0 | 2 | 0 | 2 | 0 | 2 | 0 | 2 | 0 |
| e09 | GM14311 | 2 | 0 | 2 | 0 | 2 | 0 | 2 | 0 | 1 | 1 | 2 | 0 | 1 | 1 | 2 | 0 |
| e10 | GM14313 | 1 | 1 | 1 | 1 | 2 | 0 | 2 | 0 | 1 | 1 | 2 | 0 | 2 | 0 | 2 | 0 |

| | exon -2 90090 | | exon 9 160165 | | exon 9 160376 | | exon 9 160602 | | exon 10 303073 | | exon 10 302972 | | exon 10 302848 | | exon 10 302699 | | exon 10 302681 | | exon 10 302556 | |
|---|---|---|---|---|---|---|---|---|---|---|---|---|---|---|---|---|---|---|---|---|
| | A | G | A | G | C | G | G | C | T | C | G | T | A | G | T | C | C | T | A | G |
| total | 1 | 0 | 0.99 | 0.01 | 0.89 | 0.11 | 1 | 0 | 0.99 | 0.01 | 0.93 | 0.07 | 0.98 | 0.02 | 0.79 | 0.21 | 0.97 | 0.03 | 0.77 | 0.23 |
| N.Eur | 1 | 0 | 1 | 0 | 0.89 | 0.11 | 1 | 0 | 1.00 | 0.00 | 0.94 | 0.06 | 0.89 | 0.11 | 0.83 | 0.17 | 1.00 | 0.00 | 0.83 | 0.17 |
| a01 | 2 | 0 | 2 | 0 | n/a | n/a | 2 | 0 | 2 | 0 | 2 | 0 | 2 | 0 | 2 | 0 | 2 | 0 | 2 | 0 |
| a02 | 2 | 0 | 2 | 0 | 2 | 0 | 2 | 0 | 2 | 0 | 2 | 0 | 1 | 1 | 2 | 0 | 2 | 0 | 2 | 0 |
| a03 | 2 | 0 | 2 | 0 | 2 | 0 | 2 | 0 | 2 | 0 | 2 | 0 | 1 | 1 | 2 | 0 | 2 | 0 | 2 | 0 |
| a04 | 2 | 0 | 1 | n/a | 2 | 0 | 2 | 0 | 2 | 0 | 2 | 0 | 2 | 0 | 1 | 1 | 2 | 0 | 1 | 1 |
| a05 | 2 | 0 | 2 | 0 | 2 | 0 | 2 | 0 | n/a | n/a | n/a | n/a | n/a | n/a | n/a | n/a | n/a | n/a | n/a | n/a |
| a06 | 2 | 0 | 2 | 0 | 2 | 0 | 2 | 0 | 2 | 0 | 2 | 0 | 2 | 0 | 2 | 0 | 2 | 0 | 2 | 0 |
| a07 | 2 | 0 | 2 | 0 | 2 | 0 | n/a | n/a | 2 | 0 | 2 | 0 | 2 | 0 | 2 | 0 | 2 | 0 | 2 | 0 |
| a08 | 2 | 0 | 1 | n/a | 1 | 1 | 2 | 0 | 2 | 0 | 2 | 0 | 2 | 0 | 1 | 1 | 2 | 0 | 1 | 1 |
| a09 | 2 | 0 | 2 | 0 | 1 | 1 | 2 | 0 | 2 | 0 | 1 | 1 | 2 | 0 | 1 | 1 | 2 | 0 | 1 | 1 |
| a10 | 2 | 0 | 2 | 0 | 2 | 0 | 2 | 0 | 2 | 0 | 2 | 0 | 2 | 0 | 2 | 0 | 2 | 0 | 2 | 0 |
| Chi | 1 | 0 | 1 | 0 | 0.83 | 0.17 | 1 | 0 | 1 | 0 | 1.00 | 0.00 | 1.00 | 0.00 | 0.85 | 0.15 | 1.00 | 0.00 | 0.75 | 0.25 |
| b01 | 2 | 0 | n/a | n/a | n/a | n/a | 2 | 0 | 2 | 0 | 2 | 0 | 2 | 0 | 2 | 0 | 2 | 0 | 2 | 0 |
| b02 | 2 | 0 | 2 | 0 | 2 | 0 | 2 | 0 | 2 | 0 | 2 | 0 | 2 | 0 | 2 | 0 | 2 | 0 | 1 | 1 |
| b03 | 2 | 0 | 2 | 0 | 2 | 0 | 2 | 0 | 2 | 0 | 2 | 0 | 2 | 0 | 2 | 0 | 2 | 0 | 2 | 0 |
| b04 | 2 | 0 | 2 | 0 | 2 | 0 | 2 | 0 | 2 | 0 | 2 | 0 | 2 | 0 | 2 | 0 | 2 | 0 | 2 | 0 |
| b05 | 2 | 0 | n/a | n/a | n/a | n/a | 2 | 0 | 2 | 0 | 2 | 0 | 2 | 0 | 2 | 0 | 2 | 0 | 2 | 0 |
| b06 | 2 | 0 | n/a | n/a | n/a | n/a | 2 | 0 | 2 | 0 | 2 | 0 | 2 | 0 | 1 | 1 | 2 | 0 | 1 | 1 |
| b07 | 2 | 0 | 2 | 0 | 2 | 0 | 2 | 0 | 2 | 0 | 2 | 0 | 2 | 0 | 2 | 0 | 2 | 0 | 1 | 1 |
| b08 | 2 | 0 | n/a | n/a | n/a | n/a | 2 | 0 | n/a | n/a | n/a | n/a | 2 | 0 | 1 | 1 | 2 | 0 | 1 | 1 |
| b09 | 2 | 0 | 2 | 0 | 2 | 0 | 2 | 0 | 2 | 0 | 2 | 0 | 2 | 0 | 1 | 1 | 2 | 0 | 1 | 1 |
| b10 | 2 | 0 | 1 | n/a | 0 | 2 | 2 | 0 | 2 | 0 | 2 | 0 | 2 | 0 | 2 | 0 | 2 | 0 | 2 | 0 |
| In Pak | 1 | 0 | 1 | 0 | 1 | 0 | 1 | 0 | 1 | 0 | 0.90 | 0.10 | 1.00 | 0.00 | 0.85 | 0.15 | 1.00 | 0.00 | 0.80 | 0.20 |
| c01 | 2 | 0 | 2 | 0 | 2 | 0 | 2 | 0 | 2 | 0 | 2 | 0 | 2 | 0 | 2 | 0 | 2 | 0 | 2 | 0 |
| c02 | 2 | 0 | 2 | 0 | 2 | 0 | 2 | 0 | 2 | 0 | 2 | 0 | 2 | 0 | 2 | 0 | 2 | 0 | 2 | 0 |
| c03 | 2 | 0 | 2 | 0 | 2 | 0 | 2 | 0 | 2 | 0 | 2 | 0 | 2 | 0 | 1 | 1 | 2 | 0 | 1 | 1 |
| c04 | 2 | 0 | 2 | 0 | 2 | 0 | 2 | 0 | 2 | 0 | 2 | 0 | 2 | 0 | 2 | 0 | 2 | 0 | 2 | 0 |
| c05 | 2 | 0 | 2 | 0 | 2 | 0 | 2 | 0 | 2 | 0 | 2 | 0 | 2 | 0 | 2 | 0 | 2 | 0 | 2 | 0 |
| c06 | 2 | 0 | 2 | 0 | 2 | 0 | 2 | 0 | 2 | 0 | 2 | 0 | 2 | 0 | 2 | 0 | 2 | 0 | 2 | 0 |
| c07 | 2 | 0 | 2 | 0 | 2 | 0 | 2 | 0 | 2 | 0 | 2 | 0 | 2 | 0 | 1 | 1 | 2 | 0 | 1 | 1 |
| c08 | 2 | 0 | 2 | 0 | 2 | 0 | 2 | 0 | 2 | 0 | 2 | 0 | 2 | 0 | 2 | 0 | 2 | 0 | 2 | 0 |
| c09 | 2 | 0 | 2 | 0 | 2 | 0 | 2 | 0 | 2 | 0 | 1 | 1 | 2 | 0 | 2 | 0 | 2 | 0 | 1 | 1 |
| c10 | 2 | 0 | n/a | n/a | n/a | n/a | 2 | 0 | 2 | 0 | 1 | 1 | 2 | 0 | 1 | 1 | 2 | 0 | 1 | 1 |
| Af. Amer | 1 | 0 | 0.93 | 0.07 | 0.72 | 0.28 | 1 | 0 | 0.95 | 0.05 | 0.95 | 0.05 | 1 | 0 | 0.55 | 0.45 | 0.85 | 0.15 | 0.6 | 0.4 |
| d01 | 2 | 0 | 2 | 0 | 2 | 0 | 2 | 0 | 2 | 0 | 2 | 0 | 2 | 0 | 2 | 0 | 2 | 0 | 2 | 0 |
| d02 | 2 | 0 | 2 | 0 | 2 | 0 | 2 | 0 | 2 | 0 | 2 | 0 | 2 | 0 | 1 | 1 | 1 | 1 | 1 | 1 |
| d03 | 2 | 0 | 2 | 0 | 2 | 0 | 2 | 0 | 2 | 0 | 2 | 0 | 2 | 0 | 1 | 1 | 2 | 0 | 1 | 1 |
| d04 | 2 | 0 | n/a | n/a | 2 | 0 | 2 | 0 | 2 | 0 | 2 | 0 | 2 | 0 | 2 | 0 | 2 | 0 | 2 | 0 |
| d05 | 2 | 0 | 2 | 0 | 2 | 0 | 2 | 0 | 2 | 0 | 2 | 0 | 2 | 0 | 1 | 1 | 2 | 0 | 1 | 1 |
| d06 | 2 | 0 | 2 | 0 | 1 | 1 | 2 | 0 | 2 | 0 | 1 | 1 | 2 | 0 | 1 | 1 | 2 | 0 | 1 | 1 |
| d07 | 2 | 0 | 1 | n/a | 1 | 1 | 2 | 0 | 2 | 0 | 2 | 0 | 2 | 0 | 2 | 0 | 2 | 0 | 2 | 0 |
| d08 | 2 | 0 | n/a | n/a | n/a | n/a | 2 | 0 | 2 | 0 | 2 | 0 | 2 | 0 | 1 | 1 | 2 | 0 | 1 | 1 |
| d09 | 2 | 0 | 1 | n/a | 1 | 1 | 2 | 0 | 1 | 1 | 2 | 0 | 2 | 0 | 0 | 2 | 1 | 1 | 1 | 1 |
| d10 | 2 | 0 | 1 | 1 | 0 | 2 | 2 | 0 | 2 | 0 | 2 | 0 | 2 | 0 | 0 | 2 | 1 | 1 | 0 | 2 |
| Nat. Amer | 1 | 0 | 1 | 0 | 1 | 0 | 1 | 0 | 1 | 0 | 0.85 | 0.15 | 1 | 0 | 0.85 | 0.15 | 1 | 0 | 0.85 | 0.15 |
| e01 | 2 | 0 | 2 | 0 | 2 | 0 | n/a | n/a | 2 | 0 | 1 | 1 | 2 | 0 | 1 | 1 | 2 | 0 | 1 | 1 |
| e02 | 2 | 0 | n/a | n/a | 2 | 0 | 2 | 0 | 2 | 0 | 2 | 0 | 2 | 0 | 2 | 0 | 2 | 0 | 2 | 0 |
| e03 | 2 | 0 | 2 | 0 | 2 | 0 | 2 | 0 | 2 | 0 | 2 | 0 | 2 | 0 | 2 | 0 | 2 | 0 | 2 | 0 |
| e04 | 2 | 0 | n/a | n/a | 2 | 0 | 2 | 0 | 2 | 0 | 1 | 1 | 2 | 0 | 1 | 1 | 2 | 0 | 1 | 1 |
| e05 | 2 | 0 | 2 | 0 | 2 | 0 | 2 | 0 | 2 | 0 | 1 | 1 | 2 | 0 | 1 | 1 | 2 | 0 | 1 | 1 |
| e06 | 2 | 0 | 2 | 0 | 2 | 0 | 2 | 0 | 2 | 0 | 2 | 0 | 2 | 0 | 2 | 0 | 2 | 0 | 2 | 0 |
| e07 | 2 | 0 | 2 | 0 | 2 | 0 | 2 | 0 | 2 | 0 | 2 | 0 | 2 | 0 | 2 | 0 | 2 | 0 | 2 | 0 |
| e08 | 2 | 0 | 2 | 0 | 2 | 0 | 2 | 0 | 2 | 0 | 2 | 0 | 2 | 0 | 2 | 0 | 2 | 0 | 2 | 0 |
| e09 | 2 | 0 | n/a | n/a | n/a | n/a | n/a | n/a | 2 | 0 | 2 | 0 | 2 | 0 | 2 | 0 | 2 | 0 | 2 | 0 |
| e10 | 2 | 0 | n/a | n/a | n/a | n/a | n/a | n/a | n/a | n/a | 2 | 0 | 2 | 0 | 2 | 0 | 2 | 0 | 2 | 0 |

| | exon -7 49904 | | exon -7 49934 | | exon -7 49994 | | exon -7 49671 | | exon -5 83980 | | exon -4 85938 | | exon -2 89837 | | exon -2 89889 | | exon -2 90090 | |
|---|---|---|---|---|---|---|---|---|---|---|---|---|---|---|---|---|---|---|
| | A | G | C | A | A | G | A | T | G | A | G | A | C | T | T | C | T | C |
| | 1.00 | 0.00 | 1.00 | 0.00 | 1.00 | 0.00 | 0.98 | 0.02 | 1.00 | 0.00 | 0.71 | 0.29 | 0.85 | 0.15 | 1.00 | 0.00 | 1.00 | 0.00 |
| T1 | 2 | 0 | 2 | 0 | 2 | 0 | 2 | 0 | 2 | 0 | 2 | 0 | 2 | 0 | 2 | 0 | 2 | 0 |
| T2 | 2 | 0 | 2 | 0 | 2 | 0 | 2 | 0 | 2 | 0 | 2 | 0 | 2 | 0 | 2 | 0 | 2 | 0 |
| T3 | 2 | 0 | 2 | 0 | 2 | 0 | 2 | 0 | 2 | 0 | 1 | 1 | 2 | 0 | 2 | 0 | 2 | 0 |
| T4 | 2 | 0 | 2 | 0 | 2 | 0 | 2 | 0 | 2 | 0 | 2 | 0 | 2 | 0 | 2 | 0 | 2 | 0 |
| T5 | 2 | 0 | 2 | 0 | n/a | n/a | 2 | 0 | 2 | 0 | 2 | 0 | 2 | 0 | 2 | 0 | 2 | 0 |
| T6 | 2 | 0 | 2 | 0 | 2 | 0 | 2 | 0 | 2 | 0 | 2 | 0 | n/a | n/a | 2 | 0 | 2 | 0 |
| T7 | 2 | 0 | 2 | 0 | 2 | 0 | 2 | 0 | 2 | 0 | 2 | 0 | 1 | 1 | 2 | 0 | 2 | 0 |
| T8 | 2 | 0 | 2 | 0 | 2 | 0 | 2 | 0 | 2 | 0 | 2 | 0 | 1 | 1 | 2 | 0 | 2 | 0 |
| T9 | 2 | 0 | 2 | 0 | 2 | 0 | 2 | 0 | n/a | n/a | 1 | 1 | 2 | 0 | 2 | 0 | 2 | 0 |
| T10 | 2 | 0 | 2 | 0 | 2 | 0 | 2 | 0 | n/a | n/a | 1 | 1 | 2 | 0 | 2 | 0 | 2 | 0 |
| T11 | 2 | 0 | 2 | 0 | 2 | 0 | 2 | 0 | n/a | n/a | 2 | 0 | 2 | 0 | 2 | 0 | 2 | 0 |
| T12 | 2 | 0 | 2 | 0 | 2 | 0 | 2 | 0 | n/a | n/a | 1 | 1 | 1 | 1 | 2 | 0 | 2 | 0 |
| T13 | 2 | 0 | 2 | 0 | 2 | 0 | 2 | 0 | n/a | n/a | 1 | 1 | 1 | 1 | 2 | 0 | 2 | 0 |
| T14 | 2 | 0 | 2 | 0 | 2 | 0 | 2 | 0 | n/a | n/a | 0 | 2 | 2 | 0 | 2 | 0 | 2 | 0 |
| T15 | 2 | 0 | 2 | 0 | 2 | 0 | 2 | 0 | n/a | n/a | 1 | 1 | 2 | 0 | 2 | 0 | 2 | 0 |
| T16 | 2 | 0 | 2 | 0 | 2 | 0 | 2 | 0 | 2 | 0 | 2 | 0 | 1 | 1 | 2 | 0 | 2 | 0 |
| T17 | 2 | 0 | 2 | 0 | 2 | 0 | 2 | 0 | 2 | 0 | 1 | 1 | 2 | 0 | 2 | 0 | 2 | 0 |
| T18 | 2 | 0 | 2 | 0 | 2 | 0 | 2 | 0 | n/a | n/a | 2 | 0 | 2 | 0 | 2 | 0 | 2 | 0 |
| T19 | 2 | 0 | 2 | 0 | 2 | 0 | 2 | 0 | n/a | n/a | 2 | 0 | 2 | 0 | 2 | 0 | 2 | 0 |
| T20 | 2 | 0 | 2 | 0 | 2 | 0 | 2 | 0 | 2 | 0 | 0 | 2 | 2 | 0 | 2 | 0 | n/a | n/a |
| T21 | 2 | 0 | 2 | 0 | 2 | 0 | 2 | 0 | n/a | n/a | 1 | 1 | 2 | 0 | 2 | 0 | 2 | 0 |
| T22 | 2 | 0 | 2 | 0 | 2 | 0 | 0 | 2 | 2 | 0 | 2 | 0 | 2 | 0 | 2 | 0 | 2 | 0 |
| T23 | 2 | 0 | 2 | 0 | 2 | 0 | 2 | 0 | 2 | 0 | 2 | 0 | n/a | n/a | n/a | n/a | 2 | 0 |
| T24 | 2 | 0 | 2 | 0 | 2 | 0 | 2 | 0 | 2 | 0 | 0 | 2 | 2 | 0 | 2 | 0 | 2 | 0 |
| T25 | 2 | 0 | 2 | 0 | 2 | 0 | 2 | 0 | 2 | 0 | 0 | 2 | n/a | n/a | 2 | 0 | 2 | 0 |
| T26 | 2 | 0 | 2 | 0 | 2 | 0 | 2 | 0 | 2 | 0 | 2 | 0 | 2 | 0 | 2 | 0 | 2 | 0 |
| T27 | 2 | 0 | 2 | 0 | 2 | 0 | 2 | 0 | 2 | 0 | 1 | 1 | 2 | 0 | 2 | 0 | 2 | 0 |
| T28 | 2 | 0 | 2 | 0 | 2 | 0 | 2 | 0 | n/a | n/a | 0 | 2 | 2 | 0 | 2 | 0 | 2 | 0 |
| T29 | 2 | 0 | 2 | 0 | 2 | 0 | 2 | 0 | 2 | 0 | 2 | 0 | n/a | n/a | 2 | 0 | 2 | 0 |
| T30 | 2 | 0 | 2 | 0 | 2 | 0 | 2 | 0 | 2 | 0 | 2 | 0 | 2 | 0 | 2 | 0 | 2 | 0 |
| T31 | 2 | 0 | 2 | 0 | 2 | 0 | 2 | 0 | n/a | n/a | 1 | 1 | 2 | 0 | n/a | n/a | 2 | 0 |
| T32 | 2 | 0 | 2 | 0 | 2 | 0 | 2 | 0 | 2 | 0 | 2 | 0 | 1 | 1 | 2 | 0 | 2 | 0 |
| T33 | 2 | 0 | 2 | 0 | 2 | 0 | 2 | 0 | n/a | n/a | 1 | 1 | 2 | 0 | 2 | 0 | 2 | 0 |
| T34 | 2 | 0 | 2 | 0 | 2 | 0 | 2 | 0 | n/a | n/a | 2 | 0 | 2 | 0 | 2 | 0 | 2 | 0 |
| T35 | 2 | 0 | 2 | 0 | 2 | 0 | 2 | 0 | n/a | n/a | 1 | 1 | 2 | 0 | 2 | 0 | 2 | 0 |
| T36 | 2 | 0 | 2 | 0 | 2 | 0 | 2 | 0 | n/a | n/a | 2 | 0 | 1 | 1 | 2 | 0 | 2 | 0 |
| T37 | 2 | 0 | 2 | 0 | 2 | 0 | 2 | 0 | 2 | 0 | 2 | 0 | 1 | 1 | 2 | 0 | 2 | 0 |
| T38 | 2 | 0 | 2 | 0 | 2 | 0 | 2 | 0 | n/a | n/a | 0 | 2 | 2 | 0 | 2 | 0 | 2 | 0 |
| T39 | 2 | 0 | 2 | 0 | 2 | 0 | 2 | 0 | 2 | 0 | n/a | n/a | 1 | 1 | 2 | 0 | 2 | 0 |
| T40 | 2 | 0 | 2 | 0 | 2 | 0 | 2 | 0 | n/a | n/a | 1 | 1 | 1 | 1 | 2 | 0 | 2 | 0 |
| T41 | 2 | 0 | 2 | 0 | 2 | 0 | 2 | 0 | 2 | 0 | 2 | 0 | 0 | 2 | 2 | 0 | 2 | 0 |
| T42 | 2 | 0 | 2 | 0 | 2 | 0 | 2 | 0 | n/a | n/a | 2 | 0 | 2 | 0 | 2 | 0 | 2 | 0 |
| T43 | 2 | 0 | 2 | 0 | 2 | 0 | 2 | 0 | 2 | 0 | 2 | 0 | 1 | 1 | 2 | 0 | 2 | 0 |
| T44 | 2 | 0 | 2 | 0 | 2 | 0 | 2 | 0 | n/a | n/a | 2 | 0 | 2 | 0 | 2 | 0 | 2 | 0 |
| T45 | 2 | 0 | 2 | 0 | 2 | 0 | 2 | 0 | 2 | 0 | 1 | 1 | 2 | 0 | 2 | 0 | 2 | 0 |
| T46 | 2 | 0 | 2 | 0 | 2 | 0 | 2 | 0 | n/a | n/a | 1 | 1 | 2 | 0 | 2 | 0 | 2 | 0 |
| T47 | 2 | 0 | 2 | 0 | 2 | 0 | 2 | 0 | n/a | n/a | 2 | 0 | 2 | 0 | 2 | 0 | 2 | 0 |
| T48 | 2 | 0 | 2 | 0 | 2 | 0 | 2 | 0 | 2 | 0 | 2 | 0 | 2 | 0 | 2 | 0 | 2 | 0 |

| | intron 3 126711 | | exon 5 130189 | | intron 7 154138 | | intron 7 154202 | | exon 8 154431 | | exon 9 160052 | | exon 9 160089 | | exon 9 160165 | | exon 9 160376 | |
|---|---|---|---|---|---|---|---|---|---|---|---|---|---|---|---|---|---|---|
| | A | G | G | A | G | A | A | G | G | A | A | G | A | G | A | G | C | G |
| | 0.98 | 0.02 | 0.99 | 0.01 | 0.97 | 0.03 | 0.98 | 0.02 | 0.64 | 0.36 | 0.64 | 0.36 | 0.83 | 0.17 | 0.92 | 0.08 | 0.91 | 0.09 |
| T1 | 2 | 0 | 2 | 0 | 2 | 0 | 2 | 0 | 1 | 1 | 1 | 1 | 2 | 0 | 2 | 0 | 2 | 0 |
| T2 | 2 | 0 | 2 | 0 | 2 | 0 | 2 | 0 | 2 | 0 | 0 | 2 | 2 | 0 | 2 | 0 | 2 | 0 |
| T3 | 2 | 0 | 2 | 0 | 2 | 0 | 2 | 0 | 2 | 0 | 1 | 1 | 2 | 0 | 1 | 1 | 2 | 0 |
| T4 | 2 | 0 | 2 | 0 | 1 | 1 | 2 | 0 | 1 | 1 | 1 | 1 | 2 | 0 | 2 | 0 | 2 | 0 |
| T5 | 2 | 0 | 2 | 0 | 2 | 0 | 2 | 0 | 2 | 0 | 0 | 2 | 2 | 0 | 2 | 0 | 2 | 0 |
| T6 | 2 | 0 | 2 | 0 | 2 | 0 | 2 | 0 | 1 | 1 | 2 | 0 | 0 | 2 | 2 | 0 | 2 | 0 |
| T7 | 2 | 0 | 2 | 0 | 1 | 1 | 2 | 0 | 1 | 1 | 2 | 0 | 1 | 1 | 2 | 0 | 2 | 0 |
| T8 | 2 | 0 | 2 | 0 | 2 | 0 | 2 | 0 | 2 | 0 | 2 | 0 | 0 | 2 | 2 | 0 | 2 | 0 |
| T9 | 2 | 0 | 2 | 0 | 2 | 0 | 2 | 0 | 2 | 0 | 1 | 1 | 2 | 0 | 2 | 0 | 2 | 0 |
| T10 | 2 | 0 | 2 | 0 | 2 | 0 | 2 | 0 | 0 | 2 | 2 | 0 | 2 | 0 | 2 | 0 | 2 | 0 |
| T11 | 2 | 0 | 2 | 0 | 2 | 0 | 2 | 0 | 2 | 0 | 0 | 2 | 2 | 0 | 2 | 0 | 2 | 0 |
| T12 | 2 | 0 | 2 | 0 | 2 | 0 | 1 | 1 | 2 | 0 | 1 | 1 | 2 | 0 | 2 | 0 | 2 | 0 |
| T13 | 2 | 0 | 2 | 0 | 2 | 0 | 2 | 0 | 2 | 0 | 2 | 0 | 1 | 1 | 1 | 1 | 1 | 1 |
| T14 | 2 | 0 | 2 | 0 | 2 | 0 | 2 | 0 | 1 | 1 | 1 | 1 | 2 | 0 | 2 | 0 | 2 | 0 |
| T15 | 2 | 0 | 2 | 0 | 2 | 0 | 2 | 0 | 0 | 2 | 2 | 0 | 2 | 0 | 2 | 0 | 2 | 0 |
| T16 | 2 | 0 | 2 | 0 | 2 | 0 | 2 | 0 | 2 | 0 | 0 | 2 | 2 | 0 | 2 | 0 | 2 | 0 |
| T17 | 2 | 0 | 2 | 0 | 2 | 0 | 2 | 0 | 1 | 1 | 1 | 1 | 2 | 0 | 2 | 0 | 2 | 0 |
| T18 | 2 | 0 | 2 | 0 | 2 | 0 | 2 | 0 | 1 | 1 | 1 | 1 | 2 | 0 | 2 | 0 | 2 | 0 |
| T19 | 2 | 0 | 2 | 0 | 1 | 1 | 2 | 0 | 1 | 1 | 1 | 1 | 2 | 0 | 2 | 0 | 2 | 0 |
| T20 | 2 | 0 | 2 | 0 | 2 | 0 | 2 | 0 | 0 | 2 | 2 | 0 | 2 | 0 | 2 | 0 | 2 | 0 |
| T21 | 2 | 0 | 2 | 0 | 2 | 0 | 2 | 0 | 1 | 1 | 1 | 1 | 2 | 0 | 2 | 0 | 2 | 0 |
| T22 | 2 | 0 | 2 | 0 | 2 | 0 | 2 | 0 | 2 | 0 | 2 | 0 | 2 | 0 | 0 | 2 | 0 | 2 |
| T23 | 2 | 0 | 2 | 0 | 2 | 0 | 2 | 0 | 2 | 0 | 0 | 2 | 2 | 0 | 2 | 0 | 2 | 0 |
| T24 | 2 | 0 | 2 | 0 | 2 | 0 | 2 | 0 | 2 | 0 | 2 | 0 | 2 | 0 | 0 | 2 | 0 | 2 |
| T25 | 2 | 0 | 2 | 0 | 2 | 0 | 2 | 0 | 0 | 2 | 2 | 0 | 2 | 0 | 2 | 0 | 2 | 0 |
| T26 | 1 | 1 | 2 | 0 | 2 | 0 | 2 | 0 | 1 | 1 | 1 | 1 | 2 | 0 | 2 | 0 | 2 | 0 |
| T27 | 2 | 0 | 2 | 0 | 2 | 0 | 2 | 0 | 1 | 1 | 1 | 1 | 2 | 0 | 2 | 0 | 2 | 0 |
| T28 | 2 | 0 | 2 | 0 | 2 | 0 | 2 | 0 | 0 | 2 | 2 | 0 | 2 | 0 | 2 | 0 | 2 | 0 |
| T29 | 2 | 0 | 2 | 0 | 2 | 0 | 2 | 0 | 2 | 0 | 1 | 1 | 2 | 0 | 2 | 0 | 2 | 0 |
| T30 | 1 | 1 | 2 | 0 | 2 | 0 | 2 | 0 | 1 | 1 | 1 | 1 | 2 | 0 | 2 | 0 | 2 | 0 |
| T31 | 2 | 0 | 2 | 0 | 2 | 0 | 2 | 0 | 1 | 1 | 1 | 1 | 2 | 0 | 2 | 0 | 2 | 0 |
| T32 | 2 | 0 | 2 | 0 | 2 | 0 | 2 | 0 | 2 | 0 | 1 | 1 | 1 | 1 | 2 | 0 | 2 | 0 |
| T33 | 2 | 0 | 2 | 0 | 2 | 0 | 2 | 0 | 1 | 1 | 1 | 1 | 2 | 0 | 2 | 0 | 2 | 0 |
| T34 | 2 | 0 | 2 | 0 | 2 | 0 | 2 | 0 | 0 | 2 | 2 | 0 | 2 | 0 | 2 | 0 | 2 | 0 |
| T35 | 2 | 0 | 2 | 0 | 2 | 0 | 2 | 0 | 0 | 2 | 2 | 0 | 2 | 0 | 2 | 0 | 2 | 0 |
| T36 | 2 | 0 | 2 | 0 | 2 | 0 | 2 | 0 | 1 | 1 | 2 | 0 | 1 | 1 | 2 | 0 | 2 | 0 |
| T37 | 2 | 0 | 2 | 0 | 2 | 0 | 2 | 0 | 2 | 0 | 1 | 1 | 1 | 1 | 2 | 0 | 2 | 0 |
| T38 | 2 | 0 | 2 | 0 | 2 | 0 | 2 | 0 | 1 | 1 | 2 | 0 | 2 | 0 | 1 | 1 | 1 | 1 |
| T39 | 2 | 0 | 2 | 0 | 2 | 0 | 2 | 0 | 2 | 0 | 2 | 0 | 1 | 1 | 1 | 1 | 1 | 1 |
| T40 | 2 | 0 | 2 | 0 | 2 | 0 | 2 | 0 | 1 | 1 | 2 | 0 | 0 | 2 | 2 | 0 | 2 | 0 |
| T41 | 2 | 0 | 2 | 0 | 2 | 0 | 2 | 0 | 2 | 0 | 2 | 0 | 0 | 2 | 2 | 0 | 2 | 0 |
| T42 | 2 | 0 | 2 | 0 | 2 | 0 | 2 | 0 | 2 | 0 | 1 | 1 | 2 | 0 | 2 | 0 | 2 | 0 |
| T43 | 2 | 0 | 2 | 0 | 2 | 0 | 2 | 0 | 2 | 0 | 1 | 1 | 0 | 2 | 2 | 0 | 2 | 0 |
| T44 | 2 | 0 | 1 | 1 | 2 | 0 | 1 | 1 | 2 | 0 | 1 | 1 | 2 | 0 | 2 | 0 | 0 | 2 |
| T45 | 2 | 0 | 2 | 0 | 2 | 0 | 2 | 0 | 0 | 2 | 2 | 0 | 2 | 0 | 2 | 0 | 2 | 0 |
| T46 | 2 | 0 | 2 | 0 | 2 | 0 | 2 | 0 | 1 | 1 | 1 | 1 | 2 | 0 | 2 | 0 | 2 | 0 |
| T47 | 2 | 0 | 2 | 0 | 2 | 0 | 2 | 0 | 1 | 1 | 1 | 1 | 2 | 0 | 2 | 0 | 2 | 0 |
| T48 | 2 | 0 | 2 | 0 | 2 | 0 | 2 | 0 | 2 | 0 | 0 | 2 | 2 | 0 | 2 | 0 | 2 | 0 |

| | exon 9 160602 | | exon 10 303073 | | exon 10 302972 | | exon 10 302848 | | exon 10 302699 | | exon 10 302681 | | exon 10 302556 | |
|---|---|---|---|---|---|---|---|---|---|---|---|---|---|---|
| | G | C | T | C | G | T | A | G | T | C | C | T | A | G |
| | 0.99 | 0.01 | 1.00 | 0.00 | 0.93 | 0.07 | 0.91 | 0.09 | 0.88 | 0.12 | 1.00 | 0.00 | 0.85 | 0.15 |
| T1 | 2 | 0 | 2 | 0 | 2 | 0 | 1 | 1 | 2 | 0 | 2 | 0 | 2 | 0 |
| T2 | 2 | 0 | 2 | 0 | 2 | 0 | 1 | 1 | 2 | 0 | 2 | 0 | 2 | 0 |
| T3 | 2 | 0 | 2 | 0 | 2 | 0 | 2 | 0 | 1 | 1 | 2 | 0 | 1 | 1 |
| T4 | 2 | 0 | 2 | 0 | 2 | 0 | 2 | 0 | 2 | 0 | 2 | 0 | 2 | 0 |
| T5 | 2 | 0 | 2 | 0 | 2 | 0 | 2 | 0 | 2 | 0 | 2 | 0 | 2 | 0 |
| T6 | 2 | 0 | 2 | 0 | 2 | 0 | 2 | 0 | 2 | 0 | 2 | 0 | 2 | 0 |
| T7 | 2 | 0 | 2 | 0 | 2 | 0 | 2 | 0 | 2 | 0 | 2 | 0 | 2 | 0 |
| T8 | 2 | 0 | 2 | 0 | 2 | 0 | 2 | 0 | 2 | 0 | 2 | 0 | 2 | 0 |
| T9 | 2 | 0 | 2 | 0 | 2 | 0 | 2 | 0 | 2 | 0 | 2 | 0 | 2 | 0 |
| T10 | 2 | 0 | 2 | 0 | 1 | 1 | 2 | 0 | 1 | 1 | 2 | 0 | 1 | 1 |
| T11 | 2 | 0 | 2 | 0 | 2 | 0 | 2 | 0 | 2 | 0 | 2 | 0 | 2 | 0 |
| T12 | 2 | 0 | 2 | 0 | 1 | 1 | 2 | 0 | 1 | 1 | 2 | 0 | 1 | 1 |
| T13 | 1 | 1 | 2 | 0 | 2 | 0 | 2 | 0 | 1 | 1 | 2 | 0 | 1 | 1 |
| T14 | 2 | 0 | 2 | 0 | 1 | 1 | 2 | 0 | 1 | 1 | 2 | 0 | 1 | 1 |
| T15 | 2 | 0 | 2 | 0 | 2 | 0 | 2 | 0 | 2 | 0 | 2 | 0 | 2 | 0 |
| T16 | 2 | 0 | 2 | 0 | 2 | 0 | 2 | 0 | 2 | 0 | 2 | 0 | 2 | 0 |
| T17 | 2 | 0 | 2 | 0 | 2 | 0 | 2 | 0 | 2 | 0 | 2 | 0 | 2 | 0 |
| T18 | 2 | 0 | 2 | 0 | 2 | 0 | n/a | n/a | 2 | 0 | 2 | 0 | 1 | 1 |
| T19 | 2 | 0 | 2 | 0 | 2 | 0 | n/a | n/a | 2 | 0 | 2 | 0 | 2 | 0 |
| T20 | 2 | 0 | 2 | 0 | 2 | 0 | 1 | 1 | 2 | 0 | 2 | 0 | 2 | 0 |
| T21 | 2 | 0 | 2 | 0 | 2 | 0 | n/a | n/a | 2 | 0 | 2 | 0 | 2 | 0 |
| T22 | 2 | 0 | 2 | 0 | 2 | 0 | n/a | n/a | 2 | 0 | 2 | 0 | 2 | 0 |
| T23 | 2 | 0 | 2 | 0 | 2 | 0 | 2 | 0 | 2 | 0 | 2 | 0 | 2 | 0 |
| T24 | 2 | 0 | 2 | 0 | 2 | 0 | n/a | n/a | 2 | 0 | 2 | 0 | 2 | 0 |
| T25 | 2 | 0 | 2 | 0 | 2 | 0 | 2 | 0 | 2 | 0 | 2 | 0 | 2 | 0 |
| T26 | 2 | 0 | 2 | 0 | 2 | 0 | 1 | 1 | 2 | 0 | 2 | 0 | 2 | 0 |
| T27 | 2 | 0 | 2 | 0 | 2 | 0 | 2 | 0 | 2 | 0 | 2 | 0 | 2 | 0 |
| T28 | 2 | 0 | 2 | 0 | 2 | 0 | 2 | 0 | 2 | 0 | 2 | 0 | 2 | 0 |
| T29 | 2 | 0 | 2 | 0 | 2 | 0 | 2 | 0 | 2 | 0 | 2 | 0 | 2 | 0 |
| T30 | 2 | 0 | 2 | 0 | 1 | 1 | 2 | 0 | 1 | 1 | 2 | 0 | 1 | 1 |
| T31 | 2 | 0 | 2 | 0 | 2 | 0 | 2 | 0 | 1 | 1 | 2 | 0 | 1 | 1 |
| T32 | 2 | 0 | 2 | 0 | 2 | 0 | 2 | 0 | 2 | 0 | 2 | 0 | 2 | 0 |
| T33 | 2 | 0 | 2 | 0 | 2 | 0 | 1 | 1 | 2 | 0 | 2 | 0 | 2 | 0 |
| T34 | 2 | 0 | 2 | 0 | 2 | 0 | 1 | 1 | 2 | 0 | 2 | 0 | 2 | 0 |
| T35 | 2 | 0 | 2 | 0 | 2 | 0 | 2 | 0 | 2 | 0 | 2 | 0 | 2 | 0 |
| T36 | 2 | 0 | 2 | 0 | 2 | 0 | 2 | 0 | 2 | 0 | 2 | 0 | 2 | 0 |
| T37 | 2 | 0 | 2 | 0 | 2 | 0 | 2 | 0 | 2 | 0 | 2 | 0 | 2 | 0 |
| T38 | 2 | 0 | 2 | 0 | 2 | 0 | 2 | 0 | 1 | 1 | 2 | 0 | 1 | 1 |
| T39 | 2 | 0 | 2 | 0 | 2 | 0 | 1 | 1 | 1 | 1 | 2 | 0 | 1 | 1 |
| T40 | 2 | 0 | 2 | 0 | 2 | 0 | 2 | 0 | 2 | 0 | 2 | 0 | 2 | 0 |
| T41 | 2 | 0 | 2 | 0 | 2 | 0 | 2 | 0 | 2 | 0 | 2 | 0 | 2 | 0 |
| T42 | 2 | 0 | 2 | 0 | 1 | 1 | 2 | 0 | 2 | 0 | 2 | 0 | 1 | 1 |
| T43 | 2 | 0 | 2 | 0 | 1 | 1 | 2 | 0 | 1 | 1 | 2 | 0 | 1 | 1 |
| T44 | 2 | 0 | 2 | 0 | n/a | n/a | n/a | n/a | 2 | 0 | 2 | 0 | 1 | 1 |
| T45 | 2 | 0 | 2 | 0 | 2 | 0 | n/a | n/a | 1 | 1 | 2 | 0 | 1 | 1 |
| T46 | 2 | 0 | 2 | 0 | 2 | 0 | 2 | 0 | 2 | 0 | 2 | 0 | 2 | 0 |
| T47 | 2 | 0 | 2 | 0 | 2 | 0 | n/a | n/a | 2 | 0 | 2 | 0 | 2 | 0 |
| T48 | 2 | 0 | n/a | n/a | n/a | n/a | n/a | n/a | n/a | n/a | n/a | n/a | n/a | n/a |

| | exon -7 49904 | | exon -7 49934 | | exon -7 49994 | | exon -7 49671 | | exon -5 83980 | | exon -4 85938 | | exon -2 89837 | | exon -2 89889 | | exon -2 90090 | |
|---|---|---|---|---|---|---|---|---|---|---|---|---|---|---|---|---|---|---|
| | A | G | C | A | A | G | A | T | G | A | G | A | C | T | T | C | T | C |
| | 96 | 0 | 96 | 0 | 94 | 0 | 94 | 2 | 52 | 0 | 67 | 27 | 75 | 13 | 92 | 0 | 94 | 0 |
| | 1.00 | 0.00 | 1.00 | 0.00 | 1.00 | 0.00 | 0.98 | 0.02 | 1.00 | 0.00 | 0.70 | 0.30 | 0.83 | 0.17 | 0.99 | 0.01 | 0.99 | 0.01 |
| B1 | 2 | 0 | 2 | 0 | 2 | 0 | 2 | 0 | 2 | 0 | 2 | 0 | 1 | 1 | 2 | 0 | 2 | 0 |
| B2 | 2 | 0 | 2 | 0 | 2 | 0 | 2 | 0 | n/a | n/a | 2 | 0 | 2 | 0 | 2 | 0 | 2 | 0 |
| B3 | 2 | 0 | 2 | 0 | 2 | 0 | 2 | 0 | n/a | n/a | 1 | 1 | 2 | 0 | 2 | 0 | 2 | 0 |
| B4 | 2 | 0 | 2 | 0 | 2 | 0 | 2 | 0 | n/a | n/a | 2 | 0 | 2 | 0 | 2 | 0 | 2 | 0 |
| B5 | 2 | 0 | 2 | 0 | 2 | 0 | 2 | 0 | n/a | n/a | 2 | 0 | 2 | 0 | 2 | 0 | 2 | 0 |
| B6 | 2 | 0 | 2 | 0 | 2 | 0 | 2 | 0 | n/a | n/a | 1 | 1 | 1 | 1 | 2 | 0 | 2 | 0 |
| B7 | 2 | 0 | 2 | 0 | 2 | 0 | 2 | 0 | n/a | n/a | 2 | 0 | 1 | 1 | 2 | 0 | 2 | 0 |
| B8 | 2 | 0 | 2 | 0 | 2 | 0 | 2 | 0 | 2 | 0 | 2 | 0 | 1 | 1 | 2 | 0 | 2 | 0 |
| B9 | 2 | 0 | 2 | 0 | 2 | 0 | 2 | 0 | n/a | n/a | 1 | 1 | 2 | 0 | 2 | 0 | 2 | 0 |
| B10 | 2 | 0 | 2 | 0 | 2 | 0 | 2 | 0 | 2 | 0 | 1 | 1 | 2 | 0 | 2 | 0 | 2 | 0 |
| B11 | 2 | 0 | 2 | 0 | 2 | 0 | 2 | 0 | n/a | n/a | 2 | 0 | 2 | 0 | 2 | 0 | 2 | 0 |
| B12 | 2 | 0 | 2 | 0 | 2 | 0 | 2 | 0 | n/a | n/a | 1 | 1 | 2 | 0 | 2 | 0 | 2 | 0 |
| B13 | 2 | 0 | 2 | 0 | 2 | 0 | 2 | 0 | 2 | 0 | 1 | 1 | 1 | 1 | 2 | 0 | 2 | 0 |
| B14 | 2 | 0 | 2 | 0 | 2 | 0 | 2 | 0 | n/a | n/a | 0 | 2 | 2 | 0 | 2 | 0 | 2 | 0 |
| B15 | 2 | 0 | 2 | 0 | 2 | 0 | 2 | 0 | n/a | n/a | 1 | 1 | 2 | 0 | n/a | n/a | 2 | 0 |
| B16 | n/a | n/a | n/a | n/a | n/a | n/a | n/a | n/a | n/a | n/a | 2 | 0 | 2 | 0 | 2 | 0 | 2 | 0 |
| B17 | 2 | 0 | 2 | 0 | 2 | 0 | 2 | 0 | n/a | n/a | 1 | 1 | 2 | 0 | 2 | 0 | 2 | 0 |
| B18 | 2 | 0 | 2 | 0 | 2 | 0 | 2 | 0 | 2 | 0 | 2 | 0 | 2 | 0 | 2 | 0 | 2 | 0 |
| B19 | 2 | 0 | 2 | 0 | 2 | 0 | 2 | 0 | n/a | n/a | 2 | 0 | 1 | 1 | 2 | 0 | 2 | 0 |
| B20 | 2 | 0 | 2 | 0 | 2 | 0 | 2 | 0 | n/a | n/a | 0 | 2 | 2 | 0 | 2 | 0 | 2 | 0 |
| B21 | 2 | 0 | 2 | 0 | 2 | 0 | 2 | 0 | 2 | 0 | 1 | 1 | 2 | 0 | 2 | 0 | 2 | 0 |
| B22 | 2 | 0 | 2 | 0 | 2 | 0 | 0 | 2 | 2 | 0 | n/a | n/a | 2 | 0 | 2 | 0 | 2 | 0 |
| B23 | 2 | 0 | 2 | 0 | 2 | 0 | 2 | 0 | 2 | 0 | 2 | 0 | 2 | 0 | 2 | 0 | 2 | 0 |
| B24 | 2 | 0 | 2 | 0 | 2 | 0 | 2 | 0 | 2 | 0 | 0 | 2 | 2 | 0 | 2 | 0 | 2 | 0 |
| B25 | 2 | 0 | 2 | 0 | 2 | 0 | 2 | 0 | 2 | 0 | 0 | 2 | 2 | 0 | 2 | 0 | 2 | 0 |
| B26 | 2 | 0 | 2 | 0 | 2 | 0 | 2 | 0 | 2 | 0 | 2 | 0 | 2 | 0 | 2 | 0 | 2 | 0 |
| B27 | 2 | 0 | 2 | 0 | 2 | 0 | 2 | 0 | 2 | 0 | 1 | 1 | 2 | 0 | 2 | 0 | 1 | 1 |
| B28 | 2 | 0 | 2 | 0 | 2 | 0 | 2 | 0 | 2 | 0 | 0 | 2 | 1 | 1 | 2 | 0 | 2 | 0 |
| B29 | 2 | 0 | 2 | 0 | 2 | 0 | 2 | 0 | n/a | n/a | 2 | 0 | 1 | 1 | 2 | 0 | 2 | 0 |
| B30 | 2 | 0 | 2 | 0 | 2 | 0 | 2 | 0 | n/a | n/a | 2 | 0 | 2 | 0 | 2 | 0 | 2 | 0 |
| B31 | 2 | 0 | 2 | 0 | 2 | 0 | 2 | 0 | 2 | 0 | n/a | n/a | 2 | 0 | 2 | 0 | 2 | 0 |
| B32 | 2 | 0 | 2 | 0 | 2 | 0 | 2 | 0 | 2 | 0 | 2 | 0 | 1 | 1 | 2 | 0 | 2 | 0 |
| B33 | n/a | n/a | n/a | n/a | n/a | n/a | n/a | n/a | n/a | n/a | 1 | 1 | 2 | 0 | 2 | 0 | 2 | 0 |
| B34 | 2 | 0 | 2 | 0 | 2 | 0 | 2 | 0 | 2 | 0 | 2 | 0 | 2 | 0 | 2 | 0 | 2 | 0 |
| B35 | 2 | 0 | 2 | 0 | 2 | 0 | 2 | 0 | n/a | n/a | 2 | 0 | 2 | 0 | 2 | 0 | 2 | 0 |
| B36 | 2 | 0 | 2 | 0 | 2 | 0 | 2 | 0 | 2 | 0 | n/a | n/a | 1 | 1 | 2 | 0 | 2 | 0 |
| B37 | 2 | 0 | 2 | 0 | 2 | 0 | 2 | 0 | n/a | n/a | 2 | 0 | 1 | 1 | 2 | 0 | 2 | 0 |
| B38 | 2 | 0 | 2 | 0 | 2 | 0 | 2 | 0 | n/a | n/a | 1 | 1 | 2 | 0 | 2 | 0 | 2 | 0 |
| B39 | 2 | 0 | 2 | 0 | 2 | 0 | 2 | 0 | 2 | 0 | 2 | 0 | 1 | 1 | 2 | 0 | 2 | 0 |
| B40 | 2 | 0 | 2 | 0 | 2 | 0 | 2 | 0 | n/a | n/a | 1 | 1 | 1 | 1 | 2 | 0 | 2 | 0 |
| B41 | 2 | 0 | 2 | 0 | 2 | 0 | 2 | 0 | n/a | n/a | 2 | 0 | 1 | 1 | 2 | 0 | 2 | 0 |
| B42 | 2 | 0 | 2 | 0 | 2 | 0 | 2 | 0 | 2 | 0 | 2 | 0 | 2 | 0 | 2 | 0 | 2 | 0 |
| B43 | 2 | 0 | 2 | 0 | 2 | 0 | 2 | 0 | n/a | n/a | 2 | 0 | 1 | 1 | 2 | 0 | 2 | 0 |
| B44 | 2 | 0 | 2 | 0 | 2 | 0 | 2 | 0 | n/a | n/a | n/a | n/a | 2 | 0 | 2 | 0 | 2 | 0 |
| B45 | 2 | 0 | 2 | 0 | 2 | 0 | 2 | 0 | n/a | n/a | 1 | 1 | 2 | 0 | 2 | 0 | 2 | 0 |
| B46 | 2 | 0 | 2 | 0 | 2 | 0 | 2 | 0 | 2 | 0 | 1 | 1 | 2 | 0 | 2 | 0 | 2 | 0 |
| B47 | 2 | 0 | 2 | 0 | 2 | 0 | 2 | 0 | 2 | 0 | 2 | 0 | 2 | 0 | 2 | 0 | 2 | 0 |
| B48 | 2 | 0 | 2 | 0 | 2 | 0 | 2 | 0 | n/a | n/a | 1 | 1 | 1 | 1 | 1 | 1 | 2 | 0 |
| | 92 | 0 | 92 | 0 | 92 | 0 | 90 | 2 | 42 | 0 | 62 | 26 | 80 | 16 | 93 | 1 | 95 | 1 |

| | intron 3 126711 | | exon 5 130189 | | intron 7 154138 | | intron 7 154202 | | exon 8 154431 | | exon 9 160052 | | exon 9 160089 | | exon 9 160165 | | exon 9 160376 | |
|---|---|---|---|---|---|---|---|---|---|---|---|---|---|---|---|---|---|---|
| | A | G | G | A | G | A | A | G | G | A | A | G | A | G | A | G | C | G |
| | 94 | 2 | 95 | 1 | 93 | 3 | 94 | 2 | 61 | 35 | 61 | 35 | 80 | 16 | 88 | 8 | 87 | 9 |
| | 1.00 | 0.00 | 0.98 | 0.02 | 0.97 | 0.03 | 0.97 | 0.03 | 0.67 | 0.33 | 0.60 | 0.40 | 0.85 | 0.15 | 0.91 | 0.09 | 0.90 | 0.10 |
| B1 | 2 | 0 | 2 | 0 | 2 | 0 | 2 | 0 | 1 | 1 | 1 | 1 | 2 | 0 | 2 | 0 | 2 | 0 |
| B2 | 2 | 0 | 1 | 1 | 2 | 0 | 1 | 1 | 2 | 0 | 1 | 1 | 2 | 0 | 2 | 0 | 1 | 1 |
| B3 | 2 | 0 | 2 | 0 | 2 | 0 | 2 | 0 | 2 | 0 | 1 | 1 | 2 | 0 | 1 | 1 | 2 | 0 |
| B4 | 2 | 0 | 2 | 0 | 1 | 1 | 2 | 0 | 1 | 1 | 1 | 1 | 2 | 0 | 2 | 0 | 2 | 0 |
| B5 | 2 | 0 | 2 | 0 | 2 | 0 | 2 | 0 | 2 | 0 | 0 | 2 | 2 | 0 | 2 | 0 | 2 | 0 |
| B6 | 2 | 0 | 2 | 0 | 2 | 0 | 2 | 0 | 1 | 1 | 2 | 0 | 1 | 1 | 2 | 0 | 2 | 0 |
| B7 | 2 | 0 | 2 | 0 | 1 | 1 | 2 | 0 | 1 | 1 | 2 | 0 | 1 | 1 | 2 | 0 | 2 | 0 |
| B8 | 2 | 0 | 2 | 0 | 2 | 0 | 2 | 0 | 2 | 0 | 2 | 0 | 1 | 1 | 2 | 0 | 2 | 0 |
| B9 | 2 | 0 | 2 | 0 | 2 | 0 | 2 | 0 | 2 | 0 | 1 | 1 | 2 | 0 | 1 | 1 | 2 | 0 |
| B10 | 2 | 0 | 2 | 0 | 2 | 0 | 2 | 0 | 0 | 2 | 2 | 0 | 2 | 0 | 2 | 0 | 2 | 0 |
| B11 | 2 | 0 | 2 | 0 | 2 | 0 | 2 | 0 | 2 | 0 | 0 | 2 | 2 | 0 | 2 | 0 | 2 | 0 |
| B12 | 2 | 0 | 2 | 0 | 2 | 0 | 1 | 1 | 2 | 0 | 1 | 1 | 2 | 0 | 2 | 0 | 2 | 0 |
| B13 | 2 | 0 | 2 | 0 | 2 | 0 | 2 | 0 | 2 | 0 | 2 | 0 | 1 | 1 | 1 | 1 | 1 | 1 |
| B14 | 2 | 0 | 2 | 0 | 2 | 0 | 2 | 0 | 1 | 1 | 1 | 1 | 2 | 0 | 2 | 0 | 2 | 0 |
| B15 | 2 | 0 | 2 | 0 | 2 | 0 | 2 | 0 | 0 | 2 | 2 | 0 | 2 | 0 | 2 | 0 | 2 | 0 |
| B16 | 2 | 0 | 2 | 0 | 2 | 0 | 2 | 0 | 2 | 0 | 0 | 2 | 2 | 0 | 2 | 0 | 2 | 0 |
| B17 | 2 | 0 | 2 | 0 | 2 | 0 | 2 | 0 | 1 | 1 | 1 | 1 | 2 | 0 | 2 | 0 | 2 | 0 |
| B18 | 2 | 0 | 2 | 0 | 2 | 0 | 2 | 0 | 1 | 1 | 1 | 1 | 2 | 0 | 2 | 0 | 2 | 0 |
| B19 | 2 | 0 | 2 | 0 | 2 | 0 | 2 | 0 | 1 | 1 | 1 | 1 | 2 | 0 | 2 | 0 | 2 | 0 |
| B20 | 2 | 0 | 2 | 0 | 2 | 0 | 2 | 0 | 0 | 2 | 2 | 0 | 2 | 0 | 2 | 0 | 2 | 0 |
| B21 | 2 | 0 | 2 | 0 | 2 | 0 | 2 | 0 | 1 | 1 | 1 | 1 | 2 | 0 | 2 | 0 | 2 | 0 |
| B22 | 2 | 0 | 2 | 0 | 2 | 0 | 2 | 0 | 2 | 0 | 2 | 0 | 2 | 0 | 0 | 2 | 0 | 2 |
| B23 | 2 | 0 | 2 | 0 | 2 | 0 | 2 | 0 | 2 | 0 | 0 | 2 | 2 | 0 | 2 | 0 | 2 | 0 |
| B24 | 2 | 0 | 2 | 0 | 2 | 0 | 2 | 0 | 2 | 0 | 2 | 0 | 2 | 0 | 0 | 2 | 0 | 2 |
| B25 | 2 | 0 | 2 | 0 | 2 | 0 | 2 | 0 | 0 | 2 | 2 | 0 | 2 | 0 | 2 | 0 | 2 | 0 |
| B26 | 2 | 0 | 2 | 0 | 2 | 0 | 2 | 0 | 1 | 1 | 1 | 1 | 2 | 0 | 2 | 0 | 2 | 0 |
| B27 | 2 | 0 | 2 | 0 | 2 | 0 | 2 | 0 | 1 | 1 | 1 | 1 | 2 | 0 | 2 | 0 | 2 | 0 |
| B28 | 2 | 0 | 2 | 0 | 2 | 0 | 2 | 0 | 0 | 2 | 2 | 0 | 2 | 0 | 2 | 0 | 2 | 0 |
| B29 | 2 | 0 | 2 | 0 | 2 | 0 | 2 | 0 | 2 | 0 | 1 | 1 | 1 | 1 | 2 | 0 | 2 | 0 |
| B30 | 2 | 0 | 2 | 0 | 2 | 0 | 2 | 0 | 1 | 1 | 1 | 1 | 2 | 0 | 2 | 0 | 2 | 0 |
| B31 | 2 | 0 | 2 | 0 | 2 | 0 | 2 | 0 | 1 | 1 | 1 | 1 | 2 | 0 | 2 | 0 | 2 | 0 |
| B32 | 2 | 0 | 2 | 0 | 2 | 0 | 2 | 0 | 2 | 0 | 1 | 1 | 1 | 1 | 2 | 0 | 2 | 0 |
| B33 | 2 | 0 | 2 | 0 | 2 | 0 | 2 | 0 | 1 | 1 | 1 | 1 | 2 | 0 | 2 | 0 | 2 | 0 |
| B34 | 2 | 0 | 2 | 0 | 2 | 0 | 2 | 0 | 1 | 1 | 1 | 1 | 2 | 0 | 2 | 0 | 2 | 0 |
| B35 | 2 | 0 | 2 | 0 | 2 | 0 | 2 | 0 | 2 | 0 | 0 | 2 | 2 | 0 | 2 | 0 | 2 | 0 |
| B36 | 2 | 0 | 2 | 0 | 2 | 0 | 2 | 0 | 1 | 1 | 2 | 0 | 1 | 1 | 2 | 0 | 2 | 0 |
| B37 | 2 | 0 | 2 | 0 | 2 | 0 | 2 | 0 | 2 | 0 | 1 | 1 | 1 | 1 | 2 | 0 | 2 | 0 |
| B38 | 2 | 0 | 2 | 0 | 1 | 1 | 2 | 0 | 1 | 1 | 2 | 0 | 2 | 0 | 1 | 1 | 1 | 1 |
| B39 | 2 | 0 | 2 | 0 | 2 | 0 | 2 | 0 | 2 | 0 | 2 | 0 | 1 | 1 | 1 | 1 | 1 | 1 |
| B40 | 2 | 0 | 2 | 0 | 2 | 0 | 2 | 0 | 1 | 1 | 2 | 0 | 0 | 2 | 2 | 0 | 2 | 0 |
| B41 | 2 | 0 | 2 | 0 | 2 | 0 | 2 | 0 | 2 | 0 | 2 | 0 | 0 | 2 | 2 | 0 | 2 | 0 |
| B42 | 2 | 0 | 2 | 0 | 2 | 0 | 2 | 0 | 2 | 0 | 0 | 2 | 2 | 0 | 2 | 0 | 2 | 0 |
| B43 | 2 | 0 | 2 | 0 | 2 | 0 | 2 | 0 | 2 | 0 | 1 | 1 | 1 | 1 | 2 | 0 | 2 | 0 |
| B44 | 2 | 0 | 1 | 1 | 2 | 0 | 1 | 1 | 2 | 0 | 1 | 1 | 2 | 0 | 2 | 0 | 0 | 2 |
| B45 | 2 | 0 | 2 | 0 | 2 | 0 | 2 | 0 | 0 | 2 | 2 | 0 | 2 | 0 | 2 | 0 | 2 | 0 |
| B46 | 2 | 0 | 2 | 0 | 2 | 0 | 2 | 0 | 1 | 1 | 1 | 1 | 2 | 0 | 2 | 0 | 2 | 0 |
| B47 | 2 | 0 | 2 | 0 | 2 | 0 | 2 | 0 | 2 | 0 | 0 | 2 | 2 | 0 | 2 | 0 | 2 | 0 |
| B48 | 2 | 0 | 2 | 0 | 2 | 0 | 2 | 0 | 1 | 1 | 1 | 1 | 2 | 0 | 2 | 0 | 2 | 0 |
| | 96 | 0 | 94 | 2 | 93 | 3 | 93 | 3 | 64 | 32 | 58 | 38 | 82 | 14 | 87 | 9 | 86 | 10 |

| | exon 9 160602 | | exon 10 303073 | | exon 10 302972 | | exon 10 302848 | | exon 10 302699 | | exon 10 302681 | | exon 10 302556 | |
|---|---|---|---|---|---|---|---|---|---|---|---|---|---|---|
| | G | C | T | C | G | T | A | G | T | C | C | T | A | G |
| | 95 | 1 | 94 | 0 | 86 | 6 | 71 | 7 | 83 | 11 | 94 | 0 | 80 | 14 |
| | 0.99 | 0.01 | 1.00 | 0.00 | 0.92 | 0.08 | 0.93 | 0.07 | 0.90 | 0.10 | 1.00 | 0.00 | 0.83 | 0.17 |
| B1 | 2 | 0 | n/a | n/a | n/a | n/a | n/a | n/a | 2 | 0 | 2 | 0 | 2 | 0 |
| B2 | 2 | 0 | 2 | 0 | 2 | 0 | 1 | 1 | 2 | 0 | 2 | 0 | 2 | 0 |
| B3 | 2 | 0 | 2 | 0 | 2 | 0 | 2 | 0 | 1 | 1 | 2 | 0 | 1 | 1 |
| B4 | 2 | 0 | 2 | 0 | 2 | 0 | 2 | 0 | 2 | 0 | 2 | 0 | 2 | 0 |
| B5 | 2 | 0 | 2 | 0 | 2 | 0 | 2 | 0 | 2 | 0 | 2 | 0 | 2 | 0 |
| B6 | 2 | 0 | n/a | n/a | n/a | n/a | n/a | n/a | 2 | 0 | 2 | 0 | n/a | n/a |
| B7 | 2 | 0 | 2 | 0 | 2 | 0 | 2 | 0 | 2 | 0 | 2 | 0 | 2 | 0 |
| B8 | 2 | 0 | 2 | 0 | 2 | 0 | 2 | 0 | 2 | 0 | 2 | 0 | 2 | 0 |
| B9 | 2 | 0 | 2 | 0 | 2 | 0 | 2 | 0 | 2 | 0 | 2 | 0 | 2 | 0 |
| B10 | 2 | 0 | 2 | 0 | 1 | 1 | 2 | 0 | 1 | 1 | 2 | 0 | 1 | 1 |
| B11 | 2 | 0 | 2 | 0 | 2 | 0 | 2 | 0 | 2 | 0 | 2 | 0 | 2 | 0 |
| B12 | 2 | 0 | 2 | 0 | 1 | 1 | 2 | 0 | 1 | 1 | 2 | 0 | 1 | 1 |
| B13 | 1 | 1 | 2 | 0 | 2 | 0 | n/a | n/a | 2 | 0 | 2 | 0 | 1 | 1 |
| B14 | 2 | 0 | n/a | n/a | n/a | n/a | n/a | n/a | 1 | 1 | 2 | 0 | 1 | 1 |
| B15 | 2 | 0 | 2 | 0 | 2 | 0 | 2 | 0 | 2 | 0 | 2 | 0 | 2 | 0 |
| B16 | 2 | 0 | n/a | n/a | n/a | n/a | n/a | n/a | 2 | 0 | 2 | 0 | 1 | 1 |
| B17 | 2 | 0 | 2 | 0 | 2 | 0 | 2 | 0 | 2 | 0 | 2 | 0 | 2 | 0 |
| B18 | 2 | 0 | 2 | 0 | 2 | 0 | 2 | 0 | 2 | 0 | 2 | 0 | 1 | 1 |
| B19 | 2 | 0 | 2 | 0 | 2 | 0 | 2 | 0 | 2 | 0 | 2 | 0 | 2 | 0 |
| B20 | 2 | 0 | 2 | 0 | 2 | 0 | 2 | 0 | 2 | 0 | 2 | 0 | 2 | 0 |
| B21 | 2 | 0 | 2 | 0 | 2 | 0 | 2 | 0 | 2 | 0 | 2 | 0 | 2 | 0 |
| B22 | 2 | 0 | n/a | n/a | n/a | n/a | n/a | n/a | n/a | n/a | n/a | n/a | n/a | n/a |
| B23 | 2 | 0 | 2 | 0 | 2 | 0 | 2 | 0 | 2 | 0 | 2 | 0 | 2 | 0 |
| B24 | 2 | 0 | 2 | 0 | 2 | 0 | 2 | 0 | 2 | 0 | 2 | 0 | 2 | 0 |
| B25 | 2 | 0 | 2 | 0 | 2 | 0 | 2 | 0 | 2 | 0 | 2 | 0 | 2 | 0 |
| B26 | 2 | 0 | 2 | 0 | 2 | 0 | 1 | 1 | 2 | 0 | 2 | 0 | 2 | 0 |
| B27 | 2 | 0 | 2 | 0 | 2 | 0 | 2 | 0 | 2 | 0 | 2 | 0 | 2 | 0 |
| B28 | 2 | 0 | n/a | n/a | n/a | n/a | n/a | n/a | n/a | n/a | n/a | n/a | n/a | n/a |
| B29 | 2 | 0 | 2 | 0 | 2 | 0 | 2 | 0 | 2 | 0 | 2 | 0 | 2 | 0 |
| B30 | 2 | 0 | 2 | 0 | 1 | 1 | 2 | 0 | 1 | 1 | 2 | 0 | 1 | 1 |
| B31 | 2 | 0 | 2 | 0 | 2 | 0 | 2 | 0 | 1 | 1 | 2 | 0 | 1 | 1 |
| B32 | 2 | 0 | 2 | 0 | 2 | 0 | 2 | 0 | 2 | 0 | 2 | 0 | 2 | 0 |
| B33 | 2 | 0 | 2 | 0 | 2 | 0 | 1 | 1 | 2 | 0 | 2 | 0 | 2 | 0 |
| B34 | 2 | 0 | 2 | 0 | 2 | 0 | 1 | 1 | 2 | 0 | 2 | 0 | 2 | 0 |
| B35 | 2 | 0 | 2 | 0 | 2 | 0 | 2 | 0 | 2 | 0 | 2 | 0 | 2 | 0 |
| B36 | 2 | 0 | 2 | 0 | 2 | 0 | 2 | 0 | 2 | 0 | 2 | 0 | 2 | 0 |
| B37 | 2 | 0 | n/a | n/a | 2 | 0 | n/a | n/a | 2 | 0 | 2 | 0 | 1 | 1 |
| B38 | 2 | 0 | n/a | n/a | n/a | n/a | n/a | n/a | 2 | 0 | 2 | 0 | 2 | 0 |
| B39 | 2 | 0 | n/a | n/a | n/a | n/a | n/a | n/a | n/a | n/a | n/a | n/a | n/a | n/a |
| B40 | 2 | 0 | 2 | 0 | 2 | 0 | 2 | 0 | 2 | 0 | 2 | 0 | 2 | 0 |
| B41 | 2 | 0 | 2 | 0 | 2 | 0 | 2 | 0 | 2 | 0 | 2 | 0 | 2 | 0 |
| B42 | 2 | 0 | 2 | 0 | 1 | 1 | 2 | 0 | 1 | 1 | 2 | 0 | 1 | 1 |
| B43 | 2 | 0 | 2 | 0 | 1 | 1 | 2 | 0 | 1 | 1 | 2 | 0 | 1 | 1 |
| B44 | 2 | 0 | 2 | 0 | 2 | 0 | 2 | 0 | 2 | 0 | 2 | 0 | 1 | 1 |
| B45 | 2 | 0 | 2 | 0 | 1 | 1 | 2 | 0 | 1 | 1 | 2 | 0 | 1 | 1 |
| B46 | 2 | 0 | n/a | n/a | n/a | n/a | n/a | n/a | n/a | n/a | n/a | n/a | n/a | n/a |
| B47 | 2 | 0 | 2 | 0 | 2 | 0 | 1 | 1 | 2 | 0 | 2 | 0 | 2 | 0 |
| B48 | 2 | 0 | n/a | n/a | n/a | n/a | n/a | n/a | n/a | n/a | n/a | n/a | n/a | n/a |
| | 95 | 1 | 74 | 0 | 70 | 6 | 67 | 5 | 77 | 9 | 86 | 0 | 70 | 14 |

ER2 Exons with SNPs (v3.0)

```
ER2 exon -7  (AB006589: 1-199, 49552-49750 of SEQ ID NO: 1)
         CACGCGGGCTTCATAAGCTAGATGCCAGTTAACTGTcgaga
ggggacgctccctcctcgtaggcgtccacactggagaaggaataagatgg
gcgattgcctgggaagcctgacagggcggcggcagctgggatgctggaga
ggactggccccttgAgttactgagtccgatgaatgtgcttgctctgctgg  49671 A/T 3(C,S)*
aggaaccgcgctcaggttacagtcatcccaatatggttctgaagGTGCGT
GGTTCAGGTCACTTAGGACTTGACCAGATACCGGGTTTCTTTTACAAGCC
GTTTCTGACGGTGGCCTGTTTCAACTACTGGCAGAGCTCATGTAAAACAG
ACTTTTAAAAAAATTTGGGGGGCTTTTAGTATTTTTTTCTTATTCCTATA  49904 A/G 3(C,S)
TTCTGAGGATATTTTATAGTAGTCCCACATATGGAATTAGATAATCTCTT
TTTTGTTTGATTAACAGTTTTATCAAGTATAATGTACATACCATAACGTT  49994 A/G 2
CACCCATTTTAATGGATTCAATGATTTTTAGCATATTTACAGAGTGGTGC
AACC

ER2 exon -6 (AB006589: 200-507, 50928-51235 of SEQ ID NO: 1)
      GAAATAAGGTGATACTGGAAGGACCAGGTTTTGGGGGTACAATC
ATAAGTTTGGCTTTAAATGTTTTTAAATACCTTGCCTCTTAGacatccaa
gtggagatatggcatttaaattcatgagattggatgagatcccaccaaag
gaacaggtttaggtggagacaaccaaataccgatgcctaggacactgcag
tgtttagaattcaaggagatgagaaggaaacaggagggaagattgaaaag
aagagtccagtgtgttatgaggaaaaccccaagagcatgctgccttacaa
gacaggtgaaaaatgtgttctgtgaaagaaagagtaattaactgttaaat
gttacagactgatcaaataaaatgaagactgagaatggcctgtttgtaag
GTAATAAAAATACATAAAATCTTATGATAGAAATATTTATACATAAAGTT
AGTAAGGAAACAGTGTTTACTCCTTTTTGTAGAAGTGTAAATTTTTACAA
CCATTTTGAAGGGCAGTTTGATATTATCTACAACTTAAAATTGTGCTTCC
ATTGATAATTTCACCTGT

ER2 exon -5 (AB006589: 508-691, 83858-84041 of SEQ ID NO: 1)
GGCACATAGTAAGCAAATCATAAATGCTGAGTGAATGAAATATTAAATGA
ATAAAAAGGAAATTTTTGTGCTGCTATTGGAAATTAGCTCTCTATATATT
TCAACATGTTACACATATACAATGATCTAAAAACTTGTCTTACTCTTTCC
TATCCACTAGagggagacatcaacctgttgtggaaaagaatgatcactta
aagtctttagaaattctgaaccaactctctagcaggtgatccttgttaga
atttgagcccttaacgctatccaggactggagGttgaagggacgatagag  83980 G/A 3(S)
ggagcaggaggaGAATGCACATGGATTAAGGAGCGAGAACACAGGTGAAC
TTCAGCTTTTTTGCTAACAGTCAGACAAACTACTGACCCTGACTCAGTGA
TGTGCTAGTAAACCAGCTCTTTAAAAAAAAAAAAAAAGCCCTAGATTGCT
GATTTGTATGTAATGTTTATGAATTTCAGTAGAGAAAAAGACAATATTCA
AACTGAGCCATGCACCCAAAACAAGAGAACAGCCAAGAAGTGTTCACTTC
TATCAGTGCCCTGGGTT
```

ER2 exon -4 (AB006589: 692-903, 85942-86154 of SEQ ID NO: 1)

```
                GTCGAAGGGCACACAACTAGGAAGTGTTTGTGCT
GAAAACCCACCCTAGGCCCAAGCCTTGGAACTCCAAGCCTGGGTTCCATC
CCTGCACTGGGCAATTCTGATCTATGTGCGCTAGTTTCCTTGTGTTCTCT
GTTCTCTCCGTAGaaatcctgggctctcttctcccagccacaaggttagg  85938 G/A 2,3(N,C,I,A)
ttgaaaaacagagcagatggaggtagtttgtagcctacaggtgccctgaa
tgaagcttccacagtgctaaagtggaagaacgagggactccaagggaagg
attcaaggctgggcccatgcacctgtgtaattcagaagagaccccagagg
agatcagcgccctctaattagccctgGTAAGGAGCTCTGGGAGTTACTGT
AACTCTCTCAGAAGAACCCAAACATGCGGGAACGTGACTTCTTACCTTCT
GAAAGTCCACAAAATTCCTGATTGCCACCATTAATTTGTC
```

ER2 exon -3 (AB006589: 904-997, 89037-89130 of SEQ ID NO: 1)

```
        GGGGCAGTGGACAGGACAAAAAGTTATTTTTTACCTGTTTGT
TTACAAATAGCAAAGATCAAGACTGAAACACATGAGTGTGATTTAGAAAG
AGTTGGCTGCAGGTGCTGCTTGCTCAGGTGGTTCATTTAAACTGCAGGTC
AGAGCAACCTTGTCTCATGGTCCTGGTGCCCAGGTATCAGGTTGGGTCTG
TCTTGCTGCTTATGTCCTTGTTACCCTCTGAGGGCCCCAGTCCAACGCAG
ATCAATAAAGAATAAGTTACATAAATATGCTCATAGGTGGTCATTCCTAG
ACAAGAAATTGACAACATTTCATTCAACAGtatctgggctctacaggaca
gacatgcctccatttatgcaacaaataagaacagcatctcatgacagtgg
agaaaacatgggatgtgcaggtaggTAGGTAAAGTTGGGTGGAAACTTTC
ACCCTACCAAATGCACATGGGTGACTTTATAAAATAAATGTTAGCTCTCT
GAGCCTCAGTTTTCCC
```

ER2 exon -2 (AB006589: 998-1185, 89803-89988 of SEQ ID NO: 1)

```
                          TTCCTCCTTTCCCTCCACTTTTCCTA
TTAGCTTTTGCTTTCTTGCCTTTTACAGggtttgttttgcctcttggta
gtttctttcctaCggaaaattctccctctgatctttccaagtcaaaggct  89837  C/T 2,3(C,I,A,S)
tcagcaaacatttgttgaacgcgtggattgtgctaggtgggtgttatgga
ccatggagaatgctagagatgtaagacatgcgctgtccaatcgcagcgca
ggttgtgttgacagGTAAGATGAGGGCTGTGGGGGAGCCAATGTGCACGT
TCCACTGGGCTAATGTGCTCTTCACCTTATTTAGGCTCTTGGCTTTGGGA
TGTGTAAGACTTTGCTAGACAGAGAAGGGGTGGGGTGAGAAGATGAGGAA  90090 T/C 2
G
```

ER2 exon -1 (93111-93488 of SEQ ID NO: 1)
TGCATATTCTCAGGCCCTACATCCAGACCTCTTAAATCTGAGAC
TGGGGCTGCGGGGAGCGCCATCTGTGCGCCACTATCCTTGTGGGTGGACC
AGGAGTCGGTTCGAGGGTGCTCCCACTTAGAGGTCACGCGCGGCGTCGGG
CGTTCCTGAGACCGTCGGGCTCCCTGGCTCGGTCACGTGGGCTCAGGCAC
TACTCCCCTCTACCCTCCTCTCGGTCTTTAAAAGGAAGAAGGGGCTTATC
GTTAAGTCGCTTGTGATCTTTTCAGtttctccagctgctggcttttgga
cacccactcccccgccaggaggcagttgcaagcgcggaggctgcgagaaa
taactgcctcttgaaacttgcagggcgaagagcaggcggcgagcgctggg
ccggggagggaccacccgagctgcgacgggctctggggctgcggggcagg
gctggcgcccggagcctgagctgcaggaggtgcgctcgctttcctcaaca
ggtggcggcggggcgcgcgccgggagacccccccctaatgcgggaaaagca
cgtgtccgcatttagagaaggcaaggccggtgtgtttatctgcaagGTA
AGCGCCCCTTCGCTCGAGGTGTGGTTTAATTGTCTCATTTTGTTTGAAAT
CCTGCGGTGAGAAACCAGTCGTGTTGAGAACAATAAAAGACCAAAAAACG
ATCACCAAAACCAACTGTCCTGAAAGCTACTGGAAAGTTGGAAAATGCA ER2 exon 1 (104446-104897 of SEQ ID NO: 1)
CTCACATT
CCCACTCCTCTGAGGTTAATATTTTCATGTATATTTTTCAGGATGTATTT
GTAATCTCATACAAACGTATGTATTTTTTTAATGAAAATATTTAAATTTT
CATAGTTAACAGCTGTAGCTCTAACTTGGCAATATCTTCTGTGTTTCTTT
ACAGccattatacttgcccacgaatctttgagaacattataatgaccttt
gtgcctcttcttgcaaggtgttttctcagctgttatctcaagacatggat
ataaaaaactcaccatctagccttaattctccttcctcctacaactgcag
tcaatccatcttaccccctggagcacggctccatatacatacttcctcct
atgtagacagccaccatgaatatccagccatgacattctatagccctgct
gtgatgaattacagcattcccagcaatgtcactaacttggaaggtgggcc
tggtcggcagaccacaagcccaaatgtgttgtggccaacacctgggcacc
tttctcctttagtggtccatcgccagttatcacatctgtatgcggaacct
caaaagagtccctggtgtgaagcaagatcgctagaacacaccttacctgt
aaacagGTAAGTCCAGTCTTCATTCTGAATTATAGTTGCTAGCCATTTCT
CAAATCACTTTATGGTTGAGTGAGAAGGAAATAATATGTTAGACAAGGTC
TTTATTGTATTAATTACATAGTTTACTTACAGCACCCAAAACACAGGATG FIGURE 9, sheet 3 of 7

ER2 exon 2 (107368-107540 of SEQ ID NO: 1)
TTTTCCTAGAAAGCCCTTCCTTTCCCTTTTATGCTCTGTT
CAATGGATATTTTCTTTGCTCCCTAGagagacactgaaaaggaaggttag
tgggaaccgttgcgccagccctgttactggtccaggttcaaagagggatg
ctcacttctgcgctgtctgcagcgattacgcatcgggatatcactatgga
gtctggtcgtgtgaaggatgtaaggcctttttaaaagaagcattcaagG
TACAAGAGAATTGTTAACTGCTTCTTTAGTTTCCTACTTTTGATTTCAAA
CAATTTTGCAGAGATGACTTGGCAGAAATGTCACTACTGGCCTGTTTGGC
ACACAAAGTATTTGATGAGCAGTTCAGAGGATCATGTGTGTTTGGAAGTG
GGTTG ER2 exon 3 (118610-118726 of SEQ ID NO: 1)
GTAGCTTGACTTTGGCTTTGTACCTGTACTGGT
CATTAAGAAGATGTCCCCTATCTCTCAGCTGGAAAGTGTTATCAGTGTTG
TTGACCAGGAAGAGATTTAACTAAGAGATCATAGCAATAATCTTTTTTTC
CCTCCCACTCTGCTATAGGacataatgattatatttgtccagctacaaat
cagtgtacaatcgataaaaaccggcgcaagagctgccaggcctgccgact
tcggaagtgttacgaagtgggaatggtgaagtgtgGTGAGTGCTTGCTTC
CCTTCTTATTGAATATGGGCCTTGCTAAAAGCCCTGTCCTCTGAGGAACT
GGGGACAGGTAGCCGGGAAAAGAGAAGATTTGGGACATAGTAATTAAGTA
TTTGCGTGTTGTCACATTGGAGGGGGCATTGACTTATCCACAGTAACTGC
AGAGGACAGAGCTGGGGTGAATGGGAACAGATTATGGGAGGCAG ER2 exon 4 (126774-127073 of SEQ ID NO: 1)
CTGGAAATGGAGACCTAAAAAGTTTCTGAAAAGTTATGTCGTTGGT
TTTGCTAGTACGGTCACGACCATAGTAATCTTTGGTACGTGCCCCACAGG
CTCCAGAAAATAAAAGTCAAGCTGCTTTTGCTTGACTGCGGTTTTACCCT 126711 A/G 2
GGCAATTCGAATGACTCTGCTTTCCTCTTCAGgctcccggagagagagat
gtgggtaccgccttgtgcggagacagagaagtgccgacgagcagctgcac
tgtgccggcaaggccaagagaagtggcggccacgcgccccgagtgcggga
gctgctgctggacgccctgagccccgagcagctagtgctcaccctcctgg
aggctgagccgccccatgtgctgatcagccgccccagtgcgccccttcacc
gaggcctccatgatgatgtccctgaccaagttggccgacaaggagttggt
acacatgatcagctgggccaagaagattcccgGTAGGGCTTTCTGGCTAT
CAGTTTTCCATGTACTTGTAGAAAGGCCGGCCGCTAATATTTAAGGGGCA
AGAGTACAAAGTAGAGGTCCATGAGCTGTGCCTAGATATTTAACAGGTCC
TCAGCTGGATTTGTAACTTTTAAGTGCAATATGTTCCTTCCTTCTGTCTT
GGCATACCTACCTTCAACAAGGCCGTGTT FIGURE 9, sheet 4 of 7

ER2 exon 5 (130158-130296 of SEQ ID NO: 1)

```
                      GGTCGTAGTGCTTGACAAACTCTAAATGAAGTATA
TTTGTCTCTAGAAGGGGTCCAAGACTGGAAACTAAGTTGCGCAGCTTAAC
TTCAAAGTTTTCTTCCTTTAATGAGCAGTTAATCACATCTATAAAATATC
AACTCCCTAATGGTTTGTGTTTTCTTAGTGTTTTAACACTTGCCATTCTG
TCTCTACACACACAGGGAGCTGAGGAGGAGGGGTGGGGGTGTCTCACCGC
CTCTTGCTTTCCCCAGgctttgtggagctcagcctgttcgaccaagtGcg   130189 G/A 1,2,3(C),4(As),public
gctcttggagagctgttggatggaggtgttaatgatggggctgatgtggc
gctcaattgaccaccccggcaagctcatctttgctccagatcttgttctg
gacagGTGAGAAAAAATACATTGTGTTTCTTCTCTGACTTGTTTGAGTAA
GGTGCTTAGTGAGTGGGAACAAAGTCCTGGGTGCTGCAATTAAAATCTCA
CACTTGCAGGGCAGAGGATGATAGCATCAT
```

ER2 exon 6 (137853-137986 of SEQ ID NO: 1)

```
                                         TTTCATATT
GCTGGGTGTGGTCTCATTAACACCCTGTTGTAGTTAAAATGATATTATCA
GATGAACATGTTACAAGATGAAACTTGAGATTAAAAATAAAACATTCCTT
ATTGTTTTTTTGATGGTTTCCTGAAGCTATGTTCCTTAAATTTCCAAACG
AACTTTTGTAGggatgaggggaaatgcgtagaaggaattctggaaatctt
tgacatgctcctggcaactacttcaaggtttcgagagttaaaactccaac
acaaagaatatctctgtgtcaaggccatgatcctgctcaattccaGTAAG
TAATCACACAGCTGGGCCATGTTTTATCGGGGAGAGATGCTGTTTCTACA
ACTAGCGTGATATTAAGAAGAATGTTGAACTTCTATTTTATTTGAAAGGG
TAAAATGGTTTCCTTTTGGACTTCGTTTTTATTTTGATAGCGATTTAAAC
TGTAGGTAACTTTTGGTAACTTGGACATAAATTACTCATTAAGTGAATGA
CTGGCAATCA
```

ER2 exon 7 (152379-152559 of SEQ ID NO: 1)

```
                                  CAGGCTTCTCTTCTAGCT
CTGTGACGGGGCTGGCTCTCAGGGAAGATCCCCTGGGGGAGGTAAGACCA
TGCTTATAAGCTCCTGCCACACATGCAGCTGTCAAAGCAACCCAGATCAC
CTCGGAGCAGGCGCACGGAACAGCTGAGCACACGACTTCTGCTCCTTTGC
TCAGAGCAATGACTTCTGGCTTTTATTCTTTGTCCAGgtatgtaccctct
ggtcacagcgacccaggatgctgacagcagccggaagctggctcacttgc
tgaacgccgtgaccgatgctttggtttgggtgattgccaagagcggcatc
tcctcccagcagcaatccatgcgcctggctaacctcctgatgctcctgtc
ccacgtcaggcatgcgagGTACGCGCCCTAAGGAGCTGCTCTGCTTGGGC
TTGGGATGGGATTATGTGCTCCACGGAGGGTGAAGTGATTTGGGAAAAGT   152603 T/C 4(As)
GTCTGCAAGTTAAGGAAAATGAATGCCTGAAAGGGAATGGGGAATTTGTC
AGTT
```

ER2 exon 8 (154206-154500 of SEQ ID NO: 1)
GTGGGACACAGAGGCTGACAAGACATCGTCCTTGCCCTTGAGCCTAAA
TTATCAGGGGGAGCTGGATGCACGAGCCATGGATAAATGGGCTGGGGAA
GAGTGGGTTTAGGGGTGGGGTAGACTGGCTCTGAGCAAAGAGAGCCGGGG 154138 G/A 2
AAGGCTTCGGGGTTCCTGTGGCTGCCTCGGAGGAGGGAATCTCAGCACCT
TTTTGTCCCCATAGtaacaagggcatggaacatctgctcaacatgaagtg 154202 A/G 2,3(C,A,S),4(As)
caaaaatgtggtcccagtgtatgacctgctgctggagatgctgaatgccc
acgtgcttcgcgggtgcaagtcctccatcacggggtccgagtgcagcccg
gcagaggacagtaaaagcaaagagggctcccagaacccacagtctcagtG
AcgcctggccctgaggtgaactggcccacagaggtcacaGgctgaagcGT 154431 G/A 1,2,3(N,I,A),4(all)
GAACTCCAGTGTGTCAGGAGCCTGGGCTTCATCTTTCTGCTGTGTGGTCC 3rd alt. end missing (63658)
C ER2 exon 9 (159915-160827 of SEQ ID NO: 1)
ACTGAGCTTTGAGTGAAAGAAGCTGCAGTGGCCTCCCTGGAGATGGGGAG
CAAACCAGCTTAAAGGCCCTTATCCTGAGGAAGAGACAAAAATTGACATG
CACAATATTAAGCTTTGAAATGCAGACCACACTTCCTTTCACTGCAACTT
TGACTTGTCCCGCATCTCTACTTAAGggcagaaaaggcctctcaaacact
cacctcatttggaatgaagatggagactcttttgcctgaagcaacgatgg
agcagtgaccctctaatcaactcggtggcctaaagaaaaatcttgggtaa
cattttcacttcaGtttccctctgggatcattgtaatccatgaaaaaaat 160052 G/A 1,2,3(N,I,A,S),4 (all);
AattttaaagaaagagttaaaatacTTtgaagttagttatgtggttaaaa 160089 A/G 1,2,3 (N,I,A,S)
accaccttcctttctattatcaatccAacaatttgataactgtaaacgct 160165 A/G 1,2,3(A),4(all)
aaagtgaagacggattctcttcagatggtctccttaactgcccagggctt
gcagatgtctcacccatgaggggcaccaatgtagaaagctgaggcttcat
ctactgatgagcttcactggtttcccctgaggtttgtgctttggcagaga
aggggaggaggggactgggattgtgtggtcagctgtgCctgccaacagat 160376 C/G 1,2,3(N,C,A)
gcaggttaggaactgtgttcagtatcttccaataagaaaggggaaatgcc
gatgcctatcctctttgtttaggtagaaagtaaaatgctactggacttaa
atgggcaacaaggggctttgcctgttcatttgccatggagagggctggga
atccaggtgcggtggctcacacctgtaatcccaacactttgggaggccga
ggtgggcagatcaGttgaggtcaggagtttgaaaccagcctggccaacat 160602 G/C 2
ggcgaaaccccgtctctattaaaaatataataattagccaggcatggtgg
tgtgtgcttgtaatcccagctactcaggaggctgaggcatgagaatggct
tgaacctggaaggcaaaggttgcagtgagccgagattgggccaccgcact
ccagcctgggtgactgacagagtgagactctgtcaAAAAAAAAGAGTAGAG
TAAACTGGGTATAAGATCCTTCCCTTTGCGTCCACCTCTCATGCCATGCT
GCCTTTGCCATTCCCTACA FIGURE 9, sheet 6 of 7

ER2 exon 10 (302474-303300 of assembled ER2 BAC,
302474-303300 of SEQ ID NO: 1)

| | |
|---|---|
| GACAGctctctcactctcttggagattgtttatgctgagggaagccag | |
| ctgccatggtgtgaggcagactcctggaggagcccacAtgtctgtaagta | **302556 A/G** 2,3(all) |
| gaagcagatcttttgaggcctgtcaacagccacgggaatgagcttggaag | |
| cagatcccacctcctccctcacacaagtcgagccttcagatgagcctgca | |
| gcCtttgtcgacaccttgacTgcattctcatgagagaccttgagccagag | **302671 C/T** 3(A); **302689 T/C** 2,3(all) |
| atacttagctaagccatgcccatggactcctgacccacagaaactgtgat | |
| aataagtttgttgtttcaagctgctaacttatggagtaatatgttacaca | |
| aaaatagctaatatatagctcaaaactggAagcaacccaaatatctatta | **302848 A/G** 2,3(N) |
| actggtagataaacaaactactcatttccaaacttatttccaaaactgga | |
| acactacttggcaatcaaataattaactatgcattaagtgtaacaacctg | |
| gatGaatctcaaaggcattatgttaagtgaaacaagtgagccacgtaaga | **302972 A/G** 2,3(N,I,A,S) |
| ctacatactgtttgattccctctatatgatattctagaaaaggcaaaact | |
| atagtaataggaaacagtgagtgatcacctagggttgaagacaggtgaaa | |
| ggggattgactgcaaagaggcaggaggaaacgtcttgggagatggagatg | |
| ttccttatattgatggcggtggttacacaactgcacttttatcaaaa | |
| cttacctaactgctacttaaaataggtgtattaatatttttactgtatgt | |
| aaattatacctcaataaatttgatttaaaaaaCAGGCCGGGTGTGGTGGC | |
| TCACGCCTGTACTCCCAGCACTTTGGGAGGTCGAGGTGGGCAGATCAGCT | |
| GAGGTCAGGAGTTCAAGACCAGCCTTGGCCAACATGGTGAAATCCTGTCT | |
| CTACTAAAAATACAAAATAAGGTCAGCGTGGTTGGCACACGCCTGTAATC | |
| TCAGCTACTGGGGAAGCTGAGGCAGAAG | |

* Observed in: 1= cDNA, 2= Liverpool clinical, 3= Coriell (N, North Eur.; C, Chinese; A, Afric-Amer; I, Indo-Pak; S, SW Native Amer), 4= CEPH (Ca, Caucasion; As, Asian; Af, Afric-Amer)

(bold = SNP position, underlined = primer sequences, lowercase = exon, bold/italics = alternative endings to exons 8 and 9 seen in different splice variants.)

ESTROGEN RECEPTOR BETA VARIANTS AND METHODS OF DETECTION THEREOF

RELATED APPLICATIONS

The present application claims priority to provisional application U.S. Ser. No. 60/183,755, filed Feb. 22, 2000.

FIELD OF THE INVENTION

The present invention is in the field of disease detection and therapy. The present invention specifically provides the identification of previously unknown nucleic acid/amino acid polymorphisms within the estrogen receptor beta gene (ESR-beta) and the genomic sequence of this gene for use in the development of diagnostics and therapies for diseases and disorders mediated/modulated by the estrogen receptor.

BACKGROUND OFF THE INVENTION

Estrogen Receptor

The human estrogen receptor beta belongs to the nuclear hormone receptor family. Nuclear hormone receptors are a family of hormone-activated transcription factors that can initiate or enhance the transcription of genes containing specific hormone response elements.

The ER protein consists of 595 amino acids with a molecular weight of 66 kDa, 8 transcribed exons, with six different functional domains. Two of those domains are highly conserved in the primary sequence of members of the nuclear hormone receptor superfamily. One of the domains, the DNA binding domain (DBD), contains two zinc fingers that mediate receptor binding to hormone response elements in the promoters of hormone-responsive genes. In the C-terminal region, the hormone-binding domain (HBD) contains two regions of sequence homology with other hormone receptors and gives hormone specificity and selectivity. The human ER-alpha gene is located in chromosome 6q.25.1.Estrogen receptors, like other steroid receptors, are transcription factors that are activated upon binding to steroids (estradiol) or steroid analogs such as tamoxifen. Upon activation the receptors dimerize to form homodimers or heterodimers that bind to estrogen receptor elements (EREs) located in the promoter region of estrogen-activated genes and coordinate transcription by interacting with host co-activators.

Role of Estrogen in Cardiovascular Disease

Heart disease is the leading cause of mortality in women, a fact that is under appreciated by both women and physicians. One in 9 women aged 45–65 have some form of cardiovascular disease and the number increases to 1 in 3 after age 65. Each year, 240,000 U.S. women die from heart disease, and nearly 90,000 die of stroke. Moreover, approximately 44% die within one year of suffering a heart attack, compared with 26% of men (Warren M P and Kulak J Clin Obs Gyn 1998 41(4):976–987).

Estrogens exert a wide range of physiological effects on a large variety of cell types. For example, they regulate cell growth and apoptosis and a myriad of functions related to reproduction. There are two types of estrogen receptors, beta and beta. Blood vessels and bone contain beta receptors, the liver has beta receptors, and both beta and beta receptors are found in the central nervous system. The interaction of these different receptor sites influences the biological effects of estrogen and selective estrogen receptor modulators (SERMs), such as raloxifene. The binding patterns dictate whether an estrogen or a SERM acts as an estrogen agonist or an antagonist (Mendelsohn ME and Karas R H New Engl J Med 1999, 340(23):1801–1811; Grese T A and Dodge J A Curr Pharm Design 1998, 4:71–92). Tissue-specific relationships exist between SERMs and the receptor binding sites. Estrogens also increase high-density lipoprotein cholesterol levels, decrease low-density lipoprotein cholesterol, and decrease plasminogen-activating inhibitor levels (Meisler J G Jour Women's Health 1999, 8(1):51–57). All estrogens require cellular receptors for their expression. In general, estrogen receptors are ligand-inducible transcription factors, which regulate the expression of target genes after hormone binding (Faustini-Fustini et al. Eur J Endocrin 1999, 140:111–129). Estrogen may also have important effects on the vascular wall. Estradiol and progesterone receptors have been identified in arterial endothelial and smooth muscle cells (Campisi D et al. Int J Tiss React 1987, IX(5): 393–398). Estrogens act on the wall of the artery to relax vascular smooth muscle and to decrease vascular resistance. The mechanism appears to be through stimulation of endothelial-derived relaxing factors and an endogenous nitrate (Warren M P and Kulak J Clin Obs Gyn 1998 41(4):976–987). The relaxation induced by 17B-estradiol may play an important role in the regulation of coronary tone, which reduces the risk of coronary disease in postmenopausal women. The production of nitric oxide is mediated by the estrogen receptor, because when the receptor is blocked by an antiestrogen agent, nitric oxide is suppressed.

Several studies have shown that estrogen therapy reduces the risk of heart disease by up to 50% (most recently reviewed by Mendelsohn M E and Karas R H New Engl J Med 1999, 340(23):1801–1811; Rich-Edwards J W N Engl J Med, 1995, 332:1758–1765; Gerhard M, Ganz P, Circulation, 1995, 92:5–8; Grodstein F, et al N Engl J Med 1997, 336:1769–75; Chasen-Taber L and Stampfer M J Ann of Int Med, 1998, 128:467–477; Warren M P and Kulak J Clin Obstet Gyn 1998, 41(4):976–987). Loss of estrogen may be one of the most important factors in the development of cardiovascular disease in women.

While there is no direct evidence that estrogen prevents atherogenesis, considerable epidemiologic evidence exists that suggests that estrogens may have some benefit in reducing cardiovascular disease: (1) In all age groups, women have a lower incidence of cardiovascular disease than do men; (2) women who undergo a premature surgical menopause and do not take estrogens are twice as likely to have cardiovascular disease are age-matched premenopausal controls; (3) postmenopausal women who use estrogens have a significantly lower incidence of cardiovascular disease compared with those who do not; and (4) women with coronary artery disease detected by angiography have a higher survival rate if they are estrogen users.

In recent years, reports of favorable effects of estrogen therapy on cardiovascular morbidity and mortality have led to enthusiasm for widespread use of estrogens by postmenopausal women (Meinertz T Herz 1997, 22: 151–157). Guidelines for estrogen therapy issued by the American College of Physicians include the statement "Women who have coronary heart disease are likely to benefit from hormone therapy."

More than 30 prospective studies and 13 case controlled studies have examined the effect of estrogen replacement therapy on cardiovascular incidence or prevalence and all cause mortality (Stampfer M J et al. New Engl J Med 1991, 325:756–62; Grady D et al. Ann Intern Med 1992, 117:1016–37). The majority of these studies showed lower morbidity and mortality from coronary heart disease among users of postmenopausal estrogens than among non-users. Specifically, they have shown that coronary artery disease in estrogen takers is approximately 50% that in women who do not take estrogen. Overall, the bulk of the evidence strongly supports a protective effect of estrogens yielding a relative risk of 0.56 (95% confidence interval 0.50–0.61). However, a "healthy woman selection bias" is present in these studies and potentially may confound these results (estrogen takers have better weight control, exercise more, and smoke less than women who are not prescribed estrogen). Moreover, other biases such as estrogen takers tend to have higher education, higher income, etc., are confounding these epidemiologic studies (Abrams J Clin Cardiol 1998, 21:218–222).

Since the earlier observational trials were not randomized, it is believed by many that as much as 25% of this 50% reduction in risk is due to these various methodological biases (Barrett-Conner E and Grady D 1998, Ann Rev Public Health 19:55–72). Recently, 2 meta-analyses estimated the reduction in coronary heart disease associated with estrogen use to be in the range of 35 to 44%, respectively (Grodstein F and Stampfer M J Prog Cardiol Dis 1995, 38: 199–210; Barrett-Conner E and Grady D 1998, Annu Rev Public Health 19:55–72). Recent studies are exploring the issue of opposed vs unopposed estrogen, because of a documented increased risk for uterine cancer in women with an intact uterus who are taking estrogen alone. The new lines of evidence are suggesting that women taking estrogen plus a progestin (usually a medroxyprogesterone acetate) do not receive an equivalent benefit from the cardioprotective effects compared to women taking estrogen alone (Hulley S et al 1998 JAMA 280:605–613; Abrams J Clin Cardiol 1998, 21:218–222).

The loss of estrogen at menopause is associated with a 6% decline in HDL cholesterol levels and a 5% rise in LDL cholesterol levels, which may explain the higher cardiovascular disease rate among postmenopausal women compared with premenopausal women. The lower incidence of cardiovascular disease among postmenopausal women who take estrogen may be explained in part by the resultant 15% to 19% decrease in LDL cholesterol levels and the 16% to 18% increase in HDL cholesterol levels (JAMA 1995, 273:199–208). The PEPI (Postmenopausal Estrogen/Progestin Intervention, a randomized, double-blind placebo-controlled trial, showed that HDL cholesterol levels rose significantly more in women assigned to estrogen alone than in women assigned the combined estrogen (JAMA 1995, 273:199–208). Recent non-human primates studies substantiate these findings (Clarkson T B Lab An Sci 1998, 48(6): 569–72). Statistical modeling of the effect of estrogen on lipid profiles indicates that 25–50% of the apparent cardioprotection due to estrogen is mediated by favorable changes in HDL-cholesterol (Bush T L et al. 1987 Circulation 75:1102–9; Gruchow H W et al. 1988 Am Heart J 115:954–63).

Estrogen replacement therapy is not without risk. For years, studies have shown a 3–4-fold increased risk of venous thromboembolism (VTE) in users of oral contraceptives compared to non-users (Weiss G Am J Obstet Gynecol 1999 180:S295–301). One study has shown that intrinsic coagulation factors play a significant role in oral contraceptive-associated VTE (Vandenbroucke J P et al. Lancet 1994 344:1453–7; Rosing J et al. Br J Haematol 1997, 97:233–238). The Factor V Leiden mutation increases risk of VTE 5–10 fold in non users, but 30-fold in third-generation oral contraceptive users. Combined estrogens appear to induce resistance to the body's natural anticoagulation system (APC). Heterozygotes for the Factor V Leiden mutation who take oral contraceptives develop APC resistance as high as that seen in women who are homozygous.

Estrogens increase the risk of endometrial carcinoma approximately 6-fold, an effect that is eliminated, for the most part, by the addition of progestins (Barrett-Conner E and Grady D 1998, Ann Rev Public Health 19:55–72). Controversy continues over whether estrogen replacement increases the risk of breast cancer, but some studies indicate risk is elevated by as much as 30%. (Greendale GA et al. Lancet 1999, 353:571–80).

A number of prospective randomized studies designed to definitely establish whether estrogen replacement therapy reduces the risk of cardiovascular disease in women and whether it increases the risk of breast cancer, are underway. One recently completed trial (HERS—Heart and Estrogen/progestin Replacement Study) compared continuous combined estrogen plus medroxyprogesterone acetate to placebo in 2700 women with pre-existing coronary disease (Hully S et al. 1998 JAMA 280(7):605–13). Compared to controls, the intervention group had significantly more heart disease events in year one of the trial, but significantly fewer events in years 4 and 5 of the trial. Moreover, a significant increase in the rate of thromboembolic events occurred in the early years of the study in women taking hormones. Based on these results, hormone replacement therapy is not recommended for secondary prevention of heart disease.

Two other large, ongoing clinical trials on primary prevention of cardiovascular disease using estrogens are underway. The Women's Health Initiative, due to be completed in 2005 and a U.K study called WIS-DOM, due to be completed in 2010, should shed new light on the protective effects of estrogen on cardiovascular disease (Meisler J G Jour Women's Health 1999, 8(1):51–5).

In summary, ongoing research suggests that estrogen replacement therapy, particularly involving recently formulated designer estrogens or SERMs, may have beneficial effects on the cardiovascular system as well as bone, without the untoward effects on breast and endometrial tissue. Caution still needs to be observed, nonetheless. Women who take estrogens are, on average, better educated, healthier, have higher incomes and have better access to health care. These differences rather than the estrogens may account for much of the lower risk of heart disease.

For postmenopausal women without frank disease, estrogen replacement therapy appears to have a beneficial effect when one considers the magnitude, consistency, and biological plausibility of the data. For women with pre-existing disease, questions remain as to the safety and efficacy of exogenous estrogens as protective agents against cardiovascular disease.

Estrogen and Autoimmune Diseases

A. Systemic Lupus Erythematosus

There is a widely held view that estrogens play a role in Systemic lupus erythematosus because:

1. Women of child bearing age are nine times more likely to develop systemic lupus erythematosus than men. Prior to pubescence the rate is three fold higher in females, while post menopausal women have an equal chance of developing SLE as aged matched males. Many studies have been done that show that the reason for the differences in the sexes is probably estrogen related (Lahita R. G., 1986: Springer Seminars in Immunopathology 9, 305–314; Krammer, G. M. and Tsokos, G. C., 1998 Clinical Immunology and Immunopathology 89: 192–195; Rider at al., 1998 Clinical Immunology and Immunopathology 89: 171–180).

Clues to the role of estrogens in SLE came from studies that concluded that oral contraceptives adversely affected the morbidity of this illness (Buton, J. P., 1996 Ann. Med. Interne, 147:259–264; Julkunen, 1991: Scan. J. Rheumatol. 20:427–433).

2. Patients with Klinefelter syndrome (XXY), have been reported with SLE (Stern et al., 1977: Arthritis and Rheumatism 20:18–22).
3. Patients with SLE have anti-estrogen antibodies (Feldman, 1987: Biochem. Biophys. Acta, 145:1342–1348: Bucala et al., 1987: Clin. Exp. Immunol. 67:167–175)

In the past, oral contraceptives have been shown to cause flare ups of SLE, their use was discouraged in women with SLE, while the current thinking is that the lower dose birth control pills are safe for SLE patients (Julkunen H A *Scand J Rheumatol* 1991;20(6):427–33). As well hormone replacement therapy is considered safe for SLE patients (Mok et al., *Scand J Rheumatol* 1998;27(5):342–6: Kreidstein et al., 1997*, J Rheumatol* 1997 November;24(11):2149–52)

4. The estrogen antagonist tamoxofin seems to improve the course of the disease (Sthoeger, 1997*, Ann NY Acad Sci* 1997 Apr. 5;815:367–8: Sthoeger, 1994*, J Rheumatol* 1994 December;21(12):2231–8).

B. Estrogen, Rheumatoid Arthritis (RA) and Osteoarthritis

The literature surrounding the involvement of estrogens in Rheumatoid arthritis is less clear than with osteoarthritis. Epidemiological studies suggests that RA is influenced by female sex hormones, by one study states that the use of oral contraceptives may postpone the onset of RA, but that estrogens alone no not alleviate the symptoms of RA (Bijlsma *Am J Reprod Immunol* 1992 October–December;28 (3–4):231–4). Adjuvant oestrogen treatment does increase bone mineral density in postmenopausal women with RA, and may protect against osteophoresis which is often a complication of RA (van den Brink: *Ann Rheum Dis* 1993 April;52(4):302–5). While the study mentioned above indicated that estrogens did not alleviate RA symptoms, another study concluded that adjuvant estrogen therapy did not even improve the symptoms. One polymorphism has been reported in the estrogen receptor that seems to be associated with the age of onset of RA (Ushiyama *Ann Rheum Dis* 1999 January;58(1):7–10)

Osteoarthritis on the other hand is less prevalent in postmenopausal women who take estrogen replacement therapy (ERT) (Felson *Curr Opin Rheumatol* 1998 May;10 (3):269–72) suggesting that ERT may be beneficial in preventing osteoarthritis.

C. Estrogen and Osteophorosis

Osteophorosis is a metabolic bone disorder that leads to bone fragility and subsequent risk of fracture. Treatment for postmenopausal women with osteophoresis includes hormone replacement, in particular estrogen. Estrogen has shown to reduce the incidence of bone loss and fractures (Weiss et al., *N Engl J Med* 1980 Nov. 20;303(21): 1195–8:Paganini-Hill et al., *Ann Intern Med* 1981 July;95 (1):28–31: Ettinger et al., *Ann Intern Med* 1985 March;102 (3):319–24)

Further, polymorphisms in the estrogen receptor have been associated with bone loss in both humans and mice. (Kobayashi *J Bone Miner Res* 1996 March;11(3):306–11: Kurabayashi *Am J Obstet Gynecol* 1999 May; 180(5): 1115–20; Deng *Hum Genet* 1998 November;103(5):576–85)

Estrogens and Cognitive Function

Compared with men, women are at greater risk of developing Alzheimer's disease. Several studies show that women who take estrogen after menopause have a lower incidence of Alzheimer's disease. Among women with Alzheimer's, those taking estrogen suffer less severe symptoms and slower mental deterioration. The duration of estrogen use also seems to be important in reducing risk. Women with a history of long-term term use (more than 10 years) had the lowest risk. But even women who took estrogen for a short time also benefited.

Estrogen and Breast Cancer

The major risk factors for the development of breast cancer are sex, age, family history of breast cancer, age of menarche, age at first full-term pregnancy, and age of menopause. All of these factors, with the exception of family history, have been shown to be directly associated with lifetime exposure to estrogen, increased hormone exposure being associated with increased risk of developing breast cancer. The increased cancer risk is believed to be caused by an estrogen receptor-mediated proliferative response in cells of the mammary epithelium.

Tamoxifen, an estrogen receptor antagonist, has been shown to be an effective agent for both the prevention and treatment of breast cancer. Using immunohistochemical methods, it is possible to classify breast tumors as being estrogen receptor positive or negative, depending upon the amount of estrogen receptor protein expressed in the tissue. Estrogen receptor positive tumors are more likely to respond to treatment with tamoxifen than estrogen receptor negative tumors. Pre-menopausal women are more likely to develop estrogen receptor negative breast cancers than are post-menopausal women.

Mutations altering the structure and function of the estrogen receptor have been described in primary breast tumors or breast cancer cell lines. It is not clear however whether these changes are primary (and involved in the processes leading to carcinogenesis) or secondary (and a consequence of genetic instability in cancer tissues). In addition to these somatic mutations, some studies have pointed to a possible association between inherited DNA sequence changes and the development of breast cancer, but these studies are also controversial.

Further evidence for the role of estrogen receptors in breast cancer comes from the recent finding that the gene BRCA1, which when inherited in a mutant form predisposes to the development of breast cancer, inhibits estrogen receptor signaling.

Estrogens and Endometrial Cancer

Carcinoma of the endometrium is the most common pelvic malignancy in women, however because in approximately 75% of cases it is confined to the body of the uterus at the time of diagnosis, it can usually be cured by hysterectomy. Unopposed exposure of endometrial cells to estrogens dramatically increases the chance of developing this form of uterine cancer and it is for this reason that hormone replacement therapy consisting solely of estrogen should not be given to women with intact uteri. Cyclical or continuous co-administration of progesterone serves to prevent excessive proliferation of endometrial cells, reducing the risk of endometrial cancer in post-menopausal women receiving estrogen as part of hormone replacement therapy regimens.

The majority of cases of endometrial cancers express estrogen receptor and, in general, estrogen responsive tumors have a favorable prognosis. Acquired (somatic) mutations have been described in up to 8.5% of cases, however the role of these mutations in the development and progression of endometrial cancer is uncertain at present.

Although it remains somewhat controversial, studies suggest that use of tamoxifen may increase the chance of developing endometrial cancer. This may be because, in addition to its role in estrogen receptor blockade, tamoxifen has partial receptor agonist activity and results in low-grade induction of estrogen responsive genes that induce endometrial proliferation.

Given the involvement of the estrogen receptor in mediating/modulating various disorders, it is critical to identify sequence polymorphisms in the estrogen receptor and to correlate these with disease states, therapeutic effectiveness and the like. The present invention advances the art by providing a variety of previously unidentified polymorphisms in the ESR-beta protein.

SNPs

The genomes of all organisms undergo spontaneous mutation in the course of their continuing evolution, generating variant forms of progenitor sequences (Gusella, Ann. Rev. Biochem. 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. Additionally, the effect of a variant form may be both beneficial and detrimental, depending on the circumstances. For example, a heterozygous sickle cell mutation confers resistance to malaria, but a homozygous sickle cell mutation is usually lethal. In many instances, both progenitor and variant form(s) survive and co-exist in a species population. The coexistence of multiple forms of a sequence gives rise to polymorphisms, such as SNPs.

The reference allelic form is arbitrarily designated and may be, for example, the most abundant form in a population, or the first allelic form to be identified, and other allelic forms are designated as alternative, variant or polymorphic alleles. The allelic form occurring most frequently in a selected population is sometimes referred to as the "wild type" form.

Approximately 90% of all polymorphisms in the human genome are single nucleotide polymorphisms (SNPs). SNPs are single base pair positions in DNA at which different alleles, or alternative nucleotides, exist in some population. The SNP position, or SNP site, is usually preceded by and followed by highly conserved sequences of the allele (e.g., sequences that vary in less than 1/100 or 1/1000 members of the populations). An individual may be homozygous or heterozygous for an allele at each SNP position. As defined by the present invention, the least frequent allele at a SNP position can have any frequency that is less than the frequency of the more frequent allele, including a frequency of less than 1% in a population. A SNP can, in some instances, be referred to as a "cSNP" to denote that the nucleotide sequence containing the SNP is an amino acid coding sequence.

A SNP may arise due to a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion/deletion variant (referred to as "indels"). A substitution that changes a codon coding for one amino acid to a codon coding for a different amino acid is referred to as a non-synonymous codon change, or missense mutation. A synonymous codon change, or silent mutation, is one that does not result in a change of amino acid due to the degeneracy of the genetic code. A nonsense mutation is a type of non-synonymous codon change that results in the formation of a stop codon, thereby leading to premature termination of a polypeptide chain and a defective protein.

SNPs, in principle, can be bi-, tri-, or tetra-allelic. However, tri- and tetra-allelic polymorphisms are extremely rare, almost to the point of non-existence (Brookes, Gene 234 (1999) 177–186). For this reason, SNPs are often referred to as "bi-allelic markers", or "di-allelic markers".

Causative SNPs are those SNPs that produce alterations in gene expression or in the expression or function of a gene product, and therefore are most predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Such variant products can result in a pathological condition, e.g., genetic disease. Examples of genes in which a polymorphism within a coding sequence gives rise to genetic disease include sickle cell anemia and cystic fibrosis. Causative SNPs do not necessarily have to occur in coding regions; causative SNPs can occur in any region that can ultimately affect the expression and/or activity of the protein encoded by the nucleic acid. Such gene areas include those involved in transcription, such as SNPs in promoter regions, in gene areas involved in transcript processing, such as SNPs at intron-exon boundaries that may cause defective splicing, or SNPs in mRNA processing signal sequences such as polyadenylation signal regions. For example, a SNP may inhibit splicing of an intron and result in mRNA containing a premature stop codon, leading to a defective protein. Consequently, SNPs in regulatory regions can have substantial phenotypic impact.

Some SNPs that are not causative SNPs nevertheless are in close association with, and therefore segregate with, a disease-causing sequence. In this situation, the presence of the SNP correlates with the presence of, or susceptibility to, the disease. These SNPs are invaluable for diagnostics and disease susceptibility screening.

Clinical trials have shown that patient response to treatment with pharmaceuticals is often heterogeneous. Thus there is a need for improved approaches to pharmaceutical agent design and therapy. SNPs can be used to help identify patients most suited to therapy with particular pharmaceutical agents (this is often termed "pharmacogenomics"). Pharmacogenomics can also be used in pharmaceutical research to assist the drug selection process. (Linder et al. (1997), Clinical Chemistry, 43, 254; Marshall (1997), Nature Biotechnology, 15, 1249; International Patent Application WO 97/40462, Spectra Biomedical; and Schafer et al. (1998), Nature Biotechnology, 16, 3.).

Population Studies

Population Genetics is the study of how Mendel's laws and other genetic principles apply to entire. Such a study is essential to a proper understanding of evolution because, fundamentally, evolution is the result of progressive change in the genetic composition of a population. Population genetics thus seeks to understand and to predict the effects of such genetic phenomena as segregation, recombination, and mutation; at the same time, population genetics must take into account such ecological and evolutionary factors as population size, patterns of mating, geographic distribution of individuals, migration and natural selection.

Ideally, one would wish to know how to describe the types and frequencies of genes in a population, to explain how the population's genetic composition came to be the way it is, and to predict how the population would change as a result of natural selection or as a result of artificial selection.

In order to explain many of those issues it is important to understand the existing relation between loci denominated: Linkage.

Linkage is the coinheritance of two or more nonallelic genes because their loci are in close proximity on the same chromosome, such that after meiosis they remain associated more often than the 50% expected for unlinked genes. During meiosis, there is a physical crossing over, it is clear that during the production of germ cells there is a physical exchange of maternal and paternal genetic contributions between individual chromatids. This exchange necessarily separates genes in chromosomal regions that were contiguous in each parent and, by mixing them with retained linear order, results in "recombinants". The process of forming recombinants through meiotic crossing-over is an essential feature in the reassortment of genetic traits and is central to understanding the transmission of genes.

Recombination generally occurs between large segments of DNA. This means that contiguous stretches of DNA and genes are likely to be moved together. Conversely, regions of the DNA that are far apart on a given chromosome are likely to become separated during the process of crossing-over.

It is possible to use molecular markers to clarify the recombination events that take place during meiosis. Some markers as (CA)n repeats of different lengths are dispersed throughout human DNA and there is little selective pressure in their lengths are used as position markers and regional identifying characters along chromosomes. Those markers can be used to distinguished paternally derived from maternally derived gene regions.

Other markers are Single Nucleotide Polymorphism (SNP), those are biallelic markers, also used to analyzed the transmission of those markers to offspring.

The pattern of a set of markers along a chromosome is referred to as a "Haplotype". Therefore sets of alleles on the same small chromosmal segment tend to be transmitted as a block through a pedigree. By analyzing the haplotypes in a series of offspring of parents whose haplotypes are known, it is possible to establish which parental segment of which chromosome was transmitted to which child. When not broken up by recombinations, haplotypes can be treated for mapping purposes as alleles at a single highly polymorphic locus.

The existence of a preferential occurrence of a disease gene in association with specific alleles of linked markers is called "Linkage Disequilibrium" (LD). This sort of disequilibrium generally implies that most of the disease chromosomes carry the same mutation and the markers being tested are quite close to the disease gene. For example, there is considerable linkage disequilibrium across the entire HLA locus. The A3 allele is in LD with the B7 and B14 alleles, and as a result B7 and B14 are also highly associated with hemochromatosis. Thus, HLA typing alone can significantly alter the estimate of risk for hemochromatosis, even if other family members are not available for formal linkage analysis. As a result, using a combination of several markers surrounding the presumptive location of the gene, a haplotype can be determined for affected and unaffected family members.

SNP-Based Association Analysis and Linkage Disequilibrium Mapping

SNPs are useful in association studies for identifying particular SNPs, or other polymorphisms, associated with pathological conditions, such as breast cancer. Association studies may be conducted within the general population and are not limited to studies performed on related individuals in affected families (linkage studies). An association study using SNPs involves determining the frequency of the SNP allele in many patients with the disorder of interest, such as breast cancer, as well as controls of similar age and race. The appropriate selection of patients and controls is critical to the success of SNP association studies. Therefore, a pool of individuals with well-characterized phenotypes is extremely desirable. For example, blood pressure and heart rate can be correlated with SNP patterns in hypertensive individuals in whom these physiological parameters are known in order to find associations between particular SNP genotypes and known phenotypes. Significant associations between particular SNPs or SNP haplotypes and phenotypic characteristics can be determined by standard statistical methods. Association analysis can either be direct or LD based. In direct association analysis, causative SNPs are tested that are candidates for the pathogenic sequence itself In LD based SNP association analysis, random SNPs are tested over a large genomic region, possibly the entire genome, in order to find a SNP in LD with the true pathogenic sequence or pathogenic SNP. For this approach, high density SNP maps are required in order for random SNPs to be located close enough to an unknown pathogenic locus to be in linkage disequilibrium with that locus in order to detect an association. SNPs tend to occur with great frequency and are spaced uniformly throughout the genome. The frequency and uniformity of SNPs means that there is a greater probability, compared with other types of polymorphisms such as tandem repeat polymorphisms, that a SNP will be found in close proximity to a genetic locus of interest. SNPs are also mutationally more stable than tandem repeat polymorphisms, such as VNTRs. LD-based association studies are capable of finding a disease susceptibility gene without any a priori assumptions about what or where the gene is.

Currently, however, it is not feasible to do SNP association studies over the entire human genome, therefore candidate genes associated with breast cancer are targeted for SNP identification and association analysis. The candidate gene approach uses a priori knowledge of disease pathogenesis to identify genes that are hypothesized to directly influence development of the disease. The candidate gene approach may focus on a gene that is directly targeted by a drug used to treat the disorder. To discover SNPs associated with an increased susceptibility to breast cancer candidate genes can be selected from systems physiologically implicated in the disease pathway. SNPs found in these genes are then tested for statistical association with disease in individuals who have the disease compared with appropriate controls. The candidate gene approach has the advantages of drastically reducing the number of candidate SNPs, and the number of individuals, that need to be typed, compared with LD-based association studies of random SNPs over large areas of, or complete, genomes. Furthermore, in the candidate gene approach, no assumptions are made about the extent of LD over any particular area of the genome.

Combined with the use of a high density map of appropriately spaced, sufficiently informative SNP markers, association studies, including linkage disequilibrium-based genome wide association studies, will enable the identification of most genes involved in complex disorders, such as cardiovascular diseases, cancer etc. This will enhance the selection of candidate genes most likely to contain causative SNPs associated with a particular disease. All of the SNPs disclosed by the present invention can be employed as part of genome-wide association studies or as part of candidate gene association studies. The present invention advances the state of the art and provides commercially useful embodiments by providing previously unidentified SNPs in the estrogen receptor genes.

SUMMARY OF THE INVENTION

The present invention is based on sequencing genomic DNA from human chromosome 6 and cDNAs to define the genomic structure of estrogen receptor beta genes, novel polymorphisms in the estrogen receptor gene/protein. Such polymorphisms can lead to a variety of disorders that are mediated/modulated by a variant estrogen receptor, such as a susceptibility to cancer, osteoporosis, cardiovascular disorders, etc. Based on this sequencing approach, the present invention provides genomic nucleotide sequences, cDNA sequences, amino acid sequences, sequence polymorphisms in the ESR-beta gene, methods of detecting these sequences/polymorphisms in a sample, methods of determining a risk of having or developing a disorder mediated by a variant estrogen receptor and methods of screening for compounds used to treat disorders mediated by a variant estrogen receptor.

DESCRIPTION OF THE FIGURES

FIG. 1. Shows the Complete genomic sequence of the estrogen receptor beta gene.

FIG. 2. Shows sequence polymorphisms found in the ESR-beta genomic DNA (nucleotide position is based on the sequence provided in FIGS. 1 and 3).

Figure 7:
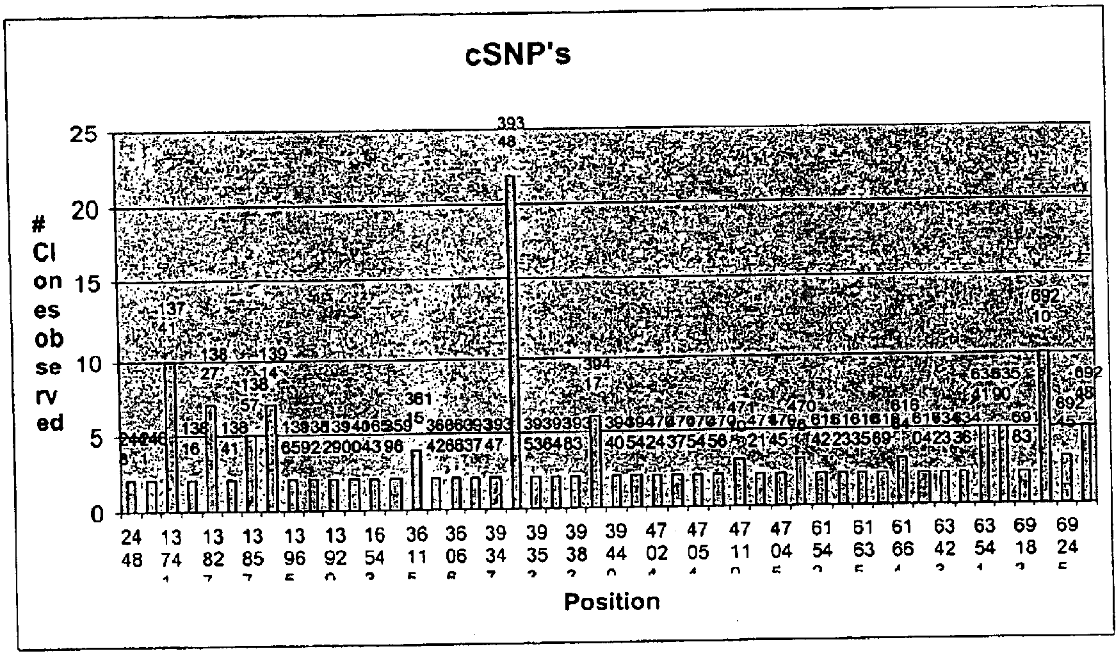

a) SNPs in Liverpool clinical tissue samples.

b) SNPs in pooled Coriell Diversity panels.

c) SNPs in unpooled Coriell Diversity panels.

d) SNPs in CEPH families.

e) PCR primers.

f) Sequencing primers.

FIG. 3. Shows the nucleic acid sequence of a cDNA covering the ESR-beta gene.

FIG. 4. Shows the amino acid sequence of the estrogen receptor beta protein.

FIG. 5. A graphic representation of the human ESR 2 locus.

(a) Complete structure of the human synaptic nuclei expressed gene 2 (syne-2) contained within intron 9 of ERβ. Exons are represented by filled boxes and introns by horizontal lines. Note that the gene is on the opposite strand as ERβ. (b) Complete structure of the human estrogen receptor beta (ERβ). Exons are represented by filled boxes and introns by horizontal lines. (c) Order and names of contigs used to complete the genomic sequence. GA numbers represent Celera contig numbers. Research genetics BAC clones are represented by standard plate and well numbering.

FIG. 6. The exon structure of the genomic ESR-beta gene.

FIG. 7. Shows the distribution and frequency of the SNPs of the present invention in the ESR-beta gene.

FIG. 8. ESR-beta SNPs: a) in Coriell Samples, b) in Liverpool Samples (T=tumor sample, B=blood sample).

FIG. 9. ESR-beta exons with SNPs. (see FIG. 2 for "N", "C", "I", "A", "S" representations). Underlined sequences indicate the primer sequences.

DETAILED DESCRIPTION OF THE INVENTION

General Description

The present invention is based on sequencing genomic DNA from human and cDNAs to define the genomic structure of estrogen receptor beta genes and novel polymorphisms in the estrogen receptor gene/protein. Such polymorphisms can lead to a variety of disorders that are mediated/modulated by a variant estrogen receptor, such as a susceptibility to cancer, osteoporosis, cardiovascular disorders, etc. Based on this sequencing approach, the present invention provides genomic nucleotide sequences, cDNA sequences, amino acid sequences and sequence polymorphisms in the ESR-beta gene, methods of detecting these sequences/polymorphisms in a sample, methods of determining a risk of having or developing a disorder mediated by a variant estrogen receptor and methods of screening for compounds used to treat disorders mediated by a variant estrogen receptor.

Isolated SNP-Containing Nucleic Acid Molecules

The present invention provides isolated nucleic acid molecules that contain one or more SNPs disclosed by the present invention. The present invention further provides isolated nucleic acid molecules that encode the variant protein. Such nucleic acid molecules will consist of, consist essentially of, or comprise one or more SNPs of the present invention. The nucleic acid molecule can have additional nucleic acid residues, such as nucleic acid residues that are naturally associated with it or heterologous nucleotide sequences.

As used herein, an "isolated" SNP-containing nucleic acid molecule is one that contains a SNP of the present invention and is separated from other nucleic acid present in the natural source of the nucleic acid. Generally, the isolated SNP-containing nucleic acid, as used herein, will be comprised of one or more SNP positions disclosed by the present invention with flanking nucleotide sequence on either side of the SNP positions. Preferably the flanking sequence is up to about 300 bases, 100 bases, 50 bases, 30 bases, 15 bases, 10 bases, or 4 bases on either side of a SNP position for detection reagents or as long as the entire protein encoding sequence if it is to be used to produce a protein containing the coding variants disclosed in Figures. The important point is that the nucleic acid is isolated from remote and unimportant flanking sequences and is of appropriate length such that it can be subjected to the specific manipulations or uses described herein such as recombinant expression, preparation of probes and primers for the SNP position, and other uses specific to the SNP-containing nucleic acid sequences.

Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. However, the nucleic acid molecule can be fused to other coding or regulatory sequences and still be considered isolated. For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

Isolated SNP-containing nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The present invention further provides related nucleic acid molecules that hybridize under stringent conditions to the nucleic acid molecules disclosed herein. As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80%, or at least about 90% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45° C., followed by one or more washes in 0.2×SSC, 0.1% SDS at 5065° C. Examples of moderate to low stringency hybridization conditions are well known in the art.

Specific Embodiments

Peptide Molecules

The present invention provides nucleic acid sequences that encode variants of the estrogen receptor. These variant molecule/sequences will be referred to herein as the estrogen receptor variants of the present invention, the estrogen receptor proteins of the present invention, or peptides/proteins of the present invention.

The present invention provides isolated estrogen receptor protein molecules that consist of, consist essentially of or are comprised of the amino acid sequences of the estrogen receptor variant proteins disclosed herein.

As used herein, a protein or peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the estrogen receptor protein having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated estrogen receptor proteins can be purified from cells that naturally express it, purified from cells that have been altered to express it (recombinant), or synthesized using known protein synthesis methods. For example, a nucleic acid molecule encoding the estrogen receptor protein is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that are encoded by an ESR-beta gene that consist of the ESR-beta encoding nucleic acid sequence provided in FIGS. 1 and 3, including one or more of the sequence polymorphisms provided in FIG. 2. A protein consists of an amino acid sequence when the amino acid sequence is the final amino acid sequence of the protein.

The present invention further provides proteins that are encoded by an ESR-beta gene that consist essentially of the ESR-beta encoding nucleic acid sequence provided in FIGS. 1 and 3, including one or more of the sequence polymorphisms provided in FIG. 2. A protein consists essentially of an amino acid sequence when such an amino acid sequence is present with only a few additional amino acid residues in the final protein.

The present invention further provides a that are encoded by an ESR-beta gene that comprises the ESR-beta encoding nucleic acid sequence provided in FIGS. 1 and 3, including one or more of the sequence polymorphisms provided in FIG. 2. A protein is comprised of an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. A brief description of how various types of these proteins can be made/isolated is provided below.

The estrogen receptor protein of the present invention can be attached to heterologous sequences to form chimeric or fusion proteins. Such chimeric and fusion proteins comprise a estrogen receptor protein operatively linked to a heterologous protein having an amino acid sequence not substantially homologous to the estrogen receptor protein. "Operatively linked" indicates that the estrogen receptor protein and the heterologous protein are fused in-frame. The heterologous protein can be fused to the N-terminus or C-terminus of the estrogen receptor protein.

In some uses, the fusion protein does not affect the activity of the estrogen receptor protein per se. For example, the fusion protein can include, but is not limited to, enzymatic fusion proteins, for example beta-galactosidase fusions, yeast two-hybrid GAL fusions, poly-His fusions, MYC-tagged, FE-tagged and Ig fusions. Such fusion proteins, particularly poly-His fusions, can facilitate the purification of recombinant estrogen receptor protein. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A estrogen receptor protein-encoding nucleic acid can be cloned into such an expression vector such that the fusion moiety is linked in-frame to the estrogen receptor protein.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Post-translational Covalent Modification of Proteins*, B. C. Johnson, Ed., Academic Press, New York 1–12 (1983); Seifter et al. (*Meth Enzymol.* 182: 626–646 (1990)) and Rattan et al. (*Ann. N.Y. Acad. Sci.* 663:48–62 (1992)).

The present invention further provides fragments of the estrogen receptor proteins of the present invention, in addition to proteins and peptides that comprise and consist of such fragments. The fragments to which the invention pertains, however, are not to be construed as encompassing fragments that may be disclosed publicly prior to the present invention.

As used herein, a fragment comprises at least 8 or more contiguous amino acid residues from a estrogen receptor protein. Such fragments can be chosen based on the ability to retain one or more of the biological activities of the estrogen receptor protein or could be chosen for the ability to perform a function, e.g. act as an immunogen. Particularly important fragments are biologically active fragments, peptides which are, for example, about 8 or more amino acids in length, that contain a variant amino acid residue (FIG. 2). Such fragments will typically comprise a domain or motif of the estrogen receptor proteins of the present invention, e.g., active site, ligand binding domain or DNA binding domain. Further, possible fragments include, but are not limited to, domain or motif containing fragments, soluble peptide fragments, and fragments containing immunogenic structures. Predicted domains and functional sites are readily identifiable by computer programs well-known and readily available to those of skill in the art (e.g., PROSITE analysis).

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its binding partner or receptor) in biological fluids; and as markers for tissues in which the corresponding protein is preferentially expressed (either constitutively or at a particular stage of tissue differentiation or development or in a disease state). Any or all of these research utilities are capable of being developed into reagent grade or kit format for commercialization as research products. Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The estrogen receptor proteins of the present invention are useful for biological assay. Such assays involve any of the known estrogen receptor functions or activities or properties useful for the diagnosis and treatment of estrogen receptor-related conditions (see Background Section).

The estrogen receptor proteins of the present invention are also useful in drug screening assays, such as in cell-based or cell-free systems. Cell-based systems can be native, i.e., cells that normally express the receptor protein, as a biopsy or expanded in cell culture. In one embodiment, however, cell-based assays involve recombinant host cells expressing the receptor protein.

The estrogen receptor proteins of the present invention can be used to identify compounds that modulate receptor activity. Both the estrogen receptor protein of the present invention and appropriate fragments can be used in high-throughput screens to assay candidate compounds for the ability to bind and/or modulate the activity of the receptor. These compounds can be further screened against a functional receptor to determine the effect of the compound on the receptor activity. Further, these compounds can be tested in animal or invertebrate systems to determine activity/ effectiveness. Compounds can be identified that activate (agonist) or inactivate (antagonist) the receptor to a desired degree. Such compounds can be selected for the ability to act on one or more of the variant estrogen receptor proteins of the present invention.

Further, the receptor polypeptides can be used to screen a compound for the ability to stimulate or inhibit interaction between the receptor protein and a target molecule that normally interacts with the receptor protein, e.g. estrogen. The target can be ligand or a binding partner that the receptor protein normally interacts (for example, an estrogen ligand or a DNA sequence). Such assays typically include the steps of combining the receptor protein with a candidate compound under conditions that allow the receptor protein, or fragment, to interact with the target molecule, and to detect the formation of a complex between the protein and the target or to detect the biochemical consequence of the interaction with the receptor protein and the target, such as any of the associated effects of DNA binding or signal transduction.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant receptors or appropriate fragments containing mutations that affect receptor function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) receptor activity. The assays typically involve an assay of events in the signal transduction pathway that indicate receptor activity. Thus, the expression of genes that are up- or down-regulated in response to the receptor protein dependent signal cascade can be assayed. In one embodiment, the regulatory region of such genes can be operably linked to a marker that is easily detectable, such as luciferase. Alternatively, phosphorylation of the receptor protein, or a receptor protein target, could also be measured. Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art.

The receptor polypeptides are also useful in competition binding assays in methods designed to discover compounds that interact with the receptor. Thus, a compound is exposed to a receptor polypeptide under conditions that allow the compound to bind or to otherwise interact with the polypeptide. Ligands to the receptor are also added to the mixture. If the test compound interacts with the receptor or ligand, it decreases the amount of complex formed or activity from the receptor target. This type of assay is particularly useful in cases in which compounds are sought that interact with specific regions of the receptor.

To perform cell free drug screening assays, it is sometimes desirable to immobilize either the receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule, as well as enzyme-linked assays which rely on detecting an enzymatic activity associated with the target molecule.

Agents that modulate the protein of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of receptor protein activity identified according to these drug screening assays can be used to treat a subject with a disorder mediated by the receptor pathway, by treating cells that express the estrogen receptor protein. These methods of treatment include the steps of administering the modulators of protein activity in a pharmaceutical composition as described herein, to a subject in need of such treatment.

This invention further pertains to novel agents identified by the above-described screening assays. Accordingly, it is within the scope of this invention to further use an agent identified as described herein in an appropriate animal model. For example, an agent identified as described herein (e.g., an estrogen receptor modulating agent, an antisense estrogen receptor nucleic acid molecule, an estrogen receptor-specific antibody, or an estrogen receptor-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The estrogen receptor proteins of the present invention are also useful to provide a a=target for diagnosing a disease or predisposition to disease mediated by the estrogen receptor. Accordingly, the invention provides methods for detecting the presence, or levels of, the estrogen receptor variants of the present invention (or encoding mRNA) in a cell, tissue, or organism. The method involves contacting a biological sample with a compound capable of interacting with the receptor protein (or gene or mRNA encoding the receptor) such that the interaction can be detected.

One agent for detecting a protein in a sample is an antibody capable of selectively binding to a variant form of the estrogen receptor protein. Such samples include tissues, cells and biological fluids isolated from a subject, as well as tissues, cells and fluids present within a subject. Other agents, such as nucleic acid based probes, primers and arrays are described below.

The estrogen receptor proteins of the present invention also provide targets for diagnosing active disease, or predisposition to disease, in a patient having a variant estrogen receptor, particularly a disease involving the estrogen pathway, such as cardiovascular disease, autoimmune disease, cell differentiation, etc (see Background Section). Thus, the receptor can be isolated from a biological sample and assayed for the presence of a genetic mutation that results in aberrant receptor activity. This includes amino acid substitution, deletion, insertion, rearrangement, (as the result of aberrant splicing events), and inappropriate post-translational modification as provided in FIG. 2. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Particularly useful are the variants provided in FIG. 2.

In vitro techniques for detection of peptide include enzyme linked immunosorbent assays (ELISAs), Western blots, immunoprecipitations and immunofluorescence. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the specific allelic variants of the estrogen receptor disclosed herein that are expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin Exp. Pharmacol. Physiol.* 23(10–11):983–985 (1996)), and Linder, M. W. (*Clin Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism/haplotype. As an alternative to genotyping, specific polymorphic peptides could be identified.

Antibodies

The invention also provides antibodies that selectively bind to the estrogen receptor proteins of the present invention as well as fragments thereof. As used herein, an antibody selectively binds a target protein when it binds the target protein and does not significantly bind to unrelated proteins. An antibody is still considered to selectively bind a protein even if it also binds to other proteins that are not substantially homologous with the target protein so long as such proteins share homology with a fragment or domain of the protein target of the antibody. In this case, it would be understood that antibody binding to the protein is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989). In general, to generate antibodies, an isolated peptide is used as an immunogen and is administered to a mammalian organism, such as a rat, rabbit or mouse. The full-length protein, an antigenic peptide fragment or a fusion protein can be used.

Antibodies are preferably prepared from regions or discrete fragments of the estrogen receptor protein. Antibodies can be prepared from any region of the peptide as described herein. However, preferred regions will include amino acids residues that are altered in the variants of the present inventions, particularly those involved in function/activity and/or receptor/binding partner interaction. An antigenic fragment will typically comprise at least 10 contiguous amino acid residues. The antigenic peptide can comprise, however, at least 12, 14, 20 or more amino acid residues. Such fragments can be selected on a physical property, such as fragments correspond to regions that are located on the surface of the protein, e.g., hydrophilic regions or can be selected based on sequence uniqueness.

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, O-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate the estrogen receptor protein of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of the estrogen receptor protein of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full length estrogen receptor protein can be used to identify turnover.

Further, the antibodies can be used to assess expression in disease states such as in active stages of the disease or in an individual with a predisposition toward disease related to the protein's function, particularly diseases involving cardiovascular disease, autoimmune disease, etc (see Background Section). When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality.

Accordingly, where treatment is ultimately aimed at correcting the expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant estrogen receptor protein analyzed by electrophoretic mobility, isoelectric point, tryptic peptide digest, and other physical assays known to those in the art.

The antibodies are also useful for inhibiting protein function, for example, blocking the binding of the estrogen receptor protein to a binding partner such as a ligand. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane.

The invention also encompasses kits for using antibodies to detect the presence of a protein in a biological sample. The kit can comprise antibodies such as a labeled or labelable antibody and a compound or agent for detecting estrogen receptor protein in a biological sample; means for determining the amount of protein in the sample; means for comparing the amount of estrogen receptor protein in the sample with a standard; and instructions for use.

Nucleic Acid Molecules

The present invention further provides isolated nucleic acid molecules that encode any of the estrogen receptor proteins of the present invention. Such nucleic acid molecules will consist of, consist essentially of, or comprise a nucleotide sequence that encodes one of the estrogen receptor proteins of the present invention.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the ESR-beta encoding nucleotide sequence shown in FIGS. 1 and 3, including one or more of the sequence polymorphisms provided in FIG. 2. A nucleic acid molecule consists of a nucleotide sequence when the nucleotide sequence is the complete nucleotide sequence of the nucleic acid molecule.

The present invention further provides nucleic acid molecules that consist essentially of the ESR-beta encoding nucleotide sequence shown in FIGS. 1 and 3, including one or more of the sequence polymorphisms provided in FIG. 2. A nucleic acid molecule consists essentially of a nucleotide sequence when such a nucleotide sequence is present with only a few additional nucleic acid residues in the final nucleic acid molecule.

The present invention further provides nucleic acid molecules that are comprised of the ESR-beta encoding nucleotide sequences shown in FIGS. 1 and 3, including one or more of the sequence polymorphisms provided in FIG. 2. A nucleic acid molecule is comprised of a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the estrogen receptor protein alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA, as well as genomic regulatory sequences such as promoters. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the noncoding strand (anti-sense strand).

The invention further provides nucleic acid molecules that encode fragments of the proteins of the present invention. A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides. The preferred probe/primer set will cover/span one of the variant bases identified in FIG. 2.

As used herein, the term "hybridizes under stringent conditions" is intended to describe conditions for hybridization and washing under which nucleotide sequences encoding a peptide at least 50–55% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in *Current Protocols in Molecular Biology*, John Wiley & Sons, N.Y. (1989), Sections 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65C.

Nucleic Acid Molecule Uses

The nucleic acid molecules of the present invention are useful for probes, primers, chemical intermediates, and in biological assays. The probe can correspond to any sequence along the entire length of the nucleic acid molecules provided in FIGS. 1 and 3, including one or more of the sequence polymorphisms provided in FIG. 2. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in estrogen receptor protein expression relative to normal results.

In vitro techniques for detection of mRNA include Northern hybridizations, in situ hybridizations and nucleic acid array based expression profiling. In vitro techniques for detecting DNA includes Southern hybridizations, in situ hybridization and nucleic acid array based expression profiling.

Probes can be used as a part of a diagnostic test kit or nucleic acid array format for identifying cells or tissues that express a estrogen receptor proteins of the present invention, such-as by measuring a level of a receptor-encoding nucleic acid in a sample of cells from a subject e.g., mRNA or genomic DNA, or determining if a receptor gene has been mutated.

Nucleic acid expression assays are useful for drug screening to identify compounds that modulate estrogen receptor nucleic acid expression.

The invention thus provides a method for identifying a compound that can be used to treat a disorder associated with nucleic acid expression of the estrogen receptor gene. The method typically includes assaying the ability of the compound to modulate the expression of the estrogen receptor nucleic acid and thus identifying a compound that can be used to treat a disorder characterized by undesired estrogen receptor nucleic acid expression. The assays can be performed in cell-based and cell-free systems. Cell-based assays include cells naturally expressing the estrogen receptor nucleic acid or recombinant cells genetically engineered to express specific nucleic acid sequences.

The assay for estrogen receptor nucleic acid expression can involve direct assay of nucleic acid levels, such as mRNA levels, or on collateral compounds involved in the signal pathway. Further, the expression of genes that are up- or down-regulated in response to the estrogen receptor protein signal pathway can also be assayed. In this embodiment the regulatory regions of these genes can be operably linked to a reporter gene such as luciferase.

Thus, modulators of estrogen receptor gene expression can be identified in a method wherein a cell is contacted with a candidate compound and the expression of mRNA determined. The level of expression of estrogen receptor mRNA in the presence of the candidate compound is compared to the level of expression of estrogen receptor mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate estrogen receptor nucleic acid expression. Modulation includes both up-regulation (i.e. activation or agonization) or down-regulation (suppression or antagonization) or nucleic acid expression.

Alternatively, a modulator for estrogen receptor nucleic acid expression can be a small molecule or drug identified using the screening assays described herein as long as the drug or small molecule inhibits the estrogen receptor nucleic acid expression.

The nucleic acid molecules are also useful for monitoring the effectiveness of modulating compounds on the expression or activity of the estrogen receptor gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in estrogen receptor nucleic acid, and particularly in qualitative changes that lead to pathology. The nucleic acid molecules can be used to detect mutations in estrogen receptor genes and gene expression products such as mRNA. The nucleic acid molecules can be used as hybridization probes to detect naturally-occurring genetic mutations in the estrogen receptor gene and thereby to determine whether a subject with the mutation is at risk for a disorder caused by the mutation. Mutations include deletion, addition, or substitution of one or more nucleotides in the gene, particularly those identified in FIG. 2, and chromosomal rearrangement, such as inversion or transposition, modification of genomic DNA, such as aberrant methylation patterns or changes in gene copy number, such as amplification. Detection of a mutated form of the estrogen receptor gene associated with a dysfunction provides a diagnostic tool for an active disease or susceptibility to disease when the disease results from overexpression, underexpression, or altered expression of a estrogen receptor protein.

Individuals carrying mutations in the estrogen receptor gene can be detected at the nucleic acid level by a variety of techniques. Genomic DNA can be analyzed directly or can be amplified by using PCR prior to analysis. RNA or cDNA can be used in the same way. Samples can be used to examine one variation at a time or multiplexed, such as by using a nucleic acid array, to examine many variants in a single experiment. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a estrogen receptor gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant estrogen receptor gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth Enzymol.* 217:286295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the estrogen receptor gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphism allow effective clinical design of treatment compounds and dosage regimens.

The nucleic acid molecules are thus useful as antisense constructs to control estrogen receptor gene expression in cells, tissues, and organisms. A DNA antisense nucleic acid molecule is designed to be complementary to a region of the gene involved in transcription, preventing transcription and hence production of estrogen receptor protein. An antisense RNA or DNA nucleic acid molecule would hybridize to the mRNA and thus block translation of mRNA into estrogen receptor protein.

Alternatively, a class of antisense molecules can be used to inactivate mRNA in order to decrease expression of estrogen receptor nucleic acid. Accordingly, these molecules can treat a disorder characterized by abnormal or undesired estrogen receptor nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the estrogen receptor proteins of the present invention, such as ligand binding.

The nucleic acid molecules also provide vectors for gene therapy in patients containing cells that are aberrant in estrogen receptor gene expression. Thus, recombinant cells, which include the patient's cells that have been engineered ex vivo and returned to the patient, are introduced into an individual where the cells produce the desired estrogen receptor protein to treat the individual.

The invention also encompasses kits for detecting the presence of an estrogen receptor nucleic acid in a biological sample. For example, the kit can comprise reagents such as a labeled or labelable nucleic acid or agent capable of detecting estrogen receptor nucleic acid in a biological sample; means for determining the amount of estrogen receptor nucleic acid in the sample; and means for comparing the amount of estrogen receptor nucleic acid in the sample with a standard. The compound or agent can be packaged in a suitable container. The kit can further comprise instructions for using the kit to detect estrogen receptor protein mRNA or DNA.

Design of SNP-Containing Nucleic Acids Detection Methods

The SNP-containing nucleic acid molecules of the present invention are useful as probes, primers, chemical intermediates, and in biological assays for SNPs of the present invention. The probes/primers can correspond to one or more of the SNPs provided in FIGS. 1–3, 8 and 9 or can correspond to a specific region 5' and/or 3' to a SNP position. However, as discussed above, fragments are not to be construed as encompassing fragments that are not associated with SNPs of the present invention or those known in the art for SNP detection. The SNP-containing nucleic acid molecules and information provided herein are also useful for designing primers for PCR to amplify any given SNP of the present invention and to design any formatted SNP detection reagent/kits.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides. Depending on the particular application, the consecutive nucleotides can either include the target SNP position, or be a specific region in close enough proximity 5' and/or 3' to the SNP position to carry out the desired assay.

Preferred primer and probe sequences can readily be determined using the sequences provided in FIGS. 1–3, 8 and 9. It will be apparent to one of skill in the art that such primers and probes are useful as diagnostic probes or amplification primers for genotyping SNPs of the present invention, and can be incorporated into a kit format.

For analyzing SNPs, it may be appropriate to use oligonucleotides specific to alternative SNP alleles (referred to as "allele-specific oligonucleotides", "allele-specific probes", or "allele-specific primers"). The design and use of allele-specific probes for analyzing polymorphisms is described by e.g., Saiki et al., Nature 324, 163–166 (1986); Dattagupta, EP 235,726, Saiki, WO 89/11548.

In a hybridization-based assay, allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, the "pairs" may be identical except for a one nucleotide mismatch that represents the allelic variants at the SNP position. One member of a pair perfectly matches a reference form of a target sequence and the other member perfectly matches a variant form. In the case of an array, several pairs of probes can then be immobilized on the same support for simultaneous analysis of multiple polymorphisms within the same target sequence.

In one type of PCR-based assay, an allele-specific primer hybridizes to a site on target DNA overlapping the SNP position and only primes amplification of an allelic form to which the primer exhibits perfect complementarity. See Gibbs, Nucleic Acid Res. 17 2427–2448 (1989). This primer is used in conjunction with a second primer that hybridizes at a distal site. Amplification proceeds from the two-primers, resulting in a detectable product that indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456). This PCR-based assay can be utilized as part of the TaqMan assay, described below.

SNP Detection Kits, Nucleic Acid Arrays, and Integrated Systems

The present invention further provides SNP detection kits, such as arrays or microarrays of nucleic acid molecules, or probe/primer sets, that are based on the SNPs provided in FIGS. 1–3, 8, 9.

In one embodiment of the present invention, kits are provided which contain the necessary reagents to carry out one or more assays that detect one or more SNPs disclosed herein. The present invention also provides multicomponent integrated systems for analyzing the SNPs provided by the present invention.

SNP detection kits may contain one or more oligonucleotide probes, or pairs of probes, that hybridize at or near each SNP position. Multiple pairs of allele-specific oligonucleotides may be included in the kit to simultaneously assay large numbers of SNPs, at least one of which is one of the SNPs of the present invention. In some kits, such as arrays, the allele-specific oligonucleotides are provided immobilized to a substrate. For example, the same substrate can comprise allele-specific oligonucleotide probes for detecting at least 1; 10; 100; 1000; 10,000; 100,000; 300,000 or substantially all of the polymorphisms shown in FIGS. 1–3, 8 and 9.

Specifically, the invention provides a compartmentalized kit to receive, in close confinement, one or more containers which comprises: (a) a first container comprising one of the nucleic acid probes, for example an allele-specific oligonucleotide, that can bind to a fragment of the human genome containing a SNP disclosed herein; and (b) one or more other containers comprising one or more of the following: wash reagents or reagents capable of detecting the presence of a bound probe.

In detail, a compartmentalized kit includes any kit in which reagents are contained in separate containers. Such containers include small glass containers, plastic containers, strips of plastic, glass or paper, or arraying material such as silica. Such containers allow one to efficiently transfer reagents from one compartment to another compartment such that the samples and reagents are not cross-contaminated, and the agents or solutions of each container can be added in a quantitative fashion from one compartment to another. Such containers may include a container which will accept the test sample, a container which contains the SNP probe, containers which contain wash reagents (such as phosphate buffered saline, Tris-buffers, etc.), and containers which contain the reagents used to detect the bound probe. The kit can further comprise reagents for PCR or other enzymatic reactions, and instructions for using the kit. One skilled in the art will readily recognize that the previously unidentified SNPs of the present invention can be routinely identified using the sequence information disclosed herein and can be readily incorporated into one of the established kit formats which are well known in the art.

The present invention further provides arrays or microarrays of nucleic acid molecules that are based on the sequence information provided in FIGS. 1 and 3, including one or more of the variations provided in FIG. 2.

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522. Arrays or microarrays are commonly referred to as "DNA chips".

Any number of oligonucleotide probes, such as allele-specific oligonucleotides, may be implemented in an array, wherein each probe or pair of probes corresponds to a different SNP position. The oligonucleotides are synthesized at designated areas on a substrate using a light-directed chemical process. The substrate may be paper, nylon or other type of membrane, filter, chip, glass slide or any other suitable solid support.

Hybridization assays based on oligonucleotide arrays rely on the differences in hybridization stability of short oligonucleotides probes to perfectly matched and mismatched target sequence variants. Efficient access to polymorphism information is obtained through a basic structure comprising high-density arrays of oligonucleotide probes attached to a solid support (e.g., a chip) at selected positions. Each DNA chip can contain thousands to millions of individual synthetic DNA probes arranged in a grid-like pattern and miniaturized to the size of a dime, each corresponding to a particular SNP position or allelic variant. Preferably, probes are attached to a solid support in an ordered, addressable array.

The array/chip technology has already been applied with success in numerous cases. For example, the screening of mutations has been undertaken in the BRCA 1 gene, in *S. cerevisiae* mutant strains, and in the protease gene of HIV-1 virus (Hacia et al., 1996; Shoemaker et al., 1996; Kozal et al., 1996). Chips of various formats for use in detecting SNPs can be produced on a customized basis.

An array-based tiling strategy useful for detecting SNPs is described in EP 785280. Briefly, arrays may generally be "tiled" for a large number of specific polymorphisms. "Tiling" refers to the synthesis of a defined set of oligonucleotide probes that are made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific SNPs. In particular, the array is tiled to include a number of detection blocks, each detection block being specific for a specific SNP or a set of SNPs. For example, a detection block may be tiled to include a number of probes that span the sequence segment that includes a specific SNP. To ensure probes that are complementary to each allele, the probes are synthesized in pairs differing at the SNP position. In addition to the probes differing at the SNP position, monosubstituted probes are also generally tiled within the detection block. Such methods can readily be applied to the SNP information disclosed herein.

These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the SNP. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the SNP are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of those disclosed in the FIGS. 1–3, 8 and 9, and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In some embodiments the polymorphic base is within 5, 4, 3, 2, or 1 nucleotides from the center of the polynucleotide, more preferably at the center of said polynucleotide. In other embodiments, the chip may comprise an array containing any number of polynucleotides of the present invention.

An oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number which lends itself to the efficient use of commercially available instrumentation.

Using such arrays, the present invention provides methods of identifying the SNPs of the present invention in a sample. Such methods comprise incubating a test sample with an array comprising one or more oligonucleotide probes corresponding to at least one SNP position of the present invention, and assaying for binding of a nucleic acid from the test sample with one or more of the oligonucleotide probes. Such assays will typically involve arrays comprising oligonucleotides probes corresponding to many SNP positions and/or allelic variants of those SNP positions, at least one of which is a SNP of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel SNPs disclosed herein. Examples of such assays can be found in Chard, T, An Introduction to Radioimmunoassay and Related Techniques, Elsevier Science Publishers, Amsterdam, The Netherlands (1.986); Bullock, G. R. et al., Techniques in Immunocytochemistry, Academic Press, Orlando, Fla. Vol. 1 (I 982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

The test samples of the present invention include, but are not limited to, nucleic acid extracts, cells, and protein or membrane extracts from cells, which may be obtained from any bodily fluids (such as blood, urine, saliva, phlegm, gastric juices, etc.), cultured cells, biopsies, or other tissue preparations. The test sample used in the above-described methods will vary based on the assay format, nature of the detection method and the tissues, cells or extracts used as the sample to be assayed. Methods of preparing nucleic acid, protein, or cell extracts are well known in the art and can be readily be adapted in order to obtain a sample that is compatible with the system utilized.

Multicomponent integrated systems may also be used to analyze SNPs. Such systems miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping SNPs, the microfluidic system may integrate, for example, nucleic acid amplification, minisequencing primer extension, capillary electrophoresis, and a detection method such as laser induced fluorescence detection.

In a first step, the DNA samples are amplified, preferably by PCR. Then, the amplification products are subjected to automated minisequencing reactions using ddNTPs (specific fluorescence for each ddNTP) and the appropriate oligonucleotide minisequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. This microchip can be used to process at least 96 to 384 samples, or more, in parallel.

Vectors/Host Cells

The invention also provides vectors containing the nucleic acid molecules described herein. The term "vector" refers to a vehicle, preferably a nucleic acid molecule, that can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, eg. cosmids and phagemids. Appropriate cloning and expression vectors for prokaryotic and eukaryotic hosts are described in Sambrook et al., *Molecular Cloning A Laboratory Manual.* 2nd. ed., Cold Spring Harbor Laboratory Press, Cold Spring Harbor, N.Y., (I 989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et a!, *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that pemits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual,* 2nd, ed, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as estrogen receptors, appropriate secretion signals are incorporated into the vector. The signal sequence can be endogenous to the peptides or heterologous to these peptides.

Where the peptide is not secreted into the medium, which is typically the case with estrogen receptors, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a estrogen receptor protein or peptide that can be further purified to produce desired amounts of estrogen receptor protein or fragments. Thus, host cells containing expression vectors are useful for peptide production.

Host cells are also useful for conducting cell-based assays involving the estrogen receptor protein or estrogen receptor protein fragments, such as those described above as well as other formats known in the art. Thus, a recombinant host cell expressing a native estrogen receptor protein is useful for assaying compounds that stimulate or inhibit estrogen receptor protein function.

Host cells are also useful for identifying estrogen receptor protein mutants in which these functions are affected. If the mutants naturally occur and give rise to a pathology, host cells containing the mutations are useful to assay compounds that have a desired effect on the mutant estrogen receptor protein (for example, stimulating or inhibiting function) which may not be indicated by their effect on the native estrogen receptor protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a estrogen receptor protein and identifying and evaluating modulators of estrogen receptor protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the estrogen receptor protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the estrogen receptor protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS*89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, estrogen receptor protein activation, and signal transduction, may not be evident from in vitro cell-free or cell-based assays. Accordingly, it is useful to provide non-human transgenic animals to assay in vivo estrogen receptor protein function, including ligand interaction, the effect of specific mutant estrogen receptor protein on estrogen receptor protein function and ligand interaction, and the effect of chimeric estrogen receptor protein. It is also possible to assess the effect of null mutations, that is mutations that substantially or completely eliminate one or more estrogen receptor protein functions.

EXAMPLES:

SNP Identification and Characterization

The method used to identify SNPs in the ESR-beta gene was sequencing of overlapping ESR-beta PCR products amplified by primers listed below in the tables. Using DNA extracted from the blood and tumors of 48 breast cancer (BC) patients and a Coriell Diversity Panel, PCR was performed to amplify exons—7 through 9 of ESR2, plus approximately 100 bases of each flanking intron. PCR products were sequenced. Sequences for exons—7 to −2 were compared with cDNA sequence from AB06589 and an "assembled" BAC AL161756. Sequences for exons—1 through 9 (FIG. 2) were compared to a BAC sequence representing 101 kb of ESR2 (all but the most 5' and 3' exons known to us), referred to here as Contig64 (FIG. 1), to discover single nucleotide polymorphisms (SNPs). Sequences for exon 10 were compared with an assembled BAC sequence representing all of ER2, referred to as ER2 BAC. PolyPhred version 2.0 (D. A. Nickerson, S. Taylor, N. Kolker, Univ. of Washington, 1998) was run on the sequences (with default settings) to visualize potential heterozygotes. Tagged sites were examined for quality to verify polymorphisms. 21 SNPs were found with a frequency greater than 2, with 4 being unique to the clinical samples, and 4 unique to the Coriell Samples. Six of these SNPs had been observed in ESR2 cDNA, isolated from a pool of prostate mRNA from 47 individuals (Clontech). 15 of the 16 SNPs had at least one instance of a change in heterozygosity, and 5 had at least one instance of a loss in heterozygosity. Of the three samples unique to the clinical samples, one was observed only in tumors.

TABLE 1

Summary of SNPs found in clinical samples with a frequency greater than 2 and quality score greater than 20.

| | |
|---|---|
| Total Number of SNPs | 21 |
| Number in Liverpool | 16 |
| Number in Coriell | 17 |
| Number unique to Liverpool | 4 |
| Number unique to Coriell | 4 |

TABLE 2

Summary of changes in heterozygosity in clinical samples. SNPs had a frequency greater than two and a quality score greater than 20.

| | |
|---|---|
| Number of Liverpool SNPs with >1 Change in Heterozygosity | 15 |
| Number of Liverpool SNPs with >1 case of Loss of Heterozygosity | 5 |

A summary of the SNPs that were identified is provided in FIG. 2(*a*). SNPs were observed in 48 breast cancer patients. Genomic DNA was isolated from blood (B; 96 chromosomes) and matched tumor tissue (T; 96 chromosomes).

FIG. 2(*b*) shows SNPs in pooled Coriell diversity panels. Some of the SNP sites were examined in 5 Coriell human diversity panels. Exons were PCR-amplified from pools of 3 or 4 individuals. Percent of chromosomes carrying the minor allele, calculated from peak height, was reported for each diversity panel, which represented 20 chromosomes (N. Eur, Northern European; Chi, Chinese; In-Pak, Indo-Pakistani; Af-Am, African-American; SW-NA, Southwestern Native American). As a reference, the frequency of these SNP's were observed in Liverpool BC samples was shown.

FIG. 2(*c*) shows SNPs in unpooled Coriell diversity panels: The SNP sites were examined in 5 Coriell human diversity panels of 10 individuals each.

FIG. 2(*d*) shows SNPs in CEPH families. SNP's found in clinical samples were validated in a second reference population of 3 CEPH families: Caucasian, African-American (Af-Am), and Asian. Each family represents 4 individuals, or 8 chromosomes. Percent of chromosomes carrying the minor allele (SNP allele) was also shown.

FIGS. 2(*e*) and (*f*) show the primer set and M13 primers that were used for overlapping PCR and clone sequencing. FIG. 2(*e*) shows the primers used to generate ix-(intron-exon) PCR products. Exons—7 though 8 were M13 tailed PCR primers. All sequencing done with M13 forward and reverse except for exon 9 in where the PCR primers were used for sequencing. FIG. 2(*f*) shows primers used for sequencing exon 10.

FIG. 5 shows the domain structure of the ESR-beta protein and the position of many of the SNPs disclosed herein. FIGS. 6*a*, 6*b* and 7 provide a graphical representation of introns/exons of the ESR-beta gene.

FIG. 8(*a*) shows the SNPs and frequency of occurance in Coriell Samples wherein the samples are collected from Northern European, Chinese, Indo-Pakistani, Africa American and Southwestern Native American ethnic groups. The result can be used for detection purpose among the specific ethnic groups. FIG. 8(*b*) shows the SNPs and frequence of occurance in Liverpool samples wherein the samples are selected from the groups of blood samples and breast cancer samples.

2. ESR 2 Genomic Sequencing—The Complete Genomic Structures of Estrogen Receptor Beta Estrogen receptor (ER) is a member of the nuclear hormone receptor gene superfamily. This family of genes is characterized by a modular structure with three distinct domains: a variable (N)-terminal domain, a highly conserved DNA binding domain, and a conserved (C)-terminal domain (Reviewed in 1, 2). Functionally, the (N)-terminus domain regulates transactivation, the DNA binding domain regulates dimerization and DNA binding, and the (C)-terminus domain regulates transactivation, dimerization, ligand binding, nuclear translocation, silencing, and Heat Shock Protein binding. It was shown that the functions of the individual domains of the nuclear hormone gene superfamily are independent of the receptor in which they are found, and that the domains retain their function even when placed into different heterologous proteins (3,4,5). The domain modularity in the nuclear hormone receptor gene superfamily exists because the major subfamilies of these genes evolved through a simple gene duplication early in evolution (6). The nuclear hormone receptor gene family can be separated according to two different classification schemes, one based on hormone binding, the other based on dimerization and how the receptors bind to their respective DNA response elements (for a review, see 2).

The cDNA for ERα was first cloned and sequenced from the MCF-7 breast cancer cell line and was found to have 27% identity and 41% conservation to the v-erb-A gene (7). ERα was mapped to chromosome 6q25.1 using Fluorescence In Situ Hybridization (FISH) and chromosome banding (8). In 1996, a novel estrogen receptor (ERβ) was identified by degenerate PCR (9) and mapped to 14q22–24 by FISH (10). ERα and ERβ were shown to have 96% sequence identity in the DNA binding domain, 58% identity in the ligand-binding domain, and low similarity in the 5' and 3' ends as well as in the hinge (domain D). A variety of ERα and ERβ variants have since been described, including single and multiple exon deletions, truncated transcripts, and transcripts containing insertions (11,12,13). These variants were isolated from a variety of sources, including normal tissues, tumor tissues and cell lines. The ER status of tumors in breast cancer patients has been used as an indicator of response to endocrine therapy (14,15), and many studies have examined the role of ER in breast cancer tumor progression, ER-negative status, and hormone antagonist resistance (for a complete review, see 16).

Because of the importance of the ER gene, we set about to clone it in its entirety and determine its complete structure. Initially, we used standard Bacterial Artificial Chromosome (BAC) sequencing to generate sequence information for the coding regions of the genes. As Celera's sequencing of the human genome progressed, the remaining regions of ER were filled in using Celera regional assemblies. A small region of less than 25 kb was filled in on ERα using a public BAC (A1353611.6, positions 1,497–25,941)

Materials and Methods

1) BAC Screening

Appropriate markers were designed for ERα and ERβ exons and used to obtain commercially available BAC clones from Research Genetics (Huntsville, Ala.). A number of positive BACs were selected and individual clones were re-screened for verification.

2) DNA Isolation and Library Preparation

BAC DNA was isolated from verified clones using QIAGEN columns (QIAGEN, Inc., Valencia, Calif.) according to the manufacturer's specifications. Shotgun libraries were prepared following standard protocols (17). Briefly, isolated BAC DNA was sonicated, polished, and size fractionated. Size selected DNA fragments were then subcloned into pUC19 using standard ligation techniques. Ligated DNA was transformed into Electrocompetent cells (Life Technologies, Rockville, Md.) and grown overnight.

3) DNA Sequencing and Annotation

Sequencing reactions were performed using Big Dye Terminator chemistry (Applied Biosystems, Foster City, Calif.) and run on an ABI PRISM 3700 DNA Analyzer (Applied Biosystems). Phred (18), Phrap and Consed (19) were used for base calling, assembly, and finishing, respectively. Exon locations were determined using Cross_Match to compare the published gene sequences to the genomic contig.

Results

1) Estrogen Receptor α

Alignment of the genomic sequence for ERα and published mRNA sequences for ERα show the gene consists of 14 exons and covers 446,296 bp of genomic sequence.

2) Estrogen Receptor β

Alignment of the genomic sequence for ERβ and published mRNA sequences for ERβ show the gene consists of 17 exons and covers 253,748 bp of genomic sequence (FIG. 5, Table 3). By analysis with the Celera Genome Browser, we were able to identify a gene, human synaptic nuclei expressed gene 2 (syne-2, accession number NM_015180.1), that is completely contained within intron 9 of ERβ, on the opposite strand. Further analysis of the syne-2 gene showed it consists of 21 exons, and covers 51,471 bp of genomic sequence.

Discussion

Alignment of the complete ERα genomic sequence and various ERβ transcripts shows that the gene covers 446,296 bp of genomic sequence and consists of 14 exons. The alignment of the published sequence for exon 1 E (AJ002561) (20) and the ER a genomic sequence revealed that exon 1 E actually consists of two separate exons. The newly delineated exon is referred to here as exon 1 G to conform to the naming convention previously established. Exon 1 G is located approximately 45 kb upstream of exon 1 E and conforms to the GT/AG splice site consensus sequence.

Alignment of the various ERβ transcripts to the complete ERβ genomic sequence reveals a more complex organization than was previously accepted (13). The 5' UTR of the ERβcx variant (AB006589) actually consists of seven untranslated exons (referred to here as exons −1 through −7), all of which conform to the GT/AG splice site consensus sequence (FIG. 5, table 3). Sequence alignment of ERβ variants AF061055 and AF061054 (12) showed that these transcripts both contain intron sequence and were probably partially mature transcripts. Both of these partially mature transcripts contain exon 7 and a portion of exon 9, but do not conform to the splice site consensus sequence at the sites where intron sequence is present.

By examining the ER genomic sequences using the Celera Genome Browser, we were able to identify a separate gene contained entirely within intron 9 of ERβ. This gene was identified as human synaptic nuclei expressed gene 2 (syne-2) and was shown to cover over 50 Kb of genomic sequence and consist of 21 exons, all of which conform to the GT/AG splice site consensus sequence (FIG. 5 and Table 4). The syne-2 gene is located on the antisense strand of ERβ.

Completion of the sequence and structures for ERα and ERβ should contribute to further understanding and characterization of these important receptors.

TABLE 3

Exon-Intron Boundaries and Locations in the Human Estrogen Receptor: Exon sequences are shown in upper case and intron sequences are shown in lower case. Splice sites are shown in bold.

| Gene | Exon no. | Splice variant | Contig start | Contig end | 5' splice donor | 3' splice acceptor | Exon Size (bp) | Intron size (Kb) |
|---|---|---|---|---|---|---|---|---|
| ER1 | 1G | AJ002561 | 18941 | 19032 | — | ACCAAAGAAG**gt**aagttttt | 91 | 33.79 |
| | 1F | AJ002562 | 52818 | 52940 | — | TTCTCTTCAA**gt**aggtactc | 122 | 11.21 |
| | 1E | AJ002561 | 64150 | 64280 | aaaacaaa**ag**GAAGAAGAAA | CATCACTGAG**gt**atgtgtga | 130 | 101.95 |
| | 1D | AJ002560 | 166228 | 166322 | — | GAGAGAGCCA**gt**aagtcacg | 94 | 1.68 |
| | 1C | X62462 | 168002 | 168120 | — | ATCCAGCAGG**gt**aggcttgt | 118 | 1.55 |

TABLE 3-continued

Exon-Intron Boundaries and Locations in the Human Estrogen Receptor: Exon sequences are shown in upper case and intron sequences are shown in lower case. Splice sites are shown in bold.

| Gene | Exon no. | Splice variant | Contig start | Contig end | 5' splice donor | 3' splice acceptor | Exon Size (bp) | Intron size (Kb) |
|---|---|---|---|---|---|---|---|---|
| | 1B | AJ002559 | 169674 | 169825 | — | GACAAGTAAA**gt**aaagttca | 151 | 0.04 |
| | 1A | X03635 | 169867 | 170678 | — | CATTCTACAG**gt**acccgcgc | 811 | 34.23 |
| | 2 | X03635 | 204912 | 205102 | ttcccccc**ag**GCCAAATTCA | AGTATTCAAG**gt**aatagtgt | 190 | 37.87 |
| | 3 | X03635 | 242970 | 243086 | cttttaat**ag**GACATAACGA | ATGAAAGCTG**gt**aggtacat | 116 | 63.08 |
| | 4 | X03635 | 306168 | 306503 | gtgttttc**ag**GGATACGAAA | AGGGTGCCAG**gt**aagaatgc | 335 | 67.14 |
| | 5 | X03635 | 373640 | 373778 | ttgttttc**ag**GCTTTGTGGA | TCTTGGACAG**gt**aagtgacc | 138 | 49.19 |
| | 6 | X03635 | 422964 | 423097 | gttttcat**ag**GAACCAGGGA | CTTAATTCTG**gt**gagttgat | 133 | 33.26 |
| | 7 | X03635 | 456354 | 456537 | gcgcattc**ag**GAGTGTACAC | GGCACATGAG**gt**gaggcatc | 183 | 4.16 |
| | 8 | X03635 | 460701 | 465237 | ccacctac**ag**TAACAAAGGC | — | 4536 | — |
| ER2 | −7 | AB006589 | 49552 | 49750 | — | GGTTCTGAAG**gt**gcgtggtt | 198 | 1.18 |
| | −6 | AB006589 | 50928 | 51235 | tgcctctt**ag**ACATCCAAGT | TGTTTGTAAG**gt**aataaaaa | 307 | 32.62 |
| | −5 | AB006589 | 83858 | 84041 | tatccact**ag**AGGGAGACAT | GAGAACACAG**gt**gaacttca | 183 | 1.90 |
| | −4 | AB006589 | 85942 | 86154 | ctctccat**ag**AAATCCTGGG | ATTAGCCCTG**gt**aaggagct | 212 | 2.88 |
| | −3 | AB006589 | 89037 | 89130 | cattcaac**ag**TATCTGGGCT | GTGCAGGTAG**gt**aggtaaag | 93 | 0.67 |
| | −2 | AB006589 | 89803 | 89988 | ccttttac**ag**GGTTTTGTTT | GTGTTGACAG**gt**aagatgag | 185 | 3.12 |
| | −1 | AF080555 | 93111 | 93488 | — | TATCTGCAAG**gt**aagcgccc | 377 | 10.96 |
| | 1 | AF060555 | 104446 | 104897 | ttctttac**ag**CCATTATACT | CTGTAAACAG**gt**aagtccag | 451 | 2.47 |
| | 2 | AF060555 | 107368 | 107540 | tgctccct**ag**AGAGACACTG | AGCATTCAAG**gt**acaagaga | 172 | 11.07 |
| | 3 | AF060555 | 118610 | 118726 | tctgctat**ag**GACATAATGA | GTGAAGTGTG**gt**gagtgctt | 116 | 8.05 |
| | 4 | AF06055 | 126774 | 127073 | tcctcttc**ag**GCTCCCGGAG | AAGATTCCCC**gt**agggcttt | 299 | 3.09 |
| | 5 | AF060555 | 130158 | 130296 | ctttcccc**ag**GCTTTGTGGA | TTCTGGACAG**gt**gagaaaaa | 138 | 7.56 |
| | 6 | AF060555 | 137853 | 137986 | acttttgt**ag**GGATGAGGGG | CTCAATTCCA**gt**aagtaatc | 133 | 14.39 |
| | 7 | AF060555 | 152379 | 152559 | ctttgtcc**ag**GTATGTACCC | GGCATGCGAG**gt**acgcgccc | 180 | 1.65 |
| | 8 | X99101 | 154206 | 154500 | gtccccat**ag**TAACAAGGGC | — | 826 | 5.42 |
| | 9 | AB006589 | 159915 | 160827 | tctactta**ag**GGCAGAAAAG | — | 912 | 141.65 |
| | 10 | AF060555 | 302474 | 303300 | gtcttgac**ag**CTCTCTCTCA | — | 826 | — |

TABLE 4

Exon-Intron Boundaries and Locations in the Human Synaptic Nuclei Expressed Gene 2. Exon sequences are shown in upper case and intron sequences are shown in lower case. Splice sites are shown in bold.

| Gene | Exon no. | Splice variant | Contig start | Contig end | 5' splice donor | 3' splice acceptor | Exon Size (bp) | Intron size (Kb) |
|---|---|---|---|---|---|---|---|---|
| Syne-2 | 1 | NM_015180 | 212563 | 212391 | — | CACTGTAGAG**gt**aaactcac | 172 | 2.22 |
| | 2 | NM_015180 | 210175 | 210044 | tttcaaat**ag**ACCTGGGACC | GCTGATTAAG**gt**attgaaat | 131 | 8.94 |
| | 3 | NM_015180 | 201109 | 200946 | ttaaatgc**ag**GAACTAGAAC | CTGCTTAAGG**gt**aagtcagc | 163 | 1.97 |
| | 4 | NM_015180 | 198981 | 198819 | tcatttgc**ag**GTGGCCATAC | GTTACAGAAG**gt**aagggagg | 162 | 1.36 |
| | 5 | NM_015180 | 197462 | 197290 | cctttgcc**ag**GACTGCATGG | TCGGATCAAG**gt**aagaaatg | 172 | 12.56 |
| | 6 | NM_015180 | 184732 | 184564 | atatgtgt**ag**GGTGAAGAAG | TGAGCAGCAG**gt**gggacaat | 168 | 5.79 |
| | 7 | NM_015180 | 178777 | 178584 | gtaatcac**ag**GATCTACAGC | GGCGCATGAA**gt**aagaacta | 193 | 0.48 |
| | 8 | NM_015180 | 178101 | 177949 | ctcccatc**ag**AATCGAGGAG | GAGGTTTGAG**gt**aaacacct | 152 | 0.36 |
| | 9 | NM_015180 | 177591 | 177405 | tgtgatgc**ag**GCCTTTCAGC | GAGACTCAGG**gt**gagctcct | 186 | 1.84 |
| | 10 | NM_015180 | 175570 | 175429 | acttttgc**ag**CATTTCACCA | CCAACTGAAT**gt**gagggctg | 141 | 0.71 |
| | 11 | NM_015180 | 174718 | 174522 | ctctcaac**ag**GGCTTCCAAC | CTGCACTCCG**gt**acgggcac | 196 | 1.19 |
| | 12 | NM_015180 | 173337 | 173051 | tgtggttt**ag**GGCTTGGAAG | GCACTGTCAG**gt**aacagctg | 286 | 1.76 |
| | 13 | NM_015180 | 171289 | 171140 | ttcgtttc**ag**GTAAATCCAT | ACCACCCTAT**gt**aagtctta | 149 | 2.00 |
| | 14 | NM_015180 | 169139 | 169013 | ctcattct**ag**GGAAAGCTAC | CAGCAGTCAG**gt**actgcctg | 126 | 0.69 |
| | 15 | NM_015180 | 168327 | 168117 | ttaattcc**ag**GTGCCTTCGA | GAGACTGCAG**gt**gagttaga | 210 | 1.02 |
| | 16 | NM_015180 | 167096 | 166890 | tctctggt**ag**GAGATACTGA | GCAGTGCCAG**gt**acgctgac | 206 | 0.93 |
| | 17 | NM_015180 | 165957 | 165825 | gtttttta**ag**GACTTCCACC | GGAACTAATG**gt**aagtttcc | 132 | 1.48 |
| | 18 | NM_015180 | 164342 | 164149 | ctgttttc**ag**CAACTGGAAA | GGGAACCCAG**gt**gagtctac | 193 | 1.08 |
| | 19 | NM_015180 | 163074 | 162982 | tgaatttc**ag**AACCCAGCCT | CCGAGCAAAG**gt**aagaagcc | 92 | 0.45 |
| | 20 | NM_015180 | 162537 | 162482 | ctttaccc**ag**CAGTTCAGAG | CAGAGAGCAG**gt**aacggggc | 55 | 0.27 |
| | 21 | NM_015180 | 162214 | 161092 | ctgttggc**ag**GGTCCCCGGC | — | 1122 | — |

REFERENCES

1. Ribeiro R C, Kushner P J, Baxter J D, Tenbaum S, Baniahmad A. The nuclear hormone receptor gene superfamily. Annu Rev Med 1995;46:443–53.
2. Tenbaum S, Baniahmad A. Nuclear receptors: structure, function and involvement in disease. Int J Biochem Cell Biol. 1997 December;29(12):1325–41.
3. Baniahmad C, Baniahmad A, O'Malley B W. A rapid method combining a functional test of fusion proteins in vivo and their purification. Biotechniques. 1994 February;16(2): 194–6.

4. Parker M G, White R. Nuclear receptors spring into action. Nat Struct Biol. 1996 February;3(2):113–5.
5. Schwabe J W. Transcriptional control: how nuclear receptors get turned on. Curr Biol. 1996 Apr. 1;6(4):372–4.
6. Laudet V, Hanni C, Coll J, Catzeflis F, Stehelin D. Evolution of the nuclear receptor gene superfamily. EMBO J. 1992 March;11(3):1003–13.
7. Green S, Walter P, Kumar V, Krust A, Bornert J M, Argos P, Chambon P. Human oestrogen receptor cDNA: sequence, expression and homology to v-erb-A. Nature. 1986 Mar 13–19;320(6058):134–9.
8. Menasce L P, White G R, Harrison C J, Boyle J M. Localization of the estrogen receptor locus (ESR) to chromosome 6q25.1 by FISH and a simple post-FISH banding technique. Genomics 1993 July;17(1):263–5.
9. Mosselman S, Polman J, Dijkema R. ER beta: identification and characterization of a novel human estrogen receptor. FEBS Lett. 1996 Aug. 19;392(1):49–53.
10. Enmark E, Pelto-Huikko M, Grandien K, Lagercrantz S, Lagercrantz J, Fried G, Nordenskjold M, Gustafsson J A. Human estrogen receptor beta-gene structure, chromosomal localization, and expression pattern. J Clin Endocrinol Metab. 1997 December;82(12):4258–65.
11. Murphy L C, Dotzlaw H, Leygue E, Douglas D, Coutts A, Watson P H. Estrogen receptor variants and mutations. J Steroid Biochem Mol. Biol. 1997 August;62(5–6): 363–72.
12. Moore J T, McKee D D, Slentz-Kesler K, Moore L B, Jones S A, Home E L, Su J L, Kliewer S A, Lehmann J M, Willson T M. Cloning and characterization of human estrogen receptor beta isoforms. Biochem Biophys Res Commun. 1998 Jun. 9;247(1):75–8.
13. Ogawa S, Inoue S, Watanabe T, Orimo A, Hosoi T, Ouchi Y, Muramatsu M. Molecular cloning and characterization of human estrogen receptor betacx: a potential inhibitor of estrogen action in human. Nucleic Acids Res. 1998 Aug. 1;26(15):3505–12.
14. Osborne C K, Yochmowitz M G, Knight W A 3d, McGuire W L. The value of estrogen and progesterone receptors in the treatment of breast cancer. Cancer 1980 Dec. 15;46(12 Suppl):2884–8.
15. DeSombre E R, Carbone P P, Jensen E V, McGuire W L, Wells S A Jr, Wittliff J L, Lipsett M Special report. Steriod receptors in breast cancer. N Engl J Med 1979 Nov. 1;301(18):1011–2.
16. Parl, Fritz F., Estrogens, Estrogen receptor, and Breast Cancer. IOS Press, Amsterdam, Netherlands, 2000.
17. Birren B, Green E D, Klapholz S, Myers, R, Riethman H, Roskams J, (eds.) (1997), Genome Analysis: A Laboratory Manual. Cold Spring Harbor Laboratory Press, Cold Spring Harbor, N.Y.
18. Ewing B, Hillier L, Wendi M C, Green P. Base-calling of automated sequencer traces using phred. I. Accuracy assessment. Genome Res 1998 March;8(3):175–85.
19. Gordon D, Abajian C, Green P. Consed: a graphical tool for sequence finishing. Genome Res 1998 March;8(3): 195–202.
20. Flouriot G, Griffin C, Kenealy M, Sonntag-Buck V, Gannon F. Differentially expressed messenger RNA isoforms of the human estrogen receptor-alpha gene are generated by alternative splicing and promoter usage. Mol Endocrinol 1998 December; 12(12): 1939–54.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule comprising SEQ ID NO:1, wherein position 89837 of SEQ ID NO:1 is 'T' instead of 'C'.

2. A nucleic acid probe that is complementary over the entire length of said probe to a segment of SEQ ID NO:1 that includes position 89837 of SEQ ID NO: 1, wherein position 89837 of SEQ ID NO: 1 is 'T' instead of 'C', such that the probe hybridizes under high stringency conditions to a nucleic acid molecule comprising said segment of SEQ ID NO: 1 but does not hybridize to a nucleic acid molecule comprising said segment of SEQ ID NO: 1 having a 'C' at position 89837, wherein said high stringency conditions are hybridization in 6× sodium chloride/sodium citrate (SSC) at about 45° C., followed by one or more washes in 0.2×SSC, 0.1% SDS at 50–65° C.

3. The probe of claim 2, wherein the probe is detectably labeled.

4. An isolated nucleic acid molecule that is entirely complementary to the nucleic acid molecule of claim 1.

* * * * *

SEQUENCE LISTING

```
<160> NUMBER OF SEQ ID NOS: 3

<210> SEQ ID NO 1
<211> LENGTH: 325791
<212> TYPE: DNA
<213> ORGANISM: HUMAN

<400> SEQUENCE: 1

agcccgctgt ttcaggcccc gccgatctgg aaggagtgtc agagctggag cgcgcgtggc      60

ctcatcggtg ttggggtcac cccggggttg ccagggctca tggagggtcg tagtctggat     120

tttgtcaccc ccacgtcccc gccccgcagc aagtctgggg ttggagaact cacgcggtct     180

tcgtaagcta catgccagtt gaccctcgag gagggatgct ccctcccctt aagcgtccac     240

gctggagaag gagtaagatg gacaattgcc tggggagcct gacagggcgg tggcagctgg     300

gatgctggag aggactggcc ccttgtgtta ctgagtccaa ggaatatgct tgctctgctc     360

taggaaccgc gttcaggtta cagtcatccc agtagagtcc tgaagatgcg tggttcaggt     420

cacttaggac ttgaccagat accgggtttc ttttacaagc cgtttactac tggcagagct     480

catctaaaac ttttttttgtt tgtttgtttg agacggagtc tcattctgtc gcccaggctg     540

gagtgcagtg gcacgatttt ggctcactgc aacctccgct tcccgggttc aagcagttct     600
```

-continued

```
ctgcctcagc ctcccgagta gctgggatta caggcaccac ctaattagcc cgccaccacg    660
cccggctaat tttgtattt ttagtagaga cggggtttca ccatcttggc caggctggtc    720
ttgaactcct gacctcgtga tccacccgcc tcggcctccc agagtgctgg gattacaggc    780
gtgagccacc gcacctggcc taaaactgat tttttattaa ttttggggct tttaatattt    840
ttttcttatt tctaaattct gaggttattt atagtagccc catatacggg attagataat    900
ctcttgtgat tttctatttc tggtaattat ttctaatata tgttttttttg tttttgagac    960
ggagtctcgc tatgtcgctc agggtggagt gcagtggcat gatctccgct ctttgtagcc   1020
tctgcctccc gggttcaaat gatcctccca cctcagcccc ccgagtagct tggaccacag   1080
gtgcatgcca ccacgccggc taatttttct atttttggta gagttggggt ttcactatgt   1140
tgaccagact ggtctagatc tcaagggatt agtctccctt ggcctcccaa aatgctggga   1200
taatgggcat gagccaccgt gcgtggcctt aaagttacta ttcttaaagt ttgcacaagt   1260
gatatgttaa aggcacagac ttagtaatat aatgtcatta taataataac cctaaaacac   1320
attgtctcat attgtgttgt acctaaacaa gtgaaattaa gaagaaaatt gaaggaaatg   1380
tttctggtaa attgcagata gtgaatcttt tgtcttatac tatcaaatag gtattgacta   1440
ttccagcttt cttatttgtt gaggaagatg gcagaaatcc cattttacag agggatagac   1500
tttgaaggat aatacccaaa gctgcatagc tgtggctggt ataggcccca aacctgatgt   1560
ttcttctcta aatctactgc ctttgccatc tcaacagcct ggtttttgac agttatctat   1620
gtatgagttg cataaatcgt tcattcatgg agcaaataat tattgagtgg ccactatgcc   1680
aacagcactg ctatagatgc tagagatacc ctagtgaacc agcaaagttt ctgctctcag   1740
ctcatattct ggtggaggag acaacgatca agttaaagaa atacataggc taattttaga   1800
gattatgaca tgctatattt taaaaatagg caagctaaga ggataggcag tgatgctggg   1860
aggtgggaaa gttttgtctc agaaatgtgg taagagattt ctttgggcat ctgacttcag   1920
cagaaacctt aatgaagaga ggaacttgga atgtaaaaga aagaaagcag ggatttgctc   1980
tgagcaactg gaaagatgga attgccattc gctgagttga aataaagtaa aatgtaggac   2040
taggttttgg ggttaagatt atgaattcgg ctttagacat ttttagattt ctcttagaca   2100
tccaaatgga gagaagatat ttaaatccat gggattgaat gagatccaac caagggtatt   2160
gtaggtagag agaggaccaa agactgacac ctagaacctt tcagtgttca gaatgcaagg   2220
agacaggagg aaccaagagg gaagattgaa aaggagagtc cagctgggag ctgtggctac   2280
acctttacta atcccagcac tttgggagac caaatacagg aagatcactt gaatccagga   2340
gtttgtagaa cagccttagc aacatagcaa gaccctgtct ctacaaaaat aaaaattaaa   2400
aaatttgcct gtaatccgag cattttggag gccgaggtgg gtggatcagc tgaggtcagg   2460
agtttgagac caacttggcc aacacagtga aaccccgtct ctactaaaaa tacaaaaatt   2520
agctgggcgt gatggctggt acctgtaatc ccagctactc gggaggccga ggcaggagaa   2580
tcccttgaac ctaggaggca gaggttgcag tgagccgaga tcacgccact gcactccagc   2640
ctgggagaca gagcgagact ccatctcaaa ataaataaat aaataaaaat ttaaaaagtt   2700
agctgggcgt ggtggcatgt acctgtagtc ccagttactc agaaggctga ggtgggagga   2760
tcctgtgagc ctaggagttg gaaacttcag taagctataa tcatcacact gcactccaac   2820
ctaggcaaca gagcaagacc ctgtctctta aaaggaaagg agagtccagt gtgttctaag   2880
gaaaacccca agagcatccc accttagaag acaagtgagg aggcctggca tggtgtctca   2940
tgcctgtaat cccagcactt tgggaggcca aggtgggtgg atcacttgag gtcaggagtt   3000
```

-continued

```
ctagaccagc ctgacaaaca tggcgaaacc tccgtctcta taaaaataca aaaattagcc   3060
aggtgtggta gcgcgtgcct gtaatcccag ctactaggga ggctgaggca ggagaactgc   3120
ttgaactcag gggcagagt ttgcagtgag ccgagatagt gccactgcac tccagcctga   3180
gcaacagagt gagactctgt ctcaaaaaca aacaagtaaa caaacaaaca aaaaaaacaa   3240
gacaagtgaa gaatgtgttt catggaaaaa gaggtaatta attctgtcaa gtgttgcaaa   3300
ttggtcaaat aaagaatgaa aatcaacctt tcacagcaaa tagaaggaaa aaatattttt   3360
atttaaatgc ttataaaggc agttgctaga aaaaatgttt actttttgca gaggccccgt   3420
ttttacaacc tttttcaggg gtaatttgat atgataatat ctacgggaaa aaaaatgttt   3480
ttttttgag tcgctctgtc accaggctgg agtgcagtgg catgatctcg gctcactgaa   3540
acctccgcct cccaggttca agcaattctt ctgcctcagc ctcccaagta gctgggacta   3600
caggtgggcg ccaccacacc cagctaattt ttgtattttt agtagagacg gggtttcacc   3660
atgttggcca ggatggtctc aatcttgacc tcgtgatctg ccttccttgg cctcccaaag   3720
tgctgggatt ggtacaggtg tgaaccacca tacctggccc gaaaatttta aatttgtatt   3780
ttctttgaca ttgtaattcc acttccagga tttttttttt ttggacagga ttttactctg   3840
tcacccaggc tggagtgcag taacacaatc agctcactgc aaccctgaac tcctgggcta   3900
aagtgatcct tctgagtagt tgggactata ggcacatgcc accacccctg actaattaaa   3960
aaattttcct gtagagatag tcttgctatg ttgcccagac tggtctccaa ctcctggcct   4020
caaaccatcc tcccaccttg accttccaaa acgttgggat tacaggcgtg agccacctct   4080
cccagtttag gaatttatct taaagtaata tttacatata aagaaagatg tataggctgg   4140
gtgcagtggt tcacgcctgt aatcccagca ctttggaagg ccgaggctgg tggatcaact   4200
gaggtcagga gttcaagacc aacctggcta acatggcgaa accccatctc tactaaaaat   4260
acaaaaatta gctgggcgtg gtggccagcc cctgtaatcc cagctactcg ggaggctgag   4320
gcaggaggat agcttaaacc caggagacga aggttgcagt gagccaagat tacaccattg   4380
cactccagcc tgagcaacaa aagcgaaact ccatctcaaa aaaacaaaaa ctaaaactaa   4440
acaaaacaaa aaaaccatgt gtaaaactgt taatcacaac actgatttca atagcaaaaa   4500
acaaaatttc tgtcaggatg gatgcagttg ttaaaggaac agcagataca tatgtataga   4560
catgtaagat agctttcata cttttttttt tgagatggaa tttcgttctt gtcacccagg   4620
ctggaatgca atggtgagat ctaggctccg cttctcaggt tcaagtgatt ctcctgcctc   4680
agcctcctga gtaagctggg aatacaggcg cccgccacca cgcccaggta atttttgtat   4740
gtttagtaga gacagggttt cgccatattg gcgaggcttg tctcaaactc ctgacctcag   4800
gtgatccacc cacctccaaa agtgttggga ttacaggcat cacccaccac gcgtgaccag   4860
cttttataca tttttaaatg ataaagacag gttaataaaa tgtataatat tatgttgcta   4920
tatccaaaaa aaggccttct ttgattacac tatcaaaagt tacctctcca tttacatccc   4980
cattactatc tcattaacct gttttattca tagcacttac taccatctaa aatgacttta   5040
tttctttata tttttgtttg ctacctgtct tttacaccag aatttaattt ttaagctttt   5100
tttgtttgtt tgtttgtttg ttttgagatg gagtcttgct ctgttgccca gactggagtg   5160
cagtggtgcg atctcagctc actgcaacct ctgcctcctg ggttcaatca atcctcctgc   5220
ctcagcctcc caagtagctg ggattacagg catgtgccac catgcccagc taatttttgc   5280
atttttagta cagcagggtg tcaccatgtt ggtcaggctg gtctcaaact cctgacctca   5340
```

-continued

```
ggagatccgt cagccttggc ctcccaaagt gttgggatta caggcgtgag ccacagcacc   5400
cagccagaat ttaaacttta taagagattt cctgtcttgt tcatacttat atacctgcag   5460
cttcgaaaca tatatatatg tttaatatat ataatagata tattttaaat tatatataga   5520
gagatggagt ttcactcttg ttgcccagac tggagtgcaa tggcgtgatc tcggctcacc   5580
acaacctctg ccccccgggt tcaagcaatt ctcctgcctc agcctccaga gtagttggaa   5640
ttacaggcac gtgccaccat gcctggctaa ttttgtattt ttagtagaga cagagtttct   5700
ccatgttggt caggctggtc tcgagctctt gacctcaggt agtccgcctg cctcggcctc   5760
acaaagtgct gggattacaa gcatgagtca ctgtgccctg ccagaattta agctttataa   5820
gagatttcct gtctgtttat acttaaatac ctgcagcttg gaaacatata tatgtttata   5880
tgtatatatt acatacatta tatatatatt tttatatatt ataattataa actcctgacc   5940
tcaggtgatc cacctgcctc agtctctcaa atgctgggat tacaggcgtg agccaccacg   6000
ccaggccaga aacatatttt taaaaatctt gttttagagg aaaaacagag tatttctttt   6060
tttttttat tagatggatt ctcactctat tgcccaggct ggagtacagt ggcacaatct   6120
tggctcaccg caacctcagc ctcccgggtt caagcaattc tcctgcctca gcctcccgag   6180
tagttggaac tataggcgtg agccaccatg ccctgctaat ttttgtattt ttagtacaga   6240
tggggtttca ctatgttggc caggctggtc tcgaactcct gaccttgtga tctgcccacc   6300
tcggcctccc aaagtgctgg gattacaggt gtgagccact gcgcccggcc tatttcttct   6360
tctctttgtt tagttattat ctattactct cattcctatg aacataactt gtttctcccc   6420
ccttaatttt tatcatacat gattgtagac agtgggcact gtcttcaatt atagtgaatt   6480
tagcagtaaa ttcacattag accaacttgt atagctttaa aaaatatatt tatgtctagg   6540
ttccaccctt gaccaactaa gtcagaactt gggtgggttc aaggttcatt attctttgaa   6600
gataagatga tgtttgaata aaattcctgg tgattctggt atcaaaaata caaatttggg   6660
acatactttt tctgctgtaa aaatattttc ctaaggccag gcgcagtggc tcacgcctgt   6720
aatcctagca ctttgggaga cggaggcggc agatcacttg aggccaggag ttcaagacca   6780
gtctggccaa catggtgaaa cccagtctct actaaaaata gaaaaaatta gccaggcatg   6840
gtggcacgtg cctgtagtcc cagctactca agaggctgag gcaggagaat cctttgaacc   6900
cgggaggcag aggttgcagt gagctgatat tgcagcactg cactccagcc tgggtgacag   6960
atcaaaactc tgtctcagaa aaaaaaaaaa aaaaaaaaga atttcctaga attagaatcg   7020
caggggtttt ttttgttttg tttgtttgtt tgtttgtttg tttttgagac agagtttcac   7080
tcctgtcgcc caggctggag tgcaatgcca tgatctcggc tcattgcaac ctctgcctcc   7140
tgagttcaag caatcctcct gcctcagcct cccgaatagc tgggattaca ggcacctgcc   7200
accatgccca gctaattttt gtatttttag tagagactgg gttttaccat gttggccaag   7260
ctggtctcga actcctgacg tcaggtgatc cacccagctc attctcccaa agtgctggaa   7320
ttacaagcat gagccactgc actcggcctt tatttattta tttatttttg agatgaagtc   7380
ttgctctgtt gcccaagctg gagtgcaatg gcatgatctc ggctcactgc aacctccacc   7440
tcccaggttc aagcaattct cctgcctcag ccccctgagt agctgggatt acaggcgtgc   7500
accaccacgc ctggctaatt tttgtatttt tagtagagac agggtttcac tatgttggtc   7560
aggttagtct cgagctcctg acttcgtgat ccgcccgcct cagccttcca aagtgttggg   7620
attacaggcg tgagccaccg cgcctggcca gaatcccagt tttttaacac atctaatgct   7680
ttaggaatag taaatggaaa catcatttcc ccttctttcg aagtacttct accttgatga   7740
```

-continued

```
gatgtatgta ttggagtaca atatttgacc tagccaagaa tttcacaaaa gaagcccaaa   7800
atatgatttt cacgtttact ggactgttca cttttggggg gatcactttc ttaagattac   7860
ttaaagtact aatgcttgat gaaaatcatt tgtgttttca cttcattaat tggagaaaga   7920
gctacatgtt tttgttgttg ttgttgttgt tttgagatgg tgtcttgctc tgtctcccag   7980
gctggagtgc aatggcgtga tctcagctca ctgcaacctc cgcctcccgg gttcaagcga   8040
ttctcctgcc tcagcctcct gagtagctgg gactacaggc gcctgccacc acgcccagct   8100
aatttttata cttttaatag agacagggtt tcaccatatt ggccaggatg gtctcaatct   8160
cttgaccttg tgatccaccc gccttggcct cccaaagtgc tgggattaca ggcgtgagcc   8220
actgcgccca gccagagcta caggttttac tgtaacactt tagaaggtcc tttttctttg   8280
tacctctgtg atgtgttcac ctagcaacag cttctttgat atgcaaacat tctacaggca   8340
aattgctcag agcagctact catgttggac aattcaggtc tcttctggaa actggccttg   8400
tatttggaat tttctccaga gtctgatgtg gtaaaaattt atacttttca cttcttacta   8460
aatgcagcat agcatactac atcttttgag tgtgtaaaaa ataaagtagt catgtacaaa   8520
cctaaaatca cagaataatc atgtaatggt gctatatttt atttttactt tagattccta   8580
atacattttt attgtatctt tataaggtta gtttgggaga atagcactat catcatctat   8640
attagttaac tttgcattaa ggtttttcat taaggttttt cccctgtttg gttctttcat   8700
tttacgatcc atatttttttg tgcctggtat gggatgataa agataacaga aatagctcct   8760
gtttttaggt acctttattt gtttgtttgt ttggagacag ggtcttactc tgtcacccag   8820
gctggtggca caatcatagc ttactacaga ctaactcctg gctcaagcca tcctccacct   8880
cagcctccca agtaactgag attacaggtg cacaccacca cctctggcta attattaaaa   8940
ttttcataga gacaggatct cacttggttg gccagactga tctcaaactc ctggtctcaa   9000
gtgatcctcc caccccagcc tcctgaagta ctaggattgc aggcatgaac cactgccctg   9060
gcctagatac atttaatgta gtagaggaga tgagattttt acatagtata atattgaatg   9120
agacaacagt caaaagaaaa tcacatacta taagagaaga gattaccctt accttttagg   9180
aatcaagaaa actccctgga ggagatggta cttgaactta tactggagga tttatatgtt   9240
catccttctt ggtttatatt ttgtcccaca cggtagcttg tttctttttt cttttttttc   9300
tttttctttt tttttttttt gaggcagagt tttgctctgt tgcccaggct agagtgcagt   9360
ggcgcgatct cggctcactg caacctccgc ctcctgggtt caagcgattc tcctgcctca   9420
gcctccctag tagcttgttt cttagagaca gtgtgagtga aactcattaa gtaaagtcaa   9480
tacagcacaa gtttcataaa atggtaaaga aatagaaata aaagtaaagg atgaaattct   9540
taagaacttt gtcaggccgg gcgtggtggc tcatgcctgt aatcccagca ctttgggagg   9600
ccgaggtggg tggatcacct gaggtcagga gtttgagacc agcctggcca acatggcaaa   9660
accctgtctc tctaaaaata caaaaattag ctgggcatgc tggcgggtgc ctataatccc   9720
agctactcgg gaggctgagg caggagaatc gcttgaaccc aggaggcgga ggttgcagtg   9780
agccgagatc acatcattcc actccagcct gggtgccaag agcaaaaaac tccatcttga   9840
aaaataaaga attttgtctc cagtatcatt cttgttctag gactgagaaa cagttcattc   9900
ttcattttcg tctactaaaa tttaagttct ttgattttct tctttaggtc ttggaaaaag   9960
aattaataga gtaattttct taggtatcaa gtaatgaaaa tgagaaaaga gactagtctc  10020
attatagatt tttttttttt attcttattt tattttattt gagacaaggt ctcgctctgt  10080
```

-continued

```
cacccaggct ggagtgtagt ggctccatta tggttccctg cagccttgaa ctcaggggcc  10140
caagcaatcc tcccacctca gcatcccgag cagctgggac tacaggtgca tgccaccatg  10200
cctggctaat ttttgtgctt tttcgtgtat aaagatgaga tttcgccatg ttgcccaggc  10260
tggtctcaaa ctcctgggct caagagatct gtccacctca gcctcctaaa gcgctgagat  10320
tacaggcatg agccaccacg tccagcctag agatatttat actttaatag ctgcctgcaa  10380
taccaataca cctagaatga attagaagaa tttgaaaaca gatttcagga ttagtaaaag  10440
aaagtcaagc cctatgcctc ctgttctaca ttcctcaaat cacataatcc tgattttttc  10500
ctcttcgtat gaaaattcct ctcattttgg gcctgtttga tttttggga gacaccaccc  10560
agcagaaaca caccgcactt acatgcaacc cctccattgc acagtttcta aatgcccccc  10620
ccctttttt tccattctct gatcctaaaa aaagaaatcc agtggcacaa tcacggatct  10680
ctgcagcctt gatctcttag cctcaagtga ttctcctgcc tcagcttcct aagtagctgg  10740
gaccacaggt gcttgccacc atgcccagct attttttttt ctttgttttt ttgtaaagat  10800
gtgtctcact atcttgccca ggctgatatt gaattcctgg gctcaagtga tcctcctacc  10860
ttggcctccc aaagtgctgg gattttatat atatatatat ttccatttta cttatgttaa  10920
tgctttccct cttttggcat agaaaagcta ataaagctta aacttaaatg gaacttgtat  10980
aaacacaata tatctgatga tacctttgag agatgtctta catttgtctt ttctttcagc  11040
aaaatgtgat gccagtccct gaaatgtgta gcaatttaat tatgggtagc attcttcttt  11100
ccctgtactt actatagtat taacttacta ctaatgctaa gaagtttata atttttgata  11160
attcagattt ggattagatt aagatttatg tctatgcata attcattaaa aactttttaa  11220
accaaattgt caaaaaagat tgtaggtacc ttgtttaaag aaaatatata agctagtttc  11280
aagaattcca aaatattttt taaaagcagc tctgtacatg tcgataaatt atttgctcat  11340
tgtaattttt tgaatctgtt tgtcaaagca aatgtagacg ggctcgaact cctgacctca  11400
aatgatccac ccgcctcagt ctcccaaatg ctggtattac aggcatgagc caccgctcat  11460
ggcctgttat catttttaat tgaaaatttt actgagataa ttgtagattc acttgccatt  11520
ataagaaata attcagagat atcacttgta tacttagccc agtgtccccc aaaggtaaaa  11580
ttttgcaaaa ttatagtcta atgtaacagc gtgaatattg acattaatac aatccactga  11640
gtttattcag atttccccag ttttacttgt attcaattgt gtgtttgtgt attaagttcg  11700
atataactag tcaatatact gaacagttct aacatcacaa gtatccttca ggtagccctt  11760
ttgtatccac atccacttcc ttctcatccc cagctattga caaccactaa tccctttttcc  11820
atttctaaaa tgtgatttca aaaatgttac atacttggct gggggcagtg gctcatgcct  11880
gtaatcccag cactttggat atactgtctc tactaaaaat acaaaaatta gctgggagtg  11940
gttgtgcaca cctgtaatcc caggtgcttg ggaagctgag gcaggagaat tgcttgaacc  12000
caggaggcag agcttgcagt gagccgagag tgtgccactt cactccagcc tgggcaacag  12060
agtgagactc tgtttcaaaa ataaataaat aaataaataa aatggtcttc atacagcctt  12120
tgctgctagg aaatatagtt tctaattaat gtaatttttt gtcaaataca aaatgcttct  12180
gaacgtttct ggttatcaag ctggtaatct ttcacagtgt cctcaatttt tttttctact  12240
ctcttactag ttctccagat cacatgcagg ctattaagaa atgtgaacta acaagttaaa  12300
gtagcaggac gggcgctgtg gctcacacct ataatcccag cactttggga agctgaggca  12360
ggtggatcac ttgaggtcag gagtttgaga gcagcctggc caacaaggtg aaaccacatc  12420
tctactaaaa aaaaaaaaaa tttgccaggt gtggtggtgc atacctgtaa tcctagctat  12480
```

-continued

```
ttgggaggct gaggcatgag aatcgcttga acccaggagg cagaggctgc ggggagccag  12540
gatcatagca ctgcactcca gcctgggtga cagagctaga ccctgtctga aaaaaaaaaa  12600
aaatgttagt agcagcagag cacagtggct catgcctgta atcccaacac tatgggagtc  12660
tgaggcagga ggatctcttg agcttaggag ttcaagacca gcctgacaac atagtaagac  12720
tccatctcta caaataatca ttaaaaaaat tagccgggcg tagtggcacc tacctgtagt  12780
cccagctact ggggaggctg agatgggagg atcacctgag cctgggaggt caaggctgca  12840
gtgagctgtg atcgccattg tactccaaac tgggtgacaa gagtgagacc atgcctcaaa  12900
aataataata ataaatgtat aatttaaatg tgacctaaca ttatgaagtt tttaaaaaca  12960
aaattataaa tgattttaac actttctcat tagctaagaa atcttcagaa caaacttttc  13020
ataaaagaaa cttcactgca agagttgaag cctgagctag aaagttacaa agaaaataat  13080
gtacgacagt cgttccagat aatgtccctg aaagataata tcaaggacct acagaaactt  13140
actgcttctc taaccagaat taaatatttg agaaacacca atattcagag gcttcaaaga  13200
ggcaactgga atttaactaa atgaattatt gagctagaaa ctgtctaagg tagggatttt  13260
tccagtttgt tttcaaacat gtcttttgtt gtaagcttgc aaatagcata tgaactccat  13320
actcctgatt gatcatagaa tttaaatctg cagaatttca cttaatacct gacccaacat  13380
tattatattt tgtattgaga tataacttaa atacctcggg ccaggtgtgg tggctcatgc  13440
ctataatccc agcactttgg gaggccaggg ctggtgaatc acttgaggtc aggagttcaa  13500
aaccagcctg gccaacatga caaaaccctg tctctactaa aaatacaaaa aattagctgg  13560
gcatggtggc atgcacctgt aatcccagct actcaggagg ctgaggtaga agaatcactt  13620
gaatccagga ggtgcgagac tctgtctaaa aaaaaaaaat ccaatttgag atataactta  13680
catacctcaa gattcagtta aagtgtacaa ttcaatggtt gtacaatcat caccactatc  13740
taatttcaga acaatttcat cacacctccc caccccccac tgcaaaaaaa aacccatgcc  13800
cggctgggca cggtggctca tgcctgagat cccagcactt tgggaggccg agacaggcgg  13860
atcacaaggt caggagttcg agaccagcct ggccaacatg gcgaaacccc atctctacta  13920
actacaggca ggtgcctgta atcccagcta ctcaggaggc tgaggcagga gaatagctta  13980
aatccaggag gctgaggttg tggtgagctg agatcatgcc attgcactcc agcctgagca  14040
gcaagagtga aactctgtct caaaaaaaaa aaaaaaaaaa aaaaaagatt taatgattga  14100
cctgctggat tttgaacttg catggggcct atagcctctt tcttttggcc aaattctccc  14160
ttttggaatg agagtattta cccaatgcct gcaattccca ttatatttcg gaagtcacta  14220
acttgttttg ttgttgttgt tgttgttgtt gtttgagaca gagtcttgct ctgttgccca  14280
ggctggagtg caatggcaca atctcggctc actgcaacct ctgcctcccg ggttcaagtg  14340
attctcctgc ctcggcctcc caagtagctg agatcacagg catgcaccac cacccccggc  14400
taatttttgt atttttagca gagatggggg tttcaccatg ttggccaggc tagtctccaa  14460
ctcctgactt caggtgatcc accggccttg gcctcccaaa gtgctgggat tacaggcatg  14520
agccaccgtg cccagcccga agttactaac ttgttttgga ttttacgggc tcacaggcag  14580
aagggacttg ccttgtttca gatgagactt tgttctttgg gcttttgagt taatgctgga  14640
atgagttaga actttggggg aactgttggg aaggcagatt gtattttgaa atgtgagaag  14700
gacatgagat ttgagagggc ccagtgggag aatgggataa ggcttgagtc tgtgtccctg  14760
cccaaatctg atgtcaaagt ataatcccca gtgttagggc ctggtgggag ctgattggat  14820
```

-continued

```
catgggggtg tatttcccct ttggtgctgt tctcatgata gtgagtgagt taccatgaga  14880
tctggttgtt taaaagtgtg tagcacctct cacctcactc tattccttct gctctggcca  14940
tgtaagatgt gcctgcttcc ccctcacctt ctgccatgat tgtaagtttc ctgaggcttc  15000
cctagccatg cttcccatgc agcctgtgga actgtgagcc aattaaacct cttttctttg  15060
taaattacct agtctgaagc atttctttac agaagtgcaa gaacagacta atacattgaa  15120
catctcttca tgtgcttatt ggccatgtgt atatcttctt tgtagaaata cctattcata  15180
tttgttgtcc cttttaaaat tgggttgtct ttttattgct gagttgtaag tgttctttat  15240
attttctgga tactggactt ttattaagtg tataatttgt aaatattttc tcccaatttg  15300
tgggtcatct ttccactttc ctaaaagtgt catttcaagc aaaaatttta attttgatgg  15360
agttgtgtgt gtgtgtgtgt gtgtgtgtat gtgtatgtgt gtctttggtg tcatagctga  15420
gaaattattg tcaaatccag gatcatgaaa gatttacatc tatattttct tttaagagtt  15480
atagttttgg ccgggcgtgg tggctcatgc ctgtaattcc agcactttgg gaggccaagg  15540
caggtggagt tcgagaccag cctggccaac atggtgaaac tccgtcccta ctaaaaatac  15600
aaaaattagc tgagcatggt ggcacacgcc tgtaatccca gctgctcgtg aggctgaggc  15660
agaagaatag cttgagcccg ggagacagag gttgcagtgg gccaaaatca tgccacggca  15720
ctccagcctg gccgacagac tctgtctcaa aaaaaaaaaa agatttatag ttttggctgg  15780
gcgtggtggc tcatgcctat aatcccagca tttggggagg ccaaggcagg tggataactt  15840
taggccagga gtttgagacc agccgggctg acataacaaa acctgatctc tactaaaagt  15900
acaaaactta ggctgggcac agtgactcat gcctgtaatc ccagcactct gggaggccga  15960
gatgggcaga taatttgagg ccaggcattg gagaccagcc tggccaacat ggtaaaaccc  16020
tgtctctact aaaaatacaa aaatcagctg ggcgtggtgg cacgcacctg taatttcagc  16080
tactcgggag gctgaggcgg gagaattgct tgaacccagg aggcagaggt ggcagtgaat  16140
tgagatcatg ccactacact tcagcccggg tgatagaacg agactctgtc tcaaaataat  16200
aataataata ataataatag ctggacatgg tggtgcacac ctgtagtccc agctacgtgg  16260
aaggctgaag caggagaatt gcttgaaccc agaaggtgga ggttgcagtg agccaagatt  16320
gtgccactgc actccagcct gggtgacaga gcaagacagg tgtactccag actgggtgac  16380
tgcaccccag cctgggtgac actgcactcc agcctgggtg acagagcaac taactaacta  16440
actaactaaa actacagtta gtttatatat agtttttagt taaaactata gttagtttga  16500
gccaggcgcg gtggctcacg cctgtaatcc cagcactttg ggaggccgag gcgggcggat  16560
cacgaggtca ggagatcgag accatcctgg ctaacaaggt gaaaccccgt ctctactaaa  16620
aaatacaaaa aattaggcgg gcgtggtgtg gtcccagcta gtcgggaggc tgaggcagga  16680
gaatcccttg aacccgggag gcggggcttg cagtgagccg agatcgcacc aatgcacctc  16740
cagcctgggc ggcagagcga gactccgtct caaaaaaaaa acaaaaacaa aaacaaaaaa  16800
aaagccatag tctttctaaa actatagtta gtttataatt aactatagtt ttagttataa  16860
aatataacta taaagttata gttttagcac ttacatttat gtctttgact tcttttggca  16920
aatttttatg tatgatgtga ggtaggagtc cagattcatt gtttttcata taaatatcca  16980
gttgtcctta gcacctctgt ggaactatct tggcattctt gccaagaatc aattgaccat  17040
aaatgtatgg gtttatcttt gggcacccaa ttctatttca ttggtctgta tgtctgtcct  17100
tataccagca ccacactgtc ttgattaatg tagctttgta gtaagttttg aaatgggtaa  17160
gtgtgaaaaa ttccaactta atttcatttt tttcaagatc attctggcta ttttgggtcc  17220
```

-continued

```
cttgcttttc catatgtatt ttaagatcag cttttccatg aacatggaat atttttccat  17280
ttatttaagt cttctttaat ttcttttttt tttttccccg agatggcgtc atgctctgtc  17340
gtccaggctg gagtgcagtg gcacgatctc ggctcactgc aacctctgcc tcctgggttc  17400
aagcaattct cctgcctcag cctcctgaat tgctaggatt acagatgctc accaccatgc  17460
ccagctaatt tttgtatttt tagtagagac agggtttcac catgttagcc agactggtct  17520
tgaactcctg accttgtgat ccacccgcct tggcctccca aagtgctggg attacaggcg  17580
tgagccaccg cgcctggcct tctttttctt tttcttagag acagggtctc actctgttac  17640
ccaggctgca gtgcagtggc acaatcatag ttcagtgtaa tcttgaattc ctgggctcaa  17700
gcaatcctcc tgcctcagct tcccaagtag ataggactac agatgcatgc ctccatgctt  17760
ggctaatttt taattttttt tttatataga tttggggtct tgctgtgtta cccaggctgg  17820
tctcaaactc ctggcctcaa tcaatcttac tgccttggcc ttccaaagca ctgagattac  17880
aggcatgcac caccacaccc agcctcttta aattgtttta acaatgtttt gtagttttca  17940
gtgtatgtgt gttacatttc ttttgttaaa tttattacta atattttatt ccttttatgc  18000
attgtaaatg aaactgtttc catatttcat tttttgattg tttattttta gagagtagaa  18060
atacaattga ttcgtgtata tcagtctttg tcctgcaagc ttgctgaact cacttattag  18120
ctctagggtt tttttggtat gtgtgtgtgg tttccttggg attttctcca tacaagacta  18180
tgaatctgca aatatgtggg tttttaaaaa tttactatta ttattatttt tgagatggag  18240
tcatactctg tcatccaggc tggagtgcag tggcacgatc acagctcaca acaacttctg  18300
cctcccaggc tcaagcaatt cccctgcctc agcctcctgt agctgagatt acaggagtga  18360
accaccatgc ctgactaatt tttgcatttt tagtagagat ggggttttgc catgttgcct  18420
aggcttgtct caaactcctg ggttcaggct acccacttgc cttggcctcc caaagtgctg  18480
gaattatagg cgtgagccac cacacccaaa tattgttgag tgtttttaat cacaaaagtg  18540
tgttggattt tttgtccaat gctttttttt ttttgcatct tactgaaata atcatgtgat  18600
tttatcctct atagaatttg ttattgttag acttattgta ttagttggta tacagagaga  18660
ggagatattt gataatgtgc cctcagttga caggagaaac aaagtcatta atttttcctc  18720
ttataataag aataatattt gagaaactca cacaatatga aaagctattc tattcagatg  18780
tgcacactac tgtagcctat ttctattttg tattggttag tatgcatcag gtcatctcat  18840
aggttggggc tcttctgagt cttgcatttc tcaaaacact ttttttttctt ttgctgtatt  18900
tataccaagt cactttttgt ttgtttgttg gttggttggt tggttggttg gttggttggt  18960
tggttggttt gagtcggaat ctcactctgt cgccgaggct ggagtgcagt agagtgatct  19020
tggctcactg caacctctgc ctcccaggtt caagcgattc tcctgcctca gcctcccaag  19080
tagctgggac gacaggtgca cgccactctg cccagctaat ttttgtattt ttagtagaga  19140
tggggtttca ccatgttggc caggctggtc tcgaactcct gacctcaggc aagccaccca  19200
cctcagactt tcaaagtgct gggattacag gcgtaaacca ctgcgcccag actacttttt  19260
aaaagaaatt atataggaga ctaaaattga aaaaagaaac aaacctttac tcagattgag  19320
atattagtta aacttaaggg cctgaaacaa ggaaaatggg gtttgctttt ttctggttgt  19380
gcagagagtg tatgaataaa aagatctcac aaagttcaag tgaaagactg attaaaagaa  19440
attcatcatc caaatatctt ctcagtgtta agcaagcaca tgaagttagc tatagctcga  19500
cccttaacag ctaatcaggt aaactcttca actcagtttt gaacgtaaca tagtatacta  19560
```

-continued

```
cagacttttt gtttttgtcc tcagaggtaa agagaaacaa tggctatatg gcatactatg  19620
aggattaatt ttatatgtct acttgactgg gccatagggt gcccaatata tggtcaaaca  19680
ttattttagg tgtttctgtg agagtgtttt ggataatttt aacatttaaa ttggtatact  19740
gagtaaagca gatgatactc cctattgtga gtaggcctca tccactgagt taaaggcctg  19800
aatagaacaa aaagattaac cctcccccag gtaagagcga attcttcctg cctgatggcc  19860
ttcaaaatgg gacatcagct ctttttcctg cctttggact caaaccattg gctcttcctg  19920
ggtcttgagc ctgctggcct ttggactgga gctacactat cagctctctt gattttcagg  19980
ccttcaaact tagactcaaa ctacattatt ggctcccctg ggtctcccag atcccagcag  20040
atcttgggaa ttgccagcct tcataattgc tgaggcagtt cctttttttt gagatgggat  20100
cttcctctgt cacccacact ggagtgtagt ggtacgatca tggcttactg caacctcaaa  20160
cacctgggca taagtgatgc tcctgactca gcctcctgag tagcagggac cacaggcaca  20220
tgccaccatg cccagctaat tttttaaaaa tttttttgtag atacaaggtc tcactttgtt  20280
gcccaggctg gtcttgaact gctgggctca agctatcctt ccacctcagc ctcccaaggt  20340
gctgggatta taggcatgag ccactgtgcc cagccaaaag tcagaagata attgaatggc  20400
atcttaaagt gctgaaagaa aaaatactga caacccagaa tctatactca gtgaaattat  20460
ccttcaaaat tgaagatgag gccgggcgcg gtggctcacg cctgtaatcc tagcactttg  20520
ggaggccgag gcgggcggat cacgaggtca ggagatcgag atcatcctgg ctaacatggt  20580
gaaaccccgt cagtactaaa aatacaaaaa aaattagccg ggcatggtaa cgggtgcctg  20640
tagtcccagc tactcgggag gctgaggcgg gagaatggcg tgaacccagg aggcggagct  20700
tgcagtgagc cgagatcgcg ccactgcact ccagcctggg cgagagtgag actccgtctc  20760
aaaaaaaaaa aaaaaaaaaa aaaaaaaaaa aattgaagat gaaataaaca tggtttcaga  20820
agaaaaaaaa agaaatcatt tattgtcaga agaactacac tattaagaaa cacaccaggc  20880
aatttttcag gatgaaggaa aatgatcctt ggtggctaca gagaaatgta gggtagaata  20940
aggagtaaag aaagggtaaa tagaaattaa tactgacaat taatttttaa aaatcctata  21000
caatttataa tatatgaaag agtaaaacat atcagtagta caagggcaag aaatggtaaa  21060
tggagttaag ctatcataag tgttttattt agggagtatc acaaaagtat taaagtagaa  21120
tgtaataggc cgggcggggt agctcacacc tgtaatccga gtaccttggg aggctaagga  21180
gggcggatca cttgaggtca agagttcgag atcagcctgg ccaacatggt gaaaccccac  21240
ctctactaaa aatacaaaaa ttagccaggt gtggtggcac acgtctgtaa tcccagctac  21300
ttgggaggct gaagcatgag aatagcttgc acgtgggagg cggaggttgc agtgagccga  21360
gatcctgtca ctgcactcca gcctgggcga caaagcgaga ctctcaaaaa aaaaaaaaaa  21420
aaagcatgta ataaatcaaa tatgcattat gtaatcacaa aatccagctt aacaactaaa  21480
taataattta aaagatatta aaaacttaat atggaagaaa aatgaaataa aaaactttat  21540
taatccaagg ccgggcgcgg tggctcatgc ctgtaatccc agcactttgg gaggccgagg  21600
cgggtggacc acttgaggcc aggagttcca gaccagcctg gccaacatga tgaaaccccg  21660
tctctactaa aaatacctgg gcaaagtaga gcatgcctgg ccgggcgcag tggctcatgc  21720
ctgtaatccc agcactttgg gaggctgaga cgggtggatc aggaggtcag gagatcgaga  21780
ccatcctggc caacatggtg aaaccctgtc tctactaaaa atacaagaat taactgggca  21840
tggtggcaca tgcctgtaat tccagctact ctggaagctg aggcaggaga attgcttgaa  21900
ccagggaatc aggttgcagt gagctgagat catgccactg cattgcaatc tggcgacaga  21960
```

-continued

```
gcgagattct gtctcaaaaa aaaaaaaaaa aaaaaattag agcatgccta taatctgagc  22020
tactcaggag gctgagacac gagaatcact tgaacccagg gcggcggagg tgcagtgagc  22080
agcgatcaca ccactgcatt ccagcctggg cgacagagtg agactccctc tcaaaaaaca  22140
aacaaacaaa caaacaaaca aacaaacaaa aactttatta atccaaatta aaatggtaga  22200
gtagtagtaa aggaacagag aatagatggt aaaaacaata aataacatga taaacccgac  22260
aatttcaata ataactttaa agatagatgg tattgtaact gcccaatggg ttcaccttgc  22320
ccgctgccta gacagagacg atttctcaag acaggggaat tgcaatagag aaagataaat  22380
tcacgcagag ctggctgtat gggagaccag agttttatta ttactcaaat cagtatccac  22440
aagcattccg ccttcagaat ttttaaggac aacatgttgg gtgggaggaa gccagtgagc  22500
tgggagtgct gattggtcag agctgaaatc atagggaatg gaagctgtct tcttaagctg  22560
agtcaattcc tgggtgggga ctgcaagatc agatgagtca ggttatcaat ctacgtggtg  22620
ccagctgacc catcaaatgc agggtctgca aaatatctca agcactgatc ttaggagcag  22680
tttagggagg gtcagaatct tgtagcctcc agctgcaaga ctcctaaacc ataatttcta  22740
atcttgtggt taatgttagt cctaccaagg caatctagtc tccaggcaag aaggaggtct  22800
gctttgggaa agggctgtca tctttgtttt aaactataaa ctataaagta agtttctccc  22860
aaagttagtt cagcctacac ccaggaatgc acaaggacag tttggaggtt agaaacaaga  22920
tggggtcagt taagttagat ctctttcact gtctcaggca taattttgca caggcggttt  22980
cagtataatc atttcagtac aagacaagat ttaaaaaaag aaaactaatg ctaagcattt  23040
ttcaagaaac atactgtagg ccgggtgcag tggctcacgc ctgtaattcc agcaccttgg  23100
gaggctgagg cgggcggatc acgaggtcag gagatcgaga ccatcctggc taacatggtg  23160
aaaccccgtc tctactaaaa acacaaaaaa attagccggg tgtggtggcg ggcacctgta  23220
gtcccagcta ctcaggaggc tgaggcagga gaatgggtca acccaggagg cagagcttgc  23280
agtgagccaa gatcctgcca ctgcactcca gcctgggtga cagagcgaga ctctgtctca  23340
aataaaaaaa aagaaggaaa catactgtag ccagacgcca cctatagtcc cagatacttg  23400
ggaggctgag gcaggaggat agcttgggac cagtttgaga ccagcctgag caacatagca  23460
agaccctgtc tccaaaattt aaaaatgttt aaaaagagat atattttaca tataagaaca  23520
cagaaagatg ttattaaaaa taaaaaaatg acatttgggt aatgtgaata ttaccctaaa  23580
gaaagctgca tctatgtgga actgttaccg ggaatgggtc ccaatctaga ccccaagaga  23640
gggttcttgg acctcacgca agaaagaatt aggggcaaat ccataaagtg aaagcaagtt  23700
tattgggaaa gtaaaggaat aaagaatggc tactccatag gtagagtcac agtatgggct  23760
gcttaactga gtatactcag ttatttcttg attatatgct aaacaagggg tggattattc  23820
atcagttttc tggaaaaggg gcaggcattt ctcggaactg agggttcctt ctttttttag  23880
actgtatagg gtaacttcct gatgttgcca tggtatttat aaactgtcat ggccctagtg  23940
ggagagtctt ttagcatgct aatgcattat aattagtgta taatgagcac tgaggacaac  24000
cagaggtcac ctttgtcacc atcttggttt tggtaggttt gggctatctt ctttatcgca  24060
ttctgtttca tcagcagggt ctttgtggtc tgtatcttgt gctgacctcc tatctcatcc  24120
tgtgactaag aatgcctaag ctcctgggaa tgcagccagt agttctgagc ttactttacc  24180
cagcccctat tcaagatgga gttgctctgg ttctaatgcc tctgacagaa cctcctgatt  24240
gtcacaatat taccagtagc agcaggcagc tattcacacc caaatttcac cttaaaaaga  24300
```

-continued

```
atggcttcaa aattgacctc ccccatggga aatattgcag gacttaacac aggattgttt  24360
ttctcttcat ttctctacga tttctttctt tctttttttt tcctttttc cgaggtggag  24420
tttctctctt tttgcccagg ctggagtgca ctggtgcaat cttggctcac cacaacctct  24480
gtctcccggg ttcaagcaat tctcctgcct cagcctcccg agtagctggg attacaggca  24540
tgcgccacca cgccaggcta attttgtatt tttagtagag acggtgtttc tccatgttgc  24600
aacctcaggt gacccgccca cctcggcctc ccaaagtgct gggattacag gcgtgagcca  24660
ctgcacccag cctaccattt ctttttggga cagggtcttg ctgtgttgcc caggctggtt  24720
tctaactcct gggctcaagc gatccactgg cctcagcctc ctgaagtgct gggattacag  24780
gagtcagcca ctgcaccagg cccatttctc taccatttct gatctctctc tagaaacact  24840
tggataactg cacagctcct ttcataagaa atatatttta gggccgggtg tggtggctta  24900
tgcctgtaat ctcagcactt tgggaggccg cggcaggtgg atcaaccgag gtcaggagtt  24960
caagaccagc ctggccaaga tggtgaaacc ccatctccac taaaaataca aaaaattagt  25020
caggagtggt ggtgcatgcc tgtaatccca gctactcagg aggctgaggc aggagaatca  25080
cctgaaccca ggaggcggag gttgcagtga cccaacattg cgccattgca tgccagtctg  25140
agcaacaaga gtgaaacttt gtctcaaaaa acaaataaac aaatgaacaa acaaacaaaa  25200
aatcattgtt attcctcaga gtaagagcaa agatcatccc ctgcagaagc ttaggaacta  25260
tgcacagaac tttacagaac aggggcgatg ctttaactga aggctgacta ctgaccagag  25320
aatggaattc tgagagggct caaggaataa aaggaaacta ggcagggaaa gggaaggcgc  25380
ccatctgaag caaacttcag cggccatcag gatatcttgt ggtggtcaca agttgtaggc  25440
tctgtttttg gaaggtttgg gtatagcgca ggattccatt tgtctacttg gctacacctc  25500
tgcctgaggt acactgttgc cagaaaagag ggtcccaatc cagaccccaa gagcaggtta  25560
ctggatcttg cacaggaaat aattcaaggg aagtcacaca gcacagagaa aaagcaagtt  25620
catacaatgt tactgagtaa gttatcgcca gaaagcagga ggaggaacac gccatccttg  25680
ttagtgtctc tatttataag aaacttatga gaagctataa ttaaacttgg aacatgcaga  25740
tgtgctcact aaaggtaggg gctattggtg ttatagatga ccattaatct ttcaacctaa  25800
gcctgctcat taatggcatc tttaataaag tgggctacac tcttaggaca tctggacatt  25860
ctgcaggatt ggtgggagat gttctgtatg gccaccaata ttctgtaatt ataattggtg  25920
gtcagcttgg gatgtggcta ttttcagacc acaagcatta accttacaga gtgcctagct  25980
actcatttca aggtggagtc actctggcca tgttttacca aaccagaggt ctggtaagga  26040
gaggttcctc taacaccatg aggtcaacgt cactcaagtt cctggccagc caaactctga  26100
aagcaaggag tcccaaattg aggatcaagt tcctccagaa atcattgcta tgggtggcaa  26160
agcagtagat tccctgaagc caatctccca cattgtctgg aattttggga gcttcatttg  26220
cccagttggc agtgccaatg gggaccccgc tggaagccat agtagcacct ttgggctctg  26280
cataggactt gctcaataca ccatattgga gtcgttggct ctttttgtta ttttaagttg  26340
aaatttgaag attggctgag ttggtttcat gatattgttg cctactgata tcttacacag  26400
agtacgagta catctggttg aaagagaaaa ggcagagaga aaagcagact ttttggagtt  26460
gttgttctca ggcactaaca gattcatccc ttatatgcat atgaatggac aataagattt  26520
cttggatatt ttcatggcaa aggtgaggag aaatttttat tgctttttga agaaacatga  26580
tttttattac cttgggttat tccaggagat aattgataaa tgttgagtag tttgttggtc  26640
ttcttcttaa aggaggatca agagaagcag tacagcatgg cagactagaa gcatttctgt  26700
```

-continued

```
tttttttgttt tgttttgttt gagatgaagt ctcactctgt tgccgaggct ggagtgcagt  26760
ggagtgatct ctgctcactg caagctccgc ctcctgggtt caagtgattc tcctgcctca  26820
gcctccaaag tatctgggat tacaggcatg tgccaccacg cccggctaat tttacattt  26880
ctagtagaga cggggtttca ccatgttagc caggctggtc tcaaactcct gaccttaaat  26940
gatccaccca cctcggcctc ccaaagtgct gggattacag gcatgagcca ccgcacctgg  27000
ctgaagggtc ttcagtatca tctctgtgat agataaattg tttagtgggt tatctacatt  27060
ggccattgac atctagaatt agggtatgag ttgggtttag aagaaggaaa tgaggctggt  27120
ctccaataga cagtgattca tatgataagc agaaagtgtt acagaagtct ggtagaggag  27180
gatgggagac agattattgt caaggagata gtaaaagttt attttgaaat ccttagacta  27240
tgccgggctc agtgggtcac acctgtaatc ccagcacttt gggaggccga ggcgggcgga  27300
tcacctgagg tcaggagttc gagaccagcc tgaccaacat gaagaaactc ggtctttatt  27360
aaaaatacaa aattagccag gcgtggtggt gcatgcctgt aatcccagct acttgggagg  27420
ctgaggcagg agaatcactt gaatctggga ggcggaggtt gtggtgagcc aagatcacgc  27480
cattgcactc ctgcctgggc aataagggcg aaactccatc tcaaaaaaaa gaaagaaatc  27540
cttagactat aagtttgtta tataatctgc atgtaaaaca aggtcctata tgacttaaat  27600
aatgtgcagg gttcccttta aaaagttcag caactacttt ccttttttttt tttttgagat  27660
ggagtctcac tctgtcaccc aggctggagt gggttggtgc aatcttggct cactgaaacc  27720
tctgcctcct gggctcaagc catcttctca cctcagcatc ctcggtaatt tagttgggac  27780
tactggcgtg cgccaccatg cccggctaat ttcctgtat tttgtggaga gacggggttt  27840
caccatgttg cccaggcttg tctcaaactc ctgggctcaa gtgatcctcc tgccttgatc  27900
tcccaaagtg ctaggattac aggcgtgagc caccacacct ggccaatgac tttcaaattt  27960
gtttaaagta atcccaatct ttatttgcct ctctcaagta attaatgata acactttctt  28020
taaaaaaaaa atgctgtcac taggctgggt gcggtggctc acatctgtaa tcccagcact  28080
ttgggaagcc gaggcgggtg gatcacctga ggtcaggagt tcgagaccag cctgaccaac  28140
acggtgaaac cctgtctcta ctaaatacaa aaattagcca ggtatggtgg tgggcacctg  28200
taattccagc tacttaggag gctgaggaag gagaatcact tgaaccccgg gaggtggagg  28260
ttgcattgag ccgagatggc accattgcac tccagcctgg gcaacaagag caaaactgtc  28320
tcaaaaaaaa aaaaaaaaaa aaaacaaaaa acagacgggg catggtggct cacacctgta  28380
atcccagcac tttgggaggc agaggcaggt ggatcacctg aagtcaggag tttgagacca  28440
gcctggccaa catggcaaaa ccccacctct actaaaaata caaaaaaatt agctgggcac  28500
ggtggcaggt gcctgtaatc tcatctacta gggaagctga agcaggggaa tcgcttgaac  28560
ctgggagacg gaggttgcag tgagctgagg ttgtgccatt gcactccagc ctgggagaca  28620
gagcaagact ccgtctcaaa aaaaaaaaaa aaaaatatgt cactaatctc taagatctct  28680
gaataactct ctcagaatta gagtccatac agctctgatc ttttcttctt ttatgctgct  28740
tgtttttcca aggcttttag tgatgcaaac ttatcattac tttaacaatt ccagctttcc  28800
ttctatgtct tggttttaca cgacaagaag cccagaaact gaacttgctt actcagctcc  28860
cgaggttgaa ggtggcaaga aggtggtaag aatcctagac aggctaggcc tggtggctca  28920
cgcctataat cctaacaatt tgggaggcca agacaggagg atcgcttgag gccaggagtt  28980
cgagactagc ctggggaaca tagtgagacc ctgtctctac aaaaaaaaaa aagaaaaaat  29040
```

-continued

```
tagctgggtg tggtagtgca cacctgtggt cccagctact caggaggcca agttgggagg  29100
attgcttgag cccaggaggt ggaggctaca gtgagcaatg atggcaccac actccaacct  29160
gggcgacaca gtgagactct gtctcaaaac aaaacaaaac aaaacaaaac aaagaagatt  29220
tggtagaatt ctcctgtggg agtttggaga aagaagtaga acattattat tgtttttttc  29280
ctgtcatatt tctaatggaa acaggatgat tacaagagtg caggggaaag gttggggaaa  29340
agaaatgtga cttctttcac ttttacatta ttgaaattgt tatttaaatt gtattctata  29400
accataatta aatcttcata aacttttcac ttaatgatct tagcattcat tgatggtctt  29460
tgcctgaatc ttatttcaaa aggcaaggca tttcaaaaat gctgattttt aaaatttcta  29520
tcatttctta tacacttatt agctcacatt tttctgtaat gagtttaccc ttatcaagtg  29580
ggactctttg gttagctgct cctctaagct aattttcttg tattctcaaa gcagtttctc  29640
catactatca tttcaatacc tcttgctgtt ctagtttgct gttttgagta tgtccttgtc  29700
ttacttatgt gattgacttt ttttttgaga tggagtttct ctctcgtcgc ccaggctgga  29760
gtgcaatggc accatctctg ctcactgcaa cctccgcctc ccaagttcaa gcaattctcc  29820
tacctcagct tcccgaataa ctgggattac aggcacctgc caccacaccc agataatttt  29880
tgtattttta gtagagacgg ggtttcacca tgctggtcag gctggtcttg aactcctgac  29940
ctcagaggat ccacccgcct tggccccaca aagtgctggg attccaggcg tgagccacag  30000
tgcctggcca tgactaactc attccattga gggtcttttc tcctgaagtt ttgtgctatg  30060
acttgatatt tcaaaagaag ggaaatagat gtctcagtat taaatttcaa acgggaagtt  30120
taacctgtat attggcttat ttagggtaag agtgaagcta tcctggacaa gaactttgac  30180
aggacaatac tattcactct gaaggaccaa aaaatgagca gaaaatttgg gataaatgtc  30240
aacaagattt gaaccctaaa gaaaagcaag catcgagtta gacagacgtc catattcatt  30300
caactgggaa aataaaactg cagtcccaac atcagaattt ccttggtcag ttggttattg  30360
cgggacagca ttcttctgca tgacagtatt gtctccttac cagccacaga ggaggctgtg  30420
agagagagga tttgggaaat tggtgcaaat gagaaatctt ggaaatctgt aagtatatag  30480
atataaaagt tattctttcc agtttgattc ttttatgatg tagattttaa tatcagtcaa  30540
tttaggaaac tctgtggctc tgaattatag ttataattct agttttacta ttacagtgaa  30600
agaagagaag aggctgttca ttattatatt ggaagtagtg tagcatgttt attaagagtg  30660
cagagcccca gcatgaagcc tagctctgcc atttgccagc tgtgtgtgct cttgggcaga  30720
ctacttatcc tctctgtgcc tcattttcat ttgtgaagta ggggacggtg tgtagttccc  30780
acctcacaga gtggttgcaa ggaccaaatg ggttaataca tgataaatgc ttagtttagt  30840
gtaagttcaa taaatatcaa aatagtggta tgttaaagat agtgtttaca tgataaccta  30900
aaattaattg ccagtttgtt ttaatttact ggtcaagtct atcaaatgat tgaatcagca  30960
tgtttaagtg gatatatctc atttgtgtcc agatcatttt agtatattca tgactcctca  31020
ctttaaaatt caaatgataa taggtacagt tagtcctcca tatctgtgga ttcaaccaag  31080
taaaaataaa aaattgcatc acaacaaggc atggtggctc acatctgtag tcccagcact  31140
ttgggaggct gaggcgggtg gaccgcttga ggccaggagt ttgagaccag cctggccaac  31200
atgacaaaaa cccatctcta ctaaaaatac aaaaatcagc tgggtggtgg tggcttgcac  31260
ttgtagtccc agctactcgg gaggctgagg gatgagaatt gcttgaaccc aggaggtgga  31320
ggttgcaatg ggccgacatc tcaccactac actctagccc gggcaacaaa tcaagactgt  31380
ctcttttttt tttttttttg agacgaagtc tcgctcagtc gcccaggcta gagcgcagtg  31440
```

-continued

```
gcgcaatctc ggctcactgc aagctccgcc tcccaggttc acgccattct cctgcctcag  31500
cctcccaagt agctgggact acaggcgccc accaccacgc ctggctaatt ttttgtattt  31560
ttagtagaga cggggtttca ccgtgttagc caggatggtc tcgatctcct gacctcgtga  31620
tccgcccgtc tcggcctccc aaagtgctgg gattacaagc gtgagccacc gtgcccggcc  31680
aagactgtct caaaaaaaaa aaaaattgca tctgtactga acatgtacag acattcttcc  31740
ttttcattat tctctaaaca acagagtaca actatttaca taacatttac gttatattag  31800
gtattataaa agtctcccga gagacagagg ttgcagtgag ccgagatcgc gccattgcac  31860
tccagcccgg gggaccagag cgagtcttcc tctcaaaaaa aaaaaaaaaa ttgagatgat  31920
ttaaagtgta caggaggatg tgaataggtt agatacaagc acaataccat tttgtatcaa  31980
agacttgagt attcataaat tttggcatct ctaggaggtt ctgacaccag tctcccaggg  32040
acgctaggga cgcctgtata tggcttagat tcagtgtgtt agtgaaacct gctacacagt  32100
agcctgttta gagttcccca tttttaaaaa tactctgctc ttttaaaatt cattatacag  32160
ccttatttct cagtactgac taaaatgtct tatttttata tatcgaagct ttctatttat  32220
tttttaaacc aatgtataca tgtcaaatcc taaaaatcgc ctgtattaat ctacttagta  32280
acttaatgcc actccaatgt ggatataaat agaacttgca catagttttg aaactacgta  32340
gaaagcatgg aggctgggtg cgtaggctca cgcctgtaat cccagcactt tgggaggcta  32400
aggtgggcag atcacctgaa ttcaggagtt cgagaccagc ctgaccaata tggcaaaacc  32460
ccgtctctac caaaaataca aaaattagcc tggcatggtg gcatgcacct gtagtgccag  32520
ctacttggga ggctgagaca ggataattgc ttgaacctgg gaggcggagg ttaccgtgag  32580
ccaacgtggc accactgcac tccagcctgg gtgaaagagc gagactctgt cttaagaaag  32640
aaagaaagcg ggcggggggg cggggggaag ggcaagcaag catagagcat gaggaagttt  32700
ttaatgtctt tttcttacag agaactaaag cctttcagca ggaaatccag atgctcacta  32760
agtgactaga gcagctgcat catctttaag aagaaggtgc tcaagaatca tcccaagctg  32820
aagaaaaaag tattgggaac aaaaaagacc cttgaaatgt ctagaaagaa aaattgagat  32880
caaggacttt ttcaagagag attagacttg gacaggaaga aagtaagaat ttcctgaagt  32940
ataagcattc ctttgataat gaaaatgatt gcattttatt cataacttta actttatcta  33000
atgtttgaag ctgttaatac tgttaatact tttctccaca ttgggaaagg ggggaaattt  33060
gctacaaact ctgaaagctt ccgattttat tttatttatt tatttatatt ttttgagaga  33120
gagtctcgct ctgtcaccag actggagtgc agtgacgcta tcttggctca ctgcaacctc  33180
tgcctcctgg gttcaagcga ttctcctgcc tcagcctccc gagtagctgg gactacaggc  33240
acgcgccacc atgcccagct aatttttgta tttttagtag agacgaggtt tcaccatttt  33300
agccaggatg gtctcaatct cttgacctta tgatccacct gcctcagcct cccaaagtgc  33360
tgggattaca ggcatgagcc actgccctgg cctctgattt tatttttaaa agcctcttct  33420
ctctccgtat ctccatgtct cttttgtgta cttatttgat gtttgttgtg agggcatctg  33480
tttacatata tatctcaatg tactttaagg agaggattag aagaaaagga gctcaaagga  33540
ataactctct ttttttcttt tttttcagat ggagtctcac tctgtcaccc agggtggagt  33600
gcaatggtgt gatctcggct cactgcaacc tccgcctccc aggttcaagc gattttcctg  33660
cctcagcctc ccaagtagct gggattacag gtgctcacca cccgcccggc taacttttgt  33720
atttttagta gagacaaggt ttcaccatgt tggccagtct ggtctcaaac tcctgactgc  33780
```

-continued

```
aggtgatctg cctgccttgg ccttccaaag tgctgggatt acatgtgtga gccactgtgc  33840
ccggccaaag gaataactct ctaatgggga aattttagga attgtgacag gcagatataa  33900
tgagcattga tgaggggcca ttgatgatgt ctctcaataa tcactgtata agtcattctc  33960
ttctctactc tctgcttccc tgaatctgta aggaaaaagg cagtcctaaa agttggatag  34020
aaataggtag gttgcaatac aatttatttt caggagattc tctattttac tacctcttca  34080
tagaattgcc tatcatagcc gggcacagtg gctcacacct ataatcctag cattttggga  34140
ggctgagaca ggcggatcac gaggtcagga gattgagacc atcctggcca acatggtgaa  34200
actctgtctc tactaaaaat acaataatta gctggatgtg gtggcacaca cctataatcc  34260
cagctactct ggaggctgag gcaggagaat tgcttgaact caggaggcag aaattgcagt  34320
gagccaaggt agtgccgcta cattgcagcc tggtgacaga gcaagactcc atctcaagaa  34380
aagaaaaaaa aaaaaaaaaa gaattgccta tcataaccaa attacgttat agtatttcta  34440
taattgctat ggtccaaagt ggaatcttgc tcactcattt accatttact catttagtct  34500
tttttttttt tttttttctg agactgagtc tcactccatc acccaggctg gagtgcagtg  34560
gcgcaatctc ggctcactgc aacctccacc tcccaggttc caatgattct cctgcctcag  34620
cctcccgagt agctgggact ataggtgtgt gccaccacac ccagctaatt tttgcagttt  34680
ttagtagaga tgcagggttt caccatgttg gccaggctgg tcttgaactc ctgacctcgt  34740
tatctgcctg cctcagcctc ccaaagtgct gggattatag gcatgagcca ctgcgcccag  34800
ccttcattta gtcttttggc tcattcattt gtttatccaa tatttattga gcattcagtt  34860
ttcttttctt ttctttttgg agacggagtt ttgcccttgt tgcctaggct ggagtgcaat  34920
ggcgcgatct tggctcactg caatctctgc ctcccgagct caagcgattc tcctgcctca  34980
gtctcctgag tagctgggat tacaggcatg cgccaccaca cctgtctaat tttgtatttt  35040
tagtagtgac agtgtttctc catgttgttc aggctggtct cgaactcccg acctcagatg  35100
accagcccac cttggcctcc caaagtgctg ggattacagg tgtgagccac catgcccggc  35160
ctaatagttt tctttactag agttcttggg ttttctggat ttcactgtat attgtcaaat  35220
tgtttcctag gaaataatgt atttttaaaa tttcacttat ttattttata aataatttga  35280
ttctaaaggt ggaacagttt ggaccagctc atgggagaac tgtctttttt tttttttttt  35340
tgagacagtc ttgctctgcc tcccaggctg gaatgtggtg ttaccatcac gattcactgt  35400
agcctcaacc tcctaaggct caagtgctcc tcttgcctca gactcccgag tagctgggac  35460
cacaggtgca caccactatg cccagctaat ttttgtagaa atggggtctt tccatgttgc  35520
tcaggctggt cttgaactcc ttgtggctca aatgatccgc ccatctctgc ctcccaaagt  35580
actggaatta cagcctttat ttcttttaga ttttcaattt actgccccta agttgcaaaa  35640
tgttctctta gaattatttt tatctttgca ttctgtatcc attctgtatg catatctata  35700
tattctgtat attcctcctt tctaatattg tgtattttca ctttctctct ttccttttta  35760
accaggcttg cctgaggcat ctattttatc tttccaaaga accagtggtt ctttttgaga  35820
cagggtctgg ctctgtctat tgtccaggct ggagtgcagt ggcgtgatta tggctcactg  35880
aagcctcaac cttcagggct ccagtgatcc tcctgcctca gcctcccaga tagctggaac  35940
tataggtgca cgcctccacg cctggctagc tttttgaagt ttttgtagag atgaggtttc  36000
gccatgttgc ccaggctggt ctcaaactgc tgagctcaag tgattctccc gcctcggcct  36060
cccaaagtgc tagtattaca ggcatgattc accgtgcctg gccagttctt tttttaaaat  36120
atacgtttta tggcctggca cgctggctca ccctgtaatc ccagcatttt gggaggctga  36180
```

-continued

```
ggtgggcaga tcacttgagg tcaggaattc gagaccagcc tgaccaacgt ggtaaaaccc  36240
tgtctctact aaaaatgcaa aagttaactg ggcatggtgg tgtgcacctc taatctcagc  36300
tacttgggag gctgaggcag gagaatcact tgaaccaggg aggtggaggt tgcattgagc  36360
tgagattgtg gcactgcact ccagcctggg caacagagcg agactgtctc aaaaataaat  36420
aaataaataa ataaatacac attttattag tttattttgg tttatatgta atgaatatat  36480
atagtatgtt tattaaatct gcaccctact ttctcttttc ccttcttaag taaatgtgct  36540
ttttttgtct tttgttttta aatcagaaaa agagtaagta ctattgaatg ttcctctgta  36600
gcttgtccaa tagattttta taagaaatgt ttcttttcac tgtgttctat gtatttttgt  36660
aattttagtg ttgatttcca ttttttggct gaaggtattc agaatttttg tttgtttgtt  36720
ttttgttttt gagacggagt ttcactcttg ttgccaaggc tggagtgaag tggtgcaatc  36780
tcggctcact gcaacctctg cctcccagat tcaagcaatt ctcctgcctc agcctcccta  36840
gtagctggga ttacaggtgt gcaccaccat gcccagtgaa tttttgtatt tttagtagag  36900
gtggggtttc accaccttgg ccaggctggt ctcgaattcc tgacctcagg tgatccccat  36960
gcctcgacct cccaaagtgc tgggattaca ggcgtgagcc accgcaccca gcctagaatt  37020
tttttaaccc tttatacaca cacacacaca cacacacaca cacacacttt tcaaaatcaa  37080
atataccaag agtcttttat tgaaaaggag cagccctctt ctgtacctct cttatttccc  37140
agagggaact ctttaactct tttagctgtt tctgatagta acttccattt tcctaaacaa  37200
ttttaaactg ccttatctcg agttatctat attagacatg ttgttgattt cctgttatat  37260
gatagatgaa atttcatctc tcataccact ttcctacctg ctcctttcat cttcccaatc  37320
tggttatatt gatattttaa gctaaatgca taatcagcat ttactttacc gtgatactaa  37380
atgtttacaa aagcatgaag tactatattc ttggtacatt ttctttcttg tattgcattt  37440
tatttttcct acagttaata ccttccttat attttcatac gtttaatttt cagtgttcat  37500
ttatcaaggt ttttttcctg cctaaatctg tatcagatga tcctttagtc tttaaaaatc  37560
tcccattttt tctctcccaa agtccttcat tcccttgctt cagtctggat tttactctgt  37620
gggcctgagc acagccatga tgccatgact ttccttctct aatctcctgg ttaggtttca  37680
ttgtttgccg aatcacattt cttcctcttt tttggtttcc tttcttattt tactggaaca  37740
catcctccaa tggcttccta agaaatggtg ccttggagag cgacattttt tgaggtcctt  37800
gtgtgaatga caatgtcttt ttttgtttga atcatcatac tcaattgata gctgggttta  37860
gactttattt tcacacacgg acttcattgt cttctaatct ctagggttgt tattgaggaa  37920
aatatgccat tctgattctt gttccttaat atgttatttc ttgtaatgga ttaaaacatt  37980
taccataact tttttgtaat aacattttat aactaatttt tttctcataa taaaattaat  38040
tcagctgggc atagtggctc atgtccgtaa ttccagcact tagggaggct gaggtgggtg  38100
gatagctgga acccaggaat ttgagatcag cctggacaac atggcaacac cccatctcta  38160
caaaaaattt aagaactagc caggcatggt gcacacttgt agtcccagtt actggggagg  38220
cttaggtggg aggatgggtt gagcacggga ggtcgaggct gcagtgtgct gtgattgcac  38280
cactgcactc cagcctgagc ggcagggtga gaccctgtct caaaaaatta aaaaatcatg  38340
tgtattagtg aagatttgta aagtagaaaa taatagaaat aaaattgaaa tcaccagtaa  38400
tcccaccatt ttgcgataac tagtattaaa tataggtata tttccctctg attattttcc  38460
atgtatattt ttatcatcat tgagatgtac atagtttttc ttaatcctgc ttttttcatt  38520
```

-continued

```
aactacatca ttgttaattt ttcttaataa atatttttga aaacttaatt tctagggaat  38580
aatctatcat ataataattt ttcttttttg acatttgcat tgtttcagtt ttttctatta  38640
tgaataatgt tgtaaagaat atctttgtgg gccaggtgcg gtggctcatg cctgtaatct  38700
cagcagtttg ggaggccaag gtgggcggat cacctgaggt caggagtttg cgatcagcct  38760
ggccaacatg gtgaaaccct gtctctacta aaaataaaaa aattagccag gcatggtgac  38820
aagcgcctgt aattccagct actcgggaag ctgaggctgg ggaatcactt gaacctagga  38880
ggcggagatt gcatttagcc aagattatgc cattgcactc cagcctgggc cacaagagcg  38940
aaactctcag atattcaaaa agaatatctg aatatcttta tggccgggtg cagtggctca  39000
cccttgtaat accagcacct tggatgagca acgcaggagg atcacttgag cccaggagat  39060
tgagggaaaa aaaaaaaaaa aaaaaaaaaa aaaaaaaaag cccgggtgtg cacaccctgt  39120
agtcccagct actccagatg ttgagatggg aggatcactt gagcctggga ggtcaagcct  39180
tcagtgagct gtgataacgc cactgcattc cagcatgggc gacagagcaa gaccctaact  39240
taaaaaataa aataaaataa ataatatctt tgtgtgagtc tttttttttt tccccgagac  39300
ggagtttcgc tctttcgccc aggctggagt gcagtggtgc aatctccgct cactgcagcc  39360
tccgccttcc ggtttcaagc gattctcttg cctcagcctc ctcagtagct gggattacag  39420
gcacctgcca ccacgcccag ctaatttttg tatttttagt agagaccggg tttcatcatg  39480
ttggccatgg tctcgatctc ctgacctcgt gatctgcctt cctcagcctc ccaaaatgct  39540
gggattacag gcttgagcca cagtgcccgg cccgtgtgtg aatctttatc cacatatttg  39600
attatttctt tataatacat tcctagaaaa gttgaactaa tctatgctac tgcttggtgc  39660
ttataaaatc tatttcattg tactcttggt agtcctgagt catcactttt attgtcatat  39720
tttattttct tgattatttt aataatgctt atttatggtg aaaaatattt tacttatgga  39780
agtattgtta agcctgcagt gtgttagtct ggagtggatg tggtattatg ctagtgtata  39840
ataacatctt aaagcacaat tttttacttc aatactgttg atttctgcaa aggaaaactc  39900
agggactaag cattcccaga tagacaagca tagcaagaag ttcaaaaagc tagagaaaga  39960
caacatgcaa caaaacaaat gttattgaat atttggcaga atttgcagat tgctactacg  40020
caaagattgg aggagaaaat tcagaaactt cagaaacagc tcagtgattt gaaattgtca  40080
aataaaaata tgaaaactca gctgacaaga gtaaatgtcc ttaaagtaag taaaggaagt  40140
gaggctttca gaaattcact aaagctttgg tcttttacca ttttagcagc atgcttttca  40200
ttgaagctaa aaaaattaat attaaaatta ttttacatac atacaaaaga atatatattt  40260
aagcatatag aataaaattg gaattcacca ctcattttaa gaaacaaata ttaccaatac  40320
aattgaaacc cccatatatc catatatcct cctccttgta ttctaagtgt tattattaca  40380
aatcccttgt tttttgtttt attattatta ttctttttga gacagagtct tgctctgtta  40440
cccagactgg agtacagtgg cgtgatcttg gctcactgca acctctgcct tccaggttca  40500
agtaatcctc ccacctcagc ctcccaagta gctgggaata caggcgcatg ccaccatgcc  40560
cagttaattt ttgtattttt agtagaaaca gggtttcacc atgttggcca ggctggtctc  40620
aaactcccga cctcaagtga tctgcctgcc ttggcctccc aaagtgctgg gattacaagt  40680
gtgagctacc tcacccagtc tgttttttgt tttagtttca cttgtgtctc ttattggggt  40740
aatagttaaa agttgtagtc attttgggga ctcttctttg gaccttctcc atatcaaact  40800
tcagttatac tatttcaaaa attatgcctt aagccaaaca ggcactaaat aactgatcaa  40860
ctgatatgcc agtttatcag caatatttct cttactgaaa tgccaattat cttctgtatt  40920
```

-continued

```
tctgtatttg attaatgtag ggctttaaga cctttgagga tgcagaaaac atgttaagac  40980
tctttaaatc ccaagtggcc agttaataaa agtgctaagt aatagttatt gatgagcacg  41040
atcatggaga aatgtcctct taattcagaa attttggaat gtttttcttt tccatatatc  41100
tctgtcttca taaaaaaaga aagaaaagga aaagaagcaa gagttatcat aactgttatt  41160
tagaagagat ctaatcctag ttatttcctt cctttccccc atcttatatg ctgtcacagg  41220
acaaaacaat tgaagagctc aggcaatctt tagcaaatgt tgaaaggatg aaagagaagg  41280
caaatgttga aacgatgaaa gagaaggcag ttgtgaaaac agaaaacttg aaaactacat  41340
tagactctgc agagcaaaag gcaagatcag acaaagagaa gacccagcag atgttagatg  41400
ctgtcacttc tgagccccca acagcaaaga gcgcacctga agaagtatca ggacaagaac  41460
aagaggtttt ttcaaaatag taaaattaaa attaatttag ttgaagtgat aaacacccac  41520
gcctacttag actgtaacta acttgacaaa agggaatatt ggcttatgga atcatgagtt  41580
aaacaaccta acctccaggt gggcggagat acacctgggc cccaggatca gcacctggaa  41640
cctacaagcc ctttctcatg gtcacttctt ggcatctatg tgtcagctca tctgtctgac  41700
tgctggttgg ttttctccat gacaggaaac atgatcactg gcaaccatgg agatttatat  41760
ggagtttctg tgacaggaga gagaatccca agaaaaggtc ttattgaccc agtttaggtc  41820
aagtgcttat ccctgctaaa cccacagtgg ctagggatgg gatatatgat tattttatat  41880
actctaacaa gtgaccagga gtgtagagtt ctatgacatc atgtgtcatc atgtgaagct  41940
caggggaaac catgtgtgtc actttctgtg tcactgtcta ggagaatata gtagtgcttc  42000
ttaacttgct tagattttca ctatacttat aaagcaaata tttcgagaga attttttaaa  42060
ggccaactga tcatctgggg caatttttaa attatatgtc acttctccat atattagttg  42120
cttatgaaac ttataccita agatatgctt aaaacataaa gtcatgatat tagcattttc  42180
actttttttct ctctttaact tctgtgtgtt cactttcttg attgtttcta ttcctctctt  42240
ttatttttttg agacagagtc tcactctgtt gcccaggctg gagtgcagta gcatgctcat  42300
ggctcactgc agcctcgacc tcctgagcta aagcagtcct ctcactgcag ccttccgagt  42360
agctggggct ataggcgtgc caccaccaca cctaattttt gtatgttttg tagagacagg  42420
gtttcaccat gttgcccagg ctggtctcaa actcctgggc tcaagcaatt ctcctgcctt  42480
ggcttcccaa agtgctggga ttacaggtgt gagccaccgt gtctagtccc ttattttatt  42540
ttcagtcaaa tctgttttcc tttggtcacc ttgtagttca ctcttcactt tttagatgat  42600
ttagtgtttt cttgcctgag ttcaactctc acatctagat atcttggact attctgaatt  42660
attacatttc tgattcaaaa taaagttttt ccccccattt ttgcaaatcc tttaaaaatt  42720
gatatttaat tttttcagg ggtgttgtgt caaatatttg tcctgtgttt cacggctgtg  42780
tttttttttt ttgttttttg tttttttttt ttgagatgga gtttcgctct tgtcacccag  42840
gctggagtgc aatggcatga tctcggctca ctgcaacctc cacctactgg gttcaagtaa  42900
ttctcctgcc tcaacctcct gagtagctgg gattacaggc agtgctacca tgcccggcta  42960
atttttgtat ttttagtaga gatggggttt caccatgttg gccaggctgg tcttgaactc  43020
ctgacctcag gtgatccaac ttccttggcc tcccaaagtg ttgggattac aggtgtgagc  43080
caccatgccc ggcccatggc tgtcttttgg gagtattttt tttttcatcg cctgaacagt  43140
ttagatgata gtgtctttct attttcttct taaagtaatt ttatgtgaat ataatttgcc  43200
atttgtctgt attcactttc aaattccttg aattgctctg gtcttcagat gtttctactt  43260
```

-continued

```
tagggtagct ggaggcaggg cttactcact aggttcctta gctcaatact accctcttct  43320
gttggcacag tgagtgcagt ttctaaagtt tactagatca agccttttg ggagtgaggg  43380
tttatatgat gtctgattct gtaatactgt ctcatttgta taaacatatt aatttccact  43440
gtttgctttt ttcttttcct ttattaccaa gcctccaagg aacacaacta cctccctctc  43500
ccctcagaaa ccttgccctc tacaactgcc atttttggtc tcatgtgctt ccaagaccct  43560
tgcttttcct tcatttgtca gtgttctgat ccaccagatc tcagatttgt tcttggtatt  43620
tcaccattta tgatctgtct tgtttctggg ggtaaggttg tctgtgttct acaccagtga  43680
aaattagctg caccttcctc tgtagctgcc tctgctggtt tagaatattt atttccccac  43740
taacatgcaa attgaagttt gtggtattct ctagttttgc tttaggcatg atttataggt  43800
agtttttatt tgatctccgt gttgatcact atggtttttg gaggatgggt agaaaaatgt  43860
gtttttaggg gactggtatt atcattcagc aaatcagaag tccaaaacgt aattacctta  43920
tggatgaaaa ataacaaaat aagcagcaat aaaattaagt ttactctata aaagtgtaaa  43980
agcaagaaaa aatttaaatg caaaggaaat tttaaataga gttattgtaa tagaagagac  44040
catttttcta gcttaaaaat attgtttgaa agtagaatat attacattta ataatgttta  44100
ataagactaa atttctagta ccaattcttt gtacataata cctgggtgac ccaaactaat  44160
aacatatctt gatttctgta atggttgttt gtagcttagt gactttcaag aaactattct  44220
cagctactca ggaggctgag gtggaggttg cagtgagcca agatcactgc actccagcct  44280
gggcgacaga gtgagactct gtctcaaaaa ataataaatg aataaaattt aaaatttaaa  44340
ataaaaatgg aaactgctca ccttccgagg tagttttaga tgtacccaag atatcctctg  44400
tgggaacaag tcagaatctg gacaggcctg tgggactcga tgcctgtttt agagagctct  44460
tcagcatggg cggggtgaga ttatactgga ccttacagaa gtaccatttt ggaacaaaat  44520
aattatcttg aatattcatt caagggataa atgagaatca ctttccaaat ggccacagcc  44580
atgattccca aactgtgtgc caaggcacac tggtgcactg taaggatctc agcatgccat  44640
ggaatgtttt gattttattt atatatttat tgagatggag tcttgctgtg tcacccaggc  44700
tggagtgcag tgacgtaatc tcggctcact gcaacctccg tctcccaggt tcaagcaatt  44760
ctcctgtctc agcctcctga gtagctggga ctacaggggc ctgccaccac gcccggctaa  44820
tttttgtatt tttagtggag acggggtttc accttgttgg tcaggctggt ctcgaactcc  44880
tgacctccgg tgatccaccc acttcagcct cccaaagtgt tgtgattata ggcataagcc  44940
accgtgccca gcctaaatat tttgatttta aagggaagca ctgtaatatt tgacatctgt  45000
caggaaggta catggatact agcttcaaca ttacatcacc cttcattctt tttgatgaca  45060
tacctttgtg atagaaactg cccaaggctt ctcaggattt ataaatttgt tgccgagtga  45120
acttcagtag ttagtggtat cgctaccaaa gaagctgtgc tgcaaacttg gggaaggagg  45180
ctctttcccc agattctagg atccctggct gcaatgtaag aaacttgctt atccttcctc  45240
tcaataatat caccagccta gcaaaagagg aaaagtgagg gacaccttga ccagagcctc  45300
cacttgcagc ccagcctgct caagctgtaa gaaccacctt cttattcaga atttccccag  45360
agccacggcc caagggtcat ctgcctgctg cagccttagc acacaggagc ctgggcatga  45420
aacaggcaga ccctctcctc cttccaggac acccttctct caggaaatgg aggccctacc  45480
agctcctaca gccaagctct ccatgaaggc caaggtgtta aggtgggcca gtttctgaaa  45540
gagccacttt ctgagcatat taaagaaaaa tctcttgtaa aaacaaagag ggcttagtgt  45600
taatgctcct ttatgaattg tgttagtagg aactgattgt tcaatcatgg ggcagtgcaa  45660
```

-continued aacgttagct gtgttaactc tgagcaaaca ggggagatcc ttcaaggacc tggaacactg 45720
tttcctagaa aagcttttaa tcatgtgtcc aaatcactgc cacactcttc tttaatgata 45780
agaattggat ttagatttaa ggctttagat aaatgattct caaccttcaa gatgctatga 45840
aatgacctaa ttaaggaatt attttttcct aggcctatcc agagattcca gttcagtttg 45900
tggtatgagg ctgaagtatg gatatttttt tcaaagctcc ttaagtatat aaattgataa 45960
aattactttg gaagactggc agtgtacgag ttttctgttg ctgctgtaac aaattatcat 46020
aaactttgtg gctaaaacag tacaaattta ttatcttaca gttctagagg tcccattggg 46080
ctaaaattaa agtgtcaaca gggtgtgttc cttctggaaa ggggaaaatc catttgtttg 46140
ccttttccaa cttctagagg ttacccacat tcttgcctca ttgcctcctt cctccatctt 46200
taaaactagt aggaattgat caggcccatc cagtctttct cacagctact gttctctggt 46260
tctttatctg attctacaat ttctctgatt ctccttctct tgcctccctc ttctctattt 46320
ttaagggtgc ttgtgattaa gttgggccca cctggacaat ccagaatgct ctccctattt 46380
taaggccacc tcttggcaaa ctctgtaaac ttaattctct tttgccatgt aacctaatat 46440
actcataggt tccagggatt aggacaagga tattttgggg gacccattat tttgcttgct 46500
gtagttagca tctactaaaa ttgaatacat gcatgcctta tgaagacgta gtcccacttc 46560
tacatacatg ttagaagcaa atttttcagt gccacaaaat aaaagaaaat agcactcgaa 46620
tataaatttt ctcagcaagg caaatttact ctttcaggag ggtgcccctc gtaggtctgg 46680
ttgccacgag aggacgcaca aacaaaggaa agcagggggt tttattatct ctaatgcagc 46740
ttgtccctgt tactgcgtct tgcctccatt ggctggagtt ggaccacacg atctaagctg 46800
aacctggttg gctaacttga aaagtgcagg aatgcggttt tcaagtggga aggtgggaag 46860
atcaattttt ctgggaaagc tgttacagca gggagggggt gatttcttgg ctgtcttgcc 46920
tgagcacagc aggatgggag gggctgatag attggcaggc aagattactg tagacaaaga 46980
acagagaaat aagacttcag gacagacagt acaaggaagt aaagacctct tggagaagaa 47040
taccttgttt gtaacaaagt gaaactcttt gaagaggaac tgtctaaact acttgttttt 47100
aacatatata acagaaatgt gtacatattc ttttttaaat ttttaaattt tattattttt 47160
ttggagacag agtttcgctc ttgttgccca ggctggagtg taatggcacg atcttggctt 47220
actgcaacct ctgccccctg ggttcaagtg attctcctgc ctcagcctcc agagtagctg 47280
gtattacagg catgcgccac cacacctggc ttattttttg tatttttagt agagacaggg 47340
tttctccatg ctggtccggc tgatttctcg aactcccgaa ctcaggtgat ctgcccgcct 47400
cagcctccca aagtgctggg attacagacg tgagctacct cgcctggcca gaaatgtgtg 47460
catattctat acaaagacat ttacaatatt actaacggtg gcattgttca ttattgccgg 47520
aaactggaaa ctacccaaat gaacaatggt ggcttaagta tggcaatcag atccattagt 47580
taagcattcg atctcatttg gggttggaca gggagaggtc aactggagtg ctgaattttt 47640
ctgaggccaa actagaaagt aactctagga gctgggcgtg gtggctcatg cctgttaatc 47700
ccagcacttt gggaggccaa ggcgggcaga tcacctgagg tcgggagttg gagaccagcc 47760
tgaccaacat ggagaaaccc cgtctctact aaaaatacaa aattagccag gcgtggtggc 47820
gcatgcctgt aaatctcagc aacctgggaa gctgaggcag gagaatcgct tgaacctggg 47880
aggcggaggt tgccgtgagc cgagatcgtg ctattgcact ccagctgggc aacaagagtg 47940
aaactctgtc tcaaaacaac aacaacaaca acaaaacaac aacaacaact actactctag 48000

-continued

```
gaccaggact gggagatggc aaatagggga gagcatggag ttccactaat aaaatggtaa  48060
tacactaaca gtggagaaag caatgggctt gtaaggagaa cttggttctt gttgaacatc  48120
cgtcactaat cagtcttgca acccttgatc aagtcttgtc acctcactaa actcgaattt  48180
tctttatctc aaaactagaa agaaatcgtg gcctggattt ctgaattatg ggtttcagg  48240
cagccacaag taggctggca gaaatgtttt ctggtcaaat aaaggagtct gttgccccag  48300
aacaggagcc aggggcacag ccaacagtaa aattctgctt ggggccccat tcctcagctg  48360
caaggtactt gtcttcaggt gtggcaggct gagatctgcc tccttgttcc cggcctatcc  48420
cgctgggccc ctcccctgca agtgttcgct tccatacaga gggaccatta gggcctgtac  48480
atcgtacttc aggtcccctc ctgtggtcca acattcccta ggggcaagtg caactgttta  48540
tgcggagacc acttttccgt gcagcccaac tgaaggtgca cgttccaccg caacctggtg  48600
cttacaacag ctcgggaggc cgcgctaccg cgcctgcgcc cctctgaata tggaagcgcg  48660
cgcgaggtcc ttaagggaaa aggaagtaag ggcggggacg gagggagacg acttcaacgt  48720
agggagttgc tgctgctaca ctgccggccg gagaggacaa ggaaaacgtg gaggaagtcg  48780
gtgatgactg gctgaagggg atgattggcg ggtgaaaaga gccgggccag aaagcacctt  48840
tgcatgtggc tagaaacccg cctgaagagg ggctgaaacc cacgccggaa cccgcccgat  48900
tcgagccaat cagggagagg agccgggtgg gggggcggac ggggcggcct cgcgggggt  48960
ggacggggcg gtctgcgggg aggggggcg gtctgcgggg agggggacgg ggcggcctcg  49020
cgggagggag gacagtttcg cgggttcggg cggcgagtct cccggatgct cctcagctct  49080
ggggacgcgg tgcagaagtg tgagggcgcc cggcttccag gcagtaatgg gcgggtccct  49140
gcgcgggagc gtggcgggcg ctggactcta cagcagatgt ggaactggag agcttggcgc  49200
gccttccgac tttgtcacac acctgcgccg ccagactggg gtcgggcccc tccgcgttct  49260
gctctggagt gcctgggtct gggcccagca ccgcgctttt agaatctcct cagctgaatc  49320
tgacgctcag cagtgggtga agcgcagccc cctgtttcag gccctgccga gctggaagga  49380
gtgtcagagc tggagcgcgc gtggccccct ctgtgttggg gtcaccccgg ggttgccagg  49440
gctcagggag ggtcgtagtc tggattttgt cacccgcacg tccccacccc ccagcaggtc  49500
tggggttgga gaatccacgc gggcttcata agctagatgc cagttaactg tcgagagggg  49560
acgctccctc ctcgtaggcg tccacactgg agaaggaata agatgggcga ttgcctggga  49620
agcctgacag ggcggcggca gctgggatgc tggagaggac tggccccttg agttactgag  49680
tccgatgaat gtgcttgctc tgctggagga accgcgctca ggttacagtc atcccaatat  49740
ggttctgaag gtgcgtggtt caggtcactt aggacttgac cagataccgg gtttctttta  49800
caagccgttt ctgacggtgg cctgtttcaa ctactggcag agctcatgta aaacagactt  49860
ttaaaaaaat ttggggggct tttagtattt ttttcttatt cctatattct gaggatattt  49920
tatagtagtc ccacatatgg aattagataa tctctttttt gtttgattaa cagttttatc  49980
aagtataatg tacataccat aacgttcacc cattttaatg gattcaatga tttttagcat  50040
atttacagag tggtgcaacc atcagcataa tagaattaag gaatcgtgat tttttttttc  50100
tggtaattgc ttttacagtt ctcaaagttt gcacaagcgg atattttaga ggtacagtgt  50160
aatataagag cttctgaaaa tgtccactta agttgtttta tacctgagca agtgaaatta  50220
agaagggaat tgaagcaaat attcctggta agttgtaggg agtgaaactt ttgtgtcttg  50280
taataccaag tagatattga ccatttcaac tggtttttat gctgaggaaa tgcataaacc  50340
ccattttaca gatgatgaaa tcgactttga aggataagtt gcctacagct gcatacctgt  50400
```

-continued gcctgggcta ggccccaaac ccagatgctt tatctctcaa tttgttaccc ttgctacctc 50460
aacagcttgg ttttcaacca tggtactgat gagtatgaac agtacaagcc attcatttac 50520
tgagcaaata attattgagt gccactctgt gccaagaaca ctgctatagg tgctagagat 50580
attattgaat cagataccgt agtgaactgt tcctgccctc agctcatctt ctggtgggga 50640
ggacaatgat caagtaaaga aatatatagt tttagagatt catctatttt tttaataggt 50700
aaattaaaag ggcaaggaat ggcagtggga ggcagaatct gatgagaaaa atctgaatga 50760
agagaggaag ttaggatata agaaagaaag caagggtttg atttgagcaa gcgcaaaaat 50820
agagttgtga tttactgaat tgaaataagg tgatactgga aggaccaggt tttgggggta 50880
caatcataag tttggcttta aatgttttta aataccttgc ctcttagaca tccaagtgga 50940
gatatggcat ttaaattcat gagattggat gagatcccac caaaggaaca ggtttaggtg 51000
gagacaacca aataccgatg cctaggacac tgcagtgttt agaattcaag gagatgagaa 51060
ggaaacagga gggaagattg aaaagaagag tccagtgtgt tatgaggaaa accccaagag 51120
catgctgcct tacaagacag gtgaaaaatg tgttctgtga aagaaagagt aattaactgt 51180
taaatgttac agactgatca aataaaatga agactgagaa tggcctgttt gtaaggtaat 51240
aaaaatacat aaaatcttat gatagaaata tttatacata aagttagtaa ggaaacagtg 51300
tttactcctt tttgtagaag tgtaaatttt tacaaccatt ttgaagggca gtttgatatt 51360
atctacaact taaaattgtg cttccattga taatttcacc tgtggaagtt tatcctacaa 51420
aaatattaat atgtgcacac aaatatgtgt aaaagtgttt atcacagctt gtacacatat 51480
atatttataa atgtgttgtc caggaacagt ggcttatgcc tgtaatccca gcactctggg 51540
aggccgaggt ggatggatca cctgaggtca ggagttcgag cccagcctgg ccaacatggc 51600
gaaaccccgt ctctattaaa aatacacaca cacacacaca cacacacaca cacacacaca 51660
cacacacaca caaattagct gggcgtggtg gcggacgcct gtaatcccag ctacttggaa 51720
ggctgaggca ggagaatcac ttgaacccgg gaggtggagg ttgcagtaag ccgagatcac 51780
gccactgtac ttctagcctg ggttacagag tgagacttca tctcaaaaaa aaaaaaaaaa 51840
aaaaaaaagg tgtttatcac agcattgttt acatttgtaa aaaggtacaa gttttcatca 51900
agatggatgc agttgttaaa gggaagatat aaatgtgtag atatgggaga tagctgctat 51960
agacggaatt gtgtcccctg aactttcata tgttgaagcc cttaccctga atgtggtggt 52020
atttggaggc agggcctttg ggaggtagtt tgatttagat gaggtcacgc agatggggcc 52080
cccacgatgg gagtagtgtc cttatacaaa gaagaaggga gtccagagct ttcttctgtc 52140
agtcatttaa ggacatggtg agaaggcagc catctgtaaa ttaggaagag tcctcaccag 52200
gaactgaact ggctgtcacc ttgatcttgg tctttccagg ttccacagcc atgagatatg 52260
aatgtctgtt tttaaagcca ctcagtctgt ggtattaata ttttgttata gcagcccaag 52320
ttaagacaga tagctttgtt aaatgataaa gtcaggttat ctaatagaat gcatagtata 52380
accccattta tcttaatgta tcacaggagg cctttctagt cacactaaca aaagttactc 52440
ctttgtgtgc cttccctgat cactgttaca ttattctatg tacagcactt attatctaaa 52500
attatttcat taatttttat acatgtttac tggcttgtca caatagaagg taagctctgt 52560
aaggggtttg cctctcttgt ttatatcccc agtgctaggt atatattact ttaggaaaaa 52620
ccattattta ttaaaaatat tttaggaaaa aaccctacac aaacagtatt cctgtagtgg 52680
ttttaaaata agacaacagg ctgggcgtgg tagctcatgc ttgtaatccc agcactttgg 52740

-continued

```
gtggccgagg caggcggatc acctgaggtc aggagttttg agaccagctt ggccaacatg  52800
gtgaaacccc gtctctacta aaaatacaaa agttagcctg gcctggcgtc acacgccttt  52860
aatctgagct acttgggagg ccaaggcagg agaatcactt gaacccagga ggcagaagtt  52920
gcagtgagct gagatcgcac cattgcaccg tagtctgggc aacaagagca aatgtctcaa  52980
aaaaataaaa taagaccaca atttctttga tagtgtttcc ttccaaaggt ggtggctaat  53040
tctcctcttc ttgaatgtag gctggattta gtgacttgct tctatgtgta gaatatggcc  53100
aatgtggagg tatgtcaata ggtcatgaat tcctttttgt tctctctctt cgatcattca  53160
ctctgaagta aagcagctgc cttgtcatga gaacatatca aacagtgctg tggaaaggca  53220
catttggtga gaaataggcc tactcccaac agccagggaa gaactgaagc cttctgtgac  53280
atgtgaatga gccacctgag aaatgtattt ttcatcctca gtcaatcagt gtctcaaaag  53340
aggccgttag ctggatccct caacaaagcc acttttgggt tcctttcaga taatacaggt  53400
ttgctttgta atctactagg tttggtggta gagtgagaag actgaacaca ctccccttta  53460
ggacacatca taaagcaaaa caagtatggc ccaaagtagc atacacttaa tgttcttttc  53520
tactaggatt tacagaattc attgttggta caatttactc ttttaaaaaa taatttttat  53580
gttgatcaga ataaaatacg gtattccaag ctatatgtgc taacttgatt ttattttaaa  53640
aatgtattga acactggaac acacagattt gaaagatttg accttaatat atatttatat  53700
ataaaatatg attttgaaat aatgaacttt taaatttaaa attataaata atttttaaaa  53760
tgccttctat ttaggtaaag aatcttcaaa acaaacttct catatgatat ggtttgtctg  53820
tgtccccacc caaatctcat cttgaattgt agctcccata attcccacat gttgtgggag  53880
ggacccagtg ggagataatt gaatcatggg ggtggtttcc ctccctgttg ttctcgtcgt  53940
agtgaataag tctcatggga tggttttatt agggatttcc cctcttgttt ggctctcatt  54000
ctaccttgcc tgttgccatg taagatgtat gtttcacctg ccatgattgt gaggcctccc  54060
cagccatgtg gaactgtgag tccattaaac tttttattta taaattaccc agtcttgggc  54120
atgtctttat cagcagtgtg aaaatggact aatacatcat aaaagaaatt tcattgcaaa  54180
agttgaagtc tgaactaaaa agctacaaag aaaataatgt ttaatagcca tcccagatag  54240
tgtccctgaa atacgatgtc aaggatctag aggaacatat tgtatcttta accagaatta  54300
agtctgaaaa acaagtattc agagtcttaa aagaggcaag caggacttaa cggaacgaat  54360
tataaaacta aggtagaaaa ttctagttta tttttgaaac atgtctctca tcataagctc  54420
acatatagca tatgagctcc atgctcctga ttgatcagtt taatttcatg gaatttcact  54480
tattgcctgg tataacatta ttacaatttt tcattataag acttgtgatt atcaaggtca  54540
ggatatcaag accaacctgg ctaacacggt gaaaccccat ctctactaaa aaatacaaaa  54600
aattagctgg gcgtggtggt gggcacctgt agtcccagct actcgggagg ctgaggcagg  54660
acaatggcgt gaacccagga ggcagagctt gcagtgagct gagatcgcgc cactgcccta  54720
ccctccagcc tgggcgacag agcgagactc tgtctcaaaa aaaaaaaaaa aagatttgtg  54780
attatctggt caatgtgtgt agagaggaga tgtttgatca tatacggtac ccttttttttt  54840
ttttttgaga tggagtctca ctctgtcccc caggctggag tgcagtggtg cgatctccgc  54900
tcactgcaag ctccgcctcc tgggttcatg tcattctcct gccttagcct cccgagtagc  54960
tgggactaca ggtgcccacc agcacacctg gctaattttt tgtgttttta gtagagatgg  55020
ggtttcaccg tgttagccag gatggtctcg atctcctgac ctcgtgatcc acccacctcg  55080
gcctcccaaa gtgctgggat tacaggcgtg agccaccgtg cctggttaca gtaccctttt  55140
```

-continued

```
tgatagcagg agaaaagatg gtcattaatg tatcctctta taataagagt aatatttaag  55200
aaagccacaa aatatgaaaa gcttttctat ccagatttac attctgttgt agaccatctt  55260
tattctgtta tttactgtac gttagaccaa ttgatacctt tcattttcct ctggggtttg  55320
catttcgcag atcactttta aaaggaaaac ataggagcct gaaacagaag tgggaaacaa  55380
atatttactc aaactaagag actaaactca gtagccagca acaagagatc aaggtgtgtg  55440
tgtgttttct ggttgtgcag atattgtctg aaataagatg gctgaaaagt tcaagtgaaa  55500
aagtaattaa aagcaattca tcaaccatag ccatagctgg atgtataata gctgatcagg  55560
catagcaaac tcttcaggat aatttcattt ttaaaaattt atgtctttgt ccttttcatc  55620
ttctaagcac agtttcaaat aagactacag agtgaggctc tagggaccat cagtttttgt  55680
ctttagtgct aaaatggtgg ctgagtgaca caccatgatt ttttttctca atatttcatc  55740
attctaccag tgttggaaaa gggagagaag gactctctga aggagactgt gcaaaggatt  55800
cttctttttt tttttttttt tttgagatgg agtctcactc tgttgcccgg gctggagtgc  55860
aatggcatga tctcggctca tgcaacctcc acctccctgg ttcaagggat tctcttgcct  55920
tagcctcttt agtagctggg attacaggcg cgccaccacg ctcggctaat ttcttgtatt  55980
tttagtagag aaaggatgtc accatgttgg tcaggccagt ctcgaactcc tgacctcgtg  56040
atctgcccac ctcggcctcc gaaagtgctg ggattaccag cgtgagccac tgggcccggc  56100
cccaaaggat ctttttacac catgtctggt tcccagccct ttttctatcc ttcctgtgca  56160
gtgtggactg agttgactga gatatttagg cccaggactt cttgcttgtt ctatagttat  56220
tgagaaaagt gtgtcaaaat atccatcact gattaaggat ttgtctgttt atttagttct  56280
atcaacattt attttttaac tttgaagcta tttgcataca aattgaggat ttttatcttt  56340
ctattgaatt gccccttttta tcgttatgaa atctcactta tttcatgtaa tactttttgc  56400
cctatagtct aggttgtctg atattaacat agctagataa tatttcttag attgcatggt  56460
atgtattttt ccatttttca ttttcaatct ttctatgtga ttaaagtatg tcttttgtaa  56520
acagcatata gttttgtttt ttaatctagt cttataatct ttgtctttta attggaatgt  56580
ttaggctatt tacattaaat tctgatattg ttggatttaa gtccaccata ctgctactta  56640
ctgtgttttt tctcctctgg tctttgttct tgtaataatt agtttgtttt ttgttattgt  56700
tgattttttt ttttttttgt caagatggag tcctcctctg tcacccaggc tggaacgcag  56760
tggtatgatc tcggctaact gcaacctcag cctgccaggt tcaagcaatt cttctgcctc  56820
agcctcccga gtagctggga ttacaggtgc ctgctgccat gatgattaat tttatgtgtt  56880
aacttagctg ggctgtgttg cccagatagt tggttaaaca ttattctgga tgtttctgtg  56940
aagatgtttt tggatgaggt taacatttag atcggtggac tttgagtaaa gcagattacc  57000
tttcataatt tgggtggggc tcatccaatc agttgaacat ctgaagagac caaaagactg  57060
accttctgca agcaaagaaa aattctgcca acagacagcc attggacttg aacttcaaca  57120
ttgactcttc agtctattgg cccaccctgc aaattttgga cttgccagta agtgtctgaa  57180
atctagtgag gcaatttctt tctttttttt tttttttgag atggagtttc gctcttgttg  57240
tccaggctgg agtgcagtgg tgcgatctca gctcaccgta acctctgcct cccaggttca  57300
agtgattctt ctgcctcagc ctcctgagta gctgggatta caggcatgtg ccaccacgcc  57360
tggctacttt tgtattttta gtagagatgg ggtttctcca tattggtcag gctggtctca  57420
aattcccaaa ctcaggtgat ccacccgcct tggcctccca aagtgctggg attacaggtg  57480
```

-continued

```
tgagccacag tgcccagcct aatttctttc tttctttctt tcttttttttg agacagagtt  57540
ttgctctttt tgaccagaaa ggagtgcaat gtggcaggat gttggctcac tgcaacctcc  57600
acctcctggc ctctctagta gctgggatta caggcgcctg ccaccacgcc cagctaattt  57660
ttgtattttt agtagagatg gggtttcacc atgttggcca ggctggtctc aaactcctga  57720
aattacgtga tctgcccgcc ttggcctccc aaagtgctgg gattacaggc gtgagccacc  57780
atgcctagcc gggtagttta tcttgacttg acttcaggct caccaatcct tttggctgca  57840
attctacgat agaaaaggac ataaaaaact ttaaattagc cttagaataa agagatgtta  57900
tcattcccta gcaattagta ttcaaagcaa gatccaaata tgtaattagt catttatgta  57960
tctaagctgt ttgtatgtat gatacaagtt ttcacataca aatttcttct ttctttcttt  58020
cttttttttt gatagaggca gggtttcacg acattgccca ggctggtctt gagctcaagt  58080
gatccatctg ccttggcctc ccaaagtgct gagattacag gcatgagcca cagtgcctgg  58140
cccaaattat tgtagttatt tccaattcct ttccccttc tcacatccca attaaagaat  58200
tccactcagg aattgttgta gtagaagtgc tttagtctgt gtgctacggt ttggatactg  58260
tttgtttgcc aagtctcatg ttggaatttg atcactaatg ttgaaggtgg agcctggtgg  58320
gaagtgtttg ggttgttaag gcagatccct tatgaatggt gtggtgccct tctagaggga  58380
gtaagttcgt tctcactctt ggttcccaca agatctcgtt gttgtaaaga tccttgtact  58440
taccctcct ctctctcttg ccttctcttt caccatgtga tctacacaca cagtatcata  58500
aggcatcttt ctgatccttt agtgttcact ctccagtacc tttaatattt gccttcaaat  58560
ttctcaaatt tctttattta cttccatttt tctcctacaa taattgtagg cgtacttaaa  58620
gtagaattac aatataaata atattttaaa atatctacaa ctaatactaa aggggttact  58680
ttattttatt taaattttat ttttaaataa gaatttaaaa tatctgcaac taatatcaga  58740
gccaaggggc tactttcttt gaaatacaaa gagtctttag agtcagactg tgtatgtttc  58800
aatctgggat ctacctctta tattgtaggt ttagacaaat tgctaaatat ttcttgtccc  58860
agttttctca tctacaaaat ggaaaaatta gcttcccttt gctgtctgcc ttgagtagaa  58920
gcttcctgag gccctcatcc aaaacagatg ttggtgccat gcttctagta cagtctgcag  58980
aactgtgagc caaataaacc tcttttcttt ataaattact cagcctcaag tattccctta  59040
tagcaacaca aatggactga gataccgtgt gtgatgtcct aatccttata atattatcct  59100
actacccagg cagatattgc tctccaaatg tcttcttaaa aaggatggtt tctgaaatga  59160
caccctcttg ggactattgg aattactgaa cagctgtttt cattagaaat cttttttttt  59220
ttttgagaca gggtcttgct ctgtcgccca tgctggagtg cagtggtgca atttcagctc  59280
actgcaacct ctgcctccca ggttcaagtg attctcctgt cttggcctcc tgagtacctg  59340
ggactacagg tgtgcaacac cacacccagc taatttttgt gtttttagta gagatgggtt  59400
tcattattta tttatttttt tgagacgaag tctcgttgtg tcacccaagc tggagtgcag  59460
tggcgtgatc tcggctcact gcaacctcca cctcccaggt tcaagtgatt ctcctgcctc  59520
agcctcctga gtaactggga ctacaggtgc acaccactat gcctggctaa tttttttttt  59580
tttttttttt ttgtattttt agtagagaca ggtttcacca tgttagccag gctggtctca  59640
aactcctgat ctcaggagat ccacccgctt tgcccttcca aagtgctggg attataggct  59700
tgagccactg tgcccggcct tagaaatata ttttgactat acatatattt tgtttttatt  59760
tatttttatt tttttgagat ggaggcttgc tctgttgccc aggctggagt gcagtggtgt  59820
gatctcagct cactgcaacc tctgcctcct gggttcaagt gactctcctc cctcagcctc  59880
```

-continued

```
tgaagtagct ggaattatgg gcacatgcca ccatacccag ctaatttttg tgtttgtatt  59940
tgtatttttg aggtggggtc ttgctctgtc gcccaggctg gagtgtgtgg cattatcttg  60000
gctcactgca acctccgcct cctgggttca agcaattctc ctgcctcagt ctcccgagta  60060
gctgggatta caggagcccg tcaccacacc cggctaattt ttgtattttt agtagagatg  60120
gggtttcacc atgttggcca ggctggtctc gaattcctga gctcaggtga ttcacctgcc  60180
tcagcctccc aaagtgctgg gattacaggc gtttgccact gtgcctggcc aactatatat  60240
atattttaaa aggggacatt tctttttaat tttggaatgg acatttgaaa attgtttgaa  60300
ttactttagt ctactcatat ctttcagtct attgacacaa ggtatatctg gtttaaagag  60360
aaaaggtgga acaaaaaaaa cccattctag atcaattggt agatgccaac agattcactc  60420
ccatatgaat atgaaaggac aaggaaccat gaatattttc atgatgaagg tgagaataag  60480
ttttgattga tttttgaaga aaaacaattt ttgttatctt gtttaactct aggaggtaat  60540
cgagaaatgt tgagttgttt gttggttctc tcccaaaggg agggtagaag gaagccatgg  60600
ttcctttata ccgtggttga ctgggagcct ttatgccttt ctgatatatt aagagaaaat  60660
gcaagggggg cctaaaggtc tctgtgatac tgaagagaaa ggtatagggg taatagggct  60720
gtgagaaagc tgaaagctga gatcatgtta cagaataaga tagcggagtt tcatatttct  60780
ggtatggggc aattcctgct gatgacaaaa tccagggttg tttttggatc taggtgtagg  60840
tggttgaagt agggtataaa ggcagtcatg tgctggtaaa ctggctcttg agaaaaagca  60900
cccaatttga gcattcattg acttttgata ccaacatgtc attgagcata gaattagaaa  60960
gagatatgaa taatcaactc ttgggagctg gaatgatctg gctttaacaa ccactttcta  61020
catcaaaaaa agttaatgtt attaatatta gaataataaa taattaaata ataaatgagt  61080
gtaggtgtag ggcattggaa ttaagtacac acatgaatca caaagctgta ttattggatc  61140
gatcatctac tgtgacccct gaaatcttga attatggtat gagttggtat agaagaagaa  61200
tgtgaggccc caaatcttca ttgagtgaag gagggttgag gagtagtcag tagaaaagaa  61260
taaaaagaga agattttata gaagtctgtt gggggtaaaa tattgctgag gaagtaaaat  61320
agtactgagg aagtgttctt caaattcctt cgactataac cactttttaa tgtaatctgt  61380
atgtaaagca agggtctaca tgatccaatt tatgtgttgg ctccatttat aaaagaatat  61440
ttcagttgtc aaaactagtt gaaagtacag ttaatccttt aataatctgg ggttagggga  61500
tatggccatc atgcaaaaaa aaaaaaaatc tgtgtataat tgttgactcc tcccaaactt  61560
aactactaat aacctgttgt tgactggaag acttaccagt aatataaaca gttgactaac  61620
acatattttg tatgttgtat gtattataca ctgtattctt acagtaaagc tagagaaaag  61680
aaaatgttat taagaaaatc ataaagaaga aaaaatatat ttactaatca ttaagtggaa  61740
gtggatcatc ataaaggtct tcattctcat cgtcttcact ttgagtagtc tgagaaggag  61800
gaaggaaagg aggggttggt cttgctgtct ccggggtagc agaagtagaa gaaaatccac  61860
gttatcagtg gacccatgca attcaactcg gtcttcaagg gtcaactgta attccaatct  61920
taattatttg ccttaactaa ttttcttaat aaaaggtgga atattcataa tttacaataa  61980
caccttcatt ttcttaactt ttctcactat atctctcaca tcacatccta aaccttttc  62040
tcctgtgcct aactctccat tctcttaaaa aactctccca gatccagtct atgctgctca  62100
taatttctct tcccttcctc tttttcctac cttctttcta atgcaaattc atcatttcat  62160
gaataatttt ctctcctctt atttcctact tttactcaac aaaagtccag aaactaaact  62220
```

-continued

```
tgcttactca gatcccagag ctgcataaaa ggacaggaga tcttggatga tgtgtgggtt  62280
ggaaacagaa ggtattacat tcttttgtta aataattgag gattttgcat gtggttaaaa  62340
tgatgtcaga gctaggcaag gaaacgggat tctcctacat tcctgatagg agattaaatt  62400
ggtacaaccc atttggaaat gcatttgtca atatctccta aaaccaaagt gtatccctaa  62460
aaccagaata tatcctaccc tgtgactcag caattccact ccatcaacag tggaatgtaa  62520
tgaatatggc tatcaggttt caatatgcta gtgacatctg ctacatctat taacagaagt  62580
ctataatttt ttaacctctg atctctgaaa acttatttta tgactttatt actctacaaa  62640
ctaaaatgtc ttactattgt gtatcagatc cacttctttt taaattaatt tttaaatgtc  62700
aagtcttaat agtcttcctt tagcctctat ttactaattt attgtcccca caatgtcact  62760
ctaaacgtaa ctgttaacta tcaggaagta tttccttctt tttctataga gaacagaaga  62820
tcttcagcag gaaattcaga tgcttactca gcaaatggaa cagctgtatc atctttatga  62880
acagctgttt gtgaatcatt ccaacttgaa gaaaagtata gggaacaaca aaagatcctt  62940
gaaatacctg gaaggaaaaa ttgcttttaa tgatgtttta aaagattaga ctatgaaaaa  63000
agactttcct gaattataga tgttattttg ggcaatgaaa ttaactattt attattctaa  63060
tattaataac tttaacttta tttggtgtag aaagctgata aaaactattt atatttcact  63120
taacattgga aaagtgaggg ggaaaaatcc ttagagttat gcttctaatt ttatcaaaaa  63180
acatgccctt tcccatatct tcagtttttt caccgtgtac atatttgaca gataaaacca  63240
tcaatataat atggaaagtt tagtgtcttt tataatctct tcttgtaagt tacataacat  63300
cacttctgcc atattctatc agtcaaacag accaacctga tacaatgttg ttcgagacta  63360
taagggtacc aggcggcgcg gtgcagatca ttggtggtca tcttaaaagt ctggctaccg  63420
cactcatttc ttttactcac aaactgaatg atttgcttat tcattcattt attcaatact  63480
tattgaacaa ccacagattt tacaaacata taggactggc tgggggcagt ggctcacgcc  63540
tgtaatccca gcactttggg aggctgaggt gggctgatca cctgaggtcg ggagttcaag  63600
accagcctgg ccaacatgga gaaaccctgt ctctactaaa aacacaaaaa ttagccaggt  63660
gtagtggctc acatttgtaa tcccaactac ttgggaggtt gaagcaggag aatcgattga  63720
acctgggaag tggaggttgc agtgagctga gatcgtgcca ctgcactcca gcttaggcga  63780
cagagcaaga ctccatctca aaacaaacaa acaaaatagg acttaatgaa gtaaggtcaa  63840
cagtagacca tatagagttt aaagataaat atatcatctc atctagcctc cacctctgcc  63900
tttgaatatg tgtatggaaa taatacattg aatggttaat ccatgcaaat aaaaataatc  63960
ctttattaag ttttcttaag attgtacaaa acgtgtgctt ggccaggcat ggtggctcac  64020
acctgtaatc tcaacactct gtgaggccga ggtgggatca ctcgaggtca ggagttttaa  64080
gaccagcctg gccaacatgg tgaagctctg tctctactaa aaacacaaaa attacctggg  64140
cacggtagca catgcctgtg gtcccagcta cctgggaggc tgaggtggga gaatcatttg  64200
aaactgggag gcagaggttg cagtgagcca agattgcacc actgcactcc agcctgggca  64260
acagagtgag accctgtctc aaaaaacaaa caaaaaacaa aataacatgt gcctacccca  64320
acacttaaag ctatgctaaa cagtttaaag gaaataataa ttttctctct gcccatgtca  64380
cctcagtaac caatgttaac cattcccata gttatggaaa tatgtaaaca tatataaagg  64440
gtaatggtgt cttcacaaaa ctaagatcat tctaataaaa atattctgca acttcctcta  64500
cttagtagtg cctcatggtt gtatcttaag ttaaaagata tagctcttcc tttaataact  64560
gtataatatt ctatagtatg catgtatctt aatttattca accatttctc ttttgaggga  64620
```

-continued

```
tgatataatt atttccttct tttggtcact acaaataatg tgaaaataag tatctttcaa  64680
cttatatcct tccacactgg tgcttttgtt gctaggggat taattgacaa atatgagctg  64740
atagggtcac agtgcgtatt ttaaattcta atagccattg tcagattact atttgcaaaa  64800
ggatagaagc agttcattta agagtaaatc attctccttt acatccagct agcattgaat  64860
gctgtcattc tttttttgttg ttagttgggt aaaaaaagaa acaaaaaaca aggtacctca  64920
ttattattgt aatttacatt ttcttgacta ctagtgaaga taaggatctt tttttttttt  64980
ttttttcct ttctgtggag ataaggtctt actatgttac ccagactggt ctcaaacccc  65040
tggatcaagc tatcctcctt tctcagcctc ccaaagggct gaaattacag gtgtgagtca  65100
ttgcacttag ccagtaagca tccctcttct ttaaaaaaat aatttcaggc caggtgcagt  65160
ggcacatgcc tgtaatccca gcactttggg aggtcaaggt gggtggatca cctgaggtca  65220
ggagttcgag accagcctgg ccaagatggc aaaaccctgt ctctaccaaa aatacaaaaa  65280
ttagctgggc atggtggtgg gtacctgtaa tcccagctac tcgggagcat gaggcaggag  65340
aatggcttga acccaggagg cggaggttgc agtgagctga gatcatgcta ttgcactcca  65400
gcctgggtga caagagcaaa actctgtctc aaataataat aataataatt tttattttta  65460
ttatagatta aggggtacat gtgcaggttt gttacatggg cataatgcgt gatgctgagg  65520
tttgggttac gtcaccaggt aatgagctta gtacccaata ggtgattttg catcccatgc  65580
cccctctctc ccatgtctgg tagtccccag tgtctattgt tcccaccttt atgtttatgt  65640
gtattcaatg tttagctccc acttataagt gagaacatgt ggtatttggc tttctgttct  65700
tgtgttaatc tgcttaggat aatggctgcc agttccatct atgttgctgc aaaggatgtg  65760
atctcattct ttttaatggc tggtaagcat cttcatatat gcctgttgac cactgggctt  65820
ttcttttcta caaattgcct ccttcttccc ataatttgga tcttaggtgc agaagattgt  65880
gctaatcaaa tttcttaaat agtgtcttgt cattggggac ataatggtcc atctctattt  65940
aattttattg tttttggttc cattccccac ttccattcct tatgcccata ggtagcctca  66000
cttaaatgtg tttatgtcta tcattttgtt tatgtgatta aaaaatcatt attgggatat  66060
ttacatgcca taaaattcac tcatttaaag tctacaattc aatgattttt agtaagttaa  66120
taaagttgtg caaatgccac cacaatccag gtttagaaca tttccatcac ccaaaaaaga  66180
tttttttttt tttttgcttc tagacaatta atgccctctt ccatcactag tgccgggcaa  66240
ccaccaatct gctttctgtg tgtatacatt ttcctttttt tggacatttc atagaaataa  66300
ataactttaa tatgtagtct tttgcatcta gtttttaaaa ttagcattgt ttttgaggtc  66360
catctatgtt gtagcattca tcagtattgt gttcttttta ttatttaatg gtattctatt  66420
gtgtggatat gccacattaa aaaataatac tttatttttg gaagcaatta tagggttaca  66480
gaaaaattga ctataaagta cagagatccc ataaacttcc ttccccatct tcacagtaac  66540
aaattgcatt agtgtggtaa atttgttaca attgagttaa cattaataca ttattattat  66600
tattattatt gaggcggagt ttcgctcttg ttacctaggc tggagtgcaa tggcatgatc  66660
tcagctcact gcaacctccg cctcctgggt tcaaaagatt ctcctgcctc agcctcctga  66720
gtagctggga ttacacacat gcaccaccac acccgactaa ttttgtactt tttttagtag  66780
agacaggatt tcaccatgtt ggtcaggctg gtcttgaact gctgacctca ggtgatccgc  66840
ctgcctcagc ctcccaaagt gttgggatta caggcatgag tcactgcgcc cagcctgata  66900
cattattatt aactaaagtc cggggtttac attaggattc attctgtaat gtacattcta  66960
```

-continued

```
tgggttttga aaagtgtata attacaagta tccatcatta catcatcata cagaatggtt  67020
tcactgccct aaaaatgtcc tgtgttccat ctgttcattc cttcctcctc ctgcaaacct  67080
ctggcaacca caacttttttt tttttgagat ggatgtctcg ctatgttgcc caggcttatc  67140
tcaaactcct gggctaaagc aattctcctg ccttagcctc ctgagtagct gggactacag  67200
gtgtatgcca ccatgcccgg cttgatcttt ttactacctc cgtagttttg tcttttccag  67260
aatgtcgtgt atttggaatc atacagatat aaccttttca gattggcttc tttcacttag  67320
taatatgcat taaagttttc tccatgtctt ttggtggctt aatagctcat tgctttttat  67380
tgcaatgtga ataaaaagca tttttttttt gcaaataata ttctgttgtg cagacttact  67440
acattttagc tttccattta cctaatggta aatcttcgtt gcttccaatt tttgacaatt  67500
ataaataaag ctgctataag cattcaagtg caggttttta tgtggacata aattttcact  67560
tcacctgggt aaaaaccaag gagtactatt tctgagtctt attgtaagaa tatgtttagt  67620
tttgttagaa actgccaaac tgttttacaa aatggctgtt ccattttgca tttccatcag  67680
caatgaatga gagctattgc tgtcactctc acatcctcac cagcatttgg tgttgtcagt  67740
gttctggatt ttagccattt gaataggtgt gtagtggtat ctcatcattg ttttaattgc  67800
agttccctaa tgacatatga tgttgaacat cttttcatat gcttatttgc catctgtata  67860
tcttctttga tgagaacttt tgttcagaac ttttgccatt tttaaattga gttctttatt  67920
ttctagttgt tgaattttaa attttatttg tatattttgg gataacaatc ctttatcaga  67980
tatatctttt gcaacaatta tctcccagtc tgtggcttgt ctttttttatt ttcttaatag  68040
tctctatcac agggcatact ttttagtttt aatgaagtcc aacttgtcag tttttttttt  68100
catgaatctt gcttttctat tgtatccaaa aaatcatctc taaacctagg tcacttacat  68160
tttctcctac gttgtcttct aggagtttta tagttttgta ctttacattt aggtctgtga  68220
tgtattttga gttagttttt gtgaaggtgg tatgaggtct gtgtctggat tcattttttg  68280
ttaatgtgga tatgtagttg tatgtagttg ttctagtacc atgtgttgaa aagactatcc  68340
tttcttgatt gaattgcctt gttcctttgt taaagatcag actttggatg agtctatttc  68400
tttaatttct ttcatccaag ttttaaaata gtcctcattt agactttttt ttttttttgag  68460
actgggtctc tctctttcac cagggctgga gggctggagt gcagtgatgc aatcacagct  68520
cactgcagcc ttgacctcct gggctcaagt gatcctccca tctcagcctc cctagtagct  68580
gggattacag gcacatgcca accacgcctg gctaattgta ttttttgtag agataggatt  68640
gcaccatgtt gcccaggctg gccttgaact cttgggctta agcaatctgc ctgccttggc  68700
ctgccaaagt gctgggatta caggcatgaa ccacaacacc tggctagcta atttaaaatt  68760
ttttcttttg tagagatgga atcttgctgt gttgacctgg ctagtttcta attcctggcc  68820
tcaaatgatc ctcccaccat ggcctcctgg ggtgctggga ttacagatgt gagccaccac  68880
acccagcata ttttgttaga tttatacctta agtatttaac ttgcttgata atttaaattt  68940
tttttttttt tttttttttt ttttttttttg agatggagtt tcgttcttgt cgcccaggct  69000
agagtgtggt ggcacgatct tggctcactg caacttttgc atcccagatt caaaggatgc  69060
tcctgcctaa gcctcccaag tagctgggat tacaggcatg tgccaccatg cctggctaat  69120
ttttgtattt ttagtagaga cagggtttta ctatgttggt caggctggtc tcgaactcct  69180
aacctcaagt gatccacctg ccttggcctc ccaaagtgct gggattacag gcatgaacca  69240
ccgcacccgg ccgatacttt aaatgttatt gtgcttttaa tttcaatttc taattgttca  69300
tatttggtat attaggaaag caattgactt tgtatattaa ctttgtattt tgcaaccttg  69360
```

-continued

```
ctgtaattgt ttattagttc cagaaatttt aaaagtcaat tctttgggat tctctacata  69420
gagaatcatg taatctgtga acaaaaacag tttcatttct tccttttcaa tctgtattaa  69480
ttttcttttc ttttcttgcc tcattgcact ggctagatct tctagcattg tactgaataa  69540
gaacaataag catggatatc ctgttttcaa tcttagaggg aaagcattca gtctttcacc  69600
attaaatgta atgttaaata tagatttttt tatagatgct tgttatcaag ttgagaaagc  69660
tcccctgtat tcctgttttt ctgagtttat ttttatgagt ggtgttgaat tttgtcatgc  69720
tttttctgtg tctattgata tgatcatatg tttttctttt ctagcctgtt aacatagtga  69780
gttacattga tttttgaagg ttgaaccacc cttgcatctc tggaattaag gcctgatatt  69840
gtttggatat ttatgctacc caattctcat ggtgaaatgt aatctccatt gttggaagtg  69900
tggcctggtg agaggtgttt gggttatggg ggcagatccc tcatggcttg gtgctgtcct  69960
cacgatagtg agtgagttct cacgagatct ggttaattta aaagtgtgtg gctccctccc  70020
tgtctctcta tcttgcttct gctctagtta tgtgatatgc tgtcaggtgc tgggctcccc  70080
cttcaccttc tgccatgatt gtgagcttcc tgaggcctca ctggaagctg agcagatgcc  70140
ccgcaccatg cttcctgtac agcctgtaga actatgagac aattaaacct attttctttg  70200
taaattatcc agtctcaagt atttttttgtt tgtttgtgtt gtgagatagg gtctcactct  70260
gtcgcctagg ctgtagtgca gtggtgcgac ctgggcccac tgcaacctct gcctctgggt  70320
tcaagtggtt ctcccacctc agcctcctga gtagctggaa ctacaggtgt gtgccaccac  70380
acccggctaa tttttgtatt ttttggtaga catggggttt caccatgttg gtcaggttgg  70440
tcttgaactc ctgacctcaa gtgatcagcc tgccttggcc tcccaaagtg ctgggattac  70500
cagcatgagc caccacagtt ggcctcaagt atttctttat agcaatgaaa gaatggccaa  70560
atacaacccc actttatcat ggtatataat tccttgtatg tattgctgaa tttgatttga  70620
taatattttg ttaaggattt ttgtatatat tcatgtggta tattagtctg tagttatttt  70680
attttatttt tattttttga gatggagtct tagtccattg cccaggctgg agtgcagtcg  70740
tgggatctgg gctccctgta acttccacct tctgggttca agtgattctc ttgcctcagc  70800
ctacaaagta gctggtacca caggtgcgtg ccaccatgcc tgactaattt ttgtattttt  70860
agtagagaca gggtttcacc atgttggcca ggctggtctc aaactcctga cctcaagtga  70920
tccacccacc ttggcctccc aaagtgctgg gattacaggc aagagccacc gtgcctggcc  70980
acagttatat ttttttggat tgtctttgtt tggtttttat atcagggtaa tattagtttc  71040
ataaaatgaa tttagaagta ttctctgtgt ctattttttg gaagatattg tgtaggatta  71100
gtgttaactc ttcttttaag atttgataga attctccagt gagaccatcc ggatatggag  71160
atttctgtta tgggaagttt taaaattata aattctggct gggcactgtg gctcatgcag  71220
taatcccagc acgttgggag gctgaggcag gaggatcact tgagcccagg agtttgagac  71280
cagcctgggc aatagagtga gaccctgtct ctacagaaaa aaaaaaaaaa ttagctgggc  71340
atggtggcat gtgcctatag tcttagctac tcgagaagct gaggtgggaa gatgtcttga  71400
gcctaggagt tcaaagctac aatgagctat gatcatgctg ctgcactcca gcctgggtga  71460
cagtgagaca ctgcctctaa aaaataaaaa agtaaaaata aattataaat tcaatctctt  71520
taatagttaa gggcaattaa gattatctgc ttaaggccag gcgtggtggc acatgcctgt  71580
aatcccagca ctctgggagg ctgaggcggg tggatcacga ggtcaagaga tggagaccat  71640
cctggccaac atggtgaaac actctctcta ctaaaaatac aaaaattagc tgggcgtggt  71700
```

-continued

```
ggcacgcacc tgtagttcta gctactcagg aggctgagga aggagaattg cttgaacctg  71760
ggaggcagag gttgcagtga gctgagatca tgccactgca ctccagcctg tcaacagagc  71820
aagactccat ctcaaaaaaa aaaaaaatac aaaaaataca aaaaattagc caggtgtggt  71880
ggtgcgtgcc tgtagtccca gctactcagg aggctgagac aggagaatcg cttgaacctg  71940
ggaggcagag gttgcagtga gtcaagatgg cgccactgca ctccagcctg ggcaacagag  72000
cgagactctg tctcaaaaaa ataaataaat aaaacattaa aaaaagataa cctacttaat  72060
attggatgat tgtagtagtt tgtgtttttc aaagaattgg ttcatttaat gtaaattgtc  72120
cagtttatgt gtgtagagtt gtttataata attccttatt attttttaga catctgtata  72180
gtctgtagta atagaccttg cattctgaat actggtaact agcgtcttct ctctctctcc  72240
tttttttttt tttttttttt tttgagacag actctcgctc tgttgcccaa gctggagtgc  72300
agtggtgcga tcttggctta ccacaacctc cacctcccag gttcaagtga ttttcctgcc  72360
tcagcctccc gagtagctgg gactacaggc acacaccacc atgcccagct aatttttgta  72420
tttttagtag agatggggtt tcactatgtt gccaggctgg tcttgaactc ctaaccttga  72480
gatctgcccg ccttggcctc ccagagtgct gggattacag gcatgagcca ccgcgtccat  72540
ccagtcttct ctcatttgtg ctttgttagt cttgatagaa gtttgtcaat tttattaatt  72600
tttctttttt tttttttttt tttttttttg agacggagtc ttgctctgtt acccaggcca  72660
gagtgcagta gtgtgatctc ggctcactgc aacctccgcc tcccaggttc aagtgattct  72720
cctgcatcag cctcccgagt agctggaact acaggcttgc accaccaggc ccagctaatt  72780
tttgtatttt tagtagagat ggagtttcgc catgttggcc aggctggtct tgaactcctg  72840
acctcaggtg atctgcctgc ctcaggctct caaagtgctg ggattacagg tgtgagccac  72900
cgtgcccagc cgattttatt aatttttcaa aagaaccagt tctttgtttc attggttttt  72960
ctattttttt cctgttttac atttaatcaa ttttgttctt atttttatta tttccttcct  73020
tctgcttgct ttggatttat tttgttctta ttttcctagg ttcttggtgt gggagcatag  73080
attattaatt tgagatcttc cctcttttct aatacacaca tttagtgcta taaatttccc  73140
tcttggtggt gctttagctg tgtccctcaa gtgttgatat gttttatttt cattttcatt  73200
cagttccatg tatttttaaa atttcccttg acctatgttt tatttaggag tacttgtttc  73260
atttccatgt gattggagat tttcctgtta tctgttattg gtttctagtt tgattccact  73320
gtggtcagaa atcacattct atacgatttc aattcttgta aatattttga tgtttgtttt  73380
aatgctcagg atatggtcta tcttactatt tcttgcatag accctcaaaa ggttgtgtag  73440
cctgctcttg tagggtggag tattctacaa atgtcaattg gattttgttg atgctggtgt  73500
ggttgagttt ttctatgttc gtgctgatta tctatctcat tctatcaact gagagaggag  73560
ctgaatcctc caacaatagt ggatttttct ctttcttctt tctttctttc tttctttttt  73620
tttttttgag acagagtctc cctgtgttgc cctggctgga gtgaagtggc gagatctcca  73680
ctcactgcaa gctccacctc ctgggttcat gccattctcc tacctcagcc tcccgagtag  73740
ctgggactac aggcacccgc caccacgccc ggctaatttt ttttgtattt ttggtagagg  73800
tggggtgcca ggatggtctc gatctcctga ccttgtgatc cacccgcctc agccttccaa  73860
agtgttggga ttacaggcgt gagccaccgc gcctggcctc ttctttcttt tttcttttct  73920
ttctttcttt ctctttctct ctctctttcc ttttcttttc tttttttttt ttttttgaca  73980
gagcctcact gttgccccag gctggagtgc agtggcctga tctcggctca ctggaacctc  74040
cgcctcccag gttcaagtga ttctcttgcc tcagcctcca gagtagctga gactacaggt  74100
```

-continued

```
gtgcaccacc acatctggct gatttttgta ttttttatta gagatggggt tttgccatgt  74160
tggccaggct gctttcaatc tcctgacctc aggtgataca cccgccttgg cctcccaaaa  74220
tgctgggatt ataggcatga gctatcatgc ctgacctttt ttctttcatt tctatcagtt  74280
tttgcttcac atatcttata actttgttgt ttgggggcat ttaagattac tgtgtcttct  74340
tggttgattg atccttttgt tattatataa tgtccctccc tgtgtctggt aattttattt  74400
gctctgaagt ctactttgtt tgacactttc ctttaatatt tgcataacat attttttcca  74460
tcctcttact gtcaaattcc ttatattttt atttgaagag tttcttatag ataccatata  74520
gttaaacatc ttttaaatcc cctctgctaa ctctgtcttt taactggggt atttattttt  74580
atttattttt ttctttttgt gatggagtct cactctgttc cccaggctgt agtgtagtga  74640
tgctcacttg gctcactgca acctctgcct cccgggttca agtgattctc ctgccttggc  74700
ctcccaagta gctggaattg cagatgtgca ccaccatgcc tggataattt ttttgtattt  74760
ttagtagaga ctggccaggc tggtcttgaa cttttgactg tatgggaaca gacacacaac  74820
tctcccaaat aagcacaaca aagagacaca gaagcagtcc aagcctctga taaactctcc  74880
catcctgaat ccttaaaaat gcttagtctg taagaggatg tgcctctgac ctaactcagc  74940
cagacgcccc tctcaggttt gttttttcta aaataaacct gtcttgactg gcaagccacc  75000
tttcttttct ctcctctttc tttaattcct acactgactt caagtgatct gcttgcttcg  75060
gcctcccaaa gtgctgggat tacaggtgtg agacactgcg cccggcctaa ctggtgtatc  75120
tagaccattt acatttaatg taattattgc tatattaggg cttaagtctt ccttttcatt  75180
ttgttttctc tgtttttttaa atttctgttt tctttttcct aatttcatgc ttgttcctga  75240
aacatttttt agaattccat tttgaattat ttatagtttt tgatgataaa catatatatt  75300
tggtatagct tttttagtgg ttgctccagg tattacattt tgtatatatg acttaataca  75360
gtgtattgat gtcattttac cagtttgagt aaagtataga actcttagct tccattatgt  75420
ctctactttt ccctgtttat ataattatct tagctatttc ctcttcatac atttagaacc  75480
acatcataca gtgttatagt ttttgcttta accatcaaac atattttaga aaactcaaga  75540
gaaggaaagc ctattgtatt tacccacagt tttgctcatt atattttctg tctcctgatg  75600
ttccaagatt ccttcatttt taaaaatcat tttctttctg tttggagaac ttcattattt  75660
agtaagtctt tttgtttttg tttttgtttt tttttagaga tggggtattg ctgtcaccta  75720
ggctggagtg cagtagtgtg atcatagctc actgcagcct tgaactcttg agctcaagca  75780
atccccctgc tcagcctacc aaatagctgg tactacaggc atgcaccacc atgcctggct  75840
aatttttttt tttttttttt ttctgagatg gagtctccct ctgtcaccca ggctggagtg  75900
caatggcgtg atctcagctc actgcaacct ctgcctccca ggttcaagca attattctct  75960
catctctgcc tcctgagtag ctgggactac aggcacacac caccacacct ggctcatttt  76020
tgtattttta gtagagacag ggtatcacca tgttggccag gctggtctca aactcctgac  76080
ctctagtgat ccgcctgcct cagcctccca aagtgctggg attacaggcg tgaaccacca  76140
tccccagtgt gttgtaggct tttaaaatgt aaagcaaaat tgttctacca gcagtgaatc  76200
aaacagtagg ttttgaaacg tcaagaagcc caaacacaaa tttaagttag agttttgtaa  76260
agtaatataa gttctccttt aaatgcattt taaaatatta ataattttct ttagtattgc  76320
ttaacccccct gtaagtcact agggctccat aattattttg gaaccaactc ctaagttaat  76380
attctttcac tgtaatttca gcatccttaa atcttctaag cacagctata agttgaaatg  76440
```

-continued

```
attttagaga actgtgagta aaaatctaat atgataaaat ggctccattt tgcggggaag  76500
gatgtactgg taattgacag aaaatgacca ggaacatgga aataggagta ggtcagacag  76560
attgaattgt taagtatttt gaatatacta taaatgagat ataaatgata ttttgaaatc  76620
aatatgcaat ttttgttgta tctaataagg acttttaagg atacagtcaa gaaggagaga  76680
tgcaatatta ctgtgtttag ccttactaaa gcaaaggaaa gtactgtacg taaaagttct  76740
ctggcgcggt ggctcatgcc tgtaatccca gcactttggg aggccgaggc gggcagatca  76800
cgaggtcagg agttccagac cagcctggcc aacataatga aacctcgtct ctactaaaaa  76860
tacaaaaatt agttgggcgt ggtggtgtgc acctgtaatt ccagctgctt gggaggcaga  76920
ggcaggagaa ttgcttgaaa ccggaaggca gaggttgcag tgagccaaga tcgtactact  76980
gcactccagc ctgggcaaca agagagaaac tccgtctaaa aaaaaaaaaa aaagttctcc  77040
ggcatttttt gaaaaaggca aactgcactc ataaaatttt acctttggaa cagaatcttt  77100
atagttacat aatcaatgga aagaacagat ttgatgacaa tattgagctt atgaattaat  77160
caaatttgaa gctgctctac acccagaatt attattatta ttattattat tattattatt  77220
ttttgagacg acgtcttact ttgtctcact ttgtcgccca ggctggaatg cagtggcgcg  77280
atcttggctc actgcaacct ccgcctccca gattcaagcg attctcctgc ctcagccttc  77340
cgagtagctg ggattacagg cacctgccag cgtgctcggc taagttttgt atttttagta  77400
gagacgagct ttcttttttt taagacggag tctcgctctg tcgcccaggc tgcagtacag  77460
tggcgtgatc tcggctcact gcaaactctg cttcccgggt tcacgccatt ctcctgtctc  77520
agcctcccga gtagctggga ctacaggcgc ccgccaccat gcccggctaa tttttttgtat  77580
ttttattaga gacggcgttt tgccgtgtta gccaggatgg tctcgatctc ctgaccttgt  77640
gatccgcccg cctcagcctc ccaaagtgct gggattacag gcgtgagcca ccgcgcctgg  77700
ccagagacga gctttcacca tgttagtcaa gctgtcctcg aactcctggc ctcaagccat  77760
ccacccacct cggcctctca aagtgctggg attacaggtg tgagctacca tgcccagttt  77820
atacccagtc ttgttaagtg agatgttaca tctccctctg tttagttcac ttgacgcaag  77880
attctctatt tttttttttt tttttttgag atggagtttc actcttgttg cccagggttg  77940
tagtggcaca atcttggctc attgcaacct ctgcctccca ggttcgagca attctcctgc  78000
ctcagcctcc agagtagctg gaattacagg cgcctgccac caatacaata ctttttttgta  78060
tttttagtag agatagggtt tcactatgtt ggccaggctg gtctcaaact cctgatctca  78120
ggtgatccac ccacctcggc ctcccaaagt gttgagatta taggcataag ccactgcacc  78180
cggcctaaga ttctctatta cttgagaata aaacaacctg ttaaaatatt ataccacagt  78240
gtgcttggcc tatgtaacat ctgcttagat aacatactct cttaagcagt aaatgagtat  78300
gagttacagg ggctctcctt ttgttcttta gggactctag aaatgccaga taattccact  78360
tttgtggtga cagaagaatc tggcaataat agctaccgtt tactgaacaa caactgcaca  78420
ttaagcactg tgtcatatgc tttaggtatg ttatttgatc ctcaccaaat gcctaggtat  78480
tattcctctt ttcttttctt ttcattttct tttctttctt ttctcttttc ttttttattt  78540
tctttctttt taacaaagaa agaaactgag ggggctgggt gtggtggctc aggtgtgtag  78600
tcccagcatt ttgggaagct gaggttggag gatcacttaa ggtcaagaat ttgaggttac  78660
aatgagctat gctagcacca ctgcactcca gcctgggtga caggtgagac tctgtctcta  78720
aaaaataaat aaatttacat ctgttcaaaa gataaatgac cttttaaaca aacaacatgt  78780
agtataaagt ttatgacata caatcataaa aaataattaa taaaaaaaac agccaatgtg  78840
```

-continued

```
acctgatatt tatagaacac tcttaacaat agcagaatac acatttttaa aagtacctgt  78900
agaacattta tcaaaatagg ccatactatt tttctcaata aatttaaaat tatttctgtc  78960
ataaaatata ctttctggcc acaatataat taaattagaa atcaataaaa aggatatcta  79020
gaaaatctcc aaatgtttgg aaaataaaac ttctatatca cacattagtt tcaaaaaaag  79080
aaattggaaa gtgttttgaa ctgtctgaaa attaaaacac aagataataa aacttgtgag  79140
atacaataaa atagtgctag agggagtctt gtagcactaa atgcctatat tagaaaatag  79200
gggcccggcg cggtgtctca tgcctataat cctagcactt tgggaggccg aggcaggtga  79260
tggcttgagc tcaggagttc aagaccaacc tgggcaacat ggtgagaccg cctctctaca  79320
aaaaatacaa aaattagctg ggcagggtgt catgcacttg tggtctccgc tcctcaggag  79380
gctgaggtgg gagggtggct tgagcctggg aggttgaggc tgcactgagg catgttcatg  79440
ccactgcact ccagtctgtg tgacaaagca agaccccgtc tcaacaacaa caacaaaaac  79500
aacaaacaaa caaacaaaaa acgaaattag aaaaagagta agttaaacac agaataaaat  79560
gaagacagga aataattaag attggagcag aaacttatga aatagaaaac aaaaatagca  79620
ggaaatcaat aaagcctaaa gctggttctt tgagaagatc aataaaatta ataaatccct  79680
aggccgggca tggtggctca cgcctgtaat cccagcattt ttggaggccg aggcgggtgg  79740
atcacgaggt cagaaggtga gaccaacctg gctaacacag tgtaacccag tctctaccaa  79800
aaatacaaaa aaattagccg ggcgtggtgg tgggcgcctg tagtcccacc tactcaggag  79860
gctgaggcag gagaatggcg tgaacccagg aggcggagat tgcagtgagc tgagatcatg  79920
ccactgcact ccagcctggg cgacagaatg agactctgtc tcaaaaataa acaaaacaaa  79980
acaaaacaaa aaacaggtta aaagaccggt gtggtggctc atgcctgtaa ttccagcact  80040
ttggaaggct gaggtgggcg gatcacgagg tcaggagttc gagaccaccc tgaccaacat  80100
agtgaaaccc catctctact aaaaatacaa aaaaaattag ctgggcatgg tggcacatgc  80160
ctgtaatccc aggtactcag gaggctgagg caggaggatc acttgaaccc aggaggcaga  80220
ggttgcagtg agccgagatc gtgccactgc actccagcct gggtgacaga gcaagactct  80280
gtcttaaaat aaataaataa ataaataaat aaattaaatt aaattaataa acctctagcc  80340
agactgaaca gaaaaaaagt gaaaggaaac acaaattgca aatatcagga atgaaggaga  80400
taacctacag attctacagc tattaaaata ataattagag aatattatga aaaacttttt  80460
aacaaaaaat tcaacatata taaaatggac aaaccccttg aaaaaaacca aattaccaaa  80520
aattgtacaa gaagagctga cctgagtagt cctatatcta ttttttaaaa ttgaatttgt  80580
agtttaaaac cttcctacaa ggaaaactcc aagcccagat ggcttcagtg gtgaattata  80640
ccaaatgatt aaggagaaat aacagcagtt ctctaccacc tctttcagaa aatggaagcc  80700
aatggaatac ttcccaattc atcctaggat aacagcatta ccctgatacc aaaacctgac  80760
aaagacattc ttagaaaact acagatcagt agtcttcagg aacacaggtg caaaaattct  80820
caaggaaatt ttagcaaatc caacctaaca atatgtaaaa aggacaatgc attaagacca  80880
accggagttt atttcaggca tataagtctt catttcaaag cccaatcaat ataattcact  80940
acattaacat aaaattaaac catatgatta ccccaacaga tccaccaaaa gtgtttgaca  81000
aaatctaaca tccgttccta ataaaaactc agcaaactag gtataggggc cctttgtttg  81060
tctttttctg gtttccaagt ccttgaaaca aaatccaact atgtccaaat gccatgaagg  81120
tttgtgttgc tgctgatgtc agagataaac attactttta aggacaggac ggagtggagt  81180
```

-continued

```
agtagaagca tttagatgag aaaaaagaca aattaacttg tttaattctt cttaagagcc  81240
aaaatgcagg tgtttcttgc acaatgtagt attctttttc tttttacttt cttttttttt  81300
ttcttttttt ttgagatgga gtttcgctct tgtcacccag gctggagtgc aatggcggat  81360
ctcagctcac ttctgcctcc cgggttcaag tgattctcct acctcagcct cccgagtagc  81420
tggtattaca ggcatgcgcc accatgccca gctaattttt gtatttttac tagggacggg  81480
gtttcaccat gttggtcagg atgatctcaa tctcttgacc ttgtgatccg cctgcctcgg  81540
cctcccaaag tgctgggatt acaggcgtga gccaccgtgc ccggcctatt tttctgtagt  81600
cccattttct tgcttcagag ttattcagga gttagcacgg tactacaatt gctatgcaca  81660
gaagctgagg aacatttggt agtgttaaat acctaacatt gacttaaatc tgtacatagg  81720
tagttctaga tatactatgc ttctttactg catcaaccag atggacatta aatggtagaa  81780
ttatgactaa tttgtataaa gcattttata tagtatatat attttattta tttatttatt  81840
tattgagaca gagtctcgct gtgttgccca ggctggagtg cagtggtgcg atcttggctc  81900
actgcaagct ccgctgccct ggttcacacc attctcctgc ctcagcctcc caagtagctg  81960
agactacagg tgtccgctac cacgcccgcc taattttttt gtatttttag tagagatggg  82020
gtttcactgt gttagccagg atggtctcga tctcctgacc tcgtgatccg cccgccttgg  82080
cctcccaaag tgctgggatt acaggcgtga gccactgcgc ccggcctagt ataataattt  82140
ttaaaattag ctttaaatat ttttgagtta aaatcttgat attttaaaat gttgcccatt  82200
aattaatttt tttttttttt ttttttgaga cggagtctcg ctctgtcgcc caggctggag  82260
tgcagtggca cgatctcggc tcagtgcaag ctctgcctcc tgggttcacg ccattctcct  82320
gcctcagcct ccagagtagc tgggactaca ggcgcccgcc accacgcccg gctaattttt  82380
ttgtattttt agtagagacg gggtttcacc gtgttagcca ggttggtctc gatctcctga  82440
ccttgtgatc cacccacctc agcctcccaa agagctggga ttacaggcgt gagccaccac  82500
gcctggccgc ctattaattt ttataagcag tttgctttta atattttaga agaaaatagc  82560
tctttgaata catttaaaac cagttttaac tttttaaatt ttaatacttt atttatttat  82620
ttattgtttg tttgtttgtt tgacagaatg tctcgctctg ttgcccaggc tagagtgcag  82680
tggaacaatc acagctcact gcagcctcaa actcctgggc tcaagccatc ctcccacctc  82740
agcctcccaa gtagctagga ctagaggcat gagtcaccac acccagctaa tttttaaaag  82800
attttttttt tgcagagaca tggtctcact atgttgccca ggctgatctc aaactcctga  82860
cttcaagtga tcctcctgct tcagcctccc aaagcgttgg aggttacagg catcagctac  82920
tatgcgcagg ttttaattta cttttgaata agtatgtgaa attaaataat tcaaacttaa  82980
agctgttgga actttattct gagccttgag aggtgtgtgg ctgtgcagcc tgagtcacat  83040
ggcatgcagc tgcaactttt gccttgtttt tcctttagat aattaagaac aaacagcacc  83100
aaagaccccc acagatcatt acccctcctt atagagtaat aaagtattct ttcttggaat  83160
ttagcaatct gtaaccaatc aaattgctgt ggcatatgca ctagtcttgt atgaaaagag  83220
tcttgctctg tcgcccaggc tgcagggcag tggcagtcat agctcactgc agcctcgaac  83280
ctgccgggct caggtgatcc tcccacctca gccctctgag tagctaggac tacaggcatg  83340
caccactgtg cccagctaaa tgtatttttt gtagagatgg agttttgcca tgttgctcag  83400
cctgtttttg aactgggctc aagcaatcct cccatctcag ccttccaaag tgctgggatt  83460
acaggcgtga gccaccatgc ccggccaaaa ccaactaata ttaacagtat tttgtgtgtc  83520
tctctaaata tatcctatgt gaatgtatgt atgtattctt tcttttgcct ttataaacaa  83580
```

-continued atgatagtat atttttcata acgttctgca ctctgatttt cttctcaatg tatcttggca 83640
gtctttctca gtatatagtg acttttctca tttttttatc tttatacctc aatatctggc 83700
acatagtaag caaatcataa atgctgagtg aatgaaatat taaatgaata aaaaggaaat 83760
ttttgtgctg ctattggaaa ttagctctct atatatttca acatgttaca catatacaat 83820
gatctaaaaa cttgtcttac tctttcctat ccactagagg gagacatcaa cctgttgtgg 83880
aaaagaatga tcacttaaag tctttagaaa ttctgaacca actctctagc aggtgatcct 83940
tgttagaatt tgagccctta acgctatcca ggactggagg ttgaagggac gatagaggga 84000
gcaggaggag aatgcacatg gattaaggag cgagaacaca ggtgaacttc agctttttg 84060
ctaacagtca gacaaactac tgaccctgac tcagtgatgt gctagtaaac cagctcttta 84120
aaaaaaaaaa aaaaagccct agattgctga tttgtatgta atgtttatga atttcagtag 84180
agaaaaagac aatattcaaa ctgagccatg cacccaaaac aagagaacag ccaagaagtg 84240
ttcacttcta tcagtgccct gggttgtttg aaaaaagaag ccgacctgag cacctgtgag 84300
ctcccttctg gcgaggagaa atctggagtg tagttattcc accatggcca aattcaagcc 84360
actcggggtt taatcaccga attgcaaatt ccttgaacat ttaacagtag gctctcttgg 84420
ctgggcgcgg tggctcatgc ctgtaatccc agcaatttgg gaggccatgg caggaggatt 84480
acctgaggtc gggagttgga gaccagcctg gccaacatag tgaaacccca tttctactaa 84540
aaatacaaaa aattagctgg gcgtggtggc aggtgcctgt ggtcccagct actcgggagg 84600
ctgaggcagg agaatcgctt gaacccagga ggcggaggtt gcagtgagcc gagattgtgc 84660
cactgcactc cagcctgggc gacaacagtg aaactccatc tcaaaaaaac aaaacaacaa 84720
taacaacaac agtaggctct cttgagccag cctgagcagg ctcttgcatg ctgctgaagc 84780
ttgtcgggtc ttagttactt ttcctgtaaa gtggggatga taaatctgct cattatgtag 84840
attctattac atagaggaca cataagttct ttgaatgctt aaagcaatgt ttcctaaact 84900
tctttggtca tgaaatcacc cagtggcttg tgtaaaataa acattcccag gacctgccct 84960
agagcacctg ggttagaaca ttttggggga gggggctggg aatctgtatt ttaaataagc 85020
aacccaggtg aggccgggcg cggtgcctca cacctgtaat cccagcactt tgggaggccg 85080
aggcgggtgg atcacgagat caagagattg agaccatcct ggctaacacg gtgaaattcc 85140
atctctacta aaaatacaaa agaattagcc gggcatggtg gcaggagcct gtagtcccag 85200
ctatttggga ggccgaggca ggagaatggc atgaacccgg gagacagagc ttgcagtgag 85260
ccgagattgc gccactgcac tccagcctgg gcgacagagc gagactgtct caaaaaataa 85320
ataaataaat aaataaataa ataaataaat aaataaataa aaataaaaaa taaaaaagtg 85380
acccaggtga ctcttatgac cctgtgaaat gggagaaaca ctgctgcaaa ttactcttat 85440
aattgggtca ggtgtcaggg gtctttctct aacttcacaa ttgggcctgc ttgaagagat 85500
gtgtgcagag ttccacaaca cactccaggc aggcatttaa tccgttcact gtcttctcta 85560
ccctcagagc ccaaacttcc caaagaggaa aacctgctcc ttgccatctc ttaggccaag 85620
gcttctgtac acctgggaag tccttcaatc tgaggatctc tgggttgttt tcaagctact 85680
atttattgag aatttacaaa gtgtcaggca cgttacagca atttgtcatt tctatgaaat 85740
agcttcttgt gctattccca ttttacagag aaaaatcaaa gaagttggga aaatgtcgaa 85800
gggcacacaa ctaggaagtg tttgtgctga aaacccaccc taggcccaag ccttggaact 85860
ccaagcctgg gttccatccc tgcactgggc aattctgatc tatgtgcgct agtttccttg 85920

-continued

```
tgttctctgt tctctccata gaaatcctgg gctctcttct cccagccaca aggttaggtt  85980
gaaaaacaga gcagatggag gtagtttgta gcctacaggt gccctgaatg aagcttccac  86040
agtgctaaag tggaagaacg agggactcca agggaaggat tcaaggctgg gcccatgcac  86100
ctgtgtaatt cagaagagac cccagaggag atcagcgccc tctaattagc cctggtaagg  86160
agctctggga gttactgtaa ctctctcaga agaacccaaa catgcgggaa cgtgacttct  86220
taccttctga aagtccacaa aattcctgat tgccaccatt aatttgtcac ttatcatttg  86280
caacaggcat tgtaggttgt cttatgcatt tgtcttctcc cttcagctag tgtataaagt  86340
cttagggaga ccagcagttc agagagaatg ggctttggtg tgaaacagat ctggtttgaa  86400
ccctctgcta cttactagct gttgggcaag ttccttaaat tctctgagtc ttaatcttct  86460
catctgtaaa atggagacat aaggagtacc cacctcattg gattgtttta aggataaaat  86520
taaatagtgc aggcaaagga tttacaagca actgctgaat gaatggtagt tatagcctcc  86580
tcctcatcat ctgtgagcaa acaccctcat atttccttgt gtctcaggta gacacttaag  86640
gtattgcaag cattaaggga gcattgtcac aaagagataa atgcatgagg gcaagatgca  86700
gtctcaaaga agagtgtttt atgaaagaat aaatgtaatg ctgagtgtca gaaaaaaatt  86760
ttttttttta aagatgaggt atctatcacc caggctgaag tgcagtggtg tgatcttagc  86820
tcactgaagc ctcaacctcc caggctcaag tgatcctcca gcctcagcct cccgagtagc  86880
tgggactaca ggtgccacca cacctggtta attgttgtat tttttgtaga gatgggtttt  86940
cgccatgttg tccaggctgg tcttgaactc ctgggctcga gcgatcctct catcttggcc  87000
tcccaaagtg ctgggattgc aggcatgagc caccacaccc agcctgtcag aaaaatttta  87060
aggtgaaaat aactaaagaa gttgttaaga attttctccc ttgagtggta ttttagactg  87120
agatgaggga gggtagaggt aggatgagaa ggaagggatg gggtccggtt gaaaggcctg  87180
tgagatagta gcagtgcaat atggcagatg ttgacagcct cagtgctagg aacacagaaa  87240
ctgaatctct tgcaaggagg caggtgtgca tctgtatgga agtcagatga cctgtgttcc  87300
tatgagtgca aatctggaaa acaccctcaa gtttccttgt cagcaaattg gtgataaaat  87360
caacattgta gggttggtgt gaacatgcag catgatgtgg ccatgcaagt tctttgttaa  87420
ctagaagcca gtgtcatgcc aggacagcag tcctcctagt aagctgtggc tggtggcgtg  87480
gtagaatacg tggagcaggc tgaggaagca cttgacttga ctatgagcag aaccattaag  87540
aagctagtta gctaaactgc ctggacagta gaaaaataat atgtgaggat gtaaaaggaa  87600
gagaaacaat gtgaggggag aggagaatgc agagatcctg gcccatggaa cagcattggt  87660
gatccttaag tagctgcatg aactacttgg agaagttcat tttctgttta taattcccag  87720
caaaggagag gactgaataa gagagaagaa aacgattcct ttctctggtt aggttcatca  87780
gatcaaacgg tgacatatgt gaaagaagca cgctctgtgc acaaaaaatc aagtctgtat  87840
ttttataaaa gccatttctg ggctgggcgc ggtggctgac gcctgtaatc ccagcacttt  87900
gggaggcgga ggcgggtgga tcaggaggcc aggagatcga gaccatcctg gctaccacgg  87960
tgaaaccctg tctctactaa aaaaatacaa aaaaattagc cgggtgtggt ggtgggtgcc  88020
tgtagtctca gctacttggg gggctgaggc ggaagattgt gccactgcac tctagcctgg  88080
gcgacagagc gagactccgt ctcaaaaaaa aaaaaaaaaa agctatttct gtaatgagca  88140
tcactggaga gttagttgct atgggtctaa aggacaatat gaggcagtta tagtaacttt  88200
ccatgatatg aacaaagaaa ttgaaaatgt tagatacatt tacaagaaga tgtagaaaaa  88260
actttagtca aaatttttga aatatttttt gaaatattaa actatgaaat cagacagtct  88320
```

-continued

```
tatctatggt ctcaagccat gtctgtctgt accttttttt tttttatctc atttcaggga  88380
atattacact ggctgactta ttaatatctt ctgagccaga aaatgtaagg aagctgcatt  88440
ttcagaattg catttgagtc atttgtgaaa ttgcatatta caatttgccg ccatttctaa  88500
cagtcctata actttttttt ttttttttct taactgggtg ttcacattca tgccaatgac  88560
ctctaggggc tagtttctct tctagctcaa gagaattgct gcagagttgg aagtaaggac  88620
aaaaatgtgt atgcttcatg tttgatttca aatgcataga aaattagaaa cttaaggtat  88680
gcaagggatt tgtgtggaat ttaagtacct ttgaggggca gtggacagga caaaaagtta  88740
ttttttacct gtttgtttac aaatagcaaa gatcaagact gaaacacatg agtgtgattt  88800
agaaagagtt ggctgcaggt gctgcttgct caggtggttc atttaaactg caggtcagag  88860
caaccttgtc tcatggtcct ggtgcccagg tatcaggttg ggtctgtctt gctgcttatg  88920
tccttgttac cctctgaggg ccccagtcca acgcagatca ataaagaata agttacataa  88980
atatgctcat aggtggtcat tcctagacaa gaaattgaca acatttcatt caacagtatc  89040
tgggctctac aggacagaca tgcctccatt tatgcaacaa ataagaacag catctcatga  89100
cagtggagaa aacatgggat gtgcaggtag gtaggtaaag ttgggtggaa actttcaccc  89160
taccaaatgc acatgggtga ctttataaaa taaatgttag ctctctgagc ctcagttttc  89220
ccatctgtaa aatagacagt cccagggaat tttcaaggat taaatgaaat aaaagtgaat  89280
caacctatgc aagcctgcct actgtggtgt ccaggctaga aaaatgctca ataaatatta  89340
ggtttgtttt tatttctaca aaagatgtga tcctaaagag ctctatccaa attcaagttt  89400
caaatgtcaa atcacatttt gtgaacttta tgttcagttg agatgatctc tgacatatta  89460
attagtaatc ctatcttttt cattcatcac caccaaaaaa aggtgttatt gcacgttcaa  89520
ttaatctttc ccctttatta attccataag tgtagggttt tatctctcag attctcttaa  89580
aacagaccaa tttataccca cataatataa ataagcttgt tcctataaca ctctggagca  89640
gataactatc ccagaaccca aatcctccta cttggcttca agctcagaga ataaagcaac  89700
aatccaaagg caccctttgg catgacaccc ttctagacat ctgtagcatt cctcctttcc  89760
ctccactttt cctattagct tttgctttct tgccttttac agggttttgt tttgcctctt  89820
ggtagtttct ttcctacgga aaattctccc tctgatcttt ccaagtcaaa ggcttcagca  89880
aacatttgtt gaacgcgtgg attgtgctag gtgggtgtta tggaccatgg agaatgctag  89940
agatgtaaga catgcgctgt ccaatcgcag cgcaggttgt gttgacaggt aagatgaggg  90000
ctgtagggga gccaatgtgc acgttccact gggctaatgt gctcttcacc ttatttaggc  90060
tcttggcttt gggatgtgta agactttgct agacagagaa ggggtggggt gagaagatga  90120
ggaaggtgca ccttttatgg agaggctttc cttcctcttc acagcaaacc atacctgtac  90180
tacattgact tcctttgctt tcccaggtga catctagctc atgctgcaag ctcatcttgt  90240
taatcataaa tgctagtaag ttaatattac ccatcatata taacatgact taattttaac  90300
aattcaatgc tttatcccca aaagatgact taatggtgac aatttcaatc cccattgtag  90360
gatattttgg agacaggcag tcctttcaat gtcatatgtg ggtgcttcct taggcaggtc  90420
aggggtgagg tggaaatgag gctgggaccc tgctcactta tatagcaggc atcgttctca  90480
ataccaggct tcagggggct ttttggtcta gccattggta tgaactgcct caagaataat  90540
cccttcatca ttgtggtcac aattcaggta gaattggaat aatcaccctc tccactctgc  90600
attaaaccag gcaaagtttc catctctggg taccattgtc tttcttgatg gacagggtga  90660
```

-continued

```
gtcagaagga aacttactca ctcccattca ttttctgctt attatttcct gcagtgaggt  90720
ttccttgtat aataaacagc ttctgtgggt gtttgagctg ctctgaaaag agaacatgct  90780
gttcctgtgt gtagaatgcc ttctgaagga agcatcacag tgaacacaga gcagaagctt  90840
ggcacacagg tggcagaagt ttgtctgcag tgttctgcat agagcagaga gtcaagccat  90900
tttcattctg attgattgga ggcatggtat ggaggtaaat gggtccttgg cctctctcct  90960
ggattcaagt ccttcttagc cactgatagg tcatgtgacc atagggaggt tgtttaacct  91020
tcctgaacat tcattttctc aagtataaaa tgggggtaat agaatttgcc ttataggctt  91080
gcgtataaaa taagaattat tgagagaaag cggggcataa atgtccaata agcggtagct  91140
gtctatgaag ccactgttgt tactgggttc ctttctcact aggtggcttc aggtagctga  91200
cagaagctct gtgagcctca atttcctcac tggaaaagtg gagtcaatat ctcactgagc  91260
tggtgtgagg attaaatgag atgctgtgca ggtgcttagc acagcgtcag gtatgatgtt  91320
aatattgata gatgcatttt cttcaccctc acctatcttt ttctgcctgt tggcttatgg  91380
ttgaaattcc ttcatgacgg tttccatttc cagagatatc ttgttaacaa gtatatacca  91440
ccaaatgaag ctgatttttt tttttttttt tttttttgag acagagtctc gctctgtcgc  91500
ccaggctgga atgcagtggc gcgatcttgg ctcactgcaa cctccgcctc ccatgttcaa  91560
gcgattctcc tgcctcagcc tcctgagtag ctgggattac tggcatgtgc caccacgtcc  91620
agccaatttt tgtattttta gtagagacga ggtttcacca tgttggtcag gctggtctca  91680
aactcctgac ctcgtgatcc acctgcctcg gcctcccaaa gtgctgagat tataggtgtg  91740
agccaccatg cctggccatg aagctgattt ttttaaacca tcatttaaca ttttctccat  91800
aaggtggcaa ggaggaagag catatgggga ctgggtactt tgagagaccc caggacagga  91860
gacagggagg ctgagattgg catgttgtct gctgcagtta tttgccagcg acacactctt  91920
cccgtccaaa ctaacttctc tgcctcaagg acagggagac tctgcctttc aacctgagag  91980
aaaccaggac tctcagcttt aatgaaaatt ggacttaggg tggggcagtg gagacttttc  92040
acagctattg tttagctgat gaagcagatg cttctccatc tttggagcct gtcttcatta  92100
cctgtggacc tcatctttat caacccagag cacacttgcg tctctctatt ttggctaaac  92160
accaaacagc tgaggctggt actgtaaaac tttccctcca aatgcccccc ctcgtcttcc  92220
tctattagag atctggatca caaccctcaa aaaccatgtc ccttatgcca cctgagtaga  92280
tggtttgatg attaattagg cacagatgtg acactggggg gttctcacaa tggcctgtgg  92340
gtcacatgct actttccttt tcattttcat cagcaacagc tgccttaaag ccagttaaga  92400
ctgtggtcct agtctcgcac cctggggctc ctgctggggt gggtgagggg aacaccccat  92460
taagctgggg gaactggggc tgccaccagg gggcgcgagg ggccttcgcc cgagaagagg  92520
ggtgggcagg tgcctccagc ggagaagggc gccgtggccg gaggcacagg tctccccggt  92580
gccacttcaa gtgagttcga ggaagtacct gggatctttg atctaacgcg aaaggccttc  92640
ccagtgacct cttgagagct gagaacccac tccctccacc tctagtccac ggctttgcca  92700
ctccagggcc cgaggttacg tttgctgctg gggatttgac aaacccaaag cctctctggt  92760
ttcaccactg gctccttaga atcagacatc tgttctgaat gacacttatg tgagtcaggg  92820
gctgaggacg tgatcctcga agtgtggtcc ccagactggc tgtatcagtg tcggcatccc  92880
ccaggacctg gttggaaatg catattctca ggccctactc cagacctctt aaatctgaga  92940
ctggggctgc ggggagcgcc atctgtgcgc cactatcctt gtgggtggac caggagtcgg  93000
ttcgagggtg ctcccactta gaggtcacgc gcggcgtcgg gcgttcctga gaccgtcggg  93060
```

-continued

```
ctccctggct cggtcacgtg ggctcaggca ctactcccct ctaccctcct ctcggtcttt  93120
aaaaggaaga aggggcttat cgttaagtcg cttgtgatct tttcagtttc tccagctgct  93180
ggctttttgg acacccactc ccccgccagg aggcagttgc aagcgcggag gctgcgagaa  93240
ataactgcct cttgaaactt gcagggcgaa gagcaggcgg cgagcgctgg gccggggagg  93300
gaccacccga gctgcgacgg gctctggggc tgcggggcag ggctggcgcc cggagcctga  93360
gctgcaggag gtgcgctcgc tttcctcaac aggtggcggc ggggcgcgcg ccgggagacc  93420
ccccctaatg cgggaaaagc acgtgtccgc attttagaga aggcaaggcc ggtgtgttta  93480
tctgcaaggt aagcgcccct tcgctcgagg tgtggtttaa ttgtctcatt ttgtttgaaa  93540
tcctgcggtg agaaaccagt cgtgttgaga acaataaaag accaaaaaac gatcaccaaa  93600
accaactgtc ctgaaagcta ctggaaagtt ggaaaatgca tgctttgatt aaatgtcttc  93660
attcaagaca ctggcaagtt aacttattta gtttgtgccg tgagctctgg gttgattgtg  93720
ctaatatgaa taactgaaaa acattttatt tccctatggt tttcctcgat ggacttcccc  93780
actatgggtg aaatgacaat ggagttgaat acactttctg attgaacttt gagggcctgg  93840
gaagatgtac acgtctcagg caagatgata ggggttttaa aatgtattaa ttggcattcc  93900
ttagccatgt cagcaagctg cgttcctcct ttcctgggca gaccaagcta agctctaact  93960
ggtctccttt atttgctgaa gaggagtcca acaactgccc tctaacaccc tgcgtgttat  94020
tcttattgga aggacaatat taagtcaagt gaatgtcatt tttgtgaaaa aactttgagt  94080
ggacttctat ttaggaagat aaggttgatt taattttact cgctgtttaa aaagcaggat  94140
tgtgttttgg tgtggtaggc aacattttgg aggacagact ttgccttatt ttgttatatt  94200
tctagtattt acatgggcat tccattagaa agttttactt ttgctctaag tttcgtaact  94260
cggtgtctag tgaggggaaa catgtttgta atttaaaaag tgaacatgtg aaaggaaagg  94320
cttttctgag agtgttgtaa aacaaatgta acgtgactat gaaaagaaca tgattaacat  94380
ctttgactcc tatttttttct gaagaaaatg tattttgata tgagttctag aagaaggaaa  94440
ctataaggat ctgttcatca acaggcatta gagtatacac cgtaggattg cattttacgt  94500
tcaagcattt ttttagatga atttctgaaa cattcttatt ttaaaagcca tcagatgctt  94560
gttaacactt aagtcttgct caagacatag aagtttctga aatcaattaa catgtttagg  94620
acacatttcg tagtgttctg agggatgtga ataaatctaa tcacagttta catttcttaa  94680
tgtatttata attcagaaaa ggtagaattt agtagtaaat tcaactcata accatataat  94740
taacatttaa tagatattga tatgttcact tttaagaata agaaggaaat tttctataag  94800
tgtatgttga acacataata attcaaaatt catgtgataa ttttaggtga tgctttgagt  94860
cgttttatag aatataaata tggataaaat ataaaatact gaaggctgaa ctcaaagtgt  94920
ttaatgataa gtttttgata atacatctag aaaccttgag aattgtatgc ttgaacgtta  94980
gatttcataa ttcagtgtct agcacattgt tttatatgca atagcacttt aaaaaaatta  95040
ggctacagca gtataattta catacagtaa aatttagcct ctgtaaatgt acctctatga  95100
attctgacag atgcacagtc atgtaaccag caccgcacac atgacacaga acagttccat  95160
taccccaaaa gtcccctttg tacctctacc taccccactg cccctgaaaa tcactgatca  95220
aaactacata atgattatgt ggttttgctc tttagtacgt ttttacttag acatattttc  95280
ctttacttct tttgaaagaa aaacctgttt ttccctttttt ataggatgag tcagtttgtg  95340
ctatttttaa ttctagtacc ttgggataaa tcaaggcaaa gacaatgcta tttgcaaatg  95400
```

-continued

```
ggaaacttga gacttggact aagtgttaaa ttcatatagg gctaatagat ttagttctta  95460
gcagatttag attctattgt ggtttaagcc tttggttatg gcatatatca ttagttatcc  95520
tgaattgaaa tacaaggcca ttaaaagtta tttatatcat attaatagaa tgcatcattc  95580
ttttataatc tttgaatttt aaaacttctt tattaaaaaa aaaactactt ttcattatac  95640
ctgagattaa gaaagctacc tgaaattgca tattatcaaa tagtgagaag caaaacaggg  95700
attgaaaatg acaaattgaa gacatttaaa atgcagagtg attacaattg ctgaaggtaa  95760
aatatttatc ttcatagggg cttaggtctg tgtccaactt atttgtagat gtcaggattt  95820
ttaaatttct gtgctcatgt cttgaagtct agattttcct gcagggtgga gatgtataac  95880
cttttgtaaa ctaatatttt tcactgttta acacagtatt caattcagta tacagttagg  95940
agcctgttat tggtaggtac tgctaacata tatatatata aaattgatgt ctttttcctt  96000
tttcctttgt tctatgaaaa acagcctgta ttttaaatat gtaacttacc ttgcataccc  96060
agttacagtg gtagtaacta ggatatgcag agtggcaagt ttatgaggag ctagcaaact  96120
ggatagttgg ccttcctagc tggaattatg acaggtcttg aaaatgaagg gcttttagtg  96180
gagaatcttt gtgtgggtgt acttgagaga gggcaggaga gttagggtga cctagaaaga  96240
tagattgctg gacttgtata tgtttcctca aagccagact gcagcatttt gttagtaaat  96300
tgttgtgtgt tctactgtca aacccaggcc tggaagggga gttgagtgca ttcagcctaa  96360
cttctggatt ggctgtgtca tcttgaatcc cttcactcgg aattctctct gaccctgtcc  96420
caaatgaata tttgaatttg gtccagttcc tacagagcat ggtctgtggc tgttgttggt  96480
gttagggaag agcagaaact tgctgttgag agagaagaca cttgagaaga ctgatgaact  96540
ctctcccacc cctgccttcg aggcttggtc ctcctaccct attcaaaccc ttgaaactct  96600
ttcctatcca actaaataag cgccaattgg ttactaggag aattagcttt tcctcatttt  96660
agaaggaaac agggtttcct tatgtacatg ttcttaagaa ttacatgcaa atcagttatt  96720
aatgatgagt tctctggtga ttttggagtg ttttatcttc ctaatattaa attaattgag  96780
ggccttaata ttttgttttg aaagaatata tttaaaaagg ctgggtgtgg tggctcacgc  96840
ctgtaatctc agcactttgg gaggcctagg tggctggatc acttgagggc aggagttcaa  96900
gaccagcctg gccaaataat gaaaccttgt ctctgttaag aatacaaaaa attagctggc  96960
catggtggct caagcctgta gtcccagcta ctcaggaggc tgaggcatga gaattgcttg  97020
aacctgggag gccgagttta cagtgagccg cgatcatgcc actgcattcc agcctgggca  97080
acaaagcaag actctatctc taaataaata aataaataaa taaataagaa tacatttaaa  97140
gataataatt ggccaggtgt ggtggttcat gcctgtgatc acagcacttt gggaggccga  97200
ggtgggagga ttgcttgagg caaggagttc aagatcaatc tgggcaacac agtgagaccc  97260
tatctctaca aaaatttaaa aatcagctgg gcatgatggt gcatgccttt agtcccagct  97320
acttgggggg ctgagtttgg aggatccctt gagcccagga gatcaaggct gcagtaggcc  97380
atgatcttgc cactacactc tagcctgagt tacagagcta gagtataacc ccccaccccc  97440
aaaaaagcta ataattgtca aacagctact tatgcacatc aaggatgctt gttgcttaag  97500
aaatcttttt aaatcttttc catgaaattc cttctagttg ctgctttgtg agcgtgaatt  97560
ttttacttct gcaggacaca caaatgtgga gcatttgaac tgaatgcttg ggaaagtgtg  97620
atgggcaggt ggaagaagaa tagggatgag gacttatcct ctattcttat cctcctagac  97680
ttatcctcct agtctgcaag cttgagaata tggcatcagg aatatgtggc attttgtcca  97740
cacacacagt gttggcaggc taccagcagc ccagctatct ggactagggg tgatggattt  97800
```

-continued

```
ctgtggacag aagtcaaaaa gtaaaattag gaggcaaaaa tcttcagggt ggccataaag  97860
acattgtaac ttgtctggaa attccaacca acactaaatg tgtatccagt gatataccaa  97920
tagactggct tcatcttctt ggatgtgtaa taatacctta cagaatgctt tctttttttt  97980
tttctttttc tttttcttta ttttttttga aatgaagttt tgctcttgtt gcccaggctg  98040
gagtgtaatg gcacaatctc agctcactgc aacctccacc tcccaggttc aagcgattgt  98100
cctgcctcat cctcccgagt agctgggatt acaggcatgt gccaccatgc ccggctaatt  98160
ttgtattttt agtagagacg gggtttctcc atgttggtta ggctggtctc aaactcccga  98220
cctcaggtga tctgcccacc ttggcctccc aaagtgctgg ggttacaggc gtgagccact  98280
gcgcccggcc tcagaatcct ttcacagaca tcatctcatt tcaccctcag agcaccgtga  98340
aaaggtacag caccaaatag gtacctgatt ctactgaaga agatgtggca gctcagggag  98400
tttgtggatt tgtctaagat tgcctggctt tcaggcagag ctggggctag aatgaatgtt  98460
ctgctctatc cattgataga atatacataa gaacaggctt gatggtggct gaccttttt   98520
tttttttttt ttttgagaca gagttttgct cttgtcacct aggttggagt gcagtggcgt  98580
gatctcggct caccgcaacc tccacctcct gggttcaagc gattctcctg cctcagcctt  98640
ctgagtagct gggtttacag gcaagcgctg ccacacccgg ctaattttgt atttttagta  98700
gagactgggt ttctccatgt tggccaggct ggtcccgaac tcctgatttc aggtgatctg  98760
cccaccttgg cctctcaaag tgctgggatt acaggcatga gccacccgcg cccgggtgac  98820
tgatttctta ttaactagat ttacaggtgc tttgataaaa accagtctag tcttggctgg  98880
cacggtggct catgcctgta atcccagcac tttgggagcc caaggcgggc gggtcacgag  98940
gtcaagagat caagaccatc ctggctaaca tggtgaaacc ccgtctctac taaaaaatag  99000
aaaaaattag ctgggcatgg tggcgggcac ctgtagtccc agctacttga gaggctgagg  99060
caggagaatg gctgaacccg ggaggtggag cttgcagtga gccaagattg caccactgca  99120
ctccagcctg ggcaacagag caagactcca tctcaaaaaa aaaaaaaaaa aagtgtagtc  99180
tttttggagt gtttttctgc catttctagg gccaaacttt ttcttgtcca tgaatcattg  99240
tcaaaattgg gaattttaaa tactactttt ttcttttaat tcaaaagcca tagtatgttt  99300
cccagccagt acattagaac accatgcacg atcccatgtg tacaaaaagc tttctggctg  99360
aattcagatg tgacctgaga gggccaaata caggggtgtg tgctgggaga gagagagagg  99420
tctctggaca gaaaacaaag cctgttcacc acccaggata tggaccaact attttaggtt  99480
atggtgacta aagaaaattg acatgcaaat aaatgaataa ttcttagaat caggatgtct  99540
gggtactggt tctttggttg gccaggtgaa attccatgcc aggcccaaca attaaactct  99600
ttagagacaa ttttttcctg ttgtaccaga acattgtact gaggccatgt ttgaacattc  99660
aatcgatgtg ttgggaaaac tctgccctac aatgttaaag aaattaaatc ttttggggag  99720
tctttccttt gaccagttta tatctctgtt ttagaggagg gcttctcaac cagaatgggt  99780
ttgttgactt atttttacag acctctggta gaaaggaggt cttttttgc tacctgttct   99840
cctgtctcag agaactatta caatggtgta agttcatcat ttcttcccct tattatggct  99900
ctgcttagga agaaaaactc tttgcattgg ctaccaagta cctaactatt caagatgcca  99960
ctgacaaaga gttaatctgt gaatcatgtg aatctgatat atctgaaata tatccaaaca 100020
aaaagcacct agccttttaa tgactctcca gaagtcagtt ctctaacttt aattatcatc 100080
cttctgggga tatgtggaaa ttctacagaa gttgattggt gatatgttga gatgtgagat 100140
```

-continued

```
ctgtattttc taagcaaagt tgccatgcac ctgattgatt ggctaggtgt atcctggcat 100200
ttgtcatttg ttggtggggt ctgatagttg gtttcaccac tgctgggtac ccagagtcat 100260
cacatccata gagacagaat gtaggctggt ggttgccagg ggctgggga agggaggagt 100320
ggggaatttg tttaacagag agttttagtt ttgcaagatg aaatgagttc tagagattgg 100380
ttgcacaata atgtgaatat ccttaacact actgaacttt atacttagaa atggctaaga 100440
tggtaagttt tatgttacat gtattttaac acaattaaaa aagaaaaaaa aaaaaacaac 100500
ttcaggccag gcacggtgac tcacacctgt aatcccagca ctttgggagg ctaaggcggg 100560
cagatcactt gaggtcagga gttcaagacc agcctggcca acatggtgaa accccatctc 100620
tactaaaaat acaaaaatta gcctggccta attgtgcatg cttataatcc cagctaattg 100680
tgaggctgag gcaggggaat cgcctcaaac cctggaggtg gaggttgcaa tgagccgaga 100740
tcacaccact gcactctcca gcctgggtga cagagtgaga tttcatttca aaacaaaaaa 100800
ccactttaga aactgctagt tttggcaata gttatcacta tatgttttat cctgcatatt 100860
ttctgttaag aataaggaat tgtttatgtt gatcaggaat ctaagtaatt aaaatacaaa 100920
attctggctg gtggctctcg cttgtaatcc cagcactttg ggaggccaag gcgggtggat 100980
catttgaggt cggaagttca agaccaggct ggtcaacatg gtgaaacccc atctctacta 101040
aaagtacaaa aaattagctg ggcatggtgg taggcacctg taatcccagc tactagggag 101100
gctgaggcag gagaagcact tgaagtcaag aggcggaggt tgcagtgagc caagattgta 101160
ccactgcact ccagcctggg tgacacagcg aaactccatg taaaaaaaaa atgaaatata 101220
aaattccata ctcattatta attacatata gtattaaaat aaaacccaaa caccaaacct 101280
tccttgatcc tatatccttc tccagctacc attctctctc ctctccttgg tccaaatttt 101340
tgatttacaa tgttggttgg aagtggtacc actttggtgt tagttcctta tcattttacc 101400
tggtctgtcc tgcctcttcc tggtacatta gctccctgaa ggcagggtgt atgtcccaga 101460
actccttgaa gtccctttc tcagcatact accatgccta ctgcagcacc ccccatcttt 101520
aatgtccttg acttggtgaa atattacatt ttgaacacat ttcctcactt ccttatgaca 101580
aatattgatt gagtttcagt gcaaggtgag taagaaatgg tacttgcttt caaggagcta 101640
aaaatctgaa tttcctttt tttttctttt tctttttctt tttttttttt ttttgagaca 101700
gagtctcact ctgtcacctg ggctggagtg cagtggcacg atctcagctt aatgcagcct 101760
ccgcctccca gattcagtga ttctcatgtc ttagcctctc gagtagctgg gactacaggc 101820
atgcaccacc acgcctggct aacttttgta tttttagtga agatggtgtt tcaccatctt 101880
ggccaggctg gcctcaaact cttgacctca tgtgatccac ccacctcggc ctcccaaagt 101940
gctgagatta caggcattga ctttacttct tactctccta tgcacctcta tcattttgaa 102000
gaagggttca aggtagttct gataagcagg attaggtttg tatgtaagtg attaaagggg 102060
tgctatgagc aaaaaaagtg tgaaggtata acaagccaac cacctcacaa tgcagtttgc 102120
atgtttctta atggacatag caggttttct gtaagaaaac agcaggagat tcgtgtggaa 102180
tgatgggttg aggcaacata gtggcatccc ttgaatgctc gaagaatgtg acttagagtt 102240
tggtgggaag cagagagctg ggttttaaga acatgaatct gacaactcta tggatctgga 102300
ggagaagcta actggggacg aggagcagta agaagcctgt tacagatgca ctgataagaa 102360
gtaatgagag ctggccgggc acagtggctc acgcctgtaa tcccagcact ttgggaggcc 102420
gaggcgggca aatcacaagg tcaggatttc aagacgagcc tggccaacat ggtgaaacgc 102480
cgtctctact aaaaatacaa aaagttagct gggcgtggtg gcgggcgcct ataatcccag 102540
```

-continued

```
ctactcggga tgctgaggca gaagaatcgc ttgaacctgg aaggtggagg ttgcagtgag 102600
ccgagattgc gccactgcac tccagcctgg gtgacagtgc gagactccgt ctcaaaaaaa 102660
aaaaaaaaaa gtaatgcgat aatgagagct tacttcaaga tggcagcaaa agacagtgga 102720
aaaaaggcat tgggaaaaaa agccaatgtg ccttgatgag taaagttaac tgagtcaagg 102780
ggagaagtca aaggtaacta tgatgggctt tttctattaa cacaaatagg aaatgagtgg 102840
ttttgggaaa gaaagtgatg aattacccct cagatattgt attaattgtc tattactgtg 102900
gccgggcatg gtagctcatg cctgtaatcc cagcactttg ggaggccgaa acaggcagat 102960
cacttgaggt caggagttcg agaccagcct ggccaacacg gtgaaaccct gtctctacta 103020
aaaatacaaa aattagtgtg gtggtgtatg cctgtaatcc cagctactca ggaggctgag 103080
acatgataat tgcttgaacc tgggaggcag agattgcagt gagctgatat ggcgccattg 103140
cactccagcc taggcaacaa gagtgaaact ccatctcaaa aaaaaagatt tgcctgtaat 103200
cagccagcac ccccagcctt gtgctcactt tacatacaaa aattctgttt tttagagcat 103260
aaattgaagg gcacattcaa aactgatacg taggccaggc atggtgactt atgcctgtaa 103320
tcccagcact ttgggagacc gaggcaggtg gatcactcga gatcaggagt ttgagaccag 103380
cctggccaac gtggtgaaac cccatcccta ctaaaaaata caacaaatta gccagtcaca 103440
gtggtgcgca cccatagtct cagctactcg tgaggctgag gcaggagaat cactagaacc 103500
tgggaggcag gaggttgcag tgagccgaga tcatgccact gcactccagc ctgggtgaca 103560
gagtgagacc ttgtctcaaa aacaaagaca aaaccaaaac aaaacaaaac tgagaagcaa 103620
cagattgata agtgacacag ttacactggt cagtctcttc agctaatacc cattgttttt 103680
tattattgga gattcataat gtgttttctt tcttttaaaa acttttttcg gaaatggtaa 103740
tttctctctt tttttttttt tttttttttt tttgagacag ggtctcactc tatcacccag 103800
gctggagcgc ggtggcacaa tctctgctca ctacaacctc tgcctcctgg gcttgagcaa 103860
tcacacctca gcctcttgag tagctgggac aacaggcaca tgccaccatt cctggctaat 103920
ttttagtaga gacggggttt caccatgttg cccaggctgg tctcgaactc ctgacctcaa 103980
gtaatctgcc cacctcagcc tcccaaagta ttgggattac aggcgtgagc cactacgctt 104040
ggcctcatag cgtattttaa tattggttga gactagcctt gctcattgat cttctcttag 104100
cgtttacttg gttattcttg cttatttttc cataagaact ttcattttta tttaatcctg 104160
tgtttttttgg ttttaaagac tattttataa taaattttcg tgattaaact cttgtgctta 104220
aactcttgat taaacaaaca agcaatgaag agatgaatga agcagaaaat gtgagtttca 104280
tgcctcacat tcccactcct ctgaggttaa tattttcatg tatatttttc aggatgtatt 104340
tgtaatctca tacaaacgta tgtatttttt taatgaaaat atttaaattt tcatagttaa 104400
cagctgtagc tctaacttgg caatatcttc tgtgtttctt tacagccatt atacttgccc 104460
acgaatcttt gagaacatta taatgacctt tgtgcctctt cttgcaaggt gttttctcag 104520
ctgttatctc aagacatgga tataaaaaac tcaccatcta gccttaattc tccttcctcc 104580
tacaactgca gtcaatccat cttacccctg gagcacggct ccatatacat accttcctcc 104640
tatgtagaca gccaccatga atatccagcc atgacattct atagccctgc tgtgatgaat 104700
tacagcattc ccagcaatgt cactaacttg gaaggtgggc ctggtcggca gaccacaagc 104760
ccaaatgtgt tgtggccaac acctgggcac ctttctcctt tagtggtcca tcgccagtta 104820
tcacatctgt atgcggaacc tcaaaagagt ccctggtgtg aagcaagatc gctagaacac 104880
```

-continued

```
accttacctg taaacaggta agtccagtct tcattctgaa ttatagttgc tagccatttc 104940
tcaaatcact ttatggttga gtgagaagga aataatatgt tagacaaggt ctttattgta 105000
ttaattacat agtttactta cagcacccaa aacacaggat gccctgttct attctgatat 105060
tttagttctc attaaaaact ggtatgtgta catcagtgtt gtggggagaa tttgctatca 105120
tgactattgt ctttatacag taaatactga acttaagtca ctccttttct ttttttgaga 105180
cagggtctcg ctctgtcact cagactggag tataatggca cgattgcggc tcactgcaac 105240
cttcacctcc tgggttcaag caattctcgt gccttagtct cccgagtagc tgggattaca 105300
ggcgcgtgcc accacgccca gctcattttt taaattttta gtagagacag ggtttcacca 105360
tgttggctag gctggtcttg aactcctgac ctcaaatgat ccacctgcct tggcctccca 105420
aagtgctggg attacagacg tgatgaacac tgtgcctggt ctgaacttaa gtcactctta 105480
atggagttat ttggatttga aaaatgaatt tttactttac tttcagtttc aaagtcttct 105540
tatagtgaaa ccacaattta atgttcatga caaattgttt ccaggataaa agtaactgtg 105600
atagtattac aacttaaatg aaattctaga catgcgaagc atgaaaagat agatgattgg 105660
tataagcttt ttaaccatga actaaaataa taacattata taaagattgg tggaaactat 105720
tgaagtttag gcttcagttg acattccctg aagttaaaaa ggatatgtgt actctttaaa 105780
tgcaaggtaa cataatggat tatttccatc taattattaa tatttctaat gataatcata 105840
ggtatgaagg gaatggatag tataatgaga aaggagaggg ggagataaaa atctaaaagt 105900
actaagggca tgttggatat tgaaattcac tactttcaaa tattatcata aaactttgag 105960
acagtaacat tgcaccatta tttttcttct tttaaaaaca ttttactcat tggtaaagag 106020
aatataaaca ttgtggataa ctttttaaa gtaatggttt gttttttttt tctccttcct 106080
cctttaaagg aagacatatt ttgtttctga gcatgaatta taatcaaagt tctgctaatt 106140
tttgggcaaa ttaatccatt atataattac cttcatttat aaatcaataa tacctttacc 106200
attccctttc caaaagaacc atgcctggca acatcaggaa ctagccagat gtgttttgga 106260
ggctgcctgg ggatcccttg ttagactttt cgttccttta tgaacctctt gcctgtggtc 106320
cagcattgag cctctgcttc cttccaagcc tttccaggcc aggcacttgc ttgttctctc 106380
tcttctcttc tctcttcttt tttctctctc cctttctctt ctcttccccc tttttcttgt 106440
ctcacattca tctcaaggta acttaaagtc catttgttat tcctcttaaa gttattttta 106500
ttttattttt ttgagatgga gtctcactct gttgcccagg ctggagtgca gtggcacagt 106560
cttggctcac tgcaacctct gcctcccggg ttcaagcaat ctcctgcttc atcctccaaa 106620
gtagctggga ttacaggtgt gcaccaccat gtctggctaa tttttgtatt tttagtagag 106680
atagggtttc accttgttgg ccaagctggt ctcgaacttc tggcctcagg tgatacgccc 106740
accttggctc cccaatgtgc taggattaca ggcatgaacc attgcgccca acctgaaagt 106800
tattttaaat ctagaccttt atctgaaatt gcagagtgtg agatgtttgt tctccattta 106860
aatgggaact tcaaatgtct gaagggctgc ttagcaatgc tgttgggaat gactgatgtt 106920
tggaagtggt tgaatgcctt cacacccatc catgcagcat tcgtgaactc tagtaactac 106980
agaagaccaa tgcatatcct gcctgtggtt cagacctgtg ggtaagattt gatctggcca 107040
ctcctttcat tacacttaga gatgtagctc ccaccccatg gctatgactg gtcttcggca 107100
gtgacaaatg ctcatcagca tcacgtggat gggcataaac tcacctaccc actttcaaac 107160
attagtcatt ccccacagcg tggctctttg tagatatgat atcagtatca aaagctttgc 107220
tgtatcagat ttccgggaat atatttacca ggaaccctgg aggaaaaaga gattaaatta 107280
```

-continued ggcaatgttc atgctatttt tttttcctag aaagcccttc ctttcccttt tatgctctgt 107340
tcaatggata ttttctttgc tccctagaga gacactgaaa aggaaggtta gtgggaaccg 107400
ttgcgccagc cctgttactg gtccaggttc aaagagggat gctcacttct gcgctgtctg 107460
cagcgattac gcatcgggat atcactatgg agtctggtcg tgtgaaggat gtaaggcctt 107520
ttttaaaaga agcattcaag gtacaagaga attgttaact gcttctttag tttcctactt 107580
ttgatttcaa acaattttgc agagatgact tggcagaaat gtcactactg gcctgtttgg 107640
cacacaaagt atttgatgag cagttcagag gatcatgtgt gtttggaagt gggttgggtg 107700
gtggggtgga attgcagatt tctaccccag aaccccaaga ttatacagcc aactcgaatg 107760
ggtcttaccc ctcgttcacc cacatgggtg ttggatagaa gacatcgagt tacaaccttg 107820
tgaagatgtc tcttggaaaa aatgtgctca caaggagttg caaagattgt ttctttcttt 107880
tacttaaatt taatatatag catgcttaac agtcatgatg gtgggctggc tcctgaggaa 107940
gaaagaataa acacattttt tggaaatggt cagaaatcag gaattcagct acagtggact 108000
ttgagaattg atctagacac atttcttccc ctaggctagg agggtctcag ttcacaatcc 108060
ccttgttttc tgggctgtgt ttagattatt tccctaactt tctctaaacg ccttctggat 108120
tttttttttt aaatcaactt gttgatgaaa agaatcaaac tctgtaaaat atttgaagag 108180
atttattctg agccaaatat gagtgacaaa tggcctgtga catagccctc aggagatctg 108240
agaacatgtg cccaaggtgg tcaggccaca acttggtctt atacatttta gggagacata 108300
aggcattaat caatgcatgt aagatgtaca ttgattcagc ctgaaaaggc aggacacctg 108360
aaagcagggg cttccaagtc acaggcagtt caaagatttt ctgattggca attgattgaa 108420
agaattatta tcagtaggaa gcaatgattg ggttacaata agggattgtg gagaccaagg 108480
ttttatcatg cagatgaagc ctccaggtag caggcttcag agagaataga ttgtaaatat 108540
ttcttagggg tcttaaaggg tctgttctat cagtgattcc aaaaggggag ggagggtata 108600
atgaaccatg tctgtctccc ttgttccatc atggcctaaa cttatttttc aggttaactt 108660
tgtaatgccc ttggccaaga ggagggaccc attcagatgg ttgaggggcc ttagaatttt 108720
attttttggt ttataaactt caagttgtgc acccctgatt tcaaggctgg tcagctcatc 108780
tccctgcatg tgtctttgct acactccttc tctcgtacca gccctgattt gctgaagtca 108840
ctttcttgct tactcttgtt ttctctattt gccccataac ctgtccctca actgctccct 108900
cccaggcaac accctatgtt tccatctgaa agctcccttc ctttttctat caaagcccca 108960
atgctttgtt ctttgccagt taagaaaagc aacgttgaga gaattcatag tgtgtaaatg 109020
gcaaatagca atttactaaa ttaactcacc cattgataac tctaagagga tgttttacct 109080
taagcagaga aatactgata gaatccagga tatggtgagg agtgaaatgt tggtagtcac 109140
cttcctacct gtcccctgaa attcaccctg tatgaatggc agcctctttg tcctggattt 109200
tataattact agctctgcga cttcacctcc tagcctgttt cctcctctgt gaaatggaga 109260
tactcatagg gattttctaa agatgaaata aggttgatta tatgaaaaca tattcagtgc 109320
tcaaatattt tatttgtgac aatcttaaca gtagattata aggccaagtc catttcctgg 109380
ctatatgata agaacaatat tgattttctg aaattctgaa ctgaattctt gatacgatga 109440
ctattttgta tcttgctgag tttctaggat tttacccctt aagaacgttt ggacctatta 109500
ctactaacca tatcttttaa aaagagatcc ttcttttttt tttttgcttt tggggaaaca 109560
ttggtctgct tgaaacatct ttgacccctg agactacagc taataacaat tgaaagtaaa 109620

-continued

```
tttcctttgc ttctctatgt tgtttcttcc ttcctgctgc atcagacagg aatgtcaaat 109680
tctaaatgtg caaagaggaa agagttaaag ctgttacagt tgtacagttg tagtgcctaa 109740
atgatccttt ctttgcatgc ttcctgtctt tgatataagt gcattacagt aactgaaagt 109800
ggccacttat ttttaaaatt gtctcaaata ggccaggatg gtacagtatt gagaaattcc 109860
ttgcatgtaa cttttttttt tttttttttt tttttggaga tggagtctca ttctgtcacc 109920
caggctggag tgcagtggca caatctcggc tcactgcaag ctctgcctcc cagattcaca 109980
ccattctcct gcctcagact cccaagtagc tgggattaca ggagctggcc accacaccct 110040
gctaattttt tgtattttta gtagagacag ggtttcggca tgttagccag gatggtctcg 110100
atctcctgac cttgtgatcc gcccgcctcg gcctcccaaa gtgctgggat tacaggtgtg 110160
agccaccgca cctggcccat tcttatgttt tttataattt taaacttgtc ttgctaactt 110220
gatttataag ctaattgacc atatcttagt catgtacctg tccccttcac tgtacaaatg 110280
cactggaagc tgtgttgtgc ttgcttttcc attgatactt tgttggcttc ttcacacaat 110340
gagttgccat cagagtgata agtgctgttg tttctctact gggttatgga gcacagagga 110400
aggaggacat agggagaagg acctcatcac ttcatctggt ccagatgaca gcatggctta 110460
ttttttgagc ttatccttta ctttttgttc tctttcctat tggtgttcat ttaacaaata 110520
tttattgagc attgtaccag gctctacgga tgcagtggtg aacaagacaa tagattatag 110580
attccatgag ggcaaggatt tttgtccatt ttgttcacta gtggcactta ccaattcctt 110640
gaatatgatt tttcaaaatt aattgggctt atacacagag ttctgtatca tttttcactt 110700
aatattgtcg tataagcatt tctgttgtta aatttccaga gaccctttttc acaactgcac 110760
aactgtgtaa tattctatct tatgatcaga tttaatttat ttaactcttt attattgaag 110820
gccctatcaa ttattttcat tgttttaatg ctatggttac tttatttgtt catgaagttt 110880
tgaaaaaaat aagtttctct ggatatgttt ttagaacaaa tctgtggggt cagagtgcat 110940
taatgtttaa agttcttgac agatgttttc aagtgttcaa gtcttaagaa ggttgtacag 111000
acttgctctt ttaccagcag tgtgagtgtc gctttttcca acctcttggt agcattgact 111060
cttatcaaaa agaaaaaaac cttgctacat tgatacgtga tgtatagtat cttttggttt 111120
caatttgctt ctctttatta gtgaggtaaa tgttttctca taaatctatc tgccatttgt 111180
attttctctt ttatcttctt tattcagaga ttttgcccgt ttttatattg ggttctggca 111240
tttgcttgat aaatttattg tgtgctttat atattaacct attattacat gtatgacaaa 111300
tattttttcc acttgactct gattttgata tgcagaaata gttaatcttt aaatagtcaa 111360
atattaccaa ctttgatagt tttgtgtata gtttttaagc ctaaaaaaag tcctttcata 111420
cccaggcatt atataaactt ttgcgcatat tttgttattt aatagtttgt ttttacattt 111480
tattatttaa ttcaaaagaa atttattttg gcatactgaa tgaaataacc aaatgtattt 111540
atctctcgtt aattttctcc acatcatttt acttaataaa tccattcatt tttcattgat 111600
ttaaaatatg ggagccaatt tttaaaagtt gagtttgaga tataatatgc atacaataaa 111660
atttacctat tttcattact ggtaatagta agtacataga aaaccacaga ataatataac 111720
actgttaatt gtggtttgta acctcatatt ttgagtagaa agtctaaagg aagaaccaat 111780
gaaaaacaat aactacaact ttttttttct ttttttttga gacagagtct cactctgtca 111840
tccaggctgg agtgtaatgg tgcaatctcg gctcactgaa acctccgact cccaggttca 111900
agggattctc ctgcctcagc ctcccaagta gctgggatta cagacaccca ccaccacgcc 111960
tggctaattt ttgtattttt agtagagatg ggtttcacc atattggcca ggctggtctc 112020
```

-continued gaactcctga cctcaggaga tcagcccacc tcagacacat gtagattgaa aataaaggga 112080
tggaaaaata tttcatgcaa atggaaacca aaaaagagca ggagtggcta tacttagacc 112140
agaccaaata gagttcaaga caaaaactat aaaaagagac aaaaaaggtc actaataata 112200
aagatgtcaa ttcagcaaga gaatataaca attgtaaata tgtctggagc acacagatat 112260
ataaagcaaa tattattaga gctaaagaga gagacagact gatatggtaa tagctggaca 112320
ctttaacact ccactttcag catcgaacag atcatccaga cacaaaatca acaaagaaat 112380
gtcagattta atctgcacta aagaccaaat ggacctaata gatatttaca gaatatttca 112440
tccagtggct gcaacataca cattcttttc ctcagcacat ggatcattct gaaggatata 112500
ccatatatta ggccacaaga caagtgttaa aacattcaaa aaaactggaa tcaaatcaag 112560
caccttcttt gaccacaatg gaataaaact agaaatcaat aaagaatttt ggaaactata 112620
caaacatgga aattaaacca tatactcctg aacaaccagt gtgtcaatga agaaattaag 112680
aaggaaatta aaaatttctt gaaacaaatg gtaatggaaa caacatacca aaacctatag 112740
gatacagtga aagcagtact aagaggaaag tttatagctt aagtgcctac atctaaaaag 112800
tagaaaatct tgaagtaaac aacttaatga tgtatcttaa agaactagaa aagcaagagc 112860
aagccaaacc caaaattaat agaagaaaag aaatattcat aaaaagatca aagcagaaat 112920
aaatgaaatt gaaaccaaga aaacaacaca aaagattgac aaaatatgaa ggtttttttg 112980
agaaaataaa cctgacagat ctttagccag actaattttt ttaaaaaaaa gatagaagag 113040
tcgaataaaa tcagatgaaa aaggagatgt tacaactgat accgcagaaa tctaaaggat 113100
cattataggc tattataagc aactatatga taataatttg gaaaacctag aagaaatgga 113160
taaattccta gaccacatac atactgttaa gattgaacta tgaagaaatc cgaaacctga 113220
acataccagt aacaagtaac aagattgaag ctgttataaa aagcctccca gcaagctggg 113280
cacaatggct catacctata atcccagcac tttgggaagc caaggcagga ggatcacctt 113340
aacccaggag ttcaagatta gcctggacaa cacacagaga tccctatctc tacaaaaaaa 113400
aaaaaaatta caaattagcc aggtgtggtg gtatgcatct gtagtcccag ctcttcagga 113460
ggctgaggtg ggaggatagc ttgggaccgg gaagtcaaga ctgtggtaag acaagattgc 113520
accactgcat tctagcctgg gtgatggagt gtgatcaggt ctcaaaaaaa aaaaaaaaaa 113580
gtctctcagc aaagaaaagc caggactgat ggcttcatcc agaattttac caaacattta 113640
aagaagaact aatgccaatc ctattcaaac aattctgaaa aatagagaag gaggagggaa 113700
taatttcaaa atcattccgt gagaccagta ttaccgtgat accagaacca aagaaacatc 113760
aaaagaatat gacagaccaa tatccccaat gaatattgat gtaaaaatcc tcaataaaat 113820
acaaaccaaa tgcaacaaca cgttaaaaag attattcatc ataaccaggt ggaatttatc 113880
ccagggatgc aaggatggtt caacatatgc aaattaattt gatgcaccat atcgacagaa 113940
tgaaggtgga aaaccatata atttcaattg atgctgaaaa ggcatttgat aaaattcaac 114000
atcccttcat gataaaaacc cttaaaaaac tgggtataga cagaatatac ctcagcccaa 114060
taacagacat ataacagacc cacagctagt atcacactta atggagaaaa actgaaagcc 114120
tttcctctat atggaacatg acgaggatgc ccactttcac cactgttatt caacatagta 114180
ctggaagtcc tagctagagc aatcagaaaa gagaaataaa gggcatctaa attggaaagg 114240
aagaagtcta attatcctag tttgctgatg atcttatatt tggaaaaatt gaaaaattcc 114300
accaaaaaac tattagatct aataaattca gtaaagttgc aggatcagta gcatttctat 114360

-continued atgccaacag caaacaatct gaaaaaaaaa tctaaagtga tctcatttac agtagctaca 114420
aataaaatac ctgggaatta accaaataag tgaaagttct ctacaatgaa aactataaaa 114480
cactggtgaa agaaattgaa gaggacaaaa aaaatggaaa gatattccat gttcatggaa 114540
tggaggaatt aatatgtcca tactacccaa agcaatctac agattcagtg caattttatc 114600
aaaataccaa tgatattttc acagaaatag aaaaaacaac cctaaaattt gtatggaacc 114660
acaaaagatc cagaataacc aaagctattc tgagcaaaaa tatcaaaact gtggaagaat 114720
cacattacct gactataaat tataccatag agctatagca accaaaacaa cgtggtacta 114780
gcctaaaaca gacataggga tcaatggaac agaatagaga acccagaaac aaatccatac 114840
atctacagtt aactcatttt tgaaaatagt ctcttcaata aatggtgctg ggaaaactgg 114900
atatccatgt acagaagaat aaaactagat ccctatctct caccatatac aaaaatcaag 114960
tccagatgga tcagtgactt aaatctaagg cctcaaacta tgaaactact aaaagaaaac 115020
acggggaaac tctccaggac attgggtggg gcaaatattt cttgagtaat aataccacac 115080
aagcacaggc aaccaaagta aaagtggaca aatggaatca catcaagtta aaaaactgct 115140
tgcatggcaa aggaacaatc aatgaagtga agagacaaca cacagaatgg gagaaaatat 115200
ctgcaaacat ctgacaaggt attaacaatc agaatataga aggagctcaa acaactctac 115260
aaaaaaactt aaaaatccaa tttaaaaatg ggcaaaagag ctgagtaaac atttctcaaa 115320
agaagatgta caaatggcaa atgggtatat gaaaaggagt tcaacatcat taattatcag 115380
agaaatgcaa atcaaaacta caatgagata ccatcttacc ccaaagtagc ttatatccaa 115440
aagatgggca ataacaaatg ctagtgagga tgtagagaaa agggaaccct ggtatactgt 115500
tggtcagatt gtaaattagt acaactacta tggagaacag tttgaagttt cctcaaaaaa 115560
ctacaaatag agctaccata tgatccagca atcccactgc tgggtatgca cccaaaagaa 115620
aggaaatcag tatatcgaag agatgtctgc agtcccatgt ttgttgcagc gctgttcaca 115680
atagccaaga tttggaagca acctaagtgt ccatccacag gtgaatatag ataaagaaaa 115740
tgtggaacat atacaccact attcggccat aaaatgaatg agatcctgtc acttgcaaca 115800
acacagatgc aactggaggt catgttaagt gaaataacca gacacacaaa gacaaacctc 115860
ccatgttctc acttatttgt gggagctaaa aataaaaaca attgcagtgc ctcatgcctg 115920
taatcctagc actttgggag gtcgaggcag gcagattgcc tgagctcagg agttcgagac 115980
cagcttgggc aacacggtga aaccctgtct ctactaaaat acaaaaaatt agctgggtgt 116040
ggcggcatgc gcctgtagtc ccagctactc gggaggctga ggcaggagaa ttgcttgaac 116100
ccgggaggtg gaggttgcag tgagtcgaga tcatgccact gaactccagc ctgggtgaca 116160
gagagagact ccgtctccaa aaaagaaaaa gaaagaaaac aattgaactt gtggggataa 116220
agtagcaggt tggttgccag aggctaggaa gggtagtggg agtggggaaa gtgggagtcc 116280
cagctacatg ggaggctgag atgggaggat tgcttaagct caggaggtgg aggttgcagt 116340
gagttgagat cacaccactg caactccagc ctgggcaaca gagggagacc ctgtctcgga 116400
aaaaaaaaaa gatgataaat caaagtattt taataaaatt gggccatact agagatgtta 116460
ttgtttgaaa tcaaatatat gaagtatagt taataatata agtgtaatag aagaaaagga 116520
gccttagaaa gcttgaaaaa catcgttgta cttcatatac atcttctttg cttacattat 116580
aatggacaat gctgcaacaa acatggaagt gcagatatct ctttgcaaca tgagagattc 116640
atgtagatct aagagactgt gaagactgtt tcaatattgg agttacaatt agctttttaa 116700
ttacctcttc tggccagctg tggtggctca cgcctgtaat cccagcactt tgggagacca 116760

-continued aggcgggtgg atcacctgag gtcaggaatt cgagaccaga ctggccaaca cggccaaacc 116820
ccgtctctac taaaaataca aaaattagct gggcgtggtg gtgggtgcct gaatcccagc 116880
tatttgggag gctgaggcag gagtatcact tgaacccggg gggcagaggt tgcagtgagt 116940
cgagatcgtg ccactgcgct ctaacctagg caacagagga aggttctgtc tcaaaaaaaa 117000
aaaaattacc ttttcattgt ttgctaatgt gtagaattct gcatgtaaca tgtccagttt 117060
aaagaatgat tatagagcaa atccctgtgt aaccagcgct caaacaatga aatagaatat 117120
aatggcagcc cagaatccct ttgggtggtc cctcctgcca cacctacttc cctccctgca 117180
gaggtgggac agtcctcctt tctgccttcc ttgctgtgta tggttttacc acctacacgt 117240
gcatccctaa acgatgcagg ttgattttct ctgtttttga actttatgtg ttcatgtctt 117300
ctacatatat tttgtgactt ttttctttta tgacttgctc atttcattta tcattgagat 117360
tcatttattc tccgcactga aattctggtt cattataggc ttaatgtaag atgttgaggc 117420
catattgttt attagaaagg cactaaaatg ccctattcac tttcactttt gcttctcatc 117480
tattttatta taatttctat ttcttaaccc tttctcaaac ccatgtagct gtcctcatcc 117540
tccctaccaa caccccatcc agacatctct catttgcaca actacagcag gctgtcatct 117600
ggtctcctgg cctcatcagt tttgctgcct ctgattggtt cttcgtactg catctgaaat 117660
aatttttgaa atataaatat tcttagctct tccttgcata agagaattaa aagtaccatt 117720
gtcttagaga ttgctatata actaacaagt tcaaactctt aggattttac tacaatgggc 117780
cttattttct gtacttctgt gtctttgagt tgtttagagt agctctactt cataaacttg 117840
gttctgggct tttgtgggag gtcaggtctg ttccacatgt ccccacgttc ttcttggacc 117900
agtggctacc tcacaggagc tcaagaggcc aagccaaact gttggagcag cacatctatt 117960
gatatatcat tggctataaa aagtcctgtg gtcaagccca acatcaactg gtagggaagt 118020
gtttgctctc tgcgcactct agtacactgc agggtcgcaa ggctgaggga gagaatgaag 118080
aattgagaac ggtaatccac cacaactctt gtcaatagca gtactttctg tcattattta 118140
gattgctaat ttctttattt gttccttttg ttattttatt tgactatgaa ttcccataaa 118200
aatattgtat taaacccgaa agagggatat atgtaaaaga atataagaag ttgaatttga 118260
tgacttgatt tacaactctt gagttctgtg acttggagca aatcaattta atgttagtct 118320
tattttccac atccaaagga tatattttta tatctctctt ttgagaattc taagaatatg 118380
cagagaataa catattagta aaaaaccagg atattgaaat gttcctaggt ctcctttact 118440
cattaacaag gtgacaatgt agcttgactt tggctttgta cctgtactgg tcattaagaa 118500
gatgtcccct atctctcagc tggaaagtgt tatcagtgtt gttgaccagg aagagattta 118560
actaagagat catagcaata atcttttttt ccctcccact ctgctatagg acataatgat 118620
tatatttgtc cagctacaaa tcagtgtaca atcgataaaa accggcgcaa gagctgccag 118680
gcctgccgac ttcggaagtg ttacgaagtg ggaatggtga agtgtggtga gtgcttgctt 118740
cccttcttat tgaatatggg ccttgctaaa agccctgtcc tctgaggaac tggggacagg 118800
tagccgggaa aagagaagat ttgggacata gtaattaagt atttgcgtgt tgtcacattg 118860
gagggggcat tgacttatcc acagtaactg cagaggacag agctggggtg aatgggaaca 118920
gattatggga ggcagatttt ggccccaggt agagaagagc tttctagagt tcaagtggtc 118980
tgaccacaga ataggccacc agatgggtta ggggacttct agccactgga atcctcaaac 119040
agggctgggt ggccgtctgt ctgtgatctt gaaaagtcca gttctaagga tgaagtcgtg 119100

-continued gtaaatgtcc atggttaaaa ctcgtgacaa aaaagtagga tatcttgtgg gttactgggg 119160
tagccatggg gaggctcaca cctatcccct cgtctagctt tctagaagta gaaaaatatg 119220
taggagtcag aaacataatg gaactatgaa aagtacatac agcatagatt ttgttctatg 119280
acagtcatag gtgtatacat atgtgtattt aacatattca catacatata ttcacatgta 119340
ttttgtacac tcacatacat tcgcatatat tttatgcaca aagaaaagtg agcactttgg 119400
tatataactg acaaagatgc caacacccag ctctctccac ctggctagat tttggttcac 119460
ttgtctgtac tcacttgctt gtttatatgt actcagagca gttctgcctg cacttattct 119520
tctgctagcc agtattttac ctgtggttaa ttgtaatttc tctgtgtaat tatttgaaaa 119580
tttaaaacaa aaatccatca ctttactctc tgacaatttc tttttttttt tttttttgag 119640
atggagtctc gctctgtcac ccagactgga gtgcagtggc ccattctcag cccactacaa 119700
gctctgcctc ccgggttcac atcattctcc tgcctcagcc tcccaagtag ctgggactac 119760
aggcacccac caccacgcct ggctaatttt tttttttttt gtatttttag tagagatggg 119820
gtttcatcat gttagccagg atggtctcga tctcctgacc tcgtgatctg cctgccttgg 119880
cctcccagag tgctgggatt acaggtgtga gccactgtac ccagccctcc ctgacaattt 119940
cttagtagct ttgccttgtg agcattctct gcccttttct tttctctgtg tatgtaacag 120000
attagaaccc tcagctatta tagttcagtt acagcagaag ttctcttcat ctgatcatgc 120060
ttctctggct tcctagagtc actgatgatc ttcatttcct ctgtagaaca tcctgccagt 120120
gcccatagcc tcacagcgtg tattattggt tattctctca aacacctaaa catttccatt 120180
cccaccgctt cacattatcc ttgtcagaaa ccggtgggct tcttttcaaa cctgtttcta 120240
ctcactgtaa ttgttacatt ataaaattta attaaaattt actcaaacat attatgaata 120300
ggaaaagaca agtttggttt ttttctgtga aagtttagtt aaggccgggt gcggtggctc 120360
acgcctgtaa tcccagcact ttgggaggcc aaggcatgca aatcatgagg tcaagagatc 120420
aagaccatcc tggtcaacag ggtgaaacct tgtctccact aaaaatacaa aaattagccg 120480
ggcgtggtgg catgtgcctg tagtcccagc tacttgggag gctgaggaag gagaatagtt 120540
tgaacctggg aggtggagct tgcagtgagc cgagatcgcg ccactacact ccagcctggt 120600
gacagagtga gactctgtct gggggcgggg ggaggaggaa gtttagttga aagttttgaa 120660
taaaatctta aaggactaat agctattgag ataggtatgg gtgagactgg gggaaaaaaa 120720
cccataaacc ttgggagatc ctgaattcag aattctttag aagtatctag gttcttgctc 120780
tgtttttgtt ttaaagaggc tgaaactgaa aatccagaga taatatctta tgtgtatgtt 120840
tatgcagaaa agtgactttg tctaattggc ccagatgctt aaagagaaag ccttggcact 120900
ctgacaaaag attgcaaata aatgttttaa gttttaagtt aaactatttt aaagtgagta 120960
tgtgtgtgtg tttaaaaaat gatttccaag ttagtcttaa gaatgctttt attatactag 121020
gatccgttgc acagctattg ccctcatggc tcaaggcagt gtatgcaggg aagagcatgg 121080
aggttggatc ccatagagtc tatgtttcat tttcgtttca tcacttcctg ctgactgtaa 121140
ctgtgctcaa actactgaat cacctctttg gcccttggtt ttcatgtctc tgaacagaga 121200
tatctgcttc acttggtttt gtgaacaata agtatgaaaa catatatgaa gacttagcac 121260
aatatctgac actcaatttt agttttcctt ccattctctc tccttccctg aaaaactcat 121320
atgagctttg atacaacact gtttcatgag acagagtaca gagggatagt taaagaagct 121380
ttcatagaaa agggaatgag agaaaggttg ttgtatttag ccagaaagtc taagaaaaga 121440
ctgtattctc tttggagatt atggaagaaa tgagatgggt tgttgcacat atacaatggg 121500

-continued

```
atattttgcc cttcactgac catagagaaa gatcattaga gatgaacttt cttaactctg 121560
tctctctcct ttcccatcac tcttcttatc tgccttcccc aaaaccctct atgcatgctt 121620
tttcttctat caggtttgga ggactagaga ttctacctgc ttgttggatc ctcctgcacc 121680
atcctgcttc ttttattttg aaaccatgta gtctgttatc accctttttct tctgaatttc 121740
tgatcttgtc ttttctactg aagtatggat gtggtcatat aatggtagga caacacccac 121800
ctagactaac tttatggatg aaacttcatt ataaggatat actgaaatgt aaggagccag 121860
gaaatccctc tgaatagcca tgtatttggc ctatatcccc atattgggac aatagctcaa 121920
catattttgg gtgccatatc tttatatacc tgctgtatac tcttctgtga aagggatttg 121980
ataggtgggt agtataaaat agtggttaaa agcaccagct ctggatttag gctactgctt 122040
gggtttagat cctgcttctg ctattttcta gctgtgccat cttagacaag ttatttgagc 122100
ttatgtttgg ttcctcttct gtacattgga gacagtaata gttcctgtac tgtagggtag 122160
ctgtcaggac atgtgcaata tgcaatgcct ggtgcataga agcttccagt agacattagc 122220
tgccatttag tgtcatttat cactacgatc atcatcatct ttggctgggg ctatttacca 122280
ctgcctaata tggagcactc gatttggtgg agctgctcat taagctcact cagaggcagc 122340
tgcctaggtt acagtgtcaa agccacaaca ctagaaacat ccttgataga aaaatgagct 122400
ccttgtcaag ggctttattg agtctagaac ccccagaatt cactacagga cctagaatgt 122460
tagactttgt cagtgaaaat ttgtcaagta aatttgaacg tatgaattca aaatctctca 122520
ctttgggtat gtaaagggta tataaatctg ttttgtaaat tccttatcct tatatactct 122580
atactctaca aaagagaaat gtatgatcag aaaggtgctt ttttttttt cttttttttt 122640
ttttgagaca gggtatcact ctgctgcagc ccaggctgga gtgcagtggt gcaatcttgg 122700
cttactgcaa cttttacctc ctcgggctca attgattctc ccacctcagc ctcccgagta 122760
gctgggacta caggtgtgtg caccaccatg cctggctaat ttttgtattt tttgtagaga 122820
caggatttca ctatgttgcc caggctagtc ttcaactcct gggctcaagt gatccccttg 122880
cctcagcctc tcaaagtgct gggggattac aggcatgagc caccttgcct agcagaaagg 122940
tgctttttaa aactatacat tttgcagcaa accgccatgg catgtgcata cctatgtaac 123000
aaacctgcat gttctgcaca tgtatcccag aacctaaagt atattaaaaa aattaagaaa 123060
aacatacatt ttgctccatt ttatcctggg tgtataattg accttagcat tctgcttgat 123120
tactaataaa atgaattgta ttttaggcct ttaattcttt tagcagtaaa tttggttcaa 123180
attttctgaa taaatagagc cctttcttct actataacta gtcaatgtta agaggaaatt 123240
ctgacaaatt ttcctgggag ccaataattt aaatttgctc acattttcta actaatattt 123300
atttttaaaa atgtaaacaa ttgatttagt gaataaacat aatgatgggt gtataaaacc 123360
aagcattttg cagatttcaa cttttagggt ttcttttttt aagggaaatt catataaaag 123420
ttataaccat gctaatgaca tccttactta caacatgtct ttcttaattt ccattttaca 123480
ttttttgtct ttaaccgatg aaaacttata aagatgttgg tgctcaaatg tatagggatt 123540
tggaagttat atttttgttg ttgatttcca tttttcttat cgtcagagaa tatgatctga 123600
ataataccta ttttaagatt ttcttcattg cctagcatgt gataattttt gcaaaatatc 123660
tatggccttt gtagatcaag cttgttaatt atgtggttca aatattctgc attctgactt 123720
tttgctcttt cagctgttga gagagagatt taaatagccc gttataatac tgcatctgtc 123780
agtttctctt tttctttcag ttactttttg tattgtgttt ggaggctgtg ttttattgtt 123840
```

-continued tgtctattta tttatttatt tatttatttt ttcaacccaa gtcttgctct gtcacccagg 123900
ctggagtgca tggcacggtc tcggttcact gtgcctcctg ggtttgtgcg actctcctgc 123960
ctcagcctct tgagtagctg ggactacagg aatgcaccac catgcctggg taatttttgt 124020
atttgtagta gagatggggt ttttccattt tggccaggct ggtctcaaac tcctgacctc 124080
aggtgatccg cccaccttgg cctcccaaat tgctgggatt acaggcatga gccagcgcac 124140
ctggcctttg ttgttttgaa gtatatgagt ttagaattat ttatcttttt aaaatattct 124200
agcgatgagt ctccttatct ataataataa tttttgcctt aaagtttatt tgtctggtat 124260
caatagagta atgtcaattt atttggttaa ttttgcctgt taaatatttt tctatctgtc 124320
tactttgttt ttctatatgt taggtatatc tcttacacct aatctatgtc tagatttaaa 124380
aatatgtata atttcagagt cactcttaaa tggtcaattt ggtatttttt gtttattgtg 124440
ataactgata tttgggttca tttctatcat cttatttttt gatttaaaaa attttattat 124500
gtattttcta cttcttccct tttaggagtt gatcacattt ttatgttttc tttttcttct 124560
tttgctagtt taaaagtcat acattctgtt tcaattccct tttatctttt gagacagagt 124620
ctcgctgtgt cacccaggct ggagtgcagt ggtgtgatct tggctcactg cagcctctgc 124680
ctcccaggtt caagtgattc tcctgcctca ccttcctaaa cagctaggat tacaggcatt 124740
tgccaccatg cccagctaat ttttgtatta ttagtagaga tggggtttca ccatgctgcc 124800
caggttggtc ttgaactcct ggcctcaagt gatccgtccc ctcccgcccc acccgccgaa 124860
accacctttg gcctcctaaa gttctgggat tacaagtgtg agccaccatg tttggccatg 124920
tttcaattcc tttaatgacg tttatgtttt gtaacgtgtt cttgattaat ttgagaattt 124980
aagcttctat cttcccaaaa aagaatctta gaaattctaa ccaaaatcat tcctctctga 125040
ttttgcatgt tattgtttgt tattttggtt ccaccttgtt tctatatcac taaaacttaa 125100
ttcttgggcc ggatgtggtg gcttatgcct gtaatcccag cactttcaga ggccaaggca 125160
ggaggatcac ttgagcccag gaattcgaga ccagcctggg caacatggtg agaccctgtc 125220
tttacaaaaa atacaaaaat tagtcagatg tggtggtgca cacttgtagt cccagctatc 125280
caggaggctg aggtgggagg atctcttgag cctgggaggt tgaggctgca gtgagctgtg 125340
atcatgactg taccaccata cttcagcctg ggtgacagag accttgtctc ttaaaaaaaa 125400
aaaaaaaaaa gtaaatccaa agaacaagca tataaatcaa ctttgctagt aattaaaaca 125460
tacaaagtaa agcgagatgg tttagttaga ttagcaaaca ttaaaaatga tttttaatgc 125520
ccaatgggtt ctgagaaaac agtcaaacta ttgaggactg ggtaacatag taagacccta 125580
gttctacaaa aaaatttaaa agttagctgg gcatggtggc atattcctgt agtcccagct 125640
actcaggagg ctgaggcagg aggattgctt gagtccagga gatgaaggct gcagtgagct 125700
atgattgcat cattacactc cagcttgggc aacagagcag gactctgtct caaaaataca 125760
attaaaatag tgtagatact acaatctaat tttgtgtata aaggctgggt gcagtggctc 125820
acgcctgtaa tcccagcact ttgggaggcc aagatgggca gatcacttga gaatcaggaa 125880
tttgagagca gcctggccaa catggtgaaa tcacatctct actaaaaata taaaaattag 125940
ccaggcatgg tggcgggctc ctgtaatccc agctacttgg gaggctaagg caggagaatc 126000
gcttgaaccc gggaggctga agttgcagtg agccaagaat gtgccactga actgcagcct 126060
gggtgacaga gtgagactcc gtctcaaaaa taaataaata attttgtgta taaaacgtgg 126120
aaaaatatgg tggcaggcac ccatagtcct agctactcgg gaggctgagg caggagaatg 126180
gcgtgaaccc ggtaggcgga gcttgcagtg agccgagatc acaccactgc actccagtct 126240

-continued

```
aggccacaga gcaaggctcc gtctcaaaaa aaaaaaaaaa aagaaaaaag aaaaataaaa 126300
gcattaaaaa gactgaaaga gtttatgcca aaatttattc tcttctatat ttttcagatt 126360
ttttcactta atttgttatt tgaaatatac ttgttttgtg taagtataag gaaatatata 126420
catatgcaca catgcatata aacattttaa gaatgtgtta taataaaagt atattatttg 126480
atacctttgg aaatatcccc atttttctac ctgaagaaaa ttcctaattt catggtttgg 126540
aaacaggttt atgagcactc tttatagaga aacggtgtta gtatctatag atgacctgga 126600
aatggagacc taaaaagttt ctgaaaagtt atgtcgttgg ttttgctagt acggtcacga 126660
ccatagtaat ctttggtacg tgccccacag gctccagaaa ataaaagtca agctgctttt 126720
gcttgactgc ggttttaccc tggcaattcg aatgactctg ctttcctctt caggctcccg 126780
gagagagaga tgtgggtacc gccttgtgcg gagacagaga agtgccgacg agcagctgca 126840
ctgtgccggc aaggccaaga gaagtggcgg ccacgcgccc cgagtgcggg agctgctgct 126900
ggacgccctg agccccgagc agctagtgct caccctcctg gaggctgagc cgccccatgt 126960
gctgatcagc cgccccagtg cgcccttcac cgaggcctcc atgatgatgt ccctgaccaa 127020
gttggccgac aaggagttgg tacacatgat cagctgggcc aagaagattc ccggtagggc 127080
tttctggcta tcagttttcc atgtacttgt agaaaggccg gccgctaata tttaaggggc 127140
aagagtacaa agtagaggtc catgagctgt gcctagatat ttaacaggtc ctcagctgga 127200
tttgtaactt ttaagtgcaa tatgttcctt ccttctgtct tggcatacct accttcaaca 127260
aggccgtgtt ctgatttaga attctgagac tcttctgagt tctgtaccca acatggtagt 127320
gcagaaagag ttgtgcgtgg cccagccatt tctattcttg actgccttct tttcccatgg 127380
ctagatgcat cccataccac cttgcacaaa ccctatcctg tgtgtccaca tctgctacag 127440
acactcacct gttggccacc tctcatgcct agaggtggtc tgggaggatg gacccaggga 127500
acctacctag gctctggaat tgggcttggg gtcatttggg caagaatcct agagtcctgg 127560
aacctggaac gtggttaaaa tgatagactc cacattgacc catttcttgg ctgtggattc 127620
ctcaccttga aaggaggggt ggggtagagt acagtatgac tagtttgaaa gtgaaaggtt 127680
tgtcagatgc taaatagaat tttgtaaatt attgttccag tagagaatca atattatgta 127740
cataaatgaa tatgtatgga caaacagagt aaatcagtgg ttgaagttac acgaatcatc 127800
aatgggccca taaacctgga atgccatcaa gttaaaaatg agcttagtta ctcatgagtt 127860
gtcacttgga acctgcgttt tccatcctcc aaagtgatca cttctctcaa gcccatttgt 127920
aatatatatc tgaagtgctg tatgatgcta aaattaccag ctaattatca tttgacttgg 127980
tgtttctgtg gaggagtgaa tctaggattc taacctagag tggcaacacc ccacgatccc 128040
cctgtgacag cttctccatg ctgttcttta cagtccttga agaaatgaag tctcttataa 128100
gttctgagcc actgggggca ttcccatggc ctggagggca gcgactgcac tgggcaagct 128160
gtaaagatga ggaggggtga gaagctgggg gaagagaagt tttgggtaaa gagcctgggg 128220
aactgaggcc tatggtgaca gtatcatttg gggacttttg ttggcctggg cccatttctt 128280
ctgagcttcc tgaggatttt tggtttctag ttgtattttg ttttgtctag catcttcacc 128340
tttgccagaa ttattttatt ttctctgctt tttcccaggg gaggcaatac tgatgcactt 128400
tcctctagtt tttgctttaa atgtattcca aacacgattt tgcaggacca cacatggaga 128460
gcagtggtga aattaattat tgctgaaagc tgtgcacctt ctttgtgcca taagaaatct 128520
gaactcttaa actgcattat tccttattca agcctggtgt tttgaaaagt tttcaggaaa 128580
```

-continued

```
cgtagacata atctgaaggc gtgatttttt ttctcctctc ttagctggca tagtcattgt 128640
ccaaaccaaa aaatatatat taaaatatca tctagccttg atcttgttga atatctacaa 128700
gattaagaac cgtgatctct cttgggtagg cttattgtca atcactatgg gtgagactgg 128760
gaaggtatat acacattagg aacctaaact gagcaaagca tgtggattta gaaagtattt 128820
atccatcttt acattcataa caccattaca ttctccttga ggcagatttg cgttataatt 128880
gttcaaagac ttgaaccatg tgtgttctct ctgctgtagt ttcctcatct gtaaaacaag 128940
aatgataaga gatcctgcct ataagacatt ctcagagata ggcattgtta cccccatttt 129000
cctataagaa aaacaaagac ttaatgggag attaagtgaa cagctagaaa gaggctgagc 129060
tggggttcga accagagtcc atttcactcc aaggcggtgt cttttgttat catatttata 129120
ttacatggcc ctctcttttt atcatggctt gtgaaggaag ccccggtgtt ctctgctttg 129180
cttttgaagt gcttccctcc ccagagatta cctgtttgca aacagtactg tgaccaacat 129240
gggttattag gttgtcagga cctgcttcgt tattatattt gctctttatt tatttattta 129300
tttatttatt tttgagacag ggtctcgctc tgttgcccag gctggagtgc agtggcgtga 129360
tctcagctca ctacagcctc gacctcctgg gctcaggcga tcatcccact tcagcctcca 129420
gagtatctgg gactacaggc acctgccacc atgaccagat aattttctgt agagatgggg 129480
tttctccatg ttggccaggc tggtctcaaa ctcctgggtg caggcaatcc acccaccttg 129540
acctcccaaa gtgctgggat tacaggtgtg cttggctata tttgctgttt aggatagaat 129600
cacccagaaa cagtgcttct acccagaaga aggatcttaa cactggatag gaaattttaa 129660
tcaatcagag aaatccttgc agttgaggcc ttggttttct gtgagggctg gcactgctct 129720
ctgcaagcct ccaaccccaa cctccaccta ccccatcccc cacctacccc atcccccacc 129780
ccttctgatc ccagtcaagg attgggtcag acaggcaggt cttctgactg gcagccaagc 129840
atcaacattc tcagtagtgc agaggaatta tcaggacaca gctaacaaag atcagttctg 129900
agccgaggtc gtagtgcttg acaaactcta aatgaagtat atttgtctct agaaggggtc 129960
caagactgga aactaagttg cgcagcttaa cttcaaagtt ttcttccttt aatgagcagt 130020
taatcacatc tataaaatat caactcccta atggtttgtg ttttcttagt gttttaacac 130080
ttgccattct gtctctacac acacagggag ctgaggagga ggggtggggg tgtctcaccg 130140
cctcttgctt tccccaggct ttgtggagct cagcctgttc gaccaagtgc ggctcttgga 130200
gagctgttgg atggaggtgt taatgatggg gctgatgtgg cgctcaattg accaccccgg 130260
caagctcatc tttgctccag atcttgttct ggacaggtga gaaaaaatac attgtgtttc 130320
ttctctgact tgtttgagta aggtgcttag tgagtgggaa caaagtcctg ggtgctgcaa 130380
ttaaaatctc acacttgcag ggcagaggat gatagcatca tcagctcctt cactgggtca 130440
agaaccagag aaggagagag ttgggtccaa ggattcaggg tcctgtgact catttttaat 130500
ctgtggtgca gcagcattta caggccagcg ctttaatagg ggactgtatc ccgtaggtat 130560
gtggccacta tgtgtataag tcgacacaga tttttctcca ttaaaaattc cattttcagg 130620
ttataatctt aagttgtcct gctgtttttt gtacctatag tgaccaatta tatctggagc 130680
tttctggaca ggtgataaaa ttcttagaaa tgtgccaagt ttattttcac atgctttaac 130740
tcactctttt gttttttttt gttttgtttt gttttgtttt ttgttttttt tctgagatgg 130800
agtctctctc tgttgctcag gctggagtgc agaggtgcaa tcttggctca ctgcaacctc 130860
cgcctaccgg attcaagtga tcctgctgcc tcagcctctc aagtagttgg gatcacaggt 130920
gtccaccacc atgccaggct aatttttcta tttttagtag agaagtggtt tcaccatgtt 130980
```

-continued ggccaggctg gtcttgaact cctgacctca ggcgatctgc ccacctcagc ttcccaaagc 131040
gctgggatta caggcgtgag ccaccatgcc cgatctgctt taacacattc taatgcatgt 131100
actatatagc atttttggca atagcggtgg aaggaagggt tactaaaact atatgaaact 131160
taacagaaaa tgggacatga tgctgtatct tggttgtgtt tgattttctt ttaaagatga 131220
cacagaaaag gaaacaattt ttaattgact taggtgaact gtttatggag ggaaagctgg 131280
actgtataaa aatactcaag ctttttagca ggaaagtaga acaccctctt ggtgtaaatt 131340
cgagcagttc gaaatcttct tggaaattga tttccacatc tcttttatgg aaaaagtgct 131400
aggttgaatg ttcagccaca tctgactctg catagcgtgg gaggatgcct agtgtctacc 131460
ccaactcttg cattataatc ctgttaccac tttagatcat cagaagaccc tgtgttacac 131520
agatgaagag tgatgcccca aggtatcagt ccccattctg ccttttgtca tggttgacaa 131580
tgttattaaa agagcactgt tctgcataat ggtgttttga tagagaacag atcctctgag 131640
aagagctgga ggactgatgt gacttgaaca ggagcaagcc caggtggtaa accatggagg 131700
gaggctctgg aagaccagag aagttcaggg cacaagaccc ttcagtaaca aacaaaatag 131760
ttaacctatt ggcttgtatg tgcttggcag caccttatgc atttaactta tgtcaacaca 131820
tttaatcttc acaatcttcc tgcccccttt gagggagtag gatccattat tatctctatc 131880
attcagatat tggaaatggg agattgagaa acctgcttac aggtaggata ataggtggtg 131940
gagctggact tggggggttg ccaaatggca aactaactct ctactttatt ctacctgttg 132000
ttatgggtga caatgttgac aaagagcaca ttctgcagaa cagagatgtt ttggtagaga 132060
acagccctgt tttacttgta acacactgca gaaacccact ctccccactg tcatctcagg 132120
gtaccatgtc gcaaggcagg ctgaaaagcc aagcacctag ccaagccatt gctctcattc 132180
attcattgta ttctgcttgg tgttttaact ggggccaaat atacatatgt ataaatatac 132240
acatataatt ttccttgaag ttagtcctag gaacacattc catcccttga caaataattt 132300
gcagacttta ggattatttt atcttttgtc ttgatttcta aattgatgcc aaatttagtg 132360
tttatttttg gtgactattt cattcctggt ttttagtaca attaactctc cactctccca 132420
tttctctgta tgcgttcttt aattcctgta attgtgtgta tacattacta taagtggaca 132480
caaatcctgg aaaaatatta ggcctacctt ttagttaata gaagaaaagt tatttttctt 132540
acaaattatt tctaatagac ttacactgcc tttataactt aagtgaaagt attatgttgt 132600
aaaacataaa tctagtatat ttgattgagt atagaagagg aattcttggg aattgtaaat 132660
gcattcatgt tgagcaggca tttttttttt tttttggaat gactactggt gtttatttgt 132720
tgttgcaatt tctagtagtt tttgtttgtt tgttttttgt ttttgagatg gagtctcgct 132780
ctgtcaccca ggctggaata cgatggcatg atctcagctc actgcaatct ccgcctccca 132840
agctcaagtg attcttgtgc ctcagcctcc tgagtaggtg ggattacagg catgtgccac 132900
tacggctggc caatttttgt attttttttt tttttttagt ggagacgggg ttttaccatg 132960
ttggccaagc tggtctcgag gtcctgactt caagtgatcc cccagcctca gcctcccaaa 133020
ttgttgggat tacagacgtg agtcaccacg cccagcctac agtctctagt atttttaaca 133080
cattaacttt ctgaagtctg gaacttgaag tctaagatag ttcagttact tagtcctctc 133140
ttatacaaat gaatatactt ttatgtaata ggtatatttg tagaggagtt gctcattcaa 133200
aaagtcagga gtcatgctcc ataaagactt ctattacgac tcttttttgc aaagtgaagg 133260
gaatcttcac accatttgaa aataactgtc ttctgctgga ttgtcctagc agagcttctt 133320

-continued caagtggtaa tatggctgaa taaacagtga atacaactaa cagttgccca tttgtggata 133380
ctgaaactat aatttctgtt tccctttatt cttgttgagg tgtccacaac aagaaaactt 133440
gtgtctactg aggatgagag gaaaatctca ttacttcagc ttatttctaa gcatttagtt 133500
tttcttttac taaccactaa attcatcata aattcacgtg aagatctaaa gaacctgact 133560
gtctaattgc tcaaaaaaaa gtcacatatg caaagacatt tttgtgtcct tagtatcaac 133620
aggcaactga ctaatgttaa attattagtc agaggaagtt tgtatctggc ttggatccca 133680
ttgtggacat ttgcagatag gtccgtgaaa ttgtatatgt ataaatgtct tgagtttaca 133740
ttcacattag ttatttgtat gctaaattcc ttcaagataa ccaccgaatt ttcaattccc 133800
aattctaagc cttaaacact ccctgccatt gccatacaca cagaggtaaa ccatggtctg 133860
tacccaggtg tgtgctgcga gcagagatat atatatatat atacacacac atacatacac 133920
acacacacac acacacacac acacacacac acacacacac acacacacac aaatagtgta 133980
cccctaaggg aggcccactc attcaacatt ttgttgttgt attaaacaat attcttcttt 134040
aggccaggca cggtggctca cgcctgtaat cccagcactt ggggagactg agatgggtgg 134100
atcacctgag gtcaggagtt cgagacaagc ctgagcaaca tgatgaaacc ccttctttac 134160
taaaaataca aaaattagct gggtgtggtg gcaggcgcct gtaatcccag ctacttggga 134220
agctgaggca ggagaattgc ttgaacccag gaagtggagg ttgcagtgag ccaagatcac 134280
gtcattgcac tccagctggg gcgacagagc aagactccat cttaaaaaaa ataaaaaata 134340
aaaagcaata ttcttatttt ataaagagtg attattggcc gggctcggtt gctcacacct 134400
gtagtcccag cactttggga ggctgaggtg agtggatcac ttgaggtcag gagttcaaga 134460
ccagcctggc caacatggtg aaaccccttc tctactaaaa atgcaaaaat tagccaggca 134520
tagtggtgtg tgcctgtaat cccagctaca tgggaggctg aggcaggaga atcacttgaa 134580
cctaggagga ggaggttgca gagagcagag atcatgccac tgcactccag tctgggcatc 134640
ggggtgagac cctgtctcaa aaaaaaaaag tgattgtcaa gtaataaatt tgatatggtt 134700
tggctctgtg tccccagcaa atctcatctg aaattgtaat ctccacgtgt caagggaggg 134760
atctggtggg agtgattgga tcatggggat ggtttccccc atgctgttct catgagagtg 134820
agtgagttct cacaggagct tatgctttaa aagtgtttgg cagctcccgg ctgtcttgct 134880
cagtcactcg ctctcctgcc tccatgtaag atgtgccttg gtttcccttt gctctctgcc 134940
atgattgtaa gtttcctgag gcctccccag ccatgcagaa ctgtgagtca gttaaacctt 135000
ttttcttcat agattaccca gtctcagata gtgctttata gcaatgtgaa aatggactaa 135060
tacaaagata ttccatgtta ttactgattt tatttagtag tttatggaca gatagtgtgc 135120
aaaaataaat ttcctgagta ggtcagtttg gttgatacat tgtttcaata ttttaacatt 135180
caaatcatat gccctgtttt tgtttttgtt tttttttttt tagagacggt cccgctctgt 135240
ggcccaggct ggagtgcagt ggtgccatca cggctcactg caaccttggg ctcctggcct 135300
caagtgatct tttgcttcag ccccctgagg aactgggact ataggtgtat gctaccatgc 135360
ctggtttatt attattttgt agagacaagg tcttgctaca tcgcccaggc tggtctagaa 135420
ctcttggcct caagtgatcc tcccactttg gcctccccaa agcacgagga ttacagacat 135480
gggccacttt acccagccag ccctgtcttt aattcaactc ttttaaccct gtcctaattt 135540
cttactcata attcagtttc aatctaaaat tataaaataa ataaaataga tgtcattaat 135600
ttagagtctt tactaacttt gttctgtgta actcatctga aagaccttta ctgggctgtc 135660
atttacgatg tcttatactt tattgcctct tcatttctca tttattttgt tgaaatgtat 135720

-continued

```
ttggtttctg cagactgtgg agtgaataaa aatattctaa ctttgccacc ccttgaatga 135780
aatggttgac tgtcacacct gcttaaaaag aaagcaatca gacctagttc tttagacttt 135840
gtttagaaat taactttctc catgagttat gtatggtctg attactgtga gggacagcct 135900
ttatcagggt ttaaaatacc tcagtatgcc aaccctcctc ccatttttgg aacataaatt 135960
tgcagtgaaa atggcatata ttttaatgag gaaatgatac caatttcaat attgaggaac 136020
taaggcacag gtacttctgg aaaataggat tgatttcagg tgggttccct taccatacca 136080
cttggggagg ggtgtgtgtg agtgtgtgtg tgtgtgtgta tgtattgtgc atgtgtgtat 136140
aatcccacat cagcacagaa gaataaagag ataatcaaat atcaatgcag gagttggtgg 136200
gttttttgt ttttttttt ttttgcccca tagagatatt ttcaaactag ctttccttag 136260
tatcaaatgt ccccaagtcc aacagttaca atttccaata attaattgtc cgcaggcaag 136320
gtgattcagg tgttttttgt gttatctctg tgcagggctt gtgttgtcct tactggatgc 136380
ctgcatcagg ttgcctggga gagcctagag ctggggaggt ggaaagatga ggcttcctgt 136440
agatttggca ctctttgccc agtgctctgg attctctaag acggcctttt cctatgagtg 136500
acttccaggg ggcactggtg ttttgtcact taacctgtgt acttatagaa aattgcaggt 136560
gtttacagaa tttatgattt agtaaattta gtaacttagt aatgctcata taccaaagtg 136620
agcaatttgc atgcttgtag ctctgtgtga gcgagtctgg gtgggagagt gtgagtgctt 136680
cggaatgcag gatcccggtg agtgccatgt acggcaggta atgggaaaga cttctgcagg 136740
actggtgtat ccagtggtgt cagaggctct tccctgaaat actgccatcg ctggaaatgc 136800
cctgagttcg gggaaggagg aggggagcag ccagctcttt gaagacctca aggccccttc 136860
aggggctgct agagactaaa aatggaactc gcataaaccc actgcccttt ctgtgtgctg 136920
caggcttttg ggagcaaagg gtggttttgt gacaaaatca tctaactgct tgtcaaggac 136980
ttccaataac cctgtgactg acaataatag agtgttttgg gggagcagtg aggtggaata 137040
atgtgtgtct ggctggagtg aatagaagct ggtattttcc agataaagtt caagtaattt 137100
acttccaaag tatatttaaa catttatttc tacaaggagt gctccaaaga attttgatta 137160
gatggctcaa agtttaaaga taatccttgc ttgaagataa tccttggcaa gtcaaaaatt 137220
tttccccacc tccatgtata ccttcttttc ctgattctaa tccatcttct ctaattgcga 137280
tttctttctc atagtcagct ttttcaaatt acaggtaaat gtcttagttg ctacacaagt 137340
ttctaagtga ccaccaggaa gtgagagtta agccctagat atggagtttt attcttggga 137400
tatttgcttc tgtgacacac ggtcttcctc attaatactt cccgatggga acatgaagtg 137460
tctcattttg aaatacgtgt catatctggg gctggttgac tgatatggtt ttgattgaaa 137520
acaatcaata ggagtggtat tgctgtaaga aaacatttgg tgaaaatgta gaaggaaaat 137580
attccaatgc acatttttgc ctaaataata tttattcata tatttacttc agggatttat 137640
aggaaatggc ctatcttctt tatatgaaga caattctagt aatttcatat tgctgggtgt 137700
ggtctcatta acaccctgtt gtagttaaaa tgatattatc agatgaacat gttacaagat 137760
gaaacttgag attaaaaata aaacattcct tattgttttt ttgatggttt cctgaagcta 137820
tgttccttaa atttccaaac gaacttttgt agggatgagg ggaaatgcgt agaaggaatt 137880
ctggaaatct ttgacatgct cctggcaact acttcaaggt ttcgagagtt aaaactccaa 137940
cacaaagaat atctctgtgt caaggccatg atcctgctca attccagtaa gtaatcacac 138000
agctgggcca tgttttatcg gggagagatg ctgtttctac aactagcgtg atattaagaa 138060
```

-continued gaatgttgaa cttctatttt atttgaaagg gtaaaatggt ttccttttgg acttcgtttt 138120
tattttgata gcgatttaaa ctgtaggtaa cttttggtaa cttggacata aattactcat 138180
taagtgaatg actggcaatc aatttaaaag tagctcaagc cacttgctgg aaaagaaaaa 138240
aaaaggaact ttaaattgtt tatcttttaa actttttttca gtgctcacac agacacttta 138300
catggttggc atgcatttat acttatgtct ggggtcctcc ttttttacag attcattcgt 138360
tcagtaaaga tacaatccta ccctcaaatg gctcatagtt taggcaggga gagagagaaa 138420
acaaatcatt aaaaataatg atttctgtgc tatgataaag tctacacaaa atactacggg 138480
aaaataggag gagagatgct ggagttgttg cagaagggaa tgattgaaca aatcttcagg 138540
aaagagcaga gggaagtagg tatgacttta aaatgcagtg ctgaagatta gaaactgctg 138600
cccaggcttt gggcagctta gaagaggttc aggcagggga gtgtcatgca cagatatgcg 138660
atatagaaag gtcactctgg cttccatgtg gaggactaga aagggcagag actgaagccg 138720
ggggcccatt agaggcaatg agagcctgaa ctgacattat ggcgtgaggt cagggagcaa 138780
aggacttgac ttgaaggaaa agtgggaggt agaggaggga aataaggtgt ctaggatatg 138840
cagatggttt cgttttgttg gttttatctt atataaatat ctgattattg ttaataaaca 138900
ttcaaatgag aaaaacatac aaggaagaaa ataaaatcat caggaatacc tgccctcaaa 138960
ataaccacca taactttggt gaccattcct ttctttcttt tttttttct tttttttttt 139020
ttttttgaga caggatcttg ctctgctgcc caggctggag ggcagtggca tgatcatagc 139080
tcactgtaac ctagtactga gctcaagtga tcctcccacc ttggcctcac aagtagcttg 139140
gaatacaggt gcataccacc agacctggtt aattaaaaca attttttttt gtagagacag 139200
aatcttgctg tgttgccaga ggtggccttg aactcctggc ctcaagcagt cctcccacct 139260
cagcctccca aagttctgga atttacaagc gtgagccact gtgcacagtc tgtatcttgt 139320
tttttcactt ttctttttga gacagggtgt cactctgttg cccaggctgg aatgcagtgg 139380
cacgatcatg gtttactgca gttccgacct cctgggctca agtgattctc ccacctcagc 139440
cacctgagta gctgagacca caagcacctg ccaccacacc cgaataattt ttgtattttt 139500
tgtagaggtg aggtatccct gtgttggcca agctggtctc aaactcctgt atttttgttt 139560
ttcttttcaa aatgctgtga aaccattctg ggtcaactag gagagatcta acacaatctt 139620
tgatatgagg gcattatact aaattgttca accatttctc tgttattaaa tatccagttc 139680
ctcttccttt ttaaccatta taaacattac tgcaataaat agagatgtgt tattttgtat 139740
gaatttctaa gtttctggat ggttgtcaag actggtcatt tcacgatcta cctggtgtct 139800
aagccagccg ctctagcaga tattgatggc tttgcttagc catttactct tgtcgagcct 139860
ttaggttatt gacttttttt cttcctcaaa cactgtatat ccaggtttta atgttcacct 139920
gaagacttac agatatctct atttagacaa catattgggc cttatttatc caatcttaga 139980
gttcgatact tgaaacaaca gggatatatc agatcatatt atactacggt ctttaaatca 140040
gccaaagtag cagttcctga agccaagatt caatgcagaa ttcactgtgg tcacatgttt 140100
ccagctgcct cttgatctgg ggccagctga ccttcatacg tgtcttctct cacagactct 140160
tggatattgg cactagtttt tttgtttgtt tgtttgtttt gagacagagc ctcactctgt 140220
tgaccaggct ggagtgttaa ggatagttac ttttgcaaaa tataacaaaa atgaattatg 140280
agaaaaataa aagtgtaaaa tacaagtcct agtttataat attattagtt atcacattca 140340
actgatttaa aattactctg tcgattgcta aaaatgttcc taaatgctta cactcaattt 140400
ctacccatct ctttgtaaat gggcaacaga ccatacatta gctctggaga gagcacagga 140460

-continued tactgtccaa gagttgcttg gatctagggt ggagggtggg gttagcccct gaagaactgg 140520
gtgagggaga atgaagaagg aatctgaagg ccatgtgaag gtacagagac ctggaagaca 140580
acctttgagc atttcctagt taagtctcaa tctggcctta cctgcctaac aggtcatttc 140640
ccctgcaccc aacacaccct tccctgttta ttgttaccat tcacctttta cagaataaca 140700
tgagggccca gcttatactg atgattatgt tgatgtgcat ataaggaaag tccagccagg 140760
tgtgtttttt tttttttttt tttttttttt ttttgacaga gtcttcctgt gttggccagg 140820
ctagagtgga gtgcagtggt ggaatcttgg ctcactgaaa cctccgcctc ccaggttcaa 140880
gtgattctca agcgatgcct cagcatccca agtagctggg attacaggtg catgccacca 140940
tgcctggcta atttttgtat ttttagtaga gatgatatat tagtctgttc tcacactatt 141000
atgaagaaat acctgagact gggtaattta taaaggaaag agatttaatt gactcacagt 141060
tcagtatggc tggggaggcc tcaggagact tacaataatg gcggaaagtg aagaggaagc 141120
aagatacctt cttcacaagg tgccaggaag gagaagtccc aagcaaaggc agaagagccc 141180
cttatataac catcacatct tgggagagct cactcactgt catgagaaca gcatggggga 141240
aactgccccc atgattcaat tacctccacc tggtctctct cttgacacat ggggattatg 141300
gagattacaa ttcaagatga gatttgggtg gggacacaaa gcctaaccat gtcagacagg 141360
gtttcaccat gttgtccagg ctggtcttga actcctggct tcgagtgatc tgcccacctt 141420
ggcctcccaa agtgccgtga ttacaggtgt gagccaccac atccggccca ccagccagga 141480
tatttgaaat tgatcatgga ataagatcaa ccctttctga ccttttccaa accacctacc 141540
aacattacct cacataggtg ctgccatttc tgtcaaaggg aggatctgct tgaagagtac 141600
cttcccatct tggcaatgga agatcatcaa atgccagatg atggggcttc tctcactttc 141660
agaaataatt tagatctctt ttctgtgcag gaaagtgctt ctcggaaagc actgtttgct 141720
tgttgttaca acactttaca gtataaagcc ttctgtttgg caaggctcct tataggcatt 141780
ttagcctccc agacatcata ttgtgttgtt gtcaaagcta gacgcagcat ctgtgcaaat 141840
gggaaagatg aaggctacag cattcccctg cagcatgaca gaactgccac attgagataa 141900
ttacagaagg cgagggagac atgtgatgta attaccactt gtggcagtaa acgagtaaaa 141960
tttgtttact gtaaatccaa gtttaagaaa tctttttttt tttttttttt ttttttttga 142020
cagagtcttg ccctgtcgcc caggctggag tgcaatggtg cgatcttggc tcactgcaac 142080
ctctacctcc tggcttaaaa cagttctcct gcctcagcct cctgagtagc tgggattaca 142140
ggcacccacc accacgcctg gctaattttt gtatttttag tagagatggg gtttcaccat 142200
gttggccagg ctggtctcga actcctgacc tcgtgatccg cttgcctcgg cctcccaaag 142260
tgctgggccc tcgcctggcc agagatcttc ttttaaggaa gttcctttct tggtagtcat 142320
aacaattgtc aaaataaatt gatcctgttc agcattgcta tggcgaaaat gggacaattt 142380
tcactgctag gttaagtgag tcttttctat gctaggtttt aaggatttgt aagtacaggc 142440
tttttcttc tggattattt gtggtattta aatttaaaaa aaaataggga tggaatctgc 142500
ctccccgcct taaaatttaa aaccctgaca gaatatataa aacagatatt ggacattgga 142560
caacagtgat ccccaggagg agggacacaa acgaggagag ccctttgatt gtccagttta 142620
ctgcctggag ccagtttcca ggttgcaaag cagggatggg tgtgttaggt ttctccagag 142680
aaacagaacc aataggatgg ataggtaggt aggcagataa atgagagggg atttattatg 142740
aaaactgact tgaacaatta tgaaggctga gaagtcacat gatatgcgtc tgcatgctag 142800

-continued

```
tgaaccaggg aagccagtag catggctcag tgtaaatgga aagacctgag aactagggag 142860
ctggtggtgt aaccctcagt ttgagattga aggcctgaga aactgggagg ccactggtgt 142920
gagtcccagg gtctggaggc tggagaacct ggagttctga tgtccaaggg caggagaaaa 142980
tgggtgttcc agctccgaga gagagaattc tcttcctctg ccatttcgtt ctatctgggc 143040
actcagccaa ttggacggtg cctgccaaca ttggctaagg gcagatcttc cttacttagt 143100
ccactgttct ttcttttttt ttttttttga gatgaagtct tgctttgtta ctcaggctgg 143160
agtgcagtgg tgccatcttg gctcactgca acctccacct tctgggttca agcgattctc 143220
ctgcctcagc ttccagagta gctgagatta caggcatctg ccaccacgcc tggctaattt 143280
tttgtatttt tagtagagat ggggtttcac cacattagac aggctggtct cgaactcctg 143340
acctcaagtg atccacccac tttggcctcc gaaagtgcag ggattacagg tgtgagccac 143400
tgtgcctggc cttagtccac tgactctaat gccagtctct tcctggaaca ctctcacaga 143460
catacccaga aataatgctt tatctgctat ctgggtatcc ctttatccag tcaagttgac 143520
acctaagact aaccatcaca aagggtaacc caaatagaca ccagtggtct cccttggtag 143580
caaggcagct aggacttgga ggggagagta ctgagtggga aagagctgca caaagaattt 143640
tggagatcta tggagagtcc tcttcaagtc ttcagctgag tgctaatctg cccatgctta 143700
tgaggatacc aaggacaggg aaagaaccat cagaaaggag cgggcgaaac aatccctaga 143760
gttcacacag ggccaggaac agttcacatt ctcaccagcc agtgggaaaa accttgcagt 143820
tcactgggta ttgggcactt ctcagccttc ctatagtatt cagaagggta ttgcctcagt 143880
agtgggccta gactaaaagc cattatgatc ctaccaaaca aaaaagcaag cctggaggat 143940
caaacaattg ctaagtgatt taactgcatc ccagcacaaa gctcaagagt agagacacat 144000
cccatttcat tacatgttgc tttattgtgc atcacagata ctgcatgttt ttacaaatcg 144060
aaggtttgtg gcaatgctgc attgaacaag tctgttagta ccatttttttc caacagcatg 144120
tgctcacttt atgtctgtgt caaattttga taacactttg caatatttct aactttttca 144180
ttatatctat tacagtgatc tgtaatcagt gatttttgat gttactattg taattgtttt 144240
ggggtgccac aaactatgcc catataagct ggcaaactta acctataaat ttgtgtgttc 144300
tgactgctcc accaactggt ggccccacca ccatctggaa ttctgggaga attctaccat 144360
gcatttgagg aaggaataat accaagtgat atggtttggc tctgtgtccc cacccaaatc 144420
tcatcttgta gtgcccataa ttcccacatg ttgtgggagg gacctggtgg gagatgattg 144480
aatcatggga gcaggtcttt actgtgctgt tctcatgata gtgaataaat ctcacgagat 144540
ttgatggtta tataaaaatg ggagtttccc tgcacaagcc ctcttctctt gtctgccgcc 144600
acatgagatg tgcctttcac cttctgccat gattgtgagg cttccccagc catgtggaac 144660
tgtaagtcca ataaaccttt cttttgtata ttgcccagtc ttgggtatgt ctatcagcag 144720
tgtgaaaatg gactaataca ccaagtttac acatactctt acagaaaatt gaacagcatg 144780
gaatgttttc caattcattc tgtgaggcca gcattactct gatagaacac tcagactaac 144840
acactagaag aaaagaagac aacagaccaa tttccctcat gcatgtataa gcaaaagttc 144900
tctaaatttt tttttttttg gtaactagaa tccaaaactg tattaaaaga atagcacatc 144960
atgaacaagc agaatttttg ggaatacaag gtttctttaa catttgaaaa tcaatcaaaa 145020
ttcatattaa cagaataata atgaaaaacc atatgatttt atatatatat atattttttt 145080
tttgtttgtt tgtttgtttt gttttttttt gttttttttt tttgagacag tctcactctc 145140
cgcccaggct ggagtgcatt ggtgctatct cagggctcac cgcaacctct gcctgctggg 145200
```

-continued ttcaatcaat tctgtctcaa cctcctgagt agctgggatt ataggtgcct gccaccatgc 145260
ctagctaatt tttgtgtttt tagtagagat gaggtttcac catgttggcc aggatggtct 145320
caaactgctg acctcaggtg atccacccgc cttggcctcc caaagtgcta ggattacagg 145380
tgtgagccac tgcacctagc catgattatc ttaatagatg cacacagcat ttgacaaaat 145440
ccaacatcca ctcctgctaa aaacactgta caaacaagga atagaaggaa acttcctcaa 145500
tccattaaag ggcacctatg aaaatcctac atttaatatt atacttaatc acaatcagga 145560
acaaggcaag tatgtccact gtccttaatt ctattcaaca ttttactgta agttctaccc 145620
agtgcattaa ggcaagaaaa gaggtaaaag gcatcaatat tggaaaggta gaagtgaaag 145680
tctttattta aaaacatgag aatctatgta gaaagtccta aggagtctaa aaaatgtgaa 145740
tttagcaagt ttgtaaggtg taagggcaat atatataaat caattgtatt tctgtgtggc 145800
accagtgagc aattggaaat tgaaatgaaa aaccactacc atttacaata gcatcaaaca 145860
ttgtgaaacc ttgggaataa acttgcaaaa gacatgaaac ctgcacacta aacactgcaa 145920
aatatagctg aaggaaatta aagaaatcct gaataaatgg agagagatgt taatggatca 145980
taagattcag tattgttttc aatctataga ttcaaactga taaaaatccc aggaggcttt 146040
ttggtagaaa ttgataagct gattcttaaa atcatgtgaa aatgcaatgg acatagaata 146100
gtcaaaacaa ctttgaaaaa gaacaaactg ggaggactta cactacctga tttagaagat 146160
aatgtggtat tgatgtcaac agaaacaaat agatcaatgg aacagagagt ccagaaataa 146220
tctatacaac tacagatgtt cctcaattta tgatggggtg atttcccaaa aaacccatct 146280
taagttgaaa atattgctag tcaaaaatat acttaacaca cctaacctac tgaacatcat 146340
agcttagcct agcctatctt tttttttttt tttttttttt tttgagacgg agtctcgctc 146400
tgtggcccag gcgggagtgc agtggcgcaa tctcggctca ctgcaagctc cgcctccagg 146460
gttcacgcca ttctcctgcc tcagcctccc cagtagctgg gactacaggc gcccaccatc 146520
acgcccggct aatttttttt gtatttttag tagagacggg gtttcaccgt gttagccagg 146580
atggtctcga tctcctgatc tcgtgatccg cccgcctcgg cctcccaaag tgctgggatt 146640
acaagcgtga gccaccgcgc ccggccagcc tagcctatct taaatgtgtt cagaatactt 146700
acattaccct gcagttgggc aaaatcatct aatataaagc ctattttata atacagtaat 146760
gaacatttca tgtaatttat ggaatactga aagttactgt actgaaaaac gaaaaaacac 146820
aatggttgta tgtgtactgg aagtacagtt tctactgaat gcaaaaactt gcagctgagt 146880
gtgttcatta tcttggttgt ggtgatggct ccaccatgta tatgtatgtc aaagtacatc 146940
aaatcgtaca cgcaaaatat gtgcaggtta ttgcatgtca ggtatacctg gatgaatctg 147000
taaacaatgt aatgaaagca aaacaaaaag attaagagag caaagtttgt aggctaaatg 147060
gaaaagaaat accaccaagc ggggaaccaa atcacagggt ggaggccctg gaggataagg 147120
gtcaggagag gagaaatggg ggtaggtctc ttaagtcaaa aggctgcgaa cttctctatt 147180
ccatgttagg atagcagagt ttccaagcgc tgcatttggt tgctgctaga tggccttgcc 147240
aggctagata agcattgggc tgtctgacga tggtctcctg catagtttgg tctcctgttt 147300
tcctgtgtat gtgacatgct taagttagga ttatgtcact caatcacatc tgcagtggta 147360
cagcacgcta gctggccagg tcgcggtttg tcagtagtca tgttttaaaa gctgcccatt 147420
tctgggttat gcatatctac taataatggc tataatatgg aatggaaatt aactgtgtca 147480
tccagctaaa tttcagctca gtttctggta tgtatattaa tgacttctaa atactaagga 147540

-continued tgtcaaaatg atttagatat aatgcttttg gtctagaatg ggatatatac tcaaatagtt 147600
aatcaaaggt ctgatccatg gtgggcttaa gtggagaggc acatatttct ctcttgggga 147660
ggcaagggaa aggaccacaa cattctaact ctctcagcca atcctcttcc actatgcata 147720
tataggttgt gtggtacttg gaattcctgt atcatactta gcctttgata tggctcttga 147780
gagtaagaga caacagaaaa atgttgcatt taacaacctg ttacaatgct tgttagagtg 147840
tttttataaa ctctaaggtg ttatgcaagt gtcatagtta ataaaatagc ctacccaaca 147900
cccaacagac agactggcca tcttgccacc caaatcctcc cttggataga attagagggg 147960
gtatggaatt taggaattag agtgtaatta attacattga ttatccatag tctttaaaat 148020
attttaaatt agaaacaagt ctatttaaac agttttaaga tttacaaagg atgaaacttt 148080
tcattaaatg aaagaaatag aggggttaag ccaggaaatc ctattttaca ttaagaaaat 148140
tattaagaga cactggctta aaccctagtt ccctctgagt ttatagggag agttcccatg 148200
gagtgggtgg gtggagaaga caaagacata gatggatgct gatgaggaaa gatgcggggg 148260
tccttttctg ttgaccaaga acactggggc aaagcacagt tgaacagcag cctgcagcct 148320
cacaccatgg caccttttga gtcccatctg ccctcatgtg ctgggggcag gaggtggtga 148380
cagagggcgt gggtcatggc cagaggttcc tttcctcaaa gcaaacaagc aaacgccaca 148440
tacggctccc caaagccagg acttcttccc tttggtcagt attctgggac ttctattagc 148500
acattagatt tttctcattt atttgccttc agtcaaggaa agcttatgtt ttcatccttt 148560
gaacaaatca gacgtggcaa atcttgaagg agaggtggct gtcccccacc actgtgctgc 148620
tcagaatgtc accaggtggg ctggtgagag gagcacacag ctgttcccag ctgataaagg 148680
ggagagaaga ttgtgtcctt gattttattt cactttcttt ggtatgtgtg aggcatggtg 148740
ccaagatctt ggtttttttt gttttttttt tttaaactat acttcttccg tttcatcaaa 148800
agtaatttaa ttttgtttta cagtgaatcc taactgatgt ttttactttt gggggatgga 148860
gagggtgcta tatttttgtg gttttctgtg cctgactggg cagagctttg gatcttgtcc 148920
cttgccccat gctgcccagg gcctgccact tagcaagtac tctgtagata tgtatttgat 148980
gagcaagggc ctgagcatgg atgtctgagg tgcaggcacg cactgctgac tggagagcca 149040
ggcagcagca tgggtattct tcagcacagt tcttttctgg gagggtattt cttttctatg 149100
tgatcaatga gaacaggagt ctccaggata attttatgta agtcagtctt tttgtatata 149160
cactgccccc ctaccccacc atatgtaaaa tggatttcgc atatgccttt ccacaactgc 149220
agtgcctcac ctccccaaac cgctgtggct gatggactct gggccccagg tggagctgtg 149280
ctgcccctac agcctgcaga aggcccaggg tctggccttg gcaatgactg tggttcgtga 149340
agtgggtaac acaatgacac atacgtgttc tctgagggga aacttcgttg cacacagccc 149400
agggaattta tgttattgta actttggttc tgaggcgttc ttttattatt attattacta 149460
ttatttttag taacagcttt attgtgatat aattcattta ccatataatt tatccatatt 149520
aagtatacag ttcaatgttt ttagtttatt cacggtatgt ggtgcaacca tcaccaccat 149580
caattttaga acattttcat cacctgaaaa gaaaccccat gcttcttagc catcatttcc 149640
cactccctat cccacccaca gccctaggca accactaatt tgcttttctg actctatgga 149700
tttgcctatt ctagacattt tattataaat ggaatcatac aacatgtggt cctttgtgtc 149760
tggcttattt tgcttagcct gatgttttca aggttcatct gtatcagtac ctcattcctt 149820
ttcgtagctg aatactattc cactgtatgg atagaccaca ttttgttgag ccattcgtca 149880
gttagtggac attccacttt taggctgagt tatgctgcta tgaacatttg tttataatct 149940

-continued gaggatttgt ttttatattt tcaatctttg tcactttgaa ctgagacatg tacaggcaca 150000
caattttggc tccttttgga attcccagac atagtattgc ttgatggcag cggaagtcca 150060
tggagcacat gtcatgcagc tgaacacact acggggtagt taaaaggaag tacttgttta 150120
tgcagatggg gttaatttta gggaaagtaa gcttgaaata attttctctg tacttttgat 150180
aattttctgt gtgtacctaa aacatacatt agcatgcata tttaccattt caaatatgat 150240
gtgtgtttgg ctaaaaaaaa taagggtctg gccgggcaca gtggctcacg cttgtaatcc 150300
cagcactttg ggaggctgag gcaggcggat tgcgaggtca ggagtttgag accagcctgg 150360
ccagcatggt gaaacactgt ctctactgaa aatacaaaaa atttgctggg catggtggcg 150420
catgcctgta atcccagcta ctaaggaggc tgaggcagga gaattgcttg aaaccgggag 150480
gcggaggttg cagtgagctg agattgtacc actgcactcc aggctgggtg acagagtgag 150540
actctgtctc aagaaaagaa aaaaaaaaaa aggtctgtgc cctcaaagca ctcatgtcca 150600
gtcttgctga gggcagaagg gtggctgtgg ggtgtgtgtg gggacaaggc agacatccag 150660
catgtggggc aacatggtgt ctctgctgag gatgaacagg gcactgtcag agtatcaggg 150720
gacacctcag accagactta gggtgggatg gtagggaggt tgggggaagc ttccagaagg 150780
aatttctgac caggttggaa tctacaggag gaatgggtat aaatgagcaa aagaatcagg 150840
gtagagaaag aggaaggaga gagtttccaa gcagcaagtt gagcatgttc ggagcaccac 150900
acattcaggg agttgagagg gggactcaag gcgaggtgtg gtgggaactg cagatgagag 150960
aagcggggag ggccctggta cctctgatag ctgcaccagg tggtttggac tctatcctat 151020
gagctgggaa gtcattaaac ggagccccat gagcagatct gctttttggc ctctcagaag 151080
gggacacacg gggccaaggg tggggtcttg tttcccctgc ggtgggaggg caagtcatct 151140
ctggggcgac agtgggaggt ttgaggctgt ggggggattc tggaagaacc aatgtggaga 151200
acaaagtgag cacagggatt ggagaagcag cttcagggct attgaaaaga tgaatatttt 151260
aaattcgtat catcagacat tatggaggtc cctagggatg tggcaaagca ctacacttac 151320
gtaattgtgc ttcagaatgt cccttgcctt acctgagtta aacttagttg aattgagctg 151380
ccttaattga actgaaagtg ccaataaaaa tagagaacaa aaactgccaa aacaaattct 151440
gtggttgctg gagcaccagc catcatcagt ctcatgacag ccaagactca gcagctccct 151500
ggttgatttc acatatttat tcttgctttg aaatggaaag cctggaagag aagctaatta 151560
ttaaagggaa tcaaggagtc aggcaggggt cgggggggagg agatttatct gagctgttac 151620
tttgctgcca ttgggatgcc acagtatctc aatcctagag ttggaggggga gttaaacaca 151680
gggcagggca ggatggggga ggcagcctac ccaggacgtg gctgtgggga cctaagcaga 151740
tgtgttcctg catgcgttgc tcagtgagga actgaggctc agagagctcc agatggtggc 151800
tagaaagtag gtctgtctga ctccaaatca gtggtcttcc tgccccagcc aggtgccact 151860
caagcgagat gcagaggtgg tagcaggggc cctgccatgg ctggctgcgg cacgtggtac 151920
acacaaggag gtggcagagg aggcttcatc acattggcca ttcctttgtt tattaaactc 151980
cctttagatg gggagccctc cgtggggcta aaagtagaat taatctcacc ttctgaccat 152040
ctctgtatct gttgctgcag atgagaaaca ccacgtaatg atttcgggag actagatata 152100
ctcgccacgg caaggccaca attatgggcc tggtggacac ttcaggtggc aatttagtct 152160
gtctgcatta ggccaggctt ctcttctagc tctgtgacgg ggctggctct cagggaagat 152220
cccctggggg aggtaagacc atgcttataa gctcctgcca cacatgcagc tgtcaaagca 152280

-continued acccagatca cctcggagca ggcgcacgga acagctgagc acacgacttc tgctcctttg 152340
ctcagagcaa tgacttctgg cttttattct ttgtccaggt atgtaccctc tggtcacagc 152400
gacccaggat gctgacagca gccggaagct ggctcacttg ctgaacgccg tgaccgatgc 152460
tttggtttgg gtgattgcca agagcggcat ctcctcccag cagcaatcca tgcgcctggc 152520
taacctcctg atgctcctgt cccacgtcag gcatgcgagg tacgcgccct aaggagctgc 152580
tctgcttggg cttgggatgg gattatgtgc tccacggagg gtgaagtgat ttgggaaaag 152640
tgtctgcaag ttaaggaaaa tgaatgcctg aaagggaatg gggaatttgt cagttcacac 152700
acctgtaagc aaagatgggc acagagtggg catggaagga atgtcatgtg gtatcttaca 152760
ggctctgcat ggcagccagt ggtggctcat gggtttttca attgctgggg tttatagcct 152820
gtttatggag tcctaaaagg ggcagttcct cccctaacac gaactgccac ccctgtttac 152880
accacccagg gctgaggccc tgaggccact ttttgtggag aggctaagac ccgctcccct 152940
agatggcccc tcgagctggt gatgcgaaga agtgcacaaa tgcttcccta agagttgttc 153000
tttcggtggc atcaggaaat taaggataag acttaagaga agtggtggac ccagcagatt 153060
taggaaggca gggctgtagg tagggcatgt ttctgatcag gaaacgtaat tgtgtgtgct 153120
gatgaagagg gtgtgcagtg gtggctactg ttggtacaat gatgctcagt gcttggtgtc 153180
acccacgatg agggtagcct tgccctggag ctggaggagg ggaggggagg gtggaaggta 153240
attaactggt cactgaggag gcaagtctag aggctgtgga gaaggacaat atacacctcg 153300
agaatcttaa gtgagatgaa gacctctgcc tttccccttt aatgattgct cagcacatag 153360
ccatttgcag aacagatcct gtgtttgtag attccttcat tgtgaattta tctgcttgct 153420
aaaatttatt tgtaacccca aaatcaatat ttgtggtgtt tttgaggtca tgaacagagt 153480
ggcagaaatt ttgagttgcc ctttatgtac agtcccagct gagatggaac aagcagctgc 153540
tctcatactg tcaacaagtg tcctttactt ggtctactta gtgccatggt tttacatttt 153600
tgtgcttttg gtgacttcac tgtttaaaat gcccccctgg tgtggtgctg aagacctgtc 153660
tagtgttcct cggtgtgaaa aagctgtgat gtgccttatg gagaaagtat gtgttaagct 153720
ttgctcgggt gtgagttata gtgctgctgg ccatgagttc aatgttaatg agtcaatggt 153780
atttatcaca taaggcatct ttagaaagaa acacacataa aacaaggttt tgtattgatc 153840
agctgatgaa gatgtggcca gaggcttgca ggaacctaac cctgtatttc ccctatgagt 153900
gaggattcag tgttcacagt gactttacgg aacataatta ccgcaaacaa tgaggattga 153960
ttgtcctatg tgtcaggcca ttgtaggtgt gtggtgggac acagaggctg acaagacatc 154020
gtccttgccc ttgagcctaa attatcaggg ggagctggat gcacgagcca tggataaatg 154080
ggctggggga agagtgggtt taggggtggg gtagactggc tctgagcaaa gagagccggg 154140
gaaggcttcg gggttcctgt ggctgcctcg gaggagggaa tctcagcacc tttttgtccc 154200
catagtaaca agggcatgga acatctgctc aacatgaagt gcaaaaatgt ggtcccagtg 154260
tatgacctgc tgctggagat gctgaatgcc cacgtgcttc gcgggtgcaa gtcctccatc 154320
acggggtccg agtgcagccc ggcagaggac agtaaaagca aagagggctc ccagaaccca 154380
cagtctcagt gacgcctggc cctgaggtga actggcccac agaggtcaca ggctgaagcg 154440
tgaactccag tgtgtcagga gcctgggctt catctttctg ctgtgtggtc cctcatttgg 154500
tgatggcagg cttggtcatg taccatcctt ccctccacct tcccaactct caggagtcgg 154560
tgtgaggaag ccatagtttc ccttgttagc agagggcaca tttgaatgca gcgtttccac 154620
actcaatggc ctcataggat ctcagtgtgg tctttcttac tttccttctt ccttcctccc 154680

-continued ctttgtgaaa catcttaaag gttttggaat gaatggtgga aatctgactt ggaagggctg 154740
cgaatcagaa aggggagagg aagtgacacg cttacagaag tgggctaacc cttcttgtgt 154800
ggcacacact acccttccct ctgagagttg acctttgctg ttttccggac cactccattg 154860
taagattgaa aacccctgtg gcaattgcgt acttacctcc caggcctgtg gggactgatc 154920
atatcatatg atgcttattc tgtcaaaggc cagagggact gtggttaagc tgggatgtga 154980
gtcatgttct ctccctgacc ttgctgccag ctgcacacag atttgtccct ctcgatttgt 155040
attcacagag cctgccaata atttggggta tgtgtgtatg agcgtgtgat cattttcatg 155100
caggactgtg ggagatacaa atctcgctgc ttctggagct gctcttcctt aaacctgttg 155160
tcccatgggg ccagcgtggg tgctggagaa aggccgtgtt tgcaggaatg ggggttctctc 155220
ctgtgggtgt gggtgacagc cacagtgttt ccctggggca atgtggatgc agtttccatc 155280
ttgtacaacc tcataagtag cagccacaat tgccccatca gtcaccacaa gtagtcaggg 155340
atactttggg ctgtggatgt gtgcagtgtg ctgttttatg gatggatgag tagctatgca 155400
ccccagtgtg tcagctctgg ggccacactg tatagccttg atgagtacgc cccttgaaca 155460
agacccagtt tgtgaactct ccttaaagag aaatatttag ggataattat ttatagcaag 155520
aaagaattct tttacacttg agagctcttt taaaaatatt ttcttattgg aaaatttata 155580
tggtgggcag ggtgaaaaag aaacagtaaa aatattagtt cttattccaa gtggaacata 155640
aataggacat gaagaagggc acctctgaaa tgacaacttt aactcacctt ttaaaagatg 155700
tgaaatttcc agttttggat acacggtgaa tatgtaaaat gagtaacagc atactatgga 155760
agccagcaat taaataatca tgtttcatta ttgcagtaac gttttaaaca attaccttgt 155820
gatatgatat taaatatatt ttctttttga aaatatgttc actttgggta gcacatcctg 155880
tatttactaa gtcattagga agactgcatt cagtgttacc aagactggtt tttgctagta 155940
agacctcgaa taatccataa ttttgatatt ggtgcaattt tactataagt tgagcttagc 156000
tgtttcagaa atgcttggac aagtacctag agaacacact gatgtctgtg ttctgaggca 156060
gtctgaagtt attcttagag actcagttac agctttagta agatttagta caggcaggat 156120
aagcttggtt tcataggaac cagggaacca gtgttagtgt cagcttcttt cctcctggtc 156180
agcctagaat cccccactcc caatagaggg gtttggaagc tggagagtag gaagtaagag 156240
gcaaagaagg cagccttcag caactcatta tctgccagtg aaattctatt aaatgtattt 156300
ttaaaagaga ttaccaggta acaaaaacat aaaaaaccaa aacaaggcca gatgtggtgg 156360
ctcacgcctg taatcccagc actttgggag gccgaggtgg gcgaaccact tgagcccatg 156420
agtttgactc caggctgggc aacatggaaa ccctgtccta caaaagatac aaaaattagc 156480
caggcgtggt ggtgcaggcc tgtagttcca gctacctggg aggctgaggt gggaggatca 156540
cctgagcctg gggagatcaa ggctgcagtc cattgcactc cagcctgggt gacagaggga 156600
gaccctgtct caaaaaaaaa aaaaaaaaaa ttgccacgaa atatatatat atatatatat 156660
ataatttttt ttttttgaga gtagatctta agacagagat cacttctact cctgggagtg 156720
aactggcaat ggcaatccct ttagagcctc gagtgggcag tatcaggagc gccgcacagt 156780
gagtttccag ctgagctatt ctcaccgaat ctcgctctgt tctcacagca cccctctgtc 156840
aggcctgtct catagtgact gcccaccagg actgactaca aaagacttga ccctaaaata 156900
gtcttgaagg gatttttctc aaaaaattaa ggcgggaaca caagacaaag ctgtcagcct 156960
agtcacaaat ctgaagactc aactgcatta aaaatagtgc aaaatcggca ggagctgtac 157020

-continued agtgcgagtc ttggtctgga atactccccc tgctaactca gctggaaggg caactatctt 157080
agatttcagt aaggaagaaa aatcagttac caatacttgg cagagccata ttatatatcc 157140
atatatattt atgtatataa gtggaattga agcaattcta gaattttcta gcatgtgaaa 157200
gcagggttta gttcttattt acgtctgcta agggactttt caaattcaaa gtgaaccttc 157260
tgtttatagg cctattttga aacaaagtat cctcacttaa taagatttga caccttttt 157320
ttttttttt tgagacaggg tctgactcct gttgctcagg ctagagtgca gtggcgccat 157380
catggctcac tgcagcctcg acctcctggg ctcaagcgat cctcccacca cagtgcccca 157440
tcccacccca ttcccgccct cgccgagtag ctggggtgca caccaccact cctggctaat 157500
tcttttaata tttgtagaga tggggtttta ctatgctccc caggctggtc ctgaactcct 157560
gggctccagc gatctgcctg ccaaggcctc ccaaagtgct gagattacag gcatgagcca 157620
ctgtgcccag ccccgccaca ttttttttta agttgctgaa aatcttttaa aaagataaaa 157680
acacattatt tagtatctaa agataatatc tgtgccagac acagttctca gtgcctcaga 157740
cattcacatt taatccttat tataataact gctatttcct tattttctgg ttgtggaact 157800
agacacggtc taagcaaact tgctgaaggt cacgtgggga gtaggtgatt gagctgaaca 157860
caggcagtcc aagtccagtg ctgacagtga ccatgcactt caaacagttt aaaaatttaa 157920
agaaaaatat tttaaaactg cagaatctat caggtgcaac ctgacatgca cggctgctgt 157980
gatttaaatg gggcccccctt gtgataccccc cttacctccc accacaatgt ccagaacacc 158040
cctacagaca cagtaagttt gtaaacctct cacatcaaag ttcaactcca cctttcatat 158100
ctgtgtaaat taaagcccac gggggcaaat tcacctattc aaggtcataa aactactcat 158160
ggcaaagctt ggactggcac gcaagtcttc tgcttgccta gcgggccagt attgctcctg 158220
ccccaggact tgcttctgtg agaatctgct ttgtgagctg agtcgcagca gaatggaggg 158280
gcggtgaagt tagggttgtc ttctgctgta cctttagatc ccatctcctc agcttagatg 158340
ggtctgcatg agcctttaca caacagcagc aatgacagat ggaaaaataa gatgcataat 158400
ctgttattcc cattgtccca tctcaggttc atgagctcta gtgggtactg tgatcacctc 158460
ctgtctgtga ctgctttccc caaacacgtg gaatatgttc cttggaagtg tactcatgta 158520
aaattcacat cttttaggca ctgctgcttc cctgtggagt gtgatatact acagtgtgaa 158580
aacacgtgcc acttattctt tatagctctc aaacttgctg gaattttggc tccagtggca 158640
gctcttaaga tgtgcattgt ctgtgatgta tgatcgtagt gccatttttg ttgctttgga 158700
gtcagggagg ttttttgttt gtttgtttgt ttgtttttta attccgagga tcctattcac 158760
ttgtagggcc agccactggt aaactggtgg tgggtttcct ctatgggaag cacataagga 158820
gtggtgatac cagccgcgaa cagttcctgt taactgtaca atggatgttt ttgcatttgt 158880
ttcctctgtt gggtgtctaa atgccttaac tgttggtcct atacctttttg tcattcaatg 158940
tgtacttcag agcctgttgg ttggctataa tttgccattt tctcagacga atgctttgta 159000
tcattacact aatttgttga cttcatttgc aggctttaca tttgggcctt gtagaaatga 159060
atgtttgctg ctctgtgaaa gcagattttg agacctgctt tcccttcctc cagggagtgt 159120
tttccttact gtgtcccttt aatgtctatg gcactgtcgt agagagttta acatgatata 159180
aataaagtgt ttcattattt tggctttaaa aatgtatttg ttgggggttg agtgtaagaa 159240
cttacagtaa ttaggctaag tagtgtctac attctattct gaattcttat tgtggggtta 159300
gagagtcctt tgagaatttg atgaaaacca gggctagtct tcctgggaaa gggcacctga 159360
acacaaatgc ttgagtacaa tttcagaaga gttaagaagc tctgctttaa tgtatcttct 159420

-continued taaaaagaac aatttcatct ttagtcagct aatctcacac ttgtgattga tttatgacca 159480
caggtcctgt gtatacaagt aaaatgcagc tcacaaaagt cctggtatcc agtgcatcga 159540
ttatttggat agattttctg taatcattct gagtttgatt agaattatat cctttacaga 159600
tggggagaaa agcaattcat tcatttgaag ttatcttagt gccaagagtc atgtgaaaat 159660
gtcccttgca tgtgggcaat gaaagatttg cagacgatat aaaacccaga ctacctcata 159720
aaagagtttt gggaatacac tgagctttga gtgaaagaag ctgcagtggc ctccctggag 159780
atggggagca aaccagctta aaggccctta tcctgaggaa gagacaaaaa ttgacatgca 159840
caatattaag ctttgaaatg cagaccacac ttcctttcac tgcaactttg acttgtcccg 159900
catctctact taagggcaga aaaggcctct caaacactca cctcatttgg aatgaagatg 159960
gagactcttt tgcctgaagc aacgatggag cagtgaccct ctaatcaact cggtggccta 160020
aagaaaaatc ttgggtaaca ttttcacttc agtttccctc tgggatcatt gtaatccatg 160080
aaaaaaataa ttttaaagaa agagttaaaa tactttgaag ttagttatgt ggttaaaaac 160140
caccttcctt tctattatca atccaacaat ttgataactg taaacgctaa agtgaagacg 160200
gattctcttc agatggtctc cttaactgcc cagggcttgc agatgtctca cccatgaggg 160260
gcaccaatgt agaaagctga ggcttcatct actgatgagc ttcactggtt tcccctgagg 160320
tttgtgcttt ggcagagaag gggaggaggg gactgggatt gtgtggtcag ctgtgcctgc 160380
caacagatgc aggttaggaa ctgtgttcag tatcttccaa taagaaaggg gaaatgccga 160440
tgcctatcct ctttgtttag gtagaaagta aaatgctact ggacttaaat gggcaacaag 160500
gggctttgcc tgttcatttg ccatggagag ggctgggaat ccaggtgcgg tggctcacac 160560
ctgtaatccc aacactttgg gaggccgagg tgggcagatc agttgaggtc aggagtttga 160620
aaccagcctg gccaacatgg cgaaaccccg tctctattaa aaatataata attagccagg 160680
catggtggtg tgtgcttgta atcccagcta ctcaggaggc tgaggcatga gaatggcttg 160740
aacctggaag gcaaaggttg cagtgagccg agattgggcc accgcactcc agcctgggtg 160800
actgacagag tgagactctg tcaaaaaaaa gagtagagta aactgggtat aagatccttc 160860
cctttgcgtc cacctctcat gccatgctgc ctttgccatt ccctacaata gctgagggtc 160920
acacgctgaa taatttaatt tacacataca cgagggtcca gagctaagtt aattctgtaa 160980
ataagactta gaataaaagg ccctctccaa atattttaaa aataataatt tttgtttttt 161040
ggaagattaa gcataccact gaactgcttt gttacagaat tcagtacaac agaagtctgg 161100
ctaattttgt tttttaatga gaaacatctg agttgtacat atcacaaaca gcttcaagtt 161160
tctgtaccaa ccccccgccc ccacccccgc cgtggccaaa cagttaaaac ccaaagcaaa 161220
gcatcacttt ggatgtgaaa aagtcttaga aaattaactt acaaaaacat ccctatcaag 161280
tcggtagttt ggcatttact ttacattagt caaaagctcc agctaaaatc taattttttt 161340
aaaaaaaaat cgaagtttac attattcata cagattgggc attgttaaaa aatatgcaca 161400
aataaccaca tccatgcaat acaatttctt taaaaattta aagcaatata aaagagcaga 161460
gctaggtact gaacagaaca ttttggtgta taaccggcag ctcaaaattg ccagctgatt 161520
ggagtaaaac tgattctaag cgtattaaat atgattgatt gtttccatca gctaagggtg 161580
cctatgagtt tctgaaccat ttctagggtg gaatgtcctc gcttgcttct ataatatatg 161640
tgatggacac cactgctcat tgaccatacc tacattataa taatgctgtt ttacaaacaa 161700
accagaattc acaaagtgct tggctcttca ggaaactgac atttccagag atccctaaac 161760

-continued

```
taatcaacta gttctgccaa aatacccggg gcacctgcca cacaggttcc ctgctcctgg 161820
ggaggaacac aatctgaaag ctgccctggg ctccagggag cccgtgctgg gtaagcccag 161880
aagaagtctg cacaggtccc gggaccttgc caacactaag tcactcagat tggtctgggg 161940
ccacgtgctg ggcacccttg gcaatcaggc aggtggtgta gcactgtggc cagctatgcc 162000
ctctatgtgg ggggtggccc attggtgtac ctcagcatgg ggtaaaagga ccgggcaaag 162060
ttgttggcct gagtgcagct gtagtcttct tcggaggagg gcagcaggca ggccaggagc 162120
agcagcagca ggaggagcag ctgcaggggt agggctgccc ggaccaccct tgagaggaag 162180
gagcgctgtg gccgtgtgct gccggggacc ctgccaacag aggaggttga gagctgattg 162240
ggaggctcca caggcacaac ccactctatt acctaagccc ctgcttatgt aagtaagaaa 162300
tccaagacct gagatttaaa tagggccaac agttggggtt cagtttcaga ggagaaaacc 162360
agccctttcc agacaaaaga aaaccagatt tttgcaagga ccttgatagt ggcattggca 162420
agactgagtc agtgggagtg tggagcaggg gaacgcactg ctgtcacggt aaagccccgt 162480
tacctgctct ctgtctcctc ctcgccttct gtagttctca ctgctctgaa ctgctgggta 162540
aagaaactcc agttagtaag ttgaagacag tttagtccta tcaatgataa aaaaaaaaaa 162600
aatcctccct taaattatat accaccttta tgttgtgtta cagccaaact ttggagacta 162660
gagtaataca attgagatta aacgtcacct gaagtaggaa ataattaggt taatctactc 162720
agtttcaggg tcaagtgtgt tgaagttttt aatggcaaaa tcagggaacc cctttagcga 162780
cactataaga gctctcattc acaacctact gtgatcccaa agaagagtga ctagaggcag 162840
actgtaagcc tctctatggg tcagcagaga cctgtgctgt cctgaaatgg ctaatgggct 162900
cttggaatcc caagcttccc tcatcttagt gactttaaaa aataaccagt gaggttctca 162960
cagaaggaag gggcttctta cctttgctcg gggagctggc acggatgttg caggaggctg 163020
gtcccccgag tctacctcgt cgaagctggg caggggtgag gctgggttct gaaattcaga 163080
ccccaaaggt tgagcacaga aatgtgtttc atgcatattc ttcatgatat agctcaccct 163140
cccctacctt aaatcaatct ttttttgttt tgttttgttt tagacagtct cactgtgtca 163200
cccaggctgg agtgcagtgg cacaatcaca ggtcactgca gcctcaacct cccaaactca 163260
atccttctac ctcagcctcc tgagtagctg gaactatagg catgcaccac cacacctggt 163320
tttgtatttt tttttttttt tttttttgca gagacgggat ttcaccatgt tgcccaggct 163380
ggtctcaaac tcctggactt aagtgatcca cctgccttgg cctccccaag tgctgggatt 163440
ataggcatta gccactgtgc ccagccttaa atctttcctg aaggggctct tctattgctc 163500
tcactcccaa caacaacaga ctttttcgga caaaaaggaa tgtaaacaag gaaaagccaa 163560
cccatattaa aaaccaaccc atagcacaga gctggggaga ctgagtttag cagcagcagt 163620
ttgagtagat ggtgagctca tcacaggtcg gtgatgagat catgtggcca tcaagagagt 163680
ctagttttgg ctgcttagga gaaaacagac ctgccctaag tctggtgagg ccacagtctg 163740
ggtattccct ttgttttgag ttggatccca ttttaaagta ggccagctat ggtggctcat 163800
gcctgtaatg ccagaacttt gcattgcttg aggtcaggag ttcaagacca gcctgggcag 163860
catggcaaga acccttctct acaaaaaata caaaaattag ccacttcctt taaaaaaagt 163920
ttaaaaattg tcatcccgcc actccctttt aaaaatgaca aaacagattc aaagagctca 163980
tgcagctctt taagtccaca cagctagaaa aagggcacga catgaggccc cactcggacc 164040
acctggccct tgcttctggc ctctgtctta gagcattgct acaacactgc tgtcctgtct 164100
gcatgtaata cggcaatctt tacagttaaa agctacaagt agactcacct gggttccctg 164160
```

-continued caaggccatt aaatcttggg acacttgctc ccgtaactgt ttgagtttct tctcaataac 164220
atgcaccttt tcttcagctt caatacagtc ttctccatgt cccttaatga gaaggctgtt 164280
tgaaatctcc tgtaacatgt ccacttgagg ttgacgttct accagctcct tttccagttg 164340
ctgaaaacag ataaagtgtg tgaaacagtg acctgtccaa agggaagcga gtgtggacac 164400
aggaggtttt tctcagtacc agaaaaattc cagaatgaat gatgggtagt actcaactcg 164460
agaatcctct atttctcata tctgcctgtg tcctccagcc cagcactatt tagatagcaa 164520
gtgtattatg ccctgcccct atttttaatt tcttttcact ctgaagacaa ttgtgatgct 164580
ggagaaatta gaagaaagaa gtgaggcaag tggtgtggga agaccaggtc cctcatccac 164640
cacggaagga agtaaaggga aactctaaag tcaatcaacc gagaaacagc agcgtaacca 164700
tagaggttca taccaggcaa acgggcttta attgttaagg gtggttatct tgcttgcaat 164760
atggccacta gacacatgtg gctattcatt tatttatttt tttgaggtgg agtctcactc 164820
tgtcgcccag ggtggagtac agtggcacga tctgggctca ctgcaacctc cgcctcctgg 164880
gttcaagcga ttctcgtgcc tcagcctccc aggtagctgg gattacaggc gcctgccacc 164940
atgcccagct aatttttctt gtatttttat tttattttgt atttttagta gagacagggt 165000
ttcaccatgt tggccagact ggtcttgaac tcctgacctc aggcgatccg cccgtctcag 165060
gctcccaaag tgctgggagc caccgtgccc ggcctacatg tggctattta aattaactaa 165120
aattaaaaat tcagtttcag tcataatagc cacatttcag gtgctttaag ccacatgagg 165180
ttattagaca gtgcagacac aggtcatctc tatcacttca gaaagttcta ctggacgcca 165240
ctgctttgct ttgcaaacat tttaggaagc tgtattttta aacaatggct agcactctga 165300
ttaaaattta aaatatttaa accacataca gatttatgga tgaaaatgtc accttgagca 165360
ccagtgagaa tacagaaatc tcatcttggt gtgttagtga caaatacacc aggacacgac 165420
tctcctccaa gaagaaagat ttttccatag tggatacaga aaacccattc agctcatcac 165480
aggtgtgaag caaatgagca ccatatttct ccccaatgag caggattcac gagagaaaaa 165540
tacttccact caaatggcct taagttcctc aggatatcga gagcacctat gtcctcagtt 165600
ctgtggactg tggctctcca ttcctgcaag tcatttggct tcagaactac aaagggcagc 165660
tcggtaaaca ccaactggag gaacactagg gctgaactcg tgcatttaca ggcaaacacc 165720
actggcacag ttcctgaaat actaggcgag gctacctgag tgtgctgcct ctctggggct 165780
gacagaggct ggtggcagta cagagccctt gggaggaaac ttaccattag ttccctccga 165840
cactctagga gagcccgggg gtctgccttt ggatcggtga catgagcctt ctgcctccgg 165900
ttcttggcac tcgctaacca cagcagcaga ttttgactca actggtggaa gtccttaaaa 165960
aacaacacat cagagcgcgg ccgtgtctta gagccctgga agagggtgtg ccaggaacat 166020
ggcttactgc ttccaatcca tcacagtcat ttgcttttct ggccttaccc actgaatacg 166080
aggaccagct ttaaactaaa tgccagggcc ccaaaatgag gaagaggaaa gaaggaagac 166140
actcagcaca gtgccaggag gccgcgaata aaagtgccac tatgaaggta gggctttggg 166200
atgcccagct gattttatat atgaaggcca cacgcattcc tcagccaatc tgctgggttc 166260
tctgctgggt tccagtggca gagggaaaca acccaacagg acaggctggg gtgggctcac 166320
gttccctgag acacagccag agctaggcag tggtgcagag ctcacacccg ctgtgcattt 166380
actgtgtcag gtactgggct aggattatac atactgcctc atttactcct aaaaagaacc 166440
tttttaaggt tctttctaaa aagaaaatgg gaatgattcc cattttcaga tgagaacact 166500

-continued gaggtctagg aggttcaatg ctttgctcaa agtcacatgg ctattaagca gtaactgctc 166560
ctctgcttca aggccaggtc tcttaatcac tctggcaaaa ggacaaaaag aggagttgtg 166620
gggtggcatc tctaacctac aggtcgcctg caggaaccct gactccagga gtggctctgg 166680
gcctgggcaa cagagacgag acctgggaca gggagtaggt ctctgagatg gccggtgagc 166740
ctctgtggaa acaaatggta aagcacatgt ttcctgacac cagccacatt tggctgcacg 166800
gaagcagcct gatgatgata aaaatatctg ctgctcctac cacgtgggcc tgggtaccgg 166860
ctctgggagg cgggctgctg agtcagcgta cctggcactg catgagcgac tgtcgtaagc 166920
cccctctcca gctgtccact gcgccctgtg ctgcttccca gagcaggctc agctggcgga 166980
gtctactttg gagctctgtg gattcggggc tctcggtttg cagaaattcc ttgctgctca 167040
cgttgacaga gaccactaat gccttgtaag tgtcaaaggc tttcagtatc tcctaccaga 167100
gagagaaaag atgaggttag gagctctgaa agtagggagg aggggctcat tttgaacctc 167160
agtagggaac aaattttcca cacacttttc caagctgcgg ccacagaaat gagagtgacc 167220
tcgcctggga ctggctggaa agcatcaggt gagggagctg ccttaaggtc tgtgaacttg 167280
gccaacaggg ccccaaagta gaggcctgct ggagggagga gaccctgctg acctctacag 167340
gccccgctct gcaactggct taatgtttct ggaccgacta aaggtcttcc agataaagta 167400
tatgtggtta ttctgcattt gctcctagaa atgccagaaa tgttattcct taggaggaat 167460
ggtaacccct aatatattaa cacagatagt aaaataaaag tacaaatatg aaaggtacct 167520
ggatcctcca aaacccctgc cctgggtctc aggctactgc tcatggcacc cttaaagcgc 167580
agggctcaaa ctgtcccttt gcagctccct gggctagttc cagtggggtc aggacttatg 167640
taagtgacac atcctaattg cataaaaggg taatgaggtc aggccacggg attcatcagt 167700
aggtgagccg gtcctttccc aagccctttc aaggaagatt ccaccactag tctttcgtgt 167760
aactgtgcag catacagttt ggaagagtgg ttttacactg cctgacagtg tccactagca 167820
cctccagaaa agtctagaaa tgcctcggat gtcagatttt tccatctctg gagatctgag 167880
ccacacctcc ccagtactct gggatcagga tcatttgcag atactcttcc atgtgaaaac 167940
aaaaatctgc atctatgtcc ttgccaacta tggaactgaa atggaagaga gtgacctcta 168000
catacaccat ctgcaagctg cgcctatgcc acgaatacat gggatctgct cgtccagcat 168060
agcaatgcgt tcacatgcac attctgaatc cctcttcccc accacacctc taactcacct 168120
gcagtctctt cactctcagt tctatttcct ggatatcaga gggaggcttt gccatcttta 168180
acatttccag ctctgcttca gttttttttca gccaagtagt gatggcgctg atatcagagt 168240
tcagctgttg caaattttgt tttattttga gcttattgtg aagctcctgt gcttgaatca 168300
tctcccatct gtcgaaggca cctggaatta aaaaatcgcc aattaaaaaa agcaataatg 168360
caacagattt ctctgcctcc agctaattag gggtcagggt ggttaaaaaa aaaaaaaaaa 168420
aaaacaaaaa aactgtaggg gattcccctg acagaagggt ctggttttgg gagttctctc 168480
ttctcctgga atgtggaata gcacatgatc tgaggcgtac actcccacag aggctggaat 168540
gaagtggaag gtctatgtgc tacagtttca agctcaacag ttcagttcct gctgaatttt 168600
ttcagttttc tcctttggtc cacaaatgac caggtcgatg ctgtcagctt tagatttagt 168660
tgagtaatta cttttataat tactgggctg gtcgaatgaa gagacacttg agataacact 168720
gatcatcatc ctcaagtctg atctttacac acaaatatag aaagtgaaaa cctgcacttc 168780
ctcaggaggc ttattttacc aacatttaaa gaatagtttt caaattacac tgaacagcct 168840
aggaatttgt tcgtgaatgc caatcgctga tttaaaaata acattggttg ttgtagggta 168900

-continued

```
agtcccccag ttctggcgaa tcgtatagtt ggttaatatc taatgaatgt tctcttgagc 168960
aaggacttaa ataccatact ctgcctctct ggacgactgc cagttacagg cagtacctga 169020
ctgctgctct gtgataccgg ccagtccccc gtcttcctgc tgtgggttgc cattcaggac 169080
tcgcgggcct tctttgccac catccgtgcc tggaggtaat agtagctttc cctagaatga 169140
gccagttttt aagttaccat ctgtagatat gaaggatatc tgaagaacaa ctggattcat 169200
ttcatattaa cagtgaagaa atgagatggg cccctttcct ttgaagggta tcttgctagg 169260
aatacagtgg tgctttagtg tctaggtagc atttataagc tggcaaagct gatggcagaa 169320
ataaagcctc agctaaggcc cagggagagg gaagcagatg agatgtcagt gatgggaaga 169380
aaagggtctg tttcaattgg catgcttcca aacacccctc aaatgatcca cacgaaacaa 169440
atcagaacaa tttgttgagc ttaccagacg gttactgcgt tagcactttg aattttcata 169500
gtgttttaca gaattttagt tatccctgtc actctgtaga ggtggttggc atcattatca 169560
cagaatcaga aatgcacaga ggatgaatct gcctcccagg ggcattcgtt accaagtgtt 169620
tatctttcac cgcacatact gactcttctg ttatcacaca gccgattggg ctgttatctc 169680
gggcctctcc aaaaataaat gtgtcccttt tagaaaagcc ctgctttctt tgtctttctt 169740
ctgtctgtat ggcctatttg tgcagaatga aaataataaa aaaaaaacct tcagatttgt 169800
ggtgatacat ctggcttcag acacaacaaa agggttgaga ttttgaaacc ggccaggtga 169860
ggaacacagg cgtcatcaca ggaagggata gccaagccac atgagccaag gatgtaaagc 169920
agaggtcagg gactgcggtc tttcccctgt cttattattc tttttaaaaa tgacacctgc 169980
ttgttaagca agaggaagtg tttctgaatt ggacacaaac agcccattat cagctgactt 170040
ggatttgagc atgcaaaggc agaatctcct ccaatgatgt aacaatattc tctccttaat 170100
ttctctcgct gctgccctag gctgccctcc caggagctgc ctagccagag catgccaaga 170160
actcaaggca gctgagggaa atgtaactaa gaagaaacag ccattgctat aaacaacaaa 170220
ccaatacagg aataataatc acgaccaata caggaataat aatcacgacc attacttctg 170280
aggaccttct tttaccttta tacacaataa tcttaacaac tactaggtga aatagcttta 170340
gcctcaggtg agaaaggctt acagaagcaa ggcgaagtgc ctcaggtacc atggcaatgg 170400
attggcaggg ctaggaatca aatccgtgtc cactgcagca caccatcaat gattttttgg 170460
aataggatgt atggacaaaa ggttaacata acaaaggctt gaaggttgga tgcagtggac 170520
catgcctgta atcccagcgc tttgggaggc tgaggcaggt ggatcacttg aggtcaggag 170580
ttcaagacca gcctggccaa catggtgaaa cccccatctc tactaaaaat acaaaaatta 170640
gccaggcatg gtggtgcaca cctgtaatcg cagctacttg ggaggctgag gcaggaaaat 170700
cacttgaacc caggaggcag agattgcagt aagtcaagat cgtgccagtg cactccagcc 170760
tgggtgacag aatgagactc cgtctccaca acaacaacaa aaagacaaag gcttgagagc 170820
tcaggagcag tcaggaaagc cagcaccttg cttgctcact atttgcacag acacctgact 170880
cgacagtaat aatgactgtt acaccacacc aacatacaga aagatggttt ttggccagaa 170940
cctatctcta agtctaatcg gttttgccgg ggttctaatg aagtatggac agctcaacag 171000
agacactgtc accataagaa aaccaactca aaatatgcct ggggaatgaa tacacgcagt 171060
ttacaccaaa atctctctct cttgcaaatg taagtatgac tcacagacat aggctgtact 171120
cccagtgaag ttaagactta catagggtgg tttataaggg gtgctggacg caggggggaac 171180
aggtggaaca ttcctgtcac cttccatttg cttgtagtga tgctcgggac aggaagggct 171240
```

-continued gtcgggaaca tgccacgagt ggccatccga aatggattta cctgaaacga aagacagcaa 171300
gcgacagtct attctctcct actgaacggg tcacgggtga catggcatca ggttacagta 171360
tgaaaatgag ttctgcagct ttccttgcaa agcatgcatg tttgcaaaat gtcagtatgt 171420
cccagaagag aatgagatga gtcatgcaac tcagcaacac tgtgccttca ctagatgggt 171480
acacaacgga gcacgaccaa catgatttgc tgtgggatga gtggcgtttt ggagccaggg 171540
tctcgagtgg tagggacact gagtggcaag gccgggtctg gggaccaaga tggcagaagg 171600
cctctcagga gtgaggggaa gagtgaacat caagatggac ttgggaacca aaaggctcct 171660
cagggctctc cccgacccac catggcagat agggatgggg ctaaggatga ggattagagc 171720
tgcaaatcaa ggaaaggaag gtttttttccc tcctgtggca aatcatcagc accctttacc 171780
gccccaaccc cccacccctt tccaccaggg gatcccagta aagcaaggaa acagttccaa 171840
accaagccac catgaagaaa gcttggccca tgccaaagga cttcagttag atggagaaaa 171900
aaatcatcaa aacaggcacc atgaaaaatt ccctctgcac aggcctgaag ggaggagagg 171960
gggttggcat cgagacggct ctggcttgga tggggttttg taaggagcac gcagttatgg 172020
gtgagtacgg cagtgtaaat acaccatgac acaaggacca aggcgcatgg tgtccacaga 172080
aggcagaggt agacacgaca tgggagcgag gttgaggatg cagtgtgcgc cacaggatgc 172140
tgccatgttg acacatgcat gggcgggggc ctaccagaag acgctttcaa agtttttgtg 172200
gtcattttaa gatatgcctc aggattttca gggatttcta catctgaaaa agaacaatgt 172260
catttgcctc actggaggtg cctgaagatt aatgcccaag tattaacaca cagtagaaac 172320
attgtcagct ggaaggagaa aactaccctt tattttttta attaaaagga ttttgaaaac 172380
cagaaagatt tttttttcca gccaactcct gactgtccaa agcaggacac tgggtatcaa 172440
agggagaagc tcagtctgca gacactctga gaaactcaac tgaaagggag ggtaggcaca 172500
gtggctcatg tctgcaatct cagtactttg ggaggctgag gcgggaggac ttcttgagcc 172560
caggagttca agaccagctc tggcaacata gcaagacctt gtttctacaa aaaatttaaa 172620
aactagctgg gtgtggtggc gtgtacctat agtcccagct actcaggagg ctgaggtgga 172680
aggattgctt gagccctgga ggttgaggct gcaatgagcc gtggtcgcac cactgcacct 172740
cagcctgggt gacagtgtga gaccctgtat caaaaaaaaa tcactgatga gtctcccaga 172800
cagccagagc catcactgag taaccttagt gtctgaatgt gaatttcatt tttttcccc 172860
ctttcattcc acctgtgatg agagtgagcc aattctcagg taagttaaga gatgggcagg 172920
atagagcaca ggaaaccaca gaagtcaggg tcggccacaa gatggactct tggtcattga 172980
gagctggccg tgttgctaag gggctaaaaa catagccaaa cgggtcactt tccagggtgc 173040
tgggaaccca gctgttacct gacagtgcgc tgtagtatgg gccctcctcg tcctcttcgt 173100
gagaggagga gccccccacg tcgcctgtgt ggtcccactc caggggggatg gagtccacgc 173160
tgacaggggt ctcgcagcca gaccgctcgt gccctggggc cactagatga cacagggact 173220
gaggagatga cggttcctcg ctctctcccc gtttacgcca agaatcagtc tggatttctc 173280
tggggtcttc catgtctgtt tcattctcag aggcctcctt ttcatcttcc aagccctaaa 173340
ccacagtatc cagttgttag aattaatcaa ctcataggct tctgcaatta gaagagcatg 173400
agaagtctgc ctatctagca gtttccaaaa ataactgcca atagtatttc taaggcagct 173460
ttaaaaagat caggttccca ggtcctgttt ctggttattc cagtttagac aatctggagt 173520
ggggcctaaa atctgttatt ttcccaaacc tccagctatt ttttcttagg aaaaaaaagc 173580
tgaagtttga taatctaagt taaacaactt tatctaggag ataaggaaat ggtggccaaa 173640

-continued gtttcattga tggttaatgg caggttcctc caagaatcag actatttttg aaaaggacat 173700
ttgaatgttc tgggtaagac tcaaacttca accagatgca ccaggttctt tctttcttat 173760
cctccaactt aattgctcag tgtctgtatt ctgcttgtgt cataacgtct ctttcagtct 173820
aagaaaaatg actctaagtg gctgtactta aaaatgagaa attgtggggt aatttttgag 173880
gctgtgtctg atgaaataac tacatttgaa tgtggccagt tggagacaca aaaaaagaaa 173940
gagtggccag tcgtatcggt caatggttgt cattcaagct tcaggcacac aaaggcagta 174000
cgctttgaac agtggcctta actccacctg aacttcccaa aagggccttt cgtctgggga 174060
aacatcaaag ttgcttttga aactcttgtg ttttctcttc caaggtgaga acaaagcatc 174120
agaaaggcac aaatactaaa agcttccagc ctctaagaaa gagggaaggg caaatacatt 174180
cctaagttac taatgtaata aaagccagaa gagttcttca agaattctag gggtagtgac 174240
gcatgccaga caagcccagc cctgaggaat acttaaaagc gactcgtgga gcatgcgcct 174300
cagaagtgcc atgctttcca ctggggaatg ggaacttgta agttactgtg gctctatatt 174360
aataaaagtg gaaattaaaa tgttttgata tagccctttc ttttcaacca aaaaataaac 174420
cataattaac cattataaga caggtcccct aattctttaa aaatttggtc tcacgtaaac 174480
tctgagcagc ccaggtgcca tttctaggca gcagtgcccg taccggagtg caggaggtga 174540
gccgccggtg gaaccgggag acccttccaa acacctcctg gcagtagcgg tggagttcct 174600
ccagctcatc ctcaatcagc acagcatcca ggggctcgct cttctgaatc agctgctccc 174660
caaacacaat gagctgatca atcttgttgg tatttaatgt aatttcctgt tggaagccct 174720
gttgagagag gagaaagaaa ggatttcaaa gaaagttacc ctgagcttcc actgcctgtt 174780
tcttctaaca gggccataga aaagcatcca aatgtcatta ttgttgtttt ccttcaccta 174840
ctactctagc tttagttttt aactaagtga caatgacatt ttaagaattt taagtgattg 174900
tctatattcc ccctcacggg cactggcttt tccaattaaa ataattctaa aagtttgaca 174960
cgggtggaca tttactgtta ttaggtgtga gagaaagaac ttgccatggc aaaacttgtt 175020
gggaacagaa catttcccat aataagccac gaatgggcat ttgcttttgc tgacacaata 175080
atattcactg gtgctgttat actagggaag gcaaatttcc atttctcaac ctcttccaaa 175140
atctggccaa ggagagaatt acagtgagat tagcctgtca tacagatatc agaaacaatg 175200
ggagagcgga cctctgttct tggccccact ggtgacaccc atactcctgg accgtaaaga 175260
acagtatcct tgcacgtgat aatctggtag tacacaggtg ggatgtagcc tggctgcttt 175320
aagaattctg aaatttgctc tcagagtatc gtgtgaaatt tgcacttggc cagctctccc 175380
acgcaaaggt gtgttctttt gagaagagct agggaagcag cagccctcac attcagttgg 175440
cgcatcttgt catcggcgtc actctctgag aagtgctcca cgttggtcag ctgcaggtcc 175500
atctctgtga gccacaccag aatgctctcc ctggtgccct caaattcttc cctctggttg 175560
gtgaaatgct gcaaaagtgg ggaggaaatc acatttctac tgaccacgga acaagagttc 175620
agacagacag caaggccacc ttcggccaca agaaaagggt acccagaata ctcagggaga 175680
aatctgcctc tagggtaccc agaaagcccc agaagcacta tgttgttcag aggctggggt 175740
ctggttctgg ctttgtgaga ccaaacaagc cccctcaact tctctgagcc ccagcttcta 175800
cgctggcaag tcggggagag agtgggaatg ttgattatgg tctctgaggt ccttaagcat 175860
ttgaaattct aaaattctct agtccaaatc agtgattttc ctctgtcctt tgaagagccc 175920
cctgaggggc caggccaggc cttctgcctg ttttacacat tggccttctg cagcttttgc 175980

-continued ttgacggaag gatttagtag cttcaagatg gaaaagcctt gatatcagga ttgaggccag 176040
cctggtgccc ccttctgcct tcactgatag aattctgaat gtgtcttccc agagaaagaa 176100
gactcagagc agttgtatca tctccaatta aggatgcctc tcaggttact gcttcacaga 176160
taggcagctg atgttcagat cagtatagct tcagtgccaa acgaaggcag attagccaca 176220
gccagatcgg caggagataa ttaatgcaag aggccgggca tggtggctca cacccacgat 176280
cccagcactt tgggaggcca aggtggaaga ttacttgagg ccaggagttt gagaccagcc 176340
tgggcaacat agtgagaccc catttccaca aaaattaaaa tcagccaggc acagtgatgc 176400
acgccggtaa tcctagttac tcaggaggct gaggcaggag gatcccttga gcctaggagt 176460
ttgaggctgc agtgagctat gatctcacca ctgcactcca gcctgggcaa cagagtgaga 176520
ccctgtcaag aaagaagaaa gagagaagag agagaaagaa agacggagag acaggaaagg 176580
agagagagac aggaagggag agagagacag aaagaaatgc aagggagttg tctaggttac 176640
tagaaaagcc aatgtcttcc tgagaaggag ggagggggag agagagagaa aagaaaggaa 176700
gaaaagaaag aaagcccaga tttacatctt tctagaatgg gttcaaccat gctctgccct 176760
gagaacagac gcagaaatta aaattgtgtc ctgtagtccc tgcctgtgac agtcctttca 176820
gtttataact ggattcacac aggtttacac agcacatctt ctgaatgaca gaaatctaag 176880
gtgaatattt accttcaaaa accaaacctt tgtgtgctct gaaattcaga gaataatcac 176940
agtccccaac cccccagtgc agacaggggc tcttgcattc acgtgccttg tccatcctcc 177000
tcagtgcgag agctgggggg ggtcccataa aaacagacag atgggcaaag cggggctcct 177060
tccaggggcc cacgtgttgc cttttccaga cccagcgaag cggcgccctg gactctgagc 177120
taacatgcac accaccacgg gttacagaag ttgtaaaaag agctgtgcgt tggtaacgca 177180
aatctcatca acaggccctg cctaagaagc cccacatgca aatccccctt ttaaaaaacg 177240
aacgttggca gctttgggct tctttgtgtt ggaggactgt taaaacagct caggcctgaa 177300
gtgaaacctt ctacctgctg ctttgtgcca caagcctgcc attgcgtatc gtgcgttatg 177360
tctcctggaa aatctacacc cgagccaggt gcagaggagc tcaccctgag tctccgcagg 177420
acggctgtga cccgcctctg aaggttgtcc cagcgctggt tgccctcgtg gaccatctgc 177480
ttcagcctgc tggccgtgtc tgtgcggttc tcccgggcca gccgccggta ctgcttgttg 177540
atgagctcca gctgagtgag ccgctcatga atctgccgct gaaaggcctg catcacatgg 177600
gaggggtcag agccaaagca tgcagagtgc caggacgccc tccttccctt ctacatccca 177660
agcgacctgc tgccaggggt tcatccccaa actgcaatgg cagcagaggg cctaattcac 177720
cagtcctgat gccagctaca gaacaggctt tcaagttcat tacatagcag ctggagtaca 177780
tcagcaatgt cttgcaaagc tgtctcagca gctgggggca ggctgtggtt taggcagccc 177840
ttgccagagg tgaggggaag ctggctactt agaggaagtc atttcagcag cccccaggct 177900
cgctgcaggc ttggttatga tcaggagacc gggatggaga aggtgtttac ctcaaacctc 177960
ttcagttcct ctttggcact cgtgtacaac acctctgagg aatttgggca ggctgccgtc 178020
ctctcagctg acttgagcca gtcctcaaag cgagaatagt cgtctaaaaa cttctgccac 178080
aggcgccacg tctcctcgat tctgatggga gcaaagcaac ttaacacaag ccatcccctc 178140
caagcctgtg cttttgcact tcttttatcc cctgacaccc gcacggttta gtgggggaga 178200
ccctgttacc ccttctggga aataagaggg acgccacttc ttgtctgtgc tcctcctgcc 178260
tgggagcgcc aagcagctca gagctcctgc ttcacagagg ttaaaaaacc aggagacagg 178320
gctgcctcca ctactgccca gctaggtcaa cggaagcaca gcggccagtc cacagccaca 178380

-continued ccccacacag gacagctggg gagagacatt actccggtta catttttctt gaataaatcc 178440
tttgataagc gttgggcctt ctctgccaat acctggcgca tttctaagtg aaatgaacag 178500
aatagttact gtgaatgagg tcagaagggt gtattgagtt cggctgacca cgctgaaggc 178560
atttggggga gcttagttct tacttcatgc gccgctccat ggacatggca caaatgttcc 178620
tccagcgtct gtccaggctc ctggtggtct gctggatcga gtcacactcg gtctcatttg 178680
cacaggcatc ggagtcgtgc agtaggacgt cacagatgtt aaacacggac tccacccctg 178740
cgctgtgttg ttcaatatct cgctgtagat cctgtgatta caacagagta agaaacctct 178800
tgagatgttg gtggcagcag gagggtcagc atcaaaggac ctccgttcct ccctcccttc 178860
tcccagctca ggggatactt ccctgggtgg atttccacca tgaacttggc agtacacatg 178920
gaatccctct catctttgtg ctacccttgt gctgtcagca cctgacacaa agtttaaaca 178980
ctggaaacat ctaggactta tgcgctgaac catgtgaggg gtgccacggt gatgggtgtc 179040
ctctacgcac tgacaggtgg cgccattact gttgagagcc catcgcccca cagacttcgg 179100
gtatgcatgg gatctactcc ataccaccca accccaaagg gctccagttt agacttggtt 179160
tcagggaggt ctttagaaac tgagtctctt cagcaggaac tctcaatctt ttatcagcta 179220
ccgaactctt caaacacaca ccaaattgtg catgcagcag tgtggatgcc cacagcttcc 179280
ccgtgagccc attcaagggc ttcatgagcc caagggagaa attctggcag acagaccttg 179340
cctccccaac tgataaagtc cagccaaagc tgtggtggct tggagagagg tggggtctct 179400
ggagtcttgt cctttgatga tgatagtgat gcagttcccc aatttgggaa aaataacatt 179460
tatgaagaga aaatgcatgg tcataggaaa aaactggaaa acctcttcac gaataaacat 179520
ggcattttta gtcatcatca gataatattt ctgctgtacc ccatgggtgg gctgcgggga 179580
gtgagagaga taaggaacct gttttgccat tctggaagag ttaggcatcc ctgatgtcca 179640
aattgtgtga caagtgacat gagaccacag cattaatttt aatatccaaa ttacattgtg 179700
agaaagcaaa cactaagtca aattctatct taattatttg ataatatacc aatttctaaa 179760
atctacacta ctttaaccac tattaactag actaaatcca gttcccagga ctcaacaaat 179820
ttcagttaat aagaggactg tactataaat ggtagctgtc accatctaca gaaaggcaat 179880
ataagcttca ttccaggtca ctttcatatt taaataactt gagattacta ctatattact 179940
agatgggacc actattttca tactctcttt tttttttttt ttgagacaag ggtttcactc 180000
tgttatagtg gtgcgatctt ggctcacgga aacctctacc tccgggctca agtgatcctc 180060
ccacatcagc ctcccaagca gctggccacc atactcagct aattttttgt atttttggta 180120
gagatggggt tttaccatgt tgtccaggct ggcctcaaac ttctgagctc aagtgatcca 180180
ccctccttgg cctcccaaag tgctgggatt acaggggtga gccaccacgc ccagccccta 180240
ttctcttact tttcttcata taaatacaca attccgatca ttgagtgttt aggttgatat 180300
aagaaaataa aatgctaacc cgccaactga attttaaatc aggcagttcc taacactgat 180360
cccgagtaca aatgaacacc accaggttat attcagaaga gatgtgtttt ccacttggcc 180420
accctgtgtg cactgtgaag aatgtgcagg gtgatttctt taaagctctg cagtgtgggt 180480
agaatgcctg atatgctcga atggtgggag tctccctgga gtcaatttga ggactaactt 180540
taaagttatt acatctaaat aaaattccag ttttaagaac tcttaccggt tcacagaact 180600
gtcatgggcc cttctaaaat tagaagatac atatcccatg taaatactaa aataataaat 180660
taggaaccct aatactggta ttaaaataaa taatactaat cattaataac tgaaaaatgc 180720

-continued ccatgacctc atctggctcc aggtgggtaa ggtctagttg aaaagccgag agaagttcta 180780
gtttatggac aatatgaatg ctctgtattt taataaactc tgcaattatc ctacattatt 180840
tattcagctt acattgaatc aaatggctaa agaaaactga ttaatattta gggtaaatgg 180900
ccgtaagaaa tgaactctac aataatttat aaaagaccat caacatcttg gttaaaaaaa 180960
aaaaagccca aacattttca aaacttttca aaaaacattt tcaaaaaatt tttaaaaacc 181020
atgtaaaaca ccacacaatg gcctactagt taccttgtac aaaaaaaaaa taaataaagt 181080
gatagactac attttaaaat gcagaccatt taagtgctag acaagaacat tttgcaagct 181140
gaaataatcc taccgctagt aaccacggag acctaagtct gcacaagaat caggttttag 181200
aaactgtcca aacctagaga aaaagtggat ttaagaaaca acataaaaca atgagaaaga 181260
cttttgccaa cagttctaac aggctcctgt tcatttcgtt tttctgcccc tgggcaggtg 181320
acacataacc ctgaggttgg ggaggaactt gggggccagg gggtacagag caagaggaga 181380
aggggagaca tgaaactgga gaagagaatg cagccagaag aatgagaata aaaaggaacc 181440
aaaaacagaa ggtaagggtg gctgaggaga agaaaaacag gctgaaaaga cagaaaatca 181500
tatagcgtga agcccccagt gccagctcct gaatgtgtct gtgggagggg cttgggtagc 181560
aagtgggaca ggatggtatt gggatggttc aggggggtttg aggtgaagct caactggccc 181620
acggcagggg ctattaatta gccagtggaa gggtaactaa caacaactcc aagccaccat 181680
ctggcacccc acagagaaac aagcaaccaa ccaatgaaca aactaggaca gggatcttaa 181740
agattcaatg aaagtggttc gtgatttaag tgtcacaaaa ttgccactac ttcctgtgca 181800
ttttaaagat gatatattcc gtaggaataa cccccattac cttatactta aaggtgttct 181860
atataagaaa ggtgaaacag aaaggactcc tatagggtct gacccctccc caaccaggta 181920
tattacagtg aggatccggg gacatcatgg ctcttagcta cttttggggg ctgagggctt 181980
ttgcagaagg caatactagg tgatgccatg tttttaggtc ttatttttgg aagcaattaa 182040
tttattatat ttagtttgaa aagtaaacat aggtaaggtg gttgtttttt taacccagac 182100
caaaaatggt cactaggtaa ggttttaaaa agtggcccat acataattct tttgtgtgac 182160
acatttgttt ccagtgtttt ggatggggta cttaaggtct gagtttagca taatataaac 182220
acactgtaac ttattctttt taacaaaaat actgaaagta tcctgagatc atctgtggta 182280
ggcagaataa tgacaatgac accccccaac cccccaacaa agacatccag atcctaatcc 182340
tggaatctgt gaatatgtta gattacacgg caaaggagaa ttacggttgc taatcagctg 182400
accttgaaat agggagatta tcctggatta tcagggtggg cccactgtaa tcctaagggt 182460
ccttaacagc agaagaggag tcagctagag ggagatgtga ctaggaagac agacacagag 182520
agatgcaatg ttgacggcgt tgaaggcaga agaaggcgca tgtgagccaa gcaatgtggg 182580
tggcctctaa aaaccaggaa aagcaaaaaa atggattctc cccagagctt ccagaaagga 182640
gcgtaatcct gatgacaccc tgatcttagc ccagtgagat ccatttcaga tctctaacct 182700
ccagatatat agtaaatttg cgtttttaag ctgctaaatc tgtaatttgt tacagcagta 182760
gtagaaaact aacacagcat ttaacttctt tacaataatg gtagtcctga acaccaattc 182820
cattaatttt ttttttttaa gtaaccaagg gatagaaatg tcactaaggt gatgctgaat 182880
tctataaaga cagaattttc aaatcaacca gattgaaatt atgtgccatt gtaggatggg 182940
aagaaataag gctaagagaa tagcagtggc tccaaactgt atgcttttgg gaacaaattc 183000
tctgcaattt aatgttctgt cacacttcgg atttataaaa aattaacaca caatcaacag 183060
cccctgcaaa atttagccag ccattcttta aggggaaaga tactgacagc ttccatataa 183120

-continued

```
tctacctgaa aaaactcacc actcagggta aattgttatt tgcaaggcct tgccttttca 183180
cagtctgttc aaagacattc atcctagtgg atcacacttg taagtaaaac tgatgtgttc 183240
agtagctgtg actccaatga gagacgcatt aaaatctctg taatgtccat taaaattcca 183300
taatacttat atcaatattc ttttctgcac aaagcaaaga cagagcctag atgacctcca 183360
tgaaaaagac atgcttaaag ttccaaggct aagtggaaaa accagtattt ttaatttgta 183420
gcattactaa atcatatcac tttgaaagcc agataacagg tatcttttaa acagtaattg 183480
taatagcact tagaaaagtc aagagcaggg agggccaggc atggtggcgc ctgcctgcag 183540
tgccatctac tcaggaggct ggggtgggag gatcacttga gcccagaagt taaagaccag 183600
ccggggcaat atagtgagac tccatctctt aaaaaaatgt caacagtagt atcaaatatt 183660
aaatctggtg aaaaaggttc acccccaatc cggtctccaa gcacctgtgg tatgtggtgt 183720
gtggtggagg cttaacatga agaaaacaga ttcaagtctg agaatcatac tgcttctatg 183780
gttgaaacag aatctgccca taggtctgag aaaaacaggt gaacaaaagc taaagaaaga 183840
ataagataaa cttagctatt taaaaaaaaa gtaaagacat atccaggcat tacaagtgag 183900
aatgagcatg tggccatgag accagggaag gcaggaaagt ggattcgata aaccagtgac 183960
atcaaagagc acctgtcagg tgggtacaat gagaaacact ggcagaactc agcagctttc 184020
aaactgccca atttccaggg ttggctcaga gcatgcatat ctgataacaa aaatgcacag 184080
agcattgcag ctcttaagag gcttcctaaa ctattggtcc aagcatgttc cttatcacac 184140
cttttcttgt tttaattttt taaaaaagct gtaccagaca cacagaatat aatcccataa 184200
aaaccttcct tggttagaaa agttgctttt ctttcaattc attgcctttc aaaactatat 184260
taacaaaaca caacaaagat cagttaaaaa aagacataat taaaaaaatc tcattaacca 184320
ccaagattaa ggtttgcatc ttaaacagta ttcacacagt ttcacaaaaa gctacatgaa 184380
tgtgggaggg agcactcaag agacagatat aagaacatgg aaaggtggtc agttttctct 184440
ggaaaaagca aaccaatgtt atggaatgtg agcacgtgaa aacacataga tatacgggga 184500
aggcctcagt cagtgcatat cgcggacacc gtactcttgc aagagctcat ttctgattgt 184560
cccacctgct gctcagcgag cctcttctgg atctcttgat catcgcagac atcataaaca 184620
acaggcttgg aaagctcaga ctcaattcga gccaaccagg tgcgaaggtt gctcatgttt 184680
ttgtccaact gctgaataaa agcaaaggtc tccttcagct tcttcaccct acacatattt 184740
gcagaaaaac aaaacgaaac aaaaaaaaac cagtgatgga aaacaaaagc ccaatactta 184800
gtggtggaag aatgtgccag taagagcatt gcagggtaaa aaagaatcta ttttgctttg 184860
attttatatc agaacaactc tcatgtcacc agatacgagt tctcagagaa tatgtgaagc 184920
tttgcaaggc tgttgcctct gttgattttc aaaaggactg agagttaatc cacccatgca 184980
aatggaagtc ctatcattcc cagagtgaga gcccctgaga cccagttcat cttcctgggg 185040
ctccagaggt gagaagatat gccatttttt cctaagtgaa aataaccact cctgacttct 185100
gcccagtttc tgccgtgggt atgcctgaga ctgcagcagc cggtgatcta ccctgggaga 185160
ttaaagatgt tacacgcctg gttcacttgg tggtatttgg tccacaaggc ctctcatggg 185220
accctcctct ctgagtaagc agagaacatg tgccaagccc taccgcttca gtatgagggg 185280
ttcacccagc cgtatacatt gaaccagccc atgcgggtag attatggggc atctctgtcc 185340
gtctaaaagg gagggggcaa aggaaatctg cacgcaagcg cagttctaaa tgtgatctcc 185400
ctcgccagtc tgcctcagct cccatccggc ccaactcggc gtggagcaga tttgaaagca 185460
```

-continued

```
cacgcatggc atgagtacaa cttggcgtgc acgtccacat gctgtcaagg ggacgtgatg 185520
tagctgttgg gggaaaacaa tctttttctg acatatatac taaaataaaa tgctccaata 185580
aaccgctttc cttaaagtcc taaagcagag cgaggtgagc caggatctgt cctggcgttc 185640
tgtgggattt gtagttaatt tcagacattt aaaagtaatg gctccaatgg aaagttccca 185700
cttatcaata cttacgttgg gagatgctgt cagaactgca ccccatagct gggagcacta 185760
gagagataaa tgggtgcact gaccctaact ctcaggaagc attgtgctcc atgccaccat 185820
cacctcttac ttgaccgaac aacctcctct cagcccccta gacttcctgc ccacctttgg 185880
ttctgtagcc aaagtgtaag taagttctag aaggcaagtc tgatccacgc tcaaagcctt 185940
caatagtccc tgccctaccc tgaaaaaccg gttcagcccc ttgatctctg tacctcaagc 186000
attcaggggc cactctgcct ctaaccttgc actctctcag acactgtgca cccaccagga 186060
cagggagtgc catggccagg ctgcagccgg ccagtttccg ccgcactcac agcacctccc 186120
acagggcctg gtgggcagga agctctccac aaatgcttgg tgaatggaca aatacggaca 186180
ggcacttcca tgggactgac ttctagttcc attaccagct acttttaaga tttagtgaaa 186240
gtcctttcac ctcagccccc ttatttcaag tacacccgca aagctgctta agcttcaggg 186300
aagtggtagc atcgggtgag gtgagggccg gaactccaga ggcaagcaga cctgggccca 186360
agttccattc tcccatctaa gagctctgca ccctgcaatg tacctaaccg ctgactctga 186420
gtttcttcat gatctgtaaa attatccacc ttgcaggtgg cggtgagctt gaaataagag 186480
gctgcatgta aagtcagctg cacagagtga atgctggacc acatgatgct acaatcacgc 186540
tttatttaca aggcattgga cctcacaaag ttctttcatc agtgttttat tctcaagggc 186600
aagcttggaa gaaggacatg tggtctggag gtggaagaac acagactctg tggtcagggc 186660
ctgggtttgc gtcctggcca tgtttaatgc catctataaa atggtgttaa cagtagtacc 186720
ttccttcact gggtagctga ggggactgaa tgagatataa catgtgaaag gcagaatgcc 186780
tcggagataa atgcccagca acttacagtt gtgataagtt tcaaggagcc atgttttcca 186840
aattacattc ttactgcaaa caccacaagg atacgttccc ttcaaagcca cagatgattt 186900
attaaaaaga aagtaacaga atccaggacc aggcctggat acagctgtaa cctagatcct 186960
gccttcattc ctatggcttc agaggtacac cctcctcacc ccagtatctt gccaccttga 187020
ttgccctggt tccaaaaaga acactccaga caactaccag ggtagctgag aacccctggc 187080
actgtgggac aaggagtcct ccaggcagtt cctgagggac tgccctcctg gaaggctctg 187140
ctggagaaga ggcccagcca cgagagcttc ccgggggtgg gggaagggct caggctcgtg 187200
acctctgcac agctctcctg ccctccccac ttctccctct tcccagaatg aaatctccca 187260
cggccttcat ctagcccctg accctattcc accctaagaa tctcagcctc tttcttattt 187320
tgaaaagaag agggctagaa tccaagtatt tatttatata tatttttctt tttccttgtt 187380
tcctctcttc taacttaaag caattaacac accggaagaa ttcaactggt taaatgaaag 187440
gagctaacta gcaacacaac agcctgggta cagatccaca ggactgtggt gatcttgaac 187500
tgttaaccct gggggttagg tgtgcaacac gcagaggggg tatggagaag gtgggggaat 187560
aatttgcttg gtttccccag ggctgtggta tccaaaatgg ggtgctcaga acaaaccaat 187620
ggggtgtagg aataaaatat gagactgtct actgtcatcc cattctttta aaatttctac 187680
aatgtgtatg ctttaaaatt ataaacttaa ttattaaaat aaaacatcta tatcccacgc 187740
tgatggccac atgtgctagg cctgttgtgc tccatgttag caactcatgt actttttttt 187800
tttttttttt tttttgagac agagtctcta tcgcctacgc tggagtgcag tgctgcgaca 187860
```

-continued tgggctcgct gcaacctccg cctcccaggt tcaagtgatt ctcctgcctc agactcctga 187920
gtagctggga ttacaggcac ctgccaccat gctcagctaa tttttgtatt tttactagag 187980
acagggtttc cccatgttgg ccaggctggt ctcgaactcc tgacctcaag tgatccacct 188040
gcctcaacct cccaaagcgc taggattaca ggcatcattt cctcttcata acaatgctag 188100
gagataggta gtattattat ccctacttga cagatgagga aaccgaggca cagagagtaa 188160
agagcttgcc caagtcacat ggtcaatagc ggaagcagga ttctaacctg ggtagtctgg 188220
tctggagctg ctgttcttaa gcactaccca tcctctcaca taatcccaca cacactaaca 188280
tgcacatact ggagatacag gatcattttg ctgcagtcag agaacatgac cagaagtctg 188340
gactcatagc tcaggataca ctgaggggta ggagctgata tagtagatgc tacaacctgg 188400
gctcttagca ggtgcctggg gaggaggctg gaaggctcaa tacatgctgc ccacgtttcc 188460
cctccatgat tttctttcag taaacactta accatttgcc ttgtcttgga tcctgcacag 188520
accctgagga ttcagagata gctggaagat aggacttctt cccagagagg tcatcaccta 188580
atttagatgt aatgttgaca ctgtaataca acataggagt tgctcaataa tagctgttga 188640
aggagtaaat gatgttcact catacettcc aatttgtctg atttgtcttc ttcataaaga 188700
ggtggccaaa ttagattttt aaagaaaaga ggtaaagacc agagcatatc agagcccttc 188760
tgccacaaag cagtgtgctg ccagcctagg agccactcgt gctcctcagc cctggtttca 188820
cacagggcca atgaagcagt gacggacatt cacatcacag gcatacttag tgcaagttaa 188880
agaggggggg aaggtgggag ggaaggaaaa gaaggtcacc aagtgacaaa gcactcatcc 188940
agccaggatt tagccggtat atcccaaact ccatccagag gcctaatacc tccaaatgcc 189000
tgggaatcta aatgttgttc ctctgatcat caggtaacaa cttaccctgg gactcatcag 189060
gtgcactgct gagcgtgtat cgttctgttc tgtacagaca ctgtaatcta attatcacct 189120
gtcccaggtc aggaagtatt tgtcttttgc caacccaggc aactgacctc cacattgttg 189180
ggccttgtta acactactct tgaaaaattt aaaatctcaa gttaatatct ggaaatgaga 189240
aaacctattc agaaaccaga ctgctggcac acagaagcaa ccacaacact gcctgacatc 189300
aaccacctga gcgctttgct gccgtggcca ccatctctgc acttgcccag gttttgaccc 189360
aggtgctctt aacatttctc acatagacat ttcaacaaat aacctttctc caggaaaaag 189420
cagcatgatt tcctgaatta aattccagtt atgagaatca gaaaaacaaa atttttaggt 189480
acaaaagcga agtcttccac ctgcataggc tctttattgg gagacctgaa caaaagcaaa 189540
atgttttcta tgaaaccaaa caaaagaatt atgcctaaga gccgctttaa attagaagag 189600
ttcttttgca gtgattatgg gtaaaaatgc agaaaacaat caaggcaaat aaagtttttc 189660
ttttaactag caatggatga gaatataaca ttgatgaaca ctgctctcct tccaaacaaa 189720
caaaatcaag tcaggttagc aacattctat ataccaagcc taagccttaa caatgtatga 189780
tgaaggcttt acatgtcaaa tttatacata tggaataatt taccatttag tcctatcctc 189840
tgtgctcagg agtctacagt taaattataa aagccctaaa tcagtctaag tgaacaaaaa 189900
aattcctatg cctaatttaa aaaatactaa ggaaaactga gatggttcaa gtatctgaat 189960
ttgtactgaa ataaacaaat agtcaaacct gcgggcagct gtcagttgca aaaaacactg 190020
tacaaatcct gtacaattgt atcttttcac atgactaaac atccttatgg caaaataatg 190080
cattactcca agatcctgaa gccctgattt aggggcagag gcattacaat acacgtctga 190140
gctcattgcc tctttaaagc atttttgtca ccagaggact tccattttcc acacggcata 190200

-continued atcactcctc tgccctgctt gtcagaggca gactgcagac accacacgca tgctgacgct 190260
gggaaagaac ccatcccccg atggctgagc acaaacactc cgcagccacc atctcatcgg 190320
tgatttctat tgtaaccaaa gcgacacagc cagagagcaa gacacaaggg acagcagctg 190380
gcgcctcggc ccaatgcaga gctgatgacg aaaatggcac ttactgttga tgagaaaaaa 190440
tcattcctta tgtttaagcg aaagctccaa gttcccggct gcacctccac ctcccagggc 190500
cgaggcagcc cctccccctg cccagcgtgc cctcttcact ggttcagcat cttgcacaga 190560
ggcggacgca gccctctcca aggctccttg tgagcacggc tggctggctc gcaggcacag 190620
ggcaatgcca gcgggaagga agacaccttc tcccctgcta actgcaattt ttaatctcag 190680
ttttcttcct tccagtaaac aaatatctcc agctttttcc tcacacacac agtctttgtt 190740
ctgacgctac aggattgcaa cgctggggga agaaagtcac actgttatct tggctatggg 190800
ttatttatga agtgctataa acagagagaa gaaacattta gatttggggc atgcaaaaga 190860
ggatttctgt cctcctcaaa ttaaatttct ctgtttcagg tttaaaagaa acagcaaaat 190920
ctgaagcccc tgagtccaat aggaatgcct tcctcttgtc ctcttaaaga agaaatatcc 190980 ctgtggggt tttctgctct gccctttgg tcctgaacat cctggtttag gagggtcatt 191040
tagtttatct gctttgtgca aaaaaattct attttgcagt ataaagggaa tttattgcag 191100
aggaagaaat tctgtaattt tccttgctag ctcctcccag ggtttaccat aatgtgtctg 191160
aaaattcctc cttatttata gcctcagttt cttcggacaa tcctgagtgg cagtgcttgg 191220
tttgtgtcta gtctacctta gactcattcc cagccttatt ctgagacttg atatcatttt 191280
tcaggagtcc ctaaagacca acatttagtc attattatat ccccaccttg aaacgtagca 191340
aacacgtgct ataccagtgg aatcagaagt gcagatctgg caatagttct cccaaaatgc 191400
tgcatctaac tcaggcccac gtggttggct gttcctgcaa cctgctgaac gtgaacctct 191460
gaggctcagt acactggacc tgcctgatgc tggccatcag gccgcttgct cattatcctc 191520
tttcctttgg ggagctcccc aaccctcagg aaggcatttc tgcagggtct gggaacagcg 191580
gccacccatt ctagaggcag aaggatcagg ctgatgggaa ggaaaatgga agtgaggagc 191640
ctcacatctg gctctccctg tgctaaaata atccctaaat ccttccagtc ccactggatc 191700
aggcaacctg ctaagaccaa cgcaagtcaa cttcgtgact agcagcattg tttggtgttc 191760
cagaaaacct tgagaaaata cagataaaag gagagcaatg aaaagcttta tcagtttaaa 191820
aaggcacacg tattcctgcc cattctgcaa ggcatggaaa acaatcttaa cacacaactg 191880
ccacggtcgt aacttctgag tttaacggta acattttaat tgccactact ataaagtagg 191940
tgagcttttc aggttggtag gcaaaattta gaagttatgc ttggtttaaa aagttccttt 192000
tatggatttg atatttctga tagtgagagc aattcagtgt aaacaggaag gagctaatct 192060
tcaaggtcat acggtactag gaaagtccct ccttgtcagt ggcttaataa ggacgacagg 192120
ccttgctagt ggtgctacca tcagagagaa attcaggaga gaacataaaa ttgatgacat 192180
ttgttcatga catgttataa catgacatct tccataatga acatttagaa agtacagata 192240
agcaaaaaga aaattacaat cattttcatt aaaatgattc caaccaagag aaaaaccaat 192300
gtaaactttc tgggagggta tgcttttcca cttcgctgtc caacctgtat cagatactga 192360
acgctttcat cagattattc acacatgctg ctagaaagag tctttaaaga gttcctcacc 192420
ctgatcccaa gtctctaaaa gaattcatca agatgtgcaa cctgccagag ggactcactg 192480
aagacacagc cccacctgtg tctacagagc tctggttcat aggacaagca gagttctctc 192540
attaaggaaa tggggaggga gttctgggaa acaaaagtag atgaattttt aaggagttca 192600

-continued actactgggt ttttaaaaat aaggggaggc ataggtgaga tcaggtggca ggtcaactcc 192660
ttctctggca tcagtcctat tgaggggatg agatccaagg accgtctttt cagagctttg 192720
gcccgtgctg gctgtgaacg ttaaccttgc atctttctgt ctatcaccca acaatttgta 192780
tctcaactgt tcttaggtaa tccagattcc tccaaaacag aggaacacac atattggcag 192840
ttctgaagga caccttctgt aatttagttg tctgtcttgc attcagaagt tttgctgagt 192900
cacttttcaa agacgttatc aaaggctggg tgcaggtggc tcatgcctgt aattccagca 192960
ctttgggagg cagaggtggg aggataactt gagcccagga gctcaagacc agcttgggca 193020
atatggtgaa accccatctc tacaaaaaac aaacaacaaa agcaaacaac tatccgggca 193080
tggtggtgtg tgcttgtagt cccagctacc tgggaggctg aggtaggaga attgtttgag 193140
cctgaaaggt agaggctgca gtgagctgtg actgtgccac tgtattccag cctgggccat 193200
acagccagac cttgtctcaa aaaaaaaaag aagaaaagag gagggagagg ggctaataga 193260
cacagataaa aaaagtttaa ctcttccttt aatttgacaa atgaacgtag tagcatataa 193320
tatttcttgt catcaaatca acttgggttc tacatagtta caatcaccaa acatatatat 193380
agtgctttaa atgacctgtg ttgatgaaat tacctgcatg tttcataaga gtgtagatgt 193440
caccactgta agaagctgcc tgagggccca tgaggacttt taaaagctcc cagagcaaca 193500
aggagggaca gccaatcaca ggcctcttta tacccacacc agggcccaag taatcttatg 193560
tgcacattcc tgtcccgggc agaattccca ttgtccttgg ctaaattatt taccttctct 193620
gagctgcagt ttccctctcc gtaaaatgaa gaatcacact gactttgcag tgttgtttta 193680
agaattcaaa tgaaataatc tatgtgagga gcctggcact taaaaaataa gcaatgttgg 193740
tttcctctcc tatctatcca acaatggagg ctaccacctg aaatgatcag aaatctaatg 193800
tggtttttaa ggaagcctat cctaaatccc atttttttcct ccagtgaatt aaaactgatt 193860
tattgaggcc ttggacttct gaaaaccatt cttaaccttg aagttagttt tatagttaag 193920
atcttgcagt aacaaggccg ggtacctatg taggatcacc ttccaatctt tttttttttt 193980
gagacggagt tcgctctgtc acccaggttg gagagcagtg gtgtgatcaa ggctcattgc 194040
aacctccacc tcccaggttc aagtcattct cctgcctcag cctcctgagt agctgggact 194100
acaggtgcgc accaccacgc ccaggtagtt tttgtatttt tggtagagat ggggtttcgc 194160
catgtaagcc aggctggtct caaactcccg actgcaggtg atccactggc ttcagcctcc 194220
caaagtgctg ggattacagg catgagccgc tatgcctggc cgatcttatt tttaacaaga 194280
gctgctgttc cctgcccaca gggccaaagc agaatactgt gggaaggatg gaagaggcta 194340
catggtgtcc tggatcctgt gggcaaatga agccatcagg gcatcccgca gagcaggttc 194400
ttgtcgccac tgttcaaatg taaagtttgc agcctgtgct tccaaccctt cccttccttt 194460
gtacaaggcc cagggtgaag tcagcatcag ggattctatg taaggctgat tctatgtaag 194520
gctgattatg acaggtccaa gtttgctgcc tcaacccaca gattcacctg aacaataaac 194580
tcagctaaga gcttcttaga ttctagctgt ctgtctcagc ctggcccttg ctttaaaata 194640
agaaaaatga ttccctccca aattccttag tgctgaaggg attagcactc agcacgtact 194700
gctcatttca gtgtttcaaa tgagagggtc tgggctgtca gggaagtgac actgcctaag 194760
ttgaaatcct ggttacgtca catgctggct atgtaactgt gggtaagctg cttagcttca 194820
gtcctcagtt tccttcttgg tatgtaaaat gggacaatgg tatctacttt acagaatcac 194880
agtgaagttt aagtgaaatc acacataaaa ggcatattgt taagaatata ggcagctggc 194940

-continued aatatatttg ctattatttc aactcctttt cccccagctg ttctttccaa aaagatcaat 195000
aaaattttac ccactgtttt atctctttcc caccaaaagg ttggctgaag acaggcaaag 195060
agtgagcgag gaaagcaaat agcctgttaa actccaaagt gatacaagca gagcatgaac 195120
gattaaaaat ggactgtcat tctaaccttc aggaaacatt agctagatct tgatcctgta 195180
tgatccatga atgggtttga tgccatcata ccctcgacta gtgccaaggg cccgagaaga 195240
cttaggctat aaaggcgacc acaaagacac aatttatccc acagaaatta tcttattctt 195300
aacgaatgca ctgaaacatt tactcatttc aacaaacatc tgacgcgcta ttctaagctc 195360
tgagaattag gtagtccagt tgcaggcctc actagggaaa gacctctcat cactagacat 195420
aaccaacaga atcatcttcc actcaataaa cacacgacct aagagtcttc tcatggaaaa 195480
gtaatgaaaa caaccactcc ataaatgctg gctcatatgt gctggcccca taccaaaggc 195540
atgacacata tcctcacagc agacagcacc agcggcctct gatgtaagcc aattagaccc 195600
attttacaga tttagcaact gaggcctaga aaggttaaat cacatactca agtttccaca 195660
gtgaataagt gggaaagtca agaatggttc aaaacttgtg ctcttaatcc ttacttaggt 195720
ttccatcatg catttctgta ggtttgtttt ttttccccca actggctgtg gagagaagtt 195780
gaatttgggc cagtctatgt tgccagccaa atccccctaa tatttgtctt cagcaaaccc 195840
tccactgcta aggaaccagg catgactcag atattttttc agaaggccaa gtatttagca 195900
gagatttaaa gtcttctaag atttagcccc agcccatctt tctagctcat ctcctatgct 195960
tggggccagt ggggcttctc atcacttcct gaacggcttc gatgctgctc tattctgtac 196020
ctgtttgctc tcaatgtatg tgtctctctc tctgccacca gtaaccgcaa tccctcattc 196080
aggaccatct gggaacgcag cccctctgta aggctcttcc taatcccagg aagatgggat 196140
ctgagctctc aaaccacttg gttttacaga tgctcagata cctactccca ctaatgtaac 196200
tgactcaact tacttcctgc ctgtaattct catagcattt agctcagtgc ctctgttgat 196260
tgactcaggt tcacttgtgg tttccagtaa acaatgaggt aaagaagatg ccaaacttaa 196320
taatttaaat tattaaattt aaataataat ttaaataata aatttaattt aaataataaa 196380
tttaaataat aagataaaag tatcttactt ttatcacctc ccaattcttt attcacctta 196440
taggttctcc tgtatattcc aaattctatg tgttgttcaa aacatctgag cacactgcta 196500
tggaaaggac ccgtgtggcc agtggaagca cagctgcaca agtggtccca aggccaagtg 196560
acggttcgct gtatgccacg tggccactga aaaaacatcc acctggagtt tgtctttaga 196620
gagggaattt gaagacattt aaaaattttg ggcatcatca tcattttggg aggagagata 196680
aaattatcag cgctatttct gataagattg cactggccaa tatagctttg atttgtggtc 196740
ctttgattta ggactgggct gcgcccaaat ccacatccta ggacaagaca cccatgggag 196800
acctggcact ctgagcccac acactttaag agtagactcc tgcccctgcc ttgagtgcaa 196860
gtagtggggc agtcatgggc ccccagcatc cagaagccag gcctgtgccc ttacctgatc 196920
tgccatactg aggcaggagc aacgggcatg gctccactgt ggggacacac aaatgctaac 196980
acagaggcag aatttctaaa caatacccccc tcccaaggat ccctttccaa atcagtttcc 197040
aactcttcat taaaactact ctaattcatg taaagttgta agctaaagaa aaaatattaa 197100
ggtgggatat actagcatat aattcttttt gtaacactga aagaatttcc actcattttt 197160
atcaaacttt gccttaatct gtaaacttat aaaattgctg gatcatctta gaggaagact 197220
gggttcagtt tactagatct gtaaagtaat tactgttcct ggagagtaat catttttagc 197280
ccatttctta ccttgatccg atgacatcaa aaagatgttg ccaacgatcg ttaattttgt 197340

-continued

```
tgagcttgtc atcgatctca gctgctcttg atttgttgct ggccttgatc aactggtcac 197400
ccatctgctt taactgtaac ttgttttcac taaacaagtt tatttcttcc atgcagtcct 197460
ggcaaaggca ccaaaacata aagcctggct aattagccca aactcatttc ttctccagcc 197520
acagacatag agttacctct tgaaattaaa aaaaaaaaaa aaaattggcc aggcatagtg 197580
gctcatacca ataatcccag cagtttggga agccgaggca agaggatcac tctagtccag 197640
gagttcaaga ctagcctgtg caacacagca agaccccact tctaaaaaca ctagcaaggt 197700
atgctggcac atgtctgtag tcccagctac tcaggtggct gaggtgggag gaccccttga 197760
gccaagaagg ttgaggctgc agtgagctat gatctcgcca ctgcactcca gcacagtgag 197820
acactgtctc aaaacctcat accttctaat gaagctaact tttcagtgag cagctaaaaa 197880
gtcaggcaac gcgcatcagg caaaagcaaa atatgtaagg caataattat ttttaatagt 197940
tatttaattc aaaagccctc tgtttcctct cacagatttc ttctaaccta cgtgggagct 198000
gaggacaact gagcataact aattaggctg ctatcagtta cagttttcca gaggtttgac 198060
tgggtggtgt tttaggtgac tacagcaaga atgttattac ttttccctgt ggagaccact 198120
gatcatttca aaattatgag cctcactgct gttggcctct cccctttaac aaggggagct 198180
tctttttttt ttttgagatg gaatttttgc tctgttgccc aggctggtgt gcaatggcac 198240
catctcggct cactgcaacc tccacctccc aggttcaagc aatcctcctg cctcagcctc 198300
ccaagtagct gggattacag gtgcccacca ccacaccagg ctaatttttg tatttttagt 198360
agagacgagg tttcaccatg tcagccaggc tggtcttgaa ctcttgacct caggtgatcc 198420
acccgccttg gcctcccaaa gtgctaggat tacagcaatg agccaccacg ccaggccaag 198480
gggagcttct taataacaac tagagaaacc ctaactcact tggggtatca gctgacatgt 198540
aaggatatgt aagcccccttc cctggtgaaa ctttctaatg gagagaaagc aactctcctc 198600
ggtaccatgc ccactgacaa tggtctcaca ctcccatctc tctggaacct cctctcttcc 198660
aactgttctc tcaaaaggat cgaaaatagt gaagtccctt caaatttcta aaatgctact 198720
ggaaacaccc gtaacattgc ccctgtttgg gcttaggagt gaggagggcc gacaattcca 198780
tggtagtcat aactacatcc acctgggtgt cctcccttac cttctgtaac ttttcaatca 198840
tttcttcaat actaatgtcc gctgtctgta gaactttgtt ttccatctgc accagccagg 198900
cacacaactc tttatttttt tcattgaata caacccatgt attgagtctg tcttcaatct 198960
cctgtttacg tatggccacc tgcaaatgaa aatacatttg gcagctgagt atagccagga 199020
aggaaagcac cccccttctct ccctcaaaaa aactgagttt cattcatttt aatcagtagc 199080
tctccgcact caaccttgtc tggttttgcc tcttctaaac ctagggttta gcatcaacag 199140
aagttcctta cacctgtgat aaatgtcata aaaaataaca aaataaatac tgtacctgaa 199200
atgtagctga ttggaaggat tgtttttatc caatactcgt gtgttactat ctggttatag 199260
taaaaattag aaacaggaaa ggctagatga agatataacc caaatccttg cccttataac 199320
aacgaatcaa atccttatac caacataagg acaatgtcct atttaactta aaaactatta 199380
atccagatag aatgtcaatc aaacatttat aatgcaaatg gaccaggaaa actacagccg 199440
tttaaatgtc cttagtgtta tgcttcaaaa caaagcaaaa ccaaaaacaa tgtacatcac 199500
tcatttaacc cacttgcccg ttatgcactg gattttggat ggaaaccata aaagtatcat 199560
caacagctgg tctgcagcaa gcaggctgac cccaaaatac ccaatacccc attatgcata 199620
agtaacccct aaactgacat cagctaaggg tcctcctcct taaaggttta aatttcacta 199680
```

-continued

```
aatataaatt taaataatgc aaatcagcct aactagatgt acaaaagtat tcccaggttt 199740
taagaatctt cagaatctta gcgttaaaag gggtggctaa gagttctttt ggtaaagttt 199800
tgacacccca ctatatggac caggaaacca agggtgaatt ctctgagatt ttcctgctgt 199860
gtataaagaa acctctgctc ttttcggagg agaaaatact gaatgcttat atatcctagc 199920
cagccaaacg tgttaaaaag gcttgaaaaa ctatcctaga aaaacaagtg ttgtgtttcc 199980
attcctcggg gcatctgttt atcttttaaa aatcctggca ttttgcacat tgtcattctg 200040
attgatttca taatagtaac aattaggaac atctgggccc cagtcttcct gtctacctta 200100
actttcagaa cacttttcat atattctaaa cattttcttt tgtataaaaa ttgaaaagtt 200160
ctaaaagaac atttaaaatt agggtacatt gtgaatatta aatactaaaa tcaaggagaa 200220
cgtgtctgaa tttcaacttt ttaaatacat ctcttaattc acaaaaatga gattaaggaa 200280
tttattttcg ttggaattct ctgttcttaa aacaaagatc tttaagacta tttgaacccc 200340
ttaattcaat actgatcctg tcacaagcct ataccgtgta atactctatt aatacaatcc 200400
cattcttaat aagttgaagt gatccattga gacaacatag cagttgatca tttctcttac 200460
aggattttag aaaccagcta cttgaaataa acatcaggtt cctgtgaatg cagagtactc 200520
atatgaaatg ctcccatgcc tggtgggcat gaagtaagac tcctgctgtt aggcccagaa 200580
gagactcccc agtaaaggac ctcttcactg ggtccagctt ctgatacact gattaggact 200640
tgccacctac acaagccaga gagcagtcta cacatctgat cagaattgca atttctgtct 200700
ccacttaaag tgacttttta aaaaagctca ttaaaagcgt gcaaagttct agcatttagt 200760
gctggagaaa caaaagggtc aaatctgtta aacctgttgc tgccttctaa aggagcagcg 200820
gccgggccag gggtcccact gaaaagggcc tccggttcaa tgaaattaag ctcctttcta 200880
ctttgtctgg ccttcagaga catttcaatc cactcccaaa cagccgtgcc ctgcagtgag 200940
ctgacttacc cttaagcaga ggtcctccca ttgtctgtgc aaatgctcta tttgctcctt 201000
caaaaccatc acatcttcca cgagaacgtg ccgggttaag tccgccttca tagtttgaag 201060
ttctttcaag ttctgagtcc agctagccaa agactgttct agttcctgca tttaatcaca 201120
agaagggggt aaaaagcctt caactcaagc ggctgttgtt tccaaacctg taggctaatc 201180
ctttgattag actctggggg aggggaggcc aggagagagg gagggacctt ctgaatggga 201240
aacagcccaa gacgagcgcc tgcagttgtg gttggccagt tctccaccac cttcttatca 201300
aaggaaaact ctgttctacc tttattttca tttcctcagg tagctctgat tttgatagaa 201360
tttattctat tttaaagtca cataggtctt catttagagg aaagtgtatt tggagtctaa 201420
taatctttac acacacacac acatgcacac atacaatttt taatcctgaa actacatttc 201480
agataaagtg tgattttcca tttaaaaaaa ccctaagaaa tgcattgctg ctattgtggc 201540
aatcacgtaa cagcaacaac ttctgttcac agggaattat ttttggttaa cttttgaaaa 201600
taatgagtaa gtataacgga agaaaaaata aacttttcta attggcaaag attagttagc 201660
agatattttt ctggccatgg aaacatctat cttttaaaat gcagcattgg ctgggctcag 201720
tggctcacac ctgtaatccc agcactttgg aagcccaagg tggacggatc acctgaggtc 201780
aggagttcaa gaccagcctg gccaacatga tgaaacccca tctctactaa aaatacaaaa 201840
attagctggg tgcggtggcg cgcgcctgta atcctagcta cttgggaggc tgaggcagga 201900
gaattgcttg aacccaggag gcggaggttg cagtgagaca agatcgcacc actgcattct 201960
agcctggctg acagagtgag actccacctc aaaaaaaaaa aaaaaaaaag aaaaagaaaa 202020
agaaaaagaa aaaaaaaaga agcatctgtc aaattgaaac cttctgaaat ctaggattta 202080
```

-continued

```
ctcaagagat ttactttcac agcagggaag gtaaaaggaa acaaccagaa cactcaagag 202140
tctaccagat ttttattgtg cttacaattc ttcatgactt ggcacatttt aagggtcttc 202200
actcctatct gtcaaatgaa atctgaaata agatactatg ccttttttaat ttttattttt 202260
tttttaagag acagggtctc accctgtttc ccatgctaga ctacagtggc atgatcatgg 202320
cttactgcag cctcgactga cctcttgggc tcaagtgatc ctcatgcttc agcctccaga 202380
gtagctgaga ctataggcac gcaccaccac aactggctaa tttttatatc tttttgtaga 202440
gatggaagtc tcaccatttt gcccaggctg gtctcaaact ccccagctca agtgatcccc 202500
ttgcctcagc cccctgaagt gtggggatga caagggcgag ccaccatgcc ctgctgatac 202560
tatgcctaaa atcagggata agtgtgaaag gccctaacaa tatgttaatt ctgattgatt 202620
ttcagagttc taaaagctac actggcatga tttcataact taccaacaag aatttatgtt 202680
taataaaatg gcccagagaa ttctttttaa aggttgcatg aagattgagg aattaacacc 202740
tttctcagaa gataaatcat taggtattta acatttttat tacctacttt tggtctcacg 202800
attggttcca gtagatgaca gcagattcca cagtggaaca ctttggaaag ctacataaca 202860
taaagggggc cacctgccag ctgaggtgta ccacttactg acttgaaatt ggagatctgg 202920
aaacctctga gcttcaaaca gagtttccca gtcaggtggc aggaagctca gcctgtccag 202980
tgccctgctc agaggtgctg gctcggccac cgagttatgc ccggccaggt ttcaatcagt 203040
ttggtttgaa tacttacaat attgacaatc ggaaagtgta cagtcactgg ataaggttga 203100
gactcctgtt ttactctcac tgccctgccc ttttcccctc taacactcac catgttcata 203160
cacatacaca cacacacaca cacacacaca cacacacacc cctatgcata cagtgtggct 203220
ctctggcaga ctggaccatt agctccacac atggcaggga ccatgacaac actgctcacg 203280
gattcagtgc ccagaacctg ccatggtgct gctgcacagc aagttttcag ataccaaaat 203340
gtacggctga aaggaaagca atttggctgt atgtctcgag agctttaaaa tgttcataaa 203400
gactaaatga aaaaagcagg gagtcaaaca atatatagaa tgaggtctct tgtggaagtt 203460
tactagagct gacgatcagt ttgtataaaa atgtcaacaa tcatgcctgt ctttaaatta 203520
aattgctccc tctccctctc cccctcccct cccccctccc accccctccc tctcccttct 203580
ttccacgtct ccctctgatg ccgagccccc tctcccttct ttccacggtc tccctctgat 203640
gctgagccaa agctggactg tactgctgcc atctggcctc actgcaacct ccctgcctga 203700
ttctcctgcc tcagcctgcc gagtgcctgg gattgcaggc gcacgccacc acgtctgtct 203760
ggttttcgta tttttttggt ggagacggag tttcgctgtg ttggccaggc tggtctccag 203820
ctcctaacca cgagtgatct gccagcctcg gcctcccgag gtgccgggat tgcagacgga 203880
gtctcgttca ctcagtgctc aatgttgccc aggctggagt gcagtggcgt gatctcggct 203940
cgctacaacc tccacctccc agccgcctgc cttggcctcc caaagtgccg agactgcagc 204000
ctctgcccgg ccgccaccct gtctgggaag tgaggagcgt ctctgcctgg ccgcccatcg 204060
tctgggatgt gaggagcccc tctgcctggc tgcccagtct gggaagtgag gagcgcctct 204120
tcctggctgc catcccgtct aggaagtgag gagcatctct gcccggccgc ccatcgtctg 204180
agatgtgggg agcgcctctg ccctgccgcc ccgtctggga tgggaggagc gcctctgccc 204240
ggccgccacc ctgtctggga ggtgagggga gtctctgccc ggccgccccg tctgagaagt 204300
gaggagcccc tccgcccggc agctgccacg tccgggaagt gaggagcgtc tctgcccggc 204360
agtcgccccg tccgagaagt gaggagcccc tccgcccggc agccgccccg tccgagaagt 204420
```

-continued gaggagcccc tccgcccggc agccgccccg tccgggaagt gaggagcgtc tccgcccagc 204480
agccgccccg tccgggaggg aggcgggggc agcccccgcc tggccagtcg ccccgtccgg 204540
gagggaggtg gggggggcct ctgcccggcc gccccttctg ggaagtgagg agcccctctg 204600
cccagccgtc accccgtcta ggaggtgtac ccaacagctc attaagaacg ggccatgatg 204660
actatggcgg ttttgtcaaa tagaaaaggg ggaaatgtgg ggaaaagata gagaaatcaa 204720
attgttgctg tgtctgtgta gaaagaagta gacataggag actccatttt gttctgtact 204780
aagaaaaatt ctgccttggg atgctgttaa tctatgacct tacccccaac cccatgctct 204840
ctgaaacatg tgctgtgtcc actcaggatt aaatggatta agggcggtgc aagatgtgct 204900
ttgttaaaca gatgcttgaa ggcagcatgc tcgttaagag tcatcaccac tccctaatct 204960
caagtaccca gggacacaaa cactgaggaa ggccgcaggg tcctctgcct aggaaaacca 205020
gagacctttg ttcacttgtt tatctgctga ccttccctcc actattgtcc tatgaccgtg 205080
ccaaatcccc ctctgcgaga aacacccaag aatgatcaat ataaataaat aaacaaataa 205140
ataaaaataa aaataaaaaa taaataaata aattaaattg ccccagactt gcaaccaaac 205200
tgtcaaagag ataagtttcc accatcttca ttcaaccaga taaattatct ataccacaag 205260
aatacctgaa aatttccaat tttttacgta acatgggatg taaaatttca agttgtttgg 205320
ctgcgaaaag cggtgtgttg cacaggattt gactggactc tgcagtatca ggacagcatc 205380
taagccttgc ctgtggactc aattaccagt ggaactgtca agtcccattt ctctgtacta 205440
ccatttgggt aaaggaggac caaaaaagaa cgggtatata aataaaattt gacctgcata 205500
tgcatactct atctttggaa gaaaatacaa caaacttgta acattgattg cttctgtgga 205560
gaggaactga taagagaaaa attttactta tacaaaaatt atttaaaaac caaactgttc 205620
caaggactca atctttggac aagtgttatg aaacacagat gtccattgta gcaattttca 205680
taatagtgaa gttagaatat atgtaaaaca tatatgtaag gaaattattc cattcctcaa 205740
cgtggctgta gtgggaatat aatttttctt ttttatcttt tatctttttc tttttgcagc 205800
tgtgcttaga agggaatata attttatgag gaggaaagtc aagctcaaat tggtcaagtg 205860
gctagcgtat ttcccccagg tgaatcaggg atgaaacaca ctgacctgga caagctttgg 205920
gttacttggg atcttttcag aatatggtca cgggttgaac gaactcaatg ctttttgcct 205980
ttccctgatt actttccact gataaatagg atgctgagac cgtgaaagct gaaaagatcc 206040
cactggaaac tgagaagtgt gatacttgag aaaaattatg gctgctcaag ggtttacatt 206100
tcatgttctg cacaggtttc tagaccttat ggaaggaaac tctgtgtttc agctgagagc 206160
atgactccaa attatttccg ttgttaccaa agtcttgctc taagcctaat gaggtaggga 206220
tgataaaaac tttgaaaatt tggcatagaa atcttgttaa cctaataaag ccactgactg 206280
acacatcacc accaaatatc acatttaaca gtgaaatgtt agaatcattt tcttctaaaa 206340
tcaacaatgg aagactcagc tattaatact tctgcttaac aatgttctga aggtattgac 206400
ccgtgtagga aaaataggaa aaaaaaaagt atattaaaaa gaagaaacaa acaaaaataa 206460
ccttgtcatt attgacagat gatgatggtc tcatagacac ccaaaaaaat acataaacga 206520
attattggaa ttaacataag agtttaacaa gatggttaaa cataaatatg caaagaccaa 206580
ttacatttct aggcatcagc aataatcagt taggaaatat aattagaaaa aggcagtatt 206640
ttcaatagct tcaaaaatat tgcaccaaga aataaatcta acaaaagata tatcttttgt 206700
gattaggaaa attataacaa gaataagcca ggtgtggtgg ctcaggcctg taatcccagc 206760
actttgggag gccaaagcag gtggatcacc tgaggttggg agttagagac cagcctggcc 206820

-continued aacatggtga aaccccgtct ctactaaaaa tacaaaaatt agctgggcgt ggtggcgggt 206880
gcctataatc ccagctactt gggaggctga ggcaggggaa tcccttgaac ccggaggcag 206940
aggtttcagt gagccaagat cgtgccactg cacgccagcc tgggtgacaa gaacgaagct 207000
ccatctcaaa aaaaaaaaaa aaagttataa accattagtg aaaacaacta aataatatga 207060
ccaaagggaa atatatacca cagtcatgag catgagcagg aatactaaaa ataattatcc 207120
aagttaatct aaaattcaat gcaattcaat taaaactctt atcagaactt ttcatggttt 207180
aacaagctgt tcctcaaagt tacggaagat caaagaccca gggacatcca aagtaatgtg 207240
agagaacaag gtgtgggtat acatcacacc tgaaataaag atgtgttaca ataaagtgca 207300
gtaatcaaga cagtttgata ttaaagctga catacacaga ccagtggaac agagaactga 207360
gaaacaaatc ctgcgtttat ggaaatttgg tatttgacat tagacaataa ataggcacca 207420
agacaactgg ctatccatac gaataaaatt agaaaatgga tctctgcctt aaaacgtatg 207480
caaaaatcaa ttcctcaatg aataaagatg tgaatgtgaa aatcaaaaac taaaaacttt 207540
ttgaagagaa tgtaagcacg tattttatga ctttagtatg aagattttgc aaaggaagcg 207600
gaaaatacaa atcatatagg aaaatactga ccaattcatc cacattaaca aaatatcttt 207660
tgttcagcca gcaataccaa ggaaaacgca gaaaaacagg ctctcagatg ggaaaagaca 207720
tttgcaatgt atatactcag tagaagagga atatttagaa taaataagca gctccttcaa 207780
ctcaataaga aaaagacaaa tagcccaatg gaaaaaaatc agtaaaaggc acaaataggc 207840
aattcacaaa agggcaaata tgaaaaaaat gtgcaactga ctaataaact ataaagagat 207900
actatctcac agctgctgga ttagcaaaag tttaaaaaaa aatctgacaa taccaagtga 207960
ctacagaagg gatatataaa ttgttgtata ttcttataat gcatactata cagcagtgag 208020
aatgaatgtg cattaggtgc caacatctat gactccaaat cacaatgagg gaaaaaagtt 208080
acattgtagg ccaggcgctg tggctcacgc ctgtaatccc agcactttgg gaggccgagg 208140
caggtggatc gcttgaggcc ccaggagttc aagaccagcc tggccaacgt ggcgaaacac 208200
catctctact aaaaatacaa aaaaattagc caggcctgat ggcacatgcc tgtaatccca 208260
gctacttggg aggctgaggc acgagaattg ctggaacccg aatggtggag gttacagtga 208320
gccaagattg cgccactgta ttccagcctg ggtgacagaa ggagactctg tcttaaaaaa 208380
agaaaaaaaa attacattat atatagtact gcttatataa agttttaaaa tttatgtatt 208440
ttgtttactt tttagagaca gtcttactct gtcatctagg gtggagcata gtggtgcatt 208500
catgagtcac tgtatcctcg acctactggg ctcaaaggat cctcccacct cagcctcccc 208560
agtggctagg atcacagtca agtgccacca catccagcta attaaaaaaa attttttgct 208620
gtacatatgg ggatctcact ttgttgctca ggctactttc aaactgctgg actcaaggga 208680
tcctcccgct gcagcctccc aaagtgctgg gattatagtt gtgagccacc atgcctagcc 208740
atataacgtt taaaaacaga aagcaattct acatctcatt gacagcaggc tgggcgcctg 208800
ctgtcacttt gggaggccaa ggcaggagaa ttgcttgagc ccaggagttg gagaccagtc 208860
tgggcaacat ggcaaaaccc tgtctctaca aaaaatagaa aaattagccg ggcatggcgg 208920
tgcatgcctg tactctgggc tactcggggg ggctgaggta ggaggatcgc ttgagcttgg 208980
aagttggagg ttgtagtgag ctgagactgt gccactgcac tctagcctgg aagacagagc 209040
cagaccctgt ctcttaaaaa caaacgaaca aacaacactg acacctacaa acacatgtat 209100
taaaattatt aggacatgtg taagaatgat gaacaccaaa tccagggtta ctgacacctc 209160

-continued taaggagaag ttagatcata caggacactt gaactgtgtg tatacttttt aattttttag 209220
ctaggtgatg gtgtcatggc agtttgtcat attatttgtt atgcctttta gcacatcaga 209280
catttttaca acaaagaaaa aagatgtagg gagaaagaca ctaatttctg gcctaatttg 209340
aagtataaca ctattcattt cttcctaatt ttttcaattt gatccccgaa agtcactgaa 209400
ggaagaaaaa aattaaaata ccactccaac agtctctcaa tgtcttttaa acatcaaagc 209460
tgcagacaga aaagagatgc agggagttgc tgacctggga attttcctgg ccccaattcc 209520
tatccataag tttgccttgt ctccagcaaa ggcctaaaat atccaggaag ttttgctagt 209580
gtggtattca ttaggaagaa tatatagttt ggatggtttt ataaaaatgc tatactggag 209640
caaactccaa cctactggct ttcaaaaatg aattctttag tcatatttta ctcttgtttc 209700
aaagaagagg acatttgata agggaacagc ttttacagga atctcagagg ccacatctta 209760
tattacagag gaggagcaga cagaaagaag acctgaagga gaaaacccct aagatcctaa 209820
gaagtgagtt tttgcaaaag tctttctcgt cttcaaacaa caatcgtaaa aagcatcaat 209880
tctaattcct taagagacga gcatgttatg ttagacagat cgggaaaata ttttctgatt 209940
gaaaatgaaa actcagtttc aatacagaaa gaggcaaaga agcacttcaa agtactcaga 210000
aaacagctaa gtgattatct tggccacttg tttggatttc aataccttaa tcagctcttt 210060
ttcgttatgg aggtcctcgt gaagctctgg aagaggatct tcactttgtg cctttaaaac 210120
ttgcagcctg cttttcaact ccttgatttt cttttcacac tggtcccagg tctatttgaa 210180
aacaagatta aaactggtaa gtattttgct ctttagaatg aattgtagaa atagaatagc 210240
tcatttaatc cacataatct ttctattaag tttgttttta ataaatcaca cagacaccca 210300
gttccctgtc ttaagcagac tatggtctcc aaaagcagaa ggaacaccaa tatgactcga 210360
ccctccttgc agctttacct gtggctcatt tcaaccacca ggctaggctt tgcttgaaaa 210420
tagttcttcc gggctgggca tggtggctca agcctgtaat cccagcactt tgggaggctg 210480
aggcgggtgg atcacctgag gtcaggagtt tgagaccagc ctggccaaca tggcgaaact 210540
ccgtctccac taaaaataca aaaattagct gggtgtggtg gtatgtgcct gtaatcccag 210600
ctacttggga ggctgagaca ggagaattgc ttgaacctgg gaggtggagg ctgcagtgag 210660
ccaagattgc accactgcac tccagcctgg gtgacagagc aagactccat cttaaaataa 210720
ataaataaat aaataaataa ataaataaaa ataaaaaagt tcttcctctc tccccaatcc 210780
ctctcatcta accaatgtga tttctacttt aattttggaa aagttcacac ctaaaaggct 210840
actgtacgga gtaactgtta gcattgacag tctttggtat atgctatgac agcaccacag 210900
aacacaagca ctcagccacc ttccttgtct tcttttccac cgtcacccct ctcctctgct 210960
ggctgtcttc tcctttctac agcctggctt tagtgacctt ttcacattca accttcactt 211020
tccacttctc accactgtgc tgactaccac cttctgctta aagcactttc ctgtttacaa 211080
agcattttca actttattaa ctcattgtaa ttataataac cttaggagat agacaaggaa 211140
agtattatca tatttaaaac aagtattatc atatttaaaa tgggaaaact aaggctcaga 211200
gaaaaatgac tagcccgtgg atctggggtt aaaagccaag tcaagggtca accatctctt 211260
ttcttcaaat tttaactgtt gaacaaaata ggtgcctgca ttttcaacta tagggtattt 211320
atattcgatt cattaggata aacttctttc ctgaagttac taaaactata caaacctaca 211380
atgaaacact attattcagt acagctgata cctaaacata cttgggttgg cctcagtcta 211440
tggtaacctc tcactgaagg gaggccactt gtgtagcaat attaactatc tggaactcaa 211500
ctcaaaagaa agcaaaggag aagcaaaacc atgagttctt caaactgtta tttgcaatta 211560

-continued tcattatgct tcacaaacat ggcagatgct taacaaatgt ttgctagtta atgaattcca 211620
tatagtccat atatcaaata aaattcagat actttattca caggagaaat tttcaagccc 211680
taactcagca tatatttact cttaattcag aaaaatatgt ctggtaagtt tggttatcta 211740
gttttggcac acacgacaga ctagagagag tgggctataa gaagtaagtg agcttggaga 211800
aagacaaagt aaaaatagac agtttgacat taagaggaga gaaagaaaaa tgataaaaac 211860
catatcagaa ctcaaagagc acagtagttc agggagggcc acaggttcaa agtaattcag 211920
aggccttgag aacaacttgg tatcttagca taacaaaaca ataatgattt tcctaacagt 211980
gactcaaaat ataacactgt agttcttaaa ggtataatca tacattattt ggaaaattca 212040
cttatatgga aaagtgcatt ctctgatgat agcagaaaaa tgaagtgttt ctgtctgttc 212100
catacatgga acattagttt tatgtattga actttcattg aatatgtttc ctgtttcata 212160
aaagtaagta tcttaataga atctcaagta tttaaatact aaacattgag ctcttgcaat 212220
gctatatcat catttcacat taagtaactg gcatgactta cagattacag cttgagttgg 212280
aaactcatga tactatagtt tcctaaaacc atttccattt tcacaccaca aatgaaaatc 212340
tatgtactga atttgaatat catgaatgga aaagtaagtg gtgagtttac ctctacagtg 212400
ctctggaact gcttaatcat ctctgccagc tggggctcca tgtctttcca gctgtcctga 212460
agttgactga ttctcctacc cacagactct ttagttttca ggtcagttgt gagcagtaac 212520
ttttctccag cttccaaggt tagggcacag gtagttcgcc tcctttgaaa atgaatttct 212580
ttattctaag aaaaaaaaga gaagtaattt gcttaggttt ctgatgtgtt caaaatgtga 212640
ttgtgtgtgc ctgtgtatat ttccttcaga gcttttctta agagttaaac tagatataaa 212700
ttagacaaat tgggtcagaa tgtacataca cacacacatc aaaagctaat gttttacact 212760
gagtagataa gcataccact aagtgaggtg ttcttaaaat aatttccaaa gattggtgag 212820
ataagattct cagtgtaatg attagcagca cagagaaata aaaaaatata catcatagaa 212880
taatagcctg caaggtaaat ggatctaaga gtattaagaa agtgaatgga gtaacagacc 212940
tgaaatcaag taacagacct tatattacgc taaacaaatg taaaaggaaa gaacgcgaga 213000
aagggtaaaa tacaaaaaat atacatttct taagcttttt atgagcacat aaacatgtac 213060
attgatgtgt gccccaaagg cgcagcttta aaaaatttca tccgaatatc atgtaggctt 213120
tctgaaaatt aaaaacaatt taaaaacaat agttttagac ccgaagtgat ggctcatgcc 213180
tgtaatccca gcactttggg aggccaagac aggcagatca gttgagctca ggggttcgag 213240
accagcctgg ccaacatgga gaaaccctga ctctactaaa aatacaaaaa ttagccaggc 213300
atggtggtgg atgcctgtaa ttccagctac ttgggaggct gagtcccaag aatcacttta 213360
acctgggagg cagagattgc agtgagccaa gatcacacca ctgcactcca gcctgggtga 213420
cagagtgacg ctttgtctca aggaaaaaaa aaaaaaaaaa tttaagagac aaggtcttgt 213480
ttatttttat ttttttctat attttagtgg cggtgttaca gctccgtgac tgctcctgca 213540
gagcagggcc gctccgcagg cagtgtgcag agagtagcga aggtcctgtt ttttaagaga 213600
tgcgccacca cacctggcta catgggcgtt ctttaaagag attgaaacta ggtatttata 213660
atacaaaaat aaagtaaaaa ctttaaaatt gatccatact cccaaaggca tttggtttta 213720
gaggaaaaat taaatagttt ttgtctgttc taaatatgtt ttcctggctg ggcattctgg 213780
tgagtgcctg tggtcccagc tactcgggtg gccgaggtag cctcaccaga agtttgaggt 213840
tacagtgagc tatgatcacg ccactgcact ccagcctggg agacagagtg agtacctatc 213900

-continued tctaaaaaaa taagtaaata aataaataat acataaatat tatttccttc accttgaaat 213960
ttcttgaagg agacaaagtg tgggcatttt tccaaaatgg gagctgataa acatcaacag 214020
agcatcacta atttacaaag gcatttctga gaagcctgaa gatcacccat acccaaagga 214080
ggaaagccaa atgcaccctc aggagcagca cacaaataag agaaacagca actggaccac 214140
aggcactcca cgtgcatctc tccaacatat tgtgctgcgc aaatgagcca ctcgtattag 214200
acctgctcct cccttagtct tccctaactc tgtcaacagc acactattca ccaagatgct 214260
tgagcttcaa cccagagtcg tccttcatct agcttttcct ttaccagact cacaaaccga 214320
cactccaaaa tacggtgttt tgacacgctg aactgaagaa gtctcagggt ctctctaccc 214380
taacgcactg cgtctcctac agaagctgaa gtcctttatc tgcctaagac ccggactcac 214440
caaggagaat gattgttttt tctttccctc cctgttacct cattatctta ttgcagaaaa 214500
gaagacccag atgtaaccac acccaaatag gctctttcaa gatgactgcc tccagcgatc 214560
actgaaattc caaagataac cttttttttt ttttccagac aggtcttgct ctgttaccca 214620
ggctggagtg cagtggtgtg accatggctc gttgcagcct caacctcccg ggctcaagtg 214680
tgaccctcct gcctcagcct cctgagcagc tgggagtaca ggcgtgcacc accacacctg 214740
gctaaatttt gaattttttt gtagagacag ggtctcact atgttgtaca caggctggtc 214800
tcaaactggg ctcaagggat cctcccacct cggcctccca aagtgttggg atttcagcca 214860
attctcatca aactgtggca cctctgtccc ctcctctcaa actcatgtgg acacatatga 214920
tagccttcat tgttagagtg tggcagaagc gatatatgtg acttctgagg ttgggtttat 214980
agggcaatac agcttgttct cgggataaga atctttgaaa ccattggggt accatataag 215040
aagtctggcc actggaagcc ctcacgtggt aacacaacag agaatgatgc ccaaggagag 215100
gagctccact gtcccagctc cttgctgctc cagttgttcc agcctaagca tcagtcatgt 215160
gagtgagctt cagatgacac cagccccagc caccatctga ctgcaactgc ctgagagacc 215220
ccaagcagga accaccaact cctgtcaacc ccaagaatga cgagacagaa tgatgagtgt 215280
cattatgcag cgataggtaa gtgagatgtt aggattccta cttttccttt agctccccta 215340
caatcaggaa cagccagagt gatctttaaa aaatatgggg ctgggcacag tggctcacgc 215400
ctgtaatccc agcactttgg gaagctgagg tgggtggatc acctgaggtc aggagttcga 215460
gaccagcctg gccaacaggg tgaaaccttg tctctactaa aaacacaaaa attagctggg 215520
catggtggcg ggcgcctgta atcccagcta cttgggaggc tgagacacga gaattgcttc 215580
aacctgggag gcagaggttg cagtgagcca agatcgcaac actgcactcc agcctgggcg 215640
acagagtgag actccgtccc aaaaaaaaga aaaacaagca aacagtgtca tgctgccctc 215700
tccctcagct gaaatgcttc aaaggctccc tggttccagc cagaccaggt aatccagctg 215760
ccacacccaa cctgcaaaac actcctccct acccgccttt ctagttcacc tcctgccact 215820
actgccttgc cagctctgcg ccagtcacac tggccttttt gccgttcctc tgtgctgagc 215880
ttgttctcat cttggggact tggagtaagc ctctccttca gtctgaaagg ctctttcctt 215940
agatcttgca tggctggctc cttctcatca ttcagtccca ggttaaatgt cacatggcca 216000
gagacaaccc aatctaaagg agccacacat ccccatctct actggccctg ttttaatgat 216060
ctacgtaagt cttattacaa tctgatattt tattatttat taatttatct gattaattat 216120
tctggtttac tactttgtct gcccttatga gagcgaaggt cttctctcca tccacagaat 216180
acacccagca cttaggacag tgattggcac agagaaggta ctcaattaat atgcgatgat 216240
tgcataatga gtgagggctg tacaggattt caggagggtg gtgtttgttg agaggcttct 216300

-continued

```
ctaaggtgga gagtagctct acagctccat gggacatgcc aaccacctat gctaatcctg 216360
tgctcatcag gcaagtttct tttggaaagc tttgttggct gaatgaattt gcccctttat 216420
ttttattttt tttaaatcag tttttaaaat tttgtgagtg catgaggttt ttaaatatag 216480
gcatgcaatg tccaataagc acatcatgga gaacggggtt tccatcccct caagcattta 216540
tcctttgagt tacaaataat ccaattacac tccttaagtt atttaaaaat atataattaa 216600
attattatcg actatagtca ccctactgtg ctatcaaata gtaggtctta ttcattctat 216660
ttttttgta cccattgaat ttgcccttca agagtaaaca atgccatcac tgtacattac 216720
tacactaatg gtcaatttat acattagtca gtggcttaag aatctgggtg gtttgagtct 216780
gttgccctaa acctccccca atttattcac ccatctccac tccatgcctc ctctcatggc 216840
ccaagagaac cctagtattt ctggatgaat gggtaatatc gggtttccaa ccccacaatg 216900
ctagggactg ggctgtgggg ggtggtgact gcaccttgct ggcctcacac tgcagagagc 216960
ccacttggat cacatcatca tcaaaaacat taaaccaaag gtgaatgaac atcttgcaaa 217020
caatgaccac cctgtggttc tcacactgct acgatgcata cactaccttc agctcatgga 217080
tcagacttct ggtttggtag aggctgaagc gctcctggcc cttcactgca gatagcaggt 217140
ggctggtgtc agtgaggaag cgaaacaagt tctccacaga agtagtgaaa tcttgccact 217200
gcctcaccag cccatcaacg tcacccttcc tctgccgaac accctggaca gcattctgcc 217260
accgatccgt cagctttgag aattctgtaa taaattctgg tctggggaaa aacaaatggt 217320
tatagaatcc agacatcgac atgtagaaaa aataactatc agtgggtaat agcagctcag 217380
attcagtttt tataagtaca atttacatga aaaaaatccc aacttctaaa cacctgagtg 217440
ctattcaatt taaacatgat taaggctttg ggaagggcag catgcagact gagtttagca 217500
gaaggtatct gcacgtaacc tggtattttg ccagcatgca taaccattcc cttaaacaaa 217560
ctgaagctgt tttaatatac attaggccaa acgtggaaag gaaaactaga aactggatca 217620
aagggaaaca gatgaacagg caggtacttt gtaacactat ggattacttg agtgtacttt 217680
acataatttt agcaataaag agcatgcttt attgcagcta ctcaacagtt cttttctgga 217740
taaataatat ccttcacacg agaaataagg cctcttgttt attatgggaa agtcatgttt 217800
ttctgtacag atcaaataga aattagctta tcatcctgga actggcttgc atttactgct 217860
tcagagctag ggagaaaagg gctttacatt tcttagttat gctgaaagaa gattcagagg 217920
tgtatgggtg gtgatgtgga agaaaaatca tacccattag gacatttaga gaagtattta 217980
aatggccagg ccatttccag gctatctgcc atgtgtacag ctgcatgagc agactcactc 218040
agcattagca gactggccaa aggtgctctg ttcagcctga ttggcactgc ccagtgaccc 218100
taagcccaca tatgtagcat ggagagaaag cccttctttc agacttatag gatttagcta 218160
cctactggga acattaggaa taatcatttt ttagaaatta ttttttaagt cgcaaaacat 218220
catgaggatg atggtagaga aggaaacagt acagaagaat catttggggg cacaaactta 218280
gttaactata cttgagaagt gggcattttc caaagcttct gggctgctaa ccccatccac 218340
ctaccatacg gaaaaggtgt ctgtcacaga tgtttttatg gtcacccagc aagatctagt 218400
cccactacat agttagaagc ctggtcctat ggtgatctgt caaccaacag ggcacagggc 218460
accaacatgg tcaaggttca catggtggaa agcctgccct gactgaatgc attaccttcc 218520
atccgcccac aaccttcatg aggcccagac agctcacctg ttctctattt ctgttgtgtc 218580
caggagttgt aaggactggg tgacatagga atcagcaatt gtctggttta tagaaacttc 218640
```

-continued

```
agcttctaac atctgtatat gagtccaagc agaaaatatc agctagtaaa attcatttta 218700
tgaatctcgg aacctacatt tcctattaaa atctaagctt acaaaggata tgagggataa 218760
ttaattttca tattatttga acctactgca aaaaatgttc aactatcata tcaacatcac 218820
ctacgaatat attcttaaaa gcaaacaggt ctaataataa ttacatctaa tacccatttg 218880
ttgggcattt acgatttggt aggcactgta aaacatgcat tgtctcattt atttctcagc 218940
cttaggattt aagcactatt attacatcca tttgaagagg aggaatctaa ggtataaaga 219000
ggttcagtaa cttacttaag gccactcagc tttttggcag gggtgatttc attttaattg 219060
gatgatctta atgtagcaat gtagacttca atcagttaca ttaaaaagtt gcagtgaagt 219120
aattctgcac acttttgaaa tgtgtccttt gtaatcccag cactttggga ggccgaggca 219180
ggcggatcac ttgaggtcag aagttcgaga ccagcctggc caacatggtg aaccccatct 219240
ctactaaaaa tacaaaaatt agccaggtgc agtggcacat gcctatagtc ccagctactc 219300
ggaagggtaa ggcacgagaa ttgcttgagc ctgggggtg gaagtttcag tgagccgaga 219360
ttgcgccact gcactccagc ctgggtgaca gaggaagact ctgtctcccc ccaccaaaaa 219420
aagcaggatc tgcctataac caccaggagt attttcaaat acatgtcagc ataagcactg 219480
aggaaactcc tgtgaaatta ttaacgctac agttataatt ataccaggtg ctttaatact 219540
atggagaatt attgagtgaa aatacaaaca tgagtcgaag tattttatta tactcttgat 219600
agaatggtat aatgtttgca ttttgtggaa gcaaagttgt actagaagct tccatgtact 219660
gcagaaaatc taggagtcct ctccctaata aaatagagca gtaaatgttg aaatttatga 219720
aacgtacaag aattttacaa atgaccaatt gacaactgaa tttgcttaaa ggtatacatt 219780
ctgtgtttag ggactgatag gtacactccc tgtgttttat ttaaagctat ctttccctga 219840
ctcctgcccc agatgagcgg ttcaagggtg gcagagaaca caggtttacc ttataggttt 219900
tctgctgctc caggagctca ggaaggctgt tagccacatc cactttgagt gcttcttcta 219960
tcttctccaa aagttggatc cacttttcac agcaataaag aaacttttca ttcaatccaa 220020
ttccctgaag ctcactacaa aggtttaaaa caaaacacac ccatgttaac aatgccattc 220080
ccgagctgaa gccgttaatt ttaccttaat tgaaacaacg acagagaagg gatgttctaa 220140
cctgcagcgc tccagtgccg tggccgtggc ccgaatccat tgccggttca tattttgtaa 220200
cgtcttcaca gctacgtcac taagtgggag cttgaggctc acttcattca aatgttcaat 220260
atcaggtgat tgggctgtca gtgccagcac atgattctat ttttaaaaaa ttgaagtaca 220320
ggtttttgga tgccaataag atatctagat gacaaaaaac cctccttacc tcaaagataa 220380
aggaaaactg gggcctgaac aggcaaatga cttgcccaca gtcaaacagc ttgctaatgt 220440
tagagtggga cctgaattca gctatctcaa tgctgtgcct tctagaatac caacctgcaa 220500
cacggccagc acccaaacag cccaggaaat agaaagttat ctcagatttt gtcaccgaag 220560
aatacagaaa ataggctttt ttattttttta tttttcggaa tggagtctca ttctgtcgcc 220620
caggctggac tgcagtatca tgatctcggc tcactgcaac ctccgcctcc tgggttcaaa 220680
cgattctcct gcttcagcct cccaagtagg tggaattaca agtgcctgcc accacacctg 220740
gctaattttt gtatttttag tttcaccatg ttggccagct ggtctaaaac tctgaccttg 220800
gatgatccac ctgcctcggc ctcccaaagt gctgggatta caggcgtgag ccactgcacc 220860
cagcctaaca tgctttttaa aaaaggacca attctgggct tttaagtccc atttagtctg 220920
ccaataacct ggccttcaac aaacaggtca agcacagagt gatgaaaatt tgattcttaa 220980
aataactcta gcagagcaag ggacttaaac acccatattt tgatagaaca tgacattgca 221040
```

-continued agaaagcaaa cttatcaaaa tttcattttt aaaaagatat tccagcgaca gcttctaagc 221100
tgacaagcaa acatccttaa caatattgaa gttaccacta cagaactctg ctgtaatatt 221160
ctaggtcagg ataagcaaac tttttctgta aaagggcaga tcataaatat tttaggcatt 221220
tgtgggccat atggtctctg tagcaactag tcaactctgc ccttgtagcg tgaaaactat 221280
aatagacaat atgtaaatga aagggcatgg ctgtgttcca tcaaaatttt atttaaaaaa 221340
aaatcagtga tggacagtgc accacagttt gttgactgct gatctaagtt atgaatattg 221400
attcctagga gagttacaag accagatcta attctttcag tcatttatgt ttactaaact 221460
aaacttacga aggtaaagaa aaatgcataa tagaattttt tttatattaa actaaccaga 221520
aaaattcaat taatcacaac agccaatttc tagattattt cagttcactg acggtaatta 221580
tgaaaaaaca tctactacaa attactctga cgtattacta aaagagatcc ctatgtcatc 221640
ctactttttc taggcctgag ggaaaatagg acagtaatga atggcataaa aatgactgtg 221700
ctcaagggtg agttaggcca ggcgcagtgg ctcaggcctg taatcccagc actttgggag 221760
gccgaggcag gcggatcacc tgacgtcaag agttcaagac cagcttggcc aatatggtaa 221820
aacttcatct ctactaaaaa atacaaaaat tagccggaca tggtggcaca tgtctgtagt 221880
cccagctact tgggaggctg aggcaggaga atggcttgaa cccgggaggt ggaggttgca 221940
gtgagccgag atcgtgccac tgcactccag cctgggtgac agagcgagag tccgtctcaa 222000
aaaaaaaaaa taagagtgag ttaggatgca agcattccat aagttcacag taatcagctt 222060
attttttta accttatggt gagtctaagc ccttagaaaa gacaaatatt ggcaatacca 222120
ggaatgagtc aggattttct ttttcctgtt ggtgaagtct atccaaattc tcttcttcat 222180
gcataataag accttttaaa gattccagcc ggactccaaa atccttaaac tgtgagagaa 222240
caaactagaa caagagaaat tttcattaga aactattttc atgtacatat aaaacagaat 222300
taaacacagg cttgggagct gctaaaaatt caagatgttt ttggctaggc acggtggctc 222360
atggctgtaa tcccagcact ttgggaggcc gaggtgggaa gattgcttga gcccaggagt 222420
tcaagaccag cctgagcaac ataggcagac tccatctctg caaaaaataa aaaattagct 222480
gggcatagtg gtgtgagcct gtggtcccag ctttttggga ggctgaggca ggaggatcaa 222540
ctgaacctgg gaggtcaagg ctgcagtaag ctgtaattat gccactgcac gccagcctgg 222600
gtgacagaat aagaccctgt ctccctgtct caaacaaaca aacaaacaaa caaaaaaaaa 222660
caaaaaataa aaaaaagtaa attcaagttg ttttcaacac ccagaagttc actattatct 222720
caagaatcat agataaatat tcagaagccc cctgattttt cactcgtgcc tttgagcctt 222780
cccaaatgga cagatcaccc gcctgaggag accacataga gagtcagtga gcactccgtt 222840
ctctcagtcc cactagttaa atgtgctttt ttgtttgttt gttttcctgc tggtactgag 222900
atgtgatact gcaactccat ggccttctgt gtagcttgtt gacagctcct gcactaaagg 222960
ctttataaaa agtgaatgaa ggctgagagc agtggctcat gcttgtaatc ccagcacttt 223020
gggaggccaa ggtgggtaga tcacttgagg ccaggagttc aagaccagcc tggccaatgt 223080
ggcgaaaccc catctctact aattatacaa aaattagccg gccagacaca gtggctcacg 223140
tctgtaatcc cagcattttg ggaggccaag gcaggtggat cacgaggtca ggagattgag 223200
accatcctgg ctaacatggt gaaaccctgt ctctactaaa aatacaaaaa aattagccag 223260
gcatggtggc aggcacctgt agtcccagct actcgggagg ctgaggcagg agaatggcat 223320
aaacccagga ggcggagctt gcagtgagct gagatcacac cactgtactc cagcctgggc 223380

-continued

```
gacagaacga gacatctcaa aataaataaa taaataaata aataaataaa taaataaata 223440
agcaagccag gcgtggtggt gggtgcctgt agtcccagct atccgggagg ctgaggcagg 223500
agaatcgctt gaacccggga ggtggaggtt gcagtgagcc aagattatgc cactgcactc 223560
tagcctgggt gtcaggtcaa gagtctgtct caaaataaaa aaaagtgaat gaagacacga 223620
agatatgaca aatcatcatg ctttaagcag ctacttctat ggctcaatta cttgactcag 223680
aaatccaaat aactgtgaga tctgaacaat gtatgcaata taatacatat atgacttcta 223740
gaactaacat cttcaataag gaagaaatga ttgcttaaga tctgcccatg tgattgaagc 223800
tagaatcgta tacatttggg agcagcttca gtctgtaatt ttgctaagga gcagcccgta 223860
aagcactact gcttcaaagg atacaaggga ttgaggatgg aatgcaaatg tctaagacta 223920
aaacttgaat ggaaagaaaa gatgaacctc aaattcattt gctttcacaa gcagcatctt 223980
ttccaaataa gcagccctct ggagagagtg caggggcccc gggaggagca tgtgggtgct 224040
ggactctgcg ggttgtggga gtcgatccag gacactggaa ttttggagaa aggcttcttt 224100
tgttttctgc acatcatgct gcagctcctg cagaagaaaa agggatggca aacacctctt 224160
cctcctttca aaccacaatt ccctacccgc tgctgctcca tcaaaatcta ggagaatatt 224220
tgccctgaaa acgtaggcat gatcttttgt tattatttat tttaaatagc tgaaaaggct 224280
gggctttctt gaaatgatgt atatcactgg cgcttttccg aaatttgtca gttcaaaact 224340
aaaagtgacc actgactaat agagtcgagg cttctagtgt atagaaactg gagacaacct 224400
gagtactcat gtactttata tttcagttgt caaacagttt aggtatctgc tttcatgctg 224460
tttcaagaat caatgcaact ctgacccctg cctgagactt tctgatataa atggattcac 224520
gtgcagaaac tatagaattt tattaatcag gctgatttta aggctattct ggaaatattg 224580
tgtacataaa atttgttttt ttatttttaa attatcagct caggtagaag ttaatcagat 224640
gtacagagca ttatctgttg gattctcacc taattaaatt ggttgccacg ttttgatttg 224700
acctacagta gcagaagata caaaatgcat ctgttcactc agttcagaac taaagagtat 224760
tcactttctg agcgttcatt aacaataata gaaaaaacac catagaggaa actaagcaag 224820
tctttaatgt agtctgaaat ttactatacc cacagaaaag gcctagcaac atggcaccaa 224880
gtccatgatt actgctaaaa caagagatac aacatgtatt attcttacag ggtcacactc 224940
agttgagaca cttgctttta cttcagattt catatgaagc ttttgcctta gagatgtaac 225000
actagagaga aagcacagac ttggaacgag gtgatatcga gtccccctga tccagctatt 225060
tgctgcctag acgtcacctc tgagccacca cctggtcctc ccagccttgc ctatgtccta 225120
catggcaagt tcacagcacc tgtcctgact actctgtccc tgtggtctgt ctggtcccca 225180
ggtcatggct gtcccttacc ccatctgttg ggctgacttg gccttggttt tccaaatggg 225240
ctttgtaccc acctttatgt cctgcagggc tgggggcagg atctctgcca ggttgtttcc 225300
agacatgctg atgtttgcga gctgttgaaa ctttgcttcc tgctgcttca gccttgcggc 225360
agcttcacca tgagcattgc tataggcctt ccagagctgg agcagactct gggccttctg 225420
caactggtct gcaatggctt ggttcacctg agtccacctg tcagtgcaac gcaaataaca 225480
taaccctcat tctctccttt ctcttgtagc gaaagtacaa tgcacacact ctactggtaa 225540
gttactagca gatggatcat taagaagaca ctgttaaatg gtttttaaaa ttagtggcat 225600
caccattata gaaaccatta tataaaaata aatccaaatt aggctattta cttgacttta 225660
taatattgca caaaaactac aaaatgtatg attggcaaca aatacctatg atgttatgaa 225720
tgtttcactc tcttttttta agagagggga gtgatgaagg gagctcaaac tttttttttt 225780
```

-continued

```
ttttttttgt agagacaggg ccttgatatg ttgcccagga tggtctcaaa ctctgcagct 225840
caagtaatcc tccaacctca agcaatcctc ctgcctcagc ctcccaaagt gttgggatta 225900
taggtgtgag ccatggtgcg ccccgcctat gaatgtctct ttggcaaaga tggagaaaac 225960
actgaactgt atgcctgata aaatgactcc acatgaagag gctcccagtt tatagagata 226020
tgctatcttt aaacaggttt taactttgta tttatatcaa ataaaattta ttatctgttt 226080
acacaaatgt tccttacata gaagtggaaa taaaggaaat tgttttatta ttccatatac 226140
agactctagt atcttgcctt tcttccctac tttttttttt tttctgaaac agggtcttgc 226200
tctgttgccc aggctggagt gcagtggtgc aatctcagct cactgtagcc ttgacctcct 226260
gggcttaagt gatcctccca tctcagcccc cacaagtagc taggaccaca ggtgcatgcc 226320
accacgcctg gctaattttt gttttttttgt agagatgggg tttcaccatg ctacccaggc 226380
tggtcttgaa ctcctggact caagtgatct acccacctcg gcctcccaaa gtgctgggat 226440
tacaggcatg agccactatg cctggcccat ttaactttta aaaaatattt tccccacgtt 226500
agtaataaaa gaaaataagt aaacctcatt ttaagtggct gtacaaatgg tctgtgggtt 226560
tttttttctt tgtttcctta gtttaattgc taaattcctt agtttaattc ctgtttagta 226620
tggatagtta agatatttgt aatttttgct attatgataa tgctcagata cagttttatt 226680
caaaaggctt tttttctgta tttcaagata ttagtcttag actagatttc tgggagaatt 226740
acagagtcaa agaatataaa gatgtaaata tttgtaaggc tttgggaata aatggtcaat 226800
ctcctttctg aaagcattat atttacattc taacatgaaa tacatgagaa tgtttgctcc 226860
acaatatcct caacaatatc ctcgaccctg ctgattaaag aatcaaaggt ggaaaatagc 226920
acactgcttt acttttatgc atttcaaaaa tcttatcaga actgtctttt aaaataagat 226980
tttccctaat tataaataca acatatattc actgtcaaaa agcaaacaaa atccctccag 227040
atatttttct ttttatctat ctatcctacc tacttaccaa tccatgagga agttaaaaaa 227100
tgcttgacat ctcatttatc tagaggtaac tactattagc attttagtgt tcttctcttc 227160
agtctttttg ttatgcatgt ttttcaacat gccttccaac atattcttgt gccaacaagt 227220
gaatgtgtac gtgcagcgta acaactgagt tcctttacca acagactgcc ctgccatacg 227280
ttttgacggt agccctgata ttgtatgtgg agtcagatgc atttgcaggt tcctcttagt 227340
ctgtctcctc cccgtcttcc aataaagact ggatcaagag ctaagggcac cactgcaggg 227400
tatataattt ggggtccctt gttcattact tgttcgaagt tgatttacaa gagaggctga 227460
aactgcatac aggaataatc aggaaggaca cttaagatag cataactctt catccctatc 227520
tctaatcaat tggttggagg ccaactttta tatcccactc atcaaaataa aagccctgca 227580
attaactagg gccacactcc ttaaagggag ctttcatatc ccaccataag tagttcatca 227640
aagaattcct tccaaaccca caaatgccct ccgcaacaga tactctaaca tccccttttct 227700
tccaccttat aatgtttcca gtgatgtttg aacaccccct gcaggatgcc catctggccc 227760
actcctttgt ctgtttctgc ctctgacttt ggtgtttccg agatcgaact tgacatttgg 227820
tctatactgt ctgtaagtga gtacactggg gttgttatta ggccatttct agactaatta 227880
taccaaacac ttgtacaagg gatgtcacag ccctcatgac atagaatctt acatagacta 227940
gattcatcaa agcagaagag accagaacag taggaaacca gtcatctcag aggaggaaga 228000
agactttaca atgcctatgc cccctcattc ttcacaagtc attaagataa agatatctat 228060
cattcaaatt atatctgaaa gcataccttt tatgagtatt ttggcatttc tcttcgatta 228120
```

-continued tttcagcaac agaggggcag agacctttga gtttgccgat aacctcctgg agtttctccc 228180
aactcccttc actgctctca gcttcatctt gcagagacta agagacacaa acaagaaatt 228240
taagtttcag aatggcctgg ctacttccaa agaaggtggc agcttctcaa cacttgctac 228300
tatgtagcaa taacactcaa atcttacagc tctgataaac tattaggaat gtgaagaaaa 228360
caatggagaa ggcattcttt atttgaggct gaacttttaa gtactaagta atataaagta 228420
cttagcactt aggcatactg aaaaaaaaaa ggccactcaa aaaccaaaac cttaaattgt 228480
gaaataatat ggacatggaa aataaaggaa gattcaacat tttcaactca aaattcaaac 228540
attttacaat gttttactga tttggctcat gtgacttatt ttggaatttc cagttattct 228600
tttgaaactg ctatttaaca tgctttgtgc ttctctgtgg gagggcacaa acacagttat 228660
gcccgttact gtgcttcctc ccatttgtaa tttcctgcca ataatgcacc atgccaagct 228720
ctggttaatt tacctgaagg ttctccacct ggcatctcaa ggtctccaat gataacacca 228780
caggcttgct gtgttccatg cagtaccaga atcggattgt catcatattc acttcatcat 228840
agagttgatc ataaatcttc cactcctgta aaactgactg catggaggtt ttgagctgat 228900
tgacctagac aaaaagtgga aacgtactga tttagaaaat cactgagaag acatgctctc 228960
caacagatct accattgtgt ccaatttagg catttcaatt tgagagtatt gaaggatcac 229020
cagtgattaa ctgaaggtgg aaagggtagg tcaatgcata agaacatatc agagaaggct 229080
gttttataat gagtgaatga aaaagagccc aaagatcaga aggatcagca ctgaaggagt 229140
tcagactagg aagagacagc ccagggaaag aacactgggt gagtattaga atttgtgagt 229200
gcaaggttca gttatattct attagctttc tgaccttggg caacttattg gaccctagag 229260
tcagtttcct catccacaaa acagagataa taattgaaaa cacaaataaa atagtgtctg 229320
tgaaaatgct ctgacaacag cacaacatta taaatgtaag atgttacctg gcacttaagt 229380
ctgattatta ctacagagca agcaccaatt ggagaggaac atgctctacc aaaatgatgg 229440
gcaagtgcaa agcaggaggc aagcaatggt gaatgtattt tgtccactgg tatgttctga 229500
taatgatgaa aaaagtccaa gcattctgtt gcatatccaa aatgatctca gatacaatca 229560
agagtatgta aagaaaactt acaaatcaat attaaagaca gataaactaa ctaaaaactg 229620
ggcaaaggaa gtgactaaac atttccccaa agaacatata taatggtcaa taaacatatg 229680
aaaagacact gaacatatac agtcattaag gaaacctaaa tcaaaaccac aatgagatat 229740
tatttcacat ccactttgat ggccataatc aaaaagtcag ataataatgt gttggtgacg 229800
atgtggaaaa actggaatcc tcatacattg ctggtgggaa tgtaaaatgg tacagtcact 229860
gtggaaaaca gctagatagt tcctcaaaaa attaaataga gttgccatat gacctaacaa 229920
ttgtactctt atacacacaa gagaattaaa agcgtatgtt cacataaaaa cctgacacaa 229980
atgttcatag cagcacgatt catgagagcc taaaaatgga aacaacccac atgttcatca 230040
actgatggag aggtaaacta aatatggtat atccatacaa tggaatatta gccataaaaa 230100
taaatgaagt actgtaaata ctacaacacc gatgatcttg aaaacattat gcttagtgaa 230160
ggaagccaga cccaaaaggc tatatagcat atgattctat ttatataaaa cgtccagaat 230220
aggtaaatcc ataagaaggt agactagtgg ctgccaggga ctggagaagg ggaaaagtgg 230280
ggagtgactg ccaatgggta tggaggtttc tttttgaggt aatgaaaatg ttctgtaatg 230340
agatagtggt gatggctgtg tatctctgtt aatatactaa acatcactga actatacctt 230400
agaaggtgaa ttttatggta tgtgaattat atctcaattt ttaaaaagga tctgggttga 230460
aatggaatgt gatcactata gtggctccac aggccatctt tatgggtagt gtgatgtgag 230520

-continued ttttgggtac aatcacacag ctctgcactc agaccctgtt ttctgtttaa taactacaag 230580
gaatgctggc acatccacag tgacagggag gctcctcaat ctctgcccca aacagggctg 230640
gataaaaaac caaagtggga cgctaaaatg tgagtctcat gttggcaact atgtggactg 230700
aatgtcttta caagggcagg atggctaagg aaaagaaacc aagttattta gttaagaaaa 230760
taaagaaggc ggccaggtgt ggtggctcac gcctgtaatc ccagcacttt gggaggccaa 230820
ggtggttgga tcacctaagg tcaggagttc aagaccagcc tggtcaacat ggtgaaaccc 230880
tgtctctact aataatacaa aaattagccg ggagtggtgg cacacgcctg taatcccagc 230940
tactagggag gctgaggcag gagaatcttt tgaacctgga aggtggaagt tgcagtgagc 231000
tgagatcatg ccactgccct ccagcctggg caacaagagc aaaactctgt ctccacaaaa 231060
aaaaaaaagg aaagaaaaaa gaaaataaag aagaaaggca aggaaggaat tcctcatcga 231120
tgtacatttt tgctagaaat gatctcacat ctatctgggt ggcagggata attctggcac 231180
aaagtaccgc atcatcccag agcccatata tacatgtcaa cacaagaact gccatggctc 231240
atgttgcaca aggcctttgc agcttccaca gataaaggtg gtggaacttc tagcacctta 231300
aaggccttct ggccttataa taaagcttca tggaaaagac acagtacatg aggtttgagg 231360
gaaaggatga gaaaatcatc aagtaaaatt cactatacta aaaacaagcg ggaggaatat 231420
tttcaaaatg ttccaactgg ggtcatcagc agggcagcat ttattgagca ttgtataggc 231480
atcagtatta agatagaaat aaatgactag gtgttatcat ccccatttta tagaccagaa 231540
aatcgaggct tagagaggtt aagtaacctg accgaagata cagatcaaaa atggtgccgc 231600
caggatcctt atttaggcag aaactgcaaa gcccttgctc ttaaacacta ggttgtattg 231660
actcttgttt acccctgggc tcaagtaatc ctcccatctc ggcctcccga atagctggga 231720
ttacaggtgc atgccaccac atccggctaa ctttatttac tttttgtgga gatgggatct 231780
cactctgttg cacaggctgt tcttgaactc ctggcctcaa gcgatcctcc tacctcagcc 231840
acccaaagtg ctgacattac aggtttgagc cactgggcca ggcctacatt gactcttgac 231900
agcttataga tggatgatct gtgcctcacg ccttctgcgt tttttttttt tttactttat 231960
tgaaatataa ttcatgtacc atacgattca tctatttaaa atgtgtaatc tccataatca 232020
attttagaac attttcatga ctctgaaaag aaactgcata actattagca gtcactcctc 232080
gttctcccca gccactaatc tgccttctgt ctttatagaa ttgtccattc tggttattcc 232140
acgtaaacag aatcaaacaa tatgtgacct tttgtgactg gcgtctttca ctcaccataa 232200
tgtttccaag atcatcagtg ttgtagtata tatatatata tgtatgtact acttcattcc 232260
ttttgtatgg atagaccacg ttttctttat acattcatta gtagatggac agttgggttg 232320
tttacacttt ctggctatca tgaatcatgc tatgaatatt cacgtataag tttttggcgt 232380
ggacacgttt tcatttctct tgggctatct atggaggagt agaactgcta agttgcatgg 232440
taactttatg tttaaccatt tgaggaactg ccagactctt ttccagctcc atggaacccg 232500
tccagcagtt tgtgagggtt acgtctccac atccacatta acacttgata ctgtctgtct 232560
ttttgttaca gctatcctag tgggtggcaa gtggtacttc tttgtggtgt tgattttcat 232620
ttccttgatg gttaatgaca tggaatatct tttcaatgca cttttcggcc atttgtattg 232680
tcttcttcac agaaatgttt attcagatca tttgtctttt tttttttttt ttttttgaga 232740
cagggtctca ctgtgttgcc caggctggag tgcagtggca tagtcttgcc ttactgctcc 232800
ttccacctcc caggctcagg tgatcctcgt gcctcagcct cctaagtagc tggactacag 232860

-continued gcacacacca ccacacccag ctaatttttt ctatttttgg tagagatagg gttttgccat 232920
gttggccagg ctggtcttaa actgctgaat tcaagcgatc tgcccacctt ggcctcccaa 232980
agtgctggga ttacaggcgt gagccactga gcctggcttg tatccatttt ttccatttgg 233040
tcatttttcc ttttattatc aagttgtgat aaatcttcat atattctagg tgtaagtccc 233100
ttatcaaata tatgatttat aaatactttt tttaacaatt tgtggtttgc ctttactttt 233160
ttgatgctgt gctttaaaac atcaaggtgt ttagttttga tgaagtccaa tgtatctatt 233220
tttttctttg atagcttacg attttggtgt cattctaggt aacccctgcc taatccatga 233280
agtcatgaag atttacacct gtgttttctt ctaagtttta tacttttagc tctaatactt 233340
gtgtcttttt tttttttttt aatacaaatg gggtcttgc tatgttgccc aggctggtct 233400
tgaattcctt gcctcaaatg atctcccacc tcagtctccc aaagtgttgg gattacaggc 233460
ataagccacc atgtctggcc tgcatttatg tctttgatct attttaattt ttgtatattg 233520
tatgaatgca gaggtctaac ttcattattt tacatgtgga tacatggttg tcccagcacc 233580
atttttcaag aaagtgtttt ccctcattaa attgtctgag gatccttgtt gaaaatcaat 233640
tgactacaaa tgtgagggct tatttctgga ctctcaattc cattccaagt atatatatgt 233700
ctatccttat gacagtacta tctgcatgtt ttcacatgca ttatttcatt taattttctc 233760
tttatatttt tattatattg taattatctg tttacatgtg tttcttccac tagcctatga 233820
gttctttgag ggtaggattc atttattttc ttgtttacct ttgtaaccct ggcagtgagc 233880
acagtacctc acacaatgta tgcttaacaa atgactgaat aagctcatct ctatttttct 233940
gctacattcc tgggggaatg aggactgagg aatgaggctg agtgttgcct atggatttca 234000
tgcaggttat tccctattcc ctcttggtac aaatggttga aagtagattt tagtaggtga 234060
caacccacaa tgaaggttct ctaggaaaca tggacatatc tataattgat ggtatagatt 234120
ataccattga tagattatac caattgattg gtataattgg ttagtatttt tagttctctt 234180
cctctgttgt gggaaaatgt caaggttgca atgtctagag atgcctgagc tcgctctctt 234240
ttggtgctct cctcctggaa ggggtaaaat gctgacattg acatgccttt tgtaagatta 234300
ttagatgtct tgcacccttt cttcctttat actctctctt caacaccatg tagtgtttct 234360
tccaaacttt agagtcctcc tggagctgac tatgctccta gctcatagag gctacatgat 234420
acaggatcac ttcctccctg aggcatctcc ctgtacatgg agacactgct tcatcactgt 234480
ttctgtatat cttgccagga aacaatgcca gatactctgt tgggtttggg gtatggagat 234540
atttatgtct gagtgagtac attagacaaa acaaagataa ccaagtggat ttgcagcctg 234600
tcaatgacgt tggaattggt ggctttgcct ctaattattg agtgcataaa atgggacttg 234660
aaatgcttct aatttacttc aatttttctc agcaactttt cagtgtttgg tatagagagt 234720
ctccatgagt aaaggacgaa aacaactaca acgacaaata aggtaaaaga atatgtgaag 234780
agaaatagca catttcaaat gaattctagt acctgagtga gaacactgct tctcttttga 234840
aataactcat caattcggga tgctgtatct tctaacaatg gcactgcccc actctccaaa 234900
gtcagataac tttgtttcaa ctcatctagt gctttggatt taattgcaag ttgattttct 234960
atatcctgga agagtaagag gaaaaggttt tcaatgcaca atattacaaa acaattaata 235020
aggtgtcaga gacaggagtt cactcttttc aagtaaaaat gtcattagat tatataatta 235080
aatagcatta catcaaagaa atttaaatca taatactctt agttcaatta catatgacac 235140
aactctgtat tttaggagaa tctaggcaac acgtctgaac catcatggca gagcagaaag 235200
gatgctggtc cgagatctgg tccccattcc acgtctgccc tgcactggct gtttgaccag 235260

-continued gcataagtca tcgaaccttt cagtctccat tttctcattt ggaaaaagtg atgataccca 235320
cagcatgtgt gccaagctaa gaactcaaat aaaatcacga gcaagaaggt gcctttaaac 235380
catatagcat catataaatg acagacgata taactgttgg tagttcagta ataactttaa 235440
tcattttcta cctcttagtt tattaattca ctcataagag gcaccctgac ctggtctact 235500
ctttatagat acatttttaa aaacctacag gatccctcta ctacaaagga caccatgggg 235560
ccagcagtct gaaaacagag atgaatgagg ccagcagcaa tggtgccact ctactcagag 235620
gaaggacggt cggagctgct tatttgtcct tctcaggatt gcagttgaaa tccaacttgg 235680
aaaaagttta aactttttaa aaattattaa agcattacat gctcattaca aagaaactgg 235740
aaaacacaag agatctttgg cattcagagg gattcatttt gaattcccct caagtctccc 235800
aattcacaaa tttgggacgc gcttctgcat actttcttta gcattacatt cccatccaga 235860
tgcatgtgtt ctgaatgcat ggcctcaaga taacgaccct tagctcatgt tctatttctc 235920
tcttgaaaat tgctttgcat aaggatccca gcttttttta tttttatttt ttgaaaattg 235980
ctttgcctaa ggatcccagc cttttttttt tttttttgaa aattgctttg cctaaggatc 236040
ccagcttttt ttttgaaaat tgctttgcct aaggatccca gctttttttt tttttttttt 236100
ttttttttaa atcctttgta agaatcactg catggtccat aaggaaagag aaacatgagt 236160
gcctcgtggg catggggtag ctgagcaggt ggcttgtacc ctgggaggga caagctccct 236220
tgtgctagcc tcacagagga gcactgaaat ccagtcccgc aaaactgcca gattaccacg 236280
tgaggagccc tcaggtcact cttggaaggt ggaaatcaca aactctaaac caatgaatgt 236340
caggggtctt ctggactgga aagtagaaaa agggaaaaaa atctgttcca taagaaactg 236400
atagctaggt ttgggagtaa gaacggatga tgagagaatg gagctggagg aatcttccac 236460
tgtatgaccc tctatgcttt tagaatttag agccacatga atatatagcg tatgaacaga 236520
aaacctctca ctgtcgtaac aatccaccca tactaacatg tgggtgaatt tatgaaatat 236580
tattcttctg gactggttac aaaggcaccc aggaaacaaa acgacttctc tgaaatagcc 236640
tttgccaatg agatttagtc agctgctacc tctgtccatc tctgccaccc taactcgctc 236700
cctcacaccc tgacagcctt atttattagc atgtttcttt tatcataggt ttaacttttt 236760
tcatctgcaa agttataaat gaaaacactt taatattaaa tcactttcct tctttgaatt 236820
tataaaacag tctctcctaa aggcttgact aactagattt ctaaaaacac ttatttacta 236880
ataagctgtc ataattcccc tataatgtaa agaaaactgg taagaaatga ctacaaagca 236940
gacaaaagga agtaacaaca cacacacaca cacacaccct tcaaaaatgg cagcataaac 237000
aacagccatg ccgggcacag tggctcacgc ctgtaatccc agcactttgg gaggccaagg 237060
caggtggatc acttgagccc aggagtttga caccagcctg ggaaacatga caaaactctg 237120
ccgttacaaa aaaatacaaa agttagctgg gtgtggtggc acacgcctac agtcccagct 237180
acttgagagg ctgaggcggg aggatccttt tttttttttt tttttttttt tttttttgag 237240
agagaatctt gctctgtcac ccatgctgca gtaggcatga tctcggctca ctgaaaactc 237300
cgcctccggg attcaagtca ttttcctgcc tcagtctccc aagtagctga ggctacaggc 237360
atgtgccacc atgcccagct aattttgagc caccgcgccc agagtgggag gatctcttaa 237420
gcctaggagc tcaaggctga agtgagttat gattgcaaca ctgcactcca gcctgggtga 237480
cagagtgaga ccctgtatca aaaaaaaaaa aaaaaaaaaa agaaaagaaa aaaaaaagcc 237540
atggcaatag cagcacacga acaaccacac acggtggggt tgctcgtttc ttttgctctg 237600

-continued cagaataata cggatttagc ccagtagtcc tgtcatctga ccttgcttca ctgaggccta 237660
acagtaccct tcaagtttcc caactcccac ttcaccggca aattaatttg tcttacttta 237720
acttccaatt tgctacacat aaatcagggt ggaattaaaa ataatctttt gctaattatg 237780
gagattcagt agaatttgca agtcctattt ttccattctg tgagaaccag cattaaatat 237840
ttttaaaata tctaaattcc tctgacttta tcacgaacat acttctttaa gaagctgtgc 237900
ttgcttatag tatagaggca tcaaacttga gggattaata atctcatctc aaacctcccc 237960
actctattca actatacaat tttccttgat aattataata tgtcaaacgt ggcctttttc 238020
cagtcatcaa tggcttttag aagcccttcg gaatatttca atcctaatgt cttcatgctt 238080
catcaactcc agtccttaac ttttctagag taaagccact ttagcaagct tacctgaact 238140
gaagcattct gccctgggat aagtcattaa agtatacatc aatcattttc atcatttttct 238200 tttctttttt tctttctgtt ttgttttttt agagatgggg tcttatccag gatggagtgc 238260
agtggcatga tcatggctta ctgcttgaac cttgaactcc tggctcaagt gatcctcctg 238320
cctcagctcc cgagtagcta ggattacagg tgtgcaacac tatgcccaga taactttttt 238380
ttttttggta gagactgggt cttatgttgc cctggctggt tttgaactcc tggcctcaag 238440
tgatccttct gccttagcct cccaaatttc tgggattaca ggtgtgagca actgcacctg 238500
gcctcatttt agttcttgta tgcaaagaat agtggaaaaa aaaaaaaaaa aagagaaatt 238560
aacatttata gaaaagcagc cttttaggtc tattaataga tatattcagg caactattaa 238620
gcacctatga atttcacagg cagtgacagg tataacaggc atgctgatgt gccagcctgc 238680
cttgagaatc ccacaatctg gtagacgaca gacccgtgga cagatgagcc cagtacagtc 238740
tctgacacat gatgctacat ggggtgctag ggaagcctgt tttatttatt tgcttccatc 238800
ttggccttgt ttatggcctt ttacaaagag gcatccaagc agcagcataa aaaattaaaa 238860
taggaagaaa tgagctaatg gaaatgtggg agtaggtagg aaggcacagt cagtgggcac 238920
gtggtgaggg agggggtcag ggtgctttga ttgagttctg acaaacatag aggagaacct 238980
gtgtgtggat ggtgggggcg aggggaggga agtagaaata attctgcaat cagctgcaaa 239040
tgtaatggca cagaggcaaa tggggactga cgagggatga tgccggccag gcatgtctgt 239100
aaatttcttt taaagcccct tgtctcagtc aacactagtc atttttctaa tgagcagagc 239160
aaatgtgaga aatggttttc tattggtaaa attaatggat tattattgtt attagagatg 239220
gggtcttgct ttgtcaccca ggctgaacta cagtggcatg atcatagttt actgtcacct 239280
tgaattcctg ggctcaaagg atattcttcc cttagcctct tgagtagctg ggactacagg 239340
catgcaccac catgcccggc taatttttaa atagtttttt gtagagacgg ggtctcaccg 239400
tcttgctcag gctggtctcg agctcctgga ctcaagcaat tctcccacct cagcctccca 239460
aagtgctggg attatacaca tgagccactg cgcccggcct taatggctta ttaaataaca 239520
taatgagtat tagaaatggg ttctcactag taaatttcat gtactcaaga tccatggatt 239580
ggctaaacta ccgtagatat aatttccacc cctacttgaa cggctataag aactgggcat 239640
agcctgttgc cttcaactag tgcaataatc cctaaggtaa gtccttatgt ggtttttgta 239700
tccagtttaa actccaagga ttctggttgc ctaatgttgg ccatagaaat aatggactct 239760
tgcttctgga atattactat gtctgccttt catgcaaagc ggtggttggt gtgctaaaga 239820
gggcagagag gctttgctga acttagttat ataaactatt tttagtgctt gcttgctaat 239880
ctatgtttct acagatggtg gcattgtgtc tggaatttat tttatttaca gcttggtagt 239940
gaggttgtgg gaagaatagc taaacttaat ccatttcgac cttgttccgt ggctaccatt 240000

-continued atctatcaaa aagagaaaca actgtgtaag actcacttga cttaggtcta tttgcaactc 240060
tttgtaggtg agggaccaga atgtcattct aaaacatgtg aacttcattc tgtggtccat 240120
ctggagccac tggaggattt tccagtggag agtgttgtga ccctttgcat ttcagaaata 240180
tccctctgca gcaatgtgga gaatgaatca gaaggaaatg agggaggagg ctggcaagtg 240240
ggctggaagc agctgcatga gacaggcctg cactgagggt ggtctgaagg aagccggcct 240300
gaccgagaca gactggccag acagtaagga gtaagtcaag agcacctaat gagaaactgt 240360
atgtagcgac acgcatgaaa acacctcctg ggctctggaa agaaccacct actaggggac 240420
aggccagcac caggctgcgg aatgtaggct tccagtaagg aagcacatga ctccaaggtg 240480
gctgtcagaa ggctaaagtg gagatggctc attgggaggt gggaacagta tacgagcagg 240540
tgaaaagggc cgcttacggt ggtgctgctg ctcacattta tgtccagtgc tatcccgtga 240600
cctcctcagt agaaatgggg tccggccaga ctttccagtc ctgacagtga ctattgtaag 240660
gccgtcacgc aggaagtgca gaaacagcac agcgtgtgcc gcctgccgtg atggcgatgg 240720
cagaggtcct ctgaatgggc agcagccaca agggcagtgc taaagcagga tcagtgtgca 240780
aagactgagt gatgcggcaa agcatagctg aaccacggac aacaccctca agcccaaatg 240840
tgattcagca gaggttccaa gggacaagtg aactttttaa agcataatac acaataggta 240900
gaagaaaatc attttcctcg aaaaaacaca gaatgaaatg ctaaaaataa tgaaaccttt 240960
agagtaattt tgtaacatta ggcaaaatga ttaaacaaat ggaaaattgg aaagcattta 241020
aatcaaaatt ccctttgaac atttttcccc aagagtacta ctcaaacctc ttaagagcag 241080
caatactgta acggtgaaag tacattcttc tgtttatcat aaaaaacggc actttgcaat 241140
tttgtaaaac ccatgggtca ttatctaatt gacataagaa aataagtaaa tagaggggag 241200
ctggaagaga gtttccacaa actacagcaa cttatcctcg gggcaagaga ggtgaccgaa 241260
tcaccccagc tcgcgggttg ggtgggatgc tgttcccctc ctcacctgac agtccaggag 241320
cagcttctgc actgagatca cactttcagg tttttgtaaa gttttcagtc tctcttcttg 241380
tgcttccagc cagttgttca agatctgtat tttattttca ctctcagtga tactttctag 241440
aagttgttct aaatgttgta tctaagtgaa tgtaaagatt acaaaaaatg ttaaaatgta 241500
tgttttaaaa ggtaaatgcc atgacgttat tttttaaaaa acaattttgc ttcttttcaa 241560
atttctaata tttcatgtaa taagatgctc tgataacttt tgaataaaga ttcaaaaatc 241620
agaaaacaga gttaaagctc ctcttaggaa aaaaatatca tatttaaggt gaaagctaat 241680
ctgctgagaa aggtagctgt tgtggagttt cagatgtata caaaataaaa tgttcccaac 241740
attcgatatt ttttcattgt gtcatctatt aatatatgta aagtataaga caaatttctt 241800
tcctcagact ttctgcatta gagttgctta aaatttctac caatatcaat aaaaaataat 241860
ttatcaattc aataaaataa tcattgtctt taatgtctgt gattctcatt cataataaat 241920
tttttattag gtcataatca taatatacac acatttttat attctttttt acatacatta 241980
taactactgt gtcatgacat aatttttttt tttttttttt tgagacggag tctcgctctg 242040
tcacccaggc tggagtgcaa tggtgcaatc tcggctcact gcaacctcca cctcccgggt 242100
tcaagcaatc ctcctgcctc agcctcccta gtagcaggga ttacaggcac gtgccgccat 242160
gcccagctaa tttctgtatt tttagtaggt caagaaaaca cctgaccttg tgatctgccc 242220
gcctcggcct cccaaagtgc tgggattaca ggcataagcc accacgccca gcctgtcatg 242280
acataatttt aaaaggctgc ccggccaggc gtggtggctc ttacctgtaa tcccagcatt 242340

-continued ttgggaggca gaggtgggtg tatcactgga ggtcaggagt tcgagaccat cctgaccaac 242400
atggtgaaac cctgactcta ctaaaaatac aaaaattagc taggcgtggc ggcaggcatg 242460
tgtaatatca gctatttggg aggctgaggc aggagaattg catgaatctg ggaggtggaa 242520
gttgcagtga gccgagatcg cgccactgca ctccagcctg ggaacagggc cgagactctg 242580
tctcaaaaaa aaaaaaaaaa aaaaagctgc cccaatgttt catcaaatta atacagtata 242640
attcgatgaa ctattcccct agagtgagaa ttaaggcatg gtacattttc acagctgtaa 242700
acgatgctga attgaacact ctgtgcacat catttacttt tttgaaggac tatctactta 242760
aatgtgtaag aggtgacttg cttggttaag tgataagatt attattacgg ttctttacat 242820
tttccaaatg ctttccaaga aagtacttaa gccattatca gcaatgtatg aacgtgacag 242880
ctttgggttt ttgtccttat ctgattaatt ttttttctaa ttaagtgcat tatgttacac 242940
agtgtttatt ttgagtatct gctaatgata tctttccatg tttatttgct aactataatt 243000
tcctcttttg tgaattgtct gttcatgtcc tttgtccatt catgtacttg tatcttaatt 243060
gtgtaaatcc atttgtatgc attctctaca cagtaaacac accaattatc atcatgatta 243120
tatgtaaagt attttttcag gaataagttt tccgaatctt ttcaagagtc atggagtgaa 243180
aaatctacca aaaagccaag tgcatttttc tttcttttta taaccttttc aaagctgaaa 243240
tagctttgcc ccttttgaac atctgctttc atagaaaatg taaaatctct gatcatttag 243300
gagtctgaca taatacttga catgttccta aataaaattc ctcatcttca cttgcctagc 243360
tcaatttccc actaagaaat ctcaaatata agaactattt ttatattctc ttataggtac 243420
caatggagaa tgctaaaaca taggatttat aaaagggcta tagttgagat gattattagg 243480
cttaataatc agtcaactaa ttgaacgtct tttttgattt ttcagaaagt gtgtttcata 243540
aaggtcaaac cacacatcca gttgtgacgc aggaacacac ctttctattc agcattccat 243600
gtacacggtg ccactggcgg ttcatctccc ccaggtgctc tgcaaactcc gttctttcat 243660
agcgcttgct ttctacatca caggtgctta gctgaagtaa tgactggtta acgaagtcaa 243720
ctatccactg tttatagtcc atttccattc taaactccta aaataagcaa agttaaacac 243780
caaagcagtc atgaatgttg gtcagatcaa atggatttcc ctttatgtgc tcgagggggc 243840
accaagctcc cgtccattaa tcaaggggca cctgtcagga gttctgttct accctcccca 243900
acctacacca ggagttggct ttattggagt agggattctt ttggggaatt acacagagat 243960
gcactgcttt caaataggct gaaaagtcaa aggggcacta tgtatggcag ttgctatcat 244020
ctgaaccctg accacgaccc aggatatgac aaagcttcct gggggaggct gcctgtcagc 244080
tgtgctggaa ttctgggcca tcctgagggc tcacggaaac aaccagatgg gaaataggaa 244140
gtaaagtctc tttcagaaaa cccaggacac cttaaggaac tctgtcattt aggcagcttc 244200
cctgttcctt cggggatagt taaggcctct caggtggctt tagaaagttt gggtggcttt 244260
aagttgtaca gcaatcctaa acccacccag ggccaacaac atttctgcca aacctgtcac 244320
ttactgattt tatctctgca agttctagca cctcttttgg agacacccgg gggtgacagt 244380
catgtggtat gtgctaggtt gctagagcct gtgagaatat acacgtgtag acttttcgaa 244440
gattttacta cacactgaag ttaggatgtg atggtacata aaaacaaaat tctctgctaa 244500
tatcttgctt ggtgattaag ccattcatct tctgcctacc agaagctagt tccatcagcc 244560
tgcatggtct taaagcaatg accacacttg tcactcatct ttgtattccc agtggccagc 244620
atagtgctga gcacacaata cacgtttgca tgtggctcat gaaatgttaa ttaaatctac 244680
ttgaaattaa atatcacaga gaaggccaca tttatatcta tttgtagaag gatctcaata 244740

-continued

```
ttttcttact cattctctta ctcaaagaac atttcattaa cacctgttag aggaaggcag 244800
gtattgggat aggcgtgcta tattttagca aggtgaagga tggcccctgg tctcgagaag 244860
ctcagtcaag gtggggagac aggcaaataa accaataatt ataataatgc atgataggag 244920
ctactaatag catcatggag acatctaatc caggaaagtc acctagtctg gctgggagag 244980
tcaggggtgg atttgcaaac aaggacaact cgagctgact atggaagatg actaagagga 245040
cgtatacagt taaacgtggg ccctggcatt ccaggtagag ggtgcagcat gtacacagga 245100
tgataaggga gagcaccaag aacagttaag gaatcaaaat cactctgtca ggcagagtct 245160
gtggttattg gggtggtgg gatgggggata aaaaggtgag accacagtct gttaaaagct 245220
tgcttggatt gtcctgtggt gatgggggct ggcaaaagga atttaagtgg aacaaaagca 245280
agtctactaa catctctcca gaatcatcca ccaccccagt ttcctacccc tagaattagt 245340
tttttgaaat tatatcctat gtgtcccttt gtccagcatt acccctctga ttagccttct 245400
tgtttcaatg aaaagacttc tgctcctttt gcataattac cttgtgcttc tgaagaagat 245460
gtttaacttg agatgcagaa cttggtgaat gcacggagtc ttcatctgaa gtttgatgct 245520
ccacattgtt catccagcta atcatttctg tgattgcttt acgagacggc aatttctcca 245580
tttgaagctg taagaacaaa atgatttcca tttaattgcc tgcagttaac aaaatgaatc 245640
agagcatcac taaagatgat atctggtttg ataaaaggtc ttgctatata attatgcagg 245700
ttactcaaaa aaaaaacaaa cccagcattc aaacttagaa taagcgaccc caaaacaatg 245760
acaatgacct tcacataaac taacacagtg gcaaagataa actgagaaat aaagtaatta 245820
agcctgattt ctctcttaag aaaaatccca ttggaggagg gtccagtaat taagacttat 245880
attcagtggt gccagagaaa aataggtagt gtcaatgaaa attattgagt cagagaaata 245940
attttaaaag agttatgagc taacaagtga atgctaattc aaatgctgag gctctaaaga 246000
cttacctggt gaagtttttc ttgaatatct ggaagttgag ttatgagcat tgtccatttt 246060
tgttcaaact gtgctaaaga agctctcagt gtagctgtat cagtttcttt caggtgaaga 246120
agctggttcc cgatactgat aacggcagtc ttcaaggagg atttttcatc aacttctttt 246180
gaaaactcct aaaggagagt tttaaaattt agaaacttaa aatttaaata tagcagaaag 246240
taagagtcgg aataactggc tagagtcaac aaataaacat agtaaatata cgaatgtgta 246300
tacacacaca cacacacacc ccttttttcct actgttgggc attacataca cgatggggaa 246360
caaaagagat ggaatgcata cccctcaaga agcttatcac ccagtgggtt aacattttta 246420
aaaataagtc attatttaaa tggggtaagt tttacaataa actatggaac ccaacacaaa 246480
gtgcacatta aatgaattac ttgcaacaag tttgtaatta aaatgtttaa atctttccta 246540
tgtagaaatt ctttcaagta tgttgaaaaa atttacattt taatagcaaa gttagtaatc 246600
atagctacga agtatgaaaa ataaaaaaaa aacaggaaaa gtctaacaga aaagactacg 246660
tttcataaat gcattgacca ataatcattt tgtaattata ttacaagagt aatacatttt 246720
tatttccccc aaaatttggg ggatattttt gaattttttt ccaaaaaaca cctcaaaaca 246780
atggaacaaa agctttttag tagaaatatc aattttgttt acaataattt aaaactatgc 246840
atttattaat gttaacattt ataagttaat aaccttataa agttgttttt gggtcttgta 246900
ttttttgtat ttgtaaaaca tgacctatgt cagtgcaagt tttttgagac tgagtttcac 246960
tcttgatgcc caggctggag tgcaatggcg ccatctcagc tcattgcaac ctccacccac 247020
cgcggttcaa gtgattctcc tgcctcagcc tcccgaggag ctgggattac aggcatgcac 247080
```

-continued caccatgctc ggctaattct gtatttttag tagagacagg gtttctccat gtttgtcagg 247140
ctggtatcga aatcccgatc tcagctgatc cactgcctca gcctcccaaa gtgctgggat 247200
tacaggcgtg agccactgca cctggcgcaa gttttaaatt cagatatatt ttatggggtc 247260
aattaaaaac atattttatt ataaacgaat gaacagtata aacagttcta ggtttgaaga 247320
acacagctgc cattcgccca agtcttaccc cttatccaca aataaatacg aagactatca 247380
catcaaccct gatgcttttt ccttgatatt tatttctgac cagtaattaa ctgaacatat 247440
gctattacaa cttacaaaaa aattgttgat gttgcttctg attgtatcca agtcctgaga 247500
cacattgagg gactgttctt tccagtaatt cagagtatgc tgggaagatt ccaaccactt 247560
ggttaactga tccgaatctc tgttataact aacaggagca aagtgagaga gaaggcagat 247620
tagaaacata ttctgataat gatatgcatc accagcaaat tttcttattt tattgtatgt 247680
cctcctatgt tgatcagtcc taacattcag aatatcatga cgttaataag gattatatca 247740
tgttttatac catgatgctc ctggcatttt ctaggactct cttcattaca gctcagcaag 247800
aacagtgagg attttaggcc agatgtggtg gctcatgcct gtaatcccag cactttggga 247860
ggccgaaaaa ggtggattgc ctgaggtcag gagttcgaga ccagcctgaa aaacatggta 247920
aaaccctgtc tctactaaaa aatacagaaa atacccaggc atggtggcag gcgcctgtag 247980
tcccagctac tcaggaggct gaggcaggag aatcgcctga acccaagagg tggaggttgc 248040
agtgagccga gattgcgcca ctgtactcca gcctgggcga cagagcaaga ctctgtctca 248100
aataaaaaaa aaaataataa taataatgag gaagtctaaa gcattcttta tttcttatta 248160
cagctacaca aaagtatacc caatgaagga acagagattt ttatccatca aatgtcttct 248220
ataaatttgt ttatattaaa aatataggtc aggcacagtg gctcacttct gtaatcccag 248280
cactttgggg taacaaggtg ggaggatggc ttgagcccag gaatttgaga ccagcctggg 248340
caacatggaa aaaccccatt tctacaaaaa atacaaaaat tagcagggcg tggtggcatg 248400
tgctgtggtt ccaggtactt gggaggctga ggtgggaaga ttacttgagc ccaggaggtc 248460
aaggctgcag tgagccacga tcacgccact gcactccagc ctgggtgaca cagtgagacc 248520
ctgtctcaaa aaataaataa aattacatac acacacacac acacacacac acacacacac 248580
accatacata cacacacaca cacacacaca cacacaacca gcatttgtat aagctgtata 248640
acaacaaact gctgctggct gaacacccaa cgtatttgcc cgaggtagtg aaaatattca 248700
aacaatattc tgcccttctt gtaactttta aactgcctta gattaagatg cagggatgag 248760
aatgatgttt aaatgttcta tgttctcctc cttcctcaca cggttcaaga ttataccaac 248820
taagcacaac aaattctcca aagaactcaa aagcctattt caaactattc tgttagctaa 248880
aatcatttaa ttttttttaat tttaaaactt ttggaaagag caatatcatg gtataaaggt 248940
aacctatata ttattttata acataattcc tagcttctat agaaatgtgt aaactagctg 249000
ggtgcagtgg cttacacctg taatcccagc actttgggaa gctgaggcag gaggactgct 249060
tgaggctagg agcttgagac caccctgggc aacaatgtga gaccccatct ctacaaaaaa 249120
ttttataaaa ttagccatgc acggtggcct atgcctgtag tcacaccaac ttgggaggct 249180
gaggcaggag gatcgcttga gtccaggagt tcaaggttgc agtgagctat gatagtgctg 249240
ctgcactcca tgcactccag cctgggtgac agtgcaagac cttgcctcct taaaaacaaa 249300
aaagaaaaga aaagaaaaga aaagaaaaaa cgatcacagc aaactgatta catgttatac 249360
tgtgtctagc aaaccatcag agattctaca tcgcgtttag cccagaagag ggacccaact 249420
gctttagact gcccaagaaa aaacagcata aggtgggttg caggtaaaat ttagttgact 249480

-continued acagaatccc cgaggtcttt cttcacagca caatatgaag ccaatccacc cccaaaaagg 249540
ctgacctgag cagatgcttg agaagagctt gcagcctgtg gagctcatgg tcaattttct 249600
tgttcaggga caaccactgc tcttccagtt ttgcgatctg gccctctaat tcaggacagc 249660
tcacagacgc caccaactgt ttgccttcgt tcagagtttg gtaaagccgg gcgtgttttc 249720
caccaatgtt tctttttatt tgctaataaa aagtaaagtc atagaatgaa ttatttagaa 249780
aataaagtct gccaagctat tcacaaatac tgcatttaaa actgacattt gtgtccactg 249840
ataaaacagt aacactttcc caacattcaa gactatatag tctgactgga tgcatgatta 249900
atggtttatt ggttaccttt catgataggt gtccaatctt gcatttctag agcacagatt 249960
caactttgta gacttactgg ctggatgcag tggctcatac ctgtaatccc agcactttgg 250020
gaggctgagg caggcagatc acctgaggtc tgcagttcga gaccaggctg accaacatgg 250080
tgaaacctcc tctctactaa aaatacaaaa aattagctag gtgtggtggc gcatgcctgt 250140
aatcccagct acttgggagg ctgaggcggg acttggtggc gcacacctgt aatcccagct 250200
agccaggagg ctgaggcagg agaattgctg gaacccagga ggtagaggct gcagtgagct 250260
gagattgtgc cactgcactc cagcctgagc gacagagcga gactgtgtca aaacaaaaca 250320
aaacaaaaca aaccaaccaa ccaacccaaa tcaactttat agacttattg catacaaaca 250380
aaaaacaagc tggcagtcat taggccatgc tgagctcaca gataggtttt gtgtgacctt 250440
aagatcagtt tgaaaaatca ggaaatctta cctaataatc aggattgcca gtgtctgtgg 250500
gaaaactgga agacctagca attgttggtc tgcatctcat gtggcaaagg gcggctgtaa 250560
ctgagcagca gctgctggct ctaggagagc ctactccctc tccttttccc ttggctcagt 250620
ccccaccacc cctctgattg cagagccagt agggtttcct tatttctatt ctgcccccga 250680
aagcacttca gatggtgact tagatatgaa gaggataaat aaaatagtat ttctctatta 250740
tccatgagat gcgaatacta ggcagaaaaa ttcatttcca gggtcttcta ctgaatataa 250800
agattcagta gagagaaagg aagaaaactt tagaaaaata aattaaaaca gcgtatcatt 250860
aatccaactt cacggaaaga aaaatgaaat tctttgaaga gaagtctgtc taaaggtaat 250920
tatctaacac agctggattc agctaatgcc atttatcctg acacctgttt aatcttaaaa 250980
aataaattat taacaaaaca gaaggtttgc tattttcaaa ttaagttaag ccttttaaat 251040
cattaccaaa aaattccacg tccatagccc tttccaccac tcccatttgt aatcccctcc 251100
cccccgtgtc tgagcatctg tattaaaaga aaaaaaaatc agtctaattt tctaagtgaa 251160
gtgctagatt cttcaccttt aaaacatctc tgaaaagtct taattcaccc cccaattttt 251220
ttttttttt tttttttttg agatgaagtc tcgctctgtc acccaggctg gagtacagtg 251280
gcgctatctc agctcactgc agcctccgac tcccgggttc cagcgattct cctgcctaag 251340
tctcccaagt agctgggatt ataggcacgt gccaccacac ccagctaatt tttgtatttt 251400
tagtagagat ggggttttac catattggct aggctggtct caaactcctg acctcaggtt 251460
atccacccac ctcggcctcc taaggtgcta ggattacagg catgagccac cacgcccagc 251520
ctaattcacc gattgtatgc atgggataca gtctgtgcac gagtaactag gctgagccag 251580
catttgaaca caggtttgtt gacttcaaag gccagacaac tgactcctag gttccatgcc 251640
ccacagacga cggctgatca agatgacaac atctgtcaga ctcacacaaa cctttccttg 251700
attctgaact gagaatggcc tatgaagtcc atatgtgaga tgggctttac aggatatgtc 251760
ttctttagtc tggcaaattt atttaaaagt cttagaacaa tttttttctt tttaatattt 251820

-continued caaatgtaat agaatcacac attttaacag atatggtcac ttttggagaa aacaatcaca 251880
ctcatattag gttggctaat attagactgt tgcttaaaat aataagcctt aaaatactgt 251940
tctcatctgc attctttcag ctgtttagat gataccttct gtatccctag actaacaaag 252000
agctaaacag tactctcatc acccccactc ccacccaccc cagaggactc agatttacct 252060
tagagttagg ctcaatataa ttaataaggc ggcaatgaga ccaactgtag ctttccaggc 252120
atctagggag tataaataca gtgtcccagc ctctggaaaa tgttccttat agaggttaaa 252180
atacctccat ggaaaagaga accctggaat tatttcctgc tttcattttc caactagttc 252240
attcaggcaa taaatgtgct tttgaggttt taaagttgat atttcataac tgcctctagc 252300
cgcacaactc agattctgac ggcatatatc ctaaagttaa aactaggaat tttaagttcc 252360
tggtgagaag acttaaaact tgtttttatc ttgttggtca tgttctcaat gtcacttgaa 252420
aactattttg aggttttatc ttttctttcg caccaaaatt agagacacag agacagatga 252480
taacaacgca aaaagttaca caaaaaagtt taaaagtttg agggtttttg ttttttttgtt 252540
ttgagatgga gtctcgctct gtcacccagg ctggagcgca atggcatgat cttggctcac 252600
tgcaacctcc acctcccagg tttaagcaat tctcctgcct cagcctccca agtaactggg 252660
attacaggca catgccgcca tgcccagcta attttttttt tttttttgta ttttagtaga 252720
gacagggttt caccattttg cccaggctgg tctcaaactc ctgagcccag gcaatccacc 252780
tgccttggcc tcccaaagtg ctaggattac aggtgtgagc catcgtgtcc ggcctgagat 252840
gtttttataa tgctggtgac aggtaagatt attgtctgtc ttatgggcta cgtctagtca 252900
ggacttcact gtaggaataa aacgaaatat atgtttagag gccgaaggct gacaaagttc 252960
tttccattct tcagctcatt tccatactag tagctcactg gcattcactt ccagagacag 253020
gtagaattgg ctcgattatc tgcattccac agataaagaa attgaggctt agggacagca 253080
aggtcacaga agtgataagt gatggagcca cgactcaagc aaggtcctct cccccaagcc 253140
agacatgtgg ttatgctaag gagttcacat tcaaatctgt agtctccctg aatacattca 253200
acagtgagtt gtatgatgaa cattttgttt caattcaaac cttccaaatc aagccactta 253260
gtcaaaacaa atgtaaaaca caaagtgcta tggacacgcc tttgataact taaatggaag 253320
acaaatacct ggtaaaatga aatcctttcc actaatcttt cctctgtttc ttccaccaaa 253380
ctcacagagg gcaatgtaga tataagaatt tccaggtcct tttcaagaga tgcatagttt 253440
tcatcaaatt cttcccattt ctagagaatc aaggacataa aattagtgga agccctttac 253500
cagattggtt ccagataaca acataattaa tcacaaaaca aaaatgaaca ccaagaccat 253560
acaaaattaa agcacagatt ccaggtgtgt tcgagagacg taaccccacc ctggtaagcg 253620
ctcagcatct aatggaaaag aattccatca cctttgagga caaggtttaa aaagaatctg 253680
agttggcatt tagtgtttta tgcttgtctt gtcaaactgg gtaacatgac taaaggagta 253740
atacaatgaa gttaaaatga tactcttagc aactccgtag agaccttgga gccacaagag 253800
agcctttctc ttattaggaa agggaaagag ctaactttta gacccttact caacagaagc 253860
tattaggctg ctcctgctct ccaagcccac gcccaagccc accaaacccc catgccactt 253920
gcagcatagg tctgctcaag gtgtctttga ggagtatagg cttacacttc atcaggggag 253980
gacaactgcc ttagccctag tcttgtcatc ttttagcttg ccccgtttcc atggatgccc 254040
accccgagga ccccaacaca ccacagagct gagttattga ctccaaacat tgtctgttag 254100
gaaaagaacc acctcactct tttccatatc tattcacata gtggctcact tggcttttat 254160
agaacactca ctgggtccat ggagtctttt ttaaaaaata ccatgacata ttataaatat 254220

-continued caacttgaca cactaactag aaaataaatt ttgttagcaa aaaaaataac accatattac 254280
actatcaagt taaacatttc cttccttttt tcttttttttt tttgagacag agtctcgctc 254340
tgtcgcccag gctggagtgc agtggtgcaa tctaggctca ctgcaaggtc tgcctcccgg 254400
gttcacgcca ttctcctgcc tcagcctcct gagtagctgg gactacaggc gcccaccacc 254460
acgcccagct aatttttttt ttgtattttt agtagagacg gggtttcact gtgttagcca 254520
ggatggtctc gatctcctga cctcgtgatc tgccccccctc cgcctcccaa agtgctggga 254580
ttacaggcgt gagccactgc gcccggcctc cttcctattt tatttccttt aagtactaac 254640
attggctatg aaaggtgtga ggggaatgcc tcaaaactga gaaggagctt tatgcatgct 254700
tattttttttc tttgagttta gacaagattg tcatccattt taggacatct gggcctgttc 254760
tcttgaagaa gtacagtttt taaaccaata actgtttcac ccaaatgatc tcattcaagg 254820
tctcaaagtg cttatcgttt tgcttattca tacatgaacc taaaaggcag agagacgcag 254880
taccatcccc aatctatgta tgagaaatcc cagccaactt ttccttcagg gagcggcctc 254940
agaacctgag caggggtcca cattcctcac tgtcaggctt ccatttaact atagcttaat 255000
gataactaga tacttcttct caacacctgg ggtggtgatg gaaaatcagc aattcccagc 255060
ttcagtacaa cgtttacata acccaaatac ctgcaacaaa ctctgcagct tcataccaca 255120
ttggcgtgac ttttcttcta gtattttaac ttctgttact tgttctgccc aaaatgtctc 255180
tctgttttgc aataaagaag gaagtatttt ggcagagtat gcttggatca acaacatgtc 255240
agcaacaagc ttctggaaaa aaacctatga gatggagaaa gttttaatat ttactttgaa 255300
attgtgaaaa ctcttaaaaa ccaagttact tcaactttat atccagttat ttttgtttta 255360
aatccaaaat cccaggacat ccgtgtagag tcaaattgac cagcctggcc aagatggcaa 255420
tacaaaaatt agctaggcat ggtggtgaat gcccgtaatc ccagtcattt gagagactga 255480
ggcaggagaa tcatttgaac ccgggaggcg gaggttgcag tgagccgaga ttgtgccact 255540
ggactccagc ctaggtgaca gagcaagact ccctctcaaa aaggaaaaaa aaacaaaaaa 255600
caaaaaaact cagtctttga acactagtgg aacttcaaca aattataaag tattaccctt 255660
aggtgttatt ttccactaaa taatccattt taaatgacaa acatttttgt caatttcaat 255720
ttccagatag atctttctaa atcagttgtt ttgagtctaa atgctacaaa aagatagatg 255780
ccagctaggt gtggtggcac acatctatag tcccagctac tcaggaggct gaagtgagag 255840
gattgtttga gaccaggatc tcgaggctac aatgagctat gattacacca ctgcactcca 255900
gcctggaata cagagtgaga ccgtgtctct taaaaaaaca aaaacaaaaa caaaaacaaa 255960
caaacaaaaa acagatgtca ctgtggctga tgaatttcaa gacaagttgg atggacagat 256020
gtgcaaactc aagcaaccca catattcgaa agacaggtct ccttaaccct ggctttaact 256080
tctactcaag agaatgacta aataaaggga atttgctgct ttataggaat cctggacata 256140
aagcttcctg tatttgtatt tgaacttcaa gaacctttca agaggaaggc tttatttcac 256200
atggttcttc tccatttaca gttgtctgga gggatccctc catattatgt gaatcccttc 256260
tcctaagcct tgaaaaggac atatacatag agacgtttat aaaagcatct agcaaggggc 256320
ctagcacact gcagataatc aatattattt tctcctcttc ccctccatcc ttcatacaat 256380
atttaccttt caatttttct tagactaagc tctaccttcc aaatgctaga ccataagctt 256440
acctcaggta ggaaccgtcc tacacatttt taattatcag cacctagatt actctttatc 256500
tttagttggt gatcaagaag tttttgttta atgaaatgaa ttttaaaaat caaaggattt 256560

-continued

```
actatagtct tatactacat aataacacac tttccttttg attctagttc tcaggaaagc 256620
cttttcttct tttttttttt tttttgagat agagtcttgc tgtgtcgcca ggctggagtg 256680
caggggcgtg atctcagctt actgcaacct ccgcctcctg agtttaagca attctcctgc 256740
ctcagcctcc caggtagctg ggattacagg tgcctgccac catacccagc taatttttgt 256800
atttttggta gagacagggt ttcaccatgt tggccaggct ggtctcgaac tcctgacctc 256860
aggtgatcca cccgcctcag cctcccaaag tgctgggatt acaagcataa gccactgcgc 256920
atggccagga aagccttttc taactttcct aagtcacctt ctgctattaa atgctctcat 256980
agaatgtatc ctcattttaa ttttaaattt gtttgaagac ttgttgataa atatctatct 257040
tctcaatcag gtgaaagctc tgtgaatgta aggaactgtg tctgttttta ctcataaccc 257100
aaattcctag catgtaccag ggttcctggt acacattaag cattctaata gatgtttatt 257160
aaaagaatga atagcttaaa tttcaacaaa gaagaaaaat ggatcctttc tgttcacatt 257220
cagaaatacc ttaagatttt agtctatgaa ggggtcaccc gacccatgtg tctgtctcac 257280
cttgtgattt tctatttgag cctgtaacgc cactttactt ttggtttgtt ttaagtggcc 257340
atgagcaagc ttttccttcc caatcttcac cagttccacc atgccttgca acaaagcatc 257400
ttgctggctc tcagtgacga aagggctgct gagttctgtg tacctggctc ttagcattcc 257460
ccacatactg tcaagtacat cctgaaaaga gaagagcagg tgcacacatg cattttcatc 257520
caaccggggc aataactgaa agacaaatct aaactctgct ggtggaagaa aaggatctgg 257580
ctcctcacaa tcacagtgct gagtcaatgt tttctgctca ggcatacctc taatttgtaa 257640
acctcctgga gtaaagcata aggtaaatga agcctctccc cttcatctct tagtttggcc 257700
actcggctct cggcgttctc cagctccact gtatatgcat ctgctttcta agtgagagac 257760
aatacaagaa aagaaaaccc ttcagtaagt cagagaagta cacatagtta tctaaaaaga 257820
attaaatagt acagaaaggg atgaagggaa aagcaaaaat cccagctccc gctccctcac 257880
ctcctgctct ccttaacaat cttgccagag gtcccaagtt cctaacatgc tccataccag 257940
taggggtaga catgcatatc cctaaactca atgaactgca ccacagcatt ctgtcctgcg 258000
gttagcattc ctcactcacc agctcttcag catctcttca cattggtata cacatatcta 258060
gctccttcga aacagacaca cagcatgcta ttgtaagggt gtaccctgct tttgttatca 258120
gtcagctctc aatggacttt tgggctatat acagttttta attcaagcag agctgctggg 258180
tccatcctta aatatttatg acttatttat ttatttattt agagacaaaa gtctggctct 258240
gtcacccaag ctggagtgca gtggcacaat ctcagttcac tgcaacctcc gccccccaag 258300
ctcaagcaat tatcacacct cagcctccgg agtaggtggg actacagccg tgtgccactg 258360
cacctggcta atttttgtat tttcgataga gatggggttt gccatgctgg ccaggctggt 258420
cttaaattcc tggcttcaag tgatccacct gcctcagtct cccaaggtgc tgggattaca 258480
ggcgtgagcc accaacctgg ccaaaatatt tatctttatg cacttgtctt atatccttag 258540
gaggagtaca agttcagcac ttcaaacagt gctggaacat agtggatcct caattaatat 258600
ttgctaaata catgaagtca aattattgct ggaagagaga gtattcatgt ttaaaattct 258660
gatatacaga caaaggatcc ccagggctcc cctggcaaga ggatgagggt ctcattttcc 258720
aataccctta ccaacactgg acatacacat tttgtcatgg ttgataagtg aaaatggcct 258780
ccttttgttt taatacattg tgcttcagaa aattaggaga tgtttttaaa aagtcaacat 258840
aaatagttct catttttat ttatttactt aagccttgct gctgctcaca aaggaaagta 258900
gttcagaagc acggcttata tgcaaagctc tgtggttcaa agttaagtca gtctgaatta 258960
```

-continued

```
ttttgacttg attacctgaa gctgttcagc aacactctgc ccactgattt cattcaaaga 259020
ctgttgtaaa gatgtcttac tcttaatgag ctgatgatat aatctcttta tttcattctg 259080
taagataaat gtcggaaact gagcaatctc atttaggcct tcattatctt tttttatatt 259140
tagttggttt ttataatttt tgtgacacta gaaatttcaa acaaatacaa aaatagagaa 259200
atccccattt tatcatcatt aaacttcaac aattattgat tcatggctga ccttcttccc 259260
tctacatcct ccctccagct ctcaactgta cctaatctcc tttccttcag gctattttga 259320
agcaaatccc aggtctcaag tcatttcatc agtatacgtt tcagtatata tttctaaaag 259380
ataaagatcc ttctctttac tccaacatac tcctcccctg ccatcaataa taattcctta 259440
atatgattta actatccaga cagaattcac atatccctaa ttgcctataa tttttctttt 259500
tgatttgttt caatgatgat ccaaatgagg tccacatgtc atgatggata aatacatctt 259560
agatctctct taacctgcag aatccctgac cactttttt gtttcttgaa tgtgtgtatg 259620
tgaaaaaatg ggtcatttgt tcagtacagt ttcccacagg ctggatttgg cagactgcac 259680
tcccagtgtg ctgtttaacc tgttcttctt ttcttgtgtc tgttttactt ggattctagc 259740
agcttggtca gattcaggct tgatttttat gggcaagcct cattcataaa tagtattggg 259800
tttcatttct ttttcattag ataattttag tagcttccta actcttctac ctgcctggag 259860
tctctgcctc tccaattcac tttagacaac tgctggagga atctacctga aacatacacg 259920
gattgtcatt ccttagctca aaaaccttaa tggctccctc tagctagaaa aacaaaaaca 259980
aatgcctccc ccgccccacc attttaattg ttaaatggct aaatgtaata caagaaatga 260040
aacattattt tagctcatcc taacaaattc ttactcaaga ctctactttt tttatttttt 260100
attttttac tttttcttt ttttgagatg ggatctatgt tgcccaggct ggtcttgaac 260160
tcctgggctc aagcaatcca cctacctagg cctcccaaag tgctgggatt acaggcatga 260220
gctactacgc tcggtcaaga ctttaaaggg cttcaccttt tttttttga gatggagtct 260280
tgctctgccg ctcaggctgg agtgcagtcg tgtgatctca gctcactgca acttctgcct 260340
cccaggttca agcaattctc ctgcctcagc ctcccaggta gctgggatta caggcacaca 260400
ccaccatgtc cggctaattt ttgtattttt agtagagatg gggtttcacc atgttggcca 260460
ggatggtctc aatctcctga cctcaggtga tccgcctgcc ttggcctctc ccaaagtgct 260520
aggattacag gcgtgagcca ctgcactcgg ccagggcttc actttcaaat gatctccaac 260580
catgagcaac aaacagaaga gtctcatcat ttcccttagc aattcttatt aacaaatgtc 260640
accaggaata ggaataggca ttaggggttc atgctgtaac ttaaaacagt gccaaaatag 260700
gctgtgtgct cggaatcata cctggtaact gcggttgtaa tcgaggccag ctttcaggga 260760
cttgcttcta cagacagctg cagcctgagt gtgctccagg cagacttgaa ggttgtcaaa 260820
acattcaagg agcaagttgg tgttctcgcc aggccaagtc atggctttca aaagatcacc 260880
cttcttgtca cttagcgcta aataaagttt cttcaactca agagccagcg tctggagtgg 260940
agaggaagga agacaatgaa tgagctctga cctcaagagg cttccacgtg ggcttaactc 261000
acggggctgc tgtaatggcc aacacatggg ctcgtgagaa gtgccctacc tcgtagtgca 261060
cctgctggcc agaaccatcc tccctgtaaa gtctgggcat ctccagcatc tcctccacac 261120
tgctgaggca ctgactgagg gtcaggaata gttcaaacaa ttttttatcc aaattgatat 261180
atgcttcttc tgtcatattt tcctgaatca agaggaaaaa agaaaaagaa aattaagata 261240
cctttgcctt cctagaccta tattttgcct agtttccatt atagtttatg atttatgtta 261300
```

-continued tgcttctttt gtaataagtt gcttcaaacg ctttgtgaac taggtagcag aacaaataaa 261360
taaacttacg atgttaaact tggagaaaaa tgagtttaag aagctcaacg ttaggtagtt 261420
atttgagtac tgcatggaac taaaaggtaa atcatgagat gaaggatccc ttagcagggc 261480
gatccaggtg aaagtgtggt cccagataaa ttacactgtc tcctttacca ctgtttccca 261540
ccctccacat tctaatgtag gagaaagcgg ttaatgaaat caagtatagc tgggagaagg 261600
aaaagaagtc acaaaagaga agcttgaagg ggttgattac aaagaggagg tacagtgtct 261660
taaaaacagg agcaggctgc agaggagggg gaaagtgtca tttatgagcc gattgtgaga 261720
atcaaggctt aggtgtatga ctccaagcac gtccccagtg tcatgcattg cgcctggtga 261780
gtctgggagc cacagatctg ttttagcata agctgctggg gccacctctt tttctttacc 261840
cacagttacc ctgaattctt gaacagttat aagtagttta ggagcatgcc atagctagtc 261900
atcactccaa cttgggccct gtctcctact atcttctctg atagacacct cacataacct 261960
agcattaatt acctcagtat taagtctgct cagggttgaa aaccatgcct atactccctc 262020
cctactctcc tcttcaccct tccaatccca gatcaccact gcagacggca ctcatcaatc 262080
atgatcctct ttcctgctga tcctggactc agaatccttt gcacacagtc cctagggaac 262140
cactacaaaa tatattagag ttggcaagca agatcaattc aatttgcaat cctaggaccc 262200
attccattat gtttcctttt acttgttcag tgacgacaat tatgaccaag tcacaatgat 262260
gatatctcct ttgtttatgt tattacaatg aggaaaacac attgtgtgca gcttctacct 262320
gtgtctgaag gttacttgct tcttggcgca ggtcttcaag ttgggtggta taggttttca 262380
gttcttcagt tgttgggtat ctaaagttat acatagtcac gctgggtaga atacccatat 262440
ttgtggaaac ctatttgaca aaggaaaacc ctattactga cagttttaga ccctgctgat 262500
gttaattaat ttattttttt attttcgaga tggagtcttg ctctgtcgcc caggctggag 262560
tgcagtggca tgatctcctc tcactgaaac ctctgtctcc catgttcaag agattctcct 262620
acctcagcct cccgagtagc tgggataaca ggtgcctgcc accatgcccg gctaattttt 262680
gtatttttag tagcgacggg gctttgccat gttagctagg ctattcttga actcgtgacc 262740
tcaggtgatc cacctgcctc agcctcccaa agtgctggga ttacaggcat gagccaacat 262800
gtccagcctg ctgatattaa tttaaataga aaaagatgcc ttagcatgct gtcttctgag 262860
ccactttctt ggtgaacatt tttgtctatc ttgccattta taagaaaaaa caattaagtt 262920
ttaatatttt ggacagcttt gaaaagtcat gactagttat atttagatac ttgaggtttc 262980
atttagatat caaaatgaga ggaaaggctg ggcttagtgg cttatgccta taatcctagt 263040
actttgcaag tagaggtggg aggattccta gaggccagga gtgcaaggga gttcaagacc 263100
agcctgtaca acataacaag atacattctc tgcaaaaaaa aaaaaaaaaa attatacaaa 263160
aatttttaaa gtagctggtc atggtgctgc acacctgtag tcctagctac tcggaaggct 263220
gaggcaggag atcgtttgag cccaggagtt caaagctata atgagttttg gtcatgccac 263280
tgcactccac cctgggtaac agcgagaacc cgtctctttt tttgagacgg agtctcgctg 263340
ttgtcaccag ggctggagtg caatggcaca atctcagctc actgcaacct ctgccacctg 263400
ggttccagca attttcctgc ctcagcctcc caagtagctg agattacagg tgcccaccac 263460
cacggccagc taattttcgt atttttagta gagatggggt ttcaccatgt tgactaggct 263520
ggtcttgaac tcctgacctc aggtgatcca cacgcctcag gctcctgaag tgctgggatt 263580
ataggcgtga gccactgcac ctagctgaga ccctgtctct taaaaaaaaa aaaaaaaggt 263640
ggtgtgtgtg tgtgtgtgtg aaatcattaa tctttcagtt tagtaataac aacattcacg 263700

-continued ctacagggct agctgcttat ttaccagttt acttttgaca cagccaacta ttagaataga 263760
attcaagtct cttctaaggg atgggtttgc atcttgattt gttattgaaa agctaaataa 263820
gtactgaaaa tgagctgtga tttcagaagg gtgaatgatt cagaattagc tcctttctca 263880
aactggaaag ctgacaaata aaatgaaaca gggtgaggtg gtagatgact ctgcttgggg 263940
aaagaactaa taatgagtgg agttctcctg tttgcaagag acctatgtac acgttacagt 264000
gtaatatgga gaaaccaagg ttaagggcca actgatgagt ttgattgaac tttaattggt 264060
caaataaggt ccttagcggg aaagaggaca gctgagaagt cctatcagac tgggaaattg 264120
ggaaatcacg ggtaaccttt gcccaggcaa tgtgagtatg tggtggaagg cagaagcctg 264180
ccttgtgcgc agtggggctg ttttgctcac ctgctccctg tctggagaga gacagtagtg 264240
actgacacag caagccagcc tgatagagcc tgtgacggca gtgataagga gggccaatca 264300
cagggaacac cgattggcca gtgccatcgg cacaggcgtt ggcacatggt agattccaaa 264360
gaattttctg atgaatgaat gacactcatt gtagcgctgt atagttttta aagtgttttt 264420
tttttttttg agacgcagtt tcactctcgt tgccctggct ggagtgcaat ggcgcgatct 264480
cagctcacca taacctccgc ctcccaggtt caagcaattc tcctgcctca gcctcctgag 264540
tagctgggat tacaggcatg caccaccacg gccagctaat tttgtatttt tagtagagac 264600
agggtttctc catgttgagg ctggtcttga actcctgacc tcaggtgatc cacctgcctc 264660
agcctcccaa agtgctggga ttacaggcgt gagccaccgc gcctggccaa gtgtttctta 264720
aaatacatat tcattccttt attcattcaa caaacagtaa ctgagagtct gtgatgtcct 264780
aggtacggtg cttggcactc aaatgcaaac caggcagaca tgatctgtct ttcttcccca 264840
tctaatgggg aatacagact ataaacaaac aggcggatag ttgttataaa taacagctct 264900
gatgagggaa gccctgggtg ctacagaagc acaaaggaag ggttcctaat gcaggtttcc 264960
aagatcaaga aaatgtatca gccaagtaaa aaactcactt ggcaactttg ctttctggag 265020
aatatacatg tttatttaat gaatgcttgt tggattttca aagataaaca ggctatttgc 265080
accatgtaga tacagactga cctgaggctc cacaagctga gggagtggga gctttatttt 265140
tgatgagagt tcatgatgca gatattgcca cttatctcca ttttggccct ggggtgacaa 265200
gatcgagtct ggaacgtcat tttcagggct ggatgcctgg ttgcttttga agaagaacaa 265260
aaggtgaaga gaataatcaa cactaaacat tttgtattac attcacagtt ctatgagcaa 265320
tttttaaaag aaacactctt aattctccca gtcataaaac cactgaatga ccaactctat 265380
ttttaaatgt tttaccttgc agatgattcc tgagttgtat cgttatcatg ttggcaatac 265440
tggggccaca ttttcttagc attaaattct atgaatttga tgaaatcttt ctgttccatt 265500
ggttttaact ccagaacctg taattgaatg agattcaaat ggtccaatcc atcaagcttt 265560
tcgattagta cccactagtt tcctctgctg agataaatct aattttgagc cagttcctaa 265620
atcattaatt actatttctc tttcttgcat tcctgttctt gtaaactctc acttcccaaa 265680
aacctattta aaatattcac acaataactg ttatttaaac cgcatacatg gaaaatcatc 265740
aaagacatac aaacacattt tgaaaagaca ggcaaagcag agtcgcaact acagaagttc 265800
accctgaaga cagctgatat aagatgtaag ttaataaagg agcaaagtta tggtgtcccc 265860
agtgttagca gctgaaagca aagcagatgc tatggtaaat gctgaaaact ctcagagttt 265920
ctgcacacac acaaacaccc acatgccaca ctttgcagaa attccatata gaaagctttt 265980
ttttgtttgt ttgtttttgt ttttggagac atggtctcac gctatcaccc caggttagag 266040

-continued

```
tagagtggtg tgatcttagc tcgctgcaac ctctgcctcc tggattcaag tgattcttgt 266100
gcctcagcct cctgagtagc tgggattaca ggcttgcacc accatgcctg gctcattttt 266160
ttgtattttt agtagagcta gggtttcacc atgttgtcca ggctggtttc gaactcctga 266220
cctcaaatga tctgcctgcc tcagcctccc aaagtgctgg gattacaggc atgagctact 266280
gtgcctggcc tttttttgg tttttgaaac agggtctcgc tatgttgccc aggctggcct 266340
cgaacacctg gccacaggtg atcctcccac ctcagcctcc caagtagcta ggactgtagg 266400
tttgcaccac cttgcctggt taaaaagtta tattctagtc cctacaactg ttgggggcta 266460
gaattacctg ttgctgctgg aaatcttttt gtctgctgaa ttgtggcctt tcagttacaa 266520
tggattccaa ttcagaaagg ttaactggtt ggagagcttc ttgatgctct ggctctgagg 266580
atttctttag aatggtagga tgctgcaaaa catttcataa tggcaggcta tttattttta 266640
aaaataaact ccactttatc tcaattctaa taatgggact acatagaaaa attttacatg 266700
aaataaatga tggtattttg ttatttgcta taattatata ctataatttt ttgtttttgt 266760
tttttgagat ggagtttcgc acttgttgcc caggctggag tgcaagggca tgatcttggc 266820
tcactgcaac ctccacctct tgggttcaag ggattctcct gcctcagccc cccaagtagc 266880
tgtgattgca gttgtgccca ccacacccag ctaatttttg tatttttagt ggagacgggg 266940
tttcaccatg ttggccagac tggtctcaaa ctcctgacct caggtgatct gcctgcctca 267000
gcctcccaaa gggctgggat tacaggcgtg agccaccaca cccagcctac tatgatttaa 267060
tgtacctatt tcataacaac ttcaaaaact actacatttg gtgaagtgat catcttactt 267120
cttcaagcta attcatccaa tgaattacta aaagcaagaa aatgtattgc ctttttttctt 267180
aaaaacaaat accaaataaa aaagtaccaa aaagagaaac agtattataa attcaaattt 267240
cccctatggc taaaatacat tttttttaaa aagagagaac atattaggat gaaaggggaa 267300
ccatatggcc tatgtatctg cagccagtct tatttctgtg aacataaatc tctaagtagg 267360
aaccactcat aagcacatgc aaatctttta tagtaagatc tactcataag atgcacattt 267420
gcatttataa acacagagtg cttttaaaaa tcatgagaac actttatatg atactttgat 267480
tatatatata aatacttgca aatgaataac aaagtatcct ggaaacaggt ttatgtttct 267540
gatgtcaaat tttagtcaca tctatgaaag ctttgttttc cagtcaatta gagtcacaaa 267600
attcctttat aatacatcct tcttttacga agaagcctta cactagacct cactgccaac 267660
aagaacactc agctacatta aaccaacaca aaccaaacca ccgccatcac caacaacaac 267720
ctagacagga aaactgcaaa gtagaatgaa ataaaaataa caagccagtg tactcatcta 267780
tggtgttaat gtgtgaaatt ctttcacact tagtacagtt tctctgtagc tggttcatca 267840
cttccaacca gagttctctt ctggcaggtc tgccacatat gtgtatcaag atgaatgtcc 267900
atagatagtc attttttacc tgatcttcac tgtgcttctc ctgaagcatc atctggactt 267960
tttctaaatt gcacttcact gttttcagtt tcagggaaag cgcttcagcc tcatgttgag 268020
tggctccatt atctcccagg ccctgatctt tgcaagtctc taacagaaag gcaaccttgt 268080
gctcaatctc tgttagcata gcctaggaaa taaaagcatt taattattca taatgttgtt 268140
cttgaagaag tattgtgcct gcaaacaagt taagacttac tctttttact taagtgtata 268200
caagaagtcc cagaaacaca ggatggaaga aaccctggaa aaacaaaaac ttccacagaa 268260
ttcttgtact tttcagtagg gatgcaacca aaccaatccc aattacacat gtcactctgt 268320
aaaataattt aagtaaatga ctctatagtc gccttacaaa acatagcaga atgtatccag 268380
cagaggatag tggttaagaa cacagatctt ggaactagac tatctggttt cagatcccag 268440
```

-continued tcctaccact tagtagatgt gtaaacacag gcaccttact ttagaggagt gtgcctctag 268500
tagtctgtaa aatgaagata ataaccgaac tcacctccta aggtcattat caggagtgaa 268560
tgaattaaat ccatgtactt tggccagtgc ttgatacatc tgtgcttaaa aagtgcagat 268620
attcttattt tccccctacc ttcctaatct tttttttttt ttttttctga gacggagtct 268680
cactctgttg cccaggatag agtgcagtgg tgtgatctcg gctcactgca acctccacct 268740
cccaggttca agtaattctc ctgcctcagc ctcccgagta gctgggatta caagagtgcg 268800
ccaccacgcc cagctaattt ttgtattttt agtagagatg gcgtttcgcc attttggcca 268860
ggctggtctc aaactcctga cctcgtgatc tgcccaccta ggcctcccaa agtgctggga 268920
ttacaggcat gaaccaccat gcctcgccta ccttcctaat cttttatgtt gcaatccaag 268980
tgtggagtag gaatttaaaa aagaattcca cgtaactgtt tgaaaattat ttcccttgct 269040
cttttccttc tctttctcaa gacaaataag cctccaaact ctcacaacac catagaagaa 269100
ataatttgga acctgaaata tttagttatt gatacaaccg gccaattcac acaaatctaa 269160
aaatatatca gctggatgaa gtaagtttcc cagtaagtct cggtcattgt attcctgctc 269220
aacagatcaa gtttgccctc tcctggggct cagcagcctg ctcggtcatg ccagctggct 269280
gggcactcac gtcagcagca acagacaaac tcacattcca gcaccatgat catttgtact 269340
aaaactcggt gcgtgactaa gaacaagttc cattcattga gcgaatttaa ggaattaaaa 269400
attttcctta aggacgaact ctattcttaa aacaaaattg caaataattt atcctataac 269460
tccttcatcc aagcaagctg taacaggccc ctttatctat gcttttactt tctgtggttt 269520
cagttacctg cagtcaatca gggctcaaaa atattaaatg gaaaattcca gaaataaata 269580
attcatacat tttaaatttt gcaccacctg agtagcgtga taaaattgca caccatcctg 269640
ctccatcccg cccaggatgt gaatcatccc tttgtccagc atattcatac tccagcactc 269700
ggctcattag ttacttagta gaggttgagt atacctaatc tgaaaatcca aaatcccaaa 269760
atgctccaaa acctgaaact ttttatgcac catgccagaa gtggaaaatt ccacacccaa 269820
cctcatgtga tgggtcacag ttgaactctg tttcatgtat aaaattatta aagttattat 269880
ataaaataac cttcaggata tgtatatgag gtatagataa aacataaatt gaggcctagc 269940
atggtggctc atacctgtaa tcccagcact tcgggaggct gaggcaggag gctcacttga 270000
ggccaggagt ttgagaccag cctgggcaac acagtgagac cctgagtcta caaaaaaataa 270060
aattagccag gcatggtggt gtacgcctgt agtcccagct attccggaga ctggggcagg 270120
aggattgcct gagcccgtca ggtcaaggct gcagtgagcc atgatcatgc tactgcactc 270180
cagcctgggt aacagagcaa gaccctgtta actctaatat aaataaagaa attaattaat 270240
taatttagtg tttagacttg ggtcctctct ctaagatatc tcattatgta tttgcaaata 270300
ttccaaaatc cctcccaaaa aaccaaatgc aaaatacttc tagttccaag catttgggga 270360
taagggatac tcactctgta gccatctcag ttgtcagatc gaaaaaacat aatacacaca 270420
gagtttggta ctatccacgg tttcaggcat ccattggggg tcttgtaaca caaccccccac 270480
agacaaaggt gggactactc tacttatgtc ctctatagat tcttctaagt ttaaacaata 270540
tgtacccata gactgtacag tggctataaa caaaatgtag cataatttta tgctctgttt 270600
ttcccactta actattacat actttttcat ctgtctccac acgtttcatg attttcattt 270660
taacagctac aagttgatat cccatgattc acttaccaat ttccctcttg ttaccccttt 270720
gtttctagtt cttcactttt gtaatcaatg cttctataat tatttttctc atttgggatt 270780

-continued attttcagaa ggtaaattaa aagtaatggt actggccggg cacggtggct catgcctgta 270840
atctcggcac tttgggaggc caaggcaggt ggatcacctg aggtcaggag ttcgagatca 270900
ccctggccaa catggggaaa ccgtttctac taaaaataca aaaattagcc agatgctgtg 270960
gtgcatgcct gtaatcccag ctacttggga ggctgaggca ggagaatcac ttgaacccag 271020
gaggcagaag ttgcagtgtg ccgagactgt gccactgcac tccagcctgg gtgagagcga 271080
gacttcacct caaaaaaaaa gtaatggtac ttttaactca aagaagatga acagcttata 271140
tgttgacaac tgacctccca aaacattgag ccaattagat agaactacca gacattagag 271200
tatctatttt tccagaatga tattttttta atgtaatgtg acagctgttt taatttatgt 271260
ctttaataat caaaattaaa caattctcaa atattacatt actaagcata atcctccctc 271320
cctccctccc tcccttcttt cctttctctt tctttttttt gacagtgtct tactctcttg 271380
cccaggctgg aatgcagtgg tgcaatcata gctcactgca gccttgaatt cttgggctta 271440
agagatatta gtgcctcagc ctcccaggta gctgggacta cagatacaca ccaccatgcc 271500
cagctagttt attttttaat ttttttttaa attattttgt agagacaagg tgtaactatg 271560
ttgcccaggc tggtctcaaa ctcctggcct caagcaatcc acccgccttg gcctcccaaa 271620
gtgctgggat tacaggcgtg agccaccact cctggtccat aatcttcact gaactgtttg 271680
ctcctgtcct ttggccattt ttccactgga attttgtgtt tttacagacc actttaaggt 271740
ttttatatgt ttcaataata actttattgt gttatgttat ataaatgagc caaagatgcc 271800
tttgtatgtt ggccccatgt ggtttttctt caaagcaggt cagaagcagt aagttcaaaa 271860
agtgccagca ccagactcaa atttttacac atttgacggc tttaaatgca gcccaaataa 271920
gcatatttta atccatttag agcctgtctg ctttgcatac ccctgaaaac tgcacccaac 271980
atctgccagc cacggataag actaaccctg ggctataaaa aaatcccaag cctctgctgc 272040
ccttcggcgc tctctgaccc agagaccctc cactgtgctg agacatcgct agacacataa 272100
gttccctctc cgtttctcct ctcccctggg agttcccttg ccttcctccc cctctgggtg 272160
gtggcctgac ccccagtcta tgccttagcc tctggaaggt ctcctgcagt aaagagcttc 272220
cctgtctctc acgatcataa tcttgccaaa atgctgccca aataaagctt gttgggtgca 272280
actgccacct ggtagtcatg tcttttcctt gagcagcctg gaaatccttg aactcactac 272340
aagtggcaat gaagatggga ttctggtgat aatcaacgag ttggcatagg gtctacccag 272400
tcagtagata atcagttggc aaatcaatcc tgaatggcct taagtgggtg ggactcaaaa 272460
tctggactgc ctcgagttga gtttagcata gcattgctct gtgctgtatg acgctctatg 272520
gcattcacag gctcccctgg gcctcatcag ccaggccaag cggcagtgcc agtatctgag 272580
tgaacctatc cctttagaac tgacttttgg gctgggcatg atagctcacg cctgtaatcc 272640
agcactttgg gaggctgact tgggtggatc gcttgagccc aggagttcga gaccagcctg 272700
ggcaatatag tgagacctct catctctaca aaaaaataca aaaagtagcc gggtgtggtg 272760
gtgcagggct gtagtcccag ctacccagga agctgaggtg ggaggatcac ctgagcccag 272820
gaagtcgagg ctgcaatgag ctatgattgc tccactgcac tccagcttgg gtgacagggt 272880
gagaccccga aaaaaaaaaa aaagaactga cttttgagat cagaggtgcc gagatgcaca 272940
gaaaaggagg ctggcctgtc tgtctggttc ctggatgttg ttaagactat gggcttacat 273000
agaaggggag aatgcacaac tgtggatcaa aggcaggctt cccacaacaa cataacaggc 273060
tacagcagga aacgctccct gtggcagggc tagtgatatg cgaactctga gacaagagga 273120
tgtcttcatc ctggcagaca agcccatatg ataaagacaa gtctggtctc ctaagtgcag 273180

-continued ctgggagaga ggcctttgca agcagctcgc gtgcccctgc tcttgtgaca ctcgattatg 273240
ctgttgcaat gtcatcattc tagcctctcc ctggagggat tagaaacccc aaccttcggg 273300
ctgagccggc aagctttact cagagcgact agcggcaagg aagtttatat ccctgcccct 273360
cccaagcaaa acccagggca ttcctagtaa aatggttgca aagccctttt atgctgtatc 273420
ttcaattttg caaattaata cttttggttt catttatgat gaatgaatat tctaattact 273480
tactaaaatt gaataaaata atagcattta ctgagcactt gttatatact ttatatacct 273540
atttaatcct gacaaaaatc ctatgagata actttatatc ctatgacact gctttaaata 273600
ccttatttaa atcctgcgac actactttaa ataccttatt taatcctgac aaaaatccta 273660
taagataacc tactatataa ggaaaatgag gctgagaagt tcacttcccg aagttcacag 273720
ctaatgtgac agagctggat ttagactcct agattctgaa cactactgtc ccctcaaata 273780
agatagttcc ataaagcatt tcaaagaatt accctgagaa ctaaaagctg aggccaagat 273840
aaatgtaagg gtcagagtaa cagaaagaaa aacagtgttg ctttaagaga aattcaccca 273900
atcttggcag atgattggtg gagaggcaaa ccatgaactc tgacttctca gtcttacctg 273960
gcaccctacc agctgctgtt ccagcacctg ctgcatgtct gcgtttaatg tttccggctc 274020
aactgccacg ttggcttgtt gcagccacag ctccagctcg gccacctggg tcttgcaggc 274080
atgcaggact tctgtgggct ccggcctagt tttctccacc ctgggctcca aacctccttg 274140
cgcgtcagaa gagtccagag tgtcagcctc aataggaggt gtggtgccct aagagaaatc 274200
caaagataag ccagggagtc caaagttttc agacttgggc ctgcaaagac ctgggaacct 274260
gcaacatttc cccagttaaa agaaacaaaa tcaggacaga agaaggaaga aagaaaagag 274320
aaatgcacct ccacactcat agcaacaatc acgtgacctg gtgccacagg tttccaagca 274380
gccgatctgc gagtaagcag gtacagtatt cccgggcaca gaggacgcaa acaggctcac 274440
agttcactac ccggtgagcc ccaggagaca ggtgagaatg tgagtgacag ggtgtgtgtg 274500
tgtccgaaac atttaaggga attggccagt gtttagcgtt acgtgacaca tgattaagca 274560
atgcttacat tgctgcacac tctattccaa cagaaaaaca aaacaaaaca gaacacgatc 274620
tttacctccc agcagggata caataaaata taccacataa ttttaacttg acatcttctc 274680
aaatagttag attataaaaa ttttagcttt ttaaaaacat acatggtatt acttatctaa 274740
atttttccct aataaaaaca gcttgagtca agtaatgaac ttcagtgggg taacctggaa 274800
acttttttcc tattcctcag aaggaatccc taaaatacct tccttcccct tctgcatact 274860
cgaatatgat tgagttaagg actagatgct cacagtataa agaaagtgtg gtgtgttctt 274920
tttacattga aataactggg ttgtttatca actgattgga aaattttctc ccagatacca 274980
aatgaaagta ttccagtaat tatatattag atatgttcaa cctggaggca aaagataatt 275040
ggatagagag atgtatttac ctcccactgt attatctatc cttcctcaga atatggaaaa 275100
agtagtatcg atacttctag agaaattcct ttaggaataa ggatttgtgt tttgctgtat 275160
aaaccttttg ctctcaaaaa atattttatt gattatgata aaatacaatg ttttctataa 275220
gagtttgtta acgtgttagc atctaataat aaaatgtaat tctagccaag tgacaaactt 275280
tgaatgggaa tcgattgcaa atatataccc taactcaaat gcacattctt caatgtttac 275340
ggaattttgt ttagacatag aactttcagt gtaaaagagc gaacaaaatt ggtaggtggt 275400
aacaaacacg tgtcaggcat gagaatgctg ttcattttca tgcacactga tgagtattat 275460
gaaagctggt ctggcacaag tgtcttgggt tgtacttttt acctttcacc atctattatc 275520

-continued

```
ttcacataca tgtgctgttt tctgccaaaa tgccatttct tccctgcctt cattaatcta 275580
ttattataat tttcttcaag aatcttgaaa accttctcaa ggaaactttt ccttgtgttg 275640
tgctttttct gaacttcata tatagtcaag tctatgcttg gattcaactg ttttaatttt 275700
ctttttttaat cctgaccttt ttttttcttc ttgggaagag tttccctctg tcacccaggc 275760
tggagtacag tggcatgatc tcggctcact gcaacctccg cctcccaggt tcaagtgatt 275820
ctcctgtctt ggcctcccaa ggaactggga ttacaagcac acaccaccat acctggctaa 275880
ttttgtattt ttagtagagg cagggttttg tcatgttggc caggctggtc ttgaactcct 275940
ggcctcaagt gatccacccg cctagacctc ccaaagtgct gggattacag gcataagcca 276000
cagcgcctgg ccctgatttt tttttaaaaa aagcaacagt tgtgtgattt tgcttccaga 276060
cttccagata tcaatttcta gtcatctgat taattccctt ctagttttca gatattgcta 276120
tatctagttt tcagatattg ctacagacaa agattttgga attccctttc cttttttttgc 276180
cacttgagag aacaatctat taatattaat taatctaaga caatctatta atattaatct 276240
gtaatcacag atttaccacc tgccttcatt atttattcaa aaattttatt tgagcacctg 276300
ttatatgcca cgcacatttt tttttttttg agatggggtc ttgccatgtt gcccaagtgg 276360
gtctctaact tctgggctca ggtgatcctc ctgcctcggc ctctcaaagt gctgggatta 276420
caggcatgag ccaccacacc cagccctcca cacacttttt ttaatgacag tattgagttt 276480
ctctgctttc tcatgaactc accaaattaa tgaggaaata agcaagctgc atgactaatc 276540
tgggtttttt ttgctagtta tttgaacctg aaaagaatcc aaaggggaag agaagacaaa 276600
aagaatattt ccaaccatac agcttcaaga gctgagggtg gcctgaggaa cccactagag 276660
atcagttcac ccacctcttt ttaaagtcta agaaatccaa gtgcacagaa tgttcaatca 276720
gcccacatgc ctccctttttt accatgttgc ttctgagaag cacccaagtt actaacccaa 276780
ggtcacacag ctctgtgatc ttttaattca gagttccctt gttttttaca cagtagcatc 276840
cctgtaaaat accttctcta tatgatagcc ccaaattcta aaagcaaaac ttatttaaat 276900
ggatgtttta taattgtaca ctttggcggg gggggggggg tgtaaaaagt attactataa 276960
gtatttctta ttaaataaat atgtcttctc taaagcataa ctgtaaatta ataatagcta 277020
gcctttattg ggctcttacc atgagcaggc actgtatggt cacacaacta gtaaacagaa 277080
tcaaaagcaa ttcctgcttt cactacactt tggaatctac aagtccacat tcttgatata 277140
atttcaccaa ccttttagta tccaagttaa cttttcagtt ggtgaatcac attgcttcac 277200
ttctgcatca acacaacact gatctaagta atcagtgaag taatcagtaa tcagtaaaaa 277260
aaactgcagt taaaatgcaa gttgattttc tggctattgc tacatttcat gccaaaatag 277320
caaaccttta cattttctcc ttaatatttc agtcaattct acaaatacct gcatatctcc 277380
cccactgctt atacctgcat atctccccca ctgcttatga aatgtaaaac tgcataccta 277440
aagtacagta cctaactgca catgaataaa tgaaaagcat gcccctagaa tggcatggtg 277500
gtggtttact ctgaggtcat gcctagcttg atttcacatt ttcacatttt tccatactaa 277560
atatttatcc ttggttgtaa tacgggtcaa gaatgactca gaattttact aaaaattatg 277620
caattatcat ttggtcaata cacttaacct ctgaaacaaa aggtttgttg aggctgatag 277680
aaggctgatg acattggctg cctggtttct gcaaagtccc cactttcctt ctcattagtg 277740
atgtgctgtg ccaatgagac agaaatcact aaaaggcagg aagacagtca ccaagaggta 277800
tggaacttgg agccagtaaa ggtgtccctg aataatcaga agtggacaaa ttcctcctgt 277860
agtaaagggt aacatctatt tttcctgctc caagaattcc tccccagcaa aagttctgag 277920
```

-continued

```
ttaagaagaa aatacaaata cacacataca taaattagtt caaaagagag tcactggagc 277980
ctaatagttc aaagctcagg ttttaaactc agagtcagaa agatctgggt ttgaatccta 278040
gctttgccac ttactagcta aatgaccttg ggcatcttac ttctctgagc ctcagtttct 278100
ccatctgtaa agtggggtaa cagtaatatt tatctcatag agctgttgtt aatgattaaa 278160
agagatagta tatgtaaaat cccagtacct ggcccatatt aaatgttcag taagtatttt 278220
gttatcctcc tttttcttcc tccttctctt tattgtcatc attatctagt atccacatgg 278280
ccagggaaaa gaccctagag gttatccaca ccagcagaaa caatattaag cagaatggct 278340
actgtagcta aaacaccatt gaagctacat ctgattttta attagatgtc aaaaataaca 278400
ttacggtggg cagatggttt gagaccagga gttcgagacc agcctgggca acatggcaga 278460
actgtgtgtc tgaaaaaata caaaaattag ccaggcgtga tggtgtgtgc ctgtggtcct 278520
agccatccgg gaggctaagg tgggaggatc acctgagccc aggaggttga ggctccagtg 278580
agccatgatt gtggccactg cactccagcc tgggtgaaga gtgagaccat gtccccagaa 278640
caaaacccag attaattctg aacagcaaaa aaacatactg actaggtcag caacttcctt 278700
agacctaagc attgccactg ggtgtaaacc tctgacattt gtccaccttc ctagacatat 278760
attgttaaga gagacagaga atgaaaggga gggaaagaaa gaagagaaag gagtaacaat 278820
ttgagaacta agagatattt ttgtaagact agacaaaaga ttgggagaaa aaaacataaa 278880
tagaactcag tataaaagaa gaaaagagat gcaataatta aacaataaaa acagcaaaaa 278940
catgccaata tcttttatag gagctatttg atgagaccct tggagcttta ggtccagcta 279000
aacaccaaaa ttaacttggg aaatagtacc catccccac accctgctgt aaggccttat 279060
tgagaacaac tgaggtacaa gattccaaat taggaagcca gattagaata ttctgggttt 279120
gattccttat tcctccattc acaagccata tatatatata tacatttttt taaaagacag 279180
agtcttgctc aatcgcccag gcaggctgga gtgcagtggc gcaatcttgg ctcactgaaa 279240
tctcctcctc ccaggttcaa gcgattctcc tgtctcagcc tcttgagtag ttgggattac 279300
aggcatgtgc caccacgccc ggctaatttt tgtattttta gtagagacgg ggtttcacca 279360
gcctgttggt caggctggtc tcaaactcct gacatcaggt gatccacctg cattggcctc 279420
ccaaagtgct gtgattatag gcttgagcca ccatgcctgg cccactaact atatttttac 279480
tccctgaatt ttgatttctt aatttgtaaa catatggtag gtatgaacct accttataca 279540
gtctgagggt taaacagata actataaatg ccttttatgt aacaggctat taatcaatat 279600
taacccttct ctactttctt tgccccata agttctatct acagattaaa gaagtagtca 279660
tcaacagaaa gactatttca tgatgacaaa tggtaaatga gtgaaaagcg tctaattctc 279720
tatgccatgc ctattttctt tgtaaatatc tgatgacaag tcttccagtt ctacagcttg 279780
acagcacata tcttcatatg ttaaagttca caaggaacac ttagcttgac gtacaaggta 279840
ttgcaggaca cagaacactg gtcatctcta ggtgctagtc cagctatctg agcagtttac 279900
ttattaccaa ccaggactta cctcttctgt ttggttgggc cttagggaac attctgggcc 279960
ttgctcagtg tttagtgagt ctggtgtgag gatttgtgcc atggaattat cagaggtgct 280020
tattttccca tatgcttcct gtaaagaaaa gaatcagagc tccagaaagg gtcctgccct 280080
ggtgccacat gaattcttct ttctgcgcat gctcatttta caaactacct gcttgcaaaa 280140
aagtcagata tggagaagtc agatacgatt agaaaaaagt ttgttcatta gggaaaaaat 280200
cagcttcccc aagactgtct ttatttgaaa gacttgcatt ctccacactt ctcttcttaa 280260
```

-continued tgagcacata aacaatctag agaattacgt acttaagtaa attcttccag aagtatgctt 280320
tgtcttgttg aagtattctt taaaagtatg tccttatgaa aatttaaatt acatggccag 280380
gtgtgatgtc tcacacctat aatcccagca ctttggaaga ccaaggcaga agaattgctt 280440
gtgctcagga gtttgagacc agcctgagca acatggtaag accctgtctc tatcaaaata 280500
attaatcaat taattatatg ataaaggcca catttcaaag agtggggaaa aggtgaattt 280560
attccattta ggaacaacta ccaaggcatt ttatgaaaaa tataagtaga attcttgtat 280620
tactcctaac aataaattct agttatgaaa aatataacta gaatccttgt atcacccccta 280680 acaataaatt ctcattgtat tctcaaagtt atgccataaa aattctaggt gtggggaagc 280740
atgacaagaa aggaaaataa tattagtatt gactacataa aaaaataaaa taatatgcac 280800
cacaaaagat accataatct aagttaaaga gaaatgacag actgggataa ctattacaca 280860
tagtgttaat attttttttt gagacggagt ctcgctctgt cgcccaggct ggagggcagt 280920
ggcacgatct cggctcacca caagctccgc ctcctgggtt cacgcccttc tcctgcctca 280980
gcctcccgag tagctgggac tacaggcacc cgccaccacg cccagctaat tttttgtatt 281040
tttagtagag atggggtttc accgttttag ccaggatgat cttgatctcc tgacctcgtg 281100
atccactcgc ctcggcctcc caaagtgctg ggattacagg cgtgagccac catgcccggc 281160
caatattctt aatatattaa ttactctata aataataagg aaaacatcaa cccctacata 281220
gaaaaacagt caaatggtag gaacaagcaa gtcgcaaaag aagagttaca aaagccaata 281280
ggcatctaaa gagatattca acattcttag aacataaatt aatttaaacc actggctaag 281340
tttggctaag actgacaata tcaaaaatca gcttgtgtgt tggttggggg ggggggtctg 281400
gaaatgcaat tccatgtata cctaggagaa atattgttgg tatagccttt ctttttcttt 281460
ctttcttttt tttttttttg agacagggcc tcactctgtc accaggctgt ggtgcagtgg 281520
tgcaatctta gcttcactgc aaccttcatc tcccaggctc aagtgatcct cccacctcaa 281580
tctctgggac tataggcatg caccaccacg accggctaat tttgtatttt ttacagagac 281640
agggtttcac tatgttgccc aggctggtct tgaactcctg agctcaagct gtccgcccac 281700
ctcagcctcc caaagtgcta ggattacagg catgagacaa ctgcacctag cctggtataa 281760
cctttctaga aggcagtttg aaaatgtgtg tcacatttta aatggatata tactttgatt 281820
cagcaatcct tcttttaaga ttaaccaaag ttaagcaatg ggaaaatgac atgtacacaa 281880
agaattaaca caacgtgaca gaaagcatgt ggatattata atcaaccaac cttgattgct 281940
ctacttgcaa gttgtatgat cttggacaaa ttaacctgaa ctctctgaaa cctcagttac 282000
ttcaccttta aaatgggaat aaaacctatc ttacctatgc ttgcaattaa gtgacatata 282060
taaggcattt agcatttcct aacaaaatgt tagtgtcttt tcagcttcta ctgaaaacag 282120
tgactgttat cagaaaggta taaaccaaga attaaaggta gagattagat aaaattagaa 282180
aggtaggcgg ggaccaggaa aatctggaat gtcacgctaa gtttgcattt tcttcagtag 282240
ataatcaaac tccatgaaga attttaggct gaggtttcgc atgattggtt ttaggaaaag 282300
tcatcagtat tttataagat gtattaggaa aaacaattgg agactgtaaa ccaattagag 282360
ggctactcca aaagtccagg gaagtaataa gaattgcttg aaataagacg atggcaaaaa 282420
taatgggagg agaggctgta cacagtgaat ggacatcatt ggccactgac aggatgtgac 282480
aggtgagaga aatgaggcac ctagtagaac tccaaagttt atctctgaga aaatagtggc 282540
accaacagca gacactgaga aattagtaag aggagcaagc tttgaaggaa aggtggtaaa 282600
ataggtttga gttggagaaa ctccatccca aaaaagtcta tcacgaggat agaaatgtgg 282660

-continued aatagattta tagatttaag agaaaagcca agactagaga tttagtttgg taatcactgg 282720
catagaggtg accacaagct ctcagaggaa ataaaattgc cctgaaagaa aacagagagg 282780
ccgggcgcag tggctcacac ctgtaatccc agcactttgg gaggccaagg caggtggatc 282840
atctgaggtc aggagttcaa gactagcctg gccaacatgg caaaactctg tctctactaa 282900
aaacaaaaaa aatgagccag gcatggtggc gggcacctgt aatcccagct gctcgggagg 282960
ctgaagcagg agaatcgctt gaacccagga ggcagaggtt gcagtgagct gagatcgcac 283020
cactgcactc cagcctgggc gacagatcga gactctgtct caaaaaaaaa aaaaaaaaaa 283080
aagagaaaac agggagaagg aagaggacag aacattgggg gaatgcctac catcacagac 283140
gaaagagaaa gaggggcaag aaaaggagat ggaggaggga ctagaggtag aagggacagg 283200
gaagaacaga attaagaaag ttaaaggaac accgcagtta aagaaggaag aggtggtcac 283260
tcccagagag gtcaataagg attaggacta ataaaagggt attgaatttg tactccagaa 283320
gtcaatggca gtttaagcat agccagaggc tgaaacaaga ttacaaaagg ggccgaggga 283380
gtagaacacc aaggaaagac cttcagtagc aaatgaaaga cgaagtgtag taattgacat 283440
gggaagcagg atccagaaat tcagttcatt aaagtaccat actgagctga gtataggata 283500
taaacgataa gcttctttcc actcatgaaa tcgtatcagg tgtattcata aaaatgtgct 283560
aagtcataat tgaggttcag aatcctattg gaaaacaggg aaagagacag caatttcctt 283620
tgcaggatgt caggaggttt cttggagcag gggaagttga gatgggtctt tgtggatggg 283680
aaggaagtct acagagaggc atggagaaag ggcatcccag ggaccaaagc cttctgtgga 283740
gctactgaag atgcaggctg gttctggaac tatctctctg tttgaagtag tggggccaca 283800
aggaagagaa catgttaggg aggggaagcc tgagtactga ggtagagaag gaaggaacct 283860
agccagaggc agagactgac aaggcaggta taggcagaga atggcgccaa tgattaagga 283920
aagagttggc ctgagagcag ggggaggggt cagccctgga caggaggcag gagtgagagg 283980
tttatggatc acgaggatgc agagatcttc cgggagcaaa ggaagcacgt agttttcaca 284040
tagccttaca atgattttct aaagtgagac catttgagag actggaaaat atttagaatg 284100
tcataaggag taaaaagact tagcgcatct aatttatctt acatactact ttgttccaca 284160
aaaaaaaaaa aaaaagatta tggagagacc ctccacccaa aactcccaaa agagtggcat 284220
gttaatttac atgctttggt aaaacagtgc agtgaagctt ttagctgctc ctttgaggta 284280
tctgtttggt cagtttggat tttcacatat atggagtttt cctcaaaaaa agtactctcc 284340
tgttattaag tacacaatag aaatagaacc aagcaggtgc tcattaaggc tgtctttgca 284400
tttgtgcaaa ggtaatgtga gaagctttca aagattcacg gtagccaaga tagagaagca 284460
accgaagtgt ccatcaactg atgaatggag aaagaacatg tggcatatat acacaacaga 284520
gtactagcca gccttcaaaa agaaggaggt tctgtcattt gtgacaatat ggatgaaccg 284580
gaagacatta tgttaaatga aataagccag gcacagaatg ataaatactg tatgatctca 284640
cttacatgtg taatctaaaa aatatggact gcatagaagc agagaatagg atggtggtta 284700
ccagggctgt tgggggctga gagagggcct ggggagatgt tggtcaaagg acacaaaatt 284760
tcagttgaac agcaggaata agttcaagag aatctatgta taacatggca attatagtta 284820
ataataatgt attgtatact taaaagttgc taagcgacta gattttaggt gttctaatta 284880
ctgaaaagat gacaaatatg tgaggtaatg catatgttaa ttagcttgat acagccattt 284940
ccaacgtata cacatttcaa aacatgttgt ataccataaa tatatacaat ggttgtcagc 285000

-continued taaaaaaaaa aaaaaaaaaa aaaaaaattc agcccatgca ggttccctcc ctaagcattc 285060
ctttaaacaa aatagttctt tactatcctt atttttattc ctgtctgagc tacaaatggg 285120
cattttaaag gtttaggcag tgcttgctga aaaccaaaca aaggaaagag ggaagagagg 285180
aagcaaagct aacatagaaa gtcaggcaac atggcgaaac cccgtctcta ctacaaatac 285240
aaaaattagc tgggcgtggt gacgtgtgcc tgtaatccca gctacttggg aggctgaagc 285300
aggagaattg cttgaaccta agaggcggag gttgcagtga gctgagatca tacgactgca 285360
ctccagtctg ggcgacagag cgagtccgtc tcaggggtgt agggaaagaa agtcgtgcag 285420
aaagagatcc ctgctccccc ctgggccctc gtaaccccta agcgtggctg atacgcccag 285480
cattacctga acaattgttc cagaggatga ggaagctctg tcttcttcca tgtccttgtc 285540
atgcttccaa agtgaagacc aagactgagg cgatggctct gccttctcat ctccattcta 285600
tcacagtaaa cgattggtta gcaaagggaa gagcttccct tactgtcata accggtgccc 285660
tactcactca cgtcttttat accagactca acttatcagg cagtgtaacc acagcccttt 285720
attgcagtcc tcccccattt ttttatctgt atttttttta ctaactatat catgtttaca 285780
aatgtggctg ctcttcctaa agcctagaaa atacttttaa aagtaggggc tcggctcacg 285840
tcacacaacg gaaatcttta aaatggtgct tttaggaatt taatctgctt tggtaaatgt 285900
aaccttaaat ggtatctttg aggccaggca ctgtgactca cacccataaa cccagccctt 285960
tgggaggctg aagtgggagg atcacttgag gccaggagtt ggaggttgca gtgagaacca 286020
ctgcactcta gcctaggcaa cagagtgaga tcccatctct aaataaatat ttaaaaatac 286080
gtaaaagtta gaaaaattaa aatgctatct ttaaaattac agccacgagt ataagaaaaa 286140
atgttcaacc tcactaatca ccagggaaat gcaaattaaa accacagtga gatactactt 286200
tacacctgtt agaatggctt atataaaaaa gataaaaatg acaagtggtc atgaggatgt 286260
ggagacaaca gaacccctga atactgtcgg tgggaatgta aattggtaca gtatcaaagt 286320
tcctcaaaaa actaaaaata gaaccagcaa tcccactact gagtacatat ccaaaggaaa 286380
aaactcagta tgtcaaagag atgtctgcac tcccatgttc aatgcagcac tgttcacaac 286440
aaccaagata cggaattaac ctaagtgtcc accaacaaat gaatggataa agaaaatgtg 286500
gttatataca catactgaaa tactatctgg ccttaaaaaa taaggaaatt ctgtcatttg 286560
caacaacatg ggtaaattag aggatcttct gttaagtgaa ataatccagg cacagaagga 286620
cacataccac atcatctccc tttaatgtgg aatgtaaaaa aaaaaaactc atagaagcag 286680
aaaataaaac aatggttacc agcgaccagg gattacaaaa atgtctgtca aaggacatta 286740
aaaaaagggc acaggaggaa taagttcaag ggatcttttg tatatcatgg tgactatagt 286800
taatatatgt ttgaaaatca tgaagagagt agattttaag ttttctcatt acaaaaaaaa 286860
atggtatgtg aggtaacatg tatgttaatt agctcaattt agccattcca caatgcatat 286920
atacatgtac tgtatcaaaa catcatacat gtcataaata tatatatata tatatatata 286980
tatatatata tatatatttt tttttttttt ttttgagaca gttttgctct tgtcacccag 287040
gctggagtgc aacagcgtga tctcggctca ctgcaacctc tgcctcctgg gttcaagcaa 287100
ttctcctgcc tcagcctccc aagtagctgg gactacagga acctgccacc acacctggca 287160
aattttttga atgcatacaa tttttacttg tcaatttttt taaaaaaatc acagcttgat 287220
gttccccttc atgtgtccat gtgttctcat tgttcaattc ccacctatga gtgagaatat 287280
gcggtgtttg gttttttgtt cttgcgatag tttactgaga atgatgattt tcaatttcat 287340
ccatgtccct acaaaggaca tgaactcatc attttttatg gctgcatagt attccatggt 287400

-continued gtatatgtgc cacattttct taatccagtc tatcattgtt ggacatttgg gttggttcca 287460
agtctttgct attgtgaata atgccgcagt aaacatatgt gtgcatgtgt ctttatagca 287520
gcatgattta tagtcctttg ggtatatacc cagtaatggg atggctgggt caaatggtat 287580
ttctagttct agatcatcac actctgggga gtgttgtggg ttagggggag ggggcagggc 287640
tagcattggg agatatacct aatgctagat gacgagttag tgggtacggt gcaccagcat 287700
ggcacatgta tgcatatgta actaacctgc acattgtgca catgtaccct aaaacttaaa 287760
gtataataat aattaaaaaa aagaaaaaaa aatcacagct tgatgaacat gtactttttt 287820
gttgctgtca aagacaaaca acactataaa catcagctca gaaggaaata catgtctcaa 287880
attaacatcg tactgaagtc actctttttg gcccctggtc cctccattat tttcgtagtt 287940
ctctctgcca tgaaggggta taatcagatt gcaaagttgt ttgatggtca cagagcacac 288000
agtaaagttg tactcttcct tgtcacagtt ccaccatgtc ccagcgacac actctaggac 288060
aagaggtctg ctctgtgtga gagtggagct atttaaccat ctataaaatg agcccaaaaa 288120
gtgtctggtg gttacatgta agtcacaaaa attgtaagtt gcttcaattt tcttcctttt 288180
gtcttaagac ccattgcaac ttattttttc aagtatgaaa tggaaactga cgtcagaaaa 288240
gacaactgaa aatgtctcat tcaaccagtt ataatcaagt agtacaaatt cttagtatta 288300
cttgctaaca caactcttca tgtcattgga aatactgttt tagagcaaaa gagtaattga 288360
aatgcggaaa aatacagttc taaaaatgag accaggagtg ccaaacagca tgctctcaaa 288420
acttcagaga aagtcctcag aaatcaggat actacagaga acttcttcac cttctcccgt 288480
atgccaacaa gagtgtctga attacattca tctcactctt acacagtgaa gtaggtttcc 288540
atacacttaa acattaataa cataagagaa ctacttcaat catactttta aaatatcaac 288600
attaatttta aaaattctta ggtttccatt cactttaaga tcttttcatt gacttctttt 288660
agagatctgg ttctaacaaa ctttaacaag aaaatcattt cccttacatc gctcttcacg 288720
gaactttctt ccacctcttc ctcgactgct gccaggtaag acatggagcc tcttctgttc 288780
aactgaaagg cacagcacaa gaatacctgc agtctgcttg ccagtcaaca tcaccaagat 288840
cccagtccag ctgcattttt atgtagctaa ttttttactt actttatcca agatgcccac 288900
ccccacaaga agcctgtctc ctggtccgtt cagctcctcc agccagatat ccggagtcag 288960
tcaaacctta ggtcttgtta ttttcatggc cccctgtgcc ccttcataaa cgattaaaga 289020
atgtgattca ttgatgtgaa tgcagagaag acttaggcac tgggcccttc ttgagtctgc 289080
aaagggctga cttttctgta cgaagatact tcaaagggag gcttgatcca cctgcctgtg 289140
aaattttata agcatgtcct aaagtaattc aggtgttaag aattctgggt ggagtccaga 289200
acaggcacac cctgaggatt tatattcact agtaaacaac ctcaggttga gtatttccac 289260
tttaaaaaat tcctttacta caggccatag acatagatgc cacaggtcgt tcaggtggaa 289320
aacactaccc attaatgctc ttgtggagtg tggggccagc attaacctaa agtcataccc 289380
accttccgct cagaagcatc cctctctgcc actccacctt cctctgatgt tacagctggc 289440
agcctatctc tttctactcc ttcttgttct tgcttcaaat gctggtgaag gtttagtacg 289500
gtggccttca agtccaccaa caggtcttct tttctctggt tcaaactcag aatctgtttc 289560
tccatacgtt cgatttctcc ctgtgtagaa agagtgtttg cataggtttg agaagtctga 289620
ggcctctgca ggcccagagc agcctgcttc ctttggtaca agggctgaag atttttcttt 289680
gctatttggt ttacaaagcc agaagctagt ctctggtacg gtatagctcc tttccatcct 289740

-continued ggatacaatt ccaaaggtcc tgtgtagggt ttataagcta taggatgcct cagccttacc 289800
agagaccttg tgaatcagaa tctctgcggg ttgagccaaa gcatggaaac ttgtaacatg 289860
ctccacacgt gactgtggtg tgcggccagg gttgggagct accgctctag tggccagcta 289920
caggactgag agaaccagga tccacggggc agggccccgg agtctgcaca ctaaccaaca 289980
ctgcataagt gccttatgca gactttccat tgtgtcccaa agcatattaa aaatgcatgt 290040
ccccaggaga catgttccca tgtctctcca ggaaattctt aagcagacta acatttggga 290100
accactgaga gaaaatgaag acagaaatct cattctttta ttatcatctt tgaaggcttc 290160
tttggtatta ctaaattcat ttactttttt tttaagcaga gtctatcctg ctcaatcatt 290220 tacttttttct acagtaaaat cttcctacta aataggaata ggtaaacaaa taaaggtacc 290280
atgtagtata tcttattatg ggaatgatgg acagatgatc tcaagcttcg tgatgttact 290340
tttaacattt atattattga tatgtgcaga tcaaatttct tattcatggc agatatgcag 290400
atgcccactg tatgtctgag atgactatag gattatagat tcttagcttt ggaagaaaca 290460
gcaggtgaca aatacactaa catcctcctc tctagcacct ctgagagatg tcattcaact 290520
tgcctgagct cctgaagtga gtactgcatc agaagcagcc tgctcctttt tagaaaacct 290580
tcatgtgttt gaaatttgtt cctaatatat tccttagacc cctattcttt ccttgttatg 290640
tcttcctttc ttgctgtcag ttcatccatc cacccatcct acagatagtc atagaagcaa 290700
taattttctt acaaaacaga gaaacgtaat ctgtctccac ctgcaagaga gagttctaaa 290760
ggccagagaa agaaggtgat ttgtccaaag ctgcaactag cacacagcag agcacaggcc 290820
tgggctttct cctggctgta ctgcacacat ttctatgcca atacccctat tctgtctgaa 290880
gtcaaaattt ctgtgattgc ttttgggaaa taacaactgt ttgacttaaa tctgagttgg 290940
ctgcattttg tgttccactt tcaataaaca ctaaacttca gaggtacact gcctcctgac 291000
aagagcaata ctacagccac taggataaca caaacagagt agaggcacag tcctacatgg 291060
agcagctgct ctcaaagcag catctgcaga cccctggcca cagtccatga ggtccagatc 291120
attttcataa tactaaaatg ttatttgcct tttacaccat actgacattt gcactgatgg 291180
catgaaagca atggtgggta aaactaccgg cacctaatat gaatcaaggc aggaacacca 291240
agtatattcg ttgttactgg gttcttcact ttgatgtatt tatagtaaaa aaaattccat 291300
tttccttaag aatgtccttg ataaaaatat gtgtcttagt ttatttgtgc tgccgtaaca 291360
gaatatctgt gactgggtaa cttataaaga acagaaattt atttctcaca gttctggaga 291420
ctgggaagtc caggatcaaa gtattggtac gtttggtgtc tggtgagggc tgttctctgt 291480
ttccaagatg gcgcattgaa gactacatct tcctaaaggg agatttgtcg tgttctcaca 291540
cggcacaaag cagaagggca aaaatgggtg gactccctcc ctcaagccct tttctgaggg 291600
cacctaatcc cattcatgag ggaagagccc tcatgactca atcacctccc aaaggccaca 291660
cctcccgata ctgctgtgtt ggtgattaag tttcaacatg aacaaaaatg ttggggggag 291720
gggaggcaac attttttggg aggaaaaaac attcaaacca cagcagtatg tatttttagt 291780
attctttgtg aaaaaatgga aagtatgcat atggcacttc tgctgcatac caagggccaa 291840
tggttgagaa aagcacttat gctactgttt gagttgtaag ctgaactatc ctttttattc 291900
acagaacact atttttacgt gaaaaaagcc agctgataac tgtattgctt tccttaaata 291960
ctaaaagatt tttctgaaga gataagtgtt aatattaaca actatgattt aaagaatatt 292020
agacaatgtg tcaacatttg gaagatcggc ctaactcagc taatcaggat tatccaagtg 292080
atcgagcgtg atgtataaaa tcatgcattg ttagaagatc cattcgaagt acaaagtagg 292140

-continued

```
ccagtaaatt ttaatgtaaa aacgtataaa gttcattgac atgggtttag attccgtttt 292200
acaattaata catactttgc acttgttggg ttttagtata gtttcaaaga aaaatgtcca 292260
caattattca aaaggactat taaaatattc ctccatcttc caagtgcatg tctttgagag 292320
gctggattgt cttcctatac ttaaaacaaa actacatgct tcagcagatc aaatgcagaa 292380
acatttgcag cacccacatc tgtccattag gtgggtgcaa aagtaatcgc ggtttttgtc 292440
attactttta atggtaaaaa ctggaattac ttttgcactg acctaatatt aagccagata 292500
ttaaagagat tacaaataca taaaacaatg tcactcttct cattactatt tgttttagaa 292560
aatataacta ctttaaaaaa atgttacttc tactacagcc tgggtaacac agtgagacct 292620
catctctaaa aaaaagaaaa taaaaatagt tattcctatt aatatgtagt gggtttatta 292680
ttgttgctta aaaactaaat gaatgttttt acatttctga gttttaattt agttatcaat 292740
ggatataatt catataaaca aaagctctct ggggtccttg attttttagc ataaggggaa 292800
atctaatatt tttacaatac tgagtcttca ttactgagtg ggaattattg atccaccatt 292860
taacagctgt gtcatcttgc actctcctgt acttcactgt agatgtcaaa tcacttgccc 292920
caggtctcac agctggcgag tagtgtaatc ttcttttgag taccatatta attgcttgcc 292980
tgtatcaatt tgatggcaag aaaaaaaagc agctctctat taccettagc atacaatcac 293040
gttttttgt tgttgttgtt ttttattata gaaatgctac ttcaaaaaca aagactgaaa 293100
aaacctagca acagatggtt aacatgcaaa ccattgtaac tgaatccaca ggacactgtt 293160
tttttatttt ttattttttt taattttttt gagacggagt ctcactctgt cacccaggct 293220
ggagtgcagt ggcgcgatct cggctcactg caagctctgc ctcccaggtt cactccattc 293280
tcctgcctca gcctcccgac tagctgggac tacaggcgcc caccaacaca cccagctaat 293340
tttttttgta tttttagtag agacagggtt tcaccgtgtt agccaggatg gtctcgatct 293400
cctgaccttg tgatctgccc gcctcggcct cccaaagtgc tgggattaca ggcgtgagcc 293460
accgcgcccg gcccacagga cactgttaat tctgacatat ggcaatatgt cagtatggca 293520
atactgctta gaatatggaa ttcttcatta caatagtatt cagggtcttc actgctgaag 293580
cccagcctgc ctacactgcc tgactctatc ccagaaagtc aggttgtcca aatatcctgt 293640
gtgttatatc aggttctttg gtaccagagc aaattcacat caaaatgctt caagctgagg 293700
ccatgggcac ttaaaaagcc ctccattaaa gaaggagatg cggcagccct ggctcagttt 293760
ctgggattag gactgcccag gctacaaaca gataaggctt ctcttgatca aacatcaggg 293820
gctataattt tgtcactttt tagtaatgat aattatataa tcatctattt tatgaaatag 293880
ggatggaaag taaacacaca cagaaatacc ttcaattgtt acagagaaac aggtgttaca 293940
ctgcaccact agaaaggctc ctagacacca aaggcttagt aagtattaaa taaatgcact 294000
gatggacaaa tgaaacatac ctttatgaat gaaagaaaca tacctgtagt tgtggcagct 294060
tgtcagcttg gtctggtgac atatgttcaa gggagaactg agctgaataa ttatttaaga 294120
tctgtttcaa attttctatt tcttcatccc attcattggt ctgttttatg actacctata 294180
aaataacccc cacaaaaaag aatctttgtc ataatctaag cagattaatg gactattttc 294240
attgtctagc cccatggaag ttttaatcac tcacagcaaa tatgcaccca ttgagatttc 294300
aataggacgt ggtagcctaa acagagagaa gaatgtttgc aaagctgaca cctgatcttc 294360
ttgctctact agatgccagg gcaccttggg cagtgcttaa agtacaagtc tcactggaca 294420
cacctttgct cttaagtatt tctggtccag tgggtttatt ctggaaagca ttttatggcg 294480
```

-continued

```
tgttaacata aagttgctaa cttttgagaa gttactgaca agtcacatac accattttaa 294540
tacatattcc atggccgggg gagcgggggg gctttccgca tagaaaggtg acataacaat 294600
tcagactgaa cagagcatgt gaggtcagtg atgatgggtt ttcccggtcc agactcatct 294660
tcacctggta ccccttggga tcagtgatgt gtgttttacg agtaagaggc tgagggttca 294720
agaacagtct aaatttgcag aataagaact aaccagaaca atacctggca tctagtgcta 294780
ggggagcagg aaagctcaga cctatctgtg gactaaataa tatgattaag cacgatgaaa 294840
aacaaagaaa cagacttcaa aagaaaaact agatacttct ttggtatgct acataatgaa 294900
gcaaaatgcc ttttaaaact acaaagtttc tagccaacac gaaattcttc cttgtatttt 294960
ctttaatatt taactataat tttagccata ggctggaaat gaataactat gttcactgtg 295020
cacatctgtt ccccagccct caataatgaa ctacatcccg ttctctccac aaaaggaatt 295080
tgtcttattt tctacaacga gggtacttac aatatctaaa gtagaaatca aaggaaatgt 295140
accatattct aatgattgtc ttcaccactg tcttccttag ctttgaaata tatgagggga 295200
catctgattg ccaccagcac aatgagatgg aaaatttgag cagcatagtt tgatacctaa 295260
cttggcacaa aacagaactg cctcttctat ttcacccatt tcgtctgtga agaagccact 295320
tgaaagcata gttaggaccg tggctttctt tttctgacca ggagactaat aaagcacaaa 295380
aggatgaaaa taatggatca aattttatat ttttttctct ttatattatt acaaggtagt 295440
acattgagtg ctagatcttt tttctctctg taggtgttac agaatgacat cagttgacca 295500
gcagccagac cagagaaact gagttaagac tcaaaccaga gattacagtc tcctcaaacc 295560
ttaggagaac agagtggcca ccaaaatgtg catgaaattt aagagggaaa aacatatagt 295620
catttttctt cttacaacca gaaggcggtc atgaaaaatg aaaaataacc cttacagtga 295680
cccatctaat caggaaaggc agcatgcagg aggttgacgg agacggttgg aagtctgtgc 295740
agactttctg caactttctg ttcttgtggg agtgattatt gatccaggaa tacaaactaa 295800
agattattcc taactaatga tgattcctga tggagagtag tgatttaaca aaacccaacc 295860
accaccacca ccaccacaac acaaaacccc tctggggaga agatgaagaa tatcagctct 295920
caatatgcag aaatgacacc aggagtttag aaactcaaat tcttgttcca tgtgtacata 295980
aattaacctc tacacaagtt aactctgtgg tctttcagca agtcacttaa ccctgatgcc 296040
aatttcctta tctgtaaaaa taaagataaa gtgcctactc tacctacatc acgtttggta 296100
atgagaaaat caataggaga gtcactgaga tgaacacaga gattactatg gtgatgatta 296160
ctttacagat ctgttggcct cagaggctgc aaatgccttg ttcaggtttg actctcttcc 296220
cacagcattt tgcccatgta ggtcaacaac tgtggaatga aattaaatag accataacta 296280
tgctttaatg tcttaaagga taagaactga gaaaaataac cttagctcca tttgagcatg 296340
aagatatgct tttatatcaa atgccacctc ctacaataat aggataataa tgaatttcaa 296400
ttagaagtga aaaccaaacc agcttttggt gaacattttc atccagtaag ttggatgtca 296460
tcagaaactg cttaccttta ataactcatt ttgttcttga gtcacatttt ccaatagttt 296520
tatatcttgt aaaagctgat ttgtccgctg aaacacaggc agaggtttca ttcctgtttg 296580
gggcaacctc agttccactt ggtaagacac tatctcagca atggttttct tcatgggacg 296640
tatattttca agtatgacct taattatata agaggagcat gttacagaaa tgaaaagaca 296700
atggccactg ttaaatttaa ttattcaaaa ttaaaataca gtatagtttt tatagtttgc 296760
atttttaaaa taatttctta gctcagattg aaaagaatta ttatatcact catgatccgg 296820
gagttgaaag tctcaggaaa gaataactgg ggcaagagta acctaccaat actaaattac 296880
```

-continued

```
gcatttggac aactttttct tccttttctc cctccacttt ctgtgtagaa ctggcgttct 296940
gctgtgtata ttgtcactag gcagtgagca atgtaagggc aggtactgcc tctcactttc 297000
gtagcaacta cacctagcac aggacttccc gtatagtagg ccctcaaaag tgcttattga 297060
cttgaacaga actgtgctgc atgagtccca ggagtataat tatattttgc tttaataaca 297120
tctgatccat agaaatctgg atttatgtaa ccaatacatt agaagagatt actcaccgta 297180
ctaagtcata tctcatataa tatcatttca tttaatcctc acaacccctc gagaggtaag 297240
tatcctaacc tccatttcac aggtgaggaa attgggctca cagaagttag aagatccagg 297300
taagcttagt ctgtaagagg cagagctggg aacagaatcc aggcctccct agtcctaaac 297360
cacatgctct caatcactag gctgagcagg ggatcaacat ttgcctgctg tttagtcatg 297420
tcccagctcc tctgtcaggg gctctattta cattacaatt ggccaatgta atctcctcag 297480
taccagtgca cggatatgaa agagaatcca aaaaccatta attactcagt catgcagcca 297540
gtgagcagtc tagctggggc tggaacccag ttcagcctga attaggtgct caagcccttg 297600
agtttgattt aaatgaaaaa ataacctata ggaaaattat ctttacatag gtggtactac 297660
aactacgatt taaatataca gttatagtta ttcccatcaa tttcccaacc ttattttgct 297720
attactctgg taagactaaa tgctttttta aatcacatta tattatattt tgaaaaagac 297780
ataataagta tcataagaaa atactttaaa taataatcta tgcttacctc cccatgtttg 297840
agatgttctt caggtgaaaa atcaaatatt tcttttgata ataggatagt tttgattttt 297900
gaaactcttt tttccattga ttttacttca gattcaatag caaccacatc ctagaatttc 297960
agaagaacac actgatgcaa tatatattgt atattaatca tctataaaac agtttattgg 298020
cattaatttt attctcttat ttagccaaat aatgtctgcc atctatacct ctgaaaaact 298080
aaccaagcac tatagataaa taaataatgt tcaccatttt ctttcctttt tttttttttt 298140
tttttttttt tttcctgaga cggagtttcg ctcttgttgc ccaggctgga gtgcaatgtc 298200
gcgatctctg ctcactgtaa cctccgcctc ccaggttcaa gcgattctcc tgcctcagcc 298260
tcctgaatag ctgggattac aggcacgtgc caccatgccc agttaatttt tatattttta 298320
gtagagacgg agtttcgcca tgttggccag gctggtctcc aactcctgac cgcaggtgat 298380
ccacccgcct cggcctccca aagtgctggg attacaggtg tgagccatcg ttcctggcca 298440
gggaccaaca aaactttata agaaaatgaa gcagtatgta caatagctgt ttatagtgat 298500
atcttcaaat tatgaggaaa agttaaatta catggacatt attctgtgca cctactattt 298560
aagaaggtat atagaattat acaatgtatt ttagggtaat tttcatcaaa cattatagaa 298620
gcatttaaaa attttgaaat gagcttcagt aaccaaaaat aattacttta acacttacta 298680
ttccctgaag atacatgagt gtggtgtagg gaatgtaact gagtaacaaa tgtaaataat 298740
gaagaacttt aattgcctct actatgtgac tctatcttta aataaatgct tctgatgttt 298800
caagccaaaa taaaaatcca gaggctggca aataacaacc cctcaataaa tatttgctat 298860
tggtaaataa agacttggga ctacctgttt tacacttgtt tttaattcct ttttgtggag 298920
aagggggtct tactgtagta cccaggcagg tctcaaactc ctgtgctcac attatccttc 298980
tgcctctgcc tccgtaaatg ctgggattac aggcgtgagc caccgtgctg ggcaccacgc 299040
ccagccagaa ctatctcttt taattccctc tttcctatcc agcatttaaa aatcagtagt 299100
atttctcttt gacaaagaga aaacactgag cttattttat cgggattctt tactctttaa 299160
aacagaccac ttctggattg aaaataagga gatgcttttt gttatagtta cactacaggt 299220
```

-continued tgcaaagtaa agtaaaatat aattccacaa atgagaacat acatgacatt ttaccagatc 299280
aatgtgtctt cacattgatt agttgtatag tgcttggtta gtagtataac tctaatttat 299340
ttgacagaat cctgctctgt cacccaggct ggagtgcagt ggcgcaatct tggctcactg 299400
caacctctgc ctcccaggtt caagcgattc tcctgcctca gccttccaag ttgctgggat 299460
tacaggtgtg caccacgatg cccagctaaa ttttgtattt ttagtagaga cagggtttca 299520
ccatgttggc caggcttgtc ttgaactcct gacctcaagt gatccacccg ccttggcctc 299580
ccaaagtgct ggaattatag ggatgagcca ccattgccca gcctctaatt taatcctgaa 299640
tgattaaatg aatggtgcaa acttacatca gccattcgct gaatctgtgg aaggctttcc 299700
attatttttt gttgtaaagc tgttacttga ttacttaact cttgtatgga ttgggttaat 299760
tcatctgttt caaaaattat tgacaggtct tctagatcca taaagattga atgtaaaaga 299820
ttgtgcttct gttctgaatc ttccaaagcc atctagataa acacagaatg ggaaaaatag 299880
agagaaacat caagatcctg atataagctg attaatattt aaatcagaga aaattgaaag 299940
ttatctcaac attttaaact agtcatttct agttcgataa tgaaaacaga acaccctcta 300000
ttgtcaatga cagtgaaaga cttcagagta tctacctgta taactgtaac ataataagaa 300060
acataaatat ttggtcttgg tccacttcta aaacacttgg aatcctttaa taatagggga 300120
gagagaagtg tcttttatta tacataataa gccctttcat acatgtaata actttcaaat 300180
ttaagatgtc aaaatagctc agccacctaa tgaaaatgtt cagcttgata atgtactctt 300240
caggtaattc cataaaaaat aactgatagg agaaagaaca ttcacttaca caactagaat 300300
ttcagtcaca agtcactaaa actaagtggg ttattcagaa ttttatatta atcttattca 300360
aaatccttat aggagaaaac ttttaggaaa acaaaactta aaaccaatgc tttttttttt 300420
tttttttttt tttttaccaa ttatcactga caacagcatc aaaaaccata aaatacttag 300480
gaataaattt aacagtatac atgcaagaaa tgtatactgg gccgggtgtg gtggctcctg 300540
cctataattc cagcactttg ggaggctgag gtgggtggat cacctgaggt caggagttcg 300600
agaccagcct ggccaacatg gcaaaaccct gtctctacta aaaatacaaa aattagccag 300660
gtgtggtggc ggaagcctgt aatcccagct actcaggagg ctgaggcagg agaatcgctt 300720
gaacccagga ggcggaggct gcagtgagcc attattgcac ccctgcactc cagcctgggt 300780
gacagagcaa gacaccatct caaaaaaaaa aaaaaaaaaa aaagacctgc atactgaaaa 300840
tcacaaaaca ttgttgagaa aaattaaatc cctagagaaa taaagagata taccatgttc 300900
ctggattgaa tagtcactat ggttgagatg ttaattctct tccaaattga tctacaaatc 300960
taatgcaatc ccactcaaaa ttcccacaga cctttattta gaaattaaca agcagattct 301020
aagatttata tcgaaataca aaggccttga tttagccaaa acaaatctga aaaaggacaa 301080
agttgtagaa ttgatgctac ctgatttcaa gacttactgt aaagctatag taatgaagac 301140
tgtcatattg gtgaaagtat agacatataa attaattgaa cagaagggag agcccagaaa 301200
tagatgcaca tgtataaggt caattgattt ccaacaaagt gccgaagtaa tttaatggtg 301260
attgttatca ataaatgatg cagaaacaat tggatatccc catggaaaaa aagaactttg 301320
atccttcaat cacaccttat gcaacaatta acatgaaatg aatcatagat ctaagagagt 301380
aagagttaaa actatcaagt tactggaaga aaacacagga agaaatcttt gtaaccctgg 301440
gttaggtaag gatttcttag aatgcaacac aaaagaataa tccataaaag aaaatattga 301500
tacattggac ctcatcaaat taataacatt tgctctctga aagacagtgt taaaagaatg 301560
aaaagacaag ccgcagactg gaagaaaata tttgtaaatg acatatatgt caaaagaatg 301620

-continued gttttcagaa tattttacaa aaaacttaca actcaacaag aagacaatgc aatttttaa 301680 atgggcaaaa aaaattgaac agatacttca caaaggaagt gtacaaatga ccaataaaga 301740
cataaataaa tgctcaaaat tattagtcat tagagaaaac ctgtttaaac cacaatgaaa 301800
taccactgca agtcactaaa atggctaaaa tttaaaaggc agacaatatt aagcgctgtt 301860
gaaaatatga agcaattaga actgatgttg ctggtgggaa agaaaaatga tacagccatt 301920
ttggaaaaca atttctcagt ttattattta tttaaacaca tcgtaaaagt cagagatcct 301980
acttttaggt atttattcat tgaaataaaa tgaaaacatt tgtctacaca aagatttata 302040
tataaacatt cacagcagct ttgctcataa tagcctatgg tagcagcctc taaggtagcc 302100
ctgaatgacc cctacctcct ggtattcata cccttatatc agcttccttg aatgcaggcc 302160
agacttacta atttaattct aataaaatgt ggcagaaatg atgagatgtc acttccaagg 302220
ttagattaca aagactgtgg cccagcctgg gcaacaaagt gaaacctttt tgcaaaaatt 302280
tagaaattag ccaggcatgg ttgtgtgcgc ctgtagtccc aactacctgg gaggctaagg 302340
tgggaggaac atttgaactc agaaggtgga ggctgcagtg agccgacatt gtgccactgc 302400
actccagcct gggtgacaga gcaagaccct gtctctaaaa gaaaaaaaaa aaatgtggct 302460
tctgtcttga cagctctctc tcactctctt ggagattgtt tatgctgagg gaagccagct 302520
gccatggtgt gaggcagact cctggaggag cccacatgtc tgtaagtaga agcagatctt 302580
ttgaggcctg tcaacagcca cgggaatgag cttggaagca gatcccacct cctccctcac 302640
acaagtcgag ccttcagatg agcctgcagc ctttgtcgac accttgactg cattctcatg 302700
agagaccttg agccagagat acttagctaa gccatgccca tggactcctg acccacagaa 302760
actgtgataa taagtttgtt gtttcaagct gctaacttat ggagtaatat gttacacaaa 302820
aatagctaat atatagctca aaactggaag caacccaaat atctattaac tggtagataa 302880
acaaactact catttccaaa cttatttcca aaactggaac actacttggc aatcaaataa 302940
ttaactatgc attaagtgta acaacctgga tgaatctcaa aggcattatg ttaagtgaaa 303000
caagtgagcc acgtaagact acatactgtt tgattccctc tatatgatat tctagaaaag 303060
gcaaaactat agtaatagga aacagtgagt gatcacctag ggttgaagac aggtgaaagg 303120
ggattgactg caaagaggca ggaggaaacg tcttgggaga tggagatgtt ccttatattg 303180
atggcggtgg tggttacaca actgcacttt tatcaaaact tacctaactg ctacttaaaa 303240
taggtgtatt aatattttta ctgtatgtaa attatacctc aataaatttg atttaaaaaa 303300
caggccgggt gtggtggctc acgcctgtac tcccagcact ttgggaggtc gaggtgggca 303360
gatcagctga ggtcaggagt tcaagaccag cctggccaac atggtgaaat cctgtctcta 303420
ctaaaaatac aaaataaggt cagcgtggtg gcacacgcct gtaatctcag ctactgggga 303480
agctgaggca gaagaatcac ttgaacctgg gaggtggagg ttgcggtgag ccaagatcgc 303540
accattgcac tccaggctgg gcaaaaagag tgaaactccg tctcaaaaaa aaaaaaaaat 303600
tagttttcta tttttataat gtcattttat gaatgtatgt ttcagttatt cttacaacag 303660
tagtatttgt ggaattatct ttaggttaca aagacctgtt ttaacaaatg caatccaggt 303720
agaagggtat agtgcaatta aaacaaacat ttaaagctta gttgagagtt ctgacacttc 303780
tttaaaagtc aatataaaaa ctaatacctg aatatgctag aaaatggaaa agggcatcct 303840
aaaagtaaga ttattgcaca aatgaggatt tcacatagga ctagttattt gggacttact 303900
tcccaggagg agattaggac acatcgggac acatagaaat aaacccgagc cttccttgtc 303960

-continued

```
cctacttcct ttcctcagtt ctagctcaga aagaaagtct agcaatttag aatgtcctga 304020
agtttgagag atgcttttac atttttacat gtgtatcagt agaaggtagc aaaatcccag 304080
ctgcttttgc ctgagctcac ttttgtacag tttttttttt taactcataa taagcatttg 304140
aaggaaaaaa aaaaagcatc attcctctct cttgtcttgg taaagtcctc aaaaatagtg 304200
aatcagggag gtgataaaga gtttaaaaat gacaaacttt ggggatgtgg aaagttaatc 304260
caagtggggg aaggcaaaaa aaatcacaag caaggggaag aaaagaaaaa aaaatgggta 304320
gaaatgcagc atctttacaa ctgttaccgt aagaaaaaaa tatgccaacg attctcaaac 304380
gtcagggagg tctgaggtca gcagctcact taggaacaca ctgtgccatt ccaaagataa 304440
aaaaaggagc tgaatcacct tggaagtctg attctgtaaa cactgttacc aaataagctt 304500
ttctctaagg gattccttct catggcagaa taagagaagg ggaacacacc tgcgcaatgc 304560
aacttcccta gtactcagca tccggaagat gttttgcagc cgaggcctca agtgggaaaa 304620
cactttcatt tgttttgact ttgtaagcca gcatggacac gtggggcatg tgtggagtac 304680
cagcaaggac aggaaatttg gaatcatggt gtgttagaag tggaaggaac catgggttcg 304740
ttttctattg ctgtgtaact aattaccaca aacttaatgg cttaaaacaa aacaaagtta 304800
tctcacagtg tccaagggta aggagtccag gcatagctga ggtgagtcct ccttacaggg 304860
agccacaagg atgcagtccg gtgccatctg gagcttgggg ttctctttga agatcattca 304920
ggttgttggc aaaattcagc tgtaggactg ggttccctgt ttccttgctg gctctcattg 304980
actctcagct tctagaaaaa gcctttgggc cctagctcca tggccctctg acaatatagc 305040
cgctttctca agaagaatct ctctgcactc tgctgcaggc tgagtagccc ttatctgaaa 305100
tgcttgagac cagaagcatt tcagattttg gactttttca aattttggaa tgtaagtatt 305160
atacttaccg gtggagcatt ccaaatccca aaatcccata ttagagagcc ttataatcac 305220
gttaatcaag tacttatggg agtgactacc ccattacctt aatcatataa cgtaacctag 305280
tcaatgaagg gactatccca tcatattcat attcctgccc acattcaagt attattcttt 305340
caggtcatat acaccagagg atgggaatat tggggggcat cttagaattc taacaaccaa 305400
aaccatcagc actatcctat gcacattctt tttttttttt gagacggagt cttgctttgt 305460
cgcccaggct ggagtgcagt ggtgcgatct cggctcactg caagctccgc ctcctgggtt 305520
cacgccattc tcctgcctca gcctcccgag tagctgggac tacaggcgcc cgccaccgtg 305580
cccagctaat ttttgtattt tttagtagag acagggtttc accgtgttag ccaggatggt 305640
ctcgatctcc taaccttgtg atccgcccac attcttattt catggggaga aactgaggtc 305700
catagaagat atactaaatt atccaaaaag tcataaagta gttatcagga cagtaagagc 305760
tgaatcctgg tctccaaaat ccatgtctac tgcttgccac tctctcaagc ttccttctgc 305820
cactgacatg gttagcggta aggttgtatt tcaggaaagg aggaaaaaag caccaagaca 305880
atcagctaag ccacgaatct ttatgtagat gctatgagtg gcagaaaacc tggaagaaca 305940
cttacctgca cagtgctagc atggtgactc agtgtcctca aagagtcata gtcagcagga 306000
ttggccagca aatgactggt attttctatc caagcctcag tgctcttcag aaggtcacta 306060
tattcctcca tcttaactgt ggcctgggaa agagatgcag gaccaaactt agtcagatgc 306120
cttttactgg agctgaatga ctcctagatg aagagtcaat agctgttagt caggggtgtg 306180
tcaggccttg cagatgtctg ctccccatgg ctggggctac ttattcacct gctctaggct 306240
atgacacttc tgacttttaa gactaactct gaccataggt ggaaaggatt taatcagttc 306300
tactccaacg ttatgggcct cagcaaagtt ctgggttagc cttgcaagta ttctggttct 306360
```

-continued cattttatgc ttcattttaa aaactggact gtactttgtc ctcctgttca ggaccttgcc 306420
ctacagttct tctaagacta ggatgctgcc tcactcttgc taaatcacag acacaactca 306480
gccaaccaca gctcctattt ggaaggaggg tagagagggt atcttttccc cgaatgacag 306540
tctttctcat tgttgtctcc cttactagac tcctgagacc acctgcccta aattcccatt 306600
actggtcttt atccacctgt tggggagcct ggacttccca acagtttgcc tggctcttgc 306660
tgtggtcaac ttctggattc ttggttctgt ctgcccaatc agacttcctg cctgcactag 306720
cattgaaatc tgtctcctca gcacccacac aagcctacca tggccccagc ttcaagtcca 306780
aaactgataa ttcaacagaa actgactgtt tctgaatata ttgttttgct ttaacaccat 306840
ctcaatacca ccacatgata tgaagctatt acgagtcaca gccatacctt attcaactgt 306900
gaggttctac actctgctct ctgtgatact tgctgatact gctggaaagg aatcatcaag 306960
ttatccatcc attcttgagc ctgtcctggg tcctgttcaa caatgtcctg aacttcagaa 307020
tccagctcat ttagtttgga atgccataga tctaactcgt cccacatttt ctggagaagg 307080
aaatcgtaag tcaacttgaa tgaagaggtc atagtttatg gaggcaatgc ctggttttca 307140
cacagtattt acatttataa atgctactaa aacatcacag aaacaacatc acatgaacag 307200
ttgttaattt atacccagca atttgtgatc taaactgaaa aacacttttc ctgagctctc 307260
ctaactacaa ctgtattcat ttcactacaa attagctgta ggggaacaga aagacctgga 307320
catttttaga gatgactgac acaaacaagg tcaatatagc cctcatctct caagagtgac 307380
aagcaaaaca ttctgtttaa aaagggcttg gggaaagact tgaacctatt tacactagtt 307440
catacacaca cacgcacgcg cgcacacaca cacacacaca cgctctatta atctacaaaa 307500
taatttcaag tgaaaaaata aaacaaagaa aaatatctgg gctgggtgca gtggctcaca 307560
caattttgga ggccaaggtg tgtgggctgc ttgaggccag gagttcaaga ccagcctgga 307620
caacacaggg aaacaccgtc tctacaaaac ttagccaggt gtagtggcgc acacctgcag 307680
tctcatctac ttgggagact gaggtgggag gatcaattga gccagggagg tcaaggctga 307740
agtgagtttt gatcacacca ctgcactcca gcttgggtga cagggtgaga ccctatctca 307800
aaaatttaaa aaaagaaaag aaaattatct gctgacttgg gatgaatgca gaggcagaaa 307860
gctctagaaa catgtattag gagcaactgc ttttgactca agaaaccaat aggttggatt 307920
caaatctgaa cttcgctggg cagaggaaaa tttcaaaggt aaaatattca attcttaatg 307980
tttgcttaag aacatttttt tccctatctt gaggactagg aaaatctaac ttgttaaatt 308040
aggttcctct gcttaagatt tgtccaatag tgagccatac tctgacctat tttaaaagcc 308100
ccaaattatt aaaacatttc cttaagacat agattagaac aagaatcctt tccctatgct 308160
ggagtttact tgcgaattaa gaaggagaat agtgtttatg tacagttttg cctaagattt 308220
tattttgtaa gatattttac aagggaaata aatttggaat ttttattttt atttaacctt 308280
tgcagtctaa aaaagagctt taatattttt catattctat tgaatgattt ttagtatcag 308340
tatccccaag ataagatcct tactttcctt tacttgtgaa aatgctagtt cacaatcaca 308400
ggctctcaga agtttgggta tatgcccacc atggaaaaac agaattattt ttttgagaca 308460
gagtctcact ctgtcaccca cactggagtg cagtgacatg atctcggctc attgcaacct 308520
ccatctcctg ggttcaagtg attttcgtgc ctcagcctcc cgagtagcta gaattgcagt 308580
cttgtgccac cacacccagc taatatttgt atttttagta gagatggggt tttgccatgt 308640
tggccaggct ggtctcaaac tcctaggctc aagtgatcat cccaccttgg cctcccaaag 308700

-continued

```
tgctgggatt acaggcgtgg gtcaccgcac ctggccaaga gaataatttt taaatgcaac 308760
tttccctatc aagcctctct aggtgatgcc cctgtggatt tggtttacaa tttctgtgct 308820
tcagattaat tcaaagaact caccctgtgg tgactgatga acaaggcagg agtgggtcag 308880
aagtaccaaa tgctgaaggg agttaaagga ggattttacc ttttgaattt cttgagcttt 308940
ctcaatattt ttgcttttct gctgcaacat cttttcaaca ttatgaagcc cattgttaat 309000
ttcttctatt tttctcctca ttgcatatga tggtgagctt tttaagactt cattgctaat 309060
ctgtgaaaga gacaaagacg catttggctt agagaggttg tctgcacttt attcataggt 309120
tcgaacaaca aaagtggtag tcactctgtt ttaacttgta aaaatttttt aagggctggg 309180
ggaagaaatt ctggcaaatg cattaatgag aaggtggata ggaagactaa taaatggcag 309240
gtgtgtttac ttcacctttt aaatctcatc ttaaataaaa taaaaattgg ttttttattt 309300
gtactgtaat acatgtattg taacatgtat tacagatata tgctgtgttg ggcaaaatta 309360
ctgagtggat tgtgtgaaac atttccatat ggatcaaatg atataaatga attcctgggg 309420
gataaattat ttttatacaa tctttccatt ttatgagaat ctatctgcat agatctgttt 309480
tcagtaaaac caaacttact ctcaagctga ctttttttaaa aaaatgtaat tccaatcata 309540
gtattcattt gggtgaaaca accttctaaa attgccattt cttgaggatg cacagagctt 309600
aattattctc tgtgtaacca tttgtagatg ttttcccagc catcagaaac ttagctactg 309660
aacagcgtaa ttttttttta tctaaacgat tctcttaaaa agaaacaaaa aaaaccttga 309720
gctaggaaag ataataaatg aatgttgaat gtatcacttt ccaaatacct gactgatgtg 309780
tgttcttgtt ttgctatttg ataaggcttt ctccaagcag ctactaaata accaaataat 309840
actttatgct tttgtataat cctttgtttt gtaaattaaa aaaaaataac tctatctgta 309900
taaccattga gactaaaatc atcctgtgca gacagtatac agatgctgaa actgtaacac 309960
agactaaatg acttgctaca gtcatatgtc aaggaagtag ctgaacttgt cccaagaagc 310020
gcccaagtcc ctagattgag tcccaggctc tattcacaat atcaggcctt gatactttta 310080
tatcatgtct ttattcccca gaccatactg cagtcaatat tattagaaaa aaaaaaatcc 310140
cactttggtt ccatattagc ttttcatggc tggctgtgtc acaaattacc acaagaaaag 310200
ttttctgata ttttgagcac ttattctcct ggcagaaatg tataccattg agatacatta 310260
ggacagatca tgatttagga aacatatgta gccatttgaa ttatacacaa tgttactatg 310320
tctgtccccc gggatccttg aacttccttt agctgtatca cacaataaaa attagttgct 310380
gtttgttaca aatatagagg gtcatagcgg aaattttcta ccttgaattt gaacgactga 310440
ttttgattat taatttactc tgctagggat tttcataagt attcatgagc ataacattta 310500
gtttctctca aaatatttag tattttcctg aaataaaatc aatagtaacg agatccttga 310560
gaaagtacga aataggtttt cttgtgtgtt aactaaaaaa gatttgttat aaatatacgt 310620
taagagttta catatttttt acatgtgaga ttttcctgag aaatctgtca tagaattaat 310680
gacatattct agcaactaag tttgaaatct gaatttttttg tgtttaagat ctattttatt 310740
tatcaagttg taagtattct agacaaaaaa aaaaaaaaaa atccttctgt ggataccaga 310800
ccaaacagaa ttttcttctg tttgatatgg gctgtctttc tacaatctaa tcaaaatatc 310860
ttgctaagct cctatgtttc tagtattata aaatattttc caccttttct ttaaatctgg 310920
actttcaggt ataaagattt gctcaggtac ttttcatgag aattctgtta acatcatcgt 310980
tagacagaca ctacatacta agtgctattc ctagtgagtt gtgaaatttg tattcttatt 311040
gccttagttg taatgtcaaa atgtttcaaa gaatgtattt taaagcaaag tattaacatc 311100
```

-continued caaaatgttc aagtggttgt acagtggttg tacaaaagca aacaaaacca gtaaaaaata 311160
ttatataact gtattataaa atgcaagaga agaataagca ttttgacaat taaatacata 311220
taaatcatct aattctgtta tcttatgtca catatttaga gcatctttat cttagcattc 311280
aatagacacg atggtcactt aactcttaaa agaagttata gctgaaatcc tggcaaatgg 311340
aatttgacat taaatgatat tttcctcttg atagtcattc agctccgtaa ataataacag 311400
tagtacagac attattatta ccttctcatc tatgtcttct aaagcttttc tgcattcttc 311460
cacctgggat tcaatctctg cagggactat ggtgtacatt tcggaatact tgattcgcag 311520
tttttccata atattctcaa aagttagttt ccctttctta aggatgcttt gaagctccta 311580
aaagcattaa gagagttgca atactcacga gactggggga aaagtttaat tctaaaaagt 311640
gaaagcagcc ttccagcaca tccttatgat ttaaaggagt gcagtttgca tgacaaaacc 311700
ccactagtga tacaagctga ttaagcccca gagacactca gtttagtcag atgatgcttt 311760
ctaatttgta agaattaaac ttgatatctc ttcatagtgt cacaccatta tctagaaaag 311820
acattacaac accccctgct tctaaagtac ctttaggatt taattgtatc tccattgcag 311880
tcctgatcta aaaagctgca agcagcaaaa aaaaaaaaaa aaaagtttca aagaagtttt 311940
ttgttgttgt tttaacgtgt tgctatttct acttcttcct ccattatcat cacaatgatt 312000
taaggccact aaaagcccca cacttggagc agaagtgtct actttcatgt aattagacag 312060
ccctgcagag ctcaactgct ttcaaaaggg aaggttccag ttccatacaa agaatgtagg 312120
tttttaggag ataaaagaaa cctgaacaaa tagtctattg gttgtggcct agaaaccaaa 312180
tctgatctac cttctcctgc agtaattata aaggagaaac tcatttgtat gggaaagttt 312240
cccaaagatc aagtggaaaa atacttcttg acttgactgt ggcttttttg ttgtttgttt 312300
tgtttttaca gtagctgttc agtagcatta tttgtgttca tggattgagt cactgtactg 312360
aagaatgatt acaattttaa atgactctgt aatgtgtcat tgttttcctt ttcttaatcc 312420
tcagcagagg acaaatctag agagagaaag ttagagaaca atgccattca aagatggggt 312480
ttaataagta agtgtcatcc cgttttatct acacctagtc caggagtaca ggctttcatt 312540
cagaggtaca cttagaaggc ttccccatga agactgcttc tttactttcc aatataataa 312600
ccaaaagttc tgtttagaca gcatgtgact tttttttttt ttgagatgga gccaggctgg 312660
attgcagcgg cacgatctcg gcttactaca accaccacct actgggtcca agtgattctc 312720
ctgcctcagc atcccagtag ctgggattat aggcacacgc taccatgcct ggctaatttt 312780
tgtattttta gtagagacgg agtttcccca tgttggccag gctggtcttg acctcctgac 312840
cccaagtgat ctgcctgcct ggacctctca aagtgctggg attataggtg tgagccacca 312900
tgtccggcca acacgtgact tttgaataaa cttccaaaca tacttttggg ctgtcactat 312960
tggactggaa tgaaagagga gattcttctg aagaaatgag attccagatg acctgtaggg 313020
tgtacataga ccctgtcaga gacaaggcgc catgtcctac taaaggagta atgtaacata 313080
ctacttaaga gtggtctgag gcccttgttc accaaacaca ctggaaacat agttgaaaga 313140
aggctgcttg gtccagactg gcctaccttc cagccttgtt tcaactctgt tctctgctct 313200
ccagccacac tgatcttctc ccttggttct gcccatacca tgccacaggg cctttgccta 313260
tgcctctctc tctctcccca gaccgctccc ccaaacccag ccactgagtt atctctaccc 313320
caaggacttt ggatacaaga ctgtgggcct gtacctgcca cattcactaa ttcattcctc 313380
acttacctca aattgttctg acttttctgg gtgatcctgg aatgccatat tttggaatga 313440

-continued agttgtggtc tgttgaaaga aattcttcaa agcaattatc tcttttgtga aggaatgtct 313500
ttcttggatt tcagtctgca ccaattcttt atttttctga actttctgaa gaagcctaaa 313560
agagaacgtc aaaatataat tgtttcttta tcctgctctt ctatgaataa aatgaaacag 313620
ttttattgca acaattaatg aaatgcctga atagctacta aaggatggtt atttcctcta 313680
agaaaaaaag taacaatttt caataatgga tgtaccacat ataaaaacag gtacaaaatc 313740
taccacttaa tcaaaaacct ctccaaatct ttcgcctcaa atactctctt ttcacacttt 313800
acattgtaac tgacatttct gtcctctctt tttctccacg taatccttga gctcacatga 313860
aaatgactta gaggtgtgaa tggaatcaca ggtgggctct tggggacaga caatcccact 313920
gggcttcttc tcttaagctg acccattttg ctatggatgc agcaaatatc agaagaggca 313980
ctgaagtggg taaaatcttt cctgagggtt atttggtaag tatctatgat attgtgatat 314040
aataaatata tacttgatct ctgctgtagt tcctgagaca gagctcttaa tacccttgta 314100
gataggagtg ctagctagga gagtcttttg ttctaatact tgatttttga ccagttcctg 314160
acacagagct cctaagccct ttgtaatttc ctgagtgata ggagcatctt tagttctaag 314220
aaggcaactc taggtgggat cctgagtagc ctcaggatga gggctggttg ccaggggaac 314280
caactatgtg attaaaaggt tggaactttc agtaccaccc ctacctccaa cacacacccc 314340
caacctctgg gggaggggac agaagctgaa ggttgagttg atcgccaatg gccaattaca 314400
taatcaatca tgactacata atgaagtctc cataaaaaaa cccaaaagac agggctcaga 314460
gagcttctgg attgctgaaa gcctgggggt tccaccacct agagagagca gggaagcccc 314520
aggccccttc ctataccatg ccttaggcac ctcttccatc tggctgttta tctgtatcct 314580
tcattatatc ctttattaat aaactggtaa acatgagtaa agtgttttct tgagttctgt 314640
gagccactct agcaaattaa ttgaacccaa gaaaggtatc aaaggatccc ttgatttata 314700
gcctatcagc cagaagtgta ccagcggggc gcagtggctc acgcctgtaa tcccagcact 314760
gtgggaggcc gaggcgggca gatgacctga agtcaggcgt tcgagaccac cctgggcaac 314820
atggtgaaac ccctcctcta ctaaaaatac aaagaattag ccgggtgtgg tggcacatgc 314880
gtgtaatccc agctactcag gaggctgagg caggagaatc gcttgaactc aggaagccga 314940
gtttgcagtg agccgagatc atgctattgt actccagcct aggcgacaga gcaagactct 315000
gtctcaaaaa aaaaaaaagg agaagtatag gtagcaacct actactgatg attggcatct 315060
gaagtagagg tcctcttgtg ggatggattg agccccccagc ctgtgtgatc tgatgctgtc 315120
tccgggtgga tagtgtgaga aatgaattgg tgtctgctgg agaactgcct gatgtgtggg 315180
gaacccccat aaccaacatg gtgtcagaag tgctttgttg catggtgtgt aagggtagag 315240
agaaaaaaca agtttgcttt ttcttcagag cacctctagc cataaaacta ctatattctt 315300
tgacccagtg attctacttc tcactatctt tctcaatgaa ttagtcacag atgaaaatat 315360
agattctggc ataagaatat tcactgcagt gttgttatga aaattaaaaa aaagtaattt 315420
aaagattcct tattaggggc ttggtttaac acattatggc atatcttcat ggtagaatat 315480
tatacagcta gttacatttt ttatttttat tttttgagat ggacgtttca ggctggagtg 315540
caatggcatg atctcaactc actgcaacct ctacctcttg ggttcaagtg attctcttcc 315600
ctcagcctcc tgagtagctg ggattatagg cgtgcgccac catgcccggc taattttttg 315660
tatttttagt agagacgggg ttttaccatg ttgaccaggc cagtctcgaa ctcctgacct 315720
caggtgatcc atccaccttg gcctcccaaa gtgctgggat tacaggcgtg agccaccatg 315780
cccggccaca gctagttaca ttttaaaaga acatttaatg gcataggaag acaaacatga 315840

-continued tttgctggta aattactcag cagaatacaa aacagtacaa gtattttgat ctctatttat 315900
ttaaaaacaa aatcatagta aaaaaggaga aaaaatgatt ggcagtggtt attgctgagt 315960
ggtgacatta aggtagattt ttatattaat ttttgtaatt ttcacatttt ctgaatttcc 316020
ttttttttga gacagagtct cactctgtca cccaggctgg agtgcagtgg cacgatctcg 316080
gctcactgca agctctgcct tctgggttca cgccattctc ctgcctcagc ctcccgagta 316140
gctgggacta caagctcctg ccaccacacc cggctgattt tttgtatttt tagtagagac 316200
ggggtttcac cacgttagcc aggatggtct tgatctcctg acctcgtgat ctgcccgcct 316260
cagcctccca aagtgctggg attacaggag tgagccaccg cgctcggcct gaatttccta 316320
taatgaatat gcattactaa actagaaaaa gggcaaaaac aaacaaacaa acaaaaaacc 316380
cacaaatgat aaaaaaggaa attggaagga cattcaccct cattaatacc aggatggaaa 316440
atgtgtgctt aattatagtt actaatctgt tccatccctt tttataccta tcagtgttgt 316500
ctcacctcaa ttctattgta tcatttgcca ttattctata cttttagatt ttctaaattt 316560
tgagccataa ttgtcaagca catgtcctta atagtttttc ataaatctta cttgttgcat 316620
cgttctttca tagaagtaat ttcttgaaat gctggaacag tttccacagc ccctgagctt 316680
tcaggaacat tctggatact tctgatgcgc tgaagaagta gagtcagtaa cagctgttgc 316740
ttctccacgt tctctccata ttggcataaa cagtctagca gctcagagag ttcctctgtg 316800
gtggctgcct cttttgtttt ggaaatttca gggagttctt cctgaagatt atctaaaata 316860
attgcctctc gttcaatcta attcaaaaaa caaaaagaac taaaataagt aaaatataca 316920
attacatttc aggacctgaa gtagccataa tttttgtatg ctctctcttc aaagggttcc 316980
tagtgccata tcctagtctg ttttcctata gctgggaata ttaatcctct gctatcagaa 317040
tcccataatg cccagctatt gctcatgtag atgtgtgact gaaatggagt actgctgtgg 317100
tgggctgaag gaaatgctgt tgaatatctt cataaataat gtatttctcc ttcagatttc 317160
agatggataa agcaacattt ctcctgagat aagcacatga gctccaccaa actgctttca 317220
ctaagtgtaa gaggttgggc aactattgga tatggaaaat ttttctgctg gtctcttttc 317280
tttcacttcc aatccctgta tgctaaaaaa gtaaggccag caggttctca ttaccctgac 317340
acacaacaaa ggtaaagcag ccagaattac caaaccagtg aagtatttat caatagtggt 317400
gtacacagaa ctcagaaata cataacctat tacatcacat atctagaaac tgggagttcc 317460
accagccctg aactcaacta agatgtagaa aaaagtctca aaggcccctg aatcaggtca 317520
ttcttacgcc tcccctcgaa tcccctggcc cacccctcgg ctgcagtact catttatcaa 317580
atcctgcctc agtgatggtt aactctcctg ctccacgttc aaactcattc atggatcttg 317640
cagtcatgac attacaggat atcactccag tcatctatgt ttatgatatc atgctaactg 317700
aaatggtgag gacctgaatg tccagtcaga catgccagag gctgagaaac aaagcctgtg 317760
aaaattcagg agccccagta tcaggggtct agtggcctgg ggcatgccag gacttctcct 317820
ctaagataaa ggtcaagttg ttcaatctta caactctacc actaaaaaag agacacagca 317880
ctgaacggac cttttggggt ctaggaggca gtatatgcta tccttgggat tactgctcag 317940
atgcatttat cagaatgctg ccaatgtcga gaggggcctg gggaaaaagc accgcagcag 318000
ggttgggctg tggtataagc tgccctgctg tttgggctgt atgacccagt tgggtaccca 318060
ataactagaa tacacggatg cagatgtaga ctggccactg tccaagagac ctaggtgtgc 318120
gcaatgggtg cttctcatca cctcaaacct aaattcagtt gaattagaag tcctagttct 318180

-continued ttgccagaca gctacactta caccaggaaa tgagataagg gttccattgt atcattttct 318240
gtccccctgc tggaaactag catgcaaata aagaaattgt tacatagatg ggggaattgt 318300
acatctaggg tttccaatgt gcatcagggt tgaaaaaact gtgtctgtaa tccaggattt 318360
aatggggcac ctcttggtgc ttacacacca gaaactggca gatttgactt gataataacc 318420
agaaatgggc agctgtagca agcacaatcc agtaagagta aaaagaataa aggctcagac 318480
ctttcctgtt tcggctcccc tcatctccca ctcctgttcc ctgggatcac tttccaaaat 318540
aaactaccat ttgcaagcct cagtcccaag ctctggtgtc cactgtgaag ttggtaagtg 318600
attgagaagg gggaatacaa gagggagaac aatctctttt tttttttttt tttttttgag 318660
acggagtctc tctctgtcac ccaggctgga gtgcagtggc atgatctcgg ctcactgtaa 318720
cctcccacgc cctaggttca agcaatcctc tgcctcagcc tccggagcag cggggattac 318780
aggcacctgc caccatgcct ggctattttt tttgtatttt tagtagagac agggtttcac 318840
catcttggcc aggctgatct tgaactcctg acctcgtgat ccacctgtct aggccaccca 318900
aagtgctggg attacaggcg tgagccactg ctcctggcca caatttttat taggacaata 318960
attttacccc aaagccaggc aattcttcaa cttgggaatg aataaacaaa ctgaattcac 319020
ccacccaaag caatactact caggaataaa gagaaatgaa ctactaatac aagcagcagc 319080
cagaatttca agtgcattat gcttagtgaa aaaaagtaaa ctcaaaaggc cacaaactgt 319140
aaggagtcca tggatatgac attctggaaa tggaaatact atgagaacag aaacagatta 319200
atggttccag gggctggagg ttatggaagg cactgaccac aaagaggaac gagggaaact 319260
tctagggtga cagaattgtc ttaaaccttg attttgctgg tgatcatgtg accgtgtgca 319320
cttgtcagaa caacatattt tacactaaaa agtgtgaaga cagccctagc atcagtaaaa 319380
tagttgtcaa aaagcctgtg cattcacttt tccacctaga ataggctttg caataccttg 319440
atgattttcc ttagacatgg gatcctaatc aaattggtta taaaactttc aggttcacgg 319500
tcaattgtaa agtccggtct agagagggag aaggacccat agttgcatca taagcaaatc 319560
caatgaagga gaccaaaaaa cccagaacca gcagaaaaga gacccaacaa agaaatgact 319620
gttggtgcaa gtggaagaag ccggcctcac atctccaatt atctttgaca atgtgacgtt 319680
cttctagcac attatgatca ttgaagcata aaatgatgat tctgaataac acaagtgaat 319740
agttatagta aagagattct gtttaagaaa acagggaggt aaaattttag ggggacacaa 319800
gttctatcaa aatttaaatt tagtttttaa tttgtaaact tacaaacagg catttaattt 319860
ttaaaaaagt ctgctaatat aaactttatt tcataaacac tggattatta tgttactata 319920
gatgacaggt ttaaagcaga aattcacttt gtcatatata aaagcaccaa tcatgctaac 319980
agaagcttac atgtatgggc tgttagatga tatacttttt attgaatgga taaaagctac 320040
actaaaatct tatatcaatt tgatgtatgt aaatatcatg taagttgaca gattaatgac 320100
taagcaccag cgtctaagtt tgaatcctct tctacccctt gtgaatttga gcaagttact 320160
cagtctcact gtgtctcact ttcctcatct acaaagtaag gataataaaa atatcctcac 320220
agaattcttg aatagtgctc tgaactatcc tgtcacacaa taattgctca atttagtagt 320280
tgtttttatt attgttatta cagggaagca tttttttttt gcttgtgcta ctctttgaaa 320340
aatattttgt tagcagattt tgtcaaatgc ttatgtgaat aattagaaag ttctatatga 320400
atggagtctg aattaataac acataattgt aaatgggtat atagcaataa tgtgataaaa 320460
taaaaggagc aaaatcttag aattagccca gacctgaatt tgaataagag atgtccctca 320520
acaaatattt actaagtgcc cactaagcgc agggccctag ccaggttcca aggttacagc 320580

-continued agtgagcagg acagccccag ccccagccta caggggttta cagcttaatc aatctctacc 320640
tggggacctt gtgccactac tcaatctatc agtgcttcag tttccccatc gataaaatgg 320700
tgataaaatt tacttcccag ggacaatgca aagattcagt gagaacaggt gtgaactgcc 320760
ttctcagcac agcatagtaa ctcaataaat ggtaccacta tggacaggca agcactggtg 320820
ccagcagccc caaccaaaag tgtaatttac aaagtttatt ttaacatttc aagagactat 320880
tcactagtca ggcctcacca ggaccactga cataaaattc atttttaagg ataatagtta 320940
taagcaagat aatacaatag tgctaagcat ttcatcctaa gataatttta cgttgtgttt 321000
ttgtttgttt gtttttgaga cagtgtctca ctctgttgcc caggctggaa tgctagaata 321060
cagtggcatg atcatggctc actgcagtct tgacctctca tcaagagatc ctcccacctc 321120
agcctcccaa gaagctggga ctacaggcat gtgccaccat gcccagattt tttttatttt 321180
tttgtagaga tggggttcac tccattgcct gggctgttct agaactcctg ggctcaagcg 321240
attctcctgt ctcagcctcc caaagtgctg ggattacata ggtgaaccac tgcacccggc 321300
tatctttaac tttctaaatt aattttcttt ctaaatatag ttcataccta aatcctgaac 321360
caaggttaaa ttaacatttg tgattgatat atatcatgca ggttttgaga ctattttcaa 321420
aaagaacatc ataacctcat atatttttag gtccacattt aacaattaca gttaatttcc 321480
atagttgaaa attatagata atttcaaaat tatttggtga ttacacatat tacctaattc 321540
taaaccttta gtataatgta gagacagtta tttctgagag gggttatttt cacaataaag 321600
attgtaaaac tcaaaccagc tagtagtcac ttattaataa gaattatctg ctatcaataa 321660
aggcactact ataaaataat ctgaataagt tcttgcaggt tatcttaata aggcctgaca 321720
tctataaaca tttatgtatc atgtataagt gatgtgcaca aatggtatag gctaaggact 321780
cgttttatag aaaaacaagg tgaaagtaat aaaacaattt aaataacatg ttagaaacta 321840
catggtttgt tgaaaatgaa gcactcactt cttcactgac aaatttccat tcctgcttca 321900
gttcttcgca ccacatctcc cactctttag cagcttccag caaactcagc catttctccc 321960
acagagccga cacaatcttg agcaaacata tgccatcatt ttctgtgcac ctgagtctca 322020
agagtctaag gatctgtcgt agtttcatta actcttcttt ggttgatata agatttgaca 322080
ccaaggcctt aagaaagaaa agaaaaaaaa taagagggac atactattac ggttttcctg 322140
aaacttacta actcttttaa atcctgaaca attaattatt tcaatcttcc ataagtattg 322200
catgatccac ctcttatcct tttagaagtc aatttagacc agatgagaat tatctatgta 322260
ttattgtatt ctgcatgaat ttgggattac agggacaaat aatgacccat aaaccatttt 322320
tttccaagaa agaacatact ttcaaaagca aatatttgcc agacgcagtg gctcatgcct 322380
gtgatcccag cactttggga ggccaaggtg ggtggatcat gagatcagga gatcgagacc 322440
atcctggcca acatgttgaa accctatctc tattaaaaac acaaaattta gctgggcatg 322500
gtggcatgcg cctgtagtcc cagctactca ggaggctgaa gcaggagaat tgactgaacc 322560
tgggaggcac aggttgcagg gttgcagtga gctgaaattg tgccactcac tgcactccag 322620
cctgggcaac agagtgagac tccgtataaa aaaaaaaaaa aaaagtctat aagtggctgg 322680
gcacagtggc tcatgcagca ctttgggaga ctgaggcagg aggattgctt gaggctagga 322740
attcaagaca tagcaaggca acatagcaag accctgtctc tacaaaaaat taaaaaatta 322800
accaggcatg gtggtgtatg cctgtagccc cagctactca gcgggctggg atgggaggat 322860
cccttgaggc caggagctca aggctgtgat aagccatgat tgcaccattg tactccagcc 322920

-continued

```
tgggtgacag aacaagaccc tgtcttattt aaaaaaaaaa aaaaaaaaaa aaaaatctaa 322980
aagtacaaca gccctcatta tctgggtttc tcctttcaag gtttcagtta cttgtgatta 323040
acaacggtcc aaaaatacta aaaaattcca gaaggaaaaa atgtgtaaga tttatttgta 323100
taaaatgtat gttttatttg tatataaata tataagtgct attctgacta gtgtgatgaa 323160
atctcaagcc atctctctcc atcccacctg ggatacgaat cttccctttg tccagcacat 323220
catgctgtat atgttcccca cctacgcgtc atttggtagc cttcttggtg atcagatcaa 323280
ctgttgtggt atcaaatgct tgtgctccag atgaatagta gcccaacgct acctcaccat 323340
ggctatatca tttcatttca tcacttcatt tcattacctc acttcatttc atcacctcac 323400
ttcatttcat cacccaggca ttgtatagtc tcatgtcatt acaagaaggg tgaaaacagt 323460
acaatgacat attttgagag aaagagacca cattcaccca acttttatta cagcatattg 323520
ttataatttc tctgttattg ttgttgacct ctgactgcac tttaatttat aaattaaact 323580
ttatcatagg cgtgtacagg aaaaaaatta tatacataga gttcagtgtt attcacagtc 323640
tcaagcatcc actgggtgtc ttggaacata tcccctgtgg ataaaggggg actactgtac 323700
attttgttat ttttaagtct cacattttac taagtagttc ctttgcacaa tacttcctat 323760
atcaaccacc aacacaatat tgaaaggttt ttcttggttc gcttttgttt ttggggaatg 323820
ttaactacag atgatttaga aagtcctcat ccaaatccta ataacataat accacagatt 323880
ctaacagata aaaataagta aaagctcaaa ttgctttgta acagtctaag aagtaaccag 323940
aattcagagc ttatgacagt tgcagtaagc gatcagtgga caacaaggct ctgtcactga 324000
tccagcagta tccctcaaag tcacatgaga ggtgatgctt tagaaaagcc atcagtgagg 324060
acaggatgct attgggggat gactgtctgt gaacctgatt aattaaatct ctcagtacca 324120
ctgcttcatt tccttccttc tggcttttta agcttcaata tattacataa ggccaggcgc 324180
agtggctcgc gcctataatc ccagcacttt gaaaggccga ggctggagga tggcttgaag 324240
tcaggagttc aagagcagcc tggtcaacat tgtgaaaccc cgtctctact aaaaatacaa 324300
aaatcagctg ggcatggtgg cgggcactgt aatcccagct actcaggagg ccgaggcagg 324360
agaatcaaat cacttgaagc cgggaggtag aagctgcagt gagccaagac tgcatgactg 324420
cactccagcc tgggcaagac tgtgtctcaa atatatataa aacattactc tctggctttc 324480
gatttgagga atattcatgg atatttaact cactgtgaag atttctacgc gtcttaacag 324540
gaccacattc tctgctgcct ctgccagttt gttctgcaat tttttgcaca cagacttact 324600
ggctaattgc caatactatt accttgctct gttccaagcg ctctaaagct tctctgtaag 324660
acagtggcaa cgaggacatg gactgtccaa gaactgtctc cattttgctg aggttagtgt 324720
aaatatcctc ttccattttt ctatagcatt tgtaattctc aagataccta gtgagtcaca 324780
gttagaaaaa aagtggtatt aaattttatt taacacaata aattcaaaat ttcccagaat 324840
aaatattcca cacttaattt ttaagaaaag atatgacaac tttcgttttt gctaggcaat 324900
gcattttaaa atgttttcca agaagttttt attcccaaag ggacctgcat atgggtttaa 324960
atgcaaactt gaaaaggaag caagggccgt cctctaaaat gaagattttt tttttttaaa 325020
gttcacttca gtaaaatgaa aactgcattc tcaaacacac tgatgagctg taaattggta 325080
caattcttgt ggaaaaccac ttagtcttaa aactattccc atctttgacc cattaatgca 325140
gcttctgcaa tttaccttaa gaactgtatc ctaaacatat agagcttatc ctaaatcttt 325200
tgcacagtaa aacatcttta ctcactagac tattaattaa aacatcacac attggaatac 325260
ccttatctaa caaaggtatg attaagaaat taaaacaatt catcgtatac aatattatag 325320
```

-continued agtaattaca ttacttttag aaagtatttg ttacaatcaa gaaaagaact gttataaaat 325380
tttaaaataa agctggatat ttgatatttt atatatagca tatatatttt aaaacactaa 325440
aattatgcat acaaaaacag acacagccta aatcccccat tgaatgtaac taaaaactct 325500
atatcaaatt attcttaaaa aacaactctt aaaacgcatg aataaattga caaggaatta 325560
gggagtcaaa ctgtaaaatg gaaatataca gaaataggca aagttgtagg accagttttt 325620
tgccttgagg gcacttgagt ttcaattttc tttgattcct actgaaaggt gggggacaga 325680
ccataaagct gggagccaat cccaggatgg gtgtctaata gaaaactccc tctgcaagaa 325740
tatttgtaac acatataact ataaaggacc actctctaaa atatagaatt c 325791

<210> SEQ ID NO 2
<211> LENGTH: 2011
<212> TYPE: DNA
<213> ORGANISM: Human

<400> SEQUENCE: 2
tttcagtttc tccagctgct ggctttttgg acacccactc cccgccaggg aggcagttgc 60
aagcgcggag gctgcgagaa ataactgcct cttgaaactt gcagggcgaa gagcaggcgg 120
cgagcgctgg gccggggagg gaccacccga gctgcgacgg gctctggggc tgcggggcag 180
ggctggcgcc cggagcctga gctgcaggag gtgcgctcgc tttcctcaac aggtggcggc 240
ggggcgcgcg ccgggagacc ccccctaatg cgggaaaagc acgtgtccgc attttagaga 300
aggcaaggcc ggtgtgttta tctgcaagcc attatacttg cccacgaatc tttgagaaca 360
ttataatgac ctttgtgcct cttcttgcaa ggtgttttct cagctgttat ctcaagacat 420
ggatataaaa aactcaccat ctagccttaa ttctccttcc tcctacaact gcagtcaatc 480
catcttaccc ctggagcacg gctccatata catacttcc tcctatgtag acagccacca 540
tgaatatcca gccatgacat tctatagccc tgctgtgatg aattacagca ttcccagcaa 600
tgtcactaac ttggaaggtg ggcctggtcg gcagaccaca agcccaaatg tgttgtggcc 660
aacacctggg cacctttctc ctttagtggt ccatcgccag ttatcacatc tgtatgcgga 720
acctcaaaag agtccctggt gtgaagcaag atcgctagaa cacaccttac ctgtaaacag 780
agagacactg aaaaggaagg ttagtgggaa ccgttgcgcc agccctgtta ctggtccagg 840
ttcaaagagg gatgctcact tctgcgctgt ctgcagcgat tacgcatcgg gatatcacta 900
tggagtctgg tcgtgtgaag gatgtaaggc ctttttttaaa agaagcattc aaggacataa 960
tgattatatt tgtccagcta caaatcagtg tacaatcgat aaaaaccggc gcaagagctg 1020
ccaggcctgc cgacttcgga agtgttacga agtgggaatg gtgaagtgtg gctcccggag 1080
agagagatgt gggtaccgcc ttgtgcggag acagagaagt gccgacgagc agctgcactg 1140
tgccggcaag gccaagagaa gtggcggcca cgcgccccga gtgcgggagc tgctgctgga 1200
cgccctgagc cccgagcagc tagtgctcac cctcctggag gctgagccgc cccatgtgct 1260
gatcagccgc cccagtgcgc ccttcaccga ggcctccatg atgatgtccc tgaccaagtt 1320
ggccgacaag gagttggtac acatgatcag ctgggccaag aagattcccg gctttgtgga 1380
gctcagcctg ttcgaccaag tgcggctctt ggagagctgt tggatggagg tgttaatgat 1440
ggggctgatg tggcgctcaa ttgaccaccc cggcaagctc atctttgctc cagatcttgt 1500
tctggacagg gatgaggggga aatgcgtaga aggaattctg gaaatctttg acatgctcct 1560
ggcaactact tcaaggtttc gagagttaaa actccaacac aaagaatatc tctgtgtcaa 1620

-continued

```
ggccatgatc ctgctcaatt ccagtatgta ccctctggtc acagcgaccc aggatgctga   1680

cagcagccgg aagctggctc acttgctgaa cgccgtgacc gatgctttgg tttgggtgat   1740

tgccaagagc ggcatctcct cccagcagca atccatgcgc ctggctaacc tcctgatgct   1800

cctgtcccac gtcaggcatg cgagtaacaa gggcatggaa catctgctca acatgaagtg   1860

caaaaatgtg gtcccagtgt atgacctgct gctggagatg ctgaatgccc acgtgcttcg   1920

cgggtgcaag tcctccatca cggggtccga gtgcagcccg gcagaggaca gtaaaagcaa   1980

agagggctcc cagaacccac agtctcagtg a                                   2011


<210> SEQ ID NO 3
<211> LENGTH: 530
<212> TYPE: PRT
<213> ORGANISM: Human

<400> SEQUENCE: 3

Met Asp Ile Lys Asn Ser Pro Ser Ser Leu Asn Ser Pro Ser Ser Tyr
 1               5                  10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
                 180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285

Phe Thr Glu Ala Ser Met Met Met Ser Leu Thr Lys Leu Ala Asp Lys
    290                 295                 300
```

-continued

```
Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430

Val Thr Asp Ala Leu Val Trp Val Ile Ala Lys Ser Gly Ile Ser Ser
        435                 440                 445

Gln Gln Gln Ser Met Arg Leu Ala Asn Leu Leu Met Leu Leu Ser His
    450                 455                 460

Val Arg His Ala Ser Asn Lys Gly Met Glu His Leu Leu Asn Met Lys
465                 470                 475                 480

Cys Lys Asn Val Val Pro Val Tyr Asp Leu Leu Leu Glu Met Leu Asn
                485                 490                 495

Ala His Val Leu Arg Gly Cys Lys Ser Ser Ile Thr Gly Ser Glu Cys
            500                 505                 510

Ser Pro Ala Glu Asp Ser Lys Ser Lys Glu Gly Ser Gln Asn Pro Gln
        515                 520                 525

Ser Gln
    530
```